US011034979B2

(12) United States Patent
de Bont et al.

(10) Patent No.: US 11,034,979 B2
(45) Date of Patent: Jun. 15, 2021

(54) FUNGAL PRODUCTION OF FDCA

(71) Applicant: Purac Biochem B.V., Gorinchem (NL)

(72) Inventors: Johannes Adrianus Maria de Bont, Wageningen (NL); Harald Johan Ruijssenaars, Doorn (NL); Jan Werij, Gorssel (NL)

(73) Assignee: Purac Biochem B.V., Gorinchem (NL)

( * ) Notice: Subject to any disclaimer, the term of this patent is extended or adjusted under 35 U.S.C. 154(b) by 235 days.

(21) Appl. No.: 15/761,469

(22) PCT Filed: Sep. 21, 2016

(86) PCT No.: PCT/EP2016/072406

§ 371 (c)(1),
(2) Date: Mar. 20, 2018

(87) PCT Pub. No.: WO2017/050815

PCT Pub. Date: Mar. 30, 2017

(65) Prior Publication Data

US 2018/0265896 A1 Sep. 20, 2018

(30) Foreign Application Priority Data

Sep. 21, 2015 (NL) ..................................... 2015469

(51) Int. Cl.

| | |
|---|---|
| ***C12P 1/02*** | (2006.01) |
| ***C12N 9/04*** | (2006.01) |
| ***C12N 9/02*** | (2006.01) |
| ***C12P 7/44*** | (2006.01) |
| ***C12N 15/52*** | (2006.01) |
| ***C12P 7/42*** | (2006.01) |

(52) U.S. Cl.

CPC .............. *C12P 1/02* (2013.01); *C12N 9/0006* (2013.01); *C12N 9/0073* (2013.01); *C12N 15/52* (2013.01); *C12P 7/42* (2013.01); *C12P 7/44* (2013.01)

(58) Field of Classification Search

None

See application file for complete search history.

(56) References Cited

U.S. PATENT DOCUMENTS 7,067,303 B1 6/2006 Nichols
10,457,965 B2 * 10/2019 Ruijssenaars ........ C12N 9/0008

FOREIGN PATENT DOCUMENTS

| | | |
|---|---|---|
| JP | 2014508531 | 4/2014 |
| WO | WO2011/026913 A1 | 3/2011 |
| WO | WO012/064195 | 5/2012 |

OTHER PUBLICATIONS

Feldman, D. et al (2015) Detoxification of 5-hydroxymethylfurfural by the Pleurotus ostreatus lignolytic enzymes aryl alcohol oxidase and dehydrogenase. Biotechnology for biofuels, 8(1), p. 63.

Koopman, F. et al, (2010) Efficient whole-cell biotransformation of 5-(hydroxymethyl) furfural into FDCA, 2, 5-furandicarboxylic acid. Bioresource technology, 101(16), pp. 6291-6296.

SubName: Full=Uncharacterized protein {EC0:0000313 j EMBL:CEJ57635.1}, UNIPROT, retrieved Jul. 22, 2015 [XP002756032].

SubName: Full=Uncharacterized protein {EC0:00003131EMB L:CEJ53675.1}, UNIPROT, retrieved Jul. 22, 2015 [XP002756033].

SubName: Full=Putative Alcohol dehydrogenase 1 {ECO:O000313 j EMBL:CEJ60574.1}, UNIPROT, retrieved Jul. 22, 2015 [XP002756034].

SubName: Full=Putative Podospora anserina S mat genomic DNA chromosome 1, supercontig 6 {ECO:0000313 j EMBL:CEJ58504.1}, UNIPROT, retrieved Jul. 22, 2015 [XP002756035].

SubName: Full=Uncharacterized protein {EC0:0000313lEMBL:CEJ57637.1}, UNIPROT, retrieved Jul. 22, 2015 [XP002756036].

SubName: Full=Putative Vanillin dehydrogenase {EC0:00003131EMBL:CEJ54238.1}, UNIPROT, retrieved Jul. 22, 2015 [XP002756037].

SubName: Full=Uncharacterized protein {EC0:0000313IEMBL:CE058352.1}, UNIPROT, retrieved Jul. 22, 2015 [XP002756038].

RecName: Full=Alternative oxidase {EC0:0000256 j RuleBase:RU003779}; EC=1.-.-.- {EC0:0000256 j RuleBase: RU003779}, UNIPROT, retrieved Jul. 22, 2015 [XP002756040].

SubName: Full=Uncharacterized protein {EC0:0000313 j EMBL:CEJ57640.1}, UNIPROT, retrieved Jul. 22, 2015 [XP002756041].

SubName: Full=Uncharacterized protein {EC0:0000313jEMBL:CEJ55406.1}, UNIPROT, retrieved Jul. 22, 2015 [XP002756042].

SubName: Full=Uncharacterized protein {EC0:0000313 j EMB L:CEJ58414.1}, UNIPROT, retrieved Jul. 22, 2015 [XP002756043].

SubName: Full=Putative 6-phosphogluconate dehydrogenase family protein {EC0:0000313IEMBL:CEJ53854.1}. UNIPROT, retrieved Jul. 22, 2015 [XP002756044].

SubName: Full=Uncharacterized protein {EC0:0000313 j EMBL:CEJ57639.1}, UNIPROT, Jul. 22, 2015 [XP002756045].

SubName: Full=Uncharacterized protein {EC0:0000313 j EMBL:CEJ56087.1}, Uniprot, Jul. 22, 2015 [XP002756046].

(Continued)

*Primary Examiner* — Anand U Desai

(74) *Attorney, Agent, or Firm* — N.V. Nederlandsch Octrooibureau; Catherine A. Shultz; Tamara C. Stegmann

(57) ABSTRACT

The invention relates to fungal cells for the production of FDCA. The fungal cell is genetically modified to have at least one of a) a genetic modification that confers to or increases in the cell the ability to oxidize 5-hydroxymethyl-2-furancarboxylic acid to 5-formyl-2-furoic acid; and, b) a genetic modification that reduces catabolism of 2,5-furandicarboxylic acid in the cell. The fungal cell can further be genetically modified to increase the cell's ability to oxidize furanic aldehydes to the corresponding furanic carboxylic acids. The invention also relates to a process for the production of 2,5-furan-dicarboxylic acid (FDCA) wherein the cells of the invention are used for oxidation of a furanic precursors of FDCA.

3 Claims, 1 Drawing Sheet

Specification includes a Sequence Listing.

(56) References Cited

OTHER PUBLICATIONS

SubName: Full=Putative Caffeine resistance protein 5 {EC0:0000313 j EMBL:CEJ56374.1}, UNIPROT, Jul. 22, 2015, [XP002756047].
SubName: Full=Uncharacterized protein {EC0:0000313jEMBL:CEJ57636.1}, UNIPROT, Jul. 22, 2015 [XP002756048].
SubName: Full=Putative Aspergillus niger contig Anl4c0130, genomic contig {EC0:0000313IEMBL:CEJ62390.1}, UNIPROT, Jul. 22, 2015 [XP002756049].
SubName: Full=Uncharacterized protein {EC0:0000313 j EMBL:CEJ57638.1}, UNIPROT, Jul. 22, 2015 [XP002756050].
International Search Report issued in International Patent Application No. PCT/EP2016/072406 dated Nov. 14, 2016.
De Jong E. et al, (2012). Furandicarboxylic acid (FDCA), a versatile building block for a very interesting class of polyesters. In Biobased monomers, polymers, and materials (pp. 1-13). American Chemical Society.
Wierckx, N. et al, (2011) Microbial degradation of furanic compounds: biochemistry, genetics, and impact. Applied microbiology and biotechnology, 92(6), pp. 1095-1105.
Wierckx, N. et al, N., (2010) Isolation and characterization of Cupriavidus basilensis HMF14 for biological removal of inhibitors from lignocellulosic hydrolysate, 3 (3), pp. 336-343.
Koopman et al, (2010). Identification and characterization of the furfural and 5-(hydroxymethyl) furfural degradation pathways of Cupriavidus basilensis HMF14. Proceedings of the National Academy of Sciences, 107(11), pp. 4919-4924.
Zhang et al, (2010). Biodetoxification of toxins generated from lignocellulose pretreatment using a newly isolated fungus, Amorphotheca resinae ZN1, and the consequent ethanol fermentation. Biotechnology for biofuels, 3(1), p. 26.
Ran, H. et al, (2014). Analysis of biodegradation performance of furfural and 5-hydroxymethylfurfural by Amorphotheca resinae ZN1. Biotechnology for biofuels, 7(1), p. 51.
Lopez, M.J. et al, 2004. Isolation of microorganisms for biological detoxification of lignocellulosic hydrolysates. Applied Microbiology and Biotechnology, 64(1), pp. 125-131.
Nichols, N.N. et al, 2014. Biological abatement of inhibitors in rice hull hydrolyzate and fermentation to ethanol using conventional and engineered microbes. Biomass and bioenergy, 67, pp. 79-88.
Nichols, N.N. et al, 2005. Bioabatement to remove inhibitors from biomass-derived sugar hydrolysates. Applied biochemistry and biotechnology, 121(1-3), pp. 379-390.
Nichols N.N. et al, 2010. Fermentation of bioenergy crops into ethanol using biological abatement for removal of inhibitors. Bioresource technology, 101(19), pp. 7545-7550.
Nichols N.N. et al, 2008. Fungal metabolism of fermentation inhibitors present in corn stover dilute acid hydrolysate. Enzyme and microbial technology, 42(7), pp. 624-630.
Parawira W. et al, 2011. Biotechnological strategies to overcome inhibitors in lignocellulose hydrolysates for ethanol production. Critical reviews in biotechnology, 31(1), pp. 20-31.
Rajulu et al, 2014. Several fungi from fire-prone forests of southern India can utilize furaldehydes. Mycological progress, 13(4), p. 992.
Horn et al.; "Draft Genome Sequence of the Fungus Penicillium brasilianum MG11"; Genome Anouncements, Sep. 3, 2015, vol. 3, Issue 5, e00724-15.
UniProtKB A0A0F7TQB1, [online], Jul. 22, 2015, [Searched on Jan. 27, 2021], Internet <URL:www.uniprot.org/uniprot/A0A0F7TQB1>.

* cited by examiner

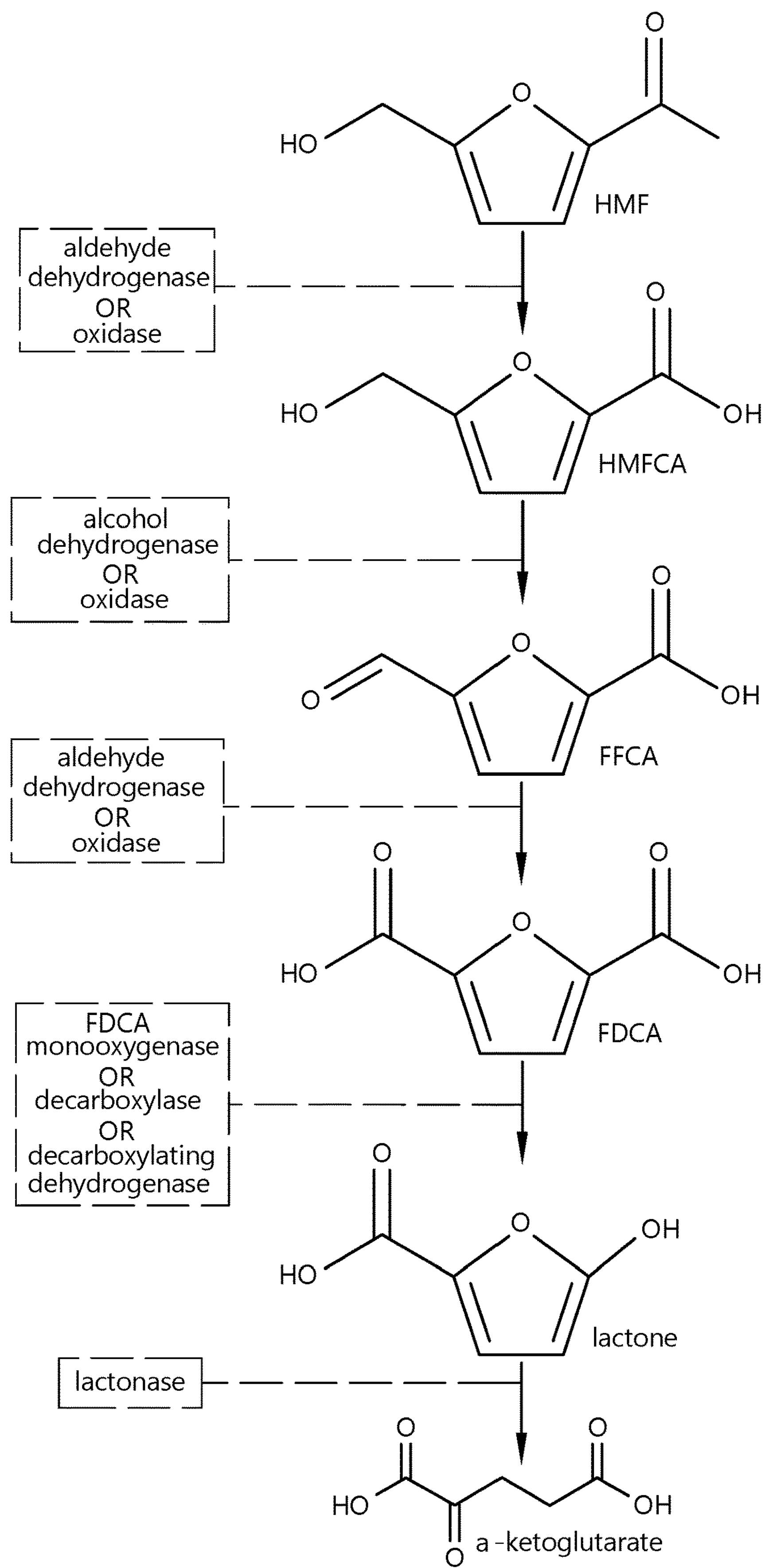
HO
O
O
HMF
aldehyde dehydrogenase OR oxidase
HO
O
O
OH
HMFCA
alcohol dehydrogenase OR oxidase
O
O
O
OH
FFCA
aldehyde dehydrogenase OR oxidase
HO
O
O
O
OH
FDCA
FDCA monooxygenase OR decarboxylase OR decarboxylating dehydrogenase
HO
O
O
OH
lactone
lactonase
HO
O
O
OH
O
a -ketoglutarate

SEQUENCE LISTING

```
<160> NUMBER OF SEQ ID NOS: 69

<210> SEQ ID NO 1
<211> LENGTH: 351
<212> TYPE: PRT
<213> ORGANISM: Penicillium brasilianum

<400> SEQUENCE: 1

Met Gly Ser Leu Ser Leu Pro Glu Thr Ser Leu Ala Ala Ile Gln Asp
1               5                   10                  15

Lys Glu Thr Lys Ala Ile Ser Val Ala Lys Arg Pro Thr Pro Val Pro
            20                  25                  30

Val Gly Thr Gln Val Leu Val Lys Leu His Tyr Ser Gly Val Cys Ala
        35                  40                  45

Thr Asp Leu His Leu Ala Arg Gly Ser Val Pro Tyr Leu Gln Pro Lys
    50                  55                  60

Val Ser Val Gly Gly His Glu Gly Thr Gly Val Ile Ala Ser Leu Gly
65                  70                  75                  80

Pro Asp Val Asp Ala Ala Glu Trp His Val Gly Asp Arg Val Ala Val
                85                  90                  95

Arg Trp Val His Ile Val Cys Gly Lys Cys Glu Val Cys Thr Thr Gly
            100                 105                 110

Phe Glu Asn Leu Cys Gln Ser Arg Lys Leu Ala Gly Lys Asp Val Glu
        115                 120                 125

Gly Thr Phe Ala Glu Tyr Ala Ile Ala Asp Ser Ser Tyr Met Val Arg
    130                 135                 140

Leu Pro Ala Gly Val Ser Asp Ala Asp Ala Ala Pro Ile Leu Cys Ala
145                 150                 155                 160

Gly Val Thr Val Tyr Lys Ala Leu Lys Ile Ala Ser Leu Arg Ala Gly
                165                 170                 175

Ser Trp Val Ala Val Ala Gly Ala Gly Gly Gly Leu Gly His Leu Ala
            180                 185                 190

Ile Gln Tyr Ala Arg Ala Met Gly Leu Lys Val Val Ala Leu Asp Ala
        195                 200                 205
```

```
Arg Lys Arg Asp Leu Cys Leu Ser Leu Gly Ala Glu Ser Tyr Ile Asp
    210                 215                 220

Val Leu Glu Thr Asp Asp Cys Val Ala Gln Val Ile Lys Val Thr Asp
225                 230                 235                 240

Gly Gly Ala His Gly Ala Leu Ile Cys Ala Ser Ser Gly Gln Ala Tyr
                245                 250                 255

Asp Asp Ala Val Lys Phe Leu Arg Trp Thr Gly Thr Leu Val Cys Ile
            260                 265                 270

Gly Leu Pro Pro Lys Pro Thr Leu Leu Ser Leu Gly Pro Ala Asp Phe
        275                 280                 285

Val Ala Arg Gly Ile Lys Val Met Gly Thr Ser Thr Gly Asp Arg Gln
    290                 295                 300

Asp Thr Val Glu Ala Leu Ala Phe Val Ala Lys Gly Gln Val Lys Pro
305                 310                 315                 320

Gln Leu Thr Glu Arg Arg Leu Glu Asp Val Glu Glu Ile Leu Lys Glu
                325                 330                 335

Ile Glu Asn Gly Thr Met Gln Gly Lys Ala Val Ile Arg Ile Ala
            340                 345                 350


<210> SEQ ID NO 2
<211> LENGTH: 339
<212> TYPE: PRT
<213> ORGANISM: Penicillium brasilianum

<400> SEQUENCE: 2

Met Ser Leu Pro Ser His Tyr Lys Arg Ala Ala Phe Lys Glu Ala Gly
1               5                   10                  15

Gly Pro Leu Thr Ile Glu Glu Val Asp Leu Thr Met Pro Asp Ala Gly
            20                  25                  30

Glu Val Leu Val Lys Val Glu Ala Cys Gly Val Cys Phe Ser Asp Thr
        35                  40                  45

Val Pro Gln Ala His Gly Leu Gly Gly Lys Phe Pro Ile Val Pro Gly
    50                  55                  60

His Glu Ile Ile Gly His Val Val Ala Thr Gly Asp Gly Val Ser Asp
65                  70                  75                  80

Trp Glu Val Gly Asp Arg Ile Gly Glu Gly Trp His Gly Gly His Asp
                85                  90                  95

Gly Thr Cys Pro Ser Cys Arg Gln Gly His Phe Gln Met Cys Asp Asn
            100                 105                 110

Gln Ser Ile Asn Gly Val Thr Lys Asn Gly Gly Tyr Ala Gln Tyr Cys
        115                 120                 125

Ile Leu Arg Ser Glu Ala Ala Val Arg Ile Pro Thr His Val Ser Ala
    130                 135                 140

Ala Glu Tyr Ala Pro Ile Leu Cys Ala Gly Val Thr Val Phe Asn Ser
145                 150                 155                 160

Met Arg Gln Ile Gly Val Lys Pro Gly Ser Thr Val Ala Ile Gln Gly
                165                 170                 175

Leu Gly Gly Leu Gly His Leu Ala Ile Gln Tyr Ala Asn Arg Phe Gly
            180                 185                 190

Phe Arg Val Val Ala Ile Ser Arg Asp Asp Gln Lys Glu Arg Phe Val
        195                 200                 205

Arg Asp Leu Gly Ala His Glu Tyr Ile Asn Thr Ser Glu Glu Asp Val
    210                 215                 220

Gly Ser Ala Leu Gln Lys Leu Gly Gly Ala Ser Leu Ile Val Ala Thr
225                 230                 235                 240
```

```
Ala Pro Asn Ala Arg Ala Ile Ser Pro Leu Leu Lys Gly Leu Arg Pro
                245                 250                 255

Leu Gly Lys Leu Leu Ile Leu Ala Val Pro Gly Glu Ile Pro Leu Asp
            260                 265                 270

Thr Arg Leu Met Val Ala Arg Gly Leu Ser Val His Gly Trp Pro Ser
        275                 280                 285

Gly His Ala Leu Asp Ser Glu Glu Thr Ile Arg Phe Thr Glu Leu Glu
    290                 295                 300

Asp Ile Lys Cys Met Ile Gln Thr Tyr Ser Leu Asp Arg Ala Asn Glu
305                 310                 315                 320

Ala Phe Asp Ala Met Ile Ser Gly Ser Val Arg Phe Arg Ala Val Ile
                325                 330                 335

Thr Met Glu


<210> SEQ ID NO 3
<211> LENGTH: 389
<212> TYPE: PRT
<213> ORGANISM: Penicillium brasilianum

<400> SEQUENCE: 3

Met Ala Pro Gln Ile Pro Glu Lys Gln Trp Ala Gln Val Val Glu Lys
1               5                   10                  15

Lys Gly Gly Pro Pro Val Tyr Lys Glu Ile Pro Val Pro Lys Pro Gly
            20                  25                  30

Pro Asp Glu Val Leu Leu Lys Ile Lys Tyr Ser Gly Val Cys His Thr
        35                  40                  45

Asp Leu His Ala Met Asn Gly Asp Trp Pro Leu Pro Val Lys Met Pro
    50                  55                  60

Leu Val Gly Gly His Glu Gly Ala Gly Ile Val Val Ala Lys Gly Glu
65                  70                  75                  80

Leu Ala Glu Gly Val Glu Ile Gly Asp His Ala Gly Ile Lys Trp Leu
                85                  90                  95

Asn Gly Ser Cys Leu Ala Cys Glu Tyr Cys Lys Thr Ser Asp Glu Pro
            100                 105                 110

Leu Cys Ala Thr Pro Gln Leu Ser Gly Tyr Thr Val Asp Gly Thr Phe
        115                 120                 125

Gln Gln Tyr Ala Ile Gly Lys Ala Ala His Val Thr Ile Leu Pro Lys
    130                 135                 140

Asp Ile Pro Leu Asp Gly Ile Ala Pro Ile Leu Cys Ala Gly Leu Thr
145                 150                 155                 160

Val Tyr Lys Gly Leu Lys Glu Ser Asn Ala Arg Pro Gly Gln Thr Val
                165                 170                 175

Ala Ile Val Gly Ala Gly Gly Gly Leu Gly Val Met Ala Gln Gln Tyr
            180                 185                 190

Ala Lys Ala Met Gly Leu Arg Val Ile Ser Ile Asp Gly Gly Asp Glu
        195                 200                 205

Lys Arg Gln Val Cys Glu Lys Leu Asp Ser Glu Ala Tyr Ile Asp Phe
    210                 215                 220

Thr Lys Ser Lys Asp Leu Val Ser Asp Val Lys Ala Ala Thr Pro Glu
225                 230                 235                 240

Gly Leu Gly Ala His Ala Val Ile Leu Leu Ala Val Ser Glu Lys Pro
                245                 250                 255

Phe Gln Gln Ala Val Glu Tyr Ser Arg Pro Arg Gly Thr Ile Val Ala
            260                 265                 270
```

```
Ile Gly Met Pro Ala Asn Ala Phe Leu Lys Ala Ser Val Phe Glu Thr
        275                 280                 285

Val Val Lys Met Ile Thr Ile Lys Gly Ser Tyr Val Gly Asn Arg Gln
    290                 295                 300

Asp Ala Ser Glu Ala Val Asp Phe Tyr Ala Arg Gly Leu Ile Lys Ala
305                 310                 315                 320

Pro Phe Lys Thr Val Pro Leu Glu Glu Leu Pro Lys Val Phe Glu Leu
                325                 330                 335

Met Gly Lys Leu Pro Asn Ser Asn Leu Leu Leu His Lys Leu Leu Ile
            340                 345                 350

Cys Phe Ser Gln Ser Lys Ala Arg Leu Pro Val Val Met Phe Ser Arg
        355                 360                 365

Cys Gln Ser Lys Cys Ile Asn Arg Arg Ala Val His Asn Arg Gln His
    370                 375                 380

Arg Met Ser Ile Ser
385


<210> SEQ ID NO 4
<211> LENGTH: 330
<212> TYPE: PRT
<213> ORGANISM: Penicillium brasilianum

<400> SEQUENCE: 4

Met Ser Leu Pro Thr Thr Met Arg Ala Val Ile Val Glu Gln Thr Gly
1               5                   10                  15

Gly Pro Glu Val Leu Gln Phe Lys Thr Asp His Pro Val Pro Thr Pro
            20                  25                  30

Gly Glu Gly Gln Leu Leu Val His Asn Asn Ile Ser Gly Val Asn Tyr
        35                  40                  45

Ile Asp Thr Tyr Phe Arg Thr Gly Leu Tyr Ala Ser Pro Lys Pro Glu
    50                  55                  60

Ile Leu Gly Arg Glu Gly Ala Gly Ile Val Ala Ala Ile Gly Pro Asn
65                  70                  75                  80

Thr Ser Gly Phe Asn Val Gly Asp Arg Val Ala Trp Leu Ala Thr Gly
                85                  90                  95

Gly Tyr Ala Glu Tyr Thr Ala Val Pro Ala Ala Lys Thr Val Lys Ile
            100                 105                 110

Pro Glu Gly Val Ser Asp Glu Asp Val Val Ala Ser Phe Leu Ser Gly
        115                 120                 125

Leu Thr Val Leu Ser Phe Ala Lys Glu Thr Tyr Pro Val Gln Lys Gly
    130                 135                 140

Asp Trp Val Leu Leu His Ala Ala Ala Gly Gly Ala Gly Phe Leu Met
145                 150                 155                 160

Thr Gln Ile Leu Lys Ser Ile Gly Ala Lys Val Ile Gly Thr Ala Gly
                165                 170                 175

Gly Ala Glu Lys Cys Ala Leu Val Lys Ser Leu Gly Ala Asp Val Val
            180                 185                 190

Ile Asp Tyr Arg Ser Glu Glu Gly Lys Asp Trp Val Lys Leu Val Lys
        195                 200                 205

Glu Ala Thr Gly Gly Arg Gly Val Asp Val Val Tyr Asp Ser Val Gly
    210                 215                 220

Lys Asp Thr Trp Glu Gly Ser Leu Glu Ala Val Lys Arg Lys Gly Thr
225                 230                 235                 240

Ile Val Trp Phe Gly Asn Ala Ser Gly Pro Val Pro Pro Ile Pro Leu
```

```
                245                 250                 255

Pro Lys Leu Ser Pro Lys Asn Val Lys Ile Ala Arg Pro Thr Leu Phe
            260                 265                 270

Gly Tyr Ile Glu Thr Arg Glu Glu Phe Glu Tyr Tyr Thr Asn Glu Leu
        275                 280                 285

Phe Ser Leu Leu Gln Ser Gly Gln Leu Lys Thr Lys Ile His Lys Val
    290                 295                 300

Tyr Pro Leu Glu Asp Ile Ala Gln Val His Lys Asp Leu Glu Gly Arg
305                 310                 315                 320

Lys Thr Met Gly Lys Ser Leu Leu Lys Pro
                325                 330


<210> SEQ ID NO 5
<211> LENGTH: 505
<212> TYPE: PRT
<213> ORGANISM: Penicillium brasilianum

<400> SEQUENCE: 5

Met Thr Gln Thr Asn Val His Val Asn Lys Ser Asp Thr Ser Leu Ala
1               5                   10                  15

Ala Pro Gln Gln Leu Phe Ile Ser Gly Lys Tyr Gln Asn Ser Gln Arg
            20                  25                  30

Asn Gly Thr Phe Pro Val Lys Asn Pro Met Thr Gly Glu Thr Ile Tyr
        35                  40                  45

Glu Cys Val Ser Ala Ser Leu Asp Asp Tyr Ala Ala Ala Ile Glu Glu
    50                  55                  60

Ala Asp Ala Ala Gln Pro Ser Trp Ala Arg Leu Gly Pro Ser Ala Arg
65                  70                  75                  80

Arg Leu Ile Leu Leu Lys Ala Ala Asp Ile Met Glu Thr Tyr Ile Glu
                85                  90                  95

Thr Asp Ala Pro Ala Ile Leu Ser Ala Glu Val Ser Ala Thr Arg Gly
            100                 105                 110

Trp Val Arg Ala Asn Ile Leu Ser Thr Ala Gly Val Phe Arg Glu Thr
        115                 120                 125

Ala Ala Leu Ala Thr His Ile Lys Gly Glu Ile Val Pro Ala Asp Arg
    130                 135                 140

Pro Gly Thr Thr Ile Leu Val Ser Arg Glu Pro Val Gly Val Val Leu
145                 150                 155                 160

Ala Ile Ser Pro Trp Asn Met Pro Ala Thr Leu Thr Ala Arg Ala Ile
                165                 170                 175

Cys Cys Pro Leu Ile Cys Gly Asn Ser Val Val Leu Arg Pro Ser Glu
            180                 185                 190

Phe Ser Pro Lys Ser Gln His Leu Val Val Arg Ala Leu Thr Glu Ala
        195                 200                 205

Gly Leu Pro Ala Gly Cys Leu Gln Phe Leu Pro Thr Ser Thr Ala Asp
    210                 215                 220

Thr Pro Arg Ala Ile Glu Phe Ala Ile Arg His Pro Lys Val Ser Arg
225                 230                 235                 240

Ala Asn Phe Thr Gly Ser Asp Arg Val Gly Arg Ile Ile Ala Gly Leu
                245                 250                 255

Ser Ala Ser Cys Leu Lys Pro Cys Val Leu Glu Leu Gly Gly Lys Ala
            260                 265                 270

Pro Val Val Val Leu Glu Asp Ala Asp Val Glu Ala Ala Val Glu Ala
        275                 280                 285
```

```
Val Val Tyr Gly Ala Met Ser Asn Ser Gly Gln Ile Cys Met Ser Thr
    290                 295                 300

Glu Arg Ala Ile Val His Arg Ser Leu Ala Ala Asp Phe Lys Ala Leu
305                 310                 315                 320

Leu Val Lys Arg Ala Glu Ser Leu Arg Val Gly Asn His Leu Glu Asp
                325                 330                 335

Pro Asp Val Gln Leu Ser Gly Leu Phe Thr Ala Ala Ser Ala Glu Arg
            340                 345                 350

Val Leu Gly Leu Ile Lys Gly Ala Val Asn Ala Gly Ala Thr Leu Leu
        355                 360                 365

Ala Gly Asp Leu Ala Leu His Gly Pro Cys Gln Thr Ile Met Ala Pro
    370                 375                 380

His Ile Leu Thr Gly Val Thr Arg Asp Met Asp Leu Phe His Arg Glu
385                 390                 395                 400

Thr Phe Gly Pro Val Leu Phe Val Ser Glu Phe Asp Thr Asp Asp Glu
                405                 410                 415

Ala Ile Ala Gln Ala Asn Asp Thr Glu Phe Ser Leu Cys Ala Ser Val
            420                 425                 430

Phe Ser Arg Asp Val Leu Arg Ala Met Asp Thr Ala Lys Arg Ile Arg
        435                 440                 445

Thr Gly Ser Cys His Val Asn Gly Pro Thr Val Tyr Ile Glu Ala Pro
    450                 455                 460

Leu Pro Asn Gly Gly Val Gly Gly Gly Ser Gly Tyr Gly Arg Phe Gly
465                 470                 475                 480

Gly Val Ala Gly Ile Glu Glu Phe Thr Glu Arg Gln Ile Val Ser Leu
                485                 490                 495

Ala Lys Pro Gly Ile Lys Tyr Ala Phe
            500                 505
```

<210> SEQ ID NO 6
<211> LENGTH: 479
<212> TYPE: PRT
<213> ORGANISM: Penicillium brasilianum

<400> SEQUENCE: 6

```
Met Ser Gln Asn Asp Ser Lys Ala Val Thr Pro Leu Leu Ile Asn Asn
1               5                   10                  15

Glu Ser Val Met Thr Asp Ile Lys Phe Glu Val His Ala Pro Ala Thr
            20                  25                  30

Gly Glu Leu Ser Ser Tyr Cys Ala Gly Ala Ser Val Glu Asp Ala Val
        35                  40                  45

Arg Ala Val Asp Asn Ala Lys Ala Ala Phe Pro Ala Trp Ser Lys Thr
    50                  55                  60

Lys Ala Tyr Asp Arg Arg Asp Ile Leu Leu Lys Ala Ala Glu Ile Met
65                  70                  75                  80

Ile Ser Arg Lys Glu Glu Leu Ile Ala Tyr Gln Gln Glu Glu Thr Gly
                85                  90                  95

Ala Gly Arg Pro Phe Cys Glu His Thr Phe Asn Met Gly Val Asn Phe
            100                 105                 110

Ile Lys Asp Phe Ala Gly Arg Ile Ser Thr Ile Glu Gly Val Val Pro
        115                 120                 125

Ser Val Thr Leu Asp Gly Glu Gly Ala Met Ile Tyr Lys Glu Pro Tyr
    130                 135                 140

Gly Val Ile Leu Ser Ile Ala Pro Trp Asn Ala Pro Phe Ile Leu Gly
145                 150                 155                 160
```

```
Thr Arg Ala Val Ala Leu Pro Leu Ala Ala Gly Asn Thr Val Val Leu
                165                 170                 175

Lys Gly Ser Glu Leu Ser Pro Lys Cys Phe Trp Ala Leu Gly Asp Ile
            180                 185                 190

Phe Arg Gln Ala Gly Leu Pro Asp Gly Cys Phe Asn Val Ile Phe His
        195                 200                 205

Gln Pro Ser Asp Ala Ala Ala Val Thr Thr Ala Leu Ile Ala His Pro
    210                 215                 220

Ala Val Arg Lys Val Asn Phe Thr Gly Ser Thr Asn Val Gly Ser Ile
225                 230                 235                 240

Ile Ala Ser Thr Ala Gly Lys Tyr Ile Lys Pro Val Leu Leu Glu Leu
                245                 250                 255

Gly Gly Lys Ala Ser Ala Ile Val Leu Asp Asp Ala Asp Leu Asp Lys
            260                 265                 270

Ala Ala Met Ser Cys Ala Leu Gly Ser Phe Leu His Ser Gly Gln Ile
        275                 280                 285

Cys Met Ser Thr Glu Arg Ile Val Val Gln Arg Ala Ile Ala Asp Glu
    290                 295                 300

Phe Arg Gln Lys Val Ala Ala Asn Ala Glu Lys Leu Phe Gly Lys Asp
305                 310                 315                 320

Ala Pro Ala Leu Gly Leu Val Asn Ala Ala Ala Val Thr Lys Asn Lys
                325                 330                 335

Lys Leu Val Ala Asp Ala Val Ser Arg Gly Ala Asn Ile Leu Phe Gly
            340                 345                 350

Asp Ala Ser Ala Asn Glu Ser Val Asn Thr Cys Met Arg Pro Ile Ile
        355                 360                 365

Val Asp Gly Val Ser Lys Glu Met Asp Leu Tyr Ala Thr Glu Ser Phe
    370                 375                 380

Gly Pro Thr Val Ser Leu Ile Val Val Asp Thr Glu Glu Glu Ala Ile
385                 390                 395                 400

Ala Val Ala Asn Asp Thr Glu Tyr Gly Leu Thr Gly Ala Val Tyr Thr
                405                 410                 415

Gln Asn Leu Phe Arg Gly Leu Arg Val Ala Lys Gln Ile Glu Ser Gly
            420                 425                 430

Ala Ile His Ile Asn Ala Leu Thr Val His Asp Glu Pro Thr Leu Pro
        435                 440                 445

His Gly Gly Trp Lys Ser Ser Gly Phe Gly Arg Phe Gly Gly Val Ala
    450                 455                 460

Gly Tyr Asp Glu Phe Leu Gln Thr Lys Thr Val Thr Trp Met Glu
465                 470                 475


<210> SEQ ID NO 7
<211> LENGTH: 473
<212> TYPE: PRT
<213> ORGANISM: Penicillium brasilianum

<400> SEQUENCE: 7

Met Thr Val Thr Thr Thr Leu Ser Leu Ile Ala Pro Pro Glu His Arg
1               5                   10                  15

His Glu Pro Ser Pro Phe Asp Pro Ala Val Asp Ile Lys Asp Ala Pro
            20                  25                  30

Ser Ile Ile Thr Ala Leu Asn Ala Ala Asp Pro Ser Leu Lys Val Tyr
        35                  40                  45

Thr Arg Ser Ser Pro Asn Phe Glu Thr Leu Arg Gly Val Tyr Asn Lys
```

```
    50                  55                  60

Leu Ile Thr His Gln Pro Leu Ala Ile Cys Arg Pro Gln Thr Ile Glu
65                  70                  75                  80

Gln Ile Gln Leu Ile Val Arg Thr Ala Arg Ala Ala Asn Pro Pro Val
                85                  90                  95

Pro Ile Val Pro Arg Cys Gly Gly His Asp Val Tyr Gly Arg Gly Leu
            100                 105                 110

Lys Pro Asp Ser Leu Ser Ile Asp Met Arg Glu Leu Asp Thr Gln Thr
        115                 120                 125

Leu Ala Glu Asp Arg Gln Ser Val Arg Ile Gly Gly Gly Val Thr Ser
    130                 135                 140

Gln Asn Phe Val Gly Phe Leu Asp Glu His Gly Leu Cys Thr Ala Asn
145                 150                 155                 160

Gly Thr Ala Gly Asn Val Gly Trp Thr Gly Trp Ala Val Trp Gly Gly
                165                 170                 175

Tyr Gly Pro Phe Asn Asp Tyr Val Gly Leu Gly Val Asp Asn Ile Leu
            180                 185                 190

Ser Ala Arg Leu Val Leu Ala Asp Gly Ser Leu Val Glu Ala Gly Pro
        195                 200                 205

Gly Ser Glu Leu Leu Trp Gly Val Arg Gly Ala Gly Gly Ser Leu Gly
    210                 215                 220

Val Ile Val Asp Val Thr Val Lys Val Tyr Pro Met Pro Val Ile Leu
225                 230                 235                 240

Ala Gly Phe Ile Ala Tyr Gln Trp Gly Glu Ser Ala Lys Val Leu Ser
                245                 250                 255

Gly Leu Gln Glu Leu Leu Asp Arg Gly Ile Pro Asp Thr Met Cys Leu
            260                 265                 270

Gln Met Gly Phe Met Lys Thr Lys Trp Gly Val Gly Met Ser Leu Ile
        275                 280                 285

Phe Ala Trp Pro Asp Ser Glu Thr Leu Asp Glu Gly Arg Thr Trp Leu
    290                 295                 300

Glu Thr Val Arg Gly Leu Gly Ala Ile Gln Val Asp Thr Val Gly Glu
305                 310                 315                 320

Thr Thr Phe Lys Ala Phe Gln Gly Ile Thr Ser Arg Val Val Asp Glu
                325                 330                 335

Pro Val Asn Val Cys Thr Arg Ser Ala Ser Val Pro Arg Phe Thr Pro
            340                 345                 350

Glu Thr Ile Ala Leu Leu Gln Lys Tyr Ser Glu Ala Ile Pro Asp Gly
        355                 360                 365

Arg Gln Tyr Asn Val Ile Ala His Ile Gly His Gly Lys Ser Thr Arg
    370                 375                 380

Pro Asn Pro Asp Thr Ser Phe Ala Thr Arg Glu Pro His Val Leu Phe
385                 390                 395                 400

His Ile Asn Ala Cys Asp Glu Pro Glu Arg Met Asp Glu Ala Arg Ser
                405                 410                 415

Trp Val Asp Gly Leu Met Lys Glu Met Asn Ala Thr Arg Gln Ala Met
            420                 425                 430

Lys Pro Val Tyr Val Ser Phe Met Gly Glu Asp Glu Asp Pro Arg Val
        435                 440                 445

Ser Phe Gly Ser His Trp Glu Arg Leu Gln Ala Leu Lys Gln Ser Val
    450                 455                 460

Asp Pro Asp Asn Val Phe Arg Phe Pro
465                 470
```

<210> SEQ ID NO 8
<211> LENGTH: 475
<212> TYPE: PRT
<213> ORGANISM: Penicillium brasilianum

<400> SEQUENCE: 8

```
Met Pro Phe Leu Pro Phe Phe Lys Val Leu Arg Leu Arg Arg Glu Leu
1               5                   10                  15

Asp Gly Thr Lys Ala Glu Ile Phe Thr Trp Gly Cys Asp Gly Tyr Asp
            20                  25                  30

Glu Ser Ile Lys Gln Trp Asn Ala Tyr Leu Thr Gln Gly Ala Thr Val
        35                  40                  45

Arg Val Thr Ser Ser Asp Glu Ala Ala Thr Val Val Arg Phe Ala Ala
    50                  55                  60

Cys His Lys Ile Pro Phe Thr Val Lys Gly Gly Gly Tyr Ser Thr Thr
65                  70                  75                  80

Gly Ala Ser Ser Ala His Gly Val Thr Ala Gln Gly Gly Ala Leu Trp
                85                  90                  95

Glu Asp Ile Asp Val Ala Ala Ala Gln His Arg Leu Ala Val Val Gly
            100                 105                 110

Ser Thr Leu Asn His Ile Gly Val Ala Gly Ala Thr Leu Gly Gly Gly
        115                 120                 125

Tyr Gly Trp Leu Thr Gly Gln Tyr Gly Leu Ala Ile Asp Asn Leu Leu
    130                 135                 140

Trp Val Lys Met Ile Leu Ala Asp Gly Ser Val Ile Ile Val Ser Glu
145                 150                 155                 160

Glu Gln Tyr Pro Asp Leu Phe Trp Ala Ile Arg Gly Ala Gly Gln Ser
                165                 170                 175

Phe Gly Val Ala Ile Glu Leu Ala Phe Arg Ala His Arg Gln Asp His
            180                 185                 190

Pro Val Phe Ala Gly Thr Leu Leu Phe Ser Ala Ser Lys Leu Ser Ala
        195                 200                 205

Ile Val Glu Phe Ala Asn Asn Phe Glu Thr Leu Thr Asn Gly Asn Gln
    210                 215                 220

Gly Phe Trp Phe Gly Phe Thr Met Pro Pro Ser Met Asp Arg Cys Ala
225                 230                 235                 240

Ile Leu Val Val Val Phe Tyr Asn Gly Pro Gln Ile Ala Ala Arg Gln
                245                 250                 255

Phe Phe Ser Pro Leu Leu Ser Ile Gly Pro Val Val Asn Glu Thr Gly
            260                 265                 270

Met Leu Pro Tyr Asp Ser Leu Asn Gly Ile Leu Asn Met Met Asp Thr
        275                 280                 285

Val Ser Arg Arg Arg Ile Leu Arg Gly Ala Asp Ile Thr Leu Pro Thr
    290                 295                 300

Asp Glu Asn Val Gly Thr Arg Lys Ser Leu Arg Gly Ser Asn Ile Thr
305                 310                 315                 320

Leu Pro Leu Asp Ile Asn Phe Thr Ala Ser Ile Tyr Ser Glu Phe Asp
                325                 330                 335

Gly Ile Leu Arg Glu Phe Thr Gln Ala Arg Asp Ser Ile Leu Leu Phe
            340                 345                 350

Glu Leu Leu Pro Tyr Thr Gln Ile Thr Lys Val Pro Asn Asp Ala Thr
        355                 360                 365

Ala Phe Ala Ser Arg Gly Pro Tyr His Asn Val Ile Ser Leu Phe Gly
```

```
    370                 375                 380

Trp Gln Asp Lys Asp Leu Asp Glu Arg Met His Ser Leu Gln Glu Asp
385                 390                 395                 400

Ile Met Asn Gln Ile Gly Lys Arg Ala Gly Ile Ala Cys Thr Pro Phe
                405                 410                 415

Tyr Asn Val Ser Lys His Gly Thr Gly Leu Tyr Ala Asn Tyr Ala Gly
            420                 425                 430

His Asn Val Pro Leu Glu Ala Ile Phe Gly Asp Asn Leu Arg Arg Leu
        435                 440                 445

Gln Glu Leu Lys Lys Lys Phe Asp Pro Asn Asn Val Phe Lys Lys Trp
    450                 455                 460

His Asn Leu Asn Thr Thr Ile Gly Thr Pro Ala
465                 470                 475


<210> SEQ ID NO 9
<211> LENGTH: 401
<212> TYPE: PRT
<213> ORGANISM: Penicillium brasilianum

<400> SEQUENCE: 9

Met Met Thr Pro Pro Ile Leu Ala Phe His Leu Phe Lys Asp Phe Glu
1               5                   10                  15

Leu Gln Arg Thr Lys Asn Tyr Phe Arg Val Leu Asn Ile Asn Tyr Lys
            20                  25                  30

Ala Asp His His Pro His Gln Leu Phe His Asp Glu Phe Thr Ile Asn
        35                  40                  45

Thr Ile Asp Asp Cys Thr Leu Ala Asn Cys Cys Lys Ala Thr Asp Leu
    50                  55                  60

Ser Leu Pro Gly Arg Ser His Leu Leu Arg Gly Arg Ser His Asn Asp
65                  70                  75                  80

Gln Leu Phe Met Ser Arg Gln Thr Thr Leu Phe Thr Met Tyr Leu His
                85                  90                  95

Ile Glu Thr Ser Asp Leu Leu Asn Ala Ser Ser Ser Asp Gln Arg Ile
            100                 105                 110

Leu Pro Ser Ser Cys Lys Pro Arg Ser Glu Arg Gly Asp Tyr Gly Met
        115                 120                 125

Val Ala Ser Asp Tyr His Ser Tyr Thr Glu Ala Gln Met Asn Asn Val
    130                 135                 140

Lys Ile Ala His Arg Glu Ala Thr Asn Trp Ser Asp Trp Val Ala Leu
145                 150                 155                 160

Gly Thr Val Arg Phe Phe Arg Trp Gly Met Asp Leu Ala Thr Gly Tyr
                165                 170                 175

Lys His Pro Gln Pro Gly Gln Glu Ala Ser Glu Lys Phe Lys Met Thr
            180                 185                 190

Glu His Lys Trp Leu Thr Arg Phe Ile Phe Leu Glu Ser Val Ala Gly
        195                 200                 205

Val Pro Gly Met Val Gly Gly Met Leu Arg His Leu Arg Ser Leu Arg
    210                 215                 220

Arg Met Lys Arg Asp Asn Gly Trp Ile Glu Thr Leu Leu Glu Glu Ala
225                 230                 235                 240

Phe Asn Glu Arg Met His Leu Leu Thr Phe Leu Lys Leu Ala Glu Pro
                245                 250                 255

Gly Trp Phe Met Arg Leu Met Val Leu Gly Ala Gln Gly Val Phe Phe
            260                 265                 270
```

```
Asn Gly Phe Phe Leu Ser Tyr Leu Ile Ser Pro Arg Ile Cys His Arg
        275                 280                 285

Phe Val Gly Tyr Leu Glu Glu Glu Ala Val Leu Thr Tyr Thr Arg Ala
    290                 295                 300

Ile Gln Glu Leu Glu Asp Gly His Leu Pro Glu Trp Lys Glu Leu Gln
305                 310                 315                 320

Ala Pro Glu Ile Ala Val His Tyr Trp Gln Met Pro Glu Asn Gln Arg
                325                 330                 335

Thr Met Arg Asp Leu Leu Leu Tyr Ile Arg Ala Asp Glu Ala Lys His
            340                 345                 350

Arg Glu Val Asn His Thr Leu Ser Asn Leu Asp Gln Ala Ala Asp Pro
        355                 360                 365

Asn Pro Tyr Gln Thr Glu Tyr Gln Asp Pro Arg Lys Asp His Pro Thr
    370                 375                 380

Arg Gly Ile Asp Asn Leu Lys Ala Thr Gly Trp Glu Arg Lys Asp Ile
385                 390                 395                 400

Phe


<210> SEQ ID NO 10
<211> LENGTH: 427
<212> TYPE: PRT
<213> ORGANISM: Penicillium brasilianum

<400> SEQUENCE: 10

Met Pro His Ala Ser Arg Ser Leu Asn Val Leu Ile Val Gly Ala Gly
1               5                   10                  15

Leu Gly Gly Leu Ala Ala Gly Leu Ala Leu Gln Thr Asp Gly His Lys
            20                  25                  30

Val Thr Ile Ile Asp Ala Ala Pro Glu Phe Ala Glu Ala Gly Ala Gly
        35                  40                  45

Ile Arg Ile Pro Pro Asn Ser Ser Arg Leu Leu Met Arg Trp Gly Val
    50                  55                  60

Asp Leu Glu Arg Met Lys Lys Ser Thr Ser Gln Arg Tyr His Phe Ile
65                  70                  75                  80

Arg Trp Lys Asp Gly Ser Thr Ile Phe Asp Leu Pro Phe Asn Asn Ile
                85                  90                  95

Val Glu Thr His Gly Ala Pro Tyr Trp Leu Val His Arg Ala Asp Leu
            100                 105                 110

His Ala Ala Leu Leu Asp Ala Thr Leu Lys Ala Gly Val Lys Val Leu
        115                 120                 125

Asn Asn Lys Leu Val Thr Ser Tyr Asp Phe Glu Ala Pro Ser Ala Thr
    130                 135                 140

Thr Gln Asp Gly Glu Thr Phe Lys Ala Asp Leu Ile Val Gly Ala Asp
145                 150                 155                 160

Gly Ile Lys Ser Ile Cys Arg Pro Leu Leu Thr Gly Gln Pro Asp Val
                165                 170                 175

Pro Arg Asp Thr Gly Asp Val Ala Tyr Arg Ile Leu Ile Pro Gly Glu
            180                 185                 190

Lys Leu Leu Ala Asp Pro Asp Leu Ala His Leu Ile Arg Asp Pro Cys
        195                 200                 205

Thr Thr Ser Trp Cys Gly Pro Asp Ala His Leu Val Gly Tyr Pro Ile
    210                 215                 220

Arg Asn Gly Glu Met Tyr Asn Ile Val Met Cys Ala Thr Ser Tyr Asn
225                 230                 235                 240
```

```
Glu Thr Thr Asp Glu Val Trp Val Val Lys Gly Asp Asn Ser Glu Leu
                245                 250                 255

Cys Lys Arg Phe Ala Ser Trp Glu Pro Gln Val Arg Lys Leu Cys Ala
            260                 265                 270

Leu Thr Gly Asp Phe Met Lys Trp Arg Leu Cys Asp Leu Pro Asn Leu
        275                 280                 285

Ala Arg Trp Thr His Pro Ser Gly Lys Ala Val Leu Leu Gly Asp Ser
    290                 295                 300

Cys His Pro Met Leu Pro Tyr Leu Ala Gln Gly Ala Ala Gln Ala Val
305                 310                 315                 320

Glu Asp Ala Ala Val Leu Arg Gln Val Leu Ala Gln Asp Met Asp Met
                325                 330                 335

Ala Ala Ala Leu Lys Gln Tyr Glu Gln Ile Arg Met Pro Arg Ala Ser
            340                 345                 350

Leu Val Gln Ala Lys Thr Arg Glu His Gln Tyr Ile Leu His Val Asp
        355                 360                 365

Asp Gly His Glu Gln Gln Asp Arg Asp Lys Lys Leu Ala Leu Asp Ala
    370                 375                 380

Ala Glu Asn Pro Val Phe Trp Gly Tyr Asp Asp Arg Arg Lys Trp Leu
385                 390                 395                 400

Phe Ser His Asp Ala Glu Val Ile Gln Lys Glu Gly Ala Asn Trp Arg
                405                 410                 415

Asp Gly Pro Asn Met Asn Gly Val His Val Ala
            420                 425


<210> SEQ ID NO 11
<211> LENGTH: 460
<212> TYPE: PRT
<213> ORGANISM: Penicillium brasilianum

<400> SEQUENCE: 11

Met Ser Pro Ser Val Thr Pro Glu Arg Tyr Pro Ile Ala Ile Val Gly
1               5                   10                  15

Gly Gly Ile Ala Gly Leu Thr Leu Ala Leu Ala Leu Glu Lys Leu Gly
            20                  25                  30

Val Arg Tyr Val Leu Phe Glu Ser Gln Ser Ser Leu Ala Pro Asp Arg
        35                  40                  45

Gly Ala Ser Val Gly Leu Gln Pro Asn Gly Leu Arg Ile Leu Asp Gln
    50                  55                  60

Leu Gly Leu Ile Asp Lys Ile Glu Gln His Thr Gly Thr Leu Gln Arg
65                  70                  75                  80

Trp Arg His Leu Asp Gly Gln Gly Glu Leu Ile Ser Glu Thr Lys Ala
                85                  90                  95

Leu Gly Tyr Tyr Gln Ser Leu Ile Gly Tyr Gly Pro Leu Phe Leu Glu
            100                 105                 110

Arg Arg Lys Leu Leu Glu Ile Met Ala Asp Glu Leu Gln Asp Lys Thr
        115                 120                 125

Ala Ala Lys Thr Ser Leu Arg Val Val Ser Ala Asn Glu Ser Ser Asp
    130                 135                 140

Gly Val Glu Leu Ala Leu Ser Asp Gly His Ser Ile Thr Ala Asp Leu
145                 150                 155                 160

Val Ile Gly Ala Asp Gly Val Arg Ser Cys Ile Arg Glu Ala Ile Asp
                165                 170                 175

Met Ser Arg Thr Glu Trp His Ser Glu Ala Asn Glu Tyr Ile Asn Thr
            180                 185                 190
```

```
Gln Phe Ala Cys Ile Tyr Gly Ile Ser Gly Ala Ile Gln Gly Ile Val
        195                 200                 205

Glu Gly Asp Cys Phe Ser Val Tyr Arg Pro Glu Ala Thr Val Leu Ile
    210                 215                 220

Phe Thr Gly Arg Asn Gly Thr Ile Phe Trp Phe Val Phe Glu Asp Leu
225                 230                 235                 240

Gly Gln Thr Tyr Gly Leu Ser Thr Thr Pro Arg Tyr Thr Asn Asp Asp
                245                 250                 255

Phe Asp Ala Leu Cys Asp Ser Ile Ala His Leu Arg Leu Thr Ala Ser
            260                 265                 270

Val Arg Phe Gly Asp Val Tyr Gly Asn Arg Ser Val Ala Met Lys Val
        275                 280                 285

Pro Leu Glu Glu Gly Leu Ala Pro Ser Trp His Thr Asp Arg Met Val
    290                 295                 300

Ile Val Gly Asp Ala Ala His Lys Met Val Pro Asn Ala Ala Met Gly
305                 310                 315                 320

Ala Asn Gln Ala Ile Glu Ser Ser Ala Thr Leu Leu Asn Glu Leu Gly
                325                 330                 335

Asn Ile Phe Thr Ala Lys Asp Gly Gly Ser Pro Gln Pro Glu Ile Leu
            340                 345                 350

Ala Asn Ala Leu Lys Arg Tyr Ala Asp Ile Arg Lys Phe Arg Ala Ser
        355                 360                 365

Glu Ile Val Lys Arg Ala Gly Thr Ile Cys Arg Ala Gln Leu Ser His
    370                 375                 380

Ser Gly Pro Ala Ala Ala Val Arg Glu Glu Leu Pro Ser Leu Thr Asp
385                 390                 395                 400

Gly Asp Trp Leu Phe Arg Gly Phe Met Gly Leu Ser Glu Ser Pro Val
                405                 410                 415

Ile Asp Ala Leu Pro Val Pro Pro Arg Gly Lys Phe Phe Gly Gln Ala
            420                 425                 430

Val Glu Lys Phe Trp Lys Arg Phe Arg Ala Arg Gln Ala Ser Gly Phe
        435                 440                 445

Lys Thr Ser Asn Leu Glu Leu Phe Gly Ile Glu Ala
    450                 455                 460


<210> SEQ ID NO 12
<211> LENGTH: 347
<212> TYPE: PRT
<213> ORGANISM: Penicillium brasilianum

<400> SEQUENCE: 12

Met Ser Ser His Thr Leu Ser Leu Leu Glu Ala Lys Pro Tyr Tyr Ser
1               5                   10                  15

Thr Glu Leu Gly Ser Leu Arg Ala Val Thr Ala Glu Gln Leu Pro Ile
            20                  25                  30

Leu Lys Asn Leu Ser Ile Lys Arg Val Val Leu Ala Pro Ser Ala Ile
        35                  40                  45

Arg Glu Pro His Trp His Ser Asn Ala Asn Glu Leu Ala Tyr Cys Leu
    50                  55                  60

Arg Gly Lys Leu Met Val Ser Ile Leu Asp Ser Gly Asn Val Phe Ala
65                  70                  75                  80

Asn Phe Val Ile Glu Ala Gly Gln Met Phe His Ile Glu Ser Gly Ser
                85                  90                  95

Leu His His Phe Glu Asn Ile Cys Asp Glu Glu Ala Glu Ile Ile Ile
```

```
            100                 105                 110

Cys Phe Arg His Glu Lys Pro Thr Asp Phe Ala Leu Ser Ala Ser Met
        115                 120                 125

Gly Ala Met Thr Asp Gly Val Leu Gly Asn Thr Tyr Gly His His Ser
    130                 135                 140

Ser Asp Trp Ala Lys Ile Asn Arg His Thr His Pro Lys Tyr Ile Val
145                 150                 155                 160

Arg Arg Asn Gly Arg Pro Thr Ile Pro Ser Thr Ala Tyr Leu Pro Asp
                165                 170                 175

Pro His Lys Phe Asp Val Glu Glu Met Asn Pro Pro Val Ser Ser Glu
            180                 185                 190

Phe Gly Ser Asn Arg Thr Ala Arg Asn Gln Phe Trp Pro Ala Leu His
        195                 200                 205

Asn Met Ser Met Tyr Ser Leu Arg Ile Glu Asp Thr Gly Met Arg Glu
    210                 215                 220

Ala His Trp His Pro Glu Thr Ser Glu Leu Gly Tyr Val Ala Glu Gly
225                 230                 235                 240

Glu Ala Arg Met Thr Val Leu Asp Pro Asp Gly Ser Thr Asp Thr Tyr
                245                 250                 255

Tyr Leu Lys Gln Gly Asp Met Tyr Tyr Val Pro Thr Ala Tyr Pro His
            260                 265                 270

Gln Ile Glu Val Ile Gly Ser Glu Arg Met His Phe Leu Ile Phe Phe
        275                 280                 285

Asp Gln Pro Tyr Pro Lys Asp Val Gly Tyr Arg Thr Ser Ala Thr Ala
    290                 295                 300

Leu Pro Arg Glu Thr Leu Ala Ser Thr Leu Glu Val Ala Glu Lys Asp
305                 310                 315                 320

Leu Pro Lys Phe Pro Leu Thr Val Lys Asp Pro Leu Phe Val Glu Lys
                325                 330                 335

Lys Asn Pro Val Asp Asn Leu Arg Pro Lys Leu
            340                 345


<210> SEQ ID NO 13
<211> LENGTH: 313
<212> TYPE: PRT
<213> ORGANISM: Penicillium brasilianum

<400> SEQUENCE: 13

Met Ala Gly Ile Arg Val Ala Trp Ile Gly Leu Gly Asn Ile Gly Arg
1               5                   10                  15

Gly Met Ser Ser Asn Ile Ala Gln Lys Gly Pro Gln Ser Ser Leu Ile
            20                  25                  30

Leu Phe Asn Arg Thr Thr Ser Arg Ala Thr Ala His Ala Glu Lys Leu
        35                  40                  45

Gly Gly Asn Val Thr Val Ala Ile Ser Leu Ile Glu Ala Val Lys Ala
    50                  55                  60

Ser Asp Leu Ile Phe Thr Cys Val Gly Asp Asp Pro Ala Ile Asp Ser
65                  70                  75                  80

Ile Thr Glu Thr Ile Leu Ser Asp Lys Glu Leu Asp Leu Ser Thr Lys
                85                  90                  95

Thr Phe Val Asp Cys Ser Thr Val His Pro Asp Thr Ser Arg Arg Thr
            100                 105                 110

Glu Ala Ala Tyr Glu Ala Arg Gly Ala Ser Phe Val Ala Cys Pro Val
        115                 120                 125
```

```
Phe Gly Ala Pro Asn Met Ala Asp Ala Gly Gln Met Ile Val Val Pro
    130                 135                 140

Ala Gly Lys Gln Ser Ala Ile Thr Lys Val Lys Pro Phe Phe Glu Gly
145                 150                 155                 160

Val Val Ala Lys Ala Thr Ile Asp Leu Ser Ala Gly Thr Gly Ala Asp
                165                 170                 175

Ile Asp Val Gly Arg Ala Ser Thr Leu Lys Val Leu Gly Asn Thr Phe
            180                 185                 190

Ile Leu Asn Thr Val Gly Val Leu Ala Glu Ala Leu Thr Ala Ala Asp
        195                 200                 205

Ala Thr Gly Leu Gly Thr Ala Pro Phe Arg Gln Trp Leu Glu Leu Phe
    210                 215                 220

Asn Pro Gly Pro Phe Ala Lys Tyr Ala Asp Arg Met Ile Ser Gly Asp
225                 230                 235                 240

Tyr Tyr Gln Arg Glu Glu Pro Leu Phe Ala Val Asp Leu Ala Arg Lys
                245                 250                 255

Asp Leu Arg His Ala Ser Asn Ile Ala Lys Glu Gly Gly Gln Arg Met
            260                 265                 270

Arg Asn Val Glu Val Thr Asp His Phe Leu Gln Glu Val Lys Ala Glu
        275                 280                 285

Lys Gly Glu Lys Gly Asp Ile Ala Ala Val Tyr Gly Ala Ala Arg Lys
    290                 295                 300

Asp Ala Gly Leu Lys Phe Glu Asn Gln
305                 310


<210> SEQ ID NO 14
<211> LENGTH: 290
<212> TYPE: PRT
<213> ORGANISM: Penicillium brasilianum

<400> SEQUENCE: 14

Met Ser Ser Thr Ser Glu Ser Phe Thr Leu Pro Asn Gly Arg Gln Met
1               5                   10                  15

Ala Tyr Thr Leu Ser Pro Gly Gly Ser Ser Asp Arg Val Val Leu Leu
            20                  25                  30

Ser Asn Ser Leu Ala Glu Asp Leu Thr Ser Trp Glu Arg Val Val Pro
        35                  40                  45

Val Val Glu Asn Gln Gly Phe Arg Val Leu Arg Tyr Asp Gln Pro Gly
    50                  55                  60

His Gly Arg Ser Gly Ala Pro Thr Glu Ala Glu Leu Thr Ser Met Thr
65                  70                  75                  80

Phe Glu Thr Leu Val Asp Asp Val Tyr Arg Leu Leu Gly His Leu Lys
                85                  90                  95

Ile Asn Asn Leu His Ala Trp Val Gly Val Ser Met Gly Gly Ile Lys
            100                 105                 110

Ala Val Tyr Phe Thr Ala Arg His Pro Gly Ile Val Asn Lys Ile Val
        115                 120                 125

Val Ala Asp Ala Ile Ala Ala Ser Pro Ser Val Val Cys Ile Pro Asp
    130                 135                 140

Asn Phe Ala Ala Arg Val Ser Ala Val Lys Gln Ser Gly Ser Ile Ser
145                 150                 155                 160

Asp Asp Leu Ser Asn Thr Arg Lys Arg Trp Phe Gly Glu Asp Trp Met
                165                 170                 175

Ala Lys His Pro Glu Glu Thr Ala Arg Met Glu Lys Ser Met Ala Thr
            180                 185                 190
```

```
Thr Thr Ile Gln Gly Leu Glu Ala Cys Cys Ala Ala Leu Ser Ser Pro
        195                 200                 205

Ser Phe Asp Leu Arg Pro Leu Tyr Thr Lys Val Gly His Gly Cys Glu
    210                 215                 220

Glu Ala Leu Ile Val Ala Gly Glu Lys Asp Ala Asp Leu Pro Val Lys
225                 230                 235                 240

Met Gln Glu Met Arg Gln Ala Ile Glu Glu Ser Leu Arg Ser Cys Gly
                245                 250                 255

Lys Lys Val Pro Val Arg Met Glu Ile Ile Lys Gly Ala Gly His Val
            260                 265                 270

Pro Tyr Ile Asp Gly Phe Glu Asp Phe Cys Glu Ile Ile Thr Lys Phe
        275                 280                 285

Leu Ala
    290


<210> SEQ ID NO 15
<211> LENGTH: 245
<212> TYPE: PRT
<213> ORGANISM: Penicillium brasilianum

<400> SEQUENCE: 15

Met Ser Leu Ser Gly Lys Val Val Leu Ile Thr Gly Ser Ser Lys Gly
1               5                   10                  15

Ile Gly Lys Ala Ala Ala Leu Arg Val Ala Ser Glu Gly Ala Asn Val
            20                  25                  30

Val Ile Asn Tyr Leu Arg Asp Pro Val Ala Ala Asn Asn Leu Val Asp
        35                  40                  45

Gln Ile Gly Ala Asp Arg Ala Leu Ala Val Gln Ala Asp Ala Ser Lys
    50                  55                  60

Leu Ala Asp Leu Asp Arg Leu Val Asn Ala Ala Val Ala Gln Phe Gly
65                  70                  75                  80

Lys Ile Asp Val Leu Ile Pro Asn Ala Gly Ile Leu Pro Leu Arg Asp
                85                  90                  95

Leu Glu His Thr Ser Glu Glu Asp Phe Asp Arg Thr Tyr Asn Leu Met
            100                 105                 110

Val Lys Gly Pro Tyr Phe Leu Ala Gln Lys Ala Val Lys His Met Pro
        115                 120                 125

Pro Gly Gly Arg Ile Ile Phe Val Ser Thr Ser Thr Ala Arg Phe Ala
    130                 135                 140

Ser Val Ala Pro Ala Tyr Leu Leu Tyr Thr Ser Ser Lys Gly Ala Ile
145                 150                 155                 160

Glu Gln Met Thr Arg Ile Met Ala Lys Asp Leu Ala Arg Lys Gly Ile
                165                 170                 175

Leu Val Asn Ala Val Ala Pro Gly Pro Thr Ser Thr Glu Leu Phe Leu
            180                 185                 190

Glu Gly Lys Pro Glu Gln Met Ile Lys Ala Ile Ser Gly Phe Ser Pro
        195                 200                 205

Phe Asn Arg Ile Gly Glu Pro Glu Glu Ile Ala Ala Val Met Ala Phe
    210                 215                 220

Leu Ser Gly Lys Asp Ser Ser Trp Ile Ser Gly Gln Val Val Ala Val
225                 230                 235                 240

Asn Gly Ala Met Ala
                245
```

<210> SEQ ID NO 16
<211> LENGTH: 581
<212> TYPE: PRT
<213> ORGANISM: Penicillium brasilianum

<400> SEQUENCE: 16

```
Met Ala Ser Leu Ile Arg Glu Ala Pro Phe Gly Gln Ile Val Arg Tyr
1               5                   10                  15

Leu Thr Asn Asn Lys Tyr Phe Gln Tyr Pro Glu Glu Lys Pro Asp Phe
            20                  25                  30

Lys Leu Pro Asp Thr Trp Leu Gln Leu Leu Asn Glu Ser Asp Ala Ala
        35                  40                  45

Thr Ile Ala Asp Pro Glu Lys Thr Glu Pro Glu Pro Glu Gly Gln Gly
    50                  55                  60

Tyr Asp Ala Thr Ser Glu Ala Ile Ser Arg Ala Ser Thr Gln Asn Ser
65                  70                  75                  80

Leu Pro Phe Thr Glu Ala Arg Leu Glu Ala Asp Glu Gln His Glu Ile
                85                  90                  95

Glu Lys Ile Lys Ser Ile Pro Ile Gln Pro Lys Lys Thr Lys Asp Gly
            100                 105                 110

Ala Ile Leu Val Asp Trp Tyr Tyr Thr Asp Asp Ala Glu Asn Pro His
        115                 120                 125

Asn Trp Ser Asn Arg Lys Arg Ala Leu Leu Thr Thr Leu Ile Cys Leu
    130                 135                 140

Tyr Thr Phe Val Val Tyr Thr Thr Ser Ala Ile Tyr Thr Ser Ser Val
145                 150                 155                 160

Pro Gly Ile Met Lys Glu Phe Gly Val Ser Asp Leu Val Ala Thr Leu
                165                 170                 175

Gly Leu Ser Leu Tyr Val Leu Gly Tyr Gly Thr Gly Pro Leu Ile Phe
            180                 185                 190

Ser Pro Leu Ser Glu Ile Pro Val Ile Gly Arg Asn Pro Val Tyr Ile
        195                 200                 205

Val Thr Met Phe Leu Phe Val Ile Leu Ser Ile Pro Thr Ala Phe Val
    210                 215                 220

Gly Asn Phe Ala Gly Leu Met Val Leu Arg Phe Leu Gln Gly Phe Phe
225                 230                 235                 240

Gly Ser Pro Cys Leu Ala Ser Gly Gly Ala Ser Ile Gly Asp Met Tyr
                245                 250                 255

Ser Leu Met Ser Leu Pro Tyr Ala Met Met Ser Trp Val Ser Ala Ala
            260                 265                 270

Tyr Cys Gly Pro Ala Leu Gly Pro Leu Ile Ser Gly Phe Ala Val Pro
        275                 280                 285

Ala Glu Thr Trp Arg Trp Ser Leu Phe Glu Ser Ile Trp Met Ser Ala
    290                 295                 300

Pro Val Leu Ile Leu Met Phe Phe Phe Leu Pro Glu Thr Ser Ser Ala
305                 310                 315                 320

Thr Ile Leu Leu Arg Arg Ala Ala Arg Leu Arg Lys Ile His Asn Asn
                325                 330                 335

Ala Arg Phe Met Ala Gln Ser Glu Ile Asp Gln Arg Asn Met Lys Val
            340                 345                 350

Ser Ala Val Ala Val Asp Ala Leu Ile Lys Pro Leu Glu Ile Thr Ile
        355                 360                 365

Lys Asp Pro Ala Val Leu Phe Val Gln Val Tyr Thr Ala Ile Ile Tyr
    370                 375                 380
```

```
Gly Ile Tyr Tyr Ser Phe Phe Glu Val Phe Pro Leu Val Tyr Pro Val
385                 390                 395                 400

Asp Tyr Gly Met Asn Leu Gly Gln Val Gly Leu Val Phe Leu Cys Ile
                405                 410                 415

Leu Val Ser Cys Ile Ile Gly Ile Ala Ile Tyr Trp Ser Tyr Leu Tyr
            420                 425                 430

Phe Trp Met Asn Pro Arg Ile Glu Arg Phe Gly Phe Pro Ala Gln Glu
        435                 440                 445

Ser Arg Leu Ile Pro Ala Leu Pro Ala Ser Ile Gly Pro Thr Ile Gly
    450                 455                 460

Leu Phe Leu Phe Ala Trp Thr Ala Arg Ala Ser Ile His Trp Ile Ala
465                 470                 475                 480

Pro Thr Ile Gly Ile Thr Ile Tyr Gly Ala Thr Val Phe Ile Val Met
                485                 490                 495

Gln Cys Leu Phe Val Tyr Ile Pro Leu Ser Tyr Pro Met Tyr Ala Ala
            500                 505                 510

Ser Leu Phe Ala Ala Asn Asp Phe Phe Arg Ser Ala Leu Ala Cys Gly
        515                 520                 525

Ser Val Leu Phe Ala His Pro Leu Phe Gly Asn Leu Gly Val Ala Arg
    530                 535                 540

Gly Thr Ser Leu Leu Gly Gly Leu Ser Val Ile Gly Ile Ile Gly Ile
545                 550                 555                 560

Trp Leu Leu Tyr Tyr Tyr Gly Ala Arg Leu Arg Ser Leu Ser Lys Phe
                565                 570                 575

Ala Ile Ser Asp Asp
            580


<210> SEQ ID NO 17
<211> LENGTH: 513
<212> TYPE: PRT
<213> ORGANISM: Penicillium brasilianum

<400> SEQUENCE: 17

Met Ser Thr Thr Lys Glu Ala Phe Pro His Thr Asp Ser Asp Ile Met
1               5                   10                  15

Glu Asp Ser Glu Lys Asn Leu Pro Glu Cys Glu His Ile Val Ser Val
            20                  25                  30

Glu Pro Thr Leu Lys Met Arg Asp Gly Ile Val Leu Met Pro Gln Pro
        35                  40                  45

Ser Asp Asp Pro Asn Asp Pro Leu Asn Trp Ser Trp Phe Arg Lys His
    50                  55                  60

Ala Ala Met Phe Thr Leu Ser Tyr Leu Ala Leu Val Cys Tyr Val Ala
65                  70                  75                  80

Val Thr Thr Leu Val Thr Gly Thr Val Pro Leu Ala Lys Ser Met His
                85                  90                  95

Val Ser Lys Ser Thr Ala Val Tyr Leu Gly Asn Thr Pro Val Ala Leu
            100                 105                 110

Tyr Ala Val Ala Pro Trp Phe Trp Ser Pro Leu Ser His Phe Ile Gly
        115                 120                 125

Arg Arg Pro Val Leu Leu Met Cys Asn Ile Ile Ala Val Val Gly Ala
    130                 135                 140

Val Val Val Thr Thr Ser Lys Thr Tyr Ala Ser Cys Met Val Gly Arg
145                 150                 155                 160

Val Ile Leu Gly Ala Gly Gly Ser Ala Phe Trp Thr Leu Gly Pro Ala
                165                 170                 175
```

```
Ser Ile Gly Asp Ile Phe Phe Arg His Glu Lys Gly Lys Lys Ile Gly
            180                 185                 190

Val Ser Thr Leu Ala Ile Val Ile Ala Pro Phe Leu Gly Thr Ile Ile
        195                 200                 205

Gly Gly Pro Ile Ile Glu Asn Glu Lys Leu Gly Trp Pro Ala Ser Gln
    210                 215                 220

Trp Ile Pro Leu Ile Phe Met Ala Ala Gly Phe Ile Met Gln Ile Phe
225                 230                 235                 240

Phe Leu Pro Glu Thr Ile Tyr Ile Arg Glu Thr Arg Ala His Pro Ala
                245                 250                 255

Ile Met Ser Thr Ser Thr Pro Gly Lys Pro Thr Phe Trp Asp Arg Tyr
            260                 265                 270

Gly Ile His Ile Pro Lys Arg Ser Glu Glu Lys Gln His Ser Phe Leu
        275                 280                 285

Phe Ile Ala Thr Arg Pro Phe Val Leu Phe Lys Phe Pro Ala Val Ile
    290                 295                 300

Leu Ser Ala Phe Trp Phe Gly Ile Ala Tyr Met Met His Val Gly Ile
305                 310                 315                 320

Thr Ser Glu Ile Pro Leu Ile Phe Glu Glu His Tyr Asp Phe Ser Val
                325                 330                 335

Leu Glu Ile Gly Leu Ser Gly Phe Ser Gly Leu Ile Gly Ala Leu Leu
            340                 345                 350

Gly Glu Val Tyr Ala Gly Pro Ser Leu Asp Phe Ile Ala Lys Arg Thr
        355                 360                 365

Met Lys Gln Gly Arg Glu Trp Arg Pro Glu Tyr Arg Leu Gln Ala Ile
    370                 375                 380

Trp Pro Ala Leu Ile Thr Val Pro Ala Gly Leu Ile Met Phe Gly Thr
385                 390                 395                 400

Ser Ile Gln Phe Gly Asn Val Trp Ile Thr Pro Leu Ile Gly Gln Ala
                405                 410                 415

Val Tyr Ile Phe Gly Ile Glu Ile Ala Thr Thr Val Ile Gln Thr Tyr
            420                 425                 430

Ile Leu Glu Cys Tyr Pro Arg Gln Gly Ala Glu Ala Asn Leu Val Phe
        435                 440                 445

Asn Leu Ile Arg Asn Leu Phe Ser Tyr Ile Ser Pro Phe Phe Val Gln
    450                 455                 460

Pro Met Ile Ala Thr Leu Gly Thr Thr Ser Pro Phe Gly Leu Ser Ala
465                 470                 475                 480

Ala Leu Thr Ala Phe Phe Phe Pro Phe Thr Val Gly Val Leu Met Trp
                485                 490                 495

Arg Gly Lys Gln Ile Arg Asp Lys Gly Gly Asp Pro Gly Trp Ser Arg
            500                 505                 510

Asp
```

<210> SEQ ID NO 18
<211> LENGTH: 1435
<212> TYPE: PRT
<213> ORGANISM: Penicillium brasilianum

<400> SEQUENCE: 18

```
Met Glu Asp His Glu Lys Glu Tyr Asp Ser Thr Ser Pro Pro Gly Thr
1               5                   10                  15

Ala Thr Glu Glu Gly Asn Gly Gly Tyr Phe Asn Thr Leu Thr Val Pro
            20                  25                  30
```

```
Glu Ile Asn Leu Arg Glu Ala Ser Ser Ala Glu Thr Leu Thr Pro His
        35                  40                  45

Ala Ser Val Val Gln Pro Pro Lys Lys Ala Ala Glu Trp His Met Thr
    50                  55                  60

Pro Gln Val Ile Arg Asn Ala Glu Arg Asp Glu Ala Ala Gly Phe Lys
65                  70                  75                  80

Arg Arg Glu Leu Gly Val Thr Trp Gln Asp Leu Ser Val Glu Val Leu
                85                  90                  95

Ala Ala Glu Ala Ala Val Lys Glu Asn Met Ile Ser Gln Phe Asn Val
            100                 105                 110

Pro Gln Leu Ile Lys Asp Phe Arg Arg Lys Pro Pro Leu Lys Ser Ile
        115                 120                 125

Leu Ser Asn Ser His Gly Cys Val Lys Pro Gly Glu Met Leu Leu Val
    130                 135                 140

Leu Gly Arg Pro Gly Ser Gly Cys Thr Thr Leu Leu Lys Met Leu Ala
145                 150                 155                 160

Asn Arg Arg Glu Gly Tyr Gln Asn Ile Thr Gly Asp Val Arg Phe Gly
                165                 170                 175

Asn Met Thr Pro Glu Glu Ala Ser Arg Tyr Gln Gly Gln Ile Val Met
            180                 185                 190

Asn Thr Glu Glu Glu Leu Phe Tyr Pro Arg Leu Thr Val Gly Gln Thr
        195                 200                 205

Met Asp Phe Ala Thr Lys Leu Lys Val Pro Tyr His Leu Pro Gly Glu
    210                 215                 220

Gly Lys Ser Val Ala Glu Tyr Thr Ala Glu Thr Lys Gln Phe Leu Leu
225                 230                 235                 240

Glu Ser Met Gly Ile Ala His Thr Ala Asp Thr Lys Val Gly Asn Glu
                245                 250                 255

Phe Val Arg Gly Val Ser Gly Gly Glu Arg Lys Arg Val Ser Ile Ile
            260                 265                 270

Glu Cys Leu Ala Thr Arg Gly Ser Val Phe Thr Trp Asp Asn Ser Thr
        275                 280                 285

Arg Gly Leu Asp Ala Ser Thr Ala Leu Glu Trp Ala Lys Ala Leu Arg
    290                 295                 300

Ala Met Thr Asp Val Gln Gly Leu Ser Thr Ile Val Thr Leu Tyr Gln
305                 310                 315                 320

Ala Gly Asn Gly Ile Tyr Asn Leu Phe Asp Lys Val Leu Val Leu Asp
                325                 330                 335

Glu Gly Lys Gln Ile Tyr Tyr Gly Pro Ala Ala Glu Ala Lys Pro Phe
            340                 345                 350

Met Glu Asn Leu Gly Phe Val Tyr Thr Asp Gly Ala Asn Ile Gly Asp
        355                 360                 365

Phe Leu Thr Gly Leu Thr Val Pro Thr Glu Arg Lys Ile Arg Pro Gly
    370                 375                 380

Trp Glu Asn Arg Phe Pro Arg Thr Ala Asp Ala Ile Leu Thr Glu Tyr
385                 390                 395                 400

Gln Asn Ser Ala Thr Tyr Lys Asn Glu Val Ser Leu Tyr Gly Tyr Pro
                405                 410                 415

Asp Thr Asp Leu Ala Ala Glu Arg Thr Glu Ala Phe Lys Glu Ser Val
            420                 425                 430

Ala Trp Glu Lys Ser Lys His Leu Pro Lys Gly Ser Asp Leu Thr Thr
        435                 440                 445
```

```
Ser Phe Trp Ala Gln Leu Met Ser Cys Thr Ala Arg Gln Tyr Gln Ile
    450                 455                 460

Leu Trp Gly Glu Lys Ser Thr Phe Leu Ile Lys Gln Ile Leu Ser Cys
465                 470                 475                 480

Val Met Ala Leu Ile Ala Gly Ser Cys Phe Tyr Asn Ser Pro Asp Thr
                485                 490                 495

Ser Ala Gly Leu Phe Thr Lys Gly Gly Ala Val Phe Phe Ser Leu Leu
            500                 505                 510

Tyr Asn Cys Ile Val Ala Met Ser Glu Val Thr Glu Ser Phe Lys Gly
        515                 520                 525

Arg Pro Ile Leu Thr Lys His Lys Ser Phe Ala Met Tyr His Pro Ala
    530                 535                 540

Ala Phe Cys Leu Ala Gln Ile Thr Ala Asp Phe Pro Val Leu Leu Phe
545                 550                 555                 560

Gln Cys Thr Ile Phe Ser Val Val Ile Tyr Trp Met Val Gly Leu Lys
                565                 570                 575

His Thr Ala Ala Ala Phe Phe Thr Phe Trp Ala Ile Leu Phe Thr Thr
            580                 585                 590

Thr Leu Cys Ile Thr Ala Leu Phe Arg Phe Ile Gly Ala Ala Phe Ser
        595                 600                 605

Ser Phe Glu Ala Ala Ser Lys Ile Ser Gly Thr Ala Val Lys Ala Ile
    610                 615                 620

Val Met Tyr Ala Gly Tyr Met Ile Pro Lys Pro Glu Ile Lys Asn Trp
625                 630                 635                 640

Phe Leu Glu Phe Tyr Tyr Thr Asn Pro Phe Ala Tyr Ala Phe Gln Ala
                645                 650                 655

Ala Leu Thr Asn Glu Phe His Asp Gln His Ile Asp Cys Val Gly Gly
            660                 665                 670

Asn Leu Ile Pro Ser Gly Pro Gly Tyr Glu Asp Val Gly Ser Gly Tyr
        675                 680                 685

Lys Ala Cys Ala Gly Val Gly Gly Ala Leu Pro Gly Ala Asp Tyr Val
    690                 695                 700

Thr Gly Asp Gln Tyr Leu Ser Ser Leu His Tyr Lys His Ser Gln Leu
705                 710                 715                 720

Trp Arg Asn Phe Gly Val Val Trp Ala Trp Trp Gly Phe Phe Ala Val
                725                 730                 735

Leu Thr Val Val Phe Thr Cys Phe Trp Lys Ser Gly Ala Ala Ser Gly
            740                 745                 750

Ser Ser Leu Leu Ile Pro Arg Glu Asn Leu Lys Lys His Gln Val Gly
        755                 760                 765

Asn Asp Glu Glu Ala Gln Asn Asn Glu Lys His Ala Ala Arg Thr Thr
    770                 775                 780

Thr Asp Glu Pro Val Gln Val Glu Asp Asp Asn Leu Val Arg Asn Thr
785                 790                 795                 800

Ser Ile Phe Thr Trp Lys Asn Leu Thr Tyr Thr Val Lys Thr Pro Thr
                805                 810                 815

Gly Asp Arg Val Leu Leu Asp Asn Ile Asn Gly Trp Val Lys Pro Gly
            820                 825                 830

Met Leu Gly Ala Leu Met Gly Ser Ser Gly Ala Gly Lys Thr Thr Leu
        835                 840                 845

Leu Asp Val Leu Ala Gln Arg Lys Thr Glu Gly Thr Ile Lys Gly Ser
    850                 855                 860

Ile Leu Val Asp Gly Arg Glu Leu Pro Val Ser Phe Gln Arg Met Ala
```

```
865                 870                 875                 880

Gly Tyr Cys Glu Gln Leu Asp Val His Glu Ser Tyr Ala Thr Val Arg
                885                 890                 895

Glu Ala Leu Glu Phe Ser Ala Leu Leu Arg Gln Ser Arg Asp Thr Pro
            900                 905                 910

Lys Ala Glu Lys Leu Lys Tyr Val Asp Thr Ile Ile Asp Leu Leu Glu
        915                 920                 925

Leu His Asp Leu Ala Asp Thr Leu Ile Gly Ser Val Gly Asn Gly Leu
    930                 935                 940

Ser Val Glu Gln Arg Lys Arg Val Thr Ile Gly Val Glu Leu Val Ser
945                 950                 955                 960

Lys Pro Ser Ile Leu Ile Phe Leu Asp Glu Pro Thr Ser Gly Leu Asp
                965                 970                 975

Gly Gln Ser Ala Tyr Asn Thr Val Arg Phe Leu Arg Lys Leu Ala Asp
            980                 985                 990

Val Gly Gln Ala Val Leu Val Thr  Ile His Gln Pro Ser  Ala Gln Leu
        995                 1000                1005

Phe Ala  Gln Phe Asp Thr Leu  Leu Leu Leu Ala Arg  Gly Gly Lys
    1010                1015                1020

Thr Val  Tyr Phe Gly Asp Ile  Gly Asp Asn Gly Ser  Thr Ile Lys
    1025                1030                1035

Gln Tyr  Phe Gly Asn Tyr Gly  Ala Ile Cys Pro Gln  Glu Ala Asn
    1040                1045                1050

Pro Ala  Glu Phe Met Ile Asp  Val Val Thr Gly Gly  Ile Gln Glu
    1055                1060                1065

Val Lys  Asp Lys Asp Trp His  Gln Ile Trp Leu Asp  Ser Pro Glu
    1070                1075                1080

Gln His  Gln Met Ile Thr Glu  Leu Asp Arg Met Ile  Ala Asp Ala
    1085                1090                1095

Ala Ser  Lys Pro Pro Gly Thr  Val Asn Asp Gly Tyr  Glu Phe Ser
    1100                1105                1110

Met Pro  Leu Trp Glu Gln Ile  Lys Ile Val Thr Gln  Arg Met Asn
    1115                1120                1125

Val Ser  Leu Phe Arg Asn Thr  Ala Tyr Val Asn Asn  Lys Phe Ser
    1130                1135                1140

Leu His  Ile Ile Ser Ala Leu  Leu Asn Gly Phe Ser  Phe Trp Arg
    1145                1150                1155

Pro Gly  Pro Ser Val Ser Ala  Leu Gln Leu Lys Met  Phe Thr Ile
    1160                1165                1170

Phe Asn  Phe Val Phe Val Ala  Pro Gly Val Ile Asn  Gln Leu Gln
    1175                1180                1185

Pro Leu  Phe Ile Gln Arg Arg  Asp Ile Tyr Asp Ala  Arg Glu Lys
    1190                1195                1200

Lys Ser  Lys Met Tyr Ser Trp  Val Ala Phe Val Thr  Gly Leu Ile
    1205                1210                1215

Val Ser  Glu Phe Pro Tyr Leu  Cys Ile Cys Ala Val  Leu Tyr Phe
    1220                1225                1230

Val Cys  Trp Tyr Trp Pro Val  Trp Arg Leu Pro His  Asp Ser Asp
    1235                1240                1245

Arg Ser  Gly Ala Ile Phe Phe  Met Met Leu Ile Tyr  Glu Phe Ile
    1250                1255                1260

Tyr Thr  Gly Ile Gly Gln Phe  Ile Ala Ala Tyr Ala  Pro Asn Pro
    1265                1270                1275
```

```
Thr Phe  Ala Ala Leu Val Asn  Pro Leu Ile Ile Ser  Val Leu Val
    1280                 1285                 1290

Leu Phe  Cys Gly Val Phe Val  Pro Tyr Asp Gln Leu  Asn Val Phe
    1295                 1300                 1305

Trp Lys  Tyr Trp Met Tyr Tyr  Leu Asn Pro Phe Asn  Tyr Val Val
    1310                 1315                 1320

Asn Gly  Met Leu Thr Phe Gly  Leu Trp Gly Gln Lys  Val Thr Cys
    1325                 1330                 1335

Asn Glu  Ser Glu Tyr Ala Val  Phe Asp Pro Leu Asn  Gly Thr Cys
    1340                 1345                 1350

Gly Glu  Tyr Leu Ala Thr Tyr  Met Ser Gly Lys Gly  Ser Gly Val
    1355                 1360                 1365

Asn Leu  Leu Asn Pro Asp Ala  Thr Ser Ser Cys Lys  Val Cys Glu
    1370                 1375                 1380

Tyr Thr  Thr Gly Ser Asp Phe  Leu Gln Thr Leu Asn  Ile Asn His
    1385                 1390                 1395

Tyr Tyr  Tyr Gly Trp Arg Asp  Ala Gly Ile Thr Val  Ile Tyr Ala
    1400                 1405                 1410

Ile Ser  Gly Tyr Ala Leu Val  Phe Gly Leu Met Lys  Leu Arg Thr
    1415                 1420                 1425

Lys Ala  Ser Lys Lys Ala Glu
    1430                 1435


<210> SEQ ID NO 19
<211> LENGTH: 872
<212> TYPE: PRT
<213> ORGANISM: Penicillium brasilianum

<400> SEQUENCE: 19

Met Cys Gln Asp His Asp Leu Glu Cys Ser Tyr Thr Leu Pro Arg Lys
1               5                   10                  15

Thr Arg Phe Tyr Gly Ser Val Asp Asp Leu Ser Asp Arg Tyr Lys Cys
            20                  25                  30

Leu Glu Ala Ile Val Arg Ala Ala Phe Pro Asn Asp Gly Ile Ser Thr
        35                  40                  45

Val Pro Glu Leu Ile Arg Leu Gly Glu Arg Met Gly Tyr Ala Met Pro
    50                  55                  60

Asp Leu Ser Gln Lys Ser Gly Glu Ser Pro Arg Ile Glu Glu Leu Val
65                  70                  75                  80

Arg Asp Phe Pro Thr Glu Ala Gly Asp Gln Gly Leu Ala Gly Ser Thr
                85                  90                  95

Gln Cys Thr Ser Ser Pro Pro Arg Thr Gly Ala Val Asn Val Pro Thr
            100                 105                 110

Glu Ser Glu Arg Arg His Ser Ser Ser Gln Val Gln Glu Asn Asn Ser
        115                 120                 125

Cys Pro Asp Glu Pro Val Gly Leu Ile Arg Asp Thr Thr Gly Arg Glu
    130                 135                 140

His Phe Ile Gly Pro Ser Gly Ser Leu Gln Phe Leu Gly Gln Leu Arg
145                 150                 155                 160

Arg Leu Leu Leu Ile Ser Arg Ser Gly Asp Ala Val Glu Ser Arg Ala
                165                 170                 175

Pro Ala Arg Leu Thr Ala Thr Phe Thr Asp Glu Asp Ala Ala Gln Ala
            180                 185                 190

Leu Glu Ala Asp Gly Asp Gln Ser Glu Leu Ala Ala Leu Pro Ser Gly
```

-continued

```
        195                 200                 205

Gly Thr Gly Asn Gly Gly Asp Glu Gly Gln Glu Ile Asp Glu Arg Ser
    210                 215                 220

Pro Ala Ser Leu Gly Ser Ala Leu Val Arg Asp Phe Ser Ser Ile Pro
225                 230                 235                 240

Val Asn Asp Ile Asp Glu Met Arg Arg Gln Leu Pro Pro Arg His Val
                245                 250                 255

Leu Asp Ser Leu Met Arg Val Tyr Phe Lys Asn Val His Pro Asp Phe
            260                 265                 270

Ala Leu Phe His Arg Gly Thr Phe Glu Glu Glu Tyr Glu Thr Phe Met
        275                 280                 285

Ser Lys Gly Arg Tyr Tyr His Gln His Ala Arg Ala Gly Val His Leu
    290                 295                 300

Ser Ser Pro Thr Leu Pro Glu Pro Gly Trp Leu Gly Cys Leu His Met
305                 310                 315                 320

Met Ile Ala Phe Ala Ser Leu Asn Gly Ser Val Asp Val Ala Pro Asp
                325                 330                 335

Leu Asp Leu Thr Ser Leu Cys Arg His Cys Ala Ser Leu Thr Arg Gln
            340                 345                 350

Leu Leu Pro Gln Phe Ile Ser Lys Cys Thr Leu Ser Asn Val Arg Ala
        355                 360                 365

Leu Leu Leu Leu Ser Leu Phe Leu His Asn His Asn Glu Arg Asn Ala
    370                 375                 380

Ala Trp Asn Leu Val Gly Thr Ala Met Arg Leu Ser Phe Ala Met Gly
385                 390                 395                 400

Leu His Arg Ala Ser Asp Asn Gly Ser His Phe Arg Pro Ile Glu Arg
                405                 410                 415

Glu Val Arg Lys Arg Val Phe Cys Thr Leu Tyr Gly Phe Glu Gln Phe
            420                 425                 430

Leu Ala Ser Ser Leu Gly Arg Pro Ser Gly Phe Tyr Asp Phe Glu Asp
        435                 440                 445

Val Glu Ile Val Pro Pro Arg Glu Gly Val Leu Asp Ser Gly Gln Asp
    450                 455                 460

Glu Asp Asp Glu Val Met Lys Leu Ser Leu Arg Leu Gln Val Ile Leu
465                 470                 475                 480

Ala Lys Ala Arg Val Ser Leu Ala Val Lys Thr Leu Ala Val Ala Asn
                485                 490                 495

Glu Arg Gly Asn Ile Asp Gly Leu Ala Arg Gln Gln Gln Ser Ser Arg
            500                 505                 510

Glu Thr Leu Glu Ile Leu Lys Ala Trp Arg Glu Asp Leu Ala Ser His
        515                 520                 525

His Ile Leu Asn Ile Pro Leu Ile Ser Glu Thr Asp Asp Pro Leu Cys
    530                 535                 540

Gln Tyr Ala Glu Glu Ile Pro Arg Met Ser Leu Gln Asp Leu Lys Ala
545                 550                 555                 560

Met Met Gly Trp Gln Ser Arg Pro Arg Leu Arg Ala Ala Leu Val Leu
                565                 570                 575

His Leu Gln Tyr Arg Tyr Ile Ala Val Leu Val Thr Arg Ser Ser Leu
            580                 585                 590

Leu Arg Tyr Val Ala Ser Ala Gln Arg Gly Glu Pro Glu His Glu Ala
        595                 600                 605

Leu Leu Ser Arg Asn Glu Ala Arg Thr Asp Pro Tyr Asn Ser Glu Ala
    610                 615                 620
```

```
Gly Glu Arg Leu Ser Asp Ile Cys Val Thr His Ala Thr Gln Leu Cys
625                 630                 635                 640

Arg Leu Ile Leu Leu Ala Asp Ser Phe Gly Leu Val Asn Gly Ile Ser
                645                 650                 655

Ala Met Asp Val Phe Tyr Val Tyr Cys Gly Val Met Val Leu Ile Leu
            660                 665                 670

Arg Ser Leu Arg Ile Ser Ser Ser Ala Ser His Tyr His Asp Gln Arg
        675                 680                 685

Glu Ala His Leu Gln Leu Glu Leu Arg Lys Leu Ile Ala Gln Thr Arg
    690                 695                 700

Glu Val Leu Ile Arg Val Asn Lys Cys Ser Thr Met Lys Arg Phe Ala
705                 710                 715                 720

Arg Val Val Ala Thr Phe Glu Asp Gly Ser Arg Gln Asp Asn Ile Arg
                725                 730                 735

Pro Ala Asp Gly Ser Thr Asn Arg Ser Thr Ala Asn Cys Glu Met Arg
            740                 745                 750

Thr Ala Arg Gln Ala Ser Arg Asp Pro Arg Gly Arg Phe Asn His Ser
        755                 760                 765

Ile His Ala Ala Leu Asp Gly Gly Arg Ala Ser Asn Leu Ala Ile Phe
    770                 775                 780

Pro Gly Ala Gly Gly Ser Leu Asp Thr Ser Ser Ser Leu Pro Val Ser
785                 790                 795                 800

Gln Gln Glu Pro Leu Asn Phe Gln His Gly Tyr Gly Asn Gly Ile Gly
                805                 810                 815

Pro Arg Leu Gly Ile Ser Asp Pro Phe Trp Gln Pro Asn Leu Leu Thr
            820                 825                 830

Ser Phe Asp Gly Glu Pro Glu Ala Asn Gly Trp Met Met Asp Pro Phe
        835                 840                 845

Leu Ala Met Asp Gly Thr Gly Val Val Asp Trp Gly Asp Ile Glu Ser
    850                 855                 860

Leu Leu Ser Arg Asn Pro Gly Gln
865                 870


<210> SEQ ID NO 20
<211> LENGTH: 1056
<212> TYPE: DNA
<213> ORGANISM: Penicillium brasilianum

<400> SEQUENCE: 20

atgggctcgc tatctctacc ggagacgtct cttgcggcaa tccaagataa ggagaccaag      60

gccatctccg tcgccaaacg cccaactcca gtccccgtcg gcactcaagt cctcgtcaag     120

ctacactact ccggtgtctg cgccacagat ctccatctgg cccgcggcag cgtcccctat     180

ctgcagccca aggtctcggt aggcggccat gagggcacgg gggtaatcgc cagcctcggc     240

cccgacgtgg acgccgcgga gtggcacgtc ggcgaccggg tcgcggtgcg gtgggtgcac     300

atcgtctgcg ggaagtgcga ggtgtgcact accggctttg agaacctgtg ccaaagccgg     360

aagctcgctg gcaaggacgt tgagggcacc tttgccgagt acgctattgc ggacagctcg     420

tacatggtcc gcctgccggc tggggtgagc gacgccgatg ccgctccgat actgtgcgcc     480

ggtgtcaccg tctacaaggc gctcaagatc gccagcctcc gggcgggctc gtgggtcgcc     540

gtggccgggg ctggtggcgg cttgggtcat ctggctattc aatatgcacg tgccatgggg     600

ctcaaggtcg tggccctgga tgctaggaaa cgggatctct gcctgagcct gggcgcggaa     660
```

```
tcgtacatcg acgtgctcga aacggacgac tgcgtagccc aggtgatcaa ggtcacggat    720

gggggcgctc atggcgcact catctgcgcc tcgtccggcc aggcctatga cgatgccgtc    780

aaattcctaa gatggaccgg caccctggtg tgtatcggcc tccccccaaa gccgacactg    840

ctctccctag gccccgcgga cttcgtcgcc cgtggcatca aggtcatggg cacatccaca    900

ggtgaccgcc aggacacggt ggaggccctc gcctttgtcg ccaagggcca ggtaaaaccg    960

cagttaactg agagaaggct ggaggatgtt gaggagatct taaaggagat cgagaatggg   1020

actatgcagg gtaaagctgt gatcaggata gcctga                              1056
```

<210> SEQ ID NO 21
<211> LENGTH: 1020
<212> TYPE: DNA
<213> ORGANISM: Penicillium brasilianum

<400> SEQUENCE: 21

```
atgagtctgc cgtctcacta caaacgggcc gcctttaaag aggctggcgg cccgctcacc     60

attgaagaag tcgacttgac catgccggat gctggcgaag tgctggtgaa ggtggaagct    120

tgcggagttt gtttctccga cacggttcca caggctcatg gcctgggggg gaaatttcca    180

atcgtacccg gtcatgaaat catcggacat gtggttgcga caggtgacgg tgtctcggac    240

tgggaggttg gcgatcgtat cggcgaagga tggcacggcg gccatgacgg aacttgtccc    300

tcctgtcgcc agggccattt ccaaatgtgc gacaatcaga gcatcaatgg ggtgaccaaa    360

aacggcggat atgcccaata ctgcattctc cgtagtgaag ctgctgtcag aattcccact    420

catgtctcag ccgccgagta tgccccaatt ctctgcgcgg gcgtgaccgt cttcaactca    480

atgcgtcaaa taggggtcaa acctggctct accgttgcca ttcagggtct gggaggtctc    540

ggccatcttg ccatccaata tgcgaatcgc ttcggcttcc gagtggtggc catctctcgc    600

gatgatcaaa aggagcgatt tgtgcgagac ctcggtgccc acgagtatat caatacaagc    660

gaagaagatg tcggaagcgc gctccagaaa ctgggaggtg cttctctgat tgtagccacc    720

gcgcccaatg cccgggccat ttcccctcta ttgaagggcc ttagacctct gggtaagctt    780

cttattctcg ccgttccggg tgaaatcccc ctcgatacac ggcttatggt cgcccgaggt    840

ctttctgtcc acggatggcc gagtgggcat gcacttgatt ctgaggaaac cattcgcttt    900

acagaattag aggatatcaa gtgtatgatc cagacatatt ctcttgatcg tgccaatgaa    960

gcattcgatg ccatgatttc ggggtcggtt cgattccgtg cggtgattac catggagtaa   1020
```

<210> SEQ ID NO 22
<211> LENGTH: 1170
<212> TYPE: DNA
<213> ORGANISM: Penicillium brasilianum

<400> SEQUENCE: 22

```
atggctcctc aaattcctga gaagcagtgg gcacaggttg tcgagaaaaa aggtgggcca     60

ccggtctaca aggaaattcc cgtccccaag cctggccccg atgaagtcct gctgaagatc    120

aagtactccg gcgtctgcca caccgatctg cacgccatga acggcgactg gcctcttcct    180

gtcaagatgc ctctggttgg tggccacgag ggtgccggta tcgttgtcgc caagggcgaa    240

ctggctgagg gcgtcgagat cggcgaccac gcaggtatca agtggctgaa cggatcgtgc    300

ctggcgtgcg aatactgcaa gacctcggac gaaccacttt gcgccacccc ccagctctcg    360

ggttacaccg tcgacggcac attccagcag tatgcgattg gcaaggctgc ccacgtcact    420

attctaccaa aggacattcc tctggatggg attgcgccaa ttctttgtgc cggacttacc    480
```

```
gtgtacaagg gtctgaagga gtctaatgct cgtcctggtc agaccgttgc catcgttggt    540

gctggtggtg gcctcggtgt gatggctcag caatatgcca aggccatggg gctgcgcgtc    600

atttccattg atggtggtga cgagaagcgt caggtctgcg agaagcttga ctcggaggcc    660

tacatcgact tcaccaaatc caaggatctc gtctctgacg tgaaggctgc cacccctgag    720

ggtttaggtg cacacgctgt gatcctgctc gccgtctccg agaagccctt ccagcaggcg    780

gttgaatact cccgtccccg cggtacaatc gtcgccattg gtatgccagc caacgcattc    840

ctcaaggctt cagttttcga gactgttgtc aagatgatca ctatcaaggg tagctacgtg    900

ggcaaccgcc aggatgcttc agaggcggtt gatttctatg ctcgtggttt gatcaaggca    960

ccattcaaga cggttcccct tgaggagctt cccaaggtgt tcgagttgat gggtaagtta   1020

ccgaattcga atttactgtt acacaagttg ctaatatgct tttcacagag caaggcaaga   1080

ttgccggtcg ttatgttctc cagatgccag agtaaatgca tcaatcgacg ggcggtgcat   1140

aaccgacaac atcgtatgag catatcttag                                    1170
```

<210> SEQ ID NO 23
<211> LENGTH: 993
<212> TYPE: DNA
<213> ORGANISM: Penicillium brasilianum

<400> SEQUENCE: 23

```
atgtccctcc caaccaccat gagagctgtg atagtcgaac aaaccggcgg cccagaagtc     60

ctccaattca aaactgacca cccggtcccg acacccgggg aaggccaact cctcgtccac    120

aacaacatct ccggcgtcaa ctatatcgac acctacttcc gcacgggtct ctacgcctct    180

cccaagcccg agattctcgg ccgggagggc gccggtatcg tcgcagccat aggccctaat    240

acctccggct tcaatgtcgg agatcgtgtt gcctggctgg ccacgggtgg gtacgcagag    300

tacactgccg tgccagcggc caagaccgtc aagatccccg agggagtcag tgacgaggac    360

gtcgtggcct cgttcttgag tggtctgacc gttttgtcct ttgcgaagga gacgtatccc    420

gtgcagaagg gcgattgggt acttttgcat gccgcggctg gtggagccgg gttcttgatg    480

acgcagattc tcaagtcgat tggggctaag gttattggta ccgctggtgg tgcggagaag    540

tgtgccctcg tcaagagctt gggggcagac gtggtgattg attatcgcag tgaggagggt    600

aaggattggg tgaaattggt caaggaggcc accggaggga ggggtgtcga tgttgtttat    660

gactccgtcg gcaaagatac gtgggagggt agcttggagg ctgtcaagcg caagggtacg    720

attgtctggt ttggtaatgc cagcggtccc gtgcccccta ttcctctgcc caaactctcg    780

cccaagaatg tcaagattgc tcgccctact ctctttggct acatcgagac ccgcgaggag    840

tttgaatact acaccaacga gctgtttagt ctgctccagt ctggccagtt gaagaccaag    900

atccacaagg tttaccctct cgaggacatc gctcaggtcc acaaggacct ggagggtcgc    960

aagaccatgg gtaagtctct tctgaagcct tag                                 993
```

<210> SEQ ID NO 24
<211> LENGTH: 1518
<212> TYPE: DNA
<213> ORGANISM: Penicillium brasilianum

<400> SEQUENCE: 24

```
atgactcaaa ccaacgtcca tgtcaacaag tctgatactt cactggcagc tccgcaacag     60

ttattcatct cgggaaaata ccagaacagc cagaggaatg ggaccttccc cgtgaagaac    120
```

```
cccatgacgg gcgagaccat atacgagtgc gtctcagcct ctctagacga ctacgccgcc    180
gccatcgagg aagcagatgc agcccaacct tcgtgggctc gcctcggccc ctcagcccgg    240
cggttgatcc ttctcaaggc cgccgacatc atggagacgt acatcgagac agacgcgccg    300
gccatccttt cagccgaggt ttcggccact aggggatggg tcagggccaa cattctgtcc    360
acagccggcg tcttccgcga gaccgccgcc ctggcaacgc atatcaaggg agagatcgtt    420
cccgcggacc ggccgggcac cacgatcctg gtgagccgcg agcccgtcgg cgtggtcctg    480
gccatcagcc cctggaatat gcccgccaca ctgacggcca gggcgatctg ctgcccgctg    540
atctgcggga atagcgtggt cctgaggccg tctgagttca gccccaagtc gcagcacctc    600
gtcgtgcgcg ctctgaccga ggctggactg ccggcggggt gcctgcagtt cctgcccacc    660
agcaccgccg acacgccgcg agcgatcgag tttgcaatcc gacacccgaa ggtgagccgc    720
gcaaacttca cgggcagcga ccgcgttggc cgcatcatcg ccgggctatc ggcatcctgt    780
ctgaagccgt gcgtgctgga gctaggcggc aaggcgcccg tcgtggtcct ggaggatgcc    840
gatgtggagg ccgccgtgga ggcagtggtg tatggcgcga tgtccaacag cgggcagata    900
tgtatgtcca cagagcgggc gatcgtgcat cgctccctgg cagcggactt caaggccctg    960
ttggtgaaac gggcggagag cctgcgggta gggaaccacc tcgaggaccc ggacgtgcag   1020
ctctcgggcc ttttcactgc cgcctccgcc gagcgtgtac tcggcctgat caagggcgcc   1080
gtcaacgcag gtgccacgct cctggcgggc gatctggctc ttcacggacc gtgccagaca   1140
atcatggctc cccacatcct cacgggcgtc acgcgggata tggacctctt ccatcgggag   1200
acgttcggcc ccgtgctctt cgtgtccgag ttcgacacgg acgatgaggc catcgcgcag   1260
gccaacgaca ccgagttctc tctgtgtgcc agcgtcttct cgcgtgacgt cctgcgcgcc   1320
atggacacgg ccaagcggat ccggacaggg agctgccacg tcaatgggcc gaccgtgtac   1380
atcgaggcgc cgctgcccaa cgggggtgtc ggcggcggga gcggctacgg ccggttcggt   1440
ggtgtggcgg gcatcgagga gtttacggag aggcagatcg tgagcttagc gaagccgggg   1500
attaagtatg cgttctag                                                 1518
```

<210> SEQ ID NO 25
<211> LENGTH: 1440
<212> TYPE: DNA
<213> ORGANISM: Penicillium brasilianum

<400> SEQUENCE: 25

```
atgtctcaga acgactccaa ggcggtgact ccgctgctta ttaacaatga atccgtcatg     60
actgatatta agttcgaggt ccacgccccc gctactggcg aattgtcgag ttactgtgct    120
ggtgcctcgg ttgaggatgc ggtgcgcgcg gtcgacaatg caaaggcggc cttcccggcc    180
tggagcaaga ccaaggctta tgatcgccgc gatattttgc tcaaggccgc cgagatcatg    240
atctcgcgca aggaggagct gatcgcatac cagcaggagg agactggtgc ggggcggccc    300
ttttgcgagc acaccttcaa catgggtgtc aacttcatca aggactttgc ggggcgcatt    360
tccaccattg agggtgtcgt acccagtgtg accttggatg gtgagggggc gatgatttat    420
aaggagcctt atggtgtgat tttgtcaatt gccccatgga acgctccctt catcttgggc    480
actcgcgcag tcgctctccc cctcgctgcc ggtaacaccg tcgtcctcaa gggttccgag    540
ctctcgccca agtgcttctg ggctctcggt gatatcttcc gccaggctgg tcttcctgat    600
gggtgcttca acgtcatttt ccaccaacct tccgatgccg cggctgtcac gaccgccctg    660
attgctcacc ctgccgttcg caaggtcaac ttcactggca gcaccaatgt cggttccatt    720
```

```
attgcctcga ctgctggcaa gtacatcaag cccgttcttt tggagctggg tggaaaggct    780

tccgcgattg tcttggacga tgcagacctc gataaggcgg ccatgagctg tgcgctcgga    840

tcattcctgc actctggaca aatttgcatg tccactgagc gcatcgtcgt gcagcgtgct    900

atcgccgacg aattccgtca gaaggttgcc gcaaatgcgg agaagctctt tggcaaggat    960

gctccagctt tgggccttgt caacgctgcc gcagtcacca agaataagaa actcgttgcg   1020

gatgccgtct cgcgcggtgc caacatcctg ttcggagatg ccagtgccaa cgagtccgtc   1080

aacacctgca tgcgccccat catcgtcgat ggagtcagca aagagatgga cctgtatgcg   1140

accgagtctt tcggcccgac cgtgtccttg atcgtcgtcg ataccgagga ggaggccatc   1200

gcagtggcca atgacaccga atacggcctg accggggcgg tctacactca aaacttgttc   1260

cgcggtcttc gtgtcgccaa gcagatcgag tctggtgcca ttcacattaa cgccctgacc   1320

gttcacgatg agcctaccct gccccacggt ggctggaaga gcagcggttt cggccgcttt   1380

ggcggcgttg ccggctatga tgagttcctg cagaccaaga ccgtcacctg gatggagtaa   1440
```

<210> SEQ ID NO 26
<211> LENGTH: 1422
<212> TYPE: DNA
<213> ORGANISM: Penicillium brasilianum

<400> SEQUENCE: 26

```
atgaccgtca ccacaactct ctccctcatc gctcctccag agcaccgcca tgagccatcc     60

cccttcgacc cggctgtcga catcaaagac gcaccctcca tcatcaccgc actcaatgcc    120

gccgatccga gtctcaaagt gtacactcga tcttctccca acttcgagac cctccgcggc    180

gtctacaaca aactaatcac ccaccagcct ctggcaatct gccgcccccca gaccattgaa    240

caaatccaac tcatcgtgcg cactgcccgt gccgcgaacc cccccgtacc catcgtcccg    300

cgctgtgggg gccacgatgt ctacggacga ggcttgaagc ctgatagcct cagcattgac    360

atgcgcgagc tcgacacgca aactctcgcc gaagatcgcc agtccgttcg catcggcggc    420

ggcgtgacgt cgcagaattt tgtcggattc ctcgacgaac acggtctctg cactgcgaat    480

gggaccgcgg ggaacgtggg atggacggga tgggccgtgt ggggcggata cgggcccttc    540

aatgactacg ttggcctggg agtcgacaat atcttgtctg cacgtctggt acttgcggat    600

ggatcgctgg tcgaggcggg tcctgggtcg gagctgttgt ggggagttcg aggcgccggt    660

ggcagtctcg ggtcatcgt tgatgtgacc gtgaaagtat acccgatgcc cgttattctg    720

gcgggtttca ttgcgtacca gtggggggag agtgcgaagg tgctctcggg tctgcaggag    780

ttgctggatc ggggaattcc cgacacgatg tgtttgcaga tgggcttcat gaagactaag    840

tggggggttg gcatgagttt gatctttgcc tggcccgatt cggagactct cgatgagggt    900

cgcacttggc tggagactgt taggggcctg ggcgcgatcc aggttgatac cgtcggtgaa    960

accacgttta aggcgtttca agggattacc tcccgtgtag tggacgagcc agtcaatgtc   1020

tgcactcgca gcgcctcggt ccctcggttt acccccgaga ctatcgcgct acttcaaaag   1080

tactccgagg ccatccccga cggtcgtcaa tacaatgtga tcgcgcatat tggacacgga   1140

aaaagtacac gaccgaaccc cgacacgtcg tttgccacgc gggaacccca cgtgctgttt   1200

catatcaacg cgtgcgatga gccagagcgc atggacgagg cccggagctg ggtcgacgga   1260

ctgatgaagg agatgaatgc tacccgccaa gccatgaagc ctgtatacgt gagttttatg   1320

ggtgaagacg aggaccctcg tgtgagcttc gggtcgcatt gggagcggtt gcaagctctc   1380
```

aagcaatcgg tggacccgga caacgttttc cgcttcccct ag 1422

<210> SEQ ID NO 27
<211> LENGTH: 1428
<212> TYPE: DNA
<213> ORGANISM: Penicillium brasilianum

<400> SEQUENCE: 27
atgccttttc tacccttctt caaggtactc aggctgcgaa gggagctgga tgggacaaag 60
gcggaaatct tcacctgggg atgtgacggg tatgatgaaa gcatcaagca atggaatgct 120
taccttaccc agggcgcgac cgtccgggtc acatcatccg atgaagccgc cacagtcgtt 180
cgctttgctg catgccacaa aattcctttc acggttaaag gagggggggta ctccaccacc 240 ggtgcctcga gcgctcatgg cgtcaccgct caaggtggcg ccctatggga agatattgat 300
gtcgcagccg ctcaacatag gctagcagtc gtcggaagca cactaaacca catcggggtg 360
gccggagcaa cattaggagg aggttatgga tggctgactg gccagtatgg cttagcgata 420
gataacttgc tctgggtgaa gatgatatta gccgatggca gcgttatcat cgtatcagaa 480
gagcaatatc cagacctatt ttgggccatt cgaggagctg gtcagagctt cggggtggcc 540
attgagttag ccttccgggc tcacagacag gaccaccctg tatttgccgg gacccttctc 600
ttctcggcga gcaagttatc cgctattgtg gagtttgcca acaacttcga gactctcaca 660
aacggtaatc aggggttctg gtttgggttt accatgccgc cctcaatgga ccggtgcgcc 720
attctcgtgg tggtcttcta caatgggccc cagatagccg cgcggcagtt cttttctcca 780
ttgctctcga taggaccggt ggtgaatgag acaggaatgc tgccgtatga tagtctcaat 840
ggtatactga atatgatgga tacagtgtcc cgacgcagaa tccttagagg tgccgatatc 900
accctcccta ccgatgaaaa cgtgggtact cgaaaaagtc ttcgaggatc aaacattact 960
ctccccctgg atatcaattt tacggcatcc atatacagtg aatttgatgg catcttgagg 1020
gagttcacac aggccaggga cagcatatta cttttcgagc tcctgccata tacacagatc 1080
accaaagttc ccaacgatgc taccgcattt gctagccgtg gtccttatca taatgtcatt 1140
tctctatttg gatggcagga taaagatctg gacgagagaa tgcactcact gcaagaggat 1200
attatgaatc agatcggaaa acgcgcaggt atcgcatgca ccccatttta taacgtttca 1260
aagcacggga caggattata tgcgaactat gctggacaca acgtgccttt agaggcaata 1320
tttggagaca atcttcgacg tctccaagag ttgaagaaga agtttgatcc caacaacgta 1380
tttaaaaagt ggcacaacct taacacgact atcggtaccc cggcatag 1428

<210> SEQ ID NO 28
<211> LENGTH: 1206
<212> TYPE: DNA
<213> ORGANISM: Penicillium brasilianum

<400> SEQUENCE: 28
atgatgacgc cgcctatact tgcttttcat cttttcaaag acttcgaact acaacgaaca 60
aagaattact ttcgagtatt gaacataaac tacaaagctg atcatcaccc acaccagctt 120
tttcatgatg aattcactat caacactatc gacgactgca cccttgcgaa ttgctgcaag 180
gccacagact tatctcttcc tggccgttcg cacctactcc ggggtcgcag ccacaacgat 240
cagctcttca tgtctcgcca gacaacgctc ttcacaatgt acctacacat cgaaacgtct 300
gatctcctca acgcctcatc ctcagatcaa agaatacttc cctcctcctg caaaccccgc 360
agtgaaagag gtgactacgg catggtcgca tccgattacc acagctatac cgaggcgcag 420

```
atgaataacg tgaaaatcgc gcatcgcgag gccaccaact ggtccgattg ggttgcactg    480

ggcacagttc gcttcttccg atggggtatg gacttggcga cgggatacaa acacccacag    540

ccgggccagg aagcatcgga gaagtttaag atgacagagc acaagtggtt gacccgtttc    600

atcttcctgg agagtgtcgc gggtgtacct gggatggttg gtggtatgct gagacatctg    660

cggagtttac gacgcatgaa gcgtgataat ggatggatcg agactctcct ggaagaagca    720

ttcaacgagc gaatgcatct cctcaccttc ctcaaactgg ccgagcctgg ctggttcatg    780

cgcttgatgg tgctcggcgc ccagggtgtc ttctttaatg gcttcttcct gtcgtatctc    840

atctctccac gaatctgcca ccgcttcgtg ggttacctgg aagaagaggc ggtgttgaca    900

tacacacggg ccattcagga actcgaagac ggccatttac ccgagtggaa ggagctccag    960

gcacccgaga ttgcagtgca ttactggcag atgcccgaga atcagcgcac gatgcgagac   1020

ttgttgctct atatccgtgc cgacgaggcc aagcaccgcg aggttaatca tacgctgtca   1080

aatctggacc aggcggctga ccccaatccc tatcagacgg agtatcagga tccgagaaag   1140

gaccatccca ctcggggcat tgataacctg aaggcgacgg gatgggagcg aaaagacatc   1200

ttttag                                                              1206
```

<210> SEQ ID NO 29
<211> LENGTH: 1284
<212> TYPE: DNA
<213> ORGANISM: Penicillium brasilianum

<400> SEQUENCE: 29

```
atgcctcacg catccagatc attgaacgtt ctcatcgtcg gtgctggctt gggcggcctc     60

gcggcgggat tagctttgca gacggacggc cacaaggtca caatcattga tgccgctcct    120

gagttcgcag aggccggagc ggggatcagg atcccaccca actcgagccg gctgctcatg    180

cgatggggcg ttgatctgga gaggatgaag aagtcgactt cacagagata tcacttcatc    240

cgctggaagg atggcagcac catcttcgac ttgcccttca acaatatcgt cgagacacac    300

ggggcgcctt actggcttgt ccatagagcc gacttgcacg ccgctctgct cgatgcgacc    360

ctgaaggccg gtgtcaaggt tctaaacaac aagcttgtca cgtcctacga cttcgaggca    420

ccgagcgcca ccacacagga tggcgagacc ttcaaggccg atcttatcgt cggtgcggac    480

ggcataaagt ccatctgccg acccccttctt accggtcagc cggacgtccc gcgggacacg    540

ggcgacgtcg cctatcggat tctcatccct ggtgagaaac tgctggccga cccggacctg    600

gcccatctga tccgcgaccc ttgcacgaca tcgtggtgtg gcccggacgc gcacctggtc    660

ggctacccga tccgcaacgg cgagatgtac aacatcgtca tgtgtgccac ctcctacaac    720

gagaccacgg acgaggtctg ggtcgtcaag ggcgacaaca gcgagctgtg caagcgcttc    780

gccagctggg aaccccaggt gcggaagctc tgcgccctca cgggcgactt catgaagtgg    840

cgcctgtgcg acctgcccaa cctcgcccgc tggacgcacc cctcgggcaa ggccgtgctg    900

ctgggcgaca gctgccaccc catgctgcct tacctggccc agggcgctgc ccaggccgtc    960

gaggatgccg ccgtcctgcg ccaggtgctc gcccaggaca tggacatggc cgcggcccta   1020

aagcagtatg agcagatccg catgccgcgg gcgagcctgg tgcaggccaa gactcgcgag   1080

caccagtaca tcctccacgt cgacgacggt cacgagcagc aagaccggga caagaagttg   1140

gctctcgatg cggcggagaa cccggtcttc tggggctacg acgaccggag aaaatggctc   1200

tttagccatg atgcagaggt gatccaaaaa gaaggtgcga actggagaga cgggcccaac   1260
```

```
atgaatggcg tgcatgttgc ttag                                          1284


<210> SEQ ID NO 30
<211> LENGTH: 1383
<212> TYPE: DNA
<213> ORGANISM: Penicillium brasilianum

<400> SEQUENCE: 30

atgtctccgt ccgtgactcc tgagcgttat ccaatcgcga tcgttggggg cggcatcgcc     60

gggctgacac tggcgttagc actggaaaag ctgggtgttc gctatgttct ctttgagtcc    120

caaagctccc tggctcctga taggggtgca agcgttggtt tacagccaaa tggcttgcgt    180

attcttgatc agctcggtct gatcgacaag attgagcaac ataccgggac gttgcagcgc    240

tggcgccatc tagatggcca aggcgagctc atctcagaaa ccaaagctct aggctattac    300

caatcattaa ttggttatgg tcctctgttc ctggaacgtc gcaagctcct cgagataatg    360

gcagatgagc tccaagacaa aacggccgcc aagacaagcc tgcgtgttgt gtcggccaac    420

gaaagttcag acggtgttga gctagcacta agtgatggcc attcaatcac agccgatctc    480

gtaattgggg cagatggtgt gcgtagctgc atccgtgaag ctattgatat gagcaggaca    540

gagtggcatt ctgaagcgaa tgagtatata aacacccagt ttgcttgcat ctatggtatc    600

tcgggtgcca tccaaggcat tgttgaaggt gactgttttt cggtataccg ccccgaggca    660

acggtcctga tctttaccgg ccgcaacggc actatatttt ggtttgtttt tgaagatttg    720

ggtcagacat atggcctatc aacaacacca agatatacaa atgacgactt cgacgcgctt    780

tgtgactcaa tcgcccatct ccgcctcact gcttcagtcc gttttggtga tgtgtatgga    840

aatagatcag tggcaatgaa agtccccttg gaggaaggct tggcgccctc atggcatacg    900

gaccgcatgg tgattgttgg ggacgctgcc cacaagatgg ttccaaatgc cgcgatggga    960

gcaaatcagg caattgagtc atccgcaact ctgctgaacg agctcggaaa tatatttact   1020

gcgaaagatg gtggctctcc acagccggaa atacttgcga atgccttgaa gagatacgca   1080

gatattcgca agttccgagc cagtgagatt gttaaaagag caggaacaat ttgcagagct   1140

cagctttcgc acagtggtcc tgctgcagct gtacgagaag aacttccgtc tttgaccgat   1200

ggtgattggc tcttccgcgg tttcatgggc ttatcagaat cgcctgtcat tgatgccctg   1260

cctgtgccac caaggggaaa gttcttcggc caagccgtgg agaaattctg gaaacgtttc   1320

cgagcccgac aagcttcggg cttcaagact tccaacttgg agttgttcgg aattgaagca   1380

tag                                                                 1383


<210> SEQ ID NO 31
<211> LENGTH: 1044
<212> TYPE: DNA
<213> ORGANISM: Penicillium brasilianum

<400> SEQUENCE: 31

atgtcttctc atacactttc tcttctcgag gccaagcctt actacagcac tgaacttggc     60

tcactccgag cagtgactgc cgagcagctt ccaattctca aaaacctttc tatcaaaaga    120

gtggttcttg cgccgtctgc aattcgggag ccccactggc attcaaatgc aaacgagcta    180

gcatactgct tgcgtggaaa attgatggtc agcattcttg actcgggtaa tgtattcgca    240

aattttgtca ttgaagcggg tcaaatgttc cacatcgaat ccggctcgtt gcatcacttc    300

gagaacattt gcgatgaaga ggcggagatc attatctgtt tccgtcatga aaagcccacg    360

gacttcgccc tatctgcctc gatgggagct atgacagatg gtgtcctggg caatacgtac    420
```

```
ggccaccatt cttctgactg ggcaaaaatc aaccgacaca cccacccgaa gtacattgtt    480

cgccgcaatg gcaggcccac aattccatcc acggcttatc tgccggatcc acataagttt    540

gacgttgagg agatgaatcc gcccgtttca tcggaatttg gatccaacag aactgcgcgc    600

aatcagttct ggccagctct tcacaatatg tcgatgtact cacttcgaat cgaggatact    660

ggtatgagag aggcacactg gcatccagaa acgtcggagc tcggttatgt tgctgagggc    720

gaagcccgta tgaccgtcct ggatccagat ggatccactg atacgtatta cctgaagcaa    780

ggcgatatgt attacgttcc aacagcgtac cctcaccaga ttgaggtgat tggatctgag    840

agaatgcatt tcttgatttt ctttgatcag ccctacccca aggatgttgg ataccggacc    900

tctgctacag cgctaccccg cgagacgtta gcgtctacat tggaagtagc ggagaaggat    960

ctccctaaat ttcctctcac tgttaaggat cccctatttg tcgagaagaa aaatcctgtg   1020

gataatttgc gaccgaagtt gtga                                          1044
```

```
<210> SEQ ID NO 32
<211> LENGTH: 942
<212> TYPE: DNA
<213> ORGANISM: Penicillium brasilianum

<400> SEQUENCE: 32

atggctggta ttcgtgtagc atggatcggc ctcggcaaca tcggccgggg catgagcagc     60

aatatcgctc agaagggacc ccaatccagc ctcatcctct tcaaccgcac cacctcacgc    120

gccaccgcac acgccgagaa actgggcggc aacgtcaccg tcgcaatctc cctcatcgaa    180

gccgtcaaag cctccgatct cattttcacc tgcgtcggcg atgaccccgc catcgactcc    240

atcaccgaga ccatcctctc cgacaaggaa ctcgacctct caacaaagac cttcgtcgac    300

tgctccaccg ttcacccgga cacctcgcgc cgcacggaag ccgcctacga agcccgcggc    360

gcctccttcg tcgcatgccc cgtcttcggt gcccccaaca tggccgacgc aggtcaaatg    420

atcgtcgtgc ccgccggcaa acaatccgct atcaccaagg tcaagccctt ctttgaaggt    480

gtcgtggcca aggccacgat tgatctctcc gccggtacgg gcgcggacat cgacgtcggc    540

cgcgcgtcca ccctcaaagt cctcggcaac acgttcatcc tcaacaccgt cggcgtgctg    600

gccgaggctc tcaccgccgc ggacgcaacg ggcctgggaa cggctccgtt ccggcagtgg    660

ctggagctgt tcaacccggg gccgtttgcc aagtatgcgg atcggatgat tagtggagat    720

tactatcagc gagaggagcc gttgtttgcg gttgatcttg cgcggaagga tttgagacat    780

gcgtctaata ttgccaagga gggtggtcag cggatgcgca atgtagaggt taccgatcac    840

tttttgcagg aggtcaaggc cgagaagggg gagaagggtg atattgccgc tgtgtatggt    900

gcggcacgga aggatgctgg cttgaagttt gagaatcagt ga                       942
```

```
<210> SEQ ID NO 33
<211> LENGTH: 873
<212> TYPE: DNA
<213> ORGANISM: Penicillium brasilianum

<400> SEQUENCE: 33

atgtcgtcta caagcgagtc cttcactctc ccaaatgggc gacagatggc ttataccctc     60

tcgcccggtg gttcctccga tcgcgtggtc cttctctcca actccttggc cgaagatctg    120

acctcctggg agcgcgtcgt acctgtggtg gaaaaccaag gcttccgcgt cctccgctac    180

gaccagccag gccatggacg ctcgggtgca cctactgaag ccgaattgac ctccatgaca    240
```

```
ttcgagacct tggtcgatga cgtctaccgc cttctcggac acctcaaaat caacaatttg    300

catgcctggg tcggcgtctc gatgggcggc atcaaggccg tgtacttcac cgcgcgccac    360

ccaggcatcg tgaacaagat cgtcgtggcc gacgccatcg ccgcttcccc gtccgtggtc    420

tgcatccccg ataacttcgc cgcgcgggta agcgctgtga agcagtcggg ttccatctcg    480

gacgacctgt caaatactcg gaagcggtgg ttcggtgaag actggatggc gaagcatccg    540

gaggagacgg cgaggatgga gaagtccatg gcgacaacta caattcaggg tctcgaggcg    600

tgctgtgctg cccttagcag cccgtctttt gacctgaggc cgctatatac gaaggtggga    660

catggctgcg aagaagcact cattgtcgcc ggggagaagg atgcggacct tccagtcaag    720

atgcaggaga tgcggcaggc aatcgaggag agcctccgga gctgtggaaa gaaggtgccc    780

gtgaggatgg agattatcaa gggtgccggg catgttccct acattgatgg tttcgaggac    840

ttctgcgaaa tcatcaccaa attccttgcc tag                                 873


<210> SEQ ID NO 34
<211> LENGTH: 738
<212> TYPE: DNA
<213> ORGANISM: Penicillium brasilianum

<400> SEQUENCE: 34

atgtctctgt ctggcaaagt cgtcctcatc accggctcct ccaagggaat cggcaaagct     60

gctgcccttc gtgtcgccag cgaaggtgcc aacgtcgtga tcaactatct tcgtgacccg    120

gttgcagcca acaatctcgt cgaccaaatc ggtgccgacc gcgcccttgc tgttcaagct    180

gatgcttcaa agctggccga cctcgatcgc ctcgtcaatg ccgctgtcgc ccagttcggc    240

aagatagatg ttcttattcc aaatgccgga atcctcccgc ttagagactt ggagcatact    300

agcgaagagg actttgacag aacctacaat ctaatggtaa agggaccata cttcctggcc    360

cagaaagccg tgaagcatat gccccctgga ggacgaatca tctttgtctc tacctcaacc    420

gcccgattcg caagcgtggc tcccgcatac ctactctaca cctcctccaa aggcgcgatc    480

gagcagatga cccgaatcat ggccaaggat ttggcgcgaa agggaatctt ggtgaatgcg    540

gtcgctcccg gtccaacttc aaccgaactc ttcctcgagg gaaagccgga gcaaatgatc    600

aaggctatct ctgggtttag tccattcaat cggatcggag agcccgagga aattgccgca    660

gtcatggcgt tcttgtctgg gaaggacagc agttggatct caggacaggt tgtggctgtg    720

aacggagcta tggcatga                                                  738


<210> SEQ ID NO 35
<211> LENGTH: 1746
<212> TYPE: DNA
<213> ORGANISM: Penicillium brasilianum

<400> SEQUENCE: 35

atggcatctc tcattcgaga ggccccctttt gggcaaatag ttcgatatct caccaacaac     60

aaatatttcc aatatcccga agaaaagccg gacttcaaac ttcccgatac atggcttcaa    120

ttattgaacg aatcggatgc cgcgacgata gccgatcccg agaaaacgga gccggagcca    180

gagggtcagg gctacgatgc aaccagcgag gcgattagtc gcgcatcaac ccaaaactcc    240

ttgcccttca cagaagctcg actggaagcg gatgagcagc atgagatcga aaagatcaag    300

tccattccta ttcagcctaa aaagaccaag gatggtgcga ttttggtcga ctggtactat    360

accgatgatg cagagaaccc acacaattgg tcgaatcgaa agcgagcact tctgacgacg    420

ctcatttgtc tttatacctt tgtggtatac acgacctctg caatttacac atcctccgtg    480
```

```
cccgggatca tgaaggagtt cggcgtcagt gacttggttg ctacactggg actgtccttg    540

tatgtccttg gctatggaac gggtccccctg atcttctcgc ctctgagtga gatccccgtg    600

attggtcgga acccggtcta tatcgtgacc atgttcctct ttgtgattct ctccattccc    660

actgcttttg tgggtaactt tgcaggactc atggtgcttc gtttcctgca aggattcttc    720

ggctcgccct gtctcgcttc tggaggtgct tcaattggcg acatgtacag tctcatgtct    780

ctcccttatg ccatgatgag ctgggtgtct gccgcttact gtggtcccgc cctgggtcct    840

ctcatcagtg gcttcgcagt tcccgccgag acctggcgct ggtccctgtt tgaatccatt    900

tggatgtcag ctccagtcct cattctgatg ttcttcttcc tccccgagac tagcagtgca    960

actatcctgc tccgtcgtgc cgctcgtctc cgcaagatcc ataacaacgc acgcttcatg   1020

gctcagtccg agattgacca gcgtaacatg aaggtctcgg ccgttgctgt cgacgccctg   1080

attaagcctt tggagattac catcaaggat cccgcggtgc tcttcgtcca ggtctacacc   1140

gccattatct acggcatcta ctactccttc ttcgaggtct tccccctggt ctaccccgtc   1200

gattatggca tgaatcttgg ccaagttggc ctggtcttcc tgtgtatcct ggtgtcctgc   1260

atcatcggta tcgccatcta ctggtcttac ctttacttct ggatgaaccc tcgcattgaa   1320

cgcttcggat tcccagctca agagtcccgt cttatccccg ccctgccagc ttctattgga   1380

cccaccattg gcttgttcct ctttgcctgg acagcccgtg cctcaatcca ctggattgcc   1440

ccgacaatcg gaatcaccat ctacggtgcg acggtcttca tcgtgatgca gtgcttgttt   1500

gtctacatcc ccttgagcta tccaatgtac gccgctagtc tgttcgctgc gaacgacttc   1560

ttccgcagtg ctctggcttg cggtagtgtc ctgtttgctc acccgttgtt tggcaacctc   1620

ggtgtcgctc ggggtaccag tctactcggt ggtctgagtg tgattggtat tatcggaata   1680

tggctgcttt actactatgg tgcccggctt cgctctttga gcaagtttgc catctccgat   1740

gattga                                                              1746
```

```
<210> SEQ ID NO 36
<211> LENGTH: 1542
<212> TYPE: DNA
<213> ORGANISM: Penicillium brasilianum

<400> SEQUENCE: 36

atgagcacga ccaaggaagc tttcccacat acggatagcg acataatgga ggactcggag     60

aagaatctcc cagagtgcga gcatatcgtc tccgtggagc ccaccctcaa gatgcgcgac    120

ggcatcgtcc tgatgccgca accgtccgac gaccccaacg acccgctcaa ctggtcctgg    180

ttccgcaagc acgccgccat gttcaccctc tcgtatttgg ccctcgtctg ttacgtggct    240

gtgaccacgc tggttacggg aacagtgccc ctagccaagt ccatgcatgt ctccaagtcg    300

acggccgtct atctgggcaa cacgcccgtc gctctctacg ccgtggcgcc ctggttctgg    360

agcccgctga gccactttat aggccgtcgc ccggtgctgc tgatgtgtaa tatcatcgcc    420

gtcgtcgggg cggtcgttgt tacgacgtcc aagacatatg cgtcttgcat ggttggccgc    480

gtcatcctcg gtgccggtgg ttcggccttc tggacactgg ggccagccag tattggggac    540

attttcttcc gccacgagaa gggcaagaag attggtgtgt cgaccttggc cattgtgatc    600

gccccattct tggggacaat catcggcgga cccatcatag aaaacgagaa gctgggctgg    660

ccggcctccc agtggatccc cctgattttc atggccgccg gcttcatcat gcagatcttc    720

ttcctcccgg agaccatcta catccgagag acacgcgcgc atcctgcaat catgtccaca    780
```

```
tctacgccgg gcaagcccac gttctgggac cgctatggga tccacatccc caagcgctcg    840
gaggagaagc agcacagctt tctcttcatc gcgacgcgcc ctttcgtcct cttcaagttc    900
cccgcggtga tactgtcggc cttctggttc ggcatcgcct acatgatgca cgtgggcatc    960
acgtccgaga tcccgctcat cttcgaggag cactacgatt tctccgtgct cgagatcggg   1020
ctgtcgggct tctcgggact catcggcgcc ctgctcggcg aggtatacgc gggaccctcg   1080
ctggatttca tcgctaagcg gaccatgaag cagggtcgcg agtggcgccc cgagtaccgc   1140
ctgcaggcga tctggccggc gcttattacc gtgccggctg gtctgatcat gttcggcaca   1200
tcgatccagt tcggaaatgt ttggatcact cctctgatcg ggcaggccgt ttatatcttc   1260
ggcatcgaga ttgccaccac ggttattcaa acctacattt tagaatgtta ccctcgccag   1320
ggcgccgagg cgaacttggt cttcaacctc atccgcaacc tgttctccta tataagtccg   1380
ttctttgtgc agccaatgat cgccaccctc ggtaccacct ctccgtttgg tctctctgct   1440
gccttgactg ccttcttctt ccctttcact gtgggtgtct tgatgtggcg gggcaaacag   1500
atccgggata aaggaggcga cccgggctgg agcagggatt aa                      1542
```

<210> SEQ ID NO 37
<211> LENGTH: 4308
<212> TYPE: DNA
<213> ORGANISM: Penicillium brasilianum

<400> SEQUENCE: 37

```
atggaggacc acgaaaaaga atacgatagt acctcacctc ccggaacggc cacggaagaa     60
gggaatggag gttacttcaa taccctcacc gttcctgaaa tcaacctccg agaagccagc    120
agtgccgaaa ccttaactcc tcacgcctcc gtcgtccaac ctcccaaaaa ggccgcagaa    180
tggcatatga caccacaagt cattcgcaat gccgaacgtg atgaagcagc tggttttaaa    240
aggcgtgagc tgggtgtcac ttggcaagac ctgtcggtcg aggttctcgc tgctgaagcg    300
gctgtcaaag agaacatgat ctcccaattc aacgttcctc aactcatcaa ggatttccgc    360
cgcaaaccac cactcaagtc gatcttgtcc aacagccatg gatgtgttaa gcctggagaa    420
atgcttctcg ttcttggaag acccggatcc ggatgcacta cccttctcaa aatgcttgcc    480
aaccgtcgtg agggatatca gaacatcacc ggagatgtaa gattcggaaa tatgactccg    540
gaagaagcat caagatatca aggccagatt gtgatgaata ccgaggagga gcttttctac    600
cctcgtttga cggtgggtca gacaatggat tttgctacca agcttaaggt cccatatcac    660
cttcctggag aagggaagag cgttgctgag tataccgccg aaacgaagca attcctcctc    720
gagtctatgg gaatcgccca tactgccgat acaaaagttg gcaatgaatt cgtccgaggt    780
gtcagtggtg gagaaagaaa gcgagtgtct attattgagt gccttgccac aagaggctct    840
gtttttactt gggataactc aacgagagga ctcgatgctt ccacggcctt agagtgggcc    900
aaagcccttc gcgccatgac cgacgtccaa ggtctttcga ctattgtaac gctctatcaa    960
gctggaaatg gaatttataa tcttttcgac aaagttctcg tcctcgacga aggaaagcag   1020
atctattacg gccctgccgc ggaagcgaaa cctttcatgg agaaccttgg ctttgtttac   1080
actgatggtg ccaacattgg tgatttcctc acggggttga ctgttccgac cgagcgaaag   1140
atcagacctg gttgggaaaa tcggttcccc aggacggccg acgccatttt gaccgagtac   1200
cagaactcgg cgacatataa gaatgaagtc tcactatacg gatatcccga cactgacctt   1260
gctgccgaac gcactgaggc cttcaaggaa tctgtggcct gggaaaagtc taaacactta   1320
cccaagggta gtgacctgac tactagtttc tgggcccagc tcatgtcatg cacggctaga   1380
```

```
cagtaccaga tcctctgggg cgagaagagc acgttcctga tcaaacagat tctgtcttgt   1440
gtcatggcct tgattgccgg gtcttgcttc tacaactctc cagatacctc tgcaggtctc   1500
ttcaccaagg gtggtgccgt tttcttctcg ttgctttaca actgcattgt ggccatgtcc   1560
gaggtcaccg aatctttcaa aggtcgtcct attttgacga aacacaaatc ttttgccatg   1620
tatcacccgg ctgctttctg tctggcccaa attactgcgg atttcccggt gttactgttc   1680
caatgcacga tcttctcggt cgttatctat tggatggttg gattgaagca taccgcggct   1740
gcatttttca ctttctgggc aatccttttc actacgacct tgtgcatcac agcgttattc   1800
agatttatcg gcgctgcttt cagtagcttc gaagctgcat ccaagatcag tggcaccgct   1860
gttaaggcaa tcgtcatgta tgcaggttac atgattccaa agccagagat caagaactgg   1920
ttcctcgagt tctactacac caatccgttt gcttatgcat tccaagctgc tttgaccaac   1980
gaattccacg accagcatat cgactgcgtt ggcggtaatc ttattcccag tggtcctgga   2040
tacgaggatg ttggatccgg ctataaagca tgtgctggag ttggtggtgc tcttcctggt   2100
gcagattatg tgactggaga tcagtatctt tcttctctac actacaagca ttctcaattg   2160
tggcgaaact tcggcgttgt ctgggcctgg tggggcttct tcgctgttct cacggtcgtc   2220
ttcacttgct tctggaaatc tggtgctgca tctggatctt cgcttctcat tccccgcgag   2280
aaccttaaga aacaccaagt tggcaatgat gaggaagccc aaaacaatga gaaacatgcc   2340
gctcggacga ccaccgatga gccagttcaa gtcgaggatg acaatcttgt gcgcaacaca   2400
tctatcttca catggaagaa tctcacctat acagtcaaaa caccaactgg cgaccgagtc   2460
ctcctggaca acatcaatgg atgggtgaaa cctggtatgc ttggtgcact catgggatct   2520
tccggagccg gcaaaacaac tctacttgat gttcttgcac agcgcaagac ggaaggtacc   2580
atcaaaggct ccattttggt tgacggtcgc gaattacctg tctctttcca aagaatggcc   2640
ggctactgtg agcaattgga tgttcatgag tcttacgcca ctgtgagaga agccctggag   2700
ttttctgctc tcctgcgaca gtctcgagat actcctaaag ctgagaaact taaatacgtc   2760
gacacaatta ttgacctctt ggagctgcat gatctcgccg acactctgat cggttccgtg   2820
ggtaatggct tgtctgttga acagcgcaaa cgtgtgacaa tcggtgtgga gctcgtgtcg   2880
aagcctagta ttctcatctt cttggatgag cccacttcag gtcttgatgg tcaatctgcg   2940
tataacactg tcagatttct tcggaaacta gccgatgtgg gccaagcagt tcttgtcacg   3000
attcaccagc cttcagctca gctattcgct caattcgata cccttctact ccttgcgaga   3060
ggtggcaaaa cggtctactt tggtgacatc ggggacaatg gatccacgat taagcagtac   3120
tttggcaatt acggggctat ctgccctcaa gaggcaaatc cagcagagtt catgattgac   3180
gtcgttaccg gtggtatcca agaagtgaag gacaaggatt ggcatcagat ctggcttgac   3240
tctcccgagc agcatcagat gatcaccgaa ttggacagaa tgattgcaga tgccgctagt   3300
aagccaccgg gaactgtcaa tgatggctat gagttttcaa tgcctctctg ggaacagatc   3360
aagattgtca ctcagcgcat gaacgtctcg cttttccgta atacggccta tgtcaacaac   3420
aagttctcgc ttcacatcat ctcagcattg ttgaacggat tctctttctg gcgacctggt   3480
cctagtgtga gtgcgttgca gctgaagatg ttcaccatct tcaattttgt tttcgtcgct   3540
ccaggtgtca tcaatcaact ccaacccctc ttcatccagc gccgcgatat ctacgatgct   3600
cgcgaaaaga agtccaagat gtattcctgg gtagctttcg tcactgggct tatcgtttcg   3660
gagttcccat atctctgcat ctgcgcagtt ctatactttg tttgctggta ctggcccgtc   3720
```

```
tggagattgc ctcatgactc tgaccgttct ggagccatct tcttcatgat gttgatctac   3780
gagttcatct acactggtat tggccagttc attgctgcgt atgcaccgaa cccaaccttt   3840
gcggcacttg tcaacccact tatcatcagt gttcttgttc tcttctgcgg tgtgtttgtg   3900
ccatatgacc agctgaacgt attctggaag tactggatgt attacctcaa cccattcaac   3960
tatgtcgtca acggcatgtt gactttcggt ctctggggcc agaaagtcac ctgcaatgag   4020
agcgagtatg cagtctttga tccgctcaat ggtacttgcg gcgagtatct ggcgacttac   4080
atgagtggca agggcagcgg agtcaatctg ctcaacccgg acgctacctc gagctgcaag   4140
gtctgtgagt acacaactgg aagtgacttc ctacagacgc tcaacatcaa ccattactat   4200
tatggatgga gagatgcggg catcactgtt atctatgcta tctcgggcta tgcacttgtg   4260
tttggtctga tgaagctccg gaccaaggcg tccaagaagg cagagtaa                4308
```

<210> SEQ ID NO 38
<211> LENGTH: 2619
<212> TYPE: DNA
<213> ORGANISM: Penicillium brasilianum

<400> SEQUENCE: 38

```
atgtgccagg accacgacct ggaatgttct tatacacttc cgcgaaagac caggttctac     60
ggcagcgtgg atgatctgag tgatcgatat aaatgcttag aggccatagt acgtgctgca    120
tttcccaatg acggcatctc caccgtcccg gagctcatcc ggctgggaga gcgcatggga    180
tatgccatgc cggacctatc tcagaaatca ggggagtcac ctaggataga ggagctggtg    240
agagacttcc ccaccgaagc tggagaccag ggccttgctg ggtccacaca gtgtacctct    300
tcgccaccaa gaacgggtgc cgtgaatgtc cctactgaga gtgaaagaag gcactcttcc    360
agccaagtcc aggaaaacaa ctcctgtcca gatgaacctg tcggactaat tagagacacc    420
actgggcgag aacatttcat cggcccgtct ggaagcctgc agtttctggg ccagctccgg    480
aggctacttc ttatatcccg cagcggggat gccgtggagt cccgggcacc cgctcgcctt    540
acggccacgt tcaccgatga agatgcagcg caagccctgg aagcagacgg tgaccagagt    600
gagctcgccg ctttgccttc tggaggcact ggcaacggtg gcgatgaagg ccaggagatt    660
gacgagcgct cccctgcctc cttgggttct gctcttgtca gggatttttc cagcattccc    720
gtcaatgaca tcgacgagat gagaaggcag cttccgcctc gccacgttct cgattctctg    780
atgcgagtat atttcaagaa tgtccatccg gactttgccc tattccaccg cggtaccttc    840
gaggaagaat acgagacctt catgtccaaa gggcggtact atcatcagca cgctcgagct    900
ggtgtacatt tatcctctcc cacgttacct gaaccaggct ggttaggctg tttgcacatg    960
atgattgcct ttgcctcgct aaatggctct gtcgatgtcg ctcccgacct ggatcttact   1020
tccctctgtc gccattgtgc cagtcttacc cgccagctcc tgcctcaatt tatctcaaag   1080
tgcaccctct ccaacgtccg ggccctccta cttctatccc ttttccttca taaccacaat   1140
gaacgtaacg cggcttggaa cctggttggg actgccatgc gcctttcctt cgccatgggg   1200
ctgcaccggg ccagcgacaa cgggtcgcac ttccggccta tagaaaggga ggtgcgcaag   1260
cgcgtcttct gcacgctcta cggctttgag caattcctcg cgtccagcct ggggagacca   1320
agcgggttct acgacttcga ggatgtggag atagttcctc cgcgtgaggg agtgctggac   1380
agtgggcagg acgaggacga cgaggtcatg aaactttcgc tgaggctgca agttatcctg   1440
gccaaggcca gggtctccct tgccgtcaag acactggccg tggccaatga gaggggcaac   1500
atcgacggtc tggctcggca acagcagtct tcaagggaga cgctggagat cttgaaggcg   1560
```

```
tggagggagg atcttgcctc ccaccacatc ttaaacatcc cgttgatcag tgagacagat   1620

gatccgcttt gccagtacgc cgaggagata ccgcgaatgt cactccaaga tctcaaggcc   1680

atgatgggtt ggcaaagccg acctcgactt cgggctgccc tggtcctgca cctccaatac   1740

aggtacattg ctgtcttggt gacgcggtct tctttgctgc gatacgtcgc gtccgcgcaa   1800

cgtggtgaac cagagcacga agccctgctc agccggaacg aggctagaac cgacccgtat   1860

aacagcgagg caggagaacg gctatcggac atctgcgtca cgcacgccac gcagctatgc   1920

cggctcatct tgcttgcaga ctcctttggc ttggtgaatg gcatatcggc catggacgtc   1980

ttctacgtct actgcggcgt catggtgctc atattgcggt cgctacggat ttctagctct   2040

gcaagccact accatgacca gcgcgaggcg catctgcagc tggagttgcg caagctgatc   2100

gcacaaacga gagaagtgct catacgtgtg aacaaatgca gcacaatgaa gcgattcgcg   2160

cgcgtggtgg ctaccttcga ggatggatca aggcaggata acatcaggcc tgccgatggt   2220

tctaccaatc ggtcaacggc caactgtgag atgcgaacgg ctcggcaggc atctcgtgac   2280

cctcggggcc ggttcaacca ttctatccac gccgccttag atggcgggcg agcgagcaac   2340

ctggcaatct ttccgggtgc aggaggatcg ctggacacgt cctcctccct gccagtctcg   2400

cagcaagagc cgcttaactt ccagcacgga tatggtaatg gaattgggcc gaggctcggt   2460

atatcagatc ctttctggca accaaactta ttgacgtcct ttgacgggga gccagaggca   2520

aacggttgga tgatggaccc attcctcgcg atggacggga ccggcgttgt ggactggggc   2580

gatattgagt ccctcttgtc acggaatcct ggtcaatag                          2619
```

```
<210> SEQ ID NO 39
<211> LENGTH: 22
<212> TYPE: DNA
<213> ORGANISM: Artificial
<220> FEATURE:
<223> OTHER INFORMATION: primers LS266

<400> SEQUENCE: 39

gcattcccaa acaactcgac tc                                              22


<210> SEQ ID NO 40
<211> LENGTH: 20
<212> TYPE: DNA
<213> ORGANISM: Artificial
<220> FEATURE:
<223> OTHER INFORMATION: primer V9G

<400> SEQUENCE: 40

ttacgtccct gccctttgta                                                 20


<210> SEQ ID NO 41
<211> LENGTH: 24
<212> TYPE: DNA
<213> ORGANISM: Artificial
<220> FEATURE:
<223> OTHER INFORMATION: primer Bt2a

<400> SEQUENCE: 41

ggtaaccaaa tcggtgctgc tttc                                            24


<210> SEQ ID NO 42
<211> LENGTH: 24
<212> TYPE: DNA
<213> ORGANISM: Artificial
<220> FEATURE:
```

<223> OTHER INFORMATION: primer Bt2b

<400> SEQUENCE: 42
accctcagtg tagtgaccct tggc 24

<210> SEQ ID NO 43
<211> LENGTH: 6752
<212> TYPE: DNA
<213> ORGANISM: Artificial
<220> FEATURE:
<223> OTHER INFORMATION: Expression construct for expression of the C. basilensis hmfH and HMF/FFA aldehyde dehydrogenase genes in the yeast

<400> SEQUENCE: 43
cggaattcac tgggatgtcg aaagctacat ataaggaacg tgctgctact catcctagtc 60
ctgttgctgc caagctattt aatatcatgc acgaaaagca aacaaacttg tgtgcttcat 120
tggatgttcg taccaccaag gaattactgg agttagttga agcaataact tcgtataatg 180
tatgctatac gaagttatta ggtctagaga tctgtttagc ttgcctcgtc cccgccgggt 240
cacccggcca gcgacatgga ggcccagaat accctccttg acagtcttga cgtgcgcagc 300
tcaggggcat gatgtgactg tcgcccgtac atttagccca tacatcccca tgtataatca 360
tttgcatcca tacattttga tggccgcacg gcgcgaagca aaaattacgg ctcctcgctg 420
cagacctgcg agcagggaaa cgctcccctc acagacgcgt tgaattgtcc ccacgccgcg 480
cccctgtaga gaaatataaa aggttaggat ttgccactga ggttcttctt tcatatactt 540
ccttttaaaa tcttgctagg atacagttct cacatcacat ccgaacataa acaaccatgg 600
gtaaggaaaa gactcacgtt tcgaggccgc gattaaattc caacatggat gctgatttat 660
atgggtataa atgggctcgc gataatgtcg ggcaatcagg tgcgacaatc tatcgattgt 720
atgggaagcc cgatgcgcca gagttgtttc tgaaacatgg caaaggtagc gttgccaatg 780
atgttacaga tgagatggtc agactaaact ggctgacgga atttatgcct cttccgacca 840
tcaagcattt tatccgtact cctgatgatg catggttact caccactgcg atccccggca 900
aaacagcatt ccaggtatta gaagaatatc ctgattcagg tgaaaatatt gttgatgcgc 960
tggcagtgtt cctgcgccgg ttgcattcga ttcctgtttg taattgtcct tttaacagcg 1020
atcgcgtatt tcgtctcgct caggcgcaat cacgaatgaa taacggtttg gttgatgcga 1080
gtgattttga tgacgagcgt aatggctggc ctgttgaaca agtctggaaa gaaatgcata 1140
agcttttgcc attctcaccg gattcagtcg tcactcatgg tgatttctca cttgataacc 1200
ttatttttga cgaggggaaa ttaataggtt gtattgatgt tggacgagtc ggaatcgcag 1260
accgatacca ggatcttgcc atcctatgga actgcctcgg tgagttttct ccttcattac 1320
agaaacggct ttttcaaaaa tatggtattg ataatcctga tatgaataaa ttgcagtttc 1380
atttgatgct cgatgagttt ttctaatcag tactgacaat aaaaagattc ttgttttcaa 1440
gaacttgtca tttgtatagt ttttttatat tgtagttgtt ctattttaat caaatgttag 1500
cgtgatttat attttttttc gcctcgacat catctgccca gatgcgaagt taagtgcgca 1560
gaaagtaata tcatgcgtca atcgtatgtg aatgctggtc gctatactgc tgtcgattcg 1620
atactaacgc cgccatccag tgtcgaaaac gagctgtcga gaacccttaa tataacttcg 1680
tataatgtat gctatacgaa gttatggccg gcctacgtag aaggcgcgcc catatgcaca 1740
caccatagct tcaaaatgtt tctactcctt ttttactctt ccagattttc tcggactccg 1800
cgcatcgccg taccacttca aaacacccaa gcacagcata ctaaatttcc cctctttctt 1860

```
cctctagggt gtcgttaatt acccgtacta aaggtttgga aaagaaaaaa gagaccgcct   1920
cgtttctttt tcttcgtcga aaaaggcaat aaaaattttt atcacgtttc tttttcttga   1980
aaattttttt ttttgatttt tttctctttc gatgacctcc cattgatatt taagttaata   2040
aacggtcttc aatttctcaa gtttcagttt catttttctt gttctattac aacttttttt   2100
acttcttgct cattagaaag aaagcatagc aatctaatct aagttttaat tacaaaatgg   2160
atacccctag agaaagattc gattatgtca ttgtcggtgg tggttcagca ggttgtgttt   2220
tagcaaatag attgtcccaa gatccagcaa taagagtcgc cttaatcgaa gctggtgtag   2280
ataccccacc tgacgccgtt cctgctgaaa tcttagattc ttatccaatg cctttgtttt   2340
tcggtgacag atacatttgg ccatccttac aagcaagagc cgttgctggt ggtagatcta   2400
aggtatacga acaaggtaga gttatgggtg gtggttcttc tattaatgtt caagctgcaa   2460
acagaggttt gcctagagat tacgacgaat gggccgctag tggtgcttct ggttggtcat   2520
ggcaagatgt cttgccttac ttcagacatt tggaaagaga tgtagactac ggtaattccc   2580
cattacatgg tagtcacggt ccagttccta ttagaagaat attgcctcaa gcatggccac   2640
ctttttgtac agaatttgca cacgccatgg gtagatccgg tttgagtgct ttagcagatc   2700
aaaatgctga atttggtgac ggttggtttc cagcagcctt ctccaactta gatgacaaaa   2760
gagttagtac agccatagct tatttggatg cagacaccag aagaagagcc aacttgagaa   2820
tctacgctga aactacagtt agaaagttgg ttgtctctgg tagagaagct agaggtgtca   2880
ttgcaatgag agccgatggt tcaagattgg ctttagacgc aggtgaagtc atagtatctg   2940
caggtgcctt gcaatcacca gccattttaa tgagagctgg tataggtgac gctggtgcat   3000
tgcaagcatt aggtattgaa gtagttgccg atagacctgg tgttggtaga aatttgcaag   3060
accatccagc tttaactttt tgtcaattct tggcaccaca atatagaatg cctttgtcta   3120
gaagaagagc atcaatgaca gctgcaagat tttccagtgg tgttcctggt ggtgaagctt   3180
ctgatatgta cttgtcttca tccactagag caggttggca cgccttaggt aatagattgg   3240
gtttattttt cttgtggtgc aacagacctt tctccagagg tcaagttagt ttggccggtg   3300
ctcaaccaga tgtcccacct atggtagaat taaatttgtt ggatgacgaa agagatttga   3360
gaagaatggt tgctggtgtc agaaaattag tacaaatagt tggtgcatcc gccttgcatc   3420
aacatccagg tgactttttc cctgccacat ttctccaag agttaaggct ttatctagag    3480
tttcaagagg taatgttttg ttaaccgaat tgttaggtgc agtcttggat gtatccggtc   3540
cattgagaag aagtttaatt gctagattcg tcactggtgg tgccaactta gcttctttgt   3600
taacagatga atcagctttg gaaggttttg ttagacaatc tgttttcggt gtctggcatg   3660
catcaggtac ctgcagaatg ggtgctcacg cagatagatc tgctgtaact gacgccgctg   3720
gtagagtaca tgatgttggt agattaagag ttatcgacgc atcattgatg ccaagattac   3780
ctaccgctaa tactaacatc ccaacaatta tgttggctga aaagattgca gatacaatgc   3840
aagccgaaag aagagcagtt agaccagcaa gttcagaagt cgcacaccca tcatagtaag   3900
gtaccatcat gtaattagtt atgtcacgct tacattcacg ccctcctccc acatccgctc   3960
taaccgaaaa ggaaggagtt agacaacctg aagtctaggt ccctatttat ttttttttaat  4020
agttatgtta gtattaagaa cgttatttat atttcaaatt tttctttttt ttctgtacaa   4080
acgcctgtac gcatgtaaca ttatactgaa aaccttgctt gagaaggttt tgggacgctc   4140
gaaggcttta atttggagct cttagtcaaa aaattagcct tttaattctg ctgtaacccg   4200
```

```
tacatgccca aaataggggg cgggttacac agaatatata acatcgtagg tgtctgggtg   4260
aacagtttat tcctggcatc cactaaatat aatggagccc gctttttaag ctggcatcca   4320
gaaaaaaaaa gaatcccagc accaaaatat tgttttcttc accaaccatc agttcatagg   4380
tccattctct tagcgcaact acagagaaca ggggcacaaa caggcaaaaa acgggcacaa   4440
cctcaatgga gtgatgcaac ctgcctggag taaatgatga cacaaggcaa ttgacccacg   4500
catgtatcta tctcattttc ttacaccttc tattaccttc tgctctctct gatttggaaa   4560
aagctgaaaa aaaaggttga aaccagttcc ctgaaattat tcccctactt gactaataag   4620
tatataaaga cggtaggtat tgattgtaat tctgtaaatc tatttcttaa acttcttaaa   4680
ttctactttt atagttagtc tttttttag ttttaaaaca ccaagaactt agtttcgaat   4740
aaacacacat aaacaaacaa aatgaacgcc caacactgga tcgccggtgc ctggactggt   4800
gaaccatctg ccgactctgt aaaccctgct gacggtacat tgatcggtca atttgctgat   4860
ggtggtacat ggcaagcaga agctgcaatt gccgctgcaa gacatgtttt cgaaagaact   4920
acatggggtc aagatgctag attaagacaa gacgttttgt tagcttgggc aggtgcctta   4980
gaagcagaaa gagaaagatt ggcttccttg ttaactgcag aaaatggtaa accagtagct   5040
caagcaagag gtgaagttgg tgccgctata agtgaagtca gatattacgc tggtttagca   5100
agacatatcc caggtcacgt tttggaacca gaacctggta ctatttccac aatattgaga   5160
gaacctgctg gtgtcgcagc cattatagta ccatggaatg cccctgctgt attgttagtt   5220
agatctttag caccagcctt ggctgcaggt tgtacagctg ttgtcaagtc agccgctcaa   5280
accactttgt ttactgcagc catgttgaga ttattcgaaa gaacagcatt acctgctggt   5340
gcagtcaact tggtatgcga aaccggttat gctgcagccg atcatttggt tagatctaga   5400
gatgtcgacg tagtttcctt tactggtagt acagctaccg gtaaaaagat catgattgct   5460
gcagccgatt ctgttaaaaa gttgtcatta gaattgggtg gtaaatcttg ttgcttagtt   5520
ttcgatgatg ttgacgccca agctgtcgca aagagattag ctttggctgc aacagttatt   5580
tcaggtcaac aatgtaccgc cgctagaaga gtcttggtac atgaagccat agctccacaa   5640
atgagaagac acttaacaga agctttggca gccttaagat tgggtccagg tattgaacct   5700
gatacccaaa tcggtccatt aattgaccat cctactagag ccatggtatc agctcaagtt   5760
gaaagagcat gtgatgaagc cgacaccgtt ttgttaagag gtactatgcc aggtggtgca   5820
ttggctagag gtgcattttt gtccccaact ttggttgaac acagtgatcc tggtgcattt   5880
ttctgccaag aagaaatttt tggtcctttc gttacctttg aaactttcgc tacagaagat   5940
gaagctttag caaaagccaa taacacagta tttggtttgt ctgcttcagt ttggacccat   6000
cacggtgaaa gagcaattag attagctaga gcattgagaa acggtactgt ttgggtcaat   6060
gatcataaca gattatttgc cgaagctgaa acaggtggtt atagacaatc tggtttaggt   6120
agattgcatg gttacgatgc attagccgac ttcactgaat tgaaacacat atgtatccaa   6180
gctggtttgc ctaagggtat gtcccaagca ggttgtagat tgagtggtgt tgccgctaga   6240
gaaagaatgg gtgtctccgt ctagtaacta gtgtgaattt actttaaatc ttgcatttaa   6300
ataaattttc tttttatagc tttatgactt agtttcaatt tatatactat tttaatgaca   6360
ttttcgattc attgattgaa agctttgtgt tttttcttga tgcgctattg cattgttctt   6420
gtctttttcg ccacatgtaa tatctgtagt agatacctga tacattgtgg atgctgagtg   6480
aaattttagt taataatgga ggcgctctta ataattttgg ggatattggc tttttttttt   6540
aaagtttaca aatgaatttt ttccgccagg atctcgagtt aattaaaccg tggatgatgt   6600
```

```
ggtctctaca ggatctgaca ttattattgt tggaagagga ctatttgcaa agggaaggga   6660

tgctaaggta gagggtgaac gttacagaaa agcaggctgg gaagcatatt tgagaagatg   6720

cggccagcaa aactaaccca gtggatccag tc                                 6752


<210> SEQ ID NO 44
<211> LENGTH: 579
<212> TYPE: PRT
<213> ORGANISM: Cupriavidus basilensis

<400> SEQUENCE: 44

Met Asp Thr Pro Arg Glu Arg Phe Asp Tyr Val Ile Val Gly Gly Gly
1               5                   10                  15

Ser Ala Gly Cys Val Leu Ala Asn Arg Leu Ser Gln Asp Pro Ala Ile
            20                  25                  30

Arg Val Ala Leu Ile Glu Ala Gly Val Asp Thr Pro Pro Asp Ala Val
        35                  40                  45

Pro Ala Glu Ile Leu Asp Ser Tyr Pro Met Pro Leu Phe Phe Gly Asp
    50                  55                  60

Arg Tyr Ile Trp Pro Ser Leu Gln Ala Arg Ala Val Ala Gly Gly Arg
65                  70                  75                  80

Ser Lys Val Tyr Glu Gln Gly Arg Val Met Gly Gly Gly Ser Ser Ile
                85                  90                  95

Asn Val Gln Ala Ala Asn Arg Gly Leu Pro Arg Asp Tyr Asp Glu Trp
            100                 105                 110

Ala Ala Ser Gly Ala Ser Gly Trp Ser Trp Gln Asp Val Leu Pro Tyr
        115                 120                 125

Phe Arg His Leu Glu Arg Asp Val Asp Tyr Gly Asn Ser Pro Leu His
    130                 135                 140

Gly Ser His Gly Pro Val Pro Ile Arg Arg Ile Leu Pro Gln Ala Trp
145                 150                 155                 160

Pro Pro Phe Cys Thr Glu Phe Ala His Ala Met Gly Arg Ser Gly Leu
                165                 170                 175

Ser Ala Leu Ala Asp Gln Asn Ala Glu Phe Gly Asp Gly Trp Phe Pro
            180                 185                 190

Ala Ala Phe Ser Asn Leu Asp Asp Lys Arg Val Ser Thr Ala Ile Ala
        195                 200                 205

Tyr Leu Asp Ala Asp Thr Arg Arg Arg Ala Asn Leu Arg Ile Tyr Ala
    210                 215                 220

Glu Thr Thr Val Arg Lys Leu Val Val Ser Gly Arg Glu Ala Arg Gly
225                 230                 235                 240

Val Ile Ala Met Arg Ala Asp Gly Ser Arg Leu Ala Leu Asp Ala Gly
                245                 250                 255

Glu Val Ile Val Ser Ala Gly Ala Leu Gln Ser Pro Ala Ile Leu Met
            260                 265                 270

Arg Ala Gly Ile Gly Asp Ala Gly Ala Leu Gln Ala Leu Gly Ile Glu
        275                 280                 285

Val Val Ala Asp Arg Pro Gly Val Gly Arg Asn Leu Gln Asp His Pro
    290                 295                 300

Ala Leu Thr Phe Cys Gln Phe Leu Ala Pro Gln Tyr Arg Met Pro Leu
305                 310                 315                 320

Ser Arg Arg Arg Ala Ser Met Thr Ala Ala Arg Phe Ser Ser Gly Val
                325                 330                 335

Pro Gly Gly Glu Ala Ser Asp Met Tyr Leu Ser Ser Ser Thr Arg Ala
```

```
            340                 345                 350

Gly Trp His Ala Leu Gly Asn Arg Leu Gly Leu Phe Phe Leu Trp Cys
        355                 360                 365

Asn Arg Pro Phe Ser Arg Gly Gln Val Ser Leu Ala Gly Ala Gln Pro
    370                 375                 380

Asp Val Pro Pro Met Val Glu Leu Asn Leu Leu Asp Asp Glu Arg Asp
385                 390                 395                 400

Leu Arg Arg Met Val Ala Gly Val Arg Lys Leu Val Gln Ile Val Gly
                405                 410                 415

Ala Ser Ala Leu His Gln His Pro Gly Asp Phe Phe Pro Ala Thr Phe
            420                 425                 430

Ser Pro Arg Val Lys Ala Leu Ser Arg Val Ser Arg Gly Asn Val Leu
        435                 440                 445

Leu Thr Glu Leu Leu Gly Ala Val Leu Asp Val Ser Gly Pro Leu Arg
    450                 455                 460

Arg Ser Leu Ile Ala Arg Phe Val Thr Gly Gly Ala Asn Leu Ala Ser
465                 470                 475                 480

Leu Leu Thr Asp Glu Ser Ala Leu Glu Gly Phe Val Arg Gln Ser Val
                485                 490                 495

Phe Gly Val Trp His Ala Ser Gly Thr Cys Arg Met Gly Ala His Ala
            500                 505                 510

Asp Arg Ser Ala Val Thr Asp Ala Ala Gly Arg Val His Asp Val Gly
        515                 520                 525

Arg Leu Arg Val Ile Asp Ala Ser Leu Met Pro Arg Leu Pro Thr Ala
    530                 535                 540

Asn Thr Asn Ile Pro Thr Ile Met Leu Ala Glu Lys Ile Ala Asp Thr
545                 550                 555                 560

Met Gln Ala Glu Arg Arg Ala Val Arg Pro Ala Ser Ser Glu Val Ala
                565                 570                 575

His Pro Ser


<210> SEQ ID NO 45
<211> LENGTH: 500
<212> TYPE: PRT
<213> ORGANISM: Cupriavidus basilensis

<400> SEQUENCE: 45

Met Asn Ala Gln His Trp Ile Ala Gly Ala Trp Thr Gly Glu Pro Ser
1               5                   10                  15

Ala Asp Ser Val Asn Pro Ala Asp Gly Thr Leu Ile Gly Gln Phe Ala
            20                  25                  30

Asp Gly Gly Thr Trp Gln Ala Glu Ala Ala Ile Ala Ala Ala Arg His
        35                  40                  45

Val Phe Glu Arg Thr Thr Trp Gly Gln Asp Ala Arg Leu Arg Gln Asp
    50                  55                  60

Val Leu Leu Ala Trp Ala Gly Ala Leu Glu Ala Glu Arg Glu Arg Leu
65                  70                  75                  80

Ala Ser Leu Leu Thr Ala Glu Asn Gly Lys Pro Val Ala Gln Ala Arg
                85                  90                  95

Gly Glu Val Gly Ala Ala Ile Ser Glu Val Arg Tyr Tyr Ala Gly Leu
            100                 105                 110

Ala Arg His Ile Pro Gly His Val Leu Glu Pro Glu Pro Gly Thr Ile
        115                 120                 125

Ser Thr Ile Leu Arg Glu Pro Ala Gly Val Ala Ala Ile Ile Val Pro
```

```
    130                 135                 140

Trp Asn Ala Pro Ala Val Leu Leu Val Arg Ser Leu Ala Pro Ala Leu
145                 150                 155                 160

Ala Ala Gly Cys Thr Ala Val Val Lys Ser Ala Ala Gln Thr Thr Leu
                165                 170                 175

Phe Thr Ala Ala Met Leu Arg Leu Phe Glu Arg Thr Ala Leu Pro Ala
            180                 185                 190

Gly Ala Val Asn Leu Val Cys Glu Thr Gly Tyr Ala Ala Ala Asp His
        195                 200                 205

Leu Val Arg Ser Arg Asp Val Asp Val Val Ser Phe Thr Gly Ser Thr
    210                 215                 220

Ala Thr Gly Lys Lys Ile Met Ile Ala Ala Ala Asp Ser Val Lys Lys
225                 230                 235                 240

Leu Ser Leu Glu Leu Gly Gly Lys Ser Cys Cys Leu Val Phe Asp Asp
                245                 250                 255

Val Asp Ala Gln Ala Val Ala Lys Arg Leu Ala Leu Ala Ala Thr Val
            260                 265                 270

Ile Ser Gly Gln Gln Cys Thr Ala Ala Arg Arg Val Leu Val His Glu
        275                 280                 285

Ala Ile Ala Pro Gln Met Arg Arg His Leu Thr Glu Ala Leu Ala Ala
    290                 295                 300

Leu Arg Leu Gly Pro Gly Ile Glu Pro Asp Thr Gln Ile Gly Pro Leu
305                 310                 315                 320

Ile Asp His Pro Thr Arg Ala Met Val Ser Ala Gln Val Glu Arg Ala
                325                 330                 335

Cys Asp Glu Ala Asp Thr Val Leu Leu Arg Gly Thr Met Pro Gly Gly
            340                 345                 350

Ala Leu Ala Arg Gly Ala Phe Leu Ser Pro Thr Leu Val Glu His Ser
        355                 360                 365

Asp Pro Gly Ala Phe Phe Cys Gln Glu Glu Ile Phe Gly Pro Phe Val
    370                 375                 380

Thr Phe Glu Thr Phe Ala Thr Glu Asp Glu Ala Leu Ala Lys Ala Asn
385                 390                 395                 400

Asn Thr Val Phe Gly Leu Ser Ala Ser Val Trp Thr His His Gly Glu
                405                 410                 415

Arg Ala Ile Arg Leu Ala Arg Ala Leu Arg Asn Gly Thr Val Trp Val
            420                 425                 430

Asn Asp His Asn Arg Leu Phe Ala Glu Ala Glu Thr Gly Gly Tyr Arg
        435                 440                 445

Gln Ser Gly Leu Gly Arg Leu His Gly Tyr Asp Ala Leu Ala Asp Phe
    450                 455                 460

Thr Glu Leu Lys His Ile Cys Ile Gln Ala Gly Leu Pro Lys Gly Met
465                 470                 475                 480

Ser Gln Ala Gly Cys Arg Leu Ser Gly Val Ala Ala Arg Glu Arg Met
                485                 490                 495

Gly Val Ser Val
            500
```

<210> SEQ ID NO 46
<211> LENGTH: 479
<212> TYPE: PRT
<213> ORGANISM: Burkholderia sp. CCGE1002

<400> SEQUENCE: 46

```
Met Asn Ala Arg His Trp Ile Ala Gly Glu Trp Thr Gly Thr Pro Asn
1               5                   10                  15

Ile Asp Ser Ile Asp Pro Ala Thr Gly Asp Ala Ile Gly Arg Phe Ala
            20                  25                  30

Asp Gly Gly Ser Ser Glu Ala Asp Ala Ala Ile Ala Ala Ala Arg His
        35                  40                  45

Ala Phe Asp Arg Thr Thr Trp Ala Gln Asp Ala Arg Leu Arg Gln Asp
    50                  55                  60

Val Leu Leu Gly Trp Ala Ser Ala Leu Glu Ala Glu Arg Asp Met Leu
65                  70                  75                  80

Ala Thr Leu Leu Thr Arg Glu Asn Gly Lys Ala Ile Ala Gln Ser Arg
                85                  90                  95

Asp Glu Ile Ala Gly Ala Ile Ser Glu Val Arg Tyr Tyr Ala Gly Leu
            100                 105                 110

Ala Arg His Ile Ala Gly His Val Leu Glu Pro Glu Pro Gly Thr Ile
        115                 120                 125

Ser Thr Met Leu Arg Glu Ala Ala Gly Val Ala Ala Ile Ile Val Pro
    130                 135                 140

Trp Asn Ala Pro Ala Val Leu Leu Val Arg Ser Leu Ala Pro Ala Leu
145                 150                 155                 160

Ala Ala Gly Cys Thr Val Ile Val Lys Pro Ala Ala Gln Thr Ser Leu
                165                 170                 175

Leu Thr Ala Ala Met Leu Arg Cys Phe Glu His Thr Ala Leu Pro Glu
            180                 185                 190

Gly Ala Val Asn Leu Val Asn Glu Arg Gly Tyr Ala Ala Ser Gln Arg
        195                 200                 205

Leu Val Asp Ser His Gly Val Asp Val Val Ser Phe Thr Gly Ser Thr
    210                 215                 220

Ala Thr Gly Lys Lys Ile Met Ala Ala Ala Ala Asp Ser Met Lys Lys
225                 230                 235                 240

Leu Ser Leu Glu Leu Gly Gly Lys Ser Cys Cys Val Val Phe Asp Asp
                245                 250                 255

Ala Asp Val Ala Ala Ile Ala Pro Arg Leu Ala Arg Ala Ala Thr Ile
            260                 265                 270

Ile Ser Gly Gln Gln Cys Thr Ala Ala Arg Arg Val Leu Val His Ala
        275                 280                 285

Ser Arg Ala Ala Gln Met Arg Glu Gln Leu Ala Ser Ala Leu Ala Ser
    290                 295                 300

Leu Arg Val Gly Pro Gly Ile Asp Pro Ala Thr Asp Ile Gly Ala Leu
305                 310                 315                 320

Ile Asp Gly Thr Thr Arg Asp Ala Val Ala Arg Thr Ile Glu Arg Ala
                325                 330                 335

Cys Gly Thr Ala Glu Arg Val Leu Leu Arg Gly Thr Cys Ser Gly His
            340                 345                 350

Ala Phe Leu Ser Pro Thr Leu Val Glu His Asp Asp Pro Lys Ala Phe
        355                 360                 365

Phe Cys Gln Asp Glu Ile Phe Gly Pro Phe Val Thr Leu Glu Val Phe
    370                 375                 380

Glu Asn Glu Met Glu Ala Ile Glu Lys Ala Asn Asp Thr Val Phe Gly
385                 390                 395                 400

Leu Ser Ala Ser Val Trp Thr His Asp Gly Ala Arg Ala Leu Arg Val
                405                 410                 415

Ala Arg Ala Leu Arg Asn Gly Thr Val Trp Ile Asn Asp His Asn Lys
```

```
            420                 425                 430

Leu Phe Ala Glu Ala Glu Thr Gly Gly Tyr Arg Gln Ser Gly Leu Gly
        435                 440                 445

Arg Leu His Gly Tyr Asp Ala Leu Ala Asp Phe Thr Glu Leu Lys His
    450                 455                 460

Ile Cys Met Pro Ala Gly Val Ala Glu Gly Ile Ala Pro Leu Arg
465                 470                 475


<210> SEQ ID NO 47
<211> LENGTH: 483
<212> TYPE: PRT
<213> ORGANISM: Burkholderia graminis C4D1M

<400> SEQUENCE: 47

Met Glu Arg Asp Ala Met Asn Trp Ile Ala Gly Glu Trp Ala Gly Lys
1               5                   10                  15

Pro Val Leu Ala Ser Ser Asp Pro Ser Asn Gly Glu Thr Leu Gly Arg
            20                  25                  30

Phe Val Ser Ser Asn Thr Gln Asp Ala Asp Ala Ala Val Ser Ala Ala
        35                  40                  45

Arg His Thr Phe Asp His Thr Thr Trp Ala Gln Asp Ala Arg Arg Arg
    50                  55                  60

Gln Asp Val Leu Leu Arg Trp Ala Gln Ala Leu Glu Leu Ser Val Glu
65                  70                  75                  80

Pro Leu Ala Glu Leu Leu Thr His Glu Asn Gly Lys Thr Ile Gly Gln
                85                  90                  95

Ala Arg Gly Glu Met Arg Ala Ala Ile Ser Glu Val Arg Tyr Tyr Ala
            100                 105                 110

Gly Leu Ala Arg His Ile Ala Gly His Val Ile Glu Pro Glu Pro Gly
        115                 120                 125

Thr Ile Ser Thr Met Leu Arg Glu Ala Ala Gly Val Ala Ala Ile Ile
    130                 135                 140

Val Pro Trp Asn Ala Pro Ala Val Leu Leu Val Arg Ser Leu Ala Pro
145                 150                 155                 160

Ala Leu Ala Ala Gly Cys Thr Ala Ile Val Lys Pro Ala Ala Gln Thr
                165                 170                 175

Ser Leu Ile Thr Ala Ala Met Ile Arg Cys Leu Asp Gln Pro Ala Leu
            180                 185                 190

Pro Ala Gly Ala Val Asn Leu Leu Leu Glu Asn Gly Ala Glu Ala Ala
        195                 200                 205

Ala Arg Leu Val Glu Ser Ala Asp Val Asp Val Ile Ser Phe Thr Gly
    210                 215                 220

Ser Thr Glu Val Gly Lys Arg Ile Met Arg Ala Ala Ala Asp Ser Met
225                 230                 235                 240

Lys Arg Leu Ser Leu Glu Leu Gly Gly Lys Ser Cys Cys Leu Val Phe
                245                 250                 255

Glu Asp Ser Asp Val Lys Ala Ile Ala Pro Arg Leu Ala Arg Ala Ala
            260                 265                 270

Thr Ile Ile Ser Gly Gln Gln Cys Thr Ala Ala Arg Arg Ile Leu Val
        275                 280                 285

His Val Ser Lys Ala Asp Gln Met Arg Asp Glu Leu Val Lys Ala Leu
    290                 295                 300

Ala Ser Leu Lys Val Gly Pro Gly Ile Asp Pro Ala Ser Asp Ile Gly
305                 310                 315                 320
```

```
Ala Leu Ile Asp Ala Ala Ser Arg Asp Ala Val Gln Thr Thr Val Glu
                325                 330                 335

Arg Ala Cys Asp Leu Ala Asp Arg Val Leu Leu Arg Gly Thr Ser Ser
            340                 345                 350

Gly Pro Gly Ala Phe Leu Ser Pro Thr Leu Val Glu His Gly Glu Pro
        355                 360                 365

His Ala Phe Phe Cys Gln Asp Glu Ile Phe Gly Pro Phe Val Thr Leu
    370                 375                 380

Glu Thr Phe Val Thr Glu Lys Glu Ala Val Glu Lys Ala Asn Asn Thr
385                 390                 395                 400

Val Phe Gly Leu Ser Ala Ser Val Trp Thr His Asp Ser Ala Arg Ala
                405                 410                 415

Phe Arg Ile Ala Arg Ala Leu Arg Asp Gly Thr Val Trp Ile Asn Asp
            420                 425                 430

His Asn Arg Leu Phe Ala Glu Ala Glu Thr Gly Gly Tyr Arg Gln Ser
        435                 440                 445

Gly Leu Gly Arg Leu His Gly Tyr Asp Ala Leu Ala Asp Phe Thr Glu
    450                 455                 460

Ile Lys His Ile Cys Val Gly Ala Gly Val Leu Glu Gly Ile Glu Val
465                 470                 475                 480

Leu Gly Ser


<210> SEQ ID NO 48
<211> LENGTH: 483
<212> TYPE: PRT
<213> ORGANISM: Azospirillum sp. B510

<400> SEQUENCE: 48

Met Thr Asn Leu Asp Ser Arg His Trp Ile Asp Gly Ala Trp Val Pro
1               5                   10                  15

Gly Thr Asp Arg Phe Ala Ser Ile Asn Pro Ala Asp Gly Ser Val Leu
            20                  25                  30

Gly His Ala Ala Asp Gly Gly Arg Ala Glu Ala Glu Ala Ala Ile Ala
        35                  40                  45

Ala Ala His Ala Ala Phe Asn Arg Pro Asp Trp Ala Gln Asn Pro Arg
    50                  55                  60

Leu Arg Gln Ser Ile Leu Leu Gly Trp Ala Asp Arg Leu Asp Thr Gln
65                  70                  75                  80

Ala Glu Asp Leu Ala Arg Leu Leu Thr Leu Glu Asn Gly Lys Ala Ile
                85                  90                  95

Ala Gln Ser Arg Gly Glu Ile Ala Gly Ala Ile Ser Glu Ile Arg Tyr
            100                 105                 110

Tyr Gly Gly Leu Ala Arg His Val Pro Gly His Val Leu Glu Val Glu
        115                 120                 125

Pro Gly Val Leu Ser Thr Met Leu Arg Glu Pro Ala Gly Val Ala Ala
    130                 135                 140

Leu Ile Ile Pro Trp Asn Ala Pro Ala Val Leu Leu Ala Arg Ala Ile
145                 150                 155                 160

Gly Pro Ala Leu Ala Cys Gly Cys Thr Val Val Val Lys Pro Ala Ala
                165                 170                 175

Gln Thr Thr Leu Leu Thr Ala Ala Phe Leu Arg Ala Leu Ser Glu Val
            180                 185                 190

Pro Ser Leu Pro Arg Gly Val Cys Asn Met Ile Ser Glu Thr Gly His
        195                 200                 205
```

```
Ala Ala Ala Ala Arg Leu Val Asp Ser Pro Leu Val Asp Val Val Ser
    210                 215                 220

Phe Thr Gly Ser Thr Ala Thr Gly Lys Arg Ile Met Val Ala Ala Ala
225                 230                 235                 240

Asp Thr Met Lys Lys Leu Ser Leu Glu Leu Gly Gly Lys Ser Cys Cys
                245                 250                 255

Leu Val Phe Pro Asp Ala Asp Pro Ala Glu Thr Ala Ala Arg Ile Ala
            260                 265                 270

Thr Ala Ala Thr Ile Ile Ser Gly Gln Gln Cys Thr Ala Ala Arg Arg
        275                 280                 285

Val Leu Val His Ala Ser Ala Phe Asp Ala Met Lys Thr His Leu Arg
    290                 295                 300

Ala Ala Leu Ala Ala Met Thr Val Gly Asn Gly Leu Asp Pro Ala Ile
305                 310                 315                 320

Arg Met Gly Pro Leu Ile Asp Arg Pro Ala Arg Asp Gln Val Gln Thr
                325                 330                 335

Gln Val Glu Arg Ala Phe Asp Ala Cys Asp Glu Val Leu Leu Arg Gly
            340                 345                 350

Gly Val Pro Thr Asp Ser Pro Ala Ala Ala Ser Phe Leu Thr Pro Ser
        355                 360                 365

Leu Val Ala His Asp Asp Pro Ser Ala Phe Phe Cys Gln Asp Glu Ile
    370                 375                 380

Phe Gly Pro Phe Val Val Leu Glu Arg Phe Glu Thr Glu Ala Glu Ala
385                 390                 395                 400

Val Ala Lys Ala Asn Asn Thr Val Phe Gly Leu Ser Ala Ser Val Trp
                405                 410                 415

Thr Arg Asp Gly Ala Arg Ala Leu Arg Met Ala Arg Ala Leu Arg Asn
            420                 425                 430

Gly Thr Val Trp Ile Asn Asp His Asn Arg Leu Phe Ala Glu Ala Glu
        435                 440                 445

Thr Gly Gly Tyr Arg Gln Ser Gly Leu Gly Arg Leu His Gly Tyr Asp
    450                 455                 460

Ala Phe Ala Asp Phe Thr Glu Leu Lys His Val Cys Gln Thr Val Gly
465                 470                 475                 480

Thr Ile Gly


<210> SEQ ID NO 49
<211> LENGTH: 480
<212> TYPE: PRT
<213> ORGANISM: Pseudomonas putida

<400> SEQUENCE: 49

Met Gln Ser Gln His Tyr Ile Asp Gly Gln Trp Thr Ser Thr Asp Arg
1               5                   10                  15

Trp Thr Asp Ser Leu Asp Pro Ala Ser Gly Glu Leu Ile Gly Cys Phe
            20                  25                  30

Ala Asp Gly Gly Glu Ala Glu Ala Glu Ala Ala Val Ala Ala Ala Ala
        35                  40                  45

Arg Ala Phe Asn Asp Pro Gln Trp Ala Gln Asn Pro Arg Leu Arg Gln
    50                  55                  60

Gln Leu Leu Leu Glu Trp Ala Ala Gly Leu Lys Ala Arg Gln Glu Gln
65                  70                  75                  80

Leu Ala Gln Leu Leu Thr Arg Glu Asn Gly Lys Ala Leu Ala Gln Ser
                85                  90                  95
```

```
Arg Gly Glu Ile Gly Gly Ala Ile Ser Glu Ile Leu Tyr Tyr Ala Gly
            100                 105                 110

Leu Ala Arg His Asn Pro Gly His Met Leu Glu Val Ala Pro Gly Glu
        115                 120                 125

Phe Ser Ser Met Leu Arg Glu Pro Ala Gly Val Ala Gly Leu Ile Ile
    130                 135                 140

Pro Trp Asn Ala Pro Ala Val Leu Leu Val Arg Ala Leu Ala Pro Ala
145                 150                 155                 160

Ile Ala Ala Gly Cys Thr Val Val Ile Lys Pro Ala Pro Gln Thr Ala
                165                 170                 175

Leu Phe Asn Ala Ala Met Leu Glu Pro Leu Phe Ala Leu Pro Gly Leu
            180                 185                 190

Pro Ala Gly Ala Val Asn Leu Phe Ala Glu Ser Gly His Ala Gly Ala
        195                 200                 205

Ala His Leu Val Ala Ser Pro Arg Val Asp Val Leu Ser Phe Thr Gly
    210                 215                 220

Ser Thr Ala Thr Gly Gln Arg Ile Met Arg Asp Cys Ala Ala Thr Met
225                 230                 235                 240

Lys Lys Leu Ser Leu Glu Leu Gly Gly Lys Ser Cys Cys Leu Val Phe
                245                 250                 255

Glu Asp Ala Asp Ile Ala Ala Ile Ala Pro Lys Leu Ala Ala Ala Ala
            260                 265                 270

Thr Ile Ile Ser Gly Gln Gln Cys Thr Ala Ala Arg Arg Val Leu Val
        275                 280                 285

His Ala Ser Arg Phe Ala Glu Met Lys Thr Ala Leu Ser Ala Ala Leu
    290                 295                 300

Gly Gln Ile Arg Leu Gly Asn Gly Leu Asp Pro Ala Asn Asn Met Gly
305                 310                 315                 320

Pro Leu Ile Asp Trp His Ser Arg Asp Ser Val Glu Arg Arg Ile Gly
                325                 330                 335

Glu Ala Leu Asp Ser Cys Asp Glu Val Leu Leu Ala Gly Gly Arg Pro
            340                 345                 350

Gln Gly Glu Leu Ser Lys Gly Ala Phe Leu Ala Pro Ser Leu Ile Ala
        355                 360                 365

His Arg Asp Ser Ser Ala Phe Phe Cys Gln Glu Glu Ile Phe Gly Pro
    370                 375                 380

Leu Leu Val Leu Glu Ser Phe Glu Asp Glu Thr Glu Ala Val Ala Arg
385                 390                 395                 400

Ala Asn His Thr Glu Phe Gly Leu Ser Ala Ser Val Trp Thr Asp Gln
                405                 410                 415

Gly Ala Arg Ala Trp Arg Val Ala Arg Ala Leu Arg Asn Gly Thr Val
            420                 425                 430

Trp Leu Asn Asp His Asn Arg Leu Phe Ala Glu Ala Glu Thr Gly Gly
        435                 440                 445

Tyr Arg Lys Ser Gly Leu Gly Arg Leu His Gly Val Asp Ala Leu Leu
    450                 455                 460

Asp Phe Ser Glu Leu Lys His Ile Tyr Gln Asn Val Gly Thr Leu Gly
465                 470                 475                 480
```

<210> SEQ ID NO 50
<211> LENGTH: 486
<212> TYPE: PRT
<213> ORGANISM: Rhodopseudomonas palustris

<400> SEQUENCE: 50

```
Met Gly Met Thr Ala Leu His Ala Asp Asn Leu Ile Asp Gly Ala Trp
1               5                   10                  15

Gln Pro Ala Gln Ser Gly Ala Thr Ala Pro Ser Leu Asp Pro Ser Ser
            20                  25                  30

Gly Gly Thr Ile Gly Gly Phe Ala Ala Gly Gly Ala Ala Asp Ala Gln
        35                  40                  45

Ala Ala Val Ala Ala Ala Arg Arg Ala Phe Glu Arg Pro Glu Trp Ser
    50                  55                  60

Gln Asn Pro Arg Ala Arg Gln Met Val Met Leu Arg Trp Ala Asp Arg
65                  70                  75                  80

Met Glu Ala Gln Ala Asp Gln Leu Ala Arg Leu Leu Thr Leu Glu Asn
                85                  90                  95

Gly Lys Pro Leu Pro Gln Ser Arg Gly Glu Ile Ala Gly Ser Val Ser
            100                 105                 110

Glu Ile Arg Tyr Tyr Ala Gly Leu Thr Arg Tyr Ile Pro Gly His Val
        115                 120                 125

Phe Glu Val Glu Pro Gly Ser Phe Ser Thr Leu Leu Lys Glu Pro Ala
    130                 135                 140

Gly Val Ala Gly Leu Ile Ile Pro Trp Asn Ala Pro Ala Val Leu Leu
145                 150                 155                 160

Ile Arg Ala Leu Thr Pro Ala Leu Ala Ala Gly Cys Thr Val Val Ile
                165                 170                 175

Lys Pro Ala Pro Gln Thr Ala Gln Ile Thr Ala Ala Ile Ile Lys Cys
            180                 185                 190

Leu His Glu Val Asp Gly Leu Pro Arg Gly Val Val Asn Leu Val Ser
        195                 200                 205

Glu Gln Gly His Gln Val Ala Glu His Leu Val Thr Ser Asn Asp Val
    210                 215                 220

Asp Val Ile Ser Phe Thr Gly Ser Asn Ala Thr Gly Ala Arg Ile Met
225                 230                 235                 240

Ala Ala Ala Ala Pro Thr Met Lys Lys Leu Ser Leu Glu Leu Gly Gly
                245                 250                 255

Lys Ser Ala Cys Leu Val Phe Asp Asp Ala Asp Ile Ala Asp Val Ala
            260                 265                 270

Pro Lys Leu Ala Ala Ala Ala Thr Ile Ile Ala Gly Gln Gln Cys Thr
        275                 280                 285

Ala Ala Arg Arg Val Leu Val His Ala Ser Arg Tyr Asp Glu Met Lys
    290                 295                 300

Ala Ala Leu Lys Ala Ala Leu Ala Asn Ile Arg Ile Ala Pro Gly Ser
305                 310                 315                 320

Ala Ala Gly Ala Glu Met Gly Pro Leu Ile Asp Ala Ala Ser Leu Ala
                325                 330                 335

Ala Val Ala Lys Arg Ala Asp Glu Ala Met Gln Ala Ala Asp Glu Val
            340                 345                 350

Val Leu Arg Gly Gly Arg Pro Ala Gly Asp Leu Ala Asn Gly Tyr Phe
        355                 360                 365

Leu Ser Pro Thr Leu Val Ala His Arg Asp Thr Ser Ala Phe Phe Val
    370                 375                 380

Gln Glu Glu Ile Phe Gly Pro Leu Val Val Leu Glu Lys Phe Glu Asp
385                 390                 395                 400

Glu Lys Glu Ala Val Ala Arg Ala Asn His Ser Asp Tyr Gly Leu Ser
                405                 410                 415
```

```
Ala Ser Val Trp Thr His Asp Gly Ala Arg Ala Met Arg Val Ala Arg
            420                 425                 430

Ala Leu Arg Asn Gly Thr Val Trp Ile Asn Asp His Asn Lys Leu Phe
        435                 440                 445

Ala Glu Ala Glu Thr Gly Gly Tyr Arg Arg Ser Gly Leu Gly Arg Leu
    450                 455                 460

His Gly Tyr Asp Ala Leu Ile Asp Phe Leu Glu Ile Lys His Val Tyr
465                 470                 475                 480

Gln Ser Cys Gly Val Val
                485


<210> SEQ ID NO 51
<211> LENGTH: 485
<212> TYPE: PRT
<213> ORGANISM: Dinoroseobacter shibae DFL 12

<400> SEQUENCE: 51

Met Thr Thr Thr Asp Leu Ile Ala Arg His Met Ile Gly Gly Ser Tyr
1               5                   10                  15

Ser Asp Ala Gly Asp Lys Ile Ala Ser Ile Asn Pro Ala Thr Gly Ala
            20                  25                  30

Val Val Gly His Val Arg Ala Asp Gly Ala Ala Gln Ala Thr Ala Ala
        35                  40                  45

Ile Ala Ala Ala Arg Ala Ala Phe Asp Thr Thr Leu Trp Pro Gln Ser
    50                  55                  60

Pro Arg Asp Arg Gln Met Ala Leu Leu Arg Trp Ala Asp Ala Leu Glu
65                  70                  75                  80

Ala Asp Leu Ala Arg Leu Ala Glu Leu Leu Thr Leu Thr Asn Gly Lys
                85                  90                  95

Pro Leu Gly Ala Ser Lys Gly Glu Leu Gly Ala Ala Ile Ser Glu Ile
            100                 105                 110

Arg Tyr Tyr Ala Gly Leu Thr Arg His Asn Pro Gly His Ala Met Glu
        115                 120                 125

Val Ala Pro Gly Glu Leu Ser Val Met Leu Arg Glu Pro Ala Gly Val
    130                 135                 140

Ala Gly Ile Ile Val Pro Trp Asn Ala Pro Ala Val Leu Leu Ile Arg
145                 150                 155                 160

Ser Leu Ala Pro Ala Leu Ala Val Gly Cys Thr Thr Val Thr Lys Pro
                165                 170                 175

Ala Pro Gln Thr Ala Leu Phe Thr Ala Ala Cys Met Ala Pro Leu Phe
            180                 185                 190

Glu Asp Ala Ala Ile Pro Ala Gly Val Val Asn Val Val Phe Glu Val
        195                 200                 205

Gly His Asp Ala Ala Gln Thr Leu Val Thr Ser Pro Asp Val Asp Val
    210                 215                 220

Ile Ser Phe Thr Gly Ser Asn Ala Val Gly Gln Arg Ile Met Ala Asp
225                 230                 235                 240

Ala Ala Pro Thr Met Lys Lys Leu Ser Leu Glu Leu Gly Gly Lys Ser
                245                 250                 255

Cys Cys Ile Val Leu Asp Asp Ala Asp Ile Gly Val Val Ala Pro Lys
            260                 265                 270

Leu Ala Ala Ala Ala Thr Ile Ile Ser Gly Gln Gln Cys Thr Ala Ala
        275                 280                 285

Arg Arg Val Leu Val His Glu Ser Arg Leu Asp Glu Ala Lys Ser Ala
    290                 295                 300
```

```
Leu Ser Ala Ala Leu Gln Ala Val Ser Ile Gly Asp Gly Met Ser Asp
305                 310                 315                 320

Gly Thr Ala Met Gly Pro Leu Ile Asp Ile Gln Ser Arg Asp Arg Val
                325                 330                 335

Met Arg Asp Cys Gly Thr Val Tyr Asp Thr Ala Asp Glu Val Val Leu
            340                 345                 350

Arg Gly Gly Pro Leu Asp Gly Pro Lys Gly Ser Ala Phe Met Ser Pro
        355                 360                 365

Ala Leu Val Val His Ser Asp Pro Asn Ala Ser Phe Val Gln Asp Glu
    370                 375                 380

Ile Phe Gly Pro Leu Val Val Leu Glu Thr Phe Arg Asp Glu Ala Asp
385                 390                 395                 400

Ala Val Ala Lys Ala Asn Asn Thr Val Tyr Gly Leu Ser Ala Ser Ile
                405                 410                 415

Trp Thr His Arg Gly Asp Ala Ser Trp Arg Leu Ala Arg Ala Leu Arg
            420                 425                 430

Asn Gly Thr Val Trp Ile Asn Asp His Asn Arg Leu Phe Ala Glu Ala
        435                 440                 445

Glu Thr Gly Gly Tyr Arg Arg Ser Gly Leu Gly Arg Leu His Gly Phe
    450                 455                 460

Asp Gly Leu Leu Asp Phe Cys Glu Leu Lys His Val Tyr Gln Asn Val
465                 470                 475                 480

Gly Val Val Gly His
                485
```

<210> SEQ ID NO 52
<211> LENGTH: 446
<212> TYPE: PRT
<213> ORGANISM: Aeribacillus pallidus

<400> SEQUENCE: 52

```
Met Lys Asn Ile Ala Asn Thr Ser Thr Glu Arg Pro Val Asn Asp Ala
1               5                   10                  15

Ser Val Lys Asn Arg Gln Met Val Arg Ala Thr Ile Ala Ser Leu Ile
            20                  25                  30

Gly Trp Ser Leu Asp Leu Tyr Asp Leu Phe Leu Leu Leu Phe Val Ala
        35                  40                  45

Thr Thr Ile Gly Asn Leu Phe Phe Pro Ala Ser Asn Gln Thr Leu Ser
    50                  55                  60

Leu Ala Ala Val Tyr Ala Ser Phe Ala Val Thr Leu Leu Met Arg Pro
65                  70                  75                  80

Leu Gly Ser Ala Ile Phe Gly Ile Tyr Ala Asp Lys Asn Gly Arg Lys
                85                  90                  95

Lys Ala Met Thr Val Ala Ile Ile Gly Ala Gly Leu Cys Thr Ala Ala
            100                 105                 110

Phe Gly Leu Leu Pro Thr Ile His Gln Val Gly Val Val Ala Ala Ile
        115                 120                 125

Ala Phe Leu Ile Leu Arg Leu Val Gln Gly Val Phe Val Gly Gly Val
    130                 135                 140

Val Ala Ser Thr His Thr Ile Gly Thr Glu Ser Ala Ser Pro Lys Tyr
145                 150                 155                 160

Arg Gly Phe Met Ser Gly Leu Ile Gly Gly Gly Gly Ala Gly Leu Gly
                165                 170                 175

Ala Leu Phe Ala Ser Ile Ser Tyr Ser Val Val Thr Ala Ile Phe Pro
```

```
            180                 185                 190

Gly Glu Ala Phe Asp Val Trp Gly Trp Arg Val Met Phe Phe Thr Gly
        195                 200                 205

Ile Ile Gly Ser Leu Phe Gly Leu Phe Ile Phe Arg Ser Leu Glu Glu
    210                 215                 220

Ser Pro Leu Trp Lys Gln Leu Lys Glu Glu Asn Ser Lys Gly Glu Val
225                 230                 235                 240

Ser Glu Phe Gln Lys Ala Pro Leu Lys Thr Phe Phe Thr Lys Tyr Tyr
                245                 250                 255

Lys Val Leu Leu Val Asn Leu Met Ile Val Ile Gly Gly Gly Ser Gly
            260                 265                 270

Tyr Tyr Leu Thr Ser Gly Phe Ile Pro Thr Phe Leu Lys Val Val Asn
        275                 280                 285

Lys Val Ser Ala Ser Val Ser Ser Gly Val Leu Ile Ala Thr Ser Ile
    290                 295                 300

Met Thr Ile Val Ala Ala Val Leu Val Gly His Leu Ser Glu Val Ile
305                 310                 315                 320

Gly Arg Lys Lys Thr Phe Leu Leu Ile Gly Ile Leu Cys Leu Val Gly
                325                 330                 335

Leu Pro Tyr Phe Tyr Leu Ser Leu Ala Asn Ser Thr Thr Thr Thr Gly
            340                 345                 350

Ile Tyr Leu Asn Ala Leu Gly Leu Ile Phe Leu Gly Asn Ala Ala Tyr
        355                 360                 365

Ala Pro Val Leu Ile Phe Leu Asn Glu Arg Phe Pro Thr Ser Ile Arg
    370                 375                 380

Ser Thr Gly Thr Gly Leu Ser Trp Asn Met Gly Phe Ala Ile Gly Gly
385                 390                 395                 400

Met Met Pro Thr Phe Val Asn Leu Ala Ser Gly Thr Val Glu His Ile
                405                 410                 415

Pro Tyr Thr Leu Met Tyr Phe Thr Ile Gly Ile Tyr Leu Val Tyr Ile
            420                 425                 430

Leu Gly Ser Leu Ile Ile Pro Glu Thr Lys Gly Asn Leu Lys
        435                 440                 445


<210> SEQ ID NO 53
<211> LENGTH: 447
<212> TYPE: PRT
<213> ORGANISM: Cupriavidus basilensis

<400> SEQUENCE: 53

Met Glu Ala Val Ala Lys Lys Arg Thr Glu Thr Ile Ser Glu Ala Leu
1               5                   10                  15

Pro Ala Ala Thr Asn Arg Gln Val Phe Gly Ala Val Thr Ala Ser Cys
            20                  25                  30

Met Gly Trp Ala Leu Asp Leu Phe Asp Leu Phe Ile Leu Leu Phe Val
        35                  40                  45

Ala Pro Val Ile Gly Arg Leu Phe Phe Pro Ser Glu His Ala Met Leu
    50                  55                  60

Ser Leu Ala Ala Val Tyr Ala Ser Phe Ala Val Thr Leu Leu Met Arg
65                  70                  75                  80

Pro Leu Gly Ser Ala Ile Phe Gly Thr Tyr Ala Asp Arg His Gly Arg
                85                  90                  95

Lys Gly Ala Met Val Val Ala Val Thr Gly Val Gly Leu Ser Thr Ala
            100                 105                 110
```

Ala Phe Gly Leu Leu Pro Thr Val Gly Gln Val Gly Leu Leu Ala Pro
115 120 125

Ala Leu Phe Ile Leu Leu Arg Leu Val Gln Gly Ile Phe Val Gly Gly
130 135 140

Val Val Ala Ser Thr His Thr Ile Gly Thr Glu Ser Val Pro Pro Ser
145 150 155 160

Trp Arg Gly Ala Val Ser Gly Leu Val Gly Gly Gly Gly Ala Gly Ile
165 170 175

Gly Ala Leu Leu Ala Ser Ile Thr Tyr Met Ala Met Thr Ala Leu Phe
180 185 190

Pro Gly Glu Ala Phe Asp Ala Trp Gly Trp Arg Cys Met Phe Phe Ser
195 200 205

Gly Ile Ile Ser Ser Val Leu Gly Leu Phe Ile Phe Asn Ser Leu Glu
210 215 220

Glu Ser Pro Leu Trp Lys Gln Leu Gln Ala Ala Lys Gly His Ala Ala
225 230 235 240

Pro Val Glu Asn Pro Leu Arg Val Ile Phe Ser Arg Gln Tyr Arg Gly
245 250 255

Val Leu Phe Val Asn Ile Leu Leu Thr Val Gly Gly Gly Ser Ala Tyr
260 265 270

Tyr Leu Thr Ser Gly Tyr Leu Pro Thr Phe Leu Lys Val Val Val Lys
275 280 285

Ala Pro Ala Gly Ala Ser Ala Ala Ile Leu Met Ala Ser Ser Val Gly
290 295 300

Val Ile Val Ala Ser Ile Ile Ala Gly His Leu Ser Thr Leu Ile Gly
305 310 315 320

Arg Lys Arg Ala Phe Leu Leu Ile Gly Ala Leu Asn Val Val Leu Leu
325 330 335

Pro Leu Ile Tyr Gln Arg Met Pro Ala Ala Pro Asp Val Thr Thr Leu
340 345 350

Gly Ile Tyr Ala Val Ala Leu Ala Met Leu Gly Ser Thr Gly Phe Ala
355 360 365

Pro Ile Leu Ile Phe Leu Asn Glu Arg Phe Pro Thr Ser Ile Arg Ala
370 375 380

Thr Gly Thr Gly Leu Ser Trp Asn Ile Gly Phe Ala Ile Gly Gly Met
385 390 395 400

Met Pro Thr Phe Ala Ser Leu Cys Ala Ser Thr Pro Ala Asp Leu Pro
405 410 415

Lys Val Leu Gly Ile Phe Val Ala Val Val Thr Ala Ile Tyr Leu Ala
420 425 430

Gly Ala Ala Ile Val Pro Glu Thr Ala Gly Arg Leu Gly Glu Lys
435 440 445

<210> SEQ ID NO 54
<211> LENGTH: 449
<212> TYPE: PRT
<213> ORGANISM: Cupriavidus basilensis

<400> SEQUENCE: 54

Met Glu Ala Val Ala Lys Lys Ser Ala Ala Thr Ile Ser Glu Ala Leu
1 5 10 15

Pro Ala Ala Ser Asn Arg Gln Val Phe Gly Ala Val Ala Ala Ser Cys
20 25 30

Met Gly Trp Ala Leu Asp Leu Phe Asp Leu Phe Ile Leu Leu Phe Val
35 40 45

```
Ala Pro Val Ile Gly Arg Leu Phe Phe Pro Ser Glu His Ala Met Leu
    50                  55                  60

Ser Leu Ala Ala Val Tyr Ala Ser Phe Ala Val Thr Leu Leu Met Arg
65                  70                  75                  80

Pro Leu Gly Ser Ala Ile Phe Gly Ser Tyr Ala Asp Arg His Gly Arg
                85                  90                  95

Lys Gly Ala Met Val Val Ala Val Thr Gly Val Gly Leu Ser Thr Ala
            100                 105                 110

Ala Phe Gly Leu Leu Pro Thr Val Gly Gln Val Gly Leu Leu Ala Pro
        115                 120                 125

Ala Leu Phe Ile Leu Leu Arg Leu Val Gln Gly Ile Phe Val Gly Gly
    130                 135                 140

Val Val Ala Ser Thr His Thr Ile Gly Thr Glu Ser Val Pro Pro Ser
145                 150                 155                 160

Trp Arg Gly Ala Val Ser Gly Leu Val Gly Gly Gly Gly Ala Gly Leu
                165                 170                 175

Gly Ala Leu Leu Ala Ser Ile Thr Tyr Met Ala Met Thr Ala Leu Phe
            180                 185                 190

Pro Gly Glu Ala Phe Asp Ala Trp Gly Trp Arg Cys Met Phe Phe Ser
        195                 200                 205

Gly Ile Ile Ser Ser Val Leu Gly Leu Phe Ile Phe Asn Ser Leu Glu
    210                 215                 220

Glu Ser Pro Leu Trp Lys Gln Leu Gln Ala Ala Lys Gly His Ala Ala
225                 230                 235                 240

Pro Val Glu Asn Pro Leu Arg Val Ile Phe Ser Arg Gln Tyr Arg Gly
                245                 250                 255

Val Leu Phe Val Asn Ile Leu Leu Thr Val Gly Gly Gly Ser Ala Tyr
            260                 265                 270

Tyr Leu Thr Ser Gly Tyr Leu Pro Thr Phe Leu Lys Val Val Val Lys
        275                 280                 285

Ala Ser Ala Gly Glu Ser Ala Ala Ile Leu Met Ala Ser Ser Leu Gly
    290                 295                 300

Val Ile Val Ala Ser Ile Leu Ala Gly His Leu Ser Thr Met Ile Gly
305                 310                 315                 320

Arg Lys Arg Ala Phe Leu Leu Ile Gly Ala Leu Asn Val Val Val Leu
                325                 330                 335

Pro Leu Leu Tyr Gln Trp Met Pro Ala Ala Pro Asp Thr Thr Thr Leu
            340                 345                 350

Gly Leu Tyr Ala Val Val Leu Ser Met Leu Gly Cys Ser Gly Phe Ala
        355                 360                 365

Pro Ile Leu Ile Phe Leu Asn Glu Arg Phe Pro Thr Ser Ile Arg Ala
    370                 375                 380

Thr Gly Thr Gly Leu Ser Trp Asn Ile Gly Phe Ala Val Gly Gly Met
385                 390                 395                 400

Met Pro Thr Phe Ala Ser Leu Cys Ala Ser Thr Pro Ala Glu Leu Pro
                405                 410                 415

Met Val Leu Gly Ile Phe Leu Ala Val Val Thr Ile Ile Tyr Leu Val
            420                 425                 430

Gly Ala Phe Ile Val Pro Glu Thr Val Gly Arg Leu Gly Asp Asn Gly
        435                 440                 445

Ala
```

<210> SEQ ID NO 55
<211> LENGTH: 449
<212> TYPE: PRT
<213> ORGANISM: Methylobacterium radiotolerans

<400> SEQUENCE: 55

```
Met Gln Thr Ala Ala Thr Phe Ala Ser Asp Pro Pro Ala Leu Ala Lys
1               5                   10                  15

Pro Thr Gly Arg Gln Thr Val Thr Ala Ala Met Ala Ser Leu Phe Gly
            20                  25                  30

Trp Gly Leu Asp Leu Phe Asp Leu Phe Ile Leu Leu Tyr Val Ala Pro
        35                  40                  45

Val Val Gly Thr Leu Phe Phe Pro Ala Asp Lys Pro Met Leu Ser Leu
    50                  55                  60

Ala Gly Ala Tyr Ala Ser Phe Ala Val Thr Leu Leu Ile Arg Pro Leu
65                  70                  75                  80

Gly Ser Ala Leu Phe Gly Ser Tyr Ala Asp Arg Phe Gly Arg Arg Arg
                85                  90                  95

Ala Leu Met Val Ala Val Val Gly Val Gly Ile Ser Thr Ala Val Phe
            100                 105                 110

Gly Leu Leu Pro Thr Val Gly Gln Ile Gly Trp Leu Ala Thr Ala Val
        115                 120                 125

Phe Leu Phe Phe Arg Leu Val Gln Gly Ile Phe Val Gly Gly Val Val
    130                 135                 140

Ala Ala Ser His Thr Ile Gly Thr Glu Ser Val Pro Glu Arg Trp Arg
145                 150                 155                 160

Gly Leu Met Ser Gly Ala Val Gly Gly Gly Gly Ser Ala Ile Gly Gly
                165                 170                 175

Leu Leu Ala Ser Leu Val Phe Tyr Val Val Ser Leu Met Ala Pro Gly
            180                 185                 190

Glu Ala Phe Ala Glu Trp Gly Trp Arg Leu Met Phe Phe Ser Gly Leu
        195                 200                 205

Leu Thr Ser Val Ile Gly Leu Ile Leu Phe Arg Asn Leu Glu Glu Ser
    210                 215                 220

Pro Ile Phe Lys Glu Leu Gln Ala Arg Lys Ala Ala Leu Arg Ala Gly
225                 230                 235                 240

Ala Pro Ala Glu Ala Ser Pro Ile Arg Ser Leu Phe Ser Pro Ser Asn
                245                 250                 255

Arg Gly Ser Phe Ala Val Ala Thr Leu Ile Ser Phe Gly Gly Gly Ala
            260                 265                 270

Ala Tyr Tyr Leu Thr Ser Gly Tyr Leu Pro Thr Leu Leu Lys Leu Val
        275                 280                 285

Asn Gly Val Pro Asn Ala Thr Ala Ser Met Ile Leu Ile Gly Ala Asn
    290                 295                 300

Val Ala Ala Ala Ile Gly Ala Cys Gly Met Gly Glu Leu Ser Gln His
305                 310                 315                 320

Ile Gly Arg Lys Arg Ser Phe Leu Leu Met Gly Val Ile Arg Leu Leu
                325                 330                 335

Ala Phe Pro Ala Leu Phe Leu Thr Met Ala Asn Thr Thr Ser Leu Val
            340                 345                 350

Gly Val Ala Ala Cys Ala Phe Leu Leu Ala Leu Ile Ala Asn Gly Ser
        355                 360                 365

Tyr Gly Pro Leu Leu Ile Phe Leu Asn Glu Lys Phe Pro Thr Ala Val
    370                 375                 380
```

```
Arg Ala Thr Gly Thr Gly Leu Thr Trp Asn Ile Gly Phe Ala Leu Gly
385                 390                 395                 400

Gly Met Leu Pro Thr Leu Val Ser Leu Val Ala Asp Gly Pro Thr Gln
                405                 410                 415

Ile Pro Met Val Leu Ala Val Ile Thr Thr Gly Val Thr Leu Val Tyr
            420                 425                 430

Leu Val Gly Ala Phe Leu Thr Asp Glu Thr Gln Gly Asn Leu Asp Arg
        435                 440                 445

Ala


<210> SEQ ID NO 56
<211> LENGTH: 443
<212> TYPE: PRT
<213> ORGANISM: Sulfolobus acidocaldarius

<400> SEQUENCE: 56

Met Lys Lys Glu Glu Lys Phe Thr Ser Asn His Phe Lys Trp Thr Leu
1               5                   10                  15

Ala Thr Phe Phe Thr Trp Thr Phe Asp Leu Tyr Asp Leu Phe Thr Ile
            20                  25                  30

Leu Leu Val Ala Pro Tyr Ile Ser Ser Leu Phe Phe Pro Ser Ser Ile
        35                  40                  45

Thr Phe Leu Ser Ile Ala Ala Thr Tyr Ala Gly Phe Ala Thr Ser Leu
    50                  55                  60

Ile Met Arg Pro Val Gly Ala Thr Val Phe Gly Ser Arg Val Ser Asp
65                  70                  75                  80

Lys Val Gly Arg Lys Arg Ala Ile Phe Tyr Gly Leu Ile Gly Leu Val
                85                  90                  95

Ile Thr Ser Thr Leu Gln Gly Ala Leu Pro Thr Tyr Gln Val Val Gly
            100                 105                 110

Val Ile Ala Pro Ile Leu Leu Leu Ala Val Arg Leu Ile Gln Gly Val
        115                 120                 125

Phe Ile Gly Gly Ile Thr Ala Gly Ser His Val Ile Gly Pro Glu Ser
    130                 135                 140

Val Pro Glu Arg Tyr Arg Gly Ile Val Gly Gly Leu Gly Phe Ser Ala
145                 150                 155                 160

Ala Gly Val Ala Tyr Leu Ile Ala Ala Gly Trp Phe Phe Leu Thr Thr
                165                 170                 175

Ile Leu Tyr Pro Gly Ser Ser Tyr Leu Val Trp Gly Trp Arg Val Met
            180                 185                 190

Phe Phe Gly Gly Leu Leu Ser Leu Ala Val Leu Gly Phe Val Asn Tyr
        195                 200                 205

Leu Val Pro Glu Ser Glu Val Trp Thr Lys Ile Lys Lys Arg Gly Ser
    210                 215                 220

Val Val Lys Ser Pro Leu Lys Glu Ile Phe Ser Lys Tyr Arg Tyr Gln
225                 230                 235                 240

Leu Gly Val Ala Leu Leu Leu Ser Ile Gly Trp Gly Ala Ser Phe Tyr
                245                 250                 255

Val Thr Asp Gly Ile Leu Pro Thr Phe Leu Ser Ser Val Asn Lys Leu
            260                 265                 270

Ala Lys Thr Glu Ile Ala Ile Val Met Ile Ile Gly Ser Ile Gly Met
        275                 280                 285

Ser Ile Gly Pro Leu Ile Gly Gly Glu Ile Ser Gln Ile Ile Gly Arg
    290                 295                 300
```

```
Lys Ile Thr Ser Leu Ile Gly Ala Ile Ile Val Leu Ala Val Val Gly
305                 310                 315                 320

Pro Leu Phe Leu Ser Leu Gly Ser Leu Lys Ser Gly Asp Leu Asn Gln
                325                 330                 335

Ile Ile Leu His Ser Phe Ala Ile Leu Phe Leu Val Asp Ile Gly Gly
            340                 345                 350

Gly Met Leu Met Thr Tyr Leu Asn Glu Ile Tyr Pro Ala Ser Val Arg
        355                 360                 365

Gly Thr Gly Val Gly Phe Thr Trp Asn Thr Gly Phe Ala Ile Gly Gly
    370                 375                 380

Thr Ile Pro Thr Ile Ile Ser Leu Ala Val Ala Ser Ala Gly Leu Ser
385                 390                 395                 400

Ala Phe Pro Ser Ile Met Phe Tyr Thr Leu Ile Val Val Ser Val Ile
                405                 410                 415

Ile Leu Val Gly Thr Val Leu Thr Lys Glu Thr Lys Gly Thr Ile Ser
            420                 425                 430

Lys Glu Glu Tyr Glu Ile Gln Lys Glu Thr Leu
        435                 440
```

<210> SEQ ID NO 57
<211> LENGTH: 1056
<212> TYPE: DNA
<213> ORGANISM: Artificial
<220> FEATURE:
<223> OTHER INFORMATION: hmfL1 coding sequence optimised for expression in yeast

<400> SEQUENCE: 57

```
atgggttcct tatccttacc agaaacatca ttagccgcaa tccaagacaa agaaacaaaa     60

gctatctcag tcgccaaaag acctacacca gtacctgttg gtacccaagt cttagtaaaa    120

ttgcattatt ccggtgtttg tgccactgat ttgcacttag ctagaggttc tgttccatac    180

ttacaaccta aggtttcagt cggtggtcat gaaggtaccg gtgttattgc ttctttgggt    240

ccagatgtcg acgcagcaga atggcatgta ggtgacagag tagcagttag atgggtacac    300

atagtttgtg gtaaatgcga agtttgtact acaggtttcg aaaatttgtg ccaatctaga    360

aagttggctg gtaaagatgt tgaaggtact ttcgccgaat atgcaattgc cgactcttca    420

tacatggtta gattaccagc tggtgtctca gatgcagacg ccgctcctat cttgtgtgct    480

ggtgtcacag tatacaaagc cttgaagatc gcttctttga gagcaggttc atgggttgct    540

gtcgcaggtg ctggtggtgg tttaggtcat ttggcaatcc aatatgctag agcaatgggt    600

ttaaaagttg tcgcattgga tgccagaaag agagacttgt gcttatcctt gggtgctgaa    660

agttacatcg acgttttaga aactgatgac tgtgtcgcac aagtaattaa agttacagat    720

ggtggtgctc acggtgcatt aatatgcgct tccagtggtc aagcctacga tgacgctgtt    780

aaatttttga gatggaccgg tactttagtc tgtataggtt tgccacctaa gccaacattg    840

ttatccttag gtcctgctga ttttgtagcc agaggtatca aggttatggg tacaagtacc    900

ggtgacagac aagacacagt tgaagccttg gctttcgtcg ctaaaggtca agtaaagcct    960

caattaaccg aaagaagatt ggaagatgtt gaagaaatct taaaggaaat agaaaatggt   1020

acaatgcaag gtaaagccgt aatcagaatc gcatag                             1056
```

<210> SEQ ID NO 58
<211> LENGTH: 1020
<212> TYPE: DNA
<213> ORGANISM: Artificial
<220> FEATURE:
<223> OTHER INFORMATION: hmfL2 coding sequence optimised for expression in yeast

<400> SEQUENCE: 58
atgagtttgc catcccacta caagagagcc gcttttaagg aagcaggtgg tccattgact 60
attgaagaag ttgatttgac tatgccagat gccggtgaag tcttggtaaa agttgaagct 120
tgtggtgtat gcttttcaga cactgttcct caagctcatg gtttgggtgg taaattccca 180
atcgttcctg gtcatgaaat tataggtcac gttgtcgcaa caggtgacgg tgtttccgac 240
tgggaagtcg gtgacagaat tggtgaaggt tggcatggtg gtcacgacgg tacatgtcca 300
tcatgcagac aaggtcattt ccaaatgtgt gataaccaat ccataaacgg tgttaccaaa 360
aatggtggtt atgctcaata ctgcattttg agaagtgaag cagcagtcag aatacctact 420
cacgtatctg ccgctgaata tgcaccaatt ttatgtgccg gtgtcaccgt ttttaattca 480
atgagacaaa tcggtgttaa gcctggttcc actgtcgcaa ttcaaggttt gggtggttta 540
ggtcatttgg ccattcaata tgctaacaga tttggtttca gagtagttgc tatatctaga 600
gatgaccaaa aggaaagatt cgttagagat ttgggtgcac acgaatacat taatacatct 660
gaagaagatg tcggttcagc tttacaaaag ttgggtggtg caagtttaat agttgcaacc 720
gccccaaacg ctagagcaat ctctcctttg ttaaaaggtt taagaccatt gggtaaattg 780
ttgatcttgg ctgttccagg tgaaatccct ttagatacca gattgatggt agcaagaggt 840
ttatccgttc atggttggcc aagtggtcac gccttggatt ctgaagaaac tataagattc 900
acagaattag aagatatcaa gtgtatgata caaacttact cattagacag agctaacgaa 960
gcctttgacg ctatgatttc aggttcagtt agattcagag cagttattac aatggaatag 1020

<210> SEQ ID NO 59
<211> LENGTH: 1518
<212> TYPE: DNA
<213> ORGANISM: Artificial
<220> FEATURE:
<223> OTHER INFORMATION: hmfN1 coding sequence optimised for expression in yeast

<400> SEQUENCE: 59
atgacccaaa ccaatgtcca cgtaaacaaa tccgacactt ccttagctgc tccacaacaa 60
ttattcatct ccggtaaata tcaaaactct caaagaaatg gtacatttcc agtcaaaaac 120
cctatgactg gtgaaacaat ctatgaatgt gtttctgcat cattagatga ctacgctgct 180
gctatagaag aagctgatgc cgcacaacca tcatgggcta gattaggtcc ttccgcaaga 240
agattgattt tgttaaaggc cgctgatata atggaaacat acatcgaaac cgacgctcca 300
gcaatcttga gtgctgaagt ttctgcaaca agaggttggg tcagagccaa tatattatct 360
accgctggtg ttttcagaga aactgctgct ttggcaacac atatcaaagg tgaaattgtt 420
ccagctgata gacctggtac tacaatctta gtttcaagag aaccagtcgg tgttgtcttg 480
gctatttccc cttggaatat gcctgcaacc ttaactgcca gagctatctg ttgccccttta 540 atttgtggta actctgtagt tttaagacca tccgaatttt ctcctaaatc tcaacatttg 600
gtcgtaagag ccttaacaga agctggtttg ccagcaggtt gcttgcaatt cttaccaaca 660
tcaaccgcag ataccccctag agccatagaa tttgctatca gacaccctaa ggttagtaga 720
gctaatttca ctggttctga tagagtcggt agaattatag caggtttatc cgccagttgt 780
ttgaaaccat gcgttttgga attgggtggt aaagccccctg ttgtcgtatt agaagatgct 840

```
gatgtcgaag ctgctgttga agcagttgtc tacggtgcca tgtctaactc aggtcaaatt    900

tgtatgagta cagaaagagc tatagttcat agatcattgg ccgctgattt taaagcattg    960

ttagtaaaga gagccgaatc attaagagtt ggtaatcact tggaagatcc agacgttcaa   1020

ttgtcaggtt tgtttactgc tgcttccgca gaaagagtct tgggtttgat taaaggtgct   1080

gtaaacgcag gtgccacctt gttagctggt gacttggcat tacatggtcc atgccaaact   1140

ataatggctc ctcacatctt aaccggtgtt actagagata tggacttgtt tcatagagaa   1200

acattcggtc cagtattgtt cgttagtgaa tttgatactg atgacgaagc tatagcacaa   1260

gccaatgaca cagaattttc tttatgtgct tcagtattct ccagagatgt tttgagagct   1320

atggataccg ctaagagaat aagaactggt tcatgccacg tcaatggtcc tactgtatat   1380

atcgaagcac cattgcctaa cggtggtgtt ggtggtggtt ctggttacgg tagatttggt   1440

ggtgttgctg gtattgaaga gtttacagaa agacaaatag ttagtttagc caagccaggt   1500

atcaagtatg ccttttag                                                 1518
```

```
<210> SEQ ID NO 60
<211> LENGTH: 2139
<212> TYPE: DNA
<213> ORGANISM: Artificial
<220> FEATURE:
<223> OTHER INFORMATION: synthetic fragment comprising hmfN1 for
      expression in yeast

<400> SEQUENCE: 60
```

```
ctcccccggg ttagtcaaaa aattagcctt ttaattctgc tgtaacccgt acatgcccaa     60

aatagggggc gggttacaca gaatatataa catcgtaggt gtctgggtga acagtttatt    120

cctggcatcc actaaatata atggagcccg ctttttaagc tggcatccag aaaaaaaaag    180

aatcccagca ccaaaatatt gttttcttca ccaaccatca gttcataggt ccattctctt    240

agcgcaacta cagagaacag gggcacaaac aggcaaaaaa cgggcacaac ctcaatggag    300

tgatgcaacc tgcctggagt aaatgatgac acaaggcaat tgacccacgc atgtatctat    360

ctcattttct tacaccttct attaccttct gctctctctg atttggaaaa agctgaaaaa    420

aaaggttgaa accagttccc tgaaattatt cccctacttg actaataagt atataaagac    480

ggtaggtatt gattgtaatt ctgtaaatct atttcttaaa cttcttaaat tctactttta    540

tagttagtct ttttttagt  tttaaaacac caagaactta gtttcgaata aacacacata    600

aacaaacaaa aatgacccaa accaatgtcc acgtaaacaa atccgacact tccttagctg    660

ctccacaaca attattcatc tccggtaaat atcaaaactc tcaaagaaat ggtacatttc    720

cagtcaaaaa ccctatgact ggtgaaacaa tctatgaatg tgtttctgca tcattagatg    780

actacgctgc tgctatagaa gaagctgatg ccgcacaacc atcatgggct agattaggtc    840

cttccgcaag aagattgatt ttgttaaagg ccgctgatat aatggaaaca tacatcgaaa    900

ccgacgctcc agcaatcttg agtgctgaag tttctgcaac aagaggttgg gtcagagcca    960

atatattatc taccgctggt gttttcagag aaactgctgc tttggcaaca catatcaaag   1020

gtgaaattgt tccagctgat agacctggta ctacaatctt agtttcaaga gaaccagtcg   1080

gtgttgtctt ggctatttcc ccttggaata tgcctgcaac cttaactgcc agagctatct   1140

gttgcccttt aatttgtggt aactctgtag ttttaagacc atccgaattt tctcctaaat   1200

ctcaacattt ggtcgtaaga gccttaacag aagctggttt gccagcaggt tgcttgcaat   1260

tcttaccaac atcaaccgca gataccccta gagccataga atttgctatc agacacccta   1320
```

```
aggttagtag agctaatttc actggttctg atagagtcgg tagaattata gcaggtttat   1380
ccgccagttg tttgaaacca tgcgttttgg aattgggtgg taaagcccct gttgtcgtat   1440
tagaagatgc tgatgtcgaa gctgctgttg aagcagttgt ctacggtgcc atgtctaact   1500
caggtcaaat ttgtatgagt acagaaagag ctatagttca tagatcattg gccgctgatt   1560
ttaaagcatt gttagtaaag agagccgaat cattaagagt tggtaatcac ttggaagatc   1620
cagacgttca attgtcaggt ttgtttactg ctgcttccgc agaaagagtc ttgggtttga   1680
ttaaaggtgc tgtaaacgca ggtgccacct tgttagctgg tgacttggca ttacatggtc   1740
catgccaaac tataatggct cctcacatct taaccggtgt tactagagat atggacttgt   1800
ttcatagaga aacattcggt ccagtattgt tcgttagtga atttgatact gatgacgaag   1860
ctatagcaca agccaatgac acagaatttt ctttatgtgc ttcagtattc tccagagatg   1920
ttttgagagc tatggatacc gctaagagaa taagaactgg ttcatgccac gtcaatggtc   1980
ctactgtata tatcgaagca ccattgccta acggtggtgt tggtggtggt tctggttacg   2040
gtagatttgg tggtgttgct ggtattgaag agtttacaga aagacaaata gttagtttag   2100
ccaagccagg tatcaagtat gccttttaga ctagtgtga                          2139
```

<210> SEQ ID NO 61
<211> LENGTH: 8645
<212> TYPE: DNA
<213> ORGANISM: Artificial
<220> FEATURE:
<223> OTHER INFORMATION: yeast/E. coli shuttle vector pTT2

<400> SEQUENCE: 61

```
ctaaattgta agcgttaata ttttgttaaa attcgcgtta aatttttgtt aaatcagctc     60
atttttaac caataggccg aaatcggcaa aatcccttat aaatcaaaag aatagaccga     120
gatagggttg agtggccgct acagggcgct cccattcgcc attcaggctg cgcaactgtt    180
gggaagggcg tttcggtgcg ggcctcttcg ctattacgcc agctggcgaa agggggatgt    240
gctgcaaggc gattaagttg ggtaacgcca gggttttccc agtcacgacg ttgtaaaacg    300
acggccagtg agcgcgacgt aatacgactc actatagggc gaattggcgg aaggccgtca    360
aggccggtac cggtcctttt catcacgtgc tataaaaata attataattt aaatttttta    420
atataaatat ataaattaaa aatagaaagt aaaaaaagaa attaaagaaa aaatagtttt    480
tgttttccga agatgtaaaa gactctaggg ggatcgccaa caaatactac cttttatctt    540
gctcttcctg ctctcaggta ttaatgccga attgtttcat cttgtctgtg tagaagacca    600
cacacgaaaa tcctgtgatt ttacatttta cttatcgtta atcgaatgta tatctattta    660
atctgctttt cttgtctaat aaatatatat gtaaagtacg ctttttgttg aaatttttta    720
aacctttgtt tatttttttt tcttcattcc gtaactcttc taccttcttt atttactttc    780
taaaatccaa atacaaaaca taaaaataaa taaacacaga gtaaattccc aaattattcc    840
atcattaaaa gatacgaggc gcgtgtaagt tacaggcaag cgatccgtcc gtttaaacat    900
gctttctgaa aacacgacta ttctgatggc taacggtgaa attaaagaca tcgcaaacgg    960
cgcgccgatt tttataatga cgaaaaaaaa aaaattggaa agaaaaagct taatgcggta   1020
gtttatcaca gttaaattgc taacgcagtc aggcaccgtg tatgaaatct aacaatgcgc   1080
tcatcgtcat cctcggcacc gtcaccctgg atgctgtagg cataggcttg gttatgccgg   1140
tactgccggg cctcttgcgg gatatcgtcc attccgacag catcgccagt cactatggcg   1200
tgctgctagc gctatatgcg ttgatgcaat ttctatgcgc acccgttctc ggagcactgt   1260
```

```
ccgaccgctt tggccgccgc ccagtcctgc tcgcttcgct acttggagcc actatcgact   1320
acgcgatcat ggcgaccaca cccgtcctgt ggatcctcta cgccggacgc atcgtggccg   1380
gcatcaccgg cgccacaggt gcggttgctg gcgcctatat cgccgacatc accgatgggg   1440
aagatcgggc tcgccacttc gggctcatga gcgcttgttt cggcgtgggt atggtggcag   1500
gccccgtggc cgggggactg ttgggcgcca tctccttgca tgcaacttct tttctttttt   1560
tttcttttct ctctcccccg ttgttgtctc accatatccg caatgacaaa aaaatgatgg   1620
aagacactaa aggaaaaaat taacgacaaa gacagcacca acagatgtcg ttgttccaga   1680
gctgatgagg ggtatctcga agcacacgaa actttttcct tccttcattc acgcacacta   1740
ctctctaatg agcaacggta tacggccttc cttccagtta cttgaatttg aaataaaaaa   1800
aagtttgctg tcttgctatc aagtataaat agacctgcaa ttattaatct tttgtttcct   1860
cgtcattgtt ctcgttccct ttcttccttg tttctttttc tgcacaatat ttcaagctat   1920
accaagcata caatcaagga attcgagcta agcggccgcc catggaagct gcaatcaaat   1980
cactggtagc aatcttaaga caagaactga cgaacttccg tatcagttgt gtttatcctg   2040
gtaattttga aagcgaaggt ttcactgtag agcagctaac gaaacccgaa attacaaagt   2100
tgatcgaagg cccctcagac gctatcccat gcaaacaagc atgtgatatc attgccaagt   2160
cgctggccag aggtgatgat gacgttttta cagattttgt cggatggatg ataatgggga   2220
tggaccttgg gctcaccgca aagaaaagcc gctttgttcc gttgcaatgg atttttggtg   2280
tcctatcaaa cattctggtc gtgccattct acacgcgtgt tattactgag tagtatttat   2340
ttaagtattg tttgtgcact tgcctgcagg cctttgaaa agcaagcata aaagatctaa    2400
acataaaatc tgtaaaataa caagatgtaa agataatgct aaatcatttg gctttttgat   2460
tgattgtaca ggaaaatata catcgcaggg ggttgacttt taccatttca ccgcaatgga   2520
atcaaacttg ttgaagagaa tgttcacagg cgcatacgct acaatgaccc gattcttgct   2580
agccttttct cggtcttgca aacaaccgcc ggcagcttct cgagccgcgg aaccgccaga   2640
tattcattac ttgacgcaaa agcgtttgaa ataatgacga aaaagaagga agaaaaaaaa   2700
agaaaaatac cgcttctagg cgggttatct actgatccga gcttccacta ggatagcacc   2760
caaacacctg catatttgga cgacctttac ttacaccacc aaaaaccact ttcgcctctc   2820
ccgcccctga taacgtccac taattgagcg attacctgag cggtcctctt ttgtttgcag   2880
catgagactt gcatactgca aatcgtaagt agcaacgtct caaggtcaaa actgtatgga   2940
aaccttgtca cctcacttaa ttctagctag cctaccctgc aagtcaagag gtctccgtga   3000
ttcctagcca cctcaaggta tgcctctccc cggaaactgt ggccttttct ggcacacatg   3060
atctccacga tttcaacata taaatagctt ttgataatgg caatattaat caaatttatt   3120
ttacttcttt cttgtaacat ctctcttgta atcccttatt ccttctagct atttttcata   3180
aaaaaccaag caactgctta tcaacacaca aacactaaat caaaatgcat tcgcgaatat   3240
ctagaataca cgtcatagaa tgcgacgtca gcttttgatt aagccttcta gtccaaaaaa   3300
cacgtttttt tgtcatttat ttcattttct tagaatagtt tagtttattc attttatagt   3360
cacgaatgtt ttatgattct atatagggtt gcaaacaagc atttttcatt ttatgttaaa   3420
acaatttcag gtttaccttt tattctgctt gtggtgacgc gggtatccgc ccgctctttt   3480
ggtcacccat gtatttaatt gcataaataa ttcttaaaag tggagctagt ctatttctat   3540
ttacatacct ctcatttctc atttcctccc ccgggttagt caaaaaatta gccttttaat   3600
```

```
tctgctgtaa cccgtacatg cccaaaatag ggggcgggtt acacagaata tataacatcg   3660
taggtgtctg ggtgaacagt ttattcctgg catccactaa atataatgga gcccgctttt   3720
taagctggca tccagaaaaa aaaagaatcc cagcaccaaa atattgtttt cttcaccaac   3780
catcagttca taggtccatt ctcttagcgc aactacagag aacaggggca caaacaggca   3840
aaaaacgggc acaacctcaa tggagtgatg caacctgcct ggagtaaatg atgacacaag   3900
gcaattgacc cacgcatgta tctatctcat ttcttacac cttctattac cttctgctct   3960
ctctgatttg gaaaaagctg aaaaaaaagg ttgaaaccag ttccctgaaa ttattcccct   4020
acttgactaa taagtatata aagacggtag gtattgattg taattctgta aatctatttc   4080
ttaaacttct taaattctac ttttatagtt agtctttttt ttagttttaa aacaccaaga   4140
acttagtttc gaataaacac acataaacaa acaaagagct ctgatcaata gtcgacatag   4200
ggcccatacc taggactagt gtgaatttac tttaaatctt gcatttaaat aaattttctt   4260
tttatagctt tatgacttag tttcaattta tatactattt taatgacatt ttcgattcat   4320
tgattgaaag ctttgtgttt tttcttgatg cgctattgca ttgttcttgt ctttttcgcc   4380
acatgtaata tctgtagtag atacctgata cattgtggat gctgagtgaa attttagtta   4440
ataatggagg cgctcttaat aattttgggg atattggctt tttttttaa agtttacaaa   4500
tgaatttttt ccgccaggat ttaattaatt gcagattccc ttttatggat tcctaaatcc   4560
tcgaggagaa cttctagtat atctacatac ctaatattat tgccttatta aaaatggaat   4620
cccaacaatt acatcaaaat ccacattctc ttcaaaatca attgtcctgt acttccttgt   4680
tcatgtgtgt tcaaaaacgt tatatttata ggataattat actctatttc tcaacaagta   4740
attggttgtt tggccgagcg gtctaaggcg cctgattcaa gaaatatctt gaccgcagtt   4800
aactgtggga atactcaggt atcgtaagat gcaagagttc gaatctctta gcaaccatta   4860
tttttttcct caacataacg agaacacaca ggggcgctat cgcacagaat caaattcgat   4920
gactggaaat tttttgttaa tttcagaggt cgcctgacgc atataccttt ttcaactgaa   4980
aaattgggag aaaaaggaaa ggtgagagcg ccggaaccgg cttttcatat agaatagaga   5040
agcgttcatg actaaatgct tgcatcacaa tacttgaagt tgacaatatt atttaaggac   5100
ctattgtttt ttccaatagg tggttagcaa tcgtcttact ttctaacttt tcttaccttt   5160
tacatttcag caatatatat atatatattt caaggatata ccattctaat gtctgcccct   5220
aagaagatcg tcgttttgcc aggtgaccac gttggtcaag aaatcacagc cgaagccatt   5280
aaggttctta aagctatttc tgatgttcgt tccaatgtca agttcgattt cgaaaatcat   5340
ttaattggtg gtgctgctat cgatgctaca ggtgttccac ttccagatga ggcgctggaa   5400
gcctccaaga aggctgatgc cgttttgtta ggtgctgtgg gtggtcctaa atggggtacc   5460
ggtagtgtta gacctgaaca aggtttacta aaaatccgta aagaacttca attgtacgcc   5520
aacttaagac catgtaactt tgcatccgac tctcttttag acttatctcc aatcaagcca   5580
caatttgcta aaggtactga cttcgttgtt gtcagagaat tagtgggagg tatttacttt   5640
ggtaagagaa aggaagacga tggtgatggt gtcgcttggg atagtgaaca atacaccgtt   5700
ccagaagtgc aaagaatcac aagaatggcc gctttcatgg ccctacaaca tgagccacca   5760
ttgcctattt ggtccttgga taaagctaat gttttggcct cttcaagatt atggagaaaa   5820
actgtggagg aaaccatcaa gaacgaattc cctacattga aggttcaaca tcaattgatt   5880
gattctgccg ccatgatcct agttaagaac ccaacccacc taaatggtat tataatcacc   5940
agcaacatgt ttggtgatat catctccgat gaagcctccg ttatcccagg ttccttgggt   6000
```

ttgttgccat ctgcgtcctt ggcctctttg ccagacaaga acaccgcatt tggtttgtac 6060
gaaccatgcc acggttctgc tccagatttg ccaaagaata aggtcaaccc tatcgccact 6120
atcttgtctg ctgcaatgat gttgaaattg tcattgaact tgcctgaaga aggtaaggcc 6180
attgaagatg cagttaaaaa ggttttggat gcaggtatca gaactggtga tttaggtggt 6240
tccaacagta ccaccgaagt cggtgatgct gtcgccgaag aagttaagaa aatccttgct 6300
taaaaagatt ctcttttttt atgatatttg tacataaact ttataaatga aattcataat 6360
agaaacgaca cgaaattaca aaatggaata tgttcatagg gtagacgaaa ctatatacgc 6420
aatctacata catttatcaa gaaggagaaa aaggaggatg taaaggaata caggtaagca 6480
aattgatact aatggctcaa cgtgataagg aaaaagaatt gcactttaac attaatattg 6540
acaaggagga gggcaccaca caaaaagtta ggtgtaacag aaaatcatga aactggccgg 6600
ccgatgctgt ccgcgggcct cataagagtt gtggtaacaa cgcaggtgcg cgcatctgct 6660
aagtttaaac ggtaccggcc tcatgggcct tccgctcact gcccgctttc cagtcgggaa 6720
acctgtcgtg ccagctgcat taacatggtc atagctgttt ccttgcgtat tgggcgctct 6780
ccgcttcctc gctcactgac tcgctgcgct cggtcgttcg ggtaaagcct ggggtgccta 6840
atgagcaaaa ggccagcaaa aggccaggaa ccgtaaaaag gccgcgttgc tggcgttttt 6900
ccataggctc cgcccccctg acgagcatca caaaaatcga cgctcaagtc agaggtggcg 6960
aaacccgaca ggactataaa gataccaggc gtttccccct ggaagctccc tcgtgcgctc 7020
tcctgttccg accctgccgc ttaccggata cctgtccgcc tttctccctt cgggaagcgt 7080
ggcgctttct catagctcac gctgtaggta tctcagttcg gtgtaggtcg ttcgctccaa 7140
gctgggctgt gtgcacgaac cccccgttca gcccgaccgc tgcgccttat ccggtaacta 7200
tcgtcttgag tccaacccgg taagacacga cttatcgcca ctggcagcag ccactggtaa 7260
caggattagc agagcgaggt atgtaggcgg tgctacagag ttcttgaagt ggtggcctaa 7320
ctacggctac actagaagaa cagtatttgg tatctgcgct ctgctgaagc cagttacctt 7380
cggaaaaaga gttggtagct cttgatccgg caaacaaacc accgctggta gcggtggttt 7440
ttttgtttgc aagcagcaga ttacgcgcag aaaaaaagga tctcaagaag atcctttgat 7500
cttttctacg gggtctgacg ctcagtggaa cgaaaactca cgttaaggga ttttggtcat 7560
gagattatca aaaaggatct tcacctagat ccttttaaat taaaaatgaa gttttaaatc 7620
aatctaaagt atatatgagt aaacttggtc tgacagttac caatgcttaa tcagtgaggc 7680
acctatctca gcgatctgtc tatttcgttc atccatagtt gcctgactcc ccgtcgtgta 7740
gataactacg atacgggagg gcttaccatc tggccccagt gctgcaatga taccgcgaga 7800
accacgctca ccggctccag atttatcagc aataaaccag ccagccggaa gggccgagcg 7860
cagaagtggt cctgcaactt tatccgcctc catccagtct attaattgtt gccgggaagc 7920
tagagtaagt agttcgccag ttaatagttt gcgcaacgtt gttgccattg ctacaggcat 7980
cgtggtgtca cgctcgtcgt ttggtatggc ttcattcagc tccggttccc aacgatcaag 8040
gcgagttaca tgatccccca tgttgtgcaa aaaagcggtt agctccttcg gtcctccgat 8100
cgttgtcaga agtaagttgg ccgcagtgtt atcactcatg gttatggcag cactgcataa 8160
ttctcttact gtcatgccat ccgtaagatg cttttctgtg actggtgagt actcaaccaa 8220
gtcattctga gaatagtgta tgcggcgacc gagttgctct tgcccggcgt caatacggga 8280
taataccgcg ccacatagca gaactttaaa agtgctcatc attggaaaac gttcttcggg 8340
gcgaaaactc tcaaggatct taccgctgtt gagatccagt tcgatgtaac ccactcgtgc 8400
acccaactga tcttcagcat cttttacttt caccagcgtt tctgggtgag caaaaacagg 8460
aaggcaaaat gccgcaaaaa agggaataag ggcgacacgg aaatgttgaa tactcatact 8520
cttccttttt caatattatt gaagcattta tcagggttat tgtctcatga gcggatacat 8580
atttgaatgt atttagaaaa ataaacaaat aggggttccg cgcacatttc cccgaaaagt 8640
gccac 8645

<210> SEQ ID NO 62
<211> LENGTH: 10125
<212> TYPE: DNA
<213> ORGANISM: Artificial
<220> FEATURE:
<223> OTHER INFORMATION: pTT2-hmfN1

<400> SEQUENCE: 62
ctcccccggg ttagtcaaaa aattagcctt ttaattctgc tgtaacccgt acatgcccaa 60
aatagggggc gggttacaca gaatatataa catcgtaggt gtctgggtga acagtttatt 120
cctggcatcc actaaatata atggagcccg ctttttaagc tggcatccag aaaaaaaaag 180
aatcccagca ccaaaatatt gttttcttca ccaaccatca gttcataggt ccattctctt 240
agcgcaacta cagagaacag gggcacaaac aggcaaaaaa cgggcacaac ctcaatggag 300
tgatgcaacc tgcctggagt aaatgatgac acaaggcaat tgacccacgc atgtatctat 360
ctcattttct tacaccttct attaccttct gctctctctg atttggaaaa agctgaaaaa 420
aaaggttgaa accagttccc tgaaattatt cccctacttg actaataagt atataaagac 480
ggtaggtatt gattgtaatt ctgtaaatct atttcttaaa cttcttaaat tctactttta 540
tagttagtct tttttttagt tttaaaacac caagaactta gtttcgaata aacacacata 600
aacaaacaaa aatgacccaa accaatgtcc acgtaaacaa atccgacact tccttagctg 660
ctccacaaca attattcatc tccggtaaat atcaaaactc tcaaagaaat ggtacatttc 720
cagtcaaaaa ccctatgact ggtgaaacaa tctatgaatg tgtttctgca tcattagatg 780
actacgctgc tgctatagaa gaagctgatg ccgcacaacc atcatgggct agattaggtc 840
cttccgcaag aagattgatt ttgttaaagg ccgctgatat aatggaaaca tacatcgaaa 900
ccgacgctcc agcaatcttg agtgctgaag tttctgcaac aagaggttgg gtcagagcca 960
atatattatc taccgctggt gttttcagag aaactgctgc tttggcaaca catatcaaag 1020
gtgaaattgt tccagctgat agacctggta ctacaatctt agtttcaaga gaaccagtcg 1080
gtgttgtctt ggctatttcc ccttggaata tgcctgcaac cttaactgcc agagctatct 1140
gttgcccttt aatttgtggt aactctgtag ttttaagacc atccgaattt tctcctaaat 1200
ctcaacattt ggtcgtaaga gccttaacag aagctggttt gccagcaggt tgcttgcaat 1260
tcttaccaac atcaaccgca gataccccta gagccataga atttgctatc agacacccta 1320
aggttagtag agctaatttc actggttctg atagagtcgg tagaattata gcaggtttat 1380
ccgccagttg tttgaaacca tgcgttttgg aattgggtgg taaagcccct gttgtcgtat 1440
tagaagatgc tgatgtcgaa gctgctgttg aagcagttgt ctacggtgcc atgtctaact 1500
caggtcaaat ttgtatgagt acagaaagag ctatagttca tagatcattg gccgctgatt 1560
ttaaagcatt gttagtaaag agagccgaat cattaagagt tggtaatcac ttggaagatc 1620
cagacgttca attgtcaggt ttgtttactg ctgcttccgc agaaagagtc ttgggtttga 1680
ttaaaggtgc tgtaaacgca ggtgccacct tgttagctgg tgacttggca ttacatggtc 1740

```
catgccaaac tataatggct cctcacatct taaccggtgt tactagagat atggacttgt   1800
ttcatagaga aacattcggt ccagtattgt tcgttagtga atttgatact gatgacgaag   1860
ctatagcaca agccaatgac acagaatttt ctttatgtgc ttcagtattc tccagagatg   1920
ttttgagagc tatggatacc gctaagagaa taagaactgg ttcatgccac gtcaatggtc   1980
ctactgtata tatcgaagca ccattgccta acggtggtgt tggtggtggt tctggttacg   2040
gtagatttgg tggtgttgct ggtattgaag agtttacaga aagacaaata gttagtttag   2100
ccaagccagg tatcaagtat gccttttaga ctagtgtgaa tttactttaa atcttgcatt   2160
taaataaatt ttctttttat agctttatga cttagtttca atttatatac tattttaatg   2220
acattttcga ttcattgatt gaaagctttg tgtttttttct tgatgcgcta ttgcattgtt   2280
cttgtctttt tcgccacatg taatatctgt agtagatacc tgatacattg tggatgctga   2340
gtgaaatttt agttaataat ggaggcgctc ttaataattt tggggatatt ggcttttttt   2400
tttaaagttt acaaatgaat tttttccgcc aggatttaat taattgcaga ttccctttta   2460
tggattccta aatcctcgag gagaacttct agtatatcta catacctaat attattgcct   2520
tattaaaaat ggaatcccaa caattacatc aaaatccaca ttctcttcaa aatcaattgt   2580
cctgtacttc cttgttcatg tgtgttcaaa aacgttatat ttataggata attatactct   2640
atttctcaac aagtaattgg ttgtttggcc gagcggtcta aggcgcctga ttcaagaaat   2700
atcttgaccg cagttaactg tgggaatact caggtatcgt aagatgcaag agttcgaatc   2760
tcttagcaac cattattttt ttcctcaaca taacgagaac acacaggggc gctatcgcac   2820
agaatcaaat tcgatgactg gaaatttttt gttaatttca gaggtcgcct gacgcatata   2880
ccttttttcaa ctgaaaaatt gggagaaaaa ggaaaggtga gagcgccgga accggctttt   2940
catatagaat agagaagcgt tcatgactaa atgcttgcat cacaatactt gaagttgaca   3000
atattattta aggacctatt gtttttttcca ataggtggtt agcaatcgtc ttactttcta   3060
acttttctta ccttttacat ttcagcaata tatatatata tatttcaagg atataccatt   3120
ctaatgtctg cccctaagaa gatcgtcgtt ttgccaggtg accacgttgg tcaagaaatc   3180
acagccgaag ccattaaggt tcttaaagct atttctgatg ttcgttccaa tgtcaagttc   3240
gatttcgaaa atcatttaat tggtggtgct gctatcgatg ctacaggtgt tccacttcca   3300
gatgaggcgc tggaagcctc caagaaggct gatgccgttt tgttaggtgc tgtgggtggt   3360
cctaaatggg gtaccggtag tgttagacct gaacaaggtt tactaaaaat ccgtaaagaa   3420
cttcaattgt acgccaactt aagaccatgt aactttgcat ccgactctct tttagactta   3480
tctccaatca agccacaatt tgctaaaggt actgacttcg ttgttgtcag agaattagtg   3540
ggaggtattt actttggtaa gagaaaggaa gacgatggtg atggtgtcgc ttgggatagt   3600
gaacaataca ccgttccaga agtgcaaaga atcacaagaa tggccgcttt catggcccta   3660
caacatgagc caccattgcc tatttggtcc ttggataaag ctaatgtttt ggcctcttca   3720
agattatgga gaaaaactgt ggaggaaacc atcaagaacg aattccctac attgaaggtt   3780
caacatcaat tgattgattc tgccgccatg atcctagtta agaacccaac ccacctaaat   3840
ggtattataa tcaccagcaa catgtttggt gatatcatct ccgatgaagc ctccgttatc   3900
ccaggttcct tgggtttgtt gccatctgcg tccttggcct ctttgccaga caagaacacc   3960
gcatttggtt tgtacgaacc atgccacggt tctgctccag atttgccaaa gaataaggtc   4020
aaccctatcg ccactatctt gtctgctgca atgatgttga aattgtcatt gaacttgcct   4080
```

```
gaagaaggta aggccattga agatgcagtt aaaaaggttt tggatgcagg tatcagaact   4140
ggtgatttag gtggttccaa cagtaccacc gaagtcggtg atgctgtcgc cgaagaagtt   4200
aagaaaatcc ttgcttaaaa agattctctt tttttatgat atttgtacat aaactttata   4260
aatgaaattc ataatagaaa cgacacgaaa ttacaaaatg gaatatgttc atagggtaga   4320
cgaaactata tacgcaatct acatacattt atcaagaagg agaaaaagga ggatgtaaag   4380
gaatacaggt aagcaaattg atactaatgg ctcaacgtga taaggaaaaa gaattgcact   4440
ttaacattaa tattgacaag gaggagggca ccacacaaaa agttaggtgt aacagaaaat   4500
catgaaactg gccggccgat gctgtccgcg ggcctcataa gagttgtggt aacaacgcag   4560
gtgcgcgcat ctgctaagtt taaacggtac cggcctcatg ggccttccgc tcactgcccg   4620
ctttccagtc gggaaacctg tcgtgccagc tgcattaaca tggtcatagc tgtttccttg   4680
cgtattgggc gctctccgct tcctcgctca ctgactcgct gcgctcggtc gttcgggtaa   4740
agcctggggt gcctaatgag caaaaggcca gcaaaaggcc aggaaccgta aaaaggccgc   4800
gttgctggcg tttttccata ggctccgccc ccctgacgag catcacaaaa atcgacgctc   4860
aagtcagagg tggcgaaacc cgacaggact ataaagatac caggcgtttc cccctggaag   4920
ctccctcgtg cgctctcctg ttccgaccct gccgcttacc ggatacctgt ccgcctttct   4980
cccttcggga agcgtggcgc tttctcatag ctcacgctgt aggtatctca gttcggtgta   5040
ggtcgttcgc tccaagctgg gctgtgtgca cgaacccccc gttcagcccg accgctgcgc   5100
cttatccggt aactatcgtc ttgagtccaa cccggtaaga cacgacttat cgccactggc   5160
agcagccact ggtaacagga ttagcagagc gaggtatgta ggcggtgcta cagagttctt   5220
gaagtggtgg cctaactacg gctacactag aagaacagta tttggtatct gcgctctgct   5280
gaagccagtt accttcggaa aaagagttgg tagctcttga tccggcaaac aaaccaccgc   5340
tggtagcggt ggtttttttg tttgcaagca gcagattacg cgcagaaaaa aaggatctca   5400
agaagatcct ttgatctttt ctacggggtc tgacgctcag tggaacgaaa actcacgtta   5460
agggattttg gtcatgagat tatcaaaaag gatcttcacc tagatccttt taaattaaaa   5520
atgaagtttt aaatcaatct aaagtatata tgagtaaact tggtctgaca gttaccaatg   5580
cttaatcagt gaggcaccta tctcagcgat ctgtctattt cgttcatcca tagttgcctg   5640
actccccgtc gtgtagataa ctacgatacg ggagggctta ccatctggcc ccagtgctgc   5700
aatgataccg cgagaaccac gctcaccggc tccagattta tcagcaataa accagccagc   5760
cggaagggcc gagcgcagaa gtggtcctgc aactttatcc gcctccatcc agtctattaa   5820
ttgttgccgg gaagctagag taagtagttc gccagttaat agtttgcgca acgttgttgc   5880
cattgctaca ggcatcgtgg tgtcacgctc gtcgtttggt atggcttcat tcagctccgg   5940
ttcccaacga tcaaggcgag ttacatgatc ccccatgttg tgcaaaaaag cggttagctc   6000
cttcggtcct ccgatcgttg tcagaagtaa gttggccgca gtgttatcac tcatggttat   6060
ggcagcactg cataattctc ttactgtcat gccatccgta agatgctttt ctgtgactgg   6120
tgagtactca accaagtcat tctgagaata gtgtatgcgg cgaccgagtt gctcttgccc   6180
ggcgtcaata cgggataata ccgcgccaca tagcagaact ttaaaagtgc tcatcattgg   6240
aaaacgttct tcggggcgaa aactctcaag gatcttaccg ctgttgagat ccagttcgat   6300
gtaacccact cgtgcaccca actgatcttc agcatctttt actttcacca gcgtttctgg   6360
gtgagcaaaa acaggaaggc aaaatgccgc aaaaaaggga ataagggcga cacggaaatg   6420
ttgaatactc atactcttcc tttttcaata ttattgaagc atttatcagg gttattgtct   6480
```

```
catgagcgga tacatatttg aatgtattta gaaaaataaa caaatagggg ttccgcgcac   6540
atttccccga aaagtgccac ctaaattgta agcgttaata ttttgttaaa attcgcgtta   6600
aatttttgtt aaatcagctc attttttaac caataggccg aaatcggcaa aatcccttat   6660
aaatcaaaag aatagaccga gatagggttg agtggccgct acagggcgct cccattcgcc   6720
attcaggctg cgcaactgtt gggaagggcg tttcggtgcg ggcctcttcg ctattacgcc   6780
agctggcgaa agggggatgt gctgcaaggc gattaagttg ggtaacgcca gggttttccc   6840
agtcacgacg ttgtaaaacg acggccagtg agcgcgacgt aatacgactc actatagggc   6900
gaattggcgg aaggccgtca aggccggtac cggtcctttt catcacgtgc tataaaaata   6960
attataattt aaatttttta atataaatat ataaattaaa aatagaaagt aaaaaaagaa   7020
attaaagaaa aaatagtttt tgttttccga agatgtaaaa gactctaggg ggatcgccaa   7080
caaatactac cttttatctt gctcttcctg ctctcaggta ttaatgccga attgtttcat   7140
cttgtctgtg tagaagacca cacacgaaaa tcctgtgatt ttacatttta cttatcgtta   7200
atcgaatgta tatctattta atctgctttt cttgtctaat aaatatatat gtaaagtacg   7260
ctttttgttg aaatttttta aacctttgtt tatttttttt tcttcattcc gtaactcttc   7320
taccttcttt atttactttc taaaatccaa atacaaaaca taaaaataaa taaacacaga   7380
gtaaattccc aaattattcc atcattaaaa gatacgaggc gcgtgtaagt tacaggcaag   7440
cgatccgtcc gtttaaacat gctttctgaa aacacgacta ttctgatggc taacggtgaa   7500
attaaagaca tcgcaaacgg cgcgccgatt tttataatga cgaaaaaaaa aaaattggaa   7560
agaaaaagct taatgcggta gtttatcaca gttaaattgc taacgcagtc aggcaccgtg   7620
tatgaaatct aacaatgcgc tcatcgtcat cctcggcacc gtcaccctgg atgctgtagg   7680
cataggcttg gttatgccgg tactgccggg cctcttgcgg gatatcgtcc attccgacag   7740
catcgccagt cactatggcg tgctgctagc gctatatgcg ttgatgcaat ttctatgcgc   7800
acccgttctc ggagcactgt ccgaccgctt tggccgccgc ccagtcctgc tcgcttcgct   7860
acttggagcc actatcgact acgcgatcat ggcgaccaca cccgtcctgt ggatcctcta   7920
cgccggacgc atcgtggccg gcatcaccgg cgccacaggt gcggttgctg gcgcctatat   7980
cgccgacatc accgatgggg aagatcgggc tcgccacttc gggctcatga gcgcttgttt   8040
cggcgtgggt atggtggcag gccccgtggc cgggggactg ttgggcgcca tctccttgca   8100
tgcaacttct ttcttttttt tttcttttct ctctcccccg ttgttgtctc accatatccg   8160
caatgacaaa aaaatgatgg aagacactaa aggaaaaaat taacgacaaa gacagcacca   8220
acagatgtcg ttgttccaga gctgatgagg ggtatctcga agcacacgaa actttttcct   8280
tccttcattc acgcacacta ctctctaatg agcaacggta tacggccttc cttccagtta   8340
cttgaatttg aaataaaaaa aagtttgctg tcttgctatc aagtataaat agacctgcaa   8400
ttattaatct tttgtttcct cgtcattgtt ctcgttccct ttcttccttg tttctttttc   8460
tgcacaatat ttcaagctat accaagcata caatcaagga attcgagcta agcggccgcc   8520
catggaagct gcaatcaaat cactggtagc aatcttaaga caagaactga cgaacttccg   8580
tatcagttgt gtttatcctg gtaattttga aagcgaaggt ttcactgtag agcagctaac   8640
gaaacccgaa attacaaagt tgatcgaagg cccctcagac gctatcccat gcaaacaagc   8700
atgtgatatc attgccaagt cgctggccag aggtgatgat gacgttttta cagattttgt   8760
cggatggatg ataatgggga tggaccttgg gctcaccgca aagaaaagcc gctttgttcc   8820
```

```
gttgcaatgg atttttggtg tcctatcaaa cattctggtc gtgccattct acacgcgtgt   8880

tattactgag tagtatttat ttaagtattg tttgtgcact tgcctgcagg ccttttgaaa   8940

agcaagcata aaagatctaa acataaaatc tgtaaaataa caagatgtaa agataatgct   9000

aaatcatttg gctttttgat tgattgtaca ggaaaatata catcgcaggg ggttgacttt   9060

taccatttca ccgcaatgga atcaaacttg ttgaagagaa tgttcacagg cgcatacgct   9120

acaatgaccc gattcttgct agccttttct cggtcttgca aacaaccgcc ggcagcttct   9180

cgagccgcgg aaccgccaga tattcattac ttgacgcaaa agcgtttgaa ataatgacga   9240

aaaagaagga agaaaaaaaa agaaaaatac cgcttctagg cgggttatct actgatccga   9300

gcttccacta ggatagcacc caaacacctg catatttgga cgacctttac ttacaccacc   9360

aaaaaccact ttcgcctctc ccgcccctga taacgtccac taattgagcg attacctgag   9420

cggtcctctt ttgtttgcag catgagactt gcatactgca aatcgtaagt agcaacgtct   9480

caaggtcaaa actgtatgga aaccttgtca cctcacttaa ttctagctag cctaccctgc   9540

aagtcaagag gtctccgtga ttcctagcca cctcaaggta tgcctctccc cggaaactgt   9600

ggccttttct ggcacacatg atctccacga tttcaacata taaatagctt ttgataatgg   9660

caatattaat caaatttatt ttacttcttt cttgtaacat ctctcttgta atcccttatt   9720

ccttctagct atttttcata aaaaaccaag caactgctta tcaacacaca aacactaaat   9780

caaaatgcat tcgcgaatat ctagaataca cgtcatagaa tgcgacgtca gcttttgatt   9840

aagccttcta gtccaaaaaa cacgtttttt tgtcatttat ttcattttct tagaatagtt   9900

tagtttattc attttatagt cacgaatgtt ttatgattct atatagggtt gcaaacaagc   9960

atttttcatt ttatgttaaa acaatttcag gtttaccttt tattctgctt gtggtgacgc  10020

gggtatccgc ccgctctttt ggtcacccat gtatttaatt gcataaataa ttcttaaaag  10080

tggagctagt ctatttctat ttacatacct ctcatttctc atttc                  10125
```

<210> SEQ ID NO 63
<211> LENGTH: 2017
<212> TYPE: DNA
<213> ORGANISM: Artificial
<220> FEATURE:
<223> OTHER INFORMATION: Synthetic fragment comprising hmfL1 coding sequence

<400> SEQUENCE: 63

```
tgcaggcgcg cctgcggtag tttatcacag ttaaattgct aacgcagtca ggcaccgtgt     60

atgaaatcta acaatgcgct catcgtcatc ctcggcaccg tcaccctgga tgctgtaggc    120

ataggcttgg ttatgccggt actgccgggc ctcttgcggg atatcgtcca ttccgacagc    180

atcgccagtc actatggcgt gctgctagcg ctatatgcgt tgatgcaatt tctatgcgca    240

cccgttctcg gagcactgtc cgaccgcttt ggccgccgcc cagtcctgct cgcttcgcta    300

cttggagcca ctatcgacta cgcgatcatg gcgaccacac ccgtcctgtg gatcctctac    360

gccggacgca tcgtggccgg catcaccggc gccacaggtg cggttgctgg cgcctatatc    420

gccgacatca ccgatgggga agatcgggct cgccacttcg ggctcatgag cgcttgtttc    480

ggcgtgggta tggtggcagg ccccgtggcc gggggactgt tgggcgccat ctccttgcat    540

gcaacttctt ttcttttttt ttcttttctc tctcccccgt tgttgtctca ccatatccgc    600

aatgacaaaa aaatgatgga agacactaaa ggaaaaaatt aacgacaaag acagcaccaa    660

cagatgtcgt tgttccagag ctgatgaggg gtatctcgaa gcacacgaaa ctttttcctt    720
```

ccttcattca cgcacactac tctctaatga gcaacggtat acggccttcc ttccagttac 780
ttgaatttga aataaaaaaa agtttgctgt cttgctatca agtataaata gacctgcaat 840
tattaatctt ttgtttcctc gtcattgttc tcgttccctt tcttccttgt ttcttttttct 900 gcacaatatt tcaagctata ccaagcatac aatcaactat ctcatacaaa aatgggttcc 960
ttatccttac cagaaacatc attagccgca atccaagaca aagaaacaaa agctatctca 1020
gtcgccaaaa gacctacacc agtacctgtt ggtacccaag tcttagtaaa attgcattat 1080
tccggtgttt gtgccactga tttgcactta gctagaggtt ctgttccata cttacaacct 1140
aaggtttcag tcggtggtca tgaaggtacc ggtgttattg cttctttggg tccagatgtc 1200
gacgcagcag aatggcatgt aggtgacaga gtagcagtta gatgggtaca catagtttgt 1260
ggtaaatgcg aagtttgtac tacaggtttc gaaaatttgt gccaatctag aaagttggct 1320
ggtaaagatg ttgaaggtac tttcgccgaa tatgcaattg ccgactcttc atacatggtt 1380
agattaccag ctggtgtctc agatgcagac gccgctccta tcttgtgtgc tggtgtcaca 1440
gtatacaaag ccttgaagat cgcttctttg agagcaggtt catgggttgc tgtcgcaggt 1500
gctggtggtg gtttaggtca tttggcaatc caatatgcta gagcaatggg tttaaaagtt 1560
gtcgcattgg atgccagaaa gagagacttg tgcttatcct tgggtgctga aagttacatc 1620
gacgttttag aaactgatga ctgtgtcgca caagtaatta aagttacaga tggtggtgct 1680
cacggtgcat taatatgcgc ttccagtggt caagcctacg atgacgctgt taaatttttg 1740
agatggaccg gtactttagt ctgtataggt ttgccaccta agccaacatt gttatcctta 1800
ggtcctgctg attttgtagc cagaggtatc aaggttatgg gtacaagtac cggtgacaga 1860
caagacacag ttgaagcctt ggctttcgtc gctaaaggtc aagtaaagcc tcaattaacc 1920
gaaagaagat tggaagatgt tgaagaaatc ttaaaggaaa tagaaaatgg tacaatgcaa 1980
ggtaaagccg taatcagaat cgcatagacg cgttgca 2017

<210> SEQ ID NO 64
<211> LENGTH: 10774
<212> TYPE: DNA
<213> ORGANISM: Artificial
<220> FEATURE:
<223> OTHER INFORMATION: pTT2-hmfLN1-hmfL1

<400> SEQUENCE: 64
cgcgtgttat tactgagtag tatttattta agtattgttt gtgcacttgc ctgcaggcct 60
tttgaaaagc aagcataaaa gatctaaaca taaaatctgt aaaataacaa gatgtaaaga 120
taatgctaaa tcatttggct ttttgattga ttgtacagga aaatatacat cgcagggggt 180
tgacttttac catttcaccg caatggaatc aaacttgttg aagagaatgt tcacaggcgc 240
atacgctaca atgacccgat tcttgctagc cttttctcgg tcttgcaaac aaccgccggc 300
agcttctcga gccgcggaac cgccagatat tcattacttg acgcaaaagc gtttgaaata 360
atgacgaaaa agaaggaaga aaaaaaaaga aaaataccgc ttctaggcgg gttatctact 420
gatccgagct tccactagga tagcacccaa acacctgcat atttggacga cctttactta 480
caccaccaaa aaccactttc gcctctcccg cccctgataa cgtccactaa ttgagcgatt 540
acctgagcgg tcctcttttg tttgcagcat gagacttgca tactgcaaat cgtaagtagc 600
aacgtctcaa ggtcaaaact gtatggaaac cttgtcacct cacttaattc tagctagcct 660
accctgcaag tcaagaggtc tccgtgattc ctagccacct caaggtatgc ctctccccgg 720
aaactgtggc cttttctggc acacatgatc tccacgattt caacatataa atagcttttg 780

```
ataatggcaa tattaatcaa atttatttta cttctttctt gtaacatctc tcttgtaatc    840
ccttattcct tctagctatt tttcataaaa aaccaagcaa ctgcttatca acacacaaac    900
actaaatcaa aatgcattcg cgaatatcta gaatacacgt catagaatgc gacgtcagct    960
tttgattaag ccttctagtc caaaaaacac gtttttttgt catttatttc attttcttag   1020
aatagtttag tttattcatt ttatagtcac gaatgtttta tgattctata tagggttgca   1080
aacaagcatt tttcatttta tgttaaaaca atttcaggtt taccttttat tctgcttgtg   1140
gtgacgcggg tatccgcccg ctcttttggt cacccatgta tttaattgca taaataattc   1200
ttaaaagtgg agctagtcta tttctattta catacctctc atttctcatt tcctccccg   1260
ggttagtcaa aaaattagcc ttttaattct gctgtaaccc gtacatgccc aaaatagggg   1320
gcgggttaca cagaatatat aacatcgtag gtgtctgggt gaacagttta ttcctggcat   1380
ccactaaata taatggagcc cgctttttaa gctggcatcc agaaaaaaaa agaatcccag   1440
caccaaaata ttgttttctt caccaaccat cagttcatag gtccattctc ttagcgcaac   1500
tacagagaac aggggcacaa acaggcaaaa aacgggcaca acctcaatgg agtgatgcaa   1560
cctgcctgga gtaaatgatg acacaaggca attgacccac gcatgtatct atctcatttt   1620
cttacacctt ctattacctt ctgctctctc tgatttggaa aaagctgaaa aaaaaggttg   1680
aaaccagttc cctgaaatta ttcccctact tgactaataa gtatataaag acggtaggta   1740
ttgattgtaa ttctgtaaat ctatttctta aacttcttaa attctacttt tatagttagt   1800
cttttttttta gttttaaaac accaagaact tagtttcgaa taaacacaca taaacaaaca   1860
aaaatgaccc aaaccaatgt ccacgtaaac aaatccgaca cttccttagc tgctccacaa   1920
caattattca tctccggtaa atatcaaaac tctcaaagaa atggtacatt tccagtcaaa   1980
aaccctatga ctggtgaaac aatctatgaa tgtgtttctg catcattaga tgactacgct   2040
gctgctatag aagaagctga tgccgcacaa ccatcatggg ctagattagg tccttccgca   2100
agaagattga ttttgttaaa ggccgctgat ataatggaaa catacatcga aaccgacgct   2160
ccagcaatct tgagtgctga agtttctgca acaagaggtt gggtcagagc caatatatta   2220
tctaccgctg gtgttttcag agaaactgct gctttggcaa cacatatcaa aggtgaaatt   2280
gttccagctg atagacctgg tactacaatc ttagtttcaa gagaaccagt cggtgttgtc   2340
ttggctattt ccccttggaa tatgcctgca accttaactg ccagagctat ctgttgccct   2400
ttaatttgtg gtaactctgt agttttaaga ccatccgaat tttctcctaa atctcaacat   2460
ttggtcgtaa gagccttaac agaagctggt ttgccagcag gttgcttgca attcttacca   2520
acatcaaccg cagatacccc tagagccata gaatttgcta tcagacaccc taaggttagt   2580
agagctaatt tcactggttc tgatagagtc ggtagaatta tagcaggttt atccgccagt   2640
tgtttgaaac catgcgtttt ggaattgggt ggtaaagccc ctgttgtcgt attagaagat   2700
gctgatgtcg aagctgctgt tgaagcagtt gtctacggtg ccatgtctaa ctcaggtcaa   2760
atttgtatga gtacagaaag agctatagtt catagatcat tggccgctga ttttaaagca   2820
ttgttagtaa agagagccga atcattaaga gttggtaatc acttggaaga tccagacgtt   2880
caattgtcag gtttgtttac tgctgcttcc gcagaaagag tcttgggttt gattaaaggt   2940
gctgtaaacg caggtgccac cttgttagct ggtgacttgg cattacatgg tccatgccaa   3000
actataatgg ctcctcacat cttaaccggt gttactagag atatggactt gtttcataga   3060
gaaacattcg gtccagtatt gttcgttagt gaatttgata ctgatgacga agctatagca   3120
```

-continued caagccaatg acacagaatt ttctttatgt gcttcagtat tctccagaga tgttttgaga 3180
gctatggata ccgctaagag aataagaact ggttcatgcc acgtcaatgg tcctactgta 3240
tatatcgaag caccattgcc taacggtggt gttggtggtg gttctggtta cggtagattt 3300
ggtggtgttg ctggtattga agagtttaca gaaagacaaa tagttagttt agccaagcca 3360
ggtatcaagt atgcctttta gactagtgtg aatttacttt aaatcttgca tttaaataaa 3420
ttttcttttt atagctttat gacttagttt caatttatat actattttaa tgacattttc 3480
gattcattga ttgaaagctt tgtgtttttt cttgatgcgc tattgcattg ttcttgtctt 3540
tttcgccaca tgtaatatct gtagtagata cctgatacat tgtggatgct gagtgaaatt 3600
ttagttaata atggaggcgc tcttaataat tttggggata ttggcttttt tttttaaagt 3660
ttacaaatga attttttccg ccaggattta attaattgca gattcccttt tatggattcc 3720
taaatcctcg aggagaactt ctagtatatc tacataccta atattattgc cttattaaaa 3780
atggaatccc aacaattaca tcaaaatcca cattctcttc aaaatcaatt gtcctgtact 3840
tccttgttca tgtgtgttca aaaacgttat atttatagga taattatact ctatttctca 3900
acaagtaatt ggttgtttgg ccgagcggtc taaggcgcct gattcaagaa atatcttgac 3960
cgcagttaac tgtgggaata ctcaggtatc gtaagatgca agagttcgaa tctcttagca 4020
accattattt ttttcctcaa cataacgaga acacacaggg gcgctatcgc acagaatcaa 4080
attcgatgac tggaaatttt ttgttaattt cagaggtcgc ctgacgcata tacctttttc 4140
aactgaaaaa ttgggagaaa aaggaaaggt gagagcgccg gaaccggctt ttcatataga 4200
atagagaagc gttcatgact aaatgcttgc atcacaatac ttgaagttga caatattatt 4260
taaggaccta ttgtttttc caataggtgg ttagcaatcg tcttactttc taacttttct 4320
taccttttac atttcagcaa tatatatata tatatttcaa ggatatacca ttctaatgtc 4380
tgcccctaag aagatcgtcg ttttgccagg tgaccacgtt ggtcaagaaa tcacagccga 4440
agccattaag gttcttaaag ctatttctga tgttcgttcc aatgtcaagt tcgatttcga 4500
aaatcattta attggtggtg ctgctatcga tgctacaggt gttccacttc cagatgaggc 4560
gctggaagcc tccaagaagg ctgatgccgt tttgttaggt gctgtgggtg gtcctaaatg 4620
gggtaccggt agtgttagac ctgaacaagg tttactaaaa atccgtaaag aacttcaatt 4680
gtacgccaac ttaagaccat gtaactttgc atccgactct cttttagact tatctccaat 4740
caagccacaa tttgctaaag gtactgactt cgttgttgtc agagaattag tgggaggtat 4800
ttactttggt aagagaaagg aagacgatgg tgatggtgtc gcttgggata gtgaacaata 4860
caccgttcca gaagtgcaaa gaatcacaag aatggccgct ttcatggccc tacaacatga 4920
gccaccattg cctatttggt ccttggataa agctaatgtt ttggcctctt caagattatg 4980
gagaaaaact gtggaggaaa ccatcaagaa cgaattccct acattgaagg ttcaacatca 5040
attgattgat tctgccgcca tgatcctagt taagaaccca acccacctaa atggtattat 5100
aatcaccagc aacatgtttg gtgatatcat ctccgatgaa gcctccgtta tcccaggttc 5160
cttgggtttg ttgccatctg cgtccttggc ctctttgcca gacaagaaca ccgcatttgg 5220
tttgtacgaa ccatgccacg gttctgctcc agatttgcca aagaataagg tcaaccctat 5280
cgccactatc ttgtctgctg caatgatgtt gaaattgtca ttgaacttgc ctgaagaagg 5340
taaggccatt gaagatgcag ttaaaaaggt tttggatgca ggtatcagaa ctggtgattt 5400
aggtggttcc aacagtacca ccgaagtcgg tgatgctgtc gccgaagaag ttaagaaaat 5460
ccttgcttaa aaagattctc ttttttatg atatttgtac ataaacttta taaatgaaat 5520

```
tcataataga aacgacacga aattacaaaa tggaatatgt tcatagggta gacgaaacta   5580
tatacgcaat ctacatacat ttatcaagaa ggagaaaaag gaggatgtaa aggaatacag   5640
gtaagcaaat tgatactaat ggctcaacgt gataaggaaa aagaattgca ctttaacatt   5700
aatattgaca aggaggaggg caccacacaa aaagttaggt gtaacagaaa atcatgaaac   5760
tggccggccg atgctgtccg cgggcctcat aagagttgtg gtaacaacgc aggtgcgcgc   5820
atctgctaag tttaaacggt accggcctca tgggccttcc gctcactgcc cgctttccag   5880
tcgggaaacc tgtcgtgcca gctgcattaa catggtcata gctgtttcct tgcgtattgg   5940
gcgctctccg cttcctcgct cactgactcg ctgcgctcgg tcgttcgggt aaagcctggg   6000
gtgcctaatg agcaaaaggc cagcaaaagg ccaggaaccg taaaaaggcc gcgttgctgg   6060
cgtttttcca taggctccgc ccccctgacg agcatcacaa aaatcgacgc tcaagtcaga   6120
ggtggcgaaa cccgacagga ctataaagat accaggcgtt tccccctgga agctccctcg   6180
tgcgctctcc tgttccgacc ctgccgctta ccggatacct gtccgccttt ctcccttcgg   6240
gaagcgtggc gctttctcat agctcacgct gtaggtatct cagttcggtg taggtcgttc   6300
gctccaagct gggctgtgtg cacgaacccc ccgttcagcc cgaccgctgc gccttatccg   6360
gtaactatcg tcttgagtcc aacccggtaa gacacgactt atcgccactg gcagcagcca   6420
ctggtaacag gattagcaga gcgaggtatg taggcggtgc tacagagttc ttgaagtggt   6480
ggcctaacta cggctacact agaagaacag tatttggtat ctgcgctctg ctgaagccag   6540
ttaccttcgg aaaaagagtt ggtagctctt gatccggcaa acaaaccacc gctggtagcg   6600
gtggtttttt tgtttgcaag cagcagatta cgcgcagaaa aaaaggatct caagaagatc   6660
ctttgatctt ttctacgggg tctgacgctc agtggaacga aaactcacgt taagggattt   6720
tggtcatgag attatcaaaa aggatcttca cctagatcct tttaaattaa aaatgaagtt   6780
ttaaatcaat ctaaagtata tatgagtaaa cttggtctga cagttaccaa tgcttaatca   6840
gtgaggcacc tatctcagcg atctgtctat ttcgttcatc catagttgcc tgactccccg   6900
tcgtgtagat aactacgata cgggagggct taccatctgg ccccagtgct gcaatgatac   6960
cgcgagaacc acgctcaccg gctccagatt tatcagcaat aaaccagcca gccggaaggg   7020
ccgagcgcag aagtggtcct gcaactttat ccgcctccat ccagtctatt aattgttgcc   7080
gggaagctag agtaagtagt tcgccagtta atagtttgcg caacgttgtt gccattgcta   7140
caggcatcgt ggtgtcacgc tcgtcgtttg gtatggcttc attcagctcc ggttcccaac   7200
gatcaaggcg agttacatga tcccccatgt tgtgcaaaaa agcggttagc tccttcggtc   7260
ctccgatcgt tgtcagaagt aagttggccg cagtgttatc actcatggtt atggcagcac   7320
tgcataattc tcttactgtc atgccatccg taagatgctt ttctgtgact ggtgagtact   7380
caaccaagtc attctgagaa tagtgtatgc ggcgaccgag ttgctcttgc ccggcgtcaa   7440
tacgggataa taccgcgcca catagcagaa ctttaaaagt gctcatcatt ggaaaacgtt   7500
cttcggggcg aaaactctca aggatcttac cgctgttgag atccagttcg atgtaaccca   7560
ctcgtgcacc caactgatct tcagcatctt ttactttcac cagcgtttct gggtgagcaa   7620
aaacaggaag gcaaaatgcc gcaaaaaagg gaataagggc gacacggaaa tgttgaatac   7680
tcatactctt cctttttcaa tattattgaa gcatttatca gggttattgt ctcatgagcg   7740
gatacatatt tgaatgtatt tagaaaaata aacaaatagg ggttccgcgc acatttcccc   7800
gaaaagtgcc acctaaattg taagcgttaa tattttgtta aaattcgcgt taaatttttg   7860
```

-continued

```
ttaaatcagc tcatttttta accaataggc cgaaatcggc aaaatccctt ataaatcaaa   7920
agaatagacc gagatagggt tgagtggccg ctacagggcg ctcccattcg ccattcaggc   7980
tgcgcaactg ttgggaaggg cgtttcggtg cgggcctctt cgctattacg ccagctggcg   8040
aaagggggat gtgctgcaag gcgattaagt tgggtaacgc cagggttttc ccagtcacga   8100
cgttgtaaaa cgacggccag tgagcgcgac gtaatacgac tcactatagg gcgaattggc   8160
ggaaggccgt caaggccggt accggtcctt ttcatcacgt gctataaaaa taattataat   8220
ttaaattttt taatataaat atataaatta aaaatagaaa gtaaaaaaag aaattaaaga   8280
aaaaatagtt tttgttttcc gaagatgtaa aagactctag ggggatcgcc aacaaatact   8340
accttttatc ttgctcttcc tgctctcagg tattaatgcc gaattgtttc atcttgtctg   8400
tgtagaagac cacacacgaa aatcctgtga ttttacattt tacttatcgt taatcgaatg   8460
tatatctatt taatctgctt ttcttgtcta ataaatatat atgtaaagta cgctttttgt   8520
tgaaattttt taaacctttg tttatttttt tttcttcatt ccgtaactct tctaccttct   8580
ttatttactt tctaaaatcc aaatacaaaa cataaaaata aataaacaca gagtaaattc   8640
ccaaattatt ccatcattaa aagatacgag gcgcgtgtaa gttacaggca agcgatccgt   8700
ccgtttaaac atgctttctg aaaacacgac tattctgatg gctaacggtg aaattaaaga   8760
catcgcaaac ggcgcgcctg cggtagttta tcacagttaa attgctaacg cagtcaggca   8820
ccgtgtatga aatctaacaa tgcgctcatc gtcatcctcg gcaccgtcac cctggatgct   8880
gtaggcatag gcttggttat gccggtactg ccgggcctct tgcgggatat cgtccattcc   8940
gacagcatcg ccagtcacta tggcgtgctg ctagcgctat atgcgttgat gcaatttcta   9000
tgcgcacccg ttctcggagc actgtccgac cgctttggcc gccgcccagt cctgctcgct   9060
tcgctacttg gagccactat cgactacgcg atcatggcga ccacacccgt cctgtggatc   9120
ctctacgccg gacgcatcgt ggccggcatc accggcgcca caggtgcggt tgctggcgcc   9180
tatatcgccg acatcaccga tggggaagat cgggctcgcc acttcgggct catgagcgct   9240
tgtttcggcg tgggtatggt ggcaggcccc gtggccgggg gactgttggg cgccatctcc   9300
ttgcatgcaa cttcttttct tttttttct tttctctctc cccgttgtt gtctcaccat   9360
atccgcaatg acaaaaaaat gatggaagac actaaaggaa aaaattaacg acaaagacag   9420
caccaacaga tgtcgttgtt ccagagctga tgaggggtat ctcgaagcac acgaaacttt   9480
ttccttcctt cattcacgca cactactctc taatgagcaa cggtatacgg ccttccttcc   9540
agttacttga atttgaaata aaaaaaagtt tgctgtcttg ctatcaagta taaatagacc   9600
tgcaattatt aatcttttgt ttcctcgtca ttgttctcgt tccctttctt ccttgtttct   9660
ttttctgcac aatatttcaa gctataccaa gcatacaatc aactatctca tacaaaaatg   9720
ggttccttat ccttaccaga aacatcatta gccgcaatcc aagacaaaga aacaaaagct   9780
atctcagtcg ccaaaagacc tacaccagta cctgttggta cccaagtctt agtaaaattg   9840
cattattccg gtgtttgtgc cactgatttg cacttagcta gaggttctgt tccatactta   9900
caacctaagg tttcagtcgg tggtcatgaa ggtaccggtg ttattgcttc tttgggtcca   9960
gatgtcgacg cagcagaatg gcatgtaggt gacagagtag cagttagatg ggtacacata  10020
gtttgtggta aatgcgaagt ttgtactaca ggtttcgaaa atttgtgcca atctagaaag  10080
ttggctggta aagatgttga aggtactttc gccgaatatg caattgccga ctcttcatac  10140
atggttagat taccagctgg tgtctcagat gcagacgccg ctcctatctt gtgtgctggt  10200
gtcacagtat acaaagcctt gaagatcgct tctttgagag caggttcatg ggttgctgtc  10260
```

```
gcaggtgctg gtggtggttt aggtcatttg gcaatccaat atgctagagc aatgggttta  10320

aaagttgtcg cattggatgc cagaaagaga gacttgtgct tatccttggg tgctgaaagt  10380

tacatcgacg ttttagaaac tgatgactgt gtcgcacaag taattaaagt tacagatggt  10440

ggtgctcacg gtgcattaat atgcgcttcc agtggtcaag cctacgatga cgctgttaaa  10500

tttttgagat ggaccggtac tttagtctgt ataggtttgc cacctaagcc aacattgtta  10560

tccttaggtc ctgctgattt tgtagccaga ggtatcaagg ttatgggtac aagtaccggt  10620

gacagacaag acacagttga agccttggct ttcgtcgcta aaggtcaagt aaagcctcaa  10680

ttaaccgaaa gaagattgga agatgttgaa gaaatcttaa aggaaataga aaatggtaca  10740

atgcaaggta aagccgtaat cagaatcgca taga                              10774
```

```
<210> SEQ ID NO 65
<211> LENGTH: 1648
<212> TYPE: DNA
<213> ORGANISM: Artificial
<220> FEATURE:
<223> OTHER INFORMATION: synthetic DNA comprising hmfL2 coding sequence
      for expression in yeast

<400> SEQUENCE: 65

gccggcagct tctcgagccg cggaaccgcc agatattcat tacttgacgc aaaagcgttt    60

gaaataatga cgaaaaagaa ggaagaaaaa aaaagaaaaa taccgcttct aggcgggtta   120

tctactgatc cgagcttcca ctaggatagc acccaaacac ctgcatattt ggacgacctt   180

tacttacacc accaaaaacc actttcgcct ctcccgcccc tgataacgtc cactaattga   240

gcgattacct gagcggtcct cttttgtttg cagcatgaga cttgcatact gcaaatcgta   300

agtagcaacg tctcaaggtc aaaactgtat ggaaaccttg tcacctcact taattctagc   360

tagcctaccc tgcaagtcaa gaggtctccg tgattcctag ccacctcaag gtatgcctct   420

ccccggaaac tgtggccttt tctggcacac atgatctcca cgatttcaac atataaatag   480

cttttgataa tggcaatatt aatcaaattt attttacttc tttcttgtaa catctctctt   540

gtaatccctt attccttcta gctatttttc ataaaaaacc aagcaactgc ttatcaacac   600

acaaacacta aatcaaaaat gagtttgcca tcccactaca agagagccgc ttttaaggaa   660

gcaggtggtc cattgactat tgaagaagtt gatttgacta tgccagatgc cggtgaagtc   720

ttggtaaaag ttgaagcttg tggtgtatgc ttttcagaca ctgttcctca agctcatggt   780

ttgggtggta aattcccaat cgttcctggt catgaaatta taggtcacgt tgtcgcaaca   840

ggtgacggtg tttccgactg ggaagtcggt gacagaattg gtgaaggttg gcatggtggt   900

cacgacggta catgtccatc atgcagacaa ggtcatttcc aaatgtgtga taaccaatcc   960

ataaacggtg ttaccaaaaa tggtggttat gctcaatact gcattttgag aagtgaagca  1020

gcagtcagaa tacctactca cgtatctgcc gctgaatatg caccaatttt atgtgccggt  1080

gtcaccgttt ttaattcaat gagacaaatc ggtgttaagc ctggttccac tgtcgcaatt  1140

caaggtttgg gtggtttagg tcatttggcc attcaatatg ctaacagatt tggtttcaga  1200

gtagttgcta tatctagaga tgaccaaaag gaaagattcg ttagagattt gggtgcacac  1260

gaatacatta atacatctga agaagatgtc ggttcagctt tacaaaagtt gggtggtgca  1320

agtttaatag ttgcaaccgc cccaaacgct agagcaatct ctcctttgtt aaaaggttta  1380

agaccattgg gtaaattgtt gatcttggct gttccaggtg aaatcccttt agataccaga  1440

ttgatggtag caagaggttt atccgttcat ggttggccaa gtggtcacgc cttggattct  1500
```

```
gaagaaacta taagattcac agaattagaa gatatcaagt gtatgataca aacttactca   1560

ttagacagag ctaacgaagc ctttgacgct atgatttcag gttcagttag attcagagca   1620

gttattacaa tggaatagga cgtcagct                                       1648


<210> SEQ ID NO 66
<211> LENGTH: 11107
<212> TYPE: DNA
<213> ORGANISM: Artificial
<220> FEATURE:
<223> OTHER INFORMATION: pTT2-hmfN1-hmfL2

<400> SEQUENCE: 66

aggtcaaaac tgtatggaaa ccttgtcacc tcacttaatt ctagctagcc taccctgcaa     60

gtcaagaggt ctccgtgatt cctagccacc tcaaggtatg cctctccccg gaaactgtgg    120

ccttttctgg cacacatgat ctccacgatt tcaacatata aatagctttt gataatggca    180

atattaatca aatttatttt acttctttct tgtaacatct ctcttgtaat cccttattcc    240

ttctagctat ttttcataaa aaaccaagca actgcttatc aacacacaaa cactaaatca    300

aaaatgagtt tgccatccca ctacaagaga gccgctttta aggaagcagg tggtccattg    360

actattgaag aagttgattt gactatgcca gatgccggtg aagtcttggt aaaagttgaa    420

gcttgtggtg tatgcttttc agacactgtt cctcaagctc atggtttggg tggtaaattc    480

ccaatcgttc ctggtcatga aattataggt cacgttgtcg caacaggtga cggtgtttcc    540

gactgggaag tcggtgacag aattggtgaa ggttggcatg gtggtcacga cggtacatgt    600

ccatcatgca gacaaggtca tttccaaatg tgtgataacc aatccataaa cggtgttacc    660

aaaaatggtg gttatgctca atactgcatt ttgagaagtg aagcagcagt cagaatacct    720

actcacgtat ctgccgctga atatgcacca attttatgtg ccggtgtcac cgtttttaat    780

tcaatgagac aaatcggtgt taagcctggt tccactgtcg caattcaagg tttgggtggt    840

ttaggtcatt tggccattca atatgctaac agatttggtt tcagagtagt tgctatatct    900

agagatgacc aaaaggaaag attcgttaga gatttgggtg cacacgaata cattaataca    960

tctgaagaag atgtcggttc agctttacaa aagttgggtg gtgcaagttt aatagttgca   1020

accgccccaa acgctagagc aatctctcct ttgttaaaag gtttaagacc attgggtaaa   1080

ttgttgatct tggctgttcc aggtgaaatc cctttagata ccagattgat ggtagcaaga   1140

ggtttatccg ttcatggttg gccaagtggt cacgccttgg attctgaaga aactataaga   1200

ttcacagaat tagaagatat caagtgtatg atacaaactt actcattaga cagagctaac   1260

gaagcctttg acgctatgat ttcaggttca gttagattca gagcagttat tacaatggaa   1320

taggacgtca gcttttgatt aagccttcta gtccaaaaaa cacgtttttt tgtcatttat   1380

ttcattttct tagaatagtt tagtttattc attttatagt cacgaatgtt ttatgattct   1440

atatagggtt gcaaacaagc atttttcatt ttatgttaaa acaatttcag gtttaccttt   1500

tattctgctt gtggtgacgc gggtatccgc ccgctctttt ggtcacccat gtatttaatt   1560

gcataaataa ttcttaaaag tggagctagt ctatttctat ttacatacct ctcatttctc   1620

atttcctccc ccgggttagt caaaaaatta gccttttaat tctgctgtaa cccgtacatg   1680

cccaaaatag ggggcgggtt acacagaata tataacatcg taggtgtctg ggtgaacagt   1740

ttattcctgg catccactaa atataatgga gcccgctttt taagctggca tccagaaaaa   1800

aaaagaatcc cagcaccaaa atattgtttt cttcaccaac catcagttca taggtccatt   1860
```

```
ctcttagcgc aactacagag aacaggggca caaacaggca aaaaacgggc acaacctcaa   1920
tggagtgatg caacctgcct ggagtaaatg atgacacaag gcaattgacc cacgcatgta   1980
tctatctcat tttcttacac cttctattac cttctgctct ctctgatttg gaaaaagctg   2040
aaaaaaaagg ttgaaaccag ttccctgaaa ttattcccct acttgactaa taagtatata   2100
aagacggtag gtattgattg taattctgta aatctatttc ttaaacttct taaattctac   2160
ttttatagtt agtctttttt ttagttttaa aacaccaaga acttagtttc gaataaacac   2220
acataaacaa acaaaaatga cccaaaccaa tgtccacgta aacaaatccg acacttcctt   2280
agctgctcca caacaattat tcatctccgg taaatatcaa aactctcaaa gaaatggtac   2340
atttccagtc aaaaacccta tgactggtga aacaatctat gaatgtgttt ctgcatcatt   2400
agatgactac gctgctgcta tagaagaagc tgatgccgca caaccatcat gggctagatt   2460
aggtccttcc gcaagaagat tgattttgtt aaaggccgct gatataatgg aaacatacat   2520
cgaaaccgac gctccagcaa tcttgagtgc tgaagtttct gcaacaagag gttgggtcag   2580
agccaatata ttatctaccg ctggtgtttt cagagaaact gctgctttgg caacacatat   2640
caaaggtgaa attgttccag ctgatagacc tggtactaca atcttagttt caagagaacc   2700
agtcggtgtt gtcttggcta tttccccttg gaatatgcct gcaaccttaa ctgccagagc   2760
tatctgttgc cctttaattt gtggtaactc tgtagtttta agaccatccg aattttctcc   2820
taaatctcaa catttggtcg taagagcctt aacagaagct ggtttgccag caggttgctt   2880
gcaattctta ccaacatcaa ccgcagatac ccctagagcc atagaatttg ctatcagaca   2940
ccctaaggtt agtagagcta atttcactgg ttctgataga gtcggtagaa ttatagcagg   3000
tttatccgcc agttgtttga aaccatgcgt tttggaattg ggtggtaaag cccctgttgt   3060
cgtattagaa gatgctgatg tcgaagctgc tgttgaagca gttgtctacg gtgccatgtc   3120
taactcaggt caaatttgta tgagtacaga aagagctata gttcatagat cattggccgc   3180
tgattttaaa gcattgttag taaagagagc cgaatcatta agagttggta atcacttgga   3240
agatccagac gttcaattgt caggtttgtt tactgctgct tccgcagaaa gagtcttggg   3300
tttgattaaa ggtgctgtaa acgcaggtgc caccttgtta gctggtgact tggcattaca   3360
tggtccatgc caaactataa tggctcctca catcttaacc ggtgttacta gagatatgga   3420
cttgtttcat agagaaacat tcggtccagt attgttcgtt agtgaatttg atactgatga   3480
cgaagctata gcacaagcca atgacacaga attttcttta tgtgcttcag tattctccag   3540
agatgttttg agagctatgg ataccgctaa gagaataaga actggttcat gccacgtcaa   3600
tggtcctact gtatatatcg aagcaccatt gcctaacggt ggtgttggtg gtggttctgg   3660
ttacggtaga tttggtggtg ttgctggtat tgaagagttt acagaaagac aaatagttag   3720
tttagccaag ccaggtatca agtatgcctt ttagactagt gtgaatttac tttaaatctt   3780
gcatttaaat aaattttctt tttatagctt tatgacttag tttcaattta tatactattt   3840
taatgacatt ttcgattcat tgattgaaag ctttgtgttt tttcttgatg cgctattgca   3900
ttgttcttgt ctttttcgcc acatgtaata tctgtagtag atacctgata cattgtggat   3960
gctgagtgaa attttagtta ataatggagg cgctcttaat aattttgggg atattggctt   4020
ttttttttaa agtttacaaa tgaatttttt ccgccaggat ttaattaatt gcagattccc   4080
ttttatggat tcctaaatcc tcgaggagaa cttctagtat atctacatac ctaatattat   4140
tgccttatta aaaatggaat cccaacaatt acatcaaaat ccacattctc ttcaaaatca   4200
attgtcctgt acttccttgt tcatgtgtgt tcaaaaacgt tatatttata ggataattat   4260
```

```
actctatttc tcaacaagta attggttgtt tggccgagcg gtctaaggcg cctgattcaa   4320
gaaatatctt gaccgcagtt aactgtggga atactcaggt atcgtaagat gcaagagttc   4380
gaatctctta gcaaccatta ttttttttcct caacataacg agaacacaca ggggcgctat   4440
cgcacagaat caaattcgat gactggaaat tttttgttaa tttcagaggt cgcctgacgc   4500
atatacctttt ttcaactgaa aaattgggag aaaaaggaaa ggtgagagcg ccggaaccgg   4560
cttttcatat agaatagaga agcgttcatg actaaatgct tgcatcacaa tacttgaagt   4620
tgacaatatt atttaaggac ctattgtttt ttccaatagg tggttagcaa tcgtcttact   4680
ttctaacttt tcttaccttt tacatttcag caatatatat atatatattt caaggatata   4740
ccattctaat gtctgcccct aagaagatcg tcgttttgcc aggtgaccac gttggtcaag   4800
aaatcacagc cgaagccatt aaggttctta aagctatttc tgatgttcgt tccaatgtca   4860
agttcgattt cgaaaatcat ttaattggtg gtgctgctat cgatgctaca ggtgttccac   4920
ttccagatga ggcgctggaa gcctccaaga aggctgatgc cgttttgtta ggtgctgtgg   4980
gtggtcctaa atggggtacc ggtagtgtta gacctgaaca aggtttacta aaaatccgta   5040
aagaacttca attgtacgcc aacttaagac catgtaactt tgcatccgac tctcttttag   5100
acttatctcc aatcaagcca caatttgcta aaggtactga cttcgttgtt gtcagagaat   5160
tagtgggagg tatttacttt ggtaagagaa aggaagacga tggtgatggt gtcgcttggg   5220
atagtgaaca atacaccgtt ccagaagtgc aaagaatcac aagaatggcc gctttcatgg   5280
ccctacaaca tgagccacca ttgcctattt ggtccttgga taaagctaat gttttggcct   5340
cttcaagatt atggagaaaa actgtggagg aaaccatcaa gaacgaattc cctacattga   5400
aggttcaaca tcaattgatt gattctgccg ccatgatcct agttaagaac ccaacccacc   5460
taaatggtat tataatcacc agcaacatgt ttggtgatat catctccgat gaagcctccg   5520
ttatcccagg ttccttgggt ttgttgccat ctgcgtcctt ggcctctttg ccagacaaga   5580
acaccgcatt tggtttgtac gaaccatgcc acggttctgc tccagatttg ccaaagaata   5640
aggtcaaccc tatcgccact atcttgtctg ctgcaatgat gttgaaattg tcattgaact   5700
tgcctgaaga aggtaaggcc attgaagatg cagttaaaaa ggttttggat gcaggtatca   5760
gaactggtga tttaggtggt tccaacagta ccaccgaagt cggtgatgct gtcgccgaag   5820
aagttaagaa aatccttgct taaaaagatt ctcttttttt atgatatttg tacataaact   5880
ttataaatga aattcataat agaaacgaca cgaaattaca aaatggaata tgttcatagg   5940
gtagacgaaa ctatatacgc aatctacata catttatcaa gaaggagaaa aaggaggatg   6000
taaaggaata caggtaagca aattgatact aatggctcaa cgtgataagg aaaaagaatt   6060
gcactttaac attaatattg acaaggagga gggcaccaca caaaaagtta ggtgtaacag   6120
aaaatcatga aactggccgg ccgatgctgt ccgcgggcct cataagagtt gtggtaacaa   6180
cgcaggtgcg cgcatctgct aagtttaaac ggtaccggcc tcatgggcct tccgctcact   6240
gcccgctttc cagtcgggaa acctgtcgtg ccagctgcat taacatggtc atagctgttt   6300
ccttgcgtat tgggcgctct ccgcttcctc gctcactgac tcgctgcgct cggtcgttcg   6360
ggtaaagcct ggggtgccta atgagcaaaa ggccagcaaa aggccaggaa ccgtaaaaag   6420
gccgcgttgc tggcgttttt ccataggctc cgcccccctg acgagcatca caaaaatcga   6480
cgctcaagtc agaggtggcg aaacccgaca ggactataaa gataccaggc gtttccccct   6540
ggaagctccc tcgtgcgctc tcctgttccg accctgccgc ttaccggata cctgtccgcc   6600
```

```
tttctccctt cgggaagcgt ggcgctttct catagctcac gctgtaggta tctcagttcg   6660
gtgtaggtcg ttcgctccaa gctgggctgt gtgcacgaac cccccgttca gcccgaccgc   6720
tgcgccttat ccggtaacta tcgtcttgag tccaacccgg taagacacga cttatcgcca   6780
ctggcagcag ccactggtaa caggattagc agagcgaggt atgtaggcgg tgctacagag   6840
ttcttgaagt ggtggcctaa ctacggctac actagaagaa cagtatttgg tatctgcgct   6900
ctgctgaagc cagttacctt cggaaaaaga gttggtagct cttgatccgg caaacaaacc   6960
accgctggta gcggtggttt ttttgtttgc aagcagcaga ttacgcgcag aaaaaaagga   7020
tctcaagaag atcctttgat cttttctacg gggtctgacg ctcagtggaa cgaaaactca   7080
cgttaaggga ttttggtcat gagattatca aaaaggatct tcacctagat ccttttaaat   7140
taaaaatgaa gttttaaatc aatctaaagt atatatgagt aaacttggtc tgacagttac   7200
caatgcttaa tcagtgaggc acctatctca gcgatctgtc tatttcgttc atccatagtt   7260
gcctgactcc ccgtcgtgta gataactacg atacgggagg gcttaccatc tggccccagt   7320
gctgcaatga taccgcgaga accacgctca ccggctccag atttatcagc aataaaccag   7380
ccagccggaa gggccgagcg cagaagtggt cctgcaactt tatccgcctc catccagtct   7440
attaattgtt gccgggaagc tagagtaagt agttcgccag ttaatagttt gcgcaacgtt   7500
gttgccattg ctacaggcat cgtggtgtca cgctcgtcgt ttggtatggc ttcattcagc   7560
tccggttccc aacgatcaag gcgagttaca tgatccccca tgttgtgcaa aaaagcggtt   7620
agctccttcg gtcctccgat cgttgtcaga agtaagttgg ccgcagtgtt atcactcatg   7680
gttatggcag cactgcataa ttctcttact gtcatgccat ccgtaagatg cttttctgtg   7740
actggtgagt actcaaccaa gtcattctga gaatagtgta tgcggcgacc gagttgctct   7800
tgcccggcgt caatacggga taataccgcg ccacatagca gaactttaaa agtgctcatc   7860
attggaaaac gttcttcggg gcgaaaactc tcaaggatct taccgctgtt gagatccagt   7920
tcgatgtaac ccactcgtgc acccaactga tcttcagcat cttttacttt caccagcgtt   7980
tctgggtgag caaaaacagg aaggcaaaat gccgcaaaaa agggaataag ggcgacacgg   8040
aaatgttgaa tactcatact cttccttttt caatattatt gaagcattta tcagggttat   8100
tgtctcatga gcggatacat atttgaatgt atttagaaaa ataaacaaat aggggttccg   8160
cgcacatttc cccgaaaagt gccacctaaa ttgtaagcgt taatattttg ttaaaattcg   8220
cgttaaattt ttgttaaatc agctcatttt ttaaccaata ggccgaaatc ggcaaaatcc   8280
cttataaatc aaaagaatag accgagatag ggttgagtgg ccgctacagg gcgctcccat   8340
tcgccattca ggctgcgcaa ctgttgggaa gggcgtttcg gtgcgggcct cttcgctatt   8400
acgccagctg gcgaaagggg gatgtgctgc aaggcgatta agttgggtaa cgccagggtt   8460
ttcccagtca cgacgttgta aaacgacggc cagtgagcgc gacgtaatac gactcactat   8520
agggcgaatt ggcggaaggc cgtcaaggcc ggtaccggtc cttttcatca cgtgctataa   8580
aaataattat aatttaaatt ttttaatata aatatataaa ttaaaaatag aaagtaaaaa   8640
aagaaattaa agaaaaaata gtttttgttt tccgaagatg taaaagactc taggggggatc  8700
gccaacaaat actacctttt atcttgctct tcctgctctc aggtattaat gccgaattgt   8760
ttcatcttgt ctgtgtagaa gaccacacac gaaaatcctg tgattttaca ttttacttat   8820
cgttaatcga atgtatatct atttaatctg cttttcttgt ctaataaata tatatgtaaa   8880
gtacgctttt tgttgaaatt ttttaaacct ttgtttattt ttttttcttc attccgtaac   8940
tcttctacct tctttattta ctttctaaaa tccaaataca aaacataaaa ataaataaac   9000
```

```
acagagtaaa ttcccaaatt attccatcat taaaagatac gaggcgcgtg taagttacag   9060
gcaagcgatc cgtccgttta aacatgcttt ctgaaaacac gactattctg atggctaacg   9120
gtgaaattaa agacatcgca aacggcgcgc cgatttttat aatgacgaaa aaaaaaaaat   9180
tggaaagaaa aagcttaatg cggtagttta tcacagttaa attgctaacg cagtcaggca   9240
ccgtgtatga aatctaacaa tgcgctcatc gtcatcctcg gcaccgtcac cctggatgct   9300
gtaggcatag gcttggttat gccggtactg ccgggcctct tgcgggatat cgtccattcc   9360
gacagcatcg ccagtcacta tggcgtgctg ctagcgctat atgcgttgat gcaatttcta   9420
tgcgcacccg ttctcggagc actgtccgac cgctttggcc gccgcccagt cctgctcgct   9480
tcgctacttg gagccactat cgactacgcg atcatggcga ccacacccgt cctgtggatc   9540
ctctacgccg gacgcatcgt ggccggcatc accggcgcca caggtgcggt tgctggcgcc   9600
tatatcgccg acatcaccga tggggaagat cgggctcgcc acttcgggct catgagcgct   9660
tgtttcggcg tgggtatggt ggcaggcccc gtggccgggg gactgttggg cgccatctcc   9720
ttgcatgcaa cttcttttct tttttttct tttctctctc cccgttgtt gtctcaccat   9780
atccgcaatg acaaaaaaat gatggaagac actaaaggaa aaaattaacg acaaagacag   9840
caccaacaga tgtcgttgtt ccagagctga tgaggggtat ctcgaagcac acgaaacttt   9900
ttccttcctt cattcacgca cactactctc taatgagcaa cggtatacgg ccttccttcc   9960
agttacttga atttgaaata aaaaaaagtt tgctgtcttg ctatcaagta taaatagacc  10020
tgcaattatt aatcttttgt ttcctcgtca ttgttctcgt tccctttctt ccttgtttct  10080
ttttctgcac aatatttcaa gctataccaa gcatacaatc aaggaattcg agctaagcgg  10140
ccgcccatgg aagctgcaat caaatcactg gtagcaatct taagacaaga actgacgaac  10200
ttccgtatca gttgtgttta tcctggtaat tttgaaagcg aaggtttcac tgtagagcag  10260
ctaacgaaac ccgaaattac aaagttgatc gaaggcccct cagacgctat cccatgcaaa  10320
caagcatgtg atatcattgc caagtcgctg gccagaggtg atgatgacgt tttacagat   10380
tttgtcggat ggatgataat ggggatggac cttgggctca ccgcaaagaa aagccgcttt  10440
gttccgttgc aatggatttt tggtgtccta tcaaacattc tggtcgtgcc attctacacg  10500
cgtgttatta ctgagtagta tttatttaag tattgtttgt gcacttgcct gcaggccttt  10560
tgaaaagcaa gcataaaaga tctaaacata aaatctgtaa aataacaaga tgtaaagata  10620
atgctaaatc atttggcttt ttgattgatt gtacaggaaa atatacatcg caggggggttg 10680
acttttacca tttcaccgca atggaatcaa acttgttgaa gagaatgttc acaggcgcat  10740
acgctacaat gacccgattc ttgctagcct tttctcggtc ttgcaaacaa ccgccggcag  10800
cttctcgagc cgcggaaccg ccagatattc attacttgac gcaaaagcgt ttgaaataat  10860
gacgaaaaag aaggaagaaa aaaaaagaaa aataccgctt ctaggcgggt tatctactga  10920
tccgagcttc cactaggata gcacccaaac acctgcatat ttggacgacc tttacttaca  10980
ccaccaaaaa ccactttcgc ctctcccgcc cctgataacg tccactaatt gagcgattac  11040
ctgagcggtc ctcttttgtt tgcagcatga gacttgcata ctgcaaatcg taagtagcaa  11100
cgtctca                                                            11107
```

<210> SEQ ID NO 67
<211> LENGTH: 11756
<212> TYPE: DNA
<213> ORGANISM: Artificial
<220> FEATURE:

<223> OTHER INFORMATION: pTT2-hmfN1-hmfL1-hmfL2

<400> SEQUENCE: 67

```
cagcttttga ttaagccttc tagtccaaaa aacacgtttt tttgtcattt atttcatttt     60
cttagaatag tttagtttat tcattttata gtcacgaatg ttttatgatt ctatataggg    120
ttgcaaacaa gcatttttca ttttatgtta aaacaatttc aggtttacct tttattctgc    180
ttgtggtgac gcgggtatcc gcccgctctt ttggtcaccc atgtatttaa ttgcataaat    240
aattcttaaa agtggagcta gtctatttct atttacatac ctctcatttc tcatttcctc    300
ccccgggtta gtcaaaaaat tagcctttta attctgctgt aacccgtaca tgcccaaaat    360
agggggcggg ttacacagaa tatataacat cgtaggtgtc tgggtgaaca gtttattcct    420
ggcatccact aaatataatg gagcccgctt tttaagctgg catccagaaa aaaaaagaat    480
cccagcacca aaatattgtt ttcttcacca accatcagtt cataggtcca ttctcttagc    540
gcaactacag agaacagggg cacaaacagg caaaaaacgg gcacaacctc aatggagtga    600
tgcaacctgc ctggagtaaa tgatgacaca aggcaattga cccacgcatg tatctatctc    660
attttcttac accttctatt accttctgct ctctctgatt tggaaaaagc tgaaaaaaaa    720
ggttgaaacc agttccctga aattattccc ctacttgact aataagtata taaagacggt    780
aggtattgat tgtaattctg taaatctatt tcttaaactt cttaaattct acttttatag    840
ttagtctttt ttttagtttt aaaacaccaa gaacttagtt tcgaataaac acacataaac    900
aaacaaaaat gacccaaacc aatgtccacg taaacaaatc cgacacttcc ttagctgctc    960
cacaacaatt attcatctcc ggtaaatatc aaaactctca aagaaatggt acatttccag   1020
tcaaaaaccc tatgactggt gaaacaatct atgaatgtgt ttctgcatca ttagatgact   1080
acgctgctgc tatagaagaa gctgatgccg cacaaccatc atgggctaga ttaggtcctt   1140
ccgcaagaag attgattttg ttaaaggccg ctgatataat ggaaacatac atcgaaaccg   1200
acgctccagc aatcttgagt gctgaagttt ctgcaacaag aggttgggtc agagccaata   1260
tattatctac cgctggtgtt ttcagagaaa ctgctgcttt ggcaacacat atcaaaggtg   1320
aaattgttcc agctgataga cctggtacta caatcttagt ttcaagagaa ccagtcggtg   1380
ttgtcttggc tatttcccct tggaatatgc ctgcaacctt aactgccaga gctatctgtt   1440
gccctttaat ttgtggtaac tctgtagttt taagaccatc cgaattttct cctaaatctc   1500
aacatttggt cgtaagagcc ttaacagaag ctggtttgcc agcaggttgc ttgcaattct   1560
taccaacatc aaccgcagat acccctagag ccatagaatt tgctatcaga caccctaagg   1620
ttagtagagc taatttcact ggttctgata gagtcggtag aattatagca ggtttatccg   1680
ccagttgttt gaaaccatgc gttttggaat tgggtggtaa agcccctgtt gtcgtattag   1740
aagatgctga tgtcgaagct gctgttgaag cagttgtcta cggtgccatg tctaactcag   1800
gtcaaatttg tatgagtaca gaaagagcta tagttcatag atcattggcc gctgatttta   1860
aagcattgtt agtaaagaga gccgaatcat taagagttgg taatcacttg gaagatccag   1920
acgttcaatt gtcaggtttg tttactgctg cttccgcaga aagagtcttg ggtttgatta   1980
aaggtgctgt aaacgcaggt gccaccttgt tagctggtga cttggcatta catggtccat   2040
gccaaactat aatggctcct cacatcttaa ccggtgttac tagagatatg gacttgtttc   2100
atagagaaac attcggtcca gtattgttcg ttagtgaatt tgatactgat gacgaagcta   2160
tagcacaagc caatgacaca gaattttctt tatgtgcttc agtattctcc agagatgttt   2220
tgagagctat ggataccgct aagagaataa gaactggttc atgccacgtc aatggtccta   2280
```

```
ctgtatatat cgaagcacca ttgcctaacg gtggtgttgg tggtggttct ggttacggta   2340
gatttggtgg tgttgctggt attgaagagt ttacagaaag acaaatagtt agtttagcca   2400
agccaggtat caagtatgcc ttttagacta gtgtgaattt actttaaatc ttgcatttaa   2460
ataaattttc tttttatagc tttatgactt agtttcaatt tatatactat tttaatgaca   2520
ttttcgattc attgattgaa agctttgtgt tttttcttga tgcgctattg cattgttctt   2580
gtctttttcg ccacatgtaa tatctgtagt agatacctga tacattgtgg atgctgagtg   2640
aaattttagt taataatgga ggcgctctta ataattttgg ggatattggc tttttttttt   2700
aaagtttaca aatgaatttt ttccgccagg atttaattaa ttgcagattc cctttttatgg   2760
attcctaaat cctcgaggag aacttctagt atatctacat acctaatatt attgccttat   2820
taaaaatgga atcccaacaa ttacatcaaa atccacattc tcttcaaaat caattgtcct   2880
gtacttcctt gttcatgtgt gttcaaaaac gttatattta taggataatt atactctatt   2940
tctcaacaag taattggttg tttggccgag cggtctaagg cgcctgattc aagaaatatc   3000
ttgaccgcag ttaactgtgg gaatactcag gtatcgtaag atgcaagagt tcgaatctct   3060
tagcaaccat tattttttc ctcaacataa cgagaacaca caggggcgct atcgcacaga   3120
atcaaattcg atgactggaa attttttgtt aatttcagag gtcgcctgac gcatatacct   3180
ttttcaactg aaaaattggg agaaaaagga aaggtgagag cgccggaacc ggcttttcat   3240
atagaataga gaagcgttca tgactaaatg cttgcatcac aatacttgaa gttgacaata   3300
ttatttaagg acctattgtt ttttccaata ggtggttagc aatcgtctta ctttctaact   3360
tttcttacct tttacatttc agcaatatat atatatatat ttcaaggata taccattcta   3420
atgtctgccc ctaagaagat cgtcgttttg ccaggtgacc acgttggtca agaaatcaca   3480
gccgaagcca ttaaggttct taaagctatt tctgatgttc gttccaatgt caagttcgat   3540
ttcgaaaatc atttaattgg tggtgctgct atcgatgcta caggtgttcc acttccagat   3600
gaggcgctgg aagcctccaa gaaggctgat gccgttttgt taggtgctgt gggtggtcct   3660
aaatggggta ccggtagtgt tagacctgaa caaggtttac taaaaatccg taaagaactt   3720
caattgtacg ccaacttaag accatgtaac tttgcatccg actctctttt agacttatct   3780
ccaatcaagc cacaatttgc taaaggtact gacttcgttg ttgtcagaga attagtggga   3840
ggtatttact ttggtaagag aaaggaagac gatggtgatg gtgtcgcttg ggatagtgaa   3900
caatacaccg ttccagaagt gcaaagaatc acaagaatgg ccgctttcat ggccctacaa   3960
catgagccac cattgcctat ttggtccttg gataaagcta atgttttggc ctcttcaaga   4020
ttatggagaa aaactgtgga ggaaaccatc aagaacgaat tccctacatt gaaggttcaa   4080
catcaattga ttgattctgc cgccatgatc ctagttaaga acccaaccca cctaaatggt   4140
attataatca ccagcaacat gtttggtgat atcatctccg atgaagcctc cgttatccca   4200
ggttccttgg gtttgttgcc atctgcgtcc ttggcctctt tgccagacaa gaacaccgca   4260
tttggtttgt acgaaccatg ccacggttct gctccagatt tgccaaagaa taaggtcaac   4320
cctatcgcca ctatcttgtc tgctgcaatg atgttgaaat tgtcattgaa cttgcctgaa   4380
gaaggtaagg ccattgaaga tgcagttaaa aaggttttgg atgcaggtat cagaactggt   4440
gatttaggtg gttccaacag taccaccgaa gtcggtgatg ctgtcgccga agaagttaag   4500
aaaatccttg cttaaaaaga ttctcttttt ttatgatatt tgtacataaa ctttataaat   4560
gaaattcata atagaaacga cacgaaatta caaaatggaa tatgttcata gggtagacga   4620
```

```
aactatatac gcaatctaca tacatttatc aagaaggaga aaaaggagga tgtaaaggaa   4680
tacaggtaag caaattgata ctaatggctc aacgtgataa ggaaaaagaa ttgcacttta   4740
acattaatat tgacaaggag gagggcacca cacaaaaagt taggtgtaac agaaaatcat   4800
gaaactggcc ggccgatgct gtccgcgggc ctcataagag ttgtggtaac aacgcaggtg   4860
cgcgcatctg ctaagtttaa acggtaccgg cctcatgggc cttccgctca ctgcccgctt   4920
tccagtcggg aaacctgtcg tgccagctgc attaacatgg tcatagctgt ttccttgcgt   4980
attgggcgct ctccgcttcc tcgctcactg actcgctgcg ctcggtcgtt cgggtaaagc   5040
ctggggtgcc taatgagcaa aaggccagca aaaggccagg aaccgtaaaa aggccgcgtt   5100
gctggcgttt ttccataggc tccgcccccc tgacgagcat cacaaaaatc gacgctcaag   5160
tcagaggtgg cgaaacccga caggactata aagataccag gcgtttcccc ctggaagctc   5220
cctcgtgcgc tctcctgttc cgaccctgcc gcttaccgga tacctgtccg cctttctccc   5280
ttcgggaagc gtggcgcttt ctcatagctc acgctgtagg tatctcagtt cggtgtaggt   5340
cgttcgctcc aagctgggct gtgtgcacga accccccgtt cagcccgacc gctgcgcctt   5400
atccggtaac tatcgtcttg agtccaaccc ggtaagacac gacttatcgc cactggcagc   5460
agccactggt aacaggatta gcagagcgag gtatgtaggc ggtgctacag agttcttgaa   5520
gtggtggcct aactacggct acactagaag aacagtattt ggtatctgcg ctctgctgaa   5580
gccagttacc ttcggaaaaa gagttggtag ctcttgatcc ggcaaacaaa ccaccgctgg   5640
tagcggtggt ttttttgttt gcaagcagca gattacgcgc agaaaaaaag gatctcaaga   5700
agatcctttg atcttttcta cggggtctga cgctcagtgg aacgaaaact cacgttaagg   5760
gattttggtc atgagattat caaaaaggat cttcacctag atccttttaa attaaaaatg   5820
aagttttaaa tcaatctaaa gtatatatga gtaaacttgg tctgacagtt accaatgctt   5880
aatcagtgag gcacctatct cagcgatctg tctatttcgt tcatccatag ttgcctgact   5940
ccccgtcgtg tagataacta cgatacggga gggcttacca tctggcccca gtgctgcaat   6000
gataccgcga gaaccacgct caccggctcc agatttatca gcaataaacc agccagccgg   6060
aagggccgag cgcagaagtg gtcctgcaac tttatccgcc tccatccagt ctattaattg   6120
ttgccgggaa gctagagtaa gtagttcgcc agttaatagt ttgcgcaacg ttgttgccat   6180
tgctacaggc atcgtggtgt cacgctcgtc gtttggtatg gcttcattca gctccggttc   6240
ccaacgatca aggcgagtta catgatcccc catgttgtgc aaaaaagcgg ttagctcctt   6300
cggtcctccg atcgttgtca gaagtaagtt ggccgcagtg ttatcactca tggttatggc   6360
agcactgcat aattctctta ctgtcatgcc atccgtaaga tgcttttctg tgactggtga   6420
gtactcaacc aagtcattct gagaatagtg tatgcggcga ccgagttgct cttgcccggc   6480
gtcaatacgg gataataccg cgccacatag cagaacttta aaagtgctca tcattggaaa   6540
acgttcttcg gggcgaaaac tctcaaggat cttaccgctg ttgagatcca gttcgatgta   6600
acccactcgt gcacccaact gatcttcagc atcttttact ttcaccagcg tttctgggtg   6660
agcaaaaaca ggaaggcaaa atgccgcaaa aaagggaata agggcgacac ggaaatgttg   6720
aatactcata ctcttccttt ttcaatatta ttgaagcatt tatcagggtt attgtctcat   6780
gagcggatac atatttgaat gtatttagaa aaataaacaa ataggggttc cgcgcacatt   6840
tccccgaaaa gtgccaccta aattgtaagc gttaatattt tgttaaaatt cgcgttaaat   6900
ttttgttaaa tcagctcatt ttttaaccaa taggccgaaa tcggcaaaat cccttataaa   6960
tcaaaagaat agaccgagat agggttgagt ggccgctaca gggcgctccc attcgccatt   7020
```

```
caggctgcgc aactgttggg aagggcgttt cggtgcgggc ctcttcgcta ttacgccagc   7080
tggcgaaagg gggatgtgct gcaaggcgat taagttgggt aacgccaggg ttttcccagt   7140
cacgacgttg taaaacgacg gccagtgagc gcgacgtaat acgactcact atagggcgaa   7200
ttggcggaag gccgtcaagg ccggtaccgg tccttttcat cacgtgctat aaaaataatt   7260
ataatttaaa ttttttaata taaatatata aattaaaaat agaaagtaaa aaaagaaatt   7320
aaagaaaaaa tagtttttgt tttccgaaga tgtaaaagac tctaggggga tcgccaacaa   7380
atactacctt ttatcttgct cttcctgctc tcaggtatta atgccgaatt gtttcatctt   7440
gtctgtgtag aagaccacac acgaaaatcc tgtgatttta cattttactt atcgttaatc   7500
gaatgtatat ctatttaatc tgcttttctt gtctaataaa tatatatgta aagtacgctt   7560
tttgttgaaa ttttttaaac ctttgtttat ttttttttct tcattccgta actcttctac   7620
cttctttatt tactttctaa aatccaaata caaaacataa aaataaataa acacagagta   7680
aattcccaaa ttattccatc attaaaagat acgaggcgcg tgtaagttac aggcaagcga   7740
tccgtccgtt taaacatgct ttctgaaaac acgactattc tgatggctaa cggtgaaatt   7800
aaagacatcg caaacggcgc gcctgcggta gtttatcaca gttaaattgc taacgcagtc   7860
aggcaccgtg tatgaaatct aacaatgcgc tcatcgtcat cctcggcacc gtcaccctgg   7920
atgctgtagg cataggcttg gttatgccgg tactgccggg cctcttgcgg gatatcgtcc   7980
attccgacag catcgccagt cactatggcg tgctgctagc gctatatgcg ttgatgcaat   8040
ttctatgcgc acccgttctc ggagcactgt ccgaccgctt tggccgccgc ccagtcctgc   8100
tcgcttcgct acttggagcc actatcgact acgcgatcat ggcgaccaca cccgtcctgt   8160
ggatcctcta cgccggacgc atcgtggccg gcatcaccgg cgccacaggt gcggttgctg   8220
gcgcctatat cgccgacatc accgatgggg aagatcgggc tcgccacttc gggctcatga   8280
gcgcttgttt cggcgtgggt atggtggcag gccccgtggc cgggggactg ttgggcgcca   8340
tctccttgca tgcaacttct ttctttttt tttcttttct ctctcccccg ttgttgtctc   8400
accatatccg caatgacaaa aaaatgatgg aagacactaa aggaaaaaat taacgacaaa   8460
gacagcacca acagatgtcg ttgttccaga gctgatgagg ggtatctcga agcacacgaa   8520
actttttcct tccttcattc acgcacacta ctctctaatg agcaacggta tacggccttc   8580
cttccagtta cttgaatttg aaataaaaaa aagtttgctg tcttgctatc aagtataaat   8640
agacctgcaa ttattaatct tttgtttcct cgtcattgtt ctcgttccct ttcttccttg   8700
tttcttttc tgcacaatat ttcaagctat accaagcata caatcaacta tctcatacaa   8760
aaatgggttc cttatcctta ccagaaacat cattagccgc aatccaagac aaagaaacaa   8820
aagctatctc agtcgccaaa agacctacac cagtacctgt tggtacccaa gtcttagtaa   8880
aattgcatta ttccggtgtt tgtgccactg atttgcactt agctagaggt tctgttccat   8940
acttacaacc taaggtttca gtcggtggtc atgaaggtac cggtgttatt gcttctttgg   9000
gtccagatgt cgacgcagca gaatggcatg taggtgacag agtagcagtt agatgggtac   9060
acatagtttg tggtaaatgc gaagtttgta ctacaggttt cgaaaatttg tgccaatcta   9120
gaaagttggc tggtaaagat gttgaaggta ctttcgccga atatgcaatt gccgactctt   9180
catacatggt tagattacca gctggtgtct cagatgcaga cgccgctcct atcttgtgtg   9240
ctggtgtcac agtatacaaa gccttgaaga tcgcttcttt gagagcaggt tcatgggttg   9300
ctgtcgcagg tgctggtggt ggtttaggtc atttggcaat ccaatatgct agagcaatgg   9360
```

```
gtttaaaagt tgtcgcattg gatgccagaa agagagactt gtgcttatcc ttgggtgctg   9420
aaagttacat cgacgtttta gaaactgatg actgtgtcgc acaagtaatt aaagttacag   9480
atggtggtgc tcacggtgca ttaatatgcg cttccagtgg tcaagcctac gatgacgctg   9540
ttaaattttt gagatggacc ggtactttag tctgtatagg tttgccacct aagccaacat   9600
tgttatcctt aggtcctgct gattttgtag ccagaggtat caaggttatg ggtacaagta   9660
ccggtgacag acaagacaca gttgaagcct tggctttcgt cgctaaaggt caagtaaagc   9720
ctcaattaac cgaaagaaga ttggaagatg ttgaagaaat cttaaaggaa atagaaaatg   9780
gtacaatgca aggtaaagcc gtaatcagaa tcgcatagac gcgtgttatt actgagtagt   9840
atttatttaa gtattgtttg tgcacttgcc tgcaggcctt ttgaaaagca agcataaaag   9900
atctaaacat aaaatctgta aaataacaag atgtaaagat aatgctaaat catttggctt   9960
tttgattgat tgtacaggaa aatatacatc gcaggggggtt gacttttacc atttcaccgc  10020
aatggaatca aacttgttga agagaatgtt cacaggcgca tacgctacaa tgacccgatt  10080
cttgctagcc ttttctcggt cttgcaaaca accgccggca gcttctcgag ccgcggaacc  10140
gccagatatt cattacttga cgcaaaagcg tttgaaataa tgacgaaaaa gaaggaagaa  10200
aaaaaaagaa aaataccgct tctaggcggg ttatctactg atccgagctt ccactaggat  10260
agcacccaaa cacctgcata tttggacgac ctttacttac accaccaaaa accactttcg  10320
cctctcccgc ccctgataac gtccactaat tgagcgatta cctgagcggt cctcttttgt  10380
ttgcagcatg agacttgcat actgcaaatc gtaagtagca acgtctcaag gtcaaaactg  10440
tatggaaacc ttgtcacctc acttaattct agctagccta ccctgcaagt caagaggtct  10500
ccgtgattcc tagccacctc aaggtatgcc tctccccgga aactgtggcc ttttctggca  10560
cacatgatct ccacgatttc aacatataaa tagcttttga taatggcaat attaatcaaa  10620
tttattttac ttctttcttg taacatctct cttgtaatcc cttattcctt ctagctattt  10680
ttcataaaaa accaagcaac tgcttatcaa cacacaaaca ctaaatcaaa aatgagtttg  10740
ccatcccact acaagagagc cgcttttaag gaagcaggtg gtccattgac tattgaagaa  10800
gttgatttga ctatgccaga tgccggtgaa gtcttggtaa aagttgaagc ttgtggtgta  10860
tgcttttcag acactgttcc tcaagctcat ggtttgggtg gtaaattccc aatcgttcct  10920
ggtcatgaaa ttataggtca cgttgtcgca acaggtgacg gtgtttccga ctgggaagtc  10980
ggtgacagaa ttggtgaagg ttggcatggt ggtcacgacg gtacatgtcc atcatgcaga  11040
caaggtcatt tccaaatgtg tgataaccaa tccataaacg gtgttaccaa aaatggtggt  11100
tatgctcaat actgcatttt gagaagtgaa gcagcagtca gaatacctac tcacgtatct  11160
gccgctgaat atgcaccaat tttatgtgcc ggtgtcaccg tttttaattc aatgagacaa  11220
atcggtgtta agcctggttc cactgtcgca attcaaggtt tgggtggttt aggtcatttg  11280
gccattcaat atgctaacag atttggtttc agagtagttg ctatatctag agatgaccaa  11340
aaggaaagat tcgttagaga tttgggtgca cacgaataca ttaatacatc tgaagaagat  11400
gtcggttcag ctttacaaaa gttgggtggt gcaagtttaa tagttgcaac cgccccaaac  11460
gctagagcaa tctctccttt gttaaaaggt ttaagaccat tgggtaaatt gttgatcttg  11520
gctgttccag gtgaaatccc tttagatacc agattgatgg tagcaagagg tttatccgtt  11580
catggttggc caagtggtca cgccttggat tctgaagaaa ctataagatt cacagaatta  11640
gaagatatca agtgtatgat acaaacttac tcattagaca gagctaacga agcctttgac  11700
gctatgattt caggttcagt tagattcaga gcagttatta caatggaata ggacgt       11756
```

<210> SEQ ID NO 68
<211> LENGTH: 8315
<212> TYPE: DNA
<213> ORGANISM: Artificial
<220> FEATURE:
<223> OTHER INFORMATION: pTT2-hmfL1

<400> SEQUENCE: 68

```
cgcgtgttat tactgagtag tatttattta agtattgttt gtgcacttgc ctgcaggcct     60

tttgaaaagc aagcataaaa gatctaaaca taaaatctgt aaaataacaa gatgtaaaga    120

taatgctaaa tcatttggct ttttgattga ttgtacagga aaatatacat cgcagggggt    180

tgacttttac catttcaccg caatggaatc aaacttgttg aagagaatgt tcacaggcgc    240

atacgctaca atgacccgat tcttgctagc cttttctcgg tcttgcaaac aaccgccggc    300

agcttctcga gccgcggaac cgccagatat tcattacttg acgcaaaagc gtttgaaata    360

atgacgaaaa agaaggaaga aaaaaaaaga aaaataccgc ttctaggcgg gttatctact    420

gatccgagct tccactagga tagcacccaa acacctgcat atttggacga cctttactta    480

caccaccaaa aaccactttc gcctctcccg cccctgataa cgtccactaa ttgagcgatt    540

acctgagcgg tcctcttttg tttgcagcat gagacttgca tactgcaaat cgtaagtagc    600

aacgtctcaa ggtcaaaact gtatggaaac cttgtcacct cacttaattc tagctagcct    660

accctgcaag tcaagaggtc tccgtgattc ctagccacct caaggtatgc ctctccccgg    720

aaactgtggc cttttctggc acacatgatc tccacgattt caacatataa atagcttttg    780

ataatggcaa tattaatcaa atttatttta cttctttctt gtaacatctc tcttgtaatc    840

ccttattcct tctagctatt tttcataaaa aaccaagcaa ctgcttatca acacacaaac    900

actaaatcaa aatgcataaa ataggacgtc agcttttgat taagccttct agtccaaaaa    960

acacgttttt ttgtcattta tttcattttc ttagaatagt ttagtttatt cattttatag   1020

tcacgaatgt tttatgattc tatatagggt tgcaaacaag catttttcat tttatgttaa   1080

aacaatttca ggtttacctt ttattctgct tgtggtgacg cgggtatccg cccgctcttt   1140

tggtcaccca tgtatttaat tgcataaata attcttaaaa gtggagctag tctatttcta   1200

tttacatacc tctcatttct catttcctcc cccctagtgc agattccctt ttatggattc   1260

ctaaatcctc gaggagaact tctagtatat ctacatacct aatattattg ccttattaaa   1320

aatggaatcc caacaattac atcaaaatcc acattctctt caaaatcaat tgtcctgtac   1380

ttccttgttc atgtgtgttc aaaaacgtta tatttatagg ataattatac tctatttctc   1440

aacaagtaat tggttgtttg gccgagcggt ctaaggcgcc tgattcaaga aatatcttga   1500

ccgcagttaa ctgtgggaat actcaggtat cgtaagatgc aagagttcga atctcttagc   1560

aaccattatt tttttcctca acataacgag aacacacagg ggcgctatcg cacagaatca   1620

aattcgatga ctggaaattt tttgttaatt tcagaggtcg cctgacgcat ataccttttt   1680

caactgaaaa attgggagaa aaaggaaagg tgagagcgcc ggaaccggct tttcatatag   1740

aatagagaag cgttcatgac taaatgcttg catcacaata cttgaagttg acaatattat   1800

ttaaggacct attgtttttt ccaataggtg gttagcaatc gtcttacttt ctaacttttc   1860

ttacctttta catttcagca atatatatat atatatttca aggatatacc attctaatgt   1920

ctgcccctaa gaagatcgtc gttttgccag gtgaccacgt tggtcaagaa atcacagccg   1980

aagccattaa ggttcttaaa gctatttctg atgttcgttc caatgtcaag ttcgatttcg   2040
```

```
aaaatcattt aattggtggt gctgctatcg atgctacagg tgttccactt ccagatgagg   2100
cgctggaagc ctccaagaag gctgatgccg ttttgttagg tgctgtgggt ggtcctaaat   2160
ggggtaccgg tagtgttaga cctgaacaag gtttactaaa aatccgtaaa gaacttcaat   2220
tgtacgccaa cttaagacca tgtaactttg catccgactc tcttttagac ttatctccaa   2280
tcaagccaca atttgctaaa ggtactgact tcgttgttgt cagagaatta gtgggaggta   2340
tttactttgg taagagaaag gaagacgatg gtgatggtgt cgcttgggat agtgaacaat   2400
acaccgttcc agaagtgcaa agaatcacaa gaatggccgc tttcatggcc ctacaacatg   2460
agccaccatt gcctatttgg tccttggata aagctaatgt tttggcctct tcaagattat   2520
ggagaaaaac tgtggaggaa accatcaaga acgaattccc tacattgaag gttcaacatc   2580
aattgattga ttctgccgcc atgatcctag ttaagaaccc aacccaccta aatggtatta   2640
taatcaccag caacatgttt ggtgatatca tctccgatga agcctccgtt atcccaggtt   2700
ccttgggttt gttgccatct gcgtccttgg cctctttgcc agacaagaac accgcatttg   2760
gtttgtacga accatgccac ggttctgctc cagatttgcc aaagaataag gtcaacccta   2820
tcgccactat cttgtctgct gcaatgatgt tgaaattgtc attgaacttg cctgaagaag   2880
gtaaggccat tgaagatgca gttaaaaagg ttttggatgc aggtatcaga actggtgatt   2940
taggtggttc caacagtacc accgaagtcg gtgatgctgt cgccgaagaa gttaagaaaa   3000
tccttgctta aaaagattct cttttttat gatatttgta cataaacttt ataaatgaaa   3060
ttcataatag aaacgacacg aaattacaaa atggaatatg ttcatagggt agacgaaact   3120
atatacgcaa tctacataca tttatcaaga aggagaaaaa ggaggatgta aaggaataca   3180
ggtaagcaaa ttgatactaa tggctcaacg tgataaggaa aaagaattgc actttaacat   3240
taatattgac aaggaggagg gcaccacaca aaaagttagg tgtaacagaa aatcatgaaa   3300
ctggccggcc gatgctgtcc gcgggcctca taagagttgt ggtaacaacg caggtgcgcg   3360
catctgctaa gtttaaacgg taccggcctc atgggccttc cgctcactgc ccgctttcca   3420
gtcgggaaac ctgtcgtgcc agctgcatta acatggtcat agctgtttcc ttgcgtattg   3480
ggcgctctcc gcttcctcgc tcactgactc gctgcgctcg gtcgttcggg taaagcctgg   3540
ggtgcctaat gagcaaaagg ccagcaaaag gccaggaacc gtaaaaaggc cgcgttgctg   3600
gcgtttttcc ataggctccg cccccctgac gagcatcaca aaaatcgacg ctcaagtcag   3660
aggtggcgaa acccgacagg actataaaga taccaggcgt ttccccctgg aagctccctc   3720
gtgcgctctc ctgttccgac cctgccgctt accggatacc tgtccgcctt tctcccttcg   3780
ggaagcgtgg cgctttctca tagctcacgc tgtaggtatc tcagttcggt gtaggtcgtt   3840
cgctccaagc tgggctgtgt gcacgaaccc cccgttcagc ccgaccgctg cgccttatcc   3900
ggtaactatc gtcttgagtc caacccggta agacacgact tatcgccact ggcagcagcc   3960
actggtaaca ggattagcag agcgaggtat gtaggcggtg ctacagagtt cttgaagtgg   4020
tggcctaact acggctacac tagaagaaca gtatttggta tctgcgctct gctgaagcca   4080
gttaccttcg gaaaaagagt tggtagctct tgatccggca aacaaaccac cgctggtagc   4140
ggtggttttt ttgtttgcaa gcagcagatt acgcgcagaa aaaaaggatc tcaagaagat   4200
cctttgatct tttctacggg gtctgacgct cagtggaacg aaaactcacg ttaagggatt   4260
ttggtcatga gattatcaaa aaggatcttc acctagatcc ttttaaatta aaaatgaagt   4320
tttaaatcaa tctaaagtat atatgagtaa acttggtctg acagttacca atgcttaatc   4380
agtgaggcac ctatctcagc gatctgtcta tttcgttcat ccatagttgc ctgactcccc   4440
```

```
gtcgtgtaga taactacgat acgggagggc ttaccatctg gccccagtgc tgcaatgata   4500
ccgcgagaac cacgctcacc ggctccagat ttatcagcaa taaaccagcc agccggaagg   4560
gccgagcgca gaagtggtcc tgcaacttta tccgcctcca tccagtctat taattgttgc   4620
cgggaagcta gagtaagtag ttcgccagtt aatagtttgc gcaacgttgt tgccattgct   4680
acaggcatcg tggtgtcacg ctcgtcgttt ggtatggctt cattcagctc cggttcccaa   4740
cgatcaaggc gagttacatg atcccccatg ttgtgcaaaa aagcggttag ctccttcggt   4800
cctccgatcg ttgtcagaag taagttggcc gcagtgttat cactcatggt tatggcagca   4860
ctgcataatt ctcttactgt catgccatcc gtaagatgct tttctgtgac tggtgagtac   4920
tcaaccaagt cattctgaga atagtgtatg cggcgaccga gttgctcttg cccggcgtca   4980
atacgggata ataccgcgcc acatagcaga actttaaaag tgctcatcat tggaaaacgt   5040
tcttcggggc gaaaactctc aaggatctta ccgctgttga gatccagttc gatgtaaccc   5100
actcgtgcac ccaactgatc ttcagcatct tttactttca ccagcgtttc tgggtgagca   5160
aaaacaggaa ggcaaaatgc cgcaaaaaag ggaataaggg cgacacggaa atgttgaata   5220
ctcatactct tcctttttca atattattga agcatttatc agggttattg tctcatgagc   5280
ggatacatat ttgaatgtat ttagaaaaat aaacaaatag gggttccgcg cacatttccc   5340
cgaaaagtgc cacctaaatt gtaagcgtta atattttgtt aaaattcgcg ttaaattttt   5400
gttaaatcag ctcatttttt aaccaatagg ccgaaatcgg caaaatccct tataaatcaa   5460
aagaatagac cgagataggg ttgagtggcc gctacagggc gctcccattc gccattcagg   5520
ctgcgcaact gttgggaagg gcgtttcggt gcgggcctct tcgctattac gccagctggc   5580
gaaaggggga tgtgctgcaa ggcgattaag ttgggtaacg ccagggtttt cccagtcacg   5640
acgttgtaaa acgacggcca gtgagcgcga cgtaatacga ctcactatag ggcgaattgg   5700
cggaaggccg tcaaggccgg taccggtcct tttcatcacg tgctataaaa ataattataa   5760
tttaaatttt ttaatataaa tatataaatt aaaaatagaa agtaaaaaaa gaaattaaag   5820
aaaaaatagt ttttgttttc cgaagatgta aaagactcta gggggatcgc caacaaatac   5880
taccttttat cttgctcttc ctgctctcag gtattaatgc cgaattgttt catcttgtct   5940
gtgtagaaga ccacacacga aaatcctgtg attttacatt ttacttatcg ttaatcgaat   6000
gtatatctat ttaatctgct tttcttgtct aataaatata tatgtaaagt acgctttttg   6060
ttgaaatttt ttaaaccttt gtttattttt ttttcttcat tccgtaactc ttctaccttc   6120
tttatttact ttctaaaatc caaatacaaa acataaaaat aaataaacac agagtaaatt   6180
cccaaattat tccatcatta aaagatacga ggcgcgtgta agttacaggc aagcgatccg   6240
tccgtttaaa catgctttct gaaaacacga ctattctgat ggctaacggt gaaattaaag   6300
acatcgcaaa cggcgcgcct gcggtagttt atcacagtta aattgctaac gcagtcaggc   6360
accgtgtatg aaatctaaca atgcgctcat cgtcatcctc ggcaccgtca ccctggatgc   6420
tgtaggcata ggcttggtta tgccggtact gccgggcctc ttgcgggata tcgtccattc   6480
cgacagcatc gccagtcact atggcgtgct gctagcgcta tatgcgttga tgcaatttct   6540
atgcgcaccc gttctcggag cactgtccga ccgctttggc cgccgcccag tcctgctcgc   6600
ttcgctactt ggagccacta tcgactacgc gatcatggcg accacacccg tcctgtggat   6660
cctctacgcc ggacgcatcg tggccggcat caccggcgcc acaggtgcgg ttgctggcgc   6720
ctatatcgcc gacatcaccg atggggaaga tcgggctcgc cacttcgggc tcatgagcgc   6780
```

```
ttgtttcggc gtgggtatgg tggcaggccc cgtggccggg ggactgttgg gcgccatctc   6840

cttgcatgca acttcttttc ttttttttc ttttctctct cccccgttgt tgtctcacca   6900

tatccgcaat gacaaaaaaa tgatggaaga cactaaagga aaaaattaac gacaaagaca   6960

gcaccaacag atgtcgttgt tccagagctg atgaggggta tctcgaagca cacgaaactt   7020

tttccttcct tcattcacgc acactactct ctaatgagca acggtatacg gccttccttc   7080

cagttacttg aatttgaaat aaaaaaaagt ttgctgtctt gctatcaagt ataaatagac   7140

ctgcaattat taatcttttg tttcctcgtc attgttctcg ttccctttct tccttgtttc   7200

tttttctgca caatatttca agctatacca agcatacaat caactatctc atacaaaaat   7260

gggttcctta tccttaccag aaacatcatt agccgcaatc caagacaaag aaacaaaagc   7320

tatctcagtc gccaaaagac ctacaccagt acctgttggt acccaagtct tagtaaaatt   7380

gcattattcc ggtgtttgtg ccactgattt gcacttagct agaggttctg ttccatactt   7440

acaacctaag gtttcagtcg gtggtcatga aggtaccggt gttattgctt ctttgggtcc   7500

agatgtcgac gcagcagaat ggcatgtagg tgacagagta gcagttagat gggtacacat   7560

agtttgtggt aaatgcgaag tttgtactac aggtttcgaa aatttgtgcc aatctagaaa   7620

gttggctggt aaagatgttg aaggtacttt cgccgaatat gcaattgccg actcttcata   7680

catggttaga ttaccagctg gtgtctcaga tgcagacgcc gctcctatct tgtgtgctgg   7740

tgtcacagta tacaaagcct tgaagatcgc ttctttgaga gcaggttcat gggttgctgt   7800

cgcaggtgct ggtggtggtt taggtcattt ggcaatccaa tatgctagag caatgggttt   7860

aaaagttgtc gcattggatg ccagaaagag agacttgtgc ttatccttgg gtgctgaaag   7920

ttacatcgac gttttagaaa ctgatgactg tgtcgcacaa gtaattaaag ttacagatgg   7980

tggtgctcac ggtgcattaa tatgcgcttc cagtggtcaa gcctacgatg acgctgttaa   8040

atttttgaga tggaccggta ctttagtctg tataggtttg ccacctaagc caacattgtt   8100

atccttaggt cctgctgatt ttgtagccag aggtatcaag gttatgggta caagtaccgg   8160

tgacagacaa gacacagttg aagccttggc tttcgtcgct aaaggtcaag taaagcctca   8220

attaaccgaa agaagattgg aagatgttga agaaatctta aaggaaatag aaaatggtac   8280

aatgcaaggt aaagccgtaa tcagaatcgc ataga                              8315
```

```
<210> SEQ ID NO 69
<211> LENGTH: 360
<212> TYPE: PRT
<213> ORGANISM: Saccharomyces cerevisiae

<400> SEQUENCE: 69

Met Ser Tyr Pro Glu Lys Phe Glu Gly Ile Ala Ile Gln Ser His Glu
1               5                   10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
```

-continued

```
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

FUNGAL PRODUCTION OF FDCA

FIELD OF THE INVENTION

The invention relates to the fields of molecular genetics, metabolic engineering, biotransformation and fermentation technology. In particular, the invention relates to fungi that are genetically modified to produce 2,5-furandicarboxylic acid from hydroxymethylfurfural. The invention further relates to the use of such fungi in processes for the biotransformation of hydroxymethylfurfural into 2,5-furandicarboxylic acid.

BACKGROUND OF THE INVENTION 2,5-furandicarboxylic acid (FDCA) is a monomeric compound which can be applied in the production of polyesters which have a tremendous economic impact. A very important compound in the field is polyethyleneterephthalate (PET) which is produced from terephthalic acid (PTA) and ethylene glycol. FDCA may substitute for PTA in the polyester PET in which case polyethylenefurandicarboxylate (PEF) results. PEF has a good potential in replacing PET in the large polyester market. Not only because it has superior properties when compared to PET, but also because it can be derived from renewable feedstocks. FDCA can be produced from sugars either chemically (De Jong et al., 2012. In: Biobased Monomers, Polymers, and Materials; Smith, P., et al.; ACS Symposium Series; American Chemical Society: Washington, D.C.) or in a combined chemical-biological route (Wiercks et al., 2011. Appl Microbiol Biotechnol 92:1095-1105). In the latter case, a monomeric sugar such as glucose or fructose is chemically transformed into 5-(hydroxymethyl)-2-furaldehyde (HMF) which subsequently can be oxidized by enzymes into FDCA.

A biological route for producing FDCA from HMF has been developed based on the isolation of the HMF-degrading strain of *Cupriavidus basilensis* HMF14 (Wierckx et al., 2010. Microbial Technology 3:336-343). A cluster of genes encoding enzymes involved in the HMF degradation route in *C. basilensis* HMF14 was identified and relevant genes heterologously expressed in a *Pseudomonas putida* S12 strain (Koopman et al., 2010. PNAS 107:4919-4924) which thereby acquired the ability to metabolize HMF. The heterologous expression of only the hmfH gene—encoding a HMF oxidoreductase that acts as an oxidase mainly at HMF-acid (HMFCA), but it also may oxidize HMF or FFCA—enables *P. putida* S12 to produce FDCA from HMF (Koopman et al., 2010. Bioresource Technology 101:6291-6296; and WO 2011/026913). In further optimization work (Wierckx et al., 2011, supra; and WO 2012/064195), two additional genes were expressed in *P. putida* S12 that encode for an HMFCA transporter and for an aldehyde dehydrogenase with unknown specificity, respectively.

Yeasts have been studied extensively for their ability to reduce HMF (Parawira and Tekere, 2011, Critical Reviews in Biotechnology 31:20-31) to the corresponding dead-end product 5-hydroxymethylfurfuryl alcohol (HMF-alcohol) for ethanol production processes. Thus far no reports have issued of yeasts that are able to completely oxidize HMF and utilize the compound for growth.

U.S. Pat. No. 7,067,303 disclose that the fungus *Coniochaeta ligniaria* (teleomorph), or its *Lecythophora* anamorph state, are capable of significantly depleting the toxic levels of furans, particularly furfural and HMF, in agricultural biomass hydrolysate. The use of *C. ligniaria* as a biological agent in detoxifying sugar-containing hydrolysates was further demonstrated in a number of subsequent papers (Lopez et al., 2004. Appl. Microbiol Biotechnol 64:125-131; Nichols et al., 2005. Appl Biochem Biotechnol. Spring; 121-124:379-90; Nichols et al., 2008. Enzyme and Microbial Technology 42:624-630; Nichols et al., 2010. Bioresource Technol 19:7545-50; Nichols et al., 2014. Biomass and Bioenergy 67:79-88). Apart from detoxification of HMF to less toxic compounds, the organism was also able to metabolize HMF for growth.

Zhang et al. (2010, Biotechnology for Biofuels 3:26) described the isolation of two HMF-metabolizing fungi that detoxified their corn stover hydrolysate, which were identified as *Amorphotheca resinae* and *Eupenicillium baarnense*, respectively. In a subsequent paper (Ran et al., 2014, Biotechnology for Biofuels 7:51) growth of the *A. resinae* strain, designated as ZN1, was reported to be supported by many compounds including HMF. HMF was degraded and HMF alcohol and HMFCA accumulated over time but no accumulation of FDCA was reported.

Govinda Rajulu et al. (2014, Mycological Progress 13:1049-1056) similarly isolated a number of fungi with the ability to utilize furfural and/or HMF as sole carbon source but again, no accumulation of FDCA was reported.

Thus, several fungi have been described that either grow at the expense of HMF or detoxify HMF-containing feedstocks. As with yeasts, the organisms were studied from the perspective of reducing HMF into HMF-alcohol for the purpose of detoxifying feedstocks. Production of FDCA by yeast or filamentous fungi, however, has not been described. Yet, fungal production of FDCA from HMF would offer several intrinsic advantages over the bacterial processes in the art. E.g., many fungi tolerate low pH values down to pH=3 or lower for growth, whereas most bacteria prefer neutral pH environments. In the specific situation of large-scale production of FDCA it would be of great advantage if whole-cell production methodologies at low pH-values would be available because of advantages in downstream processing (DSP) and for combating infections.

It is therefore an object of the present invention to provide for fungal cells and their use in processes for the production of FDCA from HMF.

SUMMARY OF THE INVENTION

In a first aspect, the invention relates to a fungal cell comprising a genetic modification that is at least one of: a) a genetic modification that confers to the cell the ability to oxidize 5-hydroxymethyl-2-furancarboxylic acid (HMFCA) to 5-formyl-2-furoic acid (FFCA) or that increases in the cell the specific activity of a enzyme that oxidizes HMFCA to FFCA as compared to a corresponding wild type cell lacking the genetic modification; and, b) a genetic modification that reduces or eliminates the specific activity of an enzyme that is involved in the catabolism of 2,5-furandicarboxylic acid, as compared to a corresponding wild type cell lacking the genetic modification. Preferably the fungal cell further comprises: c) a genetic modification that confers to the cell the ability to oxidize furanic aldehydes to the corresponding furanic carboxylic acids or a genetic modification that increases in the cell the specific activity of a enzyme that oxidizes furanic aldehydes to the corresponding furanic carboxylic acids, as compared to a corresponding wild type cell lacking the genetic modification. In a fungal cell according to the invention; a) the genetic modification in a) is at least one of: i) a modification that increases expression of a nucleotide sequence encoding a polypeptide with HMFCA dehydrogenase activity, which polypeptide comprises an amino acid sequence that has at least 45% sequence identity with the amino acid sequence of at least one of SEQ ID NO.'s: 1-4; and, ii) a modification that increases expression of a nucleotide sequence encoding a polypeptide with furanic oxidase activity, which polypeptide comprises an amino acid sequence that has at least 45% sequence identity with the amino acid sequence of at least one of SEQ ID NO.'s: 7-9; b) the genetic modification in b) is a modification that reduces or eliminates the expression of at least one of: i) a gene encoding an FDCA decarboxylating monooxygenase, wherein preferably the gene is a gene encoding a amino acid sequence with at least 45% sequence identity to at least one of SEQ ID NO.'s: 10 and 11; ii) a gene encoding an FDCA decarboxylase, wherein preferably the gene is a gene encoding a amino acid sequence with at least 45% sequence identity to SEQ ID NO: 12; iii) a gene encoding an FDCA decarboxylating dehydrogenase, wherein preferably the gene is a gene encoding a amino acid sequence with at least 45% sequence identity to SEQ ID NO: 13; and, iv) a gene encoding a lactonases that hydrolyses a lactone resulting from FDCA decarboxylation, wherein preferably the gene is a gene encoding a amino acid sequence with at least 45% sequence identity to SEQ ID NO: 14, and c) the genetic modification in c) is a modification that increases expression of a nucleotide sequence encoding a polypeptide having furanic aldehyde dehydrogenase activity, which aldehyde dehydrogenase has at least one of the abilities of i) oxidizing HMF to HMFCA, ii) oxidizing DFF to FFCA, and, iii) oxidizing FFCA into FDCA, which polypeptide comprises an amino acid sequence that has at least 45% sequence identity with the amino acid sequence of at least one of SEQ ID NO.'s: 5 and 6. A fungal cell according to the invention further preferably comprises a genetic modification selected from: a) a genetic modification that reduces or eliminates the expression of a gene encoding a short chain dehydrogenase that reduces HMF and/or FFCA to the corresponding alcohol, wherein preferably the gene is a gene encoding polypeptide comprising an amino acid sequence with at least 45% sequence identity to SEQ ID NO: 15; b) a genetic modification that increases expression of a nucleotide sequence encoding a polypeptide that transports at least one furanic compound, which polypeptide preferably comprises an amino acid sequence that has at least 45% sequence identity with the amino acid sequence of at least one of SEQ ID NO.'s: 16-18; and, c) a genetic modification that alters the expression of a gene encoding a transcriptional activator of genes involved in furan catabolism, wherein preferably the gene is a gene encoding a polypeptide comprising an amino acid sequence with at least 45% sequence identity to SEQ ID NO: 19. A preferred fungal cell according to the invention is a filamentous fungal cell selected from a genus from the group consisting of: *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, Trichoderma*, and *Ustilago*, more preferably a filamentous fungal cell selected from a species from the group consisting of *Aspergillus niger, Aspergillus awamori, Aspergillus foetidus, Aspergillus sojae, Aspergillus fumigatus, Talaromyces emersonii, Aspergillus oryzae, Myceliophthora thermophila, Trichoderma reesei, Penicillium chrysogenum, Penicillium simplicissimum* and *Penicillium brasilianum*; or, a yeast cell selected from a genus from the group consisting of: *Saccharomyces, Kluyveromyces, Candida, Pichia, Schizosaccharomyces, Hansenula, Kloeckera, Schwanniomyces, Yarrowia, Cryptococcus, Debaromyces, Saccharomycecopsis, Saccharomycodes, Wickerhamia, Debayomyces, Hanseniaspora, Ogataea, Kuraishia, Komagataella, Metschnikowia, Williopsis, Nakazawaea, Torulaspora, Bullera, Rhodotorula*, and *Sporobolomyces*, more preferably a yeast cell selected from a species from the group consisting of from *Kluyveromyces lactis, S. cerevisiae, Hansenula polymorpha, Yarrowia lipolytica, Candida tropicalis* and *Pichia pastoris.*

In a second aspect the invention relates to a process for preparing a polypeptide as defined above in the first aspect of the invention, wherein the polypeptide is: a) a HMFCA dehydrogenase; b) an aldehyde dehydrogenase that oxidizes furanic aldehydes to the corresponding furanic carboxylic acids; c) furanic alcohol/aldehyde oxidase; d) an FDCA decarboxylating monooxygenase; e) an FDCA decarboxylase; f) an FDCA decarboxylating dehydrogenase; g) a lactonase that hydrolyses a lactone resulting from FDCA decarboxylation; h) a short chain dehydrogenase that reduces HMF and/or FFCA to the corresponding alcohol; i) a transporter of at least one furanic compound; or, j) a transcriptional activator of genes involved in furan catabolism, the method comprising the step of cultivating a fungal cell as defined above in the first aspect of the invention, under conditions conducive to expression of the polypeptide and, optionally, recovering the polypeptide.

In a third aspect the invention relates to a process for oxidizing HMFCA to FFCA, the process comprising the step of incubating a fungal cell expressing enzymes that have the ability to oxidize HMFCA to FFCA, wherein preferably a fungal cell is a fungal cell as defined above in the first aspect of the invention, in the presence of HMFCA, under conditions conducive to the oxidation of HMFCA by the cell.

In a fourth aspect the invention pertains to a process for producing FDCA, the process comprising the step of incubating a fungal cell as defined above in the first aspect of the invention, in a medium comprising one or more furanic precursors of FDCA, preferably under conditions conducive to the oxidation of furanic precursors of FDCA by the cell to FDCA, and, optionally recovery of the FDCA, wherein preferably, at least one furanic precursor of FDCA is selected from the group consisting of HMF, 2,5-dihydroxymethyl furan (DHF), HMFCA, FFCA and 2,5-diformyl furan (DFF), of which HMF is most preferred, wherein the furanic precursors of FDCA are obtained from one or more hexose sugars, preferably one or more hexose sugars obtained from lignocellulosic biomass, preferably by acid-catalyzed dehydration, and, wherein preferably the FDCA is recovered from the medium by a process comprising acid precipitation followed by cooling crystallization and/or solvent extraction.

In a fifth aspect the invention pertains to a process for producing FDCA, the process comprising the step of incubating a fungal cell expressing one or more enzymes that have the ability to convert a furanic precursor of FDCA into FDCA, in a medium with a pH in the range of 2.0-3.0 and comprising one or more furanic precursors of FDCA, preferably under conditions conducive to the oxidation of furanic precursors of FDCA by the cell to FDCA, wherein preferably, at least one furanic precursor of FDCA is selected from the group consisting of HMF, 2,5-dihydroxymethyl furan (DHF), HMFCA, FFCA and 2,5-diformyl furan (DFF), of which HMF is most preferred, wherein the furanic precursors of FDCA are obtained from one or more hexose sugars, preferably one or more hexose sugars obtained from lignocellulosic biomass, preferably by acid-catalyzed dehydration, wherein preferably the FDCA precipitate from the acidic medium in which it is produced and is recovered from the medium by a process comprising acid precipitation followed by cooling crystallization. Preferably, in a process according to the fifth aspect of the invention, the fungal cell is a fungal cell as defined above in the first aspect of the invention or a fungal cell expressing one or more bacterial enzymes with the ability to convert a furanic precursors of FDCA into FDCA.

In a sixth aspect the invention pertains to a process for producing a polymer from one or more, or at least two FDCA monomers, the process comprising the steps of: preparing an FDCA monomer in a process according to the fourth or fifth aspect of the invention; and, producing a polymer from the FDCA monomer obtained in a).

In a seventh aspect the invention relates to the use of a fungal cell, preferably a fungal cell as defined above in the first aspect of the invention or a fungal cell expressing one or more bacterial enzymes with the ability to convert a furanic precursors of FDCA into FDCA, for the biotransformation of one or more of furanic precursors to FDCA, wherein preferably, at least one furanic precursor of FDCA is selected from the group consisting of HMF, DHF, HMFCA, FFCA and DFF, of which HMF is most preferred.

In an eighth aspect the invention relates to a polypeptide selected from the group consisting of: a) an HMFCA dehydrogenase having the ability to oxidize HMFCA to FFCA and comprising an amino acid sequence that is at least one of: i) an amino acid sequence with at least 73.9% sequence identity with the amino acid sequence of SEQ ID NO: 1; ii) an amino acid sequence with at least 69.4% sequence identity with the amino acid sequence of SEQ ID NO: 2; iii) an amino acid sequence with at least 84.5% sequence identity with the amino acid sequence of SEQ ID NO: 3; and, iv) an amino acid sequence with at least 88% sequence identity with the amino acid sequence of SEQ ID NO: 4; b) a furanic aldehyde dehydrogenase having the ability to oxidize at least one of i) oxidizing HMF to HMFCA, ii) oxidizing DFF to FFCA, and iii) oxidizing FFCA into FDCA and comprising an amino acid sequence that is at least one of: i) an amino acid sequence with at least 70.9% sequence identity with the amino acid sequence of SEQ ID NO: 5; and, ii) an amino acid sequence with at least 85% sequence identity with the amino acid sequence of SEQ ID NO: 6; c) a furanic oxidase activity has the ability to oxidize at least one of i) HMF to HMFCA, ii) HMF to DFF, iii) DFF to FFCA, iv) HMFCA to FFCA, and v) FFCA to FDCA and comprising an amino acid sequence that is at least one of: i) an amino acid sequence with at least 62.7% sequence identity with the amino acid sequence of SEQ ID NO: 7; ii) an amino acid sequence with at least 49.3% sequence identity with the amino acid sequence of SEQ ID NO: 8; and, ii) an amino acid sequence with at least 66.9% sequence identity with the amino acid sequence of SEQ ID NO: 9; d) an FDCA decarboxylating monooxygenase comprising an amino acid sequence that is at least one of: i) an amino acid sequence with at least 82.3% sequence identity with the amino acid sequence of SEQ ID NO: 10; and, ii) an amino acid sequence with at least 43.4% sequence identity with the amino acid sequence of SEQ ID NO: 11; e) an FDCA decarboxylase comprising an amino acid sequence that has at least 62.9% sequence identity with the amino acid sequence of SEQ ID NO: 12; and, f) FDCA decarboxylating dehydrogenase comprising an amino acid sequence that has at least 85.4% sequence identity with the amino acid sequence of SEQ ID NO: 13; g) a lactonase having the ability to hydrolyse a lactone resulting from decarboxylation of FDCA, wherein the lactonase comprises an amino acid sequence that has at least 67.5% sequence identity with the amino acid sequence of SEQ ID NO: 14; h) a short chain dehydrogenase capable of reducing at least one of HMF and FFCA to the corresponding alcohol and comprising an amino acid sequence that has at least 73.6% sequence identity with the amino acid sequence of SEQ ID NO: 15; i) a transporter of furanic compounds comprising an amino acid sequence that is at least one of: i) an amino acid sequence with at least 85.2% sequence identity with the amino acid sequence of SEQ ID NO: 16; ii) an amino acid sequence with at least 69% sequence identity with the amino acid sequence of SEQ ID NO: 17; and, ii) an amino acid sequence with at least 84.1% sequence identity with the amino acid sequence of SEQ ID NO: 18; and, j) a transcriptional activator of genes involved in furan catabolism comprising an amino acid sequence that has at least 52.4% sequence identity with the amino acid sequence of SEQ ID NO: 19.

In a ninth aspect the invention pertains to a nucleic acid molecule comprising at least one of: a) a nucleotide sequence encoding a polypeptide as defined in the eighth aspect of the invention; b) a nucleotide sequence set out in SEQ ID NO's: 20-35; c) a fragment of a nucleotide sequence as defined in (a) or (b) which is at 10, 15, 20, 30, 50 or 100 nucleotides in length; d) a nucleotide sequence the sequence of which differs from the sequence of a nucleotide sequence of b) or c) due to the degeneracy of the genetic code; and, e) a nucleotide sequence which is the reverse complement of a nucleotide sequence as defined in a) to d), wherein, preferably the nucleic acid molecule is a vector.

BRIEF DESCRIPTION OF THE FIGURE

FIG. 1: schematic representation of FDCA production from the furanic precursor HMF and the subsequent breakdown of FDCA into lactone and a-ketoglutarate.

DESCRIPTION OF THE INVENTION

Definitions

The terms "homology", "sequence identity" and the like are used interchangeably herein. Sequence identity is herein defined as a relationship between two or more amino acid (polypeptide or protein) sequences or two or more nucleic acid (polynucleotide) sequences, as determined by comparing the sequences. In the art, "identity" also means the degree of sequence relatedness between amino acid or nucleic acid sequences, as the case may be, as determined by the match between strings of such sequences. "Similarity" between two amino acid sequences is determined by comparing the amino acid sequence and its conserved amino acid substitutes of one polypeptide to the sequence of a second polypeptide. "Identity" and "similarity" can be readily calculated by known methods.

"Sequence identity" and "sequence similarity" can be determined by alignment of two peptide or two nucleotide sequences using global or local alignment algorithms, depending on the length of the two sequences. Sequences of similar lengths are preferably aligned using a global alignment algorithms (e.g. Needleman Wunsch) which aligns the sequences optimally over the entire length, while sequences of substantially different lengths are preferably aligned using a local alignment algorithm (e.g. Smith Waterman). Sequences may then be referred to as "substantially identical" or "essentially similar" when they (when optimally aligned by for example the programs GAP or BESTFIT using default parameters) share at least a certain minimal percentage of sequence identity (as defined below). GAP uses the Needleman and Wunsch global alignment algorithm to align two sequences over their entire length (full length), maximizing the number of matches and minimizing the number of gaps. A global alignment is suitably used to determine sequence identity when the two sequences have similar lengths. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA, or using open source software, such as the program "needle" (using the global Needleman Wunsch algorithm) or "water" (using the local Smith Waterman algorithm) in EmbossWIN version 2.10.0, using the same parameters as for GAP above, or using the default settings (both for 'needle' and for 'water' and both for protein and for DNA alignments, the default Gap opening penalty is 10.0 and the default gap extension penalty is 0.5; default scoring matrices are Blossum62 for proteins and DNAFull for DNA). When sequences have a substantially different overall lengths, local alignments, such as those using the Smith Waterman algorithm, are preferred.

Alternatively percentage similarity or identity may be determined by searching against public databases, using algorithms such as FASTA, BLAST, etc. Thus, the nucleic acid and protein sequences of the present invention can further be used as a "query sequence" to perform a search against public databases to, for example, identify other family members or related sequences. Such searches can be performed using the BLASTn and BLASTx programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to oxidoreductase nucleic acid molecules of the invention. BLAST protein searches can be performed with the BLASTx program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., BLASTx and BLASTn) can be used. See the homepage of the National Center for Biotechnology Information at ww.ncbi.nlm.nih.gov/.

Optionally, in determining the degree of amino acid similarity, the skilled person may also take into account so-called "conservative" amino acid substitutions, as will be clear to the skilled person. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagines and glutamine; a group of amino acids having aromatic side chains is phenylalanine, tyrosine, and tryptophan; a group of amino acids having basic side chains is lysine, arginine, and histidine; and a group of amino acids having sulphur-containing side chains is cysteine and methionine. Preferred conservative amino acids substitution groups are: valine-leucine-isoleucine, phenylalanine-tyrosine, lysine-arginine, alanine-valine, and asparagine-glutamine. Substitutional variants of the amino acid sequence disclosed herein are those in which at least one residue in the disclosed sequences has been removed and a different residue inserted in its place. Preferably, the amino acid change is conservative. Preferred conservative substitutions for each of the naturally occurring amino acids are as follows: Ala to ser; Arg to lys; Asn to gln or his; Asp to glu; Cys to ser or ala; Gln to asn; Glu to asp; Gly to pro; His to asn or gln; Ile to leu or val; Leu to ile or val; Lys to arg; gln or glu; Met to leu or ile; Phe to met, leu or tyr; Ser to thr; Thr to ser; Trp to tyr; Tyr to trp or phe; and, Val to ile or leu.

As used herein, the term "selectively hybridizing", "hybridizes selectively" and similar terms are intended to describe conditions for hybridization and washing under which nucleotide sequences at least 66%, at least 70%, at least 75%, at least 80%, more preferably at least 85%, even more preferably at least 90%, preferably at least 95%, more preferably at least 98% or more preferably at least 99% homologous to each other typically remain hybridized to each other. That is to say, such hybridizing sequences may share at least 45%, at least 50%, at least 55%, at least 60%, at least 65, at least 70%, at least 75%, at least 80%, more preferably at least 85%, even more preferably at least 90%, more preferably at least 95%, more preferably at least 98% or more preferably at least 99% sequence identity.

A preferred, non-limiting example of such hybridization conditions is hybridization in 6× sodium chloride/sodium citrate (SSC) at about 45° C., followed by one or more washes in 1×SSC, 0.1% SDS at about 50° C., preferably at about 55° C., preferably at about 60° C. and even more preferably at about 65° C.

Highly stringent conditions include, for example, hybridization at about 68° C. in 5×SSC/5×Denhardt's solution/1.0% SDS and washing in 0.2×SSC/0.1% SDS at room temperature. Alternatively, washing may be performed at 42° C.

The skilled artisan will know which conditions to apply for stringent and highly stringent hybridization conditions. Additional guidance regarding such conditions is readily available in the art, for example, in Sambrook et al., 1989, Molecular Cloning, A Laboratory Manual, Cold Spring Harbor Press, N.Y.; and Ausubel et al. (eds.), Sambrook and Russell (2001) "Molecular Cloning: A Laboratory Manual (3$^{rd}$ edition), Cold Spring Harbor Laboratory, Cold Spring Harbor Laboratory Press, New York 1995, Current Protocols in Molecular Biology, (John Wiley & Sons, N.Y.).

Of course, a polynucleotide which hybridizes only to a poly A sequence (such as the 3' terminal poly(A) tract of mRNAs), or to a complementary stretch of T (or U) resides, would not be included in a polynucleotide of the invention used to specifically hybridize to a portion of a nucleic acid of the invention, since such a polynucleotide would hybridize to any nucleic acid molecule containing a poly (A) stretch or the complement thereof (e.g., practically any double-stranded cDNA clone).

A "nucleic acid construct" or "nucleic acid vector" is herein understood to mean a man-made nucleic acid molecule resulting from the use of recombinant DNA technology. The term "nucleic acid construct" therefore does not include naturally occurring nucleic acid molecules although a nucleic acid construct may comprise (parts of) naturally occurring nucleic acid molecules. The terms "expression vector" or "expression construct" refer to nucleotide sequences that are capable of effecting expression of a gene in host cells or host organisms compatible with such sequences. These expression vectors typically include at least suitable transcription regulatory sequences and optionally, 3' transcription termination signals. Additional factors necessary or helpful in effecting expression may also be present, such as expression enhancer elements. The expression vector will be introduced into a suitable host cell and be able to effect expression of the coding sequence in an in vitro cell culture of the host cell. The expression vector will be suitable for replication in the host cell or organism of the invention.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer.

The term "selectable marker" is a term familiar to one of ordinary skill in the art and is used herein to describe any genetic entity which, when expressed, can be used to select for a cell or cells containing the selectable marker. The term "reporter" may be used interchangeably with marker, although it is mainly used to refer to visible markers, such as green fluorescent protein (GFP). Selectable markers may be dominant or recessive or bidirectional.

As used herein, the term "operably linked" refers to a linkage of polynucleotide elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means that the DNA sequences being linked are typically contiguous and, where necessary to join two protein encoding regions, contiguous and in reading frame.

The terms "protein" or "polypeptide" are used interchangeably and refer to molecules consisting of a chain of amino acids, without reference to a specific mode of action, size, 3-dimensional structure or origin.

The term "gene" means a DNA fragment comprising a region (transcribed region), which is transcribed into an RNA molecule (e.g. an mRNA) in a cell, operably linked to suitable regulatory regions (e.g. a promoter). A gene will usually comprise several operably linked fragments, such as a promoter, a 5' leader sequence, a coding region and a 3'-nontranslated sequence (3'-end) comprising a polyadenylation site. "Expression of a gene" refers to the process wherein a DNA region which is operably linked to appropriate regulatory regions, particularly a promoter, is transcribed into an RNA, which is biologically active, i.e. which is capable of being translated into a biologically active protein or peptide. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain. If homologous to a host cell, a nucleic acid sequence encoding a polypeptide will typically (but not necessarily) be operably linked to another (heterologous) promoter sequence and, if applicable, another (heterologous) secretory signal sequence and/or terminator sequence than in its natural environment. It is understood that the regulatory sequences, signal sequences, terminator sequences, etc. may also be homologous to the host cell. In this context, the use of only "homologous" sequence elements allows the construction of "self-cloned" genetically modified organisms (GMO's) (self-cloning is defined herein as in European Directive 98/81/EC Annex II). When used to indicate the relatedness of two nucleic acid sequences the term "homologous" means that one single-stranded nucleic acid sequence may hybridize to a complementary single-stranded nucleic acid sequence. The degree of hybridization may depend on a number of factors including the amount of identity between the sequences and the hybridization conditions such as temperature and salt concentration as discussed later.

The terms "heterologous" and "exogenous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous and exogenous nucleic acids or proteins are not endogenous to the cell into which it is introduced, but have been obtained from another cell or synthetically or recombinantly produced. Generally, though not necessarily, such nucleic acids encode proteins, i.e. exogenous proteins, that are not normally produced by the cell in which the DNA is transcribed or expressed. Similarly exogenous RNA encodes for proteins not normally expressed in the cell in which the exogenous RNA is present. Heterologous/exogenous nucleic acids and proteins may also be referred to as foreign nucleic acids or proteins. Any nucleic acid or protein that one of skill in the art would recognize as foreign to the cell in which it is expressed is herein encompassed by the term heterologous or exogenous nucleic acid or protein. The terms heterologous and exogenous also apply to non-natural combinations of nucleic acid or amino acid sequences, i.e. combinations where at least two of the combined sequences are foreign with respect to each other.

The "specific activity" of an enzyme is herein understood to mean the amount of activity of a particular enzyme per amount of total host cell protein, usually expressed in units of enzyme activity per mg total host cell protein. In the context of the present invention, the specific activity of a particular enzyme may be increased or decreased as compared to the specific activity of that enzyme in an (otherwise identical) wild type host cell.

"Furanic compounds" are herein understood to be 2,5-furan-dicarboxylic acid (FDCA) as well as any compound having a furan group which may be oxidized to FDCA, the latter being referred to herein as a "precursor of FDCA" or a "furanic precursor of FDCA". Precursors of FDCA at least include: 5-hydroxymethylfurfural (HMF), 2,5-dihydroxymethyl furan (DHF) or 2,5-bis(hydroxymethyl)furan (BHF) referred to as HMF-OH, 5-hydroxymethyl-2-furancarboxylic acid or 5-hydroxymethyl-2-furoic acid (HMFCA), 5-formyl-2-furoic acid (FFCA), and 2,5-diformyl furan (DFF). It is further understood that in the "furanic compounds", the furan ring or any or its substitutable sidegroup may be substituted, e.g. with OH, C1-C10 alkyl, alkyl, allyl, aryl or RO-ether moiety, including cyclic groups, in the furan ring on any available position.

"Aerobic conditions" "Oxic conditions" or an aerobic or oxic fermentation process is herein defined as conditions or a fermentation process run in the presence of oxygen and in which oxygen is consumed, preferably at a rate of at least 0.5, 1, 2, 5, 10, 20 or 50 mmol/L/h, and wherein organic molecules serve as electron donor and oxygen serves as electron acceptor.

"Anaerobic or anoxic conditions" or an "anaerobic or anoxic fermentation process" is herein defined as conditions or a fermentation process run substantially in the absence of oxygen and wherein organic molecules serve as both electron donor and electron acceptors. Under anoxic conditions substantially no oxygen is consumed, preferably less than 5, 2, 1, or 0.5 mmol/L/h, more preferably 0 mmol/L/h is consumed (i.e. oxygen consumption is not detectable), or substantially no dissolved oxygen can be detected in the fermentation medium, preferably the dissolved oxygen concentration in the medium is less than 2, 1, 0.5, 0.2, 0.1% of air saturation, i.e. below the detection limit of commercial oxygen probes.

Any reference to nucleotide or amino acid sequences accessible in public sequence databases herein refers to the version of the sequence entry as available on the filing date of this document.

DETAILED DESCRIPTION OF THE INVENTION

The Parent Host Cell

The present invention concerns the genetic modification of a host cell so as to enable the host cell to produce 2,5-furandicarboxylic acid (FDCA) from suitable furanic precursors. To this end a number of genetic modifications can be introduced in a parent host cell in accordance with the invention. These modifications include the introduction of expression of a number of heterologous genes, as well as, the modification of the expression of a number of endogenous genes already present in the parent host cell, by reducing or eliminating of some endogenous genes and/or by increasing the expression, i.e. overexpressing, other endogenous genes. These genetic modification are further set out below herein. A parent host cell is thus understood to be a host cell prior to that any of the genetic modifications in accordance with the invention have been introduced in the host cell.

A parent host cell of the invention can be any suitable host cell including e.g. eukaryotic cells such as a mammalian, insect, plant, fungal, or algal cell. Preferred mammalian cells include e.g. Chinese hamster ovary (CHO) cells, COS cells, 293 cells, PerC6 cells, and hybridomas. Preferred insect cells include e.g. Sf9 and Sf21 cells and derivatives thereof.

Preferably, however, the host cell is a microbial cell. The microbial host cell can also be a prokaryotic cell, preferably a bacterial cell. The term "bacterial cell" includes both Gram-negative and Gram-positive microorganisms. Suitable bacteria may be selected from the genera *Escherichia, Anabaena, Aeribacillus, Aneurinibacillus, Burkholderia, Bradyrhizobium, Caulobacter, Cupriavidus, Desulfotomaculum, Desulfurispora, Gluconobacter, Rhodobacter, Pelotomaculum, Pseudomonas, Paracoccus, Bacillus, Geobacillus, Brevibacillus, Brevibacterium, Corynebacterium, Rhizobium* (*Sinorhizobium*), *Flavobacterium, Klebsiella, Enterobacter, Lactobacillus, Lactococcus, Methylobacterium, Ralstonia, Rhodopseudomonas, Staphylococcus* and *Streptomyces*. Preferably, the bacterial cell is selected from a species from the group consisting of *A. pallidus, A. terranovensis, B. subtilis, B. amyloliquefaciens, B. coagulans, B. kribbensis, B. licheniformis, B. puntis, B. megaterium, B. halodurans, B. pumilus, B. thermoruber, B. panacihumi, C. basilensis, D. kuznetsovii, D. thermophila, G. kaustophilus, Gluconobacter oxydans, Caulobacter crescentus* CB 15, *Methylobacterium extorquens, Rhodobacter sphaeroides, Pelotomaculum thermopropionicum, Pseudomonas zeaxanthinifaciens, Pseudomonas putida, Paracoccus denitrificans, E. coli, C. glutamicum, Staphylococcus carnosus, Streptomyces lividans, Sinorhizobium melioti* and *Rhizobium radiobacter*. Within the species *Pseudomonas putida*, the strains *P. putida* S12 and *P. putida* KT2440 are preferred.

More preferably, however, a parent host cell of the invention is a eukaryotic microbial host cell, such as e.g. a fungal host cell. A most preferred parent host cell to be modified in accordance with the invention is a yeast or filamentous fungal host cell.

"Fungi" are herein defined as eukaryotic microorganisms and include all species of the subdivision Eumycotina (Alexopoulos, C. J., 1962, In: Introductory Mycology, John Wiley & Sons, Inc., New York). The terms "fungus" and "fungal" thus include or refers to both filamentous fungi and yeast.

"Filamentous fungi" are herein defined as eukaryotic microorganisms that include all filamentous forms of the subdivision Eumycotina and Oomycota (as defined in "Dictionary of The Fungi", 10th edition, 2008, CABI, UK, www.cabi.org). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. Filamentous fungal strains include, but are not limited to, strains of *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium, Trichoderma*, and *Ustilago*.

Preferred filamentous fungal species as parent host cells for the invention belong to a species of an *Aspergillus, Myceliophthora, Penicillium, Talaromyces* or *Trichoderma* genus, and more preferably a species selected from *Aspergillus niger, Aspergillus awamori, Aspergillus foetidus, Aspergillus sojae, Aspergillus fumigatus, Talaromyces emersonii, Aspergillus oryzae, Myceliophthora thermophila, Trichoderma reesei, Penicillium chrysogenum, Penicillium simplicissimum* and *Penicillium brasilianum*.

"Yeasts" are herein defined as eukaryotic microorganisms and include all species of the subdivision Eumycotina (Yeasts: characteristics and identification, J. A. Barnett, R. W. Payne, D. Yarrow, 2000, 3rd ed., Cambridge University Press, Cambridge UK; and, The yeasts, a taxonomic study, C P. Kurtzman and J. W. Fell (eds) 1998, 4th ed., Elsevier Science Publ. B.V., Amsterdam, The Netherlands) that predominantly grow in unicellular form. Yeasts may either grow by budding of a unicellular thallus or may grow by fission of the organism. Preferred yeasts cells for use in the present invention belong to the genera *Saccharomyces, Kluyveromyces, Candida, Pichia, Schizosaccharomyces, Hansenula, Kloeckera, Schwanniomyces, Yarrowia, Cryptococcus, Debaromyces, Saccharomycecopsis, Saccharomycodes, Wickerhamia, Debayomyces, Hanseniaspora, Ogataea, Kuraishia, Komagataella, Metschnikowia, Williopsis, Nakazawaea, Torulaspora, Bullera, Rhodotorula*, and *Sporobolomyces*. A parental yeast host cell can be a cell that is naturally capable of anaerobic fermentation, more preferably alcoholic fermentation and most preferably anaerobic alcoholic fermentation. More preferably yeasts from species such as *Kluyveromyces lactis, S. cerevisiae, Hansenula polymorpha* (new name: *Ogataea henricii*), *Yarrowia lipolytica, Candida tropicalis* and *Pichia pastoris* (new name: *Komagataella pastoris*).

Particularly when compared to bacteria, fungi, have many attractive features for industrial fermentation processes, including e.g. their high tolerance to acids, ethanol and other harmful compounds, their high osmo-tolerance, their high fermentative capacity and for some yeasts their capability of anaerobic growth.

The host cell further preferably has a high tolerance to low pH, i.e. capable of growth at a pH equal to or lower than 5.0, 4.0, 3.0, 2.9, 2.8, 2.7, 2.6, 2.5 or 2.4 and towards organic acids like lactic acid, acetic acid or formic acid and furanic acids and a high tolerance to elevated temperatures. Any of these characteristics or activities of the host cell may be naturally present in the host cell or may be introduced or modified by genetic modification, preferably by self cloning or by the methods of the invention described below.

A suitable cell is a cultured cell, a cell that may be cultured in fermentation process e.g. in submerged or solid state fermentation.

For specific uses of a compound produced in a fungal host cell according to the invention, the selection of the host cell may be made according to such use. Where e.g. the compound produced in a host cell according to the invention is to be used in food applications, a host cell may be selected from a food-grade organism such as e.g. a *Saccharomyces* species, e.g. *S. cerevisiae*, a food-grade *Penicillium* species or *Yarrowia lipolitica*. Specific uses include, but are not limited to, food, (animal) feed, pharmaceutical, agricultural such as crop-protection, and/or personal care applications.

A Genetically Modified Cell

In a first aspect, the invention pertains to a cell, preferably a fungal cell comprising a genetic modification. The genetic modification of the cell preferably is at least one of: a) a genetic modification that confers to the cell the ability to oxidize 5-hydroxymethyl-2-furancarboxylic acid (HMFCA) to 5-formyl-2-furoic acid (FFCA) or that increases in the cell the specific activity of a enzyme that oxidizes HMFCA to FFCA as compared to a corresponding wild type cell lacking the genetic modification; and, b) a genetic modification that reduces or eliminates the specific activity of an enzyme that catalyses the degradation of 2,5-furandicarboxylic acid, as compared to a corresponding wild type cell lacking the genetic modification. Preferred cells having the genetic modifications of a) and b) are further specified herein below.

A cell of the invention further preferably comprises c) a genetic modification that confers to the cell the ability to oxidize furanic aldehydes to the corresponding furanic carboxylic acids or that increases in the cell the specific activity of a enzyme that oxidizes furanic aldehydes to the corresponding furanic carboxylic acids, as compared to a corresponding wild type cell lacking the genetic modification. Preferred cells having the genetic modification of c) are also further specified herein below.

Introducing or Increasing HMFCA Dehydrogenase Activity

A cell of the invention preferably is a cell that has the ability of oxidizing 5-hydroxymethyl-2-furancarboxylic acid (HMFCA) to 5-formylfuroic acid (FFCA). The cell's ability of oxidizing HMFCA to FFCA can be an endogenous activity of the cell or it can be an exogenous activity conferred to the cell. Preferably, the ability of oxidizing HMFCA to FFCA is conferred to the cell or increased in the cell by a genetic modification of the cell, e.g. a transformation of the cell with a nucleic acid construct comprising a nucleotide sequence encoding a dehydrogenase or an oxidase that has the ability to oxidize HMFCA to FFCA. The dehydrogenase preferably is an alcohol dehydrogenase (i.e. having EC 1.1 activity). Thus, the cell is preferably a cell comprising an expression construct for expression of a nucleotide sequence encoding a dehydrogenase or an oxidase that has the ability to oxidize HMFCA to FFCA. In a preferred cell of the invention, the expression construct is expressible in the cell and expression of the dehydrogenase or oxidase preferably confers to in the cell the ability to oxidize HMFCA to FFCA or increases in the cell the specific activity of a enzyme that oxidizes HMFCA to FFCA, as compared to a corresponding cell lacking the expression construct, e.g. a wild type cell. The specific activity of the enzyme that oxidizes HMFCA to FFCA is preferably increased in the cell by at least a factor 1.05, 1.1, 1.2, 1.5, 2.0, 5.0, 10, 20, 50 or 100 as compared to a corresponding cell lacking the expression construct.

The enzyme that has the ability to oxidize HMFCA to FFCA can be an alcohol dehydrogenase or the enzyme can be an oxidase as described herein below. A preferred enzyme that has the ability to oxidize HMFCA to FFCA is an alcohol dehydrogenase that has HMFCA dehydrogenase activity. Whether or not a polypeptide has HMFCA dehydrogenase activity can be assayed by expression of the polypeptide in a suitable host cell that is incapable of oxidizing HMFCA to FFCA and detecting whether or not expression of the polypeptide confers to the cell the ability to oxidize HMFCA to FFCA. HMFCA dehydrogenase activity can e.g. be assayed using an expression construct wherein a nucleotide sequence encoding the polypeptide to be assayed for HMFCA dehydrogenase activity replaces the *C. basilensis* hmfH gene in pBT'hmfH-adh (described in WO2012/064195), after which the plasmid comprising coding sequence of the polypeptide to be assayed for HMFCA dehydrogenase activity is introduced into *P. putida* KT2440Δgcd containing pJNNhmfT1(t) (also described in WO2012/064195). The *P. putida* transformants expressing the polypeptide to be assayed for HMFCA dehydrogenase activity are incubated with HMF and samples are drawn at regular intervals for analysis of FDCA. An increase of production of FDCA, as compared to corresponding *P. putida* transformants lacking the polypeptide to be assayed for HMFCA dehydrogenase activity (and the *C. basilensis* hmfH gene) is taken as an indication that the polypeptide has HMFCA dehydrogenase activity. Alternatively, a nucleotide sequence encoding the polypeptide to be assayed for HMFCA dehydrogenase activity can be expressed in a fungal host cell, preferably a *S. cerevisiae* host cell, as e.g. described in Example 7 herein and detecting whether expression of the polypeptide confers to a fungal host cell the ability to produce both FFCA and/or FDCA from HMF.

The HMFCA dehydrogenase expressed in the cell of the invention preferably is a dehydrogenase that is dependent on a cofactor selected from an adenine dinucleotide, such as NADH or NADPH, a flavin adenine dinucleotide (FAD), a flavin mononucleotide (FMN), and pyrroloquinoline quinolone (PQQ). The HMFCA dehydrogenase expressed in the cell of the invention preferably binds a divalent cation, more preferably the HMFCA dehydrogenase is Zn-binding dehydrogenase.

The HMFCA dehydrogenase expressed in the cell of the invention further preferably is an alcohol dehydrogenase that (also) has the ability of oxidizing other furanic alcohols, preferably furanic alcohols with an hydroxy group in the 2-position, to the corresponding aldehydes. Thus, HMFCA dehydrogenase preferably has the ability of oxidizing 5-hydroxymethylfurfural (HMF) to 2,5-diformyl furan (DFF).

In one embodiment the nucleotide sequence encoding the dehydrogenase with the ability to oxidize HMFCA to FFCA is selected from the group consisting of:

(a) a nucleotide sequence encoding a polypeptide with HMFCA dehydrogenase activity, which polypeptide comprises an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of at least one of SEQ ID NO.'s: 1-4 (hmfL1, hmfL2, hmfL3 and hmfL4, respectively), more preferably at least one of SEQ ID NO.'s: 1 and 2;

(b) a nucleotide sequence the complementary strand of which hybridises to a nucleotide sequence of (a); and, (c) a nucleotide sequence the sequence of which differs from the sequence of a nucleotide sequence of (b) due to the degeneracy of the genetic code.

A preferred nucleotide sequence of the invention thus encodes a HMFCA dehydrogenase with an amino acid sequence that is identical to that of a HMFCA dehydrogenase that is obtainable from (or naturally occurs in) a fungus of a genus selected from the group consisting of *Aspergillus, Byssochlamys, Coccidioides, Chaetomium, Eutypa, Endocarpon, Fusarium, Microsporum, Neosartorya, Penicillium, Sporothrix* and *Trichophyton*, more preferably, a fungus of a species selected from the group consisting of *Coccidioides immitis, Coccidioides posadasii, Endocarpon pusillum, Microsporum gypseum, Penicillium brasilianum* and *Sporothrix schenckii*, most preferably a fungus, which is the strain *P. brasilianum* C1.

In one embodiment the nucleotide sequence encodes a polypeptide with HMFCA dehydrogenase activity as it occurs in nature, e.g. as it can isolated from a wild type source organism. Alternatively, the nucleotide sequence can encode engineered forms of any of the HMFCA dehydrogenase defined above and that comprise one or more amino acid substitutions, insertions and/or deletions as compared to the corresponding naturally occurring HMFCA dehydrogenase but that are within the ranges of identity or similarity as defined herein. Therefore, in one embodiment the nucleotide sequence of the invention encodes a HMFCA dehydrogenase the amino acid sequence of which at least comprises in each of the invariable positions (that are indicated in Tables 1-4 with a "*"), the amino acid present in a invariable position. Preferably, the amino acid sequence also comprises in the strongly conserved positions (that are indicated in Tables 1-4 with a ":") one of the amino acids present in a strongly conserved position. More preferably, the amino acid sequence further also comprises in the less strongly conserved positions (that are indicated in Tables 1-4 with a ".") one of the amino acids present in a less strongly conserved position. Amino acid substitutions outside of these invariable and conserved positions are less unlikely to affect HMFCA dehydrogenase activity. Tables 1-4 present the amino acid sequence alignments of each of *Penicillium brasilianum* hmfL1, hmfL2, hmfL3 and hmfL4, respectively with their 10 closest orthologues as available in public databases. Tables 1A-4A provide the percentages amino acid identities among the *P. brasilianum* sequences and their orthologues, as well as the accession numbers of the orthologues.

The nucleotide sequences of the invention, encoding polypeptides with HMFCA dehydrogenase activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with HMFCA dehydrogenase activity; b) the PCR fragment obtained in a) is used as probe to screen a cDNA and/or genomic library of the organism; and c) producing a cDNA or genomic DNA comprising the nucleotide sequence encoding a polypeptide with HMFCA dehydrogenase activity.

To increase the likelihood that a HMFCA dehydrogenase of the invention is expressed at sufficient levels and in active form in the cells of the invention, the nucleotide sequence encoding these enzymes, as well as other enzymes of the invention (see below), are preferably adapted to optimise their codon usage to that of the host cell in question. The adaptiveness of a nucleotide sequence encoding a polypeptide to the codon usage of a host cell may be expressed as codon adaptation index (CAI). The codon adaptation index is herein defined as a measurement of the relative adaptiveness of the codon usage of a gene towards the codon usage of highly expressed genes in a particular host cell or organism. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Jansen et al., 2003, Nucleic Acids Res. 31(8):2242-51). An adapted nucleotide sequence preferably has a CAI of at least 0.2, 0.3, 0.4, 0.5, 0.6, 0.7, 0.8 or 0.9. Most preferred are the sequences as listed in SEQ ID NO's: 57-59, which have been codon optimised for expression in yeast cells, preferably *S. cerevisiae* cells.

The fungal host cell to be transformed with a nucleic acid construct for expression of the nucleotide sequence encoding a HMFCA dehydrogenase of the invention can in principle be any fungal host cell in which the HMFCA dehydrogenase invention can suitably be expressed, preferably in functional, i.e. active form. The fungal host cell of the invention, preferably is a host cell capable of active or passive transport of furanic compounds into as well as out of the cell. A preferred host cell of the invention lacks or has no detectable activities that degrade (e.g. decarboxylate) carboxylated furanic compounds, such as in particular HMFCA, FFCA and FDCA. Such a host cell preferably naturally lacks the ability to degrade carboxylated furanic compounds. Alternatively, a fungal host cell can be genetically modified to reduce or eliminate the specific activities of one or more enzymes that catalyses the degradation of carboxylated furanic compounds, as described herein below.

The expression construct for expression of a nucleotide sequence encoding a HMFCA dehydrogenase of the invention, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a HMFCA dehydrogenase of the invention in appropriate host cells are described in more detail herein below.

Introducing or Increasing Furanic Aldehyde Dehydrogenase Activity

A cell expressing an HMFCA dehydrogenase of the invention, as described above, further preferably has aldehyde dehydrogenase activity (i.e. having EC 1.2 activity). Preferably, the aldehyde dehydrogenase is capable of converting furanic aldehydes. More preferably the aldehyde dehydrogenase activity is capable of oxidizing furanic aldehydes to the corresponding furanic carboxylic acids. More specifically, the aldehyde dehydrogenase activity is preferably capable of at least one of i) oxidizing HMF to HMFCA, ii) oxidizing 2,5-diformyl furan (DFF) to 5-formyl-2-furoic acid (FFCA), and iii) FFCA into FDCA. Such furanic aldehyde dehydrogenase activity can be an endogenous activity of the cell or it can be an exogenous activity conferred to the cell. Preferably, the furanic aldehyde dehydrogenase activity is conferred to or increased in the cell by transformation of the cell with an expression construct, e.g. a second expression construct if the cell already comprises a first expression construct for expression of the HMFCA dehydrogenase.

In a preferred cell of the invention, the expression construct for expression of the furanic aldehyde dehydrogenase is expressible in the cell and expression of the furanic aldehyde dehydrogenase preferably confers to the ability to oxidize at least one of i) oxidizing HMF to HMFCA, ii) oxidizing DFF to FFCA, and iii) oxidizing FFCA into FDCA, or increases in the cell the specific activity of a furanic aldehyde dehydrogenase with at least one of these abilities, as compared to a corresponding cell lacking the expression construct, e.g. a wild type cell. The specific activity of the furanic aldehyde dehydrogenase is preferably increased in the cell by at least a factor 1.05, 1.1, 1.2, 1.5, 2.0, 5.0, 10, 20, 50 or 100 as compared to a corresponding cell lacking the expression construct.

The ability of a polypeptide to oxidize at least one of i) HMF to HMFCA, ii) oxidizing DFF to FFCA, and iii) FFCA to FDCA, may be assayed by co-expression of a nucleotide sequence encoding the polypeptide in a *P. putida* host cell, preferably an *P. putida* KT2440 host cell, together with the HmfH and HmfT1 genes from *C. basilensis* HMF 14, incubating the *P. putida* cells in 10 mM HMF and detecting an increase in the accumulation FDCA as compared to corresponding *P. putida* cells that do not express the polypeptide, e.g. as described in Example IV of WO2012/064195. The ability of a polypeptide to oxidize HMF to HMFCA may also be assayed as described by Koopman et al 2010, PNAS supra). Strains expressing the HmfT1 gene from *C. basilensis* HMF14 are herein understood to express a gene product having the amino acid sequence of SEQ ID NO: 53. Alternatively, a nucleotide sequence encoding the polypeptide to be assayed for its ability to oxidize at least one of i) HMF to HMFCA, ii) oxidizing DFF to FFCA, and iii) FFCA to FDCA can be co-expressed in a fungal host cell, preferably a *S. cerevisiae* host cell, with an HMFCA dehydrogenase as e.g. described in Example 7 herein and detecting whether expression of the polypeptide causes an increase in the accumulation FDCA as compared to corresponding fungal host cells that do not express the polypeptide.

The furanic aldehyde dehydrogenase expressed in the cell of the invention preferably is a dehydrogenase that is dependent on a cofactor selected from an adenine dinucleotide, such as NADH or NADPH, a flavin adenine dinucleotide (FAD), a flavin mononucleotide (FMN), and pyrroloquinoline quinolone (PQQ).

In one embodiment, the nucleotide sequence encoding the furanic aldehyde dehydrogenase or oxidase is selected from the group consisting of:

a) a nucleotide sequence encoding a polypeptide having at least one of the abilities of i) oxidizing HMF to HMFCA, ii) oxidizing DFF to FFCA, and, iii) oxidizing FFCA into FDCA, which polypeptide comprising an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of at least one of SEQ ID NO's: 5 and 6 (respectively, the aldehyde dehydrogenases hmfN1 and hmfN2), of which SEQ ID NO: 5 is preferred;

b) a nucleotide sequence the complementary strand of which hybridises to a nucleotide sequence of (a); and, c) a nucleotide sequence the sequence of which differs from the sequence of a nucleotide sequence of (b) due to the degeneracy of the genetic code.

A preferred nucleotide sequence of the invention thus encodes a furanic aldehyde dehydrogenase with an amino acid sequence that is identical to that of a furanic aldehyde dehydrogenase that is obtainable from (or naturally occurs in) a fungus of a genus selected from the group consisting of *Aspergillus, Eutypa, Neosartorya, Penicillium, Podospora, Scedosporium* and *Sporothrix*, more preferably, a fungus of a species selected from the group consisting of *Eutypa lata, Penicillium brasilianum, Podospora anserina, Scedosporium apiospermum* and *Sporothrix schenckii*, most preferably a fungus, which is the strain *P. brasilianum* C1.

In one embodiment the nucleotide sequence encodes a polypeptide with furanic aldehyde dehydrogenase activity as it occurs in nature, e.g. as it can isolated from a wild type source organism. Alternatively, the nucleotide sequence can encode engineered forms of any of the furanic aldehyde dehydrogenase defined above and that comprise one or more amino acid substitutions, insertions and/or deletions as compared to the corresponding naturally occurring furanic aldehyde dehydrogenase but that are within the ranges of identity or similarity as defined herein. Therefore, in one embodiment the nucleotide sequence of the invention encodes a furanic aldehyde dehydrogenase, the amino acid sequence of which at least comprises in each of the invariable positions (that are indicated in Tables 5 and 6 with a "*"), the amino acid present in a invariable position. Preferably, the amino acid sequence also comprises in the strongly conserved positions (that are indicated in Tables 5 and 6 with a ":") one of the amino acids present in a strongly conserved position. More preferably, the amino acid sequence further also comprises in the less strongly conserved positions (that are indicated in Tables 5 and 6 with a ".") one of the amino acids present in a less strongly conserved position. Amino acid substitutions outside of these invariable and conserved positions are less unlikely to affect furanic aldehyde dehydrogenase activity. Tables 5 and 6 present the amino acid sequence alignments of each of *Penicillium brasilianum* hmfN1 and hmfN2, respectively, with their 10 closest orthologues as available in public databases. Tables 5A and 6A provide the percentages amino acid identities among the *P. brasilianum* sequences and their orthologues, as well as the accession numbers of the orthologues.

The nucleotide sequences of the invention, encoding polypeptides with furanic aldehyde dehydrogenase activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual (3rd edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with furanic aldehyde dehydrogenase activity; b) the PCR fragment obtained in a) is used as probe to screen a cDNA and/or genomic library of the organism; and c) producing a cDNA or genomic DNA comprising the nucleotide sequence encoding a polypeptide with furanic aldehyde dehydrogenase activity.

The fungal host cell to be transformed with a nucleic acid construct for expression of the nucleotide sequence encoding a furanic aldehyde dehydrogenase of the invention preferably is a fungal host cell as described above for transformation with a nucleic acid construct for expression of the nucleotide sequence encoding the HMFCA dehydrogenase, and wherein also the furanic aldehyde dehydrogenase can suitably be expressed, preferably in functional, i.e. active form. Preferably, the fungal host cell to be transformed with a nucleic acid construct for expression of the nucleotide sequence encoding a furanic aldehyde dehydrogenase also expresses nucleotide sequence encoding the HMFCA dehydrogenase, more preferably the cell comprises an expression construct for the HMFCA dehydrogenase that confers to or increases in the cell the ability to oxidize HMFCA to FFCA. As described above, such a fungal host cell, preferably is capable of active or passive transport of furanic compounds into as well as out of the cell and preferably lacks or has no detectable activities that degrade (e.g. decarboxylate) carboxylated furanic compounds.

The expression construct for expression of a nucleotide sequence encoding a furanic aldehyde dehydrogenase of the invention, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a furanic aldehyde dehydrogenase of the invention in appropriate host cells are described in more detail herein below.

Introducing or Increasing Furanic Alcohol/Aldehyde Oxidase Activity

In one embodiment, a cell of the invention that has the ability of oxidizing HMFCA to FFCA is a cell that expresses an oxidase that has the ability to oxidize HMFCA to FFCA. The oxidase preferably is capable of oxidising alcohol and aldehyde groups at the C2 and C5 positions in furanic compounds comprising such groups (i.e. having EC 1.1 and EC 1.2 activities). More specifically, the oxidase activity is preferably capable of at least one of i) oxidizing HMF to HMFCA, ii) oxidizing HMF to 2,5-diformyl furan (DFF), iii) oxidizing DFF to 5-formyl-2-furoic acid (FFCA), iv) oxidizing HMFCA to FFCA, and v) oxidizing FFCA to FDCA. Such furanic oxidase activity can be an endogenous activity of the cell or it can be an exogenous activity conferred to the cell. Preferably, the furanic oxidase activity is conferred to or increased in the cell by transformation of the cell with an expression construct. The expression construct for expression of the furanic oxidase, can be a further expression construct in a cell already comprising at least one of an expression construct for expression of the HMFCA dehydrogenase and an expression construct for expression of the furanic aldehyde dehydrogenase.

In a preferred cell of the invention, the expression construct for expression of the furanic oxidase is expressible in the cell and expression of the furanic oxidase preferably confers to the ability to oxidize at least one of i) HMF to HMFCA, ii) HMF to DFF, iii) DFF to FFCA, iv) HMFCA to FFCA, and v) FFCA to FDCA, or increases in the cell the specific activity of a furanic oxidase with at least one of these abilities, as compared to a corresponding cell lacking the expression construct, e.g. a wild type cell. The specific activity of the furanic oxidase is preferably increased in the cell by at least a factor 1.05, 1.1, 1.2, 1.5, 2.0, 5.0, 10, 20, 50 or 100 as compared to a corresponding cell lacking the expression construct.

The ability of a polypeptide to oxidize at least one of i) HMF to HMFCA, ii) HMF to DFF, iii) DFF to FFCA, iv) HMFCA to FFCA, and v) FFCA into FDCA, can e.g. be assayed using an expression construct wherein a nucleotide sequence encoding the polypeptide to be assayed for furanic oxidase activity replaces the *C. basilensis* hmfH gene in pBT'hmfH-adh (described in WO2012/064195), after which the plasmid comprising coding sequence of the polypeptide to be assayed for oxidase activity is introduced into *P. putida* KT2440Δgcd containing pJNNhmfT1(t) (also described in WO2012/064195). The *P. putida* transformants expressing the polypeptide to be assayed for furanic oxidase activity are incubated with HMF and samples are drawn at regular intervals for analysis of FDCA. An increase of production of FDCA, as compared to corresponding *P. putida* transformants lacking the polypeptide to be assayed for furanic oxidase activity (and the *C. basilensis* hmfH gene) is taken as an indication that the polypeptide has furanic oxidase activity. Alternatively, a nucleotide sequence encoding the polypeptide to be assayed for its ability to oxidize at least one of i) HMF to HMFCA, ii) HMF to DFF, iii) DFF to FFCA, iv) HMFCA to FFCA, and v) FFCA into FDCA can be expressed in a fungal host cell, preferably a *S. cerevisiae* host cell, as e.g. described in Example 7 herein and detecting whether expression of the polypeptide confers to a fungal host cell the ability to produce both FDCA from HMF.

The furanic oxidase expressed in the cell of the invention preferably is a oxidase that is dependent on a cofactor selected from an adenine dinucleotide, such as NADH or NADPH, a flavin adenine dinucleotide (FAD), a flavin mononucleotide (FMN), and pyrroloquinoline quinolone (PQQ).

In one embodiment, the nucleotide sequence encoding the furanic oxidase is selected from the group consisting of:

a) a nucleotide sequence encoding a polypeptide having at least one of the abilities of i) oxidizing HMF to HMFCA, ii)

oxidizing HMF to DFF, iii) oxidizing DFF to FFCA, iv) oxidizing HMFCA to FFCA, and v) oxidizing FFCA to FDCA, which polypeptide comprising an amino acid sequence that has at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of at least one of SEQ ID NO's: 7-9 (respectively, the furanic oxidases hmfP1, hmfP2 and hmfP3);

b) a nucleotide sequence the complementary strand of which hybridises to a nucleotide sequence of (a); and, c) a nucleotide sequence the sequence of which differs from the sequence of a nucleotide sequence of (b) due to the degeneracy of the genetic code.

A preferred nucleotide sequence of the invention thus encodes a furanic oxidase with an amino acid sequence that is identical to that of a furanic oxidase that is obtainable from (or naturally occurs in) a fungus of a genus selected from the group consisting of *Aspergillus, Arthroderma, Microsporum, Neosartorya, Penicillium, Talaromyces*, and *Trichophyton*, more preferably, a fungus of a species selected from the group consisting of *Arthroderma otae, Microsporum gypseum* and *Penicillium brasilianum*, most preferably a fungus, which is the strain *P. brasilianum* C1.

In one embodiment the nucleotide sequence encodes a polypeptide with furanic oxidase activity as it occurs in nature, e.g. as it can isolated from a wild type source organism. Alternatively, the nucleotide sequence can encode engineered forms of any of the furanic oxidase defined above and that comprise one or more amino acid substitutions, insertions and/or deletions as compared to the corresponding naturally occurring furanic oxidase but that are within the ranges of identity or similarity as defined herein. Therefore, in one embodiment the nucleotide sequence of the invention encodes a furanic oxidase, the amino acid sequence of which at least comprises in each of the invariable positions (that are indicated in Tables 7-9 with a "*"), the amino acid present in a invariable position. Preferably, the amino acid sequence also comprises in the strongly conserved positions (that are indicated in Tables 7-9 with a ":") one of the amino acids present in a strongly conserved position. More preferably, the amino acid sequence further also comprises in the less strongly conserved positions (that are indicated in Tables 7-9 with a ".") one of the amino acids present in a less strongly conserved position. Amino acid substitutions outside of these invariable and conserved positions are less unlikely to affect furanic aldehyde dehydrogenase or oxidase activity. Tables 7-9 present the amino acid sequence alignments of each of *Penicillium brasilianum* hmfP1, hmfP2 and hmfP3, respectively, with their 10 closest orthologues as available in public databases. Tables 7A-9A provide the percentages amino acid identities among the *P. brasilianum* sequences and their orthologues, as well as the accession numbers of the orthologues.

The nucleotide sequences of the invention, encoding polypeptides with furanic oxidase activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with furanic oxidase activity; b) the PCR fragment obtained in a) is used as probe to screen a cDNA and/or genomic library of the organism; and c) producing a cDNA or genomic DNA comprising the nucleotide sequence encoding a polypeptide with furanic oxidase activity.

The fungal host cell to be transformed with a nucleic acid construct for expression of the nucleotide sequence encoding a furanic oxidase of the invention preferably is a fungal host cell as described above for transformation with a nucleic acid construct for expression of the nucleotide sequence encoding the HMFCA dehydrogenase, and wherein the furanic oxidase can suitably be expressed, preferably in functional, i.e. active form. As described above, such a fungal host cell, preferably is capable of active or passive transport of furanic compounds into as well as out of the cell and preferably lacks or has no detectable activities that degrade (e.g. decarboxylate) carboxylated furanic compounds.

The expression construct for expression of a nucleotide sequence encoding a furanic oxidase of the invention, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a furanic oxidase of the invention in appropriate host cells are described in more detail herein below.

Absence of, or Reducing or Eliminating FDCA Catabolism and/or Alternative Routes for HMF Metabolism A cell of the invention preferably is a cell that lacks the ability to degrade FDCA. The cell can be of a fungal species that naturally lacks the ability to degrade FDCA. Alternatively, the cell can a genetically modified cell of fungal species that naturally has the ability to degrade FDCA, which cell has been genetically modified to reduce or eliminate its natural ability to degrade FDCA. Whether or not a given fungal strain naturally has the ability to degrade FDCA can be tested by determining the strains ability to grow at the expense of one or more of HMF, HMF-alcohol, HMFCA and FDCA as sole carbon source, as e.g. described in the Examples herein. An example of a fungal species that naturally has the ability to degrade FDCA is *Penicillium brasilianum* as shown in the Examples herein. In contrast, yeasts such as *Saccharomyces* and *Yarrowia* species, are examples of fungal species that naturally lack the ability to degrade FDCA.

Thus, in one embodiment of the invention, the cell is genetically modified to reduce or eliminate the cell's natural ability to degrade FDCA. A gene to be modified for reducing or eliminating the cell's ability to degrade FDCA can be at least one of a gene encoding an FDCA decarboxylating monooxygenase, a gene encoding an FDCA decarboxylase, a gene encoding an FDCA decarboxylating dehydrogenase and a gene encoding an lactonase (capable hydrolysing a lactone resulting from FDCA decarboxylation).

A gene encoding an FDCA decarboxylating monooxygenase to be modified for reducing or eliminating the specific FDCA decarboxylating monooxygenase activity in the cell of the invention, preferably is a gene encoding a amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to at least one of SEQ ID NO.'s: 10 and 11 (respectively, hmfK1 and hmfK2), of which SEQ ID NO: 10 is preferred. In the cells of the invention, the specific FDCA decarboxylating monooxygenase activity is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

A gene encoding an FDCA decarboxylase to be modified for reducing or eliminating the specific FDCA decarboxylase activity in the cell of the invention, preferably is a gene encoding a amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 12 (hmfQ). In the cells of the invention, the specific FDCA decarboxylase activity is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

A gene encoding an FDCA decarboxylating dehydrogenase to be modified for reducing or eliminating the specific FDCA decarboxylating dehydrogenase activity in the cell of the invention, preferably is a gene encoding a amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 13 (hmfU). In the cells of the invention, the specific FDCA decarboxylating dehydrogenase activity is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

Without wishing to be bound by theory, lactones resulting from FDCA decarboxylation are thought to exert product inhibition on FDCA carboxylases. An alternative means for reducing or eliminating a cell's ability to degrade FDCA is therefore to reduce or eliminate the specific activity of lactonases capable hydrolysing a lactone resulting from FDCA decarboxylation in a cell of the invention. A gene encoding such a lactonase to be modified for reducing or eliminating the specific activity of lactonases capable hydrolysing a lactone resulting from FDCA decarboxylation, preferably is a gene encoding a amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 14 (hmfO). In the cells of the invention, the specific lactonase activity is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

Alternative endogenous routes for metabolism of HMF and other furanic precursors of FDCA may also be present in a cell of the invention. Such alternative routes compete with the production of FDCA from HMF and other furanic precursors of FDCA. Preferably therefore the specific activity of enzymes in such alternative routes is also reduced or eliminated in a cell of the invention. One such endogenous alternative route is e.g. the reduction of HMF and/or FFCA to the corresponding alcohol by an dehydrogenase, such as e.g. a short chain dehydrogenase. A gene encoding such a short chain dehydrogenase to be modified for reducing or eliminating the specific activity of an alternative route for metabolising HMF and other furanic precursors of FDCA, preferably is a gene encoding an amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 15 (hmfM). In the cells of the invention, the specific short chain dehydrogenase activity is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

Another endogenous dehydrogenase known to reduce HMF to HMF-alcohol is the NADPH-dependent alcohol dehydrogenase encoded by the *S. cerevisiae* ADH6 gene as described by Petersson et al. (2006, Yeast, 23:455-464). Therefore, a gene to be modified for reducing or eliminating the specific activity of alternative route for metabolising HMF, preferably is the *S. cerevisiae* ADH6 gene or an orthologue thereof in another fungal host species. Preferably therefore, the gene to be modified for reducing or eliminating the specific activity of an NADPH-dependent HMF-reducing dehydrogenase is a gene encoding an amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 69 (*S. cerevisiae* ADH6). In the cells of the invention, the activity specific of the NADPH-dependent HMF-reducing dehydrogenase is preferably reduced by at least a factor 1.05, 1.1, 1.2, 1.5, 2.0, 5.0, 10, 20, 50 or 100 as compared to cells of a strain which is genetically identical except for the genetic modification causing the reduction in activity.

The nucleotide sequences of the invention, encoding enzymes the specific activities of which are preferably reduced or eliminated in a cell of the invention, are obtainable from and may be identified in genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual (3$^{rd}$ edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding enzymes the specific activities of which are preferably reduced or eliminated in a cell of the invention; b) the PCR fragment obtained in a) is used as probe to screen a cDNA and/or genomic library of the organism; and c) producing a cDNA or genomic DNA comprising the nucleotide sequence encoding the enzyme the specific activities of which is preferably reduced or eliminated in a cell of the invention. Such conserved sequences can be identified in the sequences alignments presented in Tables 10-15, wherein invariable positions are indicated with a "*" and strongly conserved positions are indicated with a ":". Also suitable host cells of the invention can be derived from Tables 10-15 wherein the host preferably is a non-pathogenic fungus or yeast that belongs to the same phylum, class, order, family or genus as the source organism of an orthologue identified in Tables 10-15. Tables 10-15 present the amino acid sequence alignments of each of *Penicillium brasilianum* hmfK1, hmfK2, hmfQ, hmfU and hmfM, respectively, with their 10 closest orthologues as available in public databases. Tables 10A-15A provide the percentages amino acid identities among the *P. brasilianum* sequences and their orthologues, as well as the accession numbers of the orthologues.

Cells Expressing a Transporter of Furanic Compounds

A cell of the invention, as described above, further preferably expresses one or more nucleotide sequences encoding a polypeptide having furanic compound transport capabilities. Such polypeptides having furanic compound transport capabilities can be an endogenous activity of the cell or it can be an exogenous activity conferred to the cell. Preferably, the activity of a polypeptides having furanic compound transport capabilities is conferred to or increased in the cell by transformation of the cell with an expression construct, e.g. a third expression construct if the cell already comprises a first expression construct for expression of the HMFCA dehydrogenase or oxidase and a second expression construct for expression of the furanic aldehyde dehydrogenase or oxidase.

Preferably the cell is transformed with an expression construct for expression of a nucleotide sequence encoding a polypeptide having furanic compound transport capabilities. The polypeptide having furanic compound transport capabilities preferably is a polypeptide having HMFCA transport capabilities, which at least includes the capability to transport HMFCA into the cell. Preferably the cell comprises an expression construct for expression of a nucleotide sequence encoding a polypeptide having the ability to transport at least HMFCA into the cell, the polypeptide comprising an amino acid sequence with at 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to at least one of SEQ ID NO: 16-18 (respectively, hmfT3, hmfT4 and hmfT5), wherein, the expression construct is expressible in the cell and expression of the polypeptide confers to or increases in the cell the ability to transport at least HMFCA into the cell, as compared to a corresponding wild type cell lacking the expression construct.

The ability of a polypeptide to transport furanic compounds, in particular HMFCA, into the cell may be assayed by co-expression of a nucleotide sequence encoding the transporter polypeptide in a yeast host cell, preferably a *S. cerevisiae* CEN.PK host cell, together with the HmfH gene from *C. basilensis* HMF 14 and a gene encoding a furanic aldehyde dehydrogenase associated with the HMF-degradation operon from *C. basilensis* HMF 14 (having the amino acid sequence of SEQ ID NO: 19 of WO2012/064195), incubating the transformed *S. cerevisiae* cells in 4 mM HMF and detecting an increase in the accumulation FDCA as compared to corresponding (i.e. otherwise identical) *S. cerevisiae* cells that do not express the transporter polypeptide, e.g. as described in Example 6 herein.

A preferred nucleotide sequence of the invention thus encodes a furanic compound transporter polypeptide with an amino acid sequence that is identical to that of a furanic compound transporter polypeptide that is obtainable from (or naturally occurs in) a fungus of a genus selected from the group consisting of *Aspergillus, Fusarium, Nectria, Penicillium, Sporothrix* and *Togninia*, more preferably, a fungus of a species selected from the group consisting of *Aspergillus terreus, Penicillium brasilianum, Penicillium digitatum, Penicillium rubens, Sporothrix schenckii* and *Togninia minima*, most preferably a fungus, which is the strain *P. brasilianum* C1.

In one embodiment the nucleotide sequence encodes a furanic compound transporter polypeptide as it occurs in nature, e.g. as it can isolated from a wild type source organism. Alternatively, the nucleotide sequence can encode engineered forms of any of the furanic compound transporter polypeptides defined above and that comprise one or more amino acid substitutions, insertions and/or deletions as compared to the corresponding naturally occurring furanic compound transporter polypeptide but that are within the ranges of identity or similarity as defined herein. Therefore, in one embodiment the nucleotide sequence of the invention encodes a furanic compound transporter polypeptide, the amino acid sequence of which at least comprises in each of the invariable positions (that are indicated in Tables 16-18 with a "*"), the amino acid present in a invariable position. Preferably, the amino acid sequence also comprises in the strongly conserved positions (that are indicated in Tables 16-18 with a ":") one of the amino acids present in a strongly conserved position. More preferably, the amino acid sequence further also comprises in the less strongly conserved positions (that are indicated in Tables 16-18 with a ".") one of the amino acids present in a less strongly conserved position. Amino acid substitutions outside of these invariable and conserved positions are less unlikely to affect furanic compound transporter polypeptide activity. Tables 16-18 present the amino acid sequence alignments of each of *Penicillium brasilianum* hmfT3, hmfT4, and hmfT5, respectively, with their 10 closest orthologues as available in public databases. Tables 16A-18A provide the percentages amino acid identities among the *P. brasilianum* sequences and their orthologues, as well as the accession numbers of the orthologues.

The nucleotide sequences of the invention, encoding polypeptides with furanic compound transporter activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual (3rd edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with the activity of a furanic compound transporter; b) the PCR fragment obtained in a) is used as probe to screen a cDNA and/or genomic library of the organism; and c) producing a cDNA or genomic DNA comprising the nucleotide sequence encoding a furanic compound transporter polypeptide.

The fungal host cell to be transformed with a nucleic acid construct for expression of the nucleotide sequence encoding a furanic compound transporter polypeptide preferably is a fungal host cell of the invention as described above.

The expression construct for expression of a nucleotide sequence encoding a furanic compound transporter polypeptide, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a furanic compound transporter polypeptide of the invention in appropriate host cells are described in more detail herein below.

Cell with Altered Regulation of Expression of a Transcriptional Activator

In one embodiment of a cell of the invention, the regulation of expression of a transcriptional activator of genes involved in furan catabolism is altered. The expression of the transcriptional activator can be reduced or eliminated to prevent degradation of FDCA in cells containing endogenous genes for FDCA degradation, and preferably containing genes coding for enzymes for converting HMF to FDCA that expressed independent from the transcriptional activator. Alternatively, the expression of the transcriptional activator can be increased and/or be made constitutive in cells genetically modified to prevent FDCA degradation, so as to increase expression of endogenous genes for converting HMF, and/or other furanic precursors, to FDCA.

Preferably, in a cell of the invention, the transcriptional activator of which the regulation of expression is altered, is encoded by a nucleotide sequence encoding a polypeptide comprising an amino acid sequence with at least 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity to SEQ ID NO: 19 (hmfR), wherein, the polypeptide has the ability to activate transcription of at least one gene involved in furan catabolism.

A preferred nucleotide sequence of the invention thus encodes a transcriptional activator with an amino acid sequence that is identical to that of a transcriptional activator that is obtainable from (or naturally occurs in) a fungus of a genus selected from the group consisting of *Fusarium, Penicillium, Scedosporium, Sporothrix* and *Stachybotrys* more preferably, a fungus of a species selected from the group consisting of *Fusarium oxysporum, Penicillium brasilianum, Scedosporium apiospermum, Sporothrix schenckii* and *Stachybotrys chlorohalonata*, most preferably a fungus, which is the strain *P. brasilianum* C1.

In one embodiment the nucleotide sequence encodes a transcriptional activator as it occurs in nature, e.g. as it can isolated from a wild type source organism. Alternatively, the nucleotide sequence can encode engineered forms of any of the transcriptional activator polypeptides defined above and that comprise one or more amino acid substitutions, insertions and/or deletions as compared to the corresponding naturally occurring transcriptional activator polypeptide but that are within the ranges of identity or similarity as defined herein. Therefore, in one embodiment the nucleotide sequence of the invention encodes a transcriptional activator polypeptide, the amino acid sequence of which at least comprises in each of the invariable positions (that are indicated in Table 19 with a "*"), the amino acid present in a invariable position. Preferably, the amino acid sequence also comprises in the strongly conserved positions (that are indicated in Table 19 with a ":") one of the amino acids present in a strongly conserved position. More preferably, the amino acid sequence further also comprises in the less strongly conserved positions (that are indicated in Table 19 with a ".") one of the amino acids present in a less strongly conserved position. Amino acid substitutions outside of these invariable and conserved positions are less unlikely to affect transcriptional activator activity. Table 19 presents the amino acid sequence alignment of *Penicillium brasilianum* hmfR, with its 10 closest orthologues as available in public databases. Table 19A provides the percentages amino acid identities among the *P. brasilianum* sequence and its orthologues, as well as the accession numbers of the orthologues.

The nucleotide sequences of the invention, encoding polypeptides with transcriptional activator activity, are obtainable from genomic and/or cDNA of a fungus, yeast or bacterium, e.g. one that belongs to the same phylum, class or genus as the source organisms described above, using methods for isolation of nucleotide sequences that are well known in the art per se (see e.g. Sambrook and Russell (2001) "Molecular Cloning: A Laboratory Manual ($3^{rd}$ edition), Cold Spring Harbor Laboratory, Cold Spring Harbor Laboratory Press, New York). The nucleotide sequences of the invention are e.g. obtainable in a process wherein a) degenerate PCR primers (designed on the basis of conserved amino acid sequences) are used on genomic and/or cDNA of a suitable organism to generate a PCR fragment comprising part of the nucleotide sequences encoding the polypeptides with the activity of a transcriptional activator; b) the PCR fragment obtained in a) is used as probe to screen a cDNA and/or genomic library of the organism; and c) producing a cDNA or genomic DNA comprising the nucleotide sequence encoding a furanic transcriptional activator.

The fungal host cell to be transformed with a nucleic acid construct for expression of the nucleotide sequence encoding a furanic transcriptional activator polypeptide preferably is a fungal host cell of the invention as described above.

The expression construct for expression of a nucleotide sequence encoding a furanic transcriptional activator polypeptide, preferably is an expression construct that is heterologous or exogenous to the host cell transformed with the construct. A construct is herein understood to be heterologous or exogenous to the host cell comprising the construct when the construct comprises at least one sequence or sequence element that does not naturally occur in the host cell and/or when construct comprises at least two sequence elements in a combination and/or order that does not naturally occur in the host cell, even if the elements themselves do naturally occur in the host cell.

Vectors and expression constructs for expression of a nucleotide sequence encoding a furanic transcriptional activator polypeptide of the invention in appropriate host cells are described in more detail herein below.

Vectors, Genetic Constructs and Methods for Genetic Modifications of Cells of the Invention For the genetic modification of the parent host cells of the invention, i.e. for the construction of the modified host cells of the invention, standard genetic and molecular biology techniques are used that are generally known in the art and have e.g. been described by Sambrook and Russell (2001, "Molecular cloning: a laboratory manual" (3rd edition), Cold Spring Harbor Laboratory, Cold Spring Harbor Laboratory Press) and Ausubel et al. (1987, eds., "Current protocols in molecular biology", Green Publishing and Wiley Interscience, New York).

More specifically, means and methods for genetic modification of yeasts are standard and known to those in the art, including e.g. promoters for (over-)expression of genes, episomal and/or integrating expression constructs and vectors, selectable markers, methods and genetic constructs for disrupting and/or deleting endogenous yeast genes or parts thereof and methods for transforming yeast. Such means and methods are e.g. described in: Sherman et al, Methods Yeast Genetics, Cold Spring Harbor Laboratory, N Y (1978); Guthrie et al. (Eds.) Guide To Yeast Genetics and Molecular Biology Vol. 194, Academic Press, San Diego (1991); Sudbery, P. E. (2001) Genetic Engineering of Yeast, in Biotechnology Set, Second Edition (eds H.-J. Rehm and G. Reed), Wiley-VCH Verlag GmbH, Weinheim, Germany. doi: 10.1002/9783527620999.ch13a; and, Gaillardin, C. and Heslot, H. (1988), Genetic engineering in *Yarrowia lipolytica*. J. Basic Microbiol., 28: 161-174. doi: 10.1002/jobm.3620280303; all of which are incorporated herein by reference.

Similarly, means and methods for genetic modification of filamentous fungi are standard and known to those in the art, including e.g. promoters for (over-)expression of genes, episomal and/or integrating expression constructs and vectors, selectable markers, and methods and genetic constructs for disrupting and/or deleting endogenous fungal genes or parts thereof and methods for transforming filamentous fungi. Such means and methods are e.g. described in Moore, M. M. (2007, "Genetic engineering of fungal cells", In Biotechnology Vol. III. (Ed. H. W. Doelle and E. J. Dasilva), EOLSS, Ontario, Canada. pp. 36-63; Lubertozzi, D., & Keasling, J. D. (2009), "Developing *Aspergillus* as a host for heterologous expression", Biotechnology advances, 27(1), 53-75; Meyer, V. (2008) "Genetic engineering of filamentous fungi—progress, obstacles and future trends", Biotechnology Advances, (26), 177-85; Kück and Hoff (2010) "New tools for the genetic manipulation of filamentous fungi. Applied microbiology and biotechnology", 86(1), 51-62; and, WO2014/142647, all of which are incorporated herein by reference.

Thus in another aspect, the invention pertains to nucleic acid constructs, such as vectors, including cloning and expression vectors, comprising a polynucleotide of the invention, e.g. a nucleotide sequence encoding a HMFCA dehydrogenase or a furanic aldehyde dehydrogenase of the invention or a functional equivalent thereof and methods of transforming or transfecting a suitable host cell with such vectors. As used herein, the terms "vector" and "construct" are used interchangeably and refers to a constructed nucleic acid molecule comprising a polynucleotide of the invention.

A vector according to the invention may be an autonomously replicating vector, i.e. a vector which exists as an extra-chromosomal entity, the replication of which is independent of chromosomal replication, e.g. a plasmid. Alternatively, the vector may be one which, when introduced into a host cell, is integrated into the host cell genome and replicated together with the chromosome (s) into which it has been integrated. For convenience the vector can be a shuttle vector, also comprising a origin of replication and selectable marker for use in a bacterium such as *E. coli*, for ease of manipulation and production.

In one embodiment, the nucleic acid constructs is an expression construct or expression vector, comprising a nucleotide sequence encoding a polypeptide of the invention to be (over-) expressed and wherein the nucleotide sequence encoding the polypeptide is operably linked to regulatory sequences that are capable of effecting and controlling (the rate of) expression of the coding nucleotide sequence in the host cells in question. Such regulatory sequences typically at least include a promoter that functions to control the transcription of the coding sequence, which is usually located upstream of, and preferably operably linked the coding sequence. In addition to the promoter, the upstream transcription regulatory sequences may comprises further elements such as enhancers, upstream activating sequences, transcription factor binding sites, repressor and activator protein binding sites and the like. The promoter sequence will usually include the transcription initiation site(s). Suitable promoters and transcription regulatory sequences for expression of coding sequences in yeast or filamentous fungi are described in the above-cited references. Downstream of the promoter and transcription initiation site(s), the expression construct will comprise the translation initiation sequences, such as the eukaryotic Kozak consensus sequence, surrounding the translation initiation codon, i.e. the first codon of the coding sequence. The coding sequence is terminated with a translation stop codon. Downstream of the coding sequence, the expression construct may comprise a 3'-untranslated region containing one or more transcription termination sites, e.g. a terminator, which preferably also includes a polyadenylation site. The origin of the terminator is less critical. The terminator can, for example, be native to the DNA sequence encoding the polypeptide. However, preferably a yeast terminator is used in yeast host cells and a filamentous fungal terminator is used in filamentous fungal host cells. More preferably, the terminator is endogenous to the host cell (in which the nucleotide sequence encoding the polypeptide is to be expressed). A functional expression unit comprising a coding sequence operably linked to the appropriate upstream- and downstream regulatory sequences may be referred to as an expression cassette. An expression vector or expression construct of the invention may comprise more than one expression cassette, optionally for the expression of more than one different coding sequences.

In addition to at least one expression cassette, an expression vector or expression construct of the invention preferably also comprises a selectable marker for selection of host cells transformed with the vector or construct. In a preferred embodiment, the selectable marker in the expression vector or expression construct in a configuration that allows excision of the marker from the expression construct/vector, once in the host cell after initial selection of the transformants, e.g. using homologous recombination as described in EP 0 635 574, or using the Cre-lox system as described by Güldener et al. (1996, Nucleic Acids Res. 24:2519-2524).

The invention further relates to method for the preparation of a polypeptide of the invention, e.g. a polypeptide having HMFCA dehydrogenase activity, a polypeptide having furanic aldehyde dehydrogenase activity and including polypeptides the expression of which is to be reduced/eliminated in the cell of the invention. The method comprises cultivating a cell according to the invention under conditions conducive to expression of the polypeptide and, optionally, recovering the expressed polypeptide. The invention also relates to a polypeptide obtainable by such a method.

Thus in another aspect, the invention pertains to means and methods for modifying endogenous target genes in the cells of the invention so as to reduce or eliminate the expression and/or activity of the encoded target proteins. Modifications that may be used to reduce or eliminate expression of a target protein are disruptions that include, but are not limited to, deletion of the entire gene or a portion of the gene encoding the target protein, inserting a DNA fragment into the target gene (in either the promoter or coding region) so that the protein is not expressed or expressed at lower levels, introducing a mutation into the target coding region which adds a stop codon or frame shift such that a functional protein is not expressed, and introducing one or more mutations into a target coding region to alter amino acids so that a non-functional target protein, or a target protein with reduced enzymatic activity is expressed. In addition, expression of the target gene may be blocked by expression of an antisense RNA or an interfering RNA, and constructs may be introduced that result in co-suppression. Moreover, a target coding sequence may be synthesized whose expression will be low because rare codons are substituted for plentiful ones, when this suboptimal coding sequence is substituted for the corresponding endogenous target coding sequence. Preferably such a suboptimal coding sequence will have a codon adaptation index (see above) of less than 0.5, 0.4, 0.3 0.2, or 0.1. Such a suboptimal coding sequence will produce the same polypeptide but at a lower rate due to inefficient translation. In addition, the synthesis or stability of the transcript may be reduced by mutation. Similarly the efficiency by which a protein is translated from mRNA may be modulated by mutation, e.g. by using suboptimal translation initiation codons. All of these methods may be readily practiced by one skilled in the art making use of the sequences encoding target proteins.

In particular, genomic DNA sequences surrounding a target coding sequence are useful for modification methods using homologous recombination. For example, in this method sequences flanking the target gene are placed on either site of a selectable marker gene to mediate homologous recombination whereby the marker gene replaces the target gene. Also partial target gene sequences and target gene flanking sequences bounding a selectable marker gene may be used to mediate homologous recombination whereby the marker gene replaces a portion of the target gene. In addition, the selectable marker in the inactivation construct can be configured in such a way so as to allow excision of the marker from the inactivation construct expression construct/vector, once integrated in the host cell's genome, e.g. using homologous recombination as described in EP 0 635 574, or using the Cre-lox system as described by Güldener et al. (1996, Nucleic Acids Res. 24:2519-2524).

Deletions of target genes may also be effected using mitotic recombination as described in Wach et al. (1994, Yeast 10:1793-1808). This method involves preparing a DNA fragment that contains a selectable marker between genomic regions that may be as short as 20 bp, and which bound, i.e. flank the target DNA sequence. This DNA fragment can be prepared by PCR amplification of the selectable marker gene using as primers oligonucleotides that hybridize to the ends of the marker gene and that include the genomic regions that can recombine with the fungal genome. The linear DNA fragment can be efficiently transformed into yeast or filamentous fungi and recombined into the genome resulting in gene replacement including with deletion of the target DNA sequence (as described in Methods in Enzymology, 1991, v 194, pp 281-301). Moreover, promoter replacement methods may be used to exchange the endogenous transcriptional control elements allowing another means to modulate expression such as described in Mnaimneh et al. (2004, Cell 118(1):31-44) and in the Examples herein.

In addition, the activity of target proteins or genes in any cell may be disrupted using random mutagenesis, which is followed by screening to identify strains with reduced activity of the target proteins. Using this type of method, the DNA sequence coding for the target protein, or any other region of the genome affecting expression of the target protein, need not even be known. Methods for creating genetic mutations are common and well known in the art and may be applied to the exercise of creating mutants. Commonly used random genetic modification methods (reviewed in Methods in Yeast Genetics, 2005, Cold Spring Harbor Laboratory Press, Cold Spring Harbor, N.Y.) include spontaneous mutagenesis, mutagenesis caused by mutator genes, chemical mutagenesis, irradiation with UV or X-rays, or transposon mutagenesis.

Chemical mutagenesis of fungi commonly involves treatment of cells with one of the following DNA mutagens: ethyl methanesulfonate (EMS), nitrous acid, diethyl sulfate, or N-methyl-N'-nitro-N-nitroso-guanidine (MNNG). These methods of mutagenesis have been reviewed in Spencer et al (Mutagenesis in Yeast, 1996, Yeast Protocols: Methods in Cell and Molecular Biology. Humana Press, Totowa, N.J.). Chemical mutagenesis with EMS may be performed as described in Methods in Yeast Genetics, 2005, Cold Spring Harbor Laboratory Press, Cold Spring Harbor, N.Y. Irradiation with ultraviolet (UV) light or X-rays can also be used to produce random mutagenesis in yeast cells. The primary effect of mutagenesis by UV irradiation is the formation of pyrimidine dimers which disrupt the fidelity of DNA replication. Protocols for UV-mutagenesis of yeast can be found in Spencer et al (Mutagenesis in Yeast, 1996, Yeast Protocols: Methods in Cell and Molecular Biology. Humana Press, Totowa, N.J.). Introduction of a mutator phenotype can also be used to generate random chromosomal mutations in yeast. Common mutator phenotypes can be obtained through disruption of one or more of the following genes: PMS1, MAG1, RAD18 or RAD51. Restoration of the non-mutator phenotype can be easily obtained by insertion of the wild type allele. Collections of modified cells produced from any of these or other known random mutagenesis processes may be screened for reduced activity of the target protein (US20090305363).

Processes for the Oxidation of Furanic Compounds

In a further aspect, the invention pertains to processes for oxidizing furanic compounds. In particular the invention pertain to process wherein furanic precursors of FDCA are oxidized. A process of the invention may comprise a single oxidation reaction step resulting in a product (e.g. the oxidation of HMFCA to FFCA). Alternatively a process of the invention may comprise more than one oxidation reaction step, each step resulting in an intermediate, where the last intermediate is the final product. Examples of such a series of steps, wherein HMF is oxidized in sequential oxidation steps to FDCA include e.g.: 1) HMF is first oxidized to HMFCA, which in a second step is oxidized to FFCA, which is then finally oxidized to FDCA, or alternatively, as described by Dijkman et al. (2014, Angew. Chem. 53 (2014) 6515-8) 2) HMF is first oxidized to DFF, which in a second step is oxidized to FFCA, which is then finally oxidized to FDCA. Thus, in a preferred process of the invention one or more furanic precursors of FDCA are oxidized in a series of steps to ultimately FDCA.

In one embodiment, the invention relates to processes comprising at least the oxidation of HMFCA to FFCA. Preferably, the process is a process for oxidizing HMFCA to FFCA, wherein the process comprises the step of incubating a cell in the presence of HMFCA. The cell preferably is a cell expressing enzymes that have the ability to oxidize HMFCA to FFCA. The cell can be cell that is genetically modified to have the ability to oxidize HMFCA to FFCA. In a preferred embodiment, the cell is a fungal as herein defined above, or below. Preferably the cell is incubated in the presence of HMFCA under conditions conducive to the oxidation of HMFCA by the cell, as e.g. specified below.

In another embodiment, the invention relates to processes for producing FDCA. A process for producing FDCA preferably comprises the step of incubating a cell in a medium comprising one or more furanic precursors of FDCA. The cell preferably is a cell expressing one or more enzymes that have the ability to convert a furanic precursor of FDCA into FDCA. The enzymes with the ability to convert a furanic precursors of FDCA into FDCA can be an enzyme having alcohol and/or aldehyde dehydrogenase activities and/or alcohol and/or aldehyde oxidase activities as described above, including the exemplified fungal enzymes. Thus, in a preferred embodiment, the cell is a cell, preferably a fungal cell, as herein defined above.

However, alternatively, the cell, preferably a fungal cell expresses bacterial enzymes with the ability to convert a furanic precursors of FDCA into FDCA. Such bacterial enzymes e.g. include the HmfH oxidase from the *Cupriavidus basilensis* strain HMF14 and related oxidases as described in WO2011/26913. Preferably therefore the fungal cell expresses an oxidase having at least one of EC 1.1 and EC 1.2 activities on a furanic precursor of FDCA, wherein the oxidase preferably comprises an amino acid sequence with at least 45, 50, 55, 60, 65, 70, 75, 80, 85, 90, 91, 92, 93, 94, 95, 96, 97, 98, 99 or 100% sequence identity with the amino acid sequence of SEQ ID NO: 44 (the amino acid sequence of the *C. basilensis* HMF14 HmfH oxidase).

The cell, preferably a fungal cell can further express a bacterial enzyme with aldehyde dehydrogenase activity (i.e. EC 1.2 activity) such as e.g. the aldehyde dehydrogenase from the *Cupriavidus basilensis* strain HMF14 and related dehydrogenases as described in WO2012/64195. Preferably, the aldehyde dehydrogenase activity is capable of converting furanic aldehydes. More preferably the aldehyde dehydrogenase activity is capable of oxidizing furanic aldehydes to the corresponding furanic carboxylic acids. More specifically, the aldehyde dehydrogenase activity is preferably capable of at least one of i) oxidizing HMF to HMFCA, ii) oxidizing 2,5-diformyl furan (DFF) to 5-formyl-2-furoic acid (FFCA), and iii) FFCA into FDCA. Preferably, the aldehyde dehydrogenase comprises an amino acid sequence that has at least 45, 50, 55, 60, 65, 70, 75, 80, 85, 90, 91, 92, 93, 94, 95, 96, 97, 98, 99 or 100% sequence identity with the amino acid sequence of any one of SEQ ID NO's: 45, 46, 47, 48, 49, 50 and 51.

The cell, preferably a fungal cell can further express a polypeptide having furanic compound transport capabilities, preferably, having HMFCA transport capabilities, such as e.g. the HmfT transporter from the *Cupriavidus basilensis* strain HMF14 and related transporters as described in WO2012/64195. HMFCA transport capabilities are understood to at least include the capability to transport HMFCA into the cell. Preferably, the polypeptide having furanic compound transport capabilities comprises an amino acid sequence that has at least 45, 50, 55, 60, 65, 70, 75, 80, 85, 90, 91, 92, 93, 94, 95, 96, 97, 98, 99 or 100% sequence identity with the amino acid sequence of any one of SEQ ID NO's: 52, 53, 54, 55 and 56.

Preferably the cell is incubated in the presence of one or more furanic precursors of FDCA under conditions conducive to the oxidation furanic precursors of FDCA by the cell to FDCA, as e.g. specified below.

Preferably in the process, at least one furanic precursor of FDCA is selected from the group consisting of HMF, DHF, HMFCA, FFCA and DFF, of which HMF is most preferred. The furanic precursors of FDCA are preferably obtained from one or more hexose sugars, preferably by acid-catalyzed dehydration, e.g. by heating in presence of acid, in a conventional manner. The technology to generate HMF from fructose is well established and robust (see e.g. van Putten et al., 2013, Chem. Rev. 113, 1499-1597). Also glucose-rich feedstock can be utilized, but the thermochemical formation of HMF proceeds more efficiently from fructose. Therefore, an additional enzymatic step can be included to convert glucose to fructose, using glucose isomerase. The latter process is well-established in food industry e.g. for producing high fructose corn syrup (HFCS) from hydrolysed starch. Glucose can also be chemically isomerised to fructose using combinations of catalysts and solvents as e.g. described in van Putten et al. (2013, supra).

The hexose sugars will usually be obtained from biomass. The term "biomass" is understood to mean the biodegradable fraction of products, waste and residues from biological origin from agriculture (including vegetal, such as crop residues, and animal substances), forestry (such as wood resources) and related industries including fisheries and aquaculture, as well as biodegradable fraction of industrial and municipal waste, such as municipal solid waste or wastepaper. In a preferred embodiment, the biomass is plant biomass, more preferably a (fermentable) hexose/glucose/sugar-rich biomass, such as e.g. sugarcane, a starch-containing biomass, for example, wheat grain, or corn straw, or even cereal grains, such as corn, wheat, barley or mixtures thereof. Preferred are agricultural crops naturally rich in fructans (e.g., topinambur or chicory roots).

The hexose sugars can be obtained by hydrolysis of such biomass Methods for hydrolysis of biomass are known in the art per se and include the use of e.g. vapour and/or carbohydrases such as glucoamylases.

Another preferred type of biomass for use in the process of the invention is a so-called "second generation" lignocellulosic feedstock, which are preferred if large volumes of FDCA are to be produced in a more sustainable way. Lignocellulosic feedstocks can be obtained from dedicated energy crops, e.g. grown on marginal lands, thus not competing directly with food crops. Or lignocellulosic feedstocks can be obtained as by-products, e.g. municipal solid wastes, wastepaper, wood residues (including sawmill and paper mill discards) and crop residues can be considered. Examples of crop residues include bagasse from sugar cane and also several corn and wheat wastes. In the case of corn by-products, three wastes are fiber, cobs and stover. Furthermore, forestry biomass may be used as feedstock. In order to convert second generation feedstocks into fermentation products of the invention, the cellulose and hemicellulose need to be released as monosaccharides. Hereto, either thermochemical approaches (usually referred to as pretreatment), enzymatic approaches or a combination of the two methodologies are applied. A pretreatment can serve to either completely liberate the sugars, or to make the polymeric compounds more accessible to subsequent enzymatic attack. Different types of pretreatment include liquid hot water, steam explosion, acid pretreatment, alkali pretreatment, and ionic liquid pretreatments. The relative amounts of the various compounds will depend both on the feedstock used and the pretreatment employed. For release of monosaccharide sugars from such lignocellulosic feedstock, appropriate carbohydrases are employed, including e.g. arabinases, xylanases, glucanases, amylases, cellulases, glucanases and the like.

The oxidation process of the invention is preferably conducted at temperature most optimal to the cell and/or the oxidoreductase enzymes contained is the cell. Thus, in case of thermophilic cells and/or thermophilic enzymes the temperature preferably is in the range between 40 and 65° C., e.g. at least 40, 42, or 45° C. and/or not higher than e.g. 65, 60, 55 or 50° C. However, in the case of a mesophilic cell and/or enzymes from mesophiles, the oxidation reactions are preferably conducted at a relatively mild temperature, e.g. in the range of 10-45° C., more preferably 20-40° C., e.g. at least 10, 15, 18, 20, 22 or 25° C. and/or not higher than e.g. 45, 42, 40, 38, 35, 32 or 30° C.

The oxidation process of the invention is preferably conducted at acidic pH. Downstream processing (DSP), i.e. recovery and purification, is of general concern in any biotechnological process but in particular in productions of monomeric compounds for polymer productions because the purity of the monomer is essential in controlled polymer formation. FDCA has a very limited solubility at pH-values below 3 (with a $pK_a$ of around 2.28). When the process is carried out at acidic pH, the FDCA produced will precipitate from the medium in which it is produced, preferably already during its production, thereby greatly facilitating its recovery. Preferably therefore, in the process of the invention, the cell, preferably a fungal cell is incubated in the presence of one or more furanic at a pH equal to or lower than 5.0, 4.0, 3.0, 2.9, 2.8, 2.7, 2.6, 2.5 or 2.4, and preferably at a pH that is equal to or higher than 2.0, 2.1, 2.2 or 2.25, 2.27 or 2.28. Preferably, in the process of the invention a cell, preferably a fungal host cell is selected that has a high tolerance to a pH in this range. An additional advantage of carrying out the process at acidic pH is that microbial contaminations of the process will be less of a problem since almost all bacteria are adversely affected at low pH. Yeasts and fungi are less of a problem compared to bacteria as source of infections and will be relatively easy to deal with.

The reaction time may be 6-150 hrs, more preferably 6-18 hrs. Preferably oxygen is supplied to the cells in the reaction medium from an oxygen source, such as molecular oxygen, e.g. as pure oxygen or in air, or water, or a different source of oxygen depending on the requirements of the furanic oxidizing enzyme. Air may be used conveniently as a source of molecular oxygen.

The reactor may be any suitable (aerated) bioreactor. It may be operated in batch, continuous or preferably in fed-batch.

The process of the invention further preferably comprises the step of recovery of the oxidation product(s) produced in the process, such as FDCA, or HMFCA. Preferably, the oxidation product is recovered from the medium in which the cell carrying out the oxidation steps is incubated. Oxidation products such as FDCA, HMFCA, etc. may be recovered from the reaction mixture or medium by e.g. (acid) precipitation, subsequent cooling crystallisation, and separation of the crystallized oxidation product, e.g., crystallized FDCA. However, other recovery methods are suitable, such as e.g. acid precipitation and solvent extraction, as known in the art.

The processes of the invention for oxidizing furanic compounds may advantageously be applied for the elimination of furanic compounds from feedstocks wherein furanic compounds are considered to be detrimental, such as feedstocks for fermentations for the production of biofuels and biochemicals. More preferably, the processes for oxidizing furanic compounds are applied in the bioproduction of FDCA as a monomeric precursor for the production of polyesters (plastics), wherein FDCA may substitute for PTA in the polyester PET in which case biobased polyethylenefurandicarboxylate (PEF) results. FDCA may also be used as a substrate for a large variety of valuable compounds, including e.g. as substrate for the production of succinic acid, 2,5-bis(aminomethyl)-tetrahydrofuran, 2,5-dihydroxymethyl-tetrahydrofuran, 2,5-dihydroxymethylfuran and 2,5-furandicarbaldehyde. FDCA may be used in the production of coatings, e.g. in alkyd resin and thermoplastic coatings. It may also be used as a xylene equivalent in biofuels and as solvent. FDCA may be esterified, and the esters may be used as plasticizers. FDCA may converted to its diol, that may be used in PET-like polyesters and polyurethanes. Further FDCA may be converted into its diamine, the diamine may be used as chain extender and the diamine may be converted into di-isocyanate, which can be used in the production of polyurethanes.

Thus, in a further aspect the invention relates to a process for producing a polymer from one or more, or at least two FDCA monomers, the process comprising the steps of: a) preparing an FDCA monomer in an oxidation process of the invention as described above; and, b) producing a polymer from the FDCA monomer(s) obtained in a). Preferably the polymer is polyethylenefurandicarboxylate (PEF).

In yet another aspect, the invention pertains to the use of a cell, preferably a cell of the invention, for the biotransformation of one or more of furanic precursors to FDCA to FDCA, wherein the cell is a cell expressing an HMFCA dehydrogenase as herein defined above, or a cell expressing polypeptide having furanic compound transport capabilities and further comprising a HMFCA dehydrogenase or oxidase activities as herein defined above. Preferably, at least one furanic precursor of FDCA that is biotransformed to FDCA is selected from the group consisting of HMF, DHF, HMFCA, FFCA and DFF, of which HMF is most preferred.

Polypeptides Having the Ability to Oxidize HMFCA to FFCA and Nucleic Acids Encoding Such Polypeptides In a further aspect the invention relates to a polypeptide having HMFCA dehydrogenase activity. Preferably the polypeptide is an alcohol dehydrogenase having the ability to oxidize HMFCA to FFCA. The polypeptide having HMFCA dehydrogenase activity preferably comprises or consist of an amino acid sequence that has at least 69, 69.4, 70, 71, 72, 73, 73.9, 74, 75, 76, 77, 78, 79, 80, 81, 82, 83, 84, 84.5, 85, 86, 87, 88, 89, 90, 91, 92, 93, 94, 95, 95, 96, 97, 98, 99 or 100% sequence identity with the amino acid sequence of at least one of SEQ ID NO.'s: 1-4, but is otherwise as herein defined above. Preferably the polypeptide is an isolated polypeptide.

The invention further relates to a nucleic acid molecule comprising at least one of:

a) a nucleotide sequence encoding a polypeptide having HMFCA dehydrogenase activity, which polypeptide comprises or consist of an amino acid sequence that has at least 69, 69.4, 70, 71, 72, 73, 73.9, 74, 75, 76, 77, 78, 79, 80, 81, 82, 83, 84, 84.5, 85, 86, 87, 88, 89, 90, 91, 92, 93, 94, 95, 95, 96, 97, 98, 99 or 100% sequence identity with the amino acid sequence of at least one of SEQ ID NO.'s: 1-4;
b) a nucleotide sequence set out in at least one of SEQ ID NO.'s: 22, 23, 57 and 58;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having HMFCA dehydrogenase activity as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

Polypeptides Having Furanic Aldehyde Dehydrogenase Activity and Nucleic Acids Encoding Such Polypeptides In a further aspect the invention relates to a polypeptide having furanic aldehyde dehydrogenase activity, i.e. a dehydrogenase that oxidizes furanic aldehydes to the corresponding furanic carboxylic acids. Preferably the furanic aldehyde dehydrogenase has the ability to oxidize at least one of i) oxidizing HMF to HMFCA, ii) oxidizing DFF to FFCA, and iii) oxidizing FFCA into FDCA and preferably comprises or consist of an amino acid sequence that has at least 50, 51, 52, 53, 54, 55, 56, 57, 58, 59, 60, 61, 62, 63, 64, 65, 66, 67, 68, 69, 70, 70.9, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of at least one of SEQ ID NO.'s: 5 and 6 but is otherwise as herein defined above. Preferably the polypeptide is an isolated polypeptide.

The invention further relates to a nucleic acid molecule comprising at least one of:

a) a nucleotide sequence encoding a polypeptide having furanic aldehyde dehydrogenase activity, which polypeptide comprises or consist of an amino acid sequence that has at least 50, 51, 52, 53, 54, 55, 56, 57, 58, 59, 60, 61, 62, 63, 64, 65, 66, 67, 68, 69, 70, 70.9, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO.'s: 5 and 6;
b) a nucleotide sequence set out in at least one of SEQ ID NO.'s: 24, 25 and 59;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having furanic aldehyde dehydrogenase activity as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

Polypeptides Having Furanic Alcohol/Aldehyde Oxidase Activity and Nucleic Acids Encoding Such Polypeptides In a further aspect the invention relates to a polypeptide having furanic alcohol/aldehyde oxidase activity. The polypeptide preferably is an oxidase activity that is capable of oxidising alcohol and aldehyde groups at the C2 and C5 positions in furanic compounds comprising such groups. The polypeptide preferably thus has EC 1.1 and EC 1.2 activities. Preferably the polypeptide with furanic oxidase activity has the ability to oxidize at least one of i) HMF to HMFCA, ii) HMF to DFF, iii) DFF to FFCA, iv) HMFCA to FFCA, and v) FFCA to FDCA, and preferably comprises or consist of an amino acid sequence that has at least 49.3, 50, 51, 52, 53, 54, 55, 56, 57, 58, 59, 60, 61, 62, 62.7, 63, 64, 65, 66, 66.9, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of at least one of SEQ ID NO.'s: 7-9 but is otherwise as herein defined above. Preferably the polypeptide is an isolated polypeptide.

The invention further relates to a nucleic acid molecule comprising at least one of:

a) a nucleotide sequence encoding a polypeptide having furanic oxidase activity, which polypeptide comprises or consist of an amino acid sequence that has at least 49.3, 50, 51, 52, 53, 54, 55, 56, 57, 58, 59, 60, 61, 62, 62.7, 63, 64, 65, 66, 66.9, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO.'s: 7-9;
b) a nucleotide sequence set out in SEQ ID NO.'s: 26-28;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having furanic oxidase activity as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

Polypeptides Involved in FDCA Catabolism and/or Polypeptides Involved in Alternative Routes for HMF Metabolism and Nucleic Acids Encoding Such Polypeptides In a further aspect the invention relates to a polypeptide having the ability to degrade FDCA. Preferably the polypeptide having the ability to degrade FDCA is at least one of a polypeptide having FDCA decarboxylating monooxygenase activity, a polypeptide having FDCA decarboxylase activity, a polypeptide having FDCA decarboxylating dehydrogenase activity, and a polypeptide lactonase activity, i.e. having the ability of hydrolysing a lactone resulting from FDCA decarboxylation.

In one embodiment, the polypeptide has FDCA decarboxylating monooxygenase activity and preferably comprises or consist of an amino acid sequence that has at least 43.4, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 82.3, 83, 84, 85, 86, 87, 88, 89, 90, 91, 92, 93, 94, 95, 95, 96, 97, 98, 99 or 100% sequence identity with the amino acid sequence of at least one of SEQ ID NO.'s: 10 and 11, but is otherwise as herein defined above. Preferably the polypeptide is an isolated polypeptide.

The invention further relates to a nucleic acid molecule comprising at least one of:

a) a nucleotide sequence encoding a polypeptide having FDCA decarboxylating monooxygenase activity, which polypeptide comprises or consist of an amino acid sequence that has at least 43.4, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 82.3, 83, 84, 85, 86, 87, 88, 89, 90, 91, 92, 93, 94, 95, 95, 96, 97, 98, 99 or 100% sequence identity with the amino acid sequence of at least one of SEQ ID NO.'s: 10 and 11;
b) a nucleotide sequence set out in at least one of SEQ ID NO.'s: 29 and 30;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In one embodiment, the polypeptide has FDCA decarboxylase activity and preferably comprises or consist of an amino acid sequence that has at least 62.9, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 12 but is otherwise as herein defined above. Preferably the polypeptide is an isolated polypeptide.

The invention further relates to a nucleic acid molecule comprising at least one of:

a) a nucleotide sequence encoding a polypeptide having FDCA decarboxylase activity, which polypeptide comprises or consist of an amino acid sequence that has at least 62.9, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 12;
b) a nucleotide sequence set out in SEQ ID NO: 31;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In one embodiment, the polypeptide has FDCA decarboxylating dehydrogenase activity and preferably comprises or consist of an amino acid sequence that has at least 85, 85.4, 86, 87, 88, 89, 90, 91, 92, 93, 94, 95, 95, 96, 97, 98, 99 or 100% sequence identity with the amino acid sequence of SEQ ID NO: 13 but is otherwise as herein defined above. Preferably the polypeptide is an isolated polypeptide.

The invention further relates to a nucleic acid molecule comprising at least one of:

a) a nucleotide sequence encoding a polypeptide having FDCA decarboxylating dehydrogenase activity, which polypeptide comprises or consist of an amino acid sequence that has at least 85, 85.4, 86, 87, 88, 89, 90, 91, 92, 93, 94, 95, 95, 96, 97, 98, 99 or 100% sequence identity with the amino acid sequence of SEQ ID NO: 13;
b) a nucleotide sequence set out in SEQ ID NO: 32;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In one embodiment, the polypeptide has lactonase activity, i.e. it has the ability of hydrolysing a lactone resulting from FDCA decarboxylation and preferably comprises or consist of an amino acid sequence that has at least 67.5, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 14 but is otherwise as herein defined above. Preferably the polypeptide is an isolated polypeptide.

The invention further relates to a nucleic acid molecule comprising at least one of:

a) a nucleotide sequence encoding a polypeptide having lactonase activity, which polypeptide comprises or consist of an amino acid sequence that has at least 67.5, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 14;
b) a nucleotide sequence set out in SEQ ID NO: 33;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In a further aspect the invention relates to a polypeptide involved in alternative endogenous routes for metabolism of HMF and other furanic precursors of FDCA, which alternative routes compete with the production of FDCA from HMF and other furanic precursors of FDCA. One such polypeptide is a dehydrogenase capable of reducing HMF and/or FFCA to the corresponding alcohol, such e.g. a short chain dehydrogenase. Preferably the polypeptide has short chain alcohol dehydrogenase activity.

In one embodiment, the polypeptide has short chain alcohol dehydrogenase activity and preferably comprises or consist of an amino acid sequence that has at least 73.6, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 15 but is otherwise as herein defined above. Preferably the polypeptide is an isolated polypeptide.

The invention further relates to a nucleic acid molecule comprising at least one of:

a) a nucleotide sequence encoding a polypeptide having FDCA decarboxylating dehydrogenase activity, which polypeptide comprises or consist of an amino acid sequence that has at least 73.6, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 15;
b) a nucleotide sequence set out in SEQ ID NO: 34;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

Specifically included in the invention are inactivation constructs for inactivation of the target coding sequences described in this section, which inactivation construct preferably comprise genomic DNA sequences surrounding or flanking the target coding sequence, as herein described above.

Polypeptides Having Furanic Transporter and Nucleic Acids Encoding Such Polypeptides In a further aspect the invention relates to a polypeptide having furanic compound transport capabilities as herein defined above. Preferably the polypeptide has the ability to transport furanic compound and preferably comprises or consist of an amino acid sequence that has at least 69, 70, 71, 72, 73, 74, 75, 76, 77, 78, 79, 80, 81, 82, 83, 84, 84.1, 85, 85.2, 86, 87, 88, 89, 90, 91, 92, 93, 94, 95, 95, 96, 97, 98, 99 or 100% sequence identity with the amino acid sequence of at least one of SEQ ID NO.'s: 16-18, but is otherwise as herein defined above. Preferably the polypeptide is an isolated polypeptide.

The invention further relates to a nucleic acid molecule comprising at least one of:

a) a nucleotide sequence encoding a polypeptide having furanic compound transport capabilities, which polypeptide comprises or consist of an amino acid sequence that has at least 69, 70, 71, 72, 73, 74, 75, 76, 77, 78, 79, 80, 81, 82, 83, 84, 84.1, 85, 85.2, 86, 87, 88, 89, 90, 91, 92, 93, 94, 95, 95, 96, 97, 98, 99 or 100% sequence identity with the amino acid sequence of at least one of SEQ ID NO.'s: 16-18;
b) a nucleotide sequence set out in SEQ ID NO.'s: 35-37;
c) a fragment of a nucleotide sequence as defined in (a) or (b) which is at 10, 15, 20, 30, 50 or 100 nucleotides in length;
d) a nucleotide sequence the sequence of which differs from the sequence of a nucleotide sequence of b) or c) due to the degeneracy of the genetic code; and,
e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having furanic compound transport capabilities as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

Polypeptides Having Regulator Furanic Aldehyde Dehydrogenase or Oxidase Activity and Nucleic Acids Encoding Such Polypeptides In a further aspect the invention relates to a polypeptide that is a transcriptional activator of genes involved in furan catabolism, as herein defined above. Preferably the transcriptional activator has the ability to activate transcription of at least one gene involved in furan catabolism and preferably comprises or consist of an amino acid sequence that has at least 52.4, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 19 but is otherwise as herein defined above. Preferably the polypeptide is an isolated polypeptide.

The invention further relates to a nucleic acid molecule comprising at least one of:

a) a nucleotide sequence encoding a polypeptide having the ability to activate transcription of at least one gene involved in furan catabolism, which polypeptide comprises or consist of an amino acid sequence that has at least 52.4, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 95, 96, 97, 98, 99 or 100% sequence identity with the amino acid sequence of SEQ ID NO: 19;
b) a nucleotide sequence set out in SEQ ID NO: 38;
c) a fragment of a nucleotide sequence as defined in (a) or (b) which is at 10, 15, 20, 30, 50 or 100 nucleotides in length;

d) a nucleotide sequence the sequence of which differs from the sequence of a nucleotide sequence of b) or c) due to the degeneracy of the genetic code; and, e) a nucleotide sequence which is the reverse complement of a nucleotide sequence as defined in a) to d).

Another aspect of the invention pertains to vectors, including cloning and expression vectors, comprising a nucleotide sequence as defined in a) to e) above in this section, which vectors are otherwise as described herein above.

In yet another aspect, the invention pertains to a cell comprising at least one of i) a polypeptide having the ability to activate transcription of at least one gene involved in furan catabolism as defined above in this section, and ii) a nucleic acid molecule as defined above in this section. Preferably the cell is a cell comprising or transformed with a nucleotide sequence as defined in a) to e) above in this section, or a vector comprising such a nucleotide sequence. The cell preferably is an isolated cell or a cultured cell, the cell preferably is otherwise as described herein above and preferably the cell comprises one or more of the genetic modifications described herein above. The cell can be applied in any of the methods, processes and uses as described above.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

TABLE 1

Amino acid sequence alignment of *Penicillium brasilianum* hmfL1 and 10 closest orthologues.

```
P_brasilianum_hmfL1   MGSLSLPETSLAAIQDK--ETKAISVAKRPTPVPVGTQVLVKLHYSGVCA
Spo_sche_ERT02385     ---MAVPTTSTAAIRDD--QGK-ISVQQRPTPVPERTQILVKVHYSGVCA
Asp_kawa_GAA84694     -MSTDNPATRKVAVCID--TQH-IKVEERPLPIPNDSEVVVLIEASGICA
Bys_spec_GAD98038     -MGSTIPATRKVAVTTS--PPT-VSITSLPIPQPAGTEVLLQIEATGICA
Asp_nige_XP_001397354 -MTTNVPATRKVAVCID--TQH-IELEERPMPTPSGSEVVVKIQATGICA
Eut_lata_XP_007796771 -MSCSPPTQSRVVVAKG--THD-LVVQERQTPEPTGKQILLRIEATGVCA
Asp_nige_EHA21652     -----------------------------MPTPSGSEVVVKIQATGICA
Fus_gram_EYB30957     -MSVQIPSQQRAAVRQGSGPDARAPIKTVPVPSPGQGQILVKVNWTGLCG
Fus_gram_XP_011318199 -MSVQIPSQQRAAVRQGSGPDARAPIKTVPVPSPGPGQILVKVNWTGLCG
Rhi_phas_WP_016737077 -MKIMTSKMMKAAVVRE--FGKPLAIECVPVPVPGPGEILVKVAACGVCH
Dye_jian_WP_038619920 ----MAPRTMKAAVAHR--FGEPLRIEEVPVPAPGRGEVLVKIVSSGVCH
                                                     * *   :::: :   *:*

P_brasilianum_hmfL1   TD---LHLARGSVPYLQPKVS--VGGHEGTGVIASLGPDVDAAEWHVGDR
Spo_sche_ERT02385     TD---VHIARGLIPYLRPKVA--VGGHEGTGVIAALGPDVDASQWAIGDR
Asp_kawa_GAA84694     TD---LHLVRRSIPYLQREVD--VCGREGVGRIVALGPDVDTSEWRLGDR
Bys_spec_GAD98038     TD---LHIVQRSLSYFQPKVD--IHGREGIGRIVALGPDVDASKWKIGDK
Asp_nige_XP_001397354 TD---LHLVRRTIPYLQRKVD--VCGREGVGHIVAVGPDVDTSKWHMGDR
Eut_lata_XP_007796771 TD---LHLIRRSIPYLQPKVD--ICGREGIGRIVRLGPEADQKRWSVGDR
Asp_nige_EHA21652     TD---LHLVRRTIPYLQRKVD--VCGREGVGHIVAVGPDVDTSKWHMGDR
Fus_gram_EYB30957     SDKSLLHDEWSDFGICMKDVTNGIAGHEGAGSVVAVGQGMEQR-WKIGDR
Fus_gram_XP_011318199 SDKSLLHDEWSDFGICMKDVTNGIAGHEGAGSVVAVGQGMEQR-WKIGDR
Rhi_phas_WP_016737077 TD---LHAAEGDWPVMPVPPF--IPGHEAAGIVAALGPDVTEF--KEGDA
Dye_jian_WP_038619920 TD---VHAVDGDWPVKPQPPF--IPGREGVGVVVALGEGVDNL--KVGDA
                      :*   :*                : ***. * :. :*          **

P_brasilianum_hmfL1   VAVRWVHIVCGKCEVCTTGF-ENLCQSRKLAGKDVEGTFAEYAIADSSYM
Spo_sche_ERT02385     VAVRWVHIVCGTCESCTTGH-ENLCAGRKLAGKDVDGTFAEYAIADSAYA
Asp_kawa_GAA84694     VAHRWIFDVCRNCEMCQEGN-EQLCDSRKLSGKDVEGCWGEYTIVNSKYL
Bys_spec_GAD98038     VAHRWIYRWCKECEPCRAGL-EQFCDKRQLSGLQVEGCWAEYTVADTEYM
Asp_nige_XP_001397354 VAHRWVFDVCLNCDMCQGGN-EQLCDSRKLSGKDVEGCWGEYTIVNSMYL
Eut_lata_XP_007796771 VAHRWIYRWCGECESCEDGN-EQLCDRRELSGKDIDGCWAEYTLVDSDYL
Asp_nige_EHA21652     VAHRWVFDVCLNCDMCQGGN-EQLCDSRKLSGKDVEGCWGEYTIVNSMYL
Fus_gram_EYB30957     AGVKWIASVCGECDFCMVGSDEVHCPEQTNSGFSVPGTFQEYVVADGKYS
Fus_gram_XP_011318199 AGVKWIASVCGECDFCMVGSDEVHCPEQTNSGFSVPGTFQEYVVADGKYS
Rhi_phas_WP_016737077 VGVAWLHDACLRCEYCETGW-ETLCAHQHNTGYSCNGGFAEYVIASAAFA
Dye_jian_WP_038619920 VGIAWLHDACGHCEYCITGW-ETLCEAQHDSGYSVNGSFAEYAIGNAAYV
                      ..  *:   *  *: *  *  *  *  :  :* .  * : **.: .  :

P_brasilianum_hmfL1   VRLPAGVSDADAAPILCAGVTVYKALKIASLRAGSWVAVAGAGGGLGHLA
Spo_sche_ERT02385     VRLPENVGDAEAAPILCAGVTVYKALKIARLRKGSWVAVAGAGGGLGHLA
Asp_kawa_GAA84694     MRISEDISATEAAPTLCAGTTAYRAIRTTGLTSGQWIAIIGAGGGLGHLA
Bys_spec_GAD98038     LRIPEGLDSAEAAPILCAGTTVYRALRTSELSPGQWVAIVGAGGGLGHLA
Asp_nige_XP_001397354 MRIPEDISAAEAAPTLCAGTTAYRAIRTAGLTSGQWIAIVGAGGGLGHLA
Eut_lata_XP_007796771 LRIPEEIDPVAAAPILCAG---------------HWVAIVGAGGGLGHLA
Asp_nige_EHA21652     MRIPEDISAAEAAPTLCAGTTAYRAIRTAGLTSGQWIAIVGAGGGLGHLA
Fus_gram_EYB30957     SKLPDGVTDEEAGPIMCGGVTAYTACKRSGVTPGQWLVIPGAGGGLGHFA
Fus_gram_XP_011318199 SKLPDGVTDEEAGPIMCGGVTAYTACKRSGVTPGQWLVIPGAGGGLGHFA
Rhi_phas_WP_016737077 ARLPAGVDFAEIAPILCAGVTTYKGLKETEARPGEWVAISGVGG-LGHVA
Dye_jian_WP_038619920 ARLPKDVDYAAMAPILCAGVTTYKGIRETEARPGEWIAISGIGG-LGHLA
                       ::.  :     .* :*.*                *:.: * ** ***.*
```

TABLE 1-continued

Amino acid sequence alignment of *Penicillium brasilianum* hmfL1 and 10 closest orthologues.

```
P_brasilianum_hmfL1   IQYARAMGLKVVALDAR--KRDLCLSLGAESYIDVLET---DDCVAQVIK
Spo_sche_ERT02385     VQYAKALGLKVVALDAN--KKDLCLSLGADAYVDVLAPGHDDGCVGAVVA
Asp_kawa_GAA84694     IQYAKASGLRVLGIDTGPSKRELSCKLGVTSYIDFMDT---PDLTADVIR
Bys_spec_GAD98038     IQYAKVQGLKVLAIDGGKEKEKLCTDLGADVYIDFTST---KDITATVID
Asp_nige_XP_001397354 VQYAKANDLQVLGIDTGPSKWELCSRLGVTSYIDFMET---RDLTADVTR
Eut_lata_XP_007796771 IQYAKVKGLKVLAIDAGGEKGAMCTKLGADAFVDFTQT---KDITSDVVK
Asp_nige_EHA21652     VQYAKANDLQVLGIDTGPSKWELCSRLGVTSYIDFMET---RDLTADVTR
Fus_gram_EYB30957     IQYAKAMGMRVIAIDGGDEKRDLCLKLGAEVFIDFKTT---KDIATQVLK
Fus_gram_XP_011318199 IQYAKAMGMRVIAIDGGDEKRDLCLKLGAEVFIDFKTT---KDIATQVLK
Rhi_phas_WP_016737077 IQYAKAMGLKVVALDVAAAKLDLARQVGADLALNARSE----DTVEKVLK
Dye_jian_WP_038619920 IQYATAMGLNVVAVDVAEEKLALARKLGASAAVDARSP----NAVEEVLD
                      :*** . .:.*:.:*    *  :.  :*.   ::        . .  *

P_brasilianum_hmfL1   VTDG-GAHGALICASSGQAYDDAVKFLRWTGTLVCIGLP----------
Spo_sche_ERT02385     ATDGVGAHGALICASSGVAYADAVKYLRKSGVLVCIGLP----------
Asp_kawa_GAA84694     VTDG-GPHGVIVVSSSSMAYEQALQYVRKMGIIVCIGIT----------
Bys_spec_GAD98038     ITSG-GAHGILVTSSSPRAYEQAITYVRKMGIIVCIGAT----------
Asp_nige_XP_001397354 VSGG-GPHGVIVVSSSTRAYEQALTYVRKMGIIVCIGISKLRWYLRATPQ
Eut_lata_XP_007796771 ITNG-GAHAILVTSSSVRAYEQAITYVRKRGIIICIGIT----------
Asp_nige_EHA21652     VSGG-GPHGVIVVSSSTRAYEQALTYVRKMGIIVCIGIK----------
Fus_gram_EYB30957     VTTH-GAHGVIVTAATRAAYESAPNYLRPNGTVVAVGLP----------
Fus_gram_XP_011318199 VTTH-GAHGVIVTAATRAAYESAPNYLRPNGTVVAVGLP----------
Rhi_phas_WP_016737077 ATNG-GAHGVVVTAVSPSAFSQALGMVRRKGTVSLVGLP----------
Dye_jian_WP_038619920 ATGG-GAHGVLVTAVSPKAFSQALNFTRRRGTMSLVGLP----------
                       :   *.*. :: : :  *: .*    *  * :  :*

P_brasilianum_hmfL1   ------PKPTLLSLGPADFVARG-IKVMGTSTGDRQDTVEALAFVAKGQV
Spo_sche_ERT02385     ------LRPTPIPVLPEDFVARG-LRLEGTSTGDRTDTAEALEFVARGQV
Asp_kawa_GAA84694     ------PNKMHFPIGPEYFVARG-VRLTGSSTGTMEDTREALQYVRDGRV
Bys_spec_GAD98038     ------STKMTFPIGPEYFVGKG-VRLTGTSTGTLRDTEEALELVRQGKV
Asp_nige_XP_001397354 ANIPQAPNKMHFPIGPEYFVARG-VRLTGSSTGTMEDTCQALQYVRDGRV
Eut_lata_XP_007796771 ------PQKMSFPIGPEYFVARG-VRLTGTSTGTIEDTKEALEYVKTGQV
Asp_nige_EHA21652     -----------------YFVARG-VRLTGSSTGTMEDTCQALQYVRDGRV
Fus_gram_EYB30957     ------QDPTVLAGAPPMLVALRRLKIVGSVTGSMKDVEEALEFTARGLV
Fus_gram_XP_011318199 ------QDPTVLAGAPPMLVALRRLKIVGSVTGSMKDVEEALEFTARGLV
Rhi_phas_WP_016737077 --------PGNFPTPIFDVVLKR-ITIRGSIVGTRRDLDEALAFAAEGRV
Dye_jian_WP_038619920 --------PGDFATPIFDVVLKR-LTIRGSIVGTRKDLAEAVAFAAEGKV
                                        .*    : : *: .*   *  :*:  .  * *

P_brasilianum_hmfL1   KPQLTERRLEDVEEILKEIENGTMQGKAVIRIA-------------
Spo_sche_ERT02385     KPQIVERQLGEIEAILEEIEKGTVHGKSVIKIA-------------
Asp_kawa_GAA84694     KPMIVEVRLEDIGACLQALEKGEGDGRFVVKF--------------
Bys_spec_GAD98038     KPIIVEKKLEDIPECLDLLAKGDAVGKFVVKL--------------
Asp_nige_XP_001397354 KPIIVEARLEEIEACLQALEKGEADGRFVVSFS-------------
Eut_lata_XP_007796771 KPITIEKRLEDIAECLSILEKGDAVGRYVVRL--------------
Asp_nige_EHA21652     KPIIVEARLEEIEACLQALEKGEADGRFVVSFS-------------
Fus_gram_EYB30957     HPILSKGKLEDLDDWVHKLATGQVAGRCVLKVAA------------
Fus_gram_XP_011318199 HPILSKGKLEDLDDWVHKLATGQVAGRCVLKVAA------------
Rhi_phas_WP_016737077 RAEIAKAPLDDINDIFASLKAGTIEGRMVLDIAGEAGVSAAAEQSAA
Dye_jian_WP_038619920 VPTIERRKLEDVNDVLQGLREGHIQGRVVLDIGTPU---SAGE----
                       .   .  * ::   .  :  *   *: *: .
```

TABLE 2

Amino acid sequence alignment of *Penicillium brasilianum* hmfL2 and 10 closest orthologues.

```
P_brasilianum_hmfL2      MS--LPSHYKRAAFKEAGGPLTIEEVDLTMPDAGEVLVKVEACGVCFSDT
Coc_immi_XP_001244132.2  MA--LPQTFKQAVFKGAGKPLVIEEVSLALPGPGEVLVKVEACGVCFSDT
Coc_posa_XP_003068662    MA--LPQTFKQAVFKGAGKPLVIEEVSLALPGPGEVLVKVEACGVCFSDT
Coc_posa_EFW20539        MA--LPQTFKQAVFKGAGKPLVIEEVSLALPGPGEVLVKVEACGVCFSDT
Tri_rubr_XP_003235253    MD--IPKTFKQAIFKEKGAPLVLEEVPMTPPGNGEVLVKVQACGVCHSDV
Tri_equi_EGE05431        MD--IPKTFKQAIFKEKGAPLVLEEVPMTPPGNGEVLVKVQACGVCHSDV
Cha_glob_XP_001220755    MT--LPKTFKQAAFHSQGAALTIEDAELRLPGPGEVLVKVEACGVCFSDM
Tri_tons_EGD92820        MD--IPKTFKQAIFKEKGAPLVLEEVPMTPPGNGEVLVKVQACGVCHSDV
Mic_gyps_XP_003173798    MD--IPKTFKQAIFKEVGAPLVLEEVPMTPPGKGEVLVKVQTCGVCYSDT
End_pusi_XP_007800835    MAPELPKTFKRAVFKEQGAPLTIEEVELRMPERGEVLVKVEACGVCHSDS
Art_otae_XP_002844685    MD--APKTFKQAIFKEAGAPLVLEEVPLTPPEKGEVLVKVQACGVCRSDF
                         *    *. :*:* *:  * .*.:*:. :  *  *******::**** **

P_brasilianum_hmfL2      VPQAHGLGGKFPIVPGHEIIGHVVATGDGVSDWEVGDRIGEGWHGGHDGT
Coc_immi_XP_001244132.2  YAQKNMLGGGFPIVPGHEIIGRVAAVGDGVSGWGLGDRIGGGWHGAHDGT
Coc_posa_XP_003068662    YAQKNMLGGGFPIVPGHEIIGRVAAVGDGVSGWGLGDRIGGGWHGAHDGT
```

TABLE 2-continued

Amino acid sequence alignment of *Penicillium brasilianum* hmfL2 and 10 closest orthologues.

```
Coc_posa_EFW20539          YAQKNMLGGGFPIVPGHEIIGRVAAVGDGVSGWGLGDRIGGGWHGAHDGT
Tri_rubr_XP_003235253      FVQNDGLGGGLPRVPGHEIIGHVAATGEGVTQWKVGDRIGGAWHGGHDGT
Tri_equi_EGE05431          FVQNDGLGAGLPRVPGHEIIGHVAAIGEGVTQWKVGDRIGGAWHGGHDGT
Cha_glob_XP_001220755      FAQQNIMGGGFPIVPGHEIIGRVAAVGDGVTAWKVGERVGAGWHGGHDGT
Tri_tons_EGD92820          FVQNDGLGAGLPRVPGHEIIGHVAAIGEGVTQWKVGDRIGGAWHGGHDGT
Mic_gyps_XP_003173798      AVQKNALGGGLPRVPGHEIIGHVAAVGEGVTQWKVGDRIGGAWHGGHDG-
End_pusi_XP_007800835      MAQMNIFGGGFPLVPGHEIIGHVAAVADGETAWKVGDRIGGPWHGGHDGT
Art_otae_XP_002844685      YVQHNAVGS-LPRVPGHEIIGHVAAVGEGVTQWKVGDRIGGAWHGGHDGT
                             * . .*. :* ********:*.* .:* : * :*:*:*  ***.***

P_brasilianum_hmfL2        CPSCRQGHFQMCDNQSINGVTKNGGYAQYCILRSEAAVRIPTHVSAAEYA
Coc_immi_XP_001244132.2    CKSCKKGLFQMCSNKLINGETRSGGYAEYCTLRAEAAVRVPDHIDAAKYA
Coc_posa_XP_003068662      CKSCKKGLFQMCSNKLINGETRSGGYAEYCTLRAEAAVRVPDHVDAAKYA
Coc_posa_EFW20539          CKSCKKGLFQMCSNKLINGETRSGGYAEYCTLRAEAAVRVPDHVDAAKYA
Tri_rubr_XP_003235253      CRQCKKGYYQMCDNELVNGVNKGGGYAEYCLLRAEAGVRVPADVDAAVYA
Tri_equi_EGE05431          CRQCKKGYYQMCDNELINGVNKGGGYAEYCLLRAEAGVRVPEDVDAAVYA
Cha_glob_XP_001220755      CFACKKGLYQMCDNQVVNGETKAGGYAEYVLLRSEATVRVPERVSAAKYA
Tri_tons_EGD92820          CRQCKKGYYQMCDNELINGVNKGGGYAEYCLLRAEAGVRVPEDVDAAVYA
Mic_gyps_XP_003173798      -------YYQMCDNALVNGVNKGGGYAEYCLLRSEAGVRIPPDVDAAKFA
End_pusi_XP_007800835      CKACKTGFFQMCDNEKINGITRNGGYAQYCTLRSEAGVSIPSHLDAAEYA
Art_otae_XP_002844685      CKPCKKGYFQMCDNALVNGVNKGGGYAEYCKLRAEAGVRIPADIDAAKYA
                                   :***.*  :** .: ****:*  **:** * :* .:.** :*

P_brasilianum_hmfL2        PILCAGVTVFNSMRQIGVKPGSTVAIQGLGGLGHLAIQYANRFGFRVVAI
Coc_immi_XP_001244132.2    PILCAGVTVFNSMRHMNVPPGETVAIQGLGGLGHLAIQCANRFGYRVVAI
Coc_posa_XP_003068662      PILCAGVTVFNSMRHMNVPPGETVAIQGLGGLGHLAIQCANRFGYRVVAI
Coc_posa_EFW20539          PILCAGVTVFNSMRHMNVPPGETVAIQGLGGLGHLAIQCANRFGYRVVAI
Tri_rubr_XP_003235253      PILCAGVTVFNSMRNMKLGPGSTVAIQGLGGLGHLAIQYANKFGYRVVAL
Tri_equi_EGE05431          PILCAGVTVFNSMRNMKLMPGSTVAIQGLGGLGHLAIQYANKFGYRVVAL
Cha_glob_XP_001220755      PILCAGMTVFNSLRHMDVQPGETVAVQGLGGLGHLAIQAAQRMGYRVVAI
Tri_tons_EGD92820          PILCAGVTVFNSMRNMKLMPGSTVAIQGLGGLGHLAIQYANKFGYRVVAL
Mic_gyps_XP_003173798      PILCAGVTVFNSMRNMNLIPGSTVAIQGLGGLGHLAIQYANRFGYRVVAL
End_pusi_XP_007800835      PILCAGVTVFNSMRRMQISPGSLVAVQGLGGLGHLALQFANKFGFRVAAL
Art_otae_XP_002844685      PILCAGVTVFNSMRHMNMMPGSTVAVQGLGGLGHLAIQYANKFGYRVVAL
                           ******:*****:*.: : **. **:**********:* *:::*:**.*:

P_brasilianum_hmfL2        SRDDQKERFVRDLGAHEYINTSEEDVGSALQKLGGASLIVATAPNARAIS
Coc_immi_XP_001244132.2    SRDSKKEKFARALGAHEYIDTSKEDVSKALRRLGKASMIVLTAPNADVVN
Coc_posa_XP_003068662      SRDSKKEKFARALGAHEYIDTSKEDVSKALRRLGKASMIVLTAPNADVVN
Coc_posa_EFW20539          SRDSKKEKFARALGAHEYIDTSKEDVSKALRRLGKASMIVLTAPNADVVN
Tri_rubr_XP_003235253      SRGSDKEKFAKELGAHIYIDGGKGDIGEQLQAIGGADMIVSTAPSRSAVE
Tri_equi_EGE05431          SRGSDKEKFAKELGAHIYIDGGKGDIGEQLQAIGGADMIVSTAPSRSAVE
Cha_glob_XP_001220755      SRGADKEAFARQLGAHEYIDSSKGDVGEALRRLGGARLAMTTAPTAEVMG
Tri_tons_EGD92820          SRGSDKEKFAKELGAHIYIDGGKGDIGEQLQAIGGADMIVSTAPSRSAVE
Mic_gyps_XP_003173798      SRGSDKEKFARDLGAHIYIDGSKGDVGEQLQKLGGVDMIVSTAPSKNAVE
End_pusi_XP_007800835      SRNADKEKFARDLGAHEYIDGSKGDQGEALQKLGGASLIVVTAPDAKVIS
Art_otae_XP_002844685      SRGSEKEKFARDLGAHEYLDASKGDIGEQLQNLGGASMIVSTAPSKDAVE
                           **. .** *.: **** *:: .: * .. *: :* . : : ***   .:

P_brasilianum_hmfL2        PLLKGLRPLGKLLILAVPGEIPLDTRLM----------VARGLSVHGWPS
Coc_immi_XP_001244132.2    PLLNGLEARGKLLMLSGPGEVTINSSLM----------VVSGLSIHAWPS
Coc_posa_XP_003068662      PLLNGLEARGKLLMLSGPGEVPINSSLM----------VVSGLSIHAWPS
Coc_posa_EFW20539          PLLNGLEARGKLLMLSGPGEVPINSSLM----------VVSGLSIHAWPS
Tri_rubr_XP_003235253      PLLKGLGMLGKLLVLSIPGDITVNTGLM----------LRRGLTVQCWPS
Tri_equi_EGE05431          PLLKGLGMLGKLLILSIPGDITINTGLM----------VRRGLTVQCWPS
Cha_glob_XP_001220755      TLLKGLGPMGKLLILSVPGDVPVNTGVM----------LKYALSVQSWPC
Tri_tons_EGD92820          PLLKGLGMLGKLLIPSIPGDITINTGLM----------VRRGLTVQCWPS
Mic_gyps_XP_003173798      PLLKGLGMLGKLLVLSVPGDITINTGLM----------VRRGLSVQCWPS
End_pusi_XP_007800835      PLMKGLGIMGKLLILAAAGEVPVDTGAM----------IHYGLSVHSWPS
Art_otae_XP_002844685      PLLKGLGMLGKLLILSVPGDITINTGLMNKAVDLLASQVRQGLSVQCWPS
                           .*::**   ****: : .*::.:::  *          :  .*::: **.

P_brasilianum_hmfL2        GHALDSEETIRFTELEDIKCMIQTYSLDRANEAFDAMISGSVRFRAVITM
Coc_immi_XP_001244132.2    GHATDSEEAIAFTELQNINCMVETFPLARANDAFEAMLKGTVRFRAVITM
Coc_posa_XP_003068662      GHATDSEEAIAFTELQNINCMVETFPLARANDAFGKNSHKN---------
Coc_posa_EFW20539          GHATDSEEAIAFTELQNINCMVETFPLARANDAFGNVERDGSV-------
Tri_rubr_XP_003235253      GHATDSEDAIEFTKLENINCMVEKFPLAKVQEAYDAMVKGTVRFRAVITM
Tri_equi_EGE05431          GHATDSEDAIEFTKLENINCMVEKFPLAKVQEAYDAMVKGTVRFRAVITM
Cha_glob_XP_001220755      GHATDSEDAIQFMDLQKVDCIVQTFPLAKANEAFNAMMDGSVRFRTVIVM
Tri_tons_EGD92820          GHATDSEDAIEFTKLENINCMVEKFPLAKVQEAYDAMVKGTVRFRAVITM
Mic_gyps_XP_003173798      GHATDSEDAIEFAKLEGINCMVETFPLAKVNEAYDAMVKGTVRFRAVITM
End_pusi_XP_007800835      GHSLDSEEAIAFTELENIKCMVEKFQLEKCNDAMDAMMKGTVKVEEAAEL
Art_otae_XP_002844685      GHATDSEEAIEFTKLENINCMVETFPLEKVNDAYDAMVKGSEPIMGTPUS
                           **: ***::* * .*: :.*:::.: * : ::*

P_brasilianum_hmfL2        E-------------------------------------------------
Coc_immi_XP_001244132.2    E-------------------------------------------------
```

TABLE 2-continued

Amino acid sequence alignment of *Penicillium brasilianum* hmfL2 and 10 closest orthologues.

```
Coc_posa_XP_003068662     --------------------------------------------------
Coc_posa_EFW20539         --------------------------------------------------
Tri_rubr_XP_003235253     E-------------------------------------------------
Tri_equi_EGE05431         E-------------------------------------------------
Cha_glob_XP_001220755     E-------------------------------------------------
Tri_tons_EGD92820         E-------------------------------------------------
Mic_gyps_XP_003173798     E-------------------------------------------------
End_pusi_XP_007800835     CRRIGEWFAELEVPGRSSAGWLEDIQPDSWVGHVFCIWKREPGVVVGIEL
Art_otae_XP_002844685     AGE-----------------------------------------------

P_brasilianum_hmfL2       --------------------------------------------------
Coc_immi_XP_001244132.2   --------------------------------------------------
Coc_posa_XP_003068662     --------------------------------------------------
Coc_posa_EFW20539         --------------------------------------------------
Tri_rubr_XP_003235253     --------------------------------------------------
Tri_equi_EGE05431         --------------------------------------------------
Cha_glob_XP_001220755     --------------------------------------------------
Tri_tons_EGD92820         --------------------------------------------------
Mic_gyps_XP_003173798     --------------------------------------------------
End_pusi_XP_007800835     GPVVTDEGCSGPICGVEDPRLNLVIVELLGVVALSGSNVQDCSSSLGKLE
Art_otae_XP_002844685     --------------------------------------------------

P_brasilianum_hmfL2       --------------------------------------------------
Coc_immi_XP_001244132.2   --------------------------------------------------
Coc_posa_XP_003068662     --------------------------------------------------
Coc_posa_EFW20539         --------------------------------------------------
Tri_rubr_XP_003235253     --------------------------------------------------
Tri_equi_EGE05431         --------------------------------------------------
Cha_glob_XP_001220755     --------------------------------------------------
Tri_tons_EGD92820         --------------------------------------------------
Mic_gyps_XP_003173798     --------------------------------------------------
End_pusi_XP_007800835     ATGSLKEILAPGPMGPKSSHSKFQAVASMMFTVAGMPEESQALLKKVFDV
Art_otae_XP_002844685     --------------------------------------------------

P_brasilianum_hmfL2       --------------------------------
Coc_immi_XP_001244132.2   --------------------------------
Coc_posa_XP_003068662     --------------------------------
Coc_posa_EFW20539         --------------------------------
Tri_rubr_XP_003235253     --------------------------------
Tri_equi_EGE05431         --------------------------------
Cha_glob_XP_001220755     --------------------------------
Tri_tons_EGD92820         --------------------------------
Mic_gyps_XP_003173798     --------------------------------
End_pusi_XP_007800835     FDRTFVMIPLLLSGLRSQSRPSEDQYNDTNGC
Art_otae_XP_002844685     --------------------------------
```

TABLE 3

Amino acid sequence alignment of *Penicillium brasilianum* hmfL3 and 10 closest orthologues.

```
P_brasilianum_hmfL3     -MAPQIPEKQWAQVVEKKGGPPVYKEIPVPKPGPDEVLLKIKYSGVCHTD
Pen_oxal_EPS34335       -MAPQVPDKQWAQVVEQKGGPPVYKEIPVPKPGPDEVLVQIKYSGVCHTD
Pen_rube_XP_002557546   MS--PIPETQWAQVVEKKGGPPVYKQIPVPKPGPDEVLVKMKYTGVCHTD
Pen_digi_EKV11985       MSSFTIPETQWAQVIEQPGASPVYKQIPVPKPGPDEVLVKIRYTGVCHTD
Neo_fisc_XP_001262738   MTKDSVPSMQWAQVAEKVGGPLVLKQIPVPKPGPDEILVKIRYSGVCHTD
Neo_fisc_XP_001266013   ---MTIPDKQWAQVVEKKGSPPIYKEIPVPKPGPDEILVKIHYSGVCHTD
Asp_kawa_GAA89866       ---MTIPEKQWAQVVEKKGGPLVYKEIPVAKPGPDEILVKIRYTGVCHTD
Asp_fumi_EDP48048       MTKFDIPSMQWAQVAEQVGGPLVLKQIPVPKPGPDEILVKIRYSGVCHTD
Asp_nige_XP_001398382   ---MTIPEKQWAQVVEKKGGPPVYKQIPVAKPGPDEILVKIRYTGVCHTD
Asp_clav_XP_001273959   ---MSLPEKQWAQVVEKKGGPPVYKEIPVPKPGPDQILVKIRYTGVCHTD
Asp_fumi_XP_746830      MTKFDIPSMQWAQVAEQVGGPLVLKQIPVPKPGPDEILVKIRYSGVCHTD
                             :*. ***** *: *.. : *:***.*****::*::::*:******

P_brasilianum_hmfL3     LHAMNGDWPLPVKMPLVGGHEGAGIVVAKGELAEGVEIGDHAGIKWLNGS
Pen_oxal_EPS34335       LHAMKGDWPLPLKMPLVGGHEGAGIVVAKGELADGVEIGDHVGIKWLNGS
Pen_rube_XP_002557546   LHAMNGDWPLTVKQNLVGGHEGAGIVVAKGSLAQGIEIGDHAGIKWLNGS
Pen_digi_EKV11985       LHAMNGDWPMPVKKNLVGGHEGAGVVVATGSLVKGIEVGDHAGIKWLNGS
Neo_fisc_XP_001262738   LHAMKGDWPLPVKMPLVGGHEGAGIVVAKGDLVTEFEIGDHAGIKWLNGS
Neo_fisc_XP_001266013   LHAMKGDWPLPLKLPLVGGHEGAGVVVAKGELVTGFEIGDHAGIKWLNGS
Asp_kawa_GAA89866       LHAMKGDWPLDLKLPLVGGHEGAGVVVATGELVNEFEVGDHAGIKWLNGS
Asp_fumi_EDP48048       LHAMKGDWPLPVKMPLVGGHEGAGVVVAKGDLVTEFEIGDHAGIKWLNGS
Asp_nige_XP_001398382   LHAMKGDWPLGLKLPLVGGHEGAGVVVATGDLVNEFEVGDHAGIKWLNGS
Asp_clav_XP_001273959   LHAMKGDWPLEVKMPLVGGHEGAGVVVAKGELVTGFEIGDHAGIKWLNGS
```

TABLE 3-continued

Amino acid sequence alignment of *Penicillium brasilianum* hmfL3 and 10 closest orthologues.

```
Asp_fumi_XP_746830       LHAMKGDWPLPVKMPLVGGHEGAGVVVAKGDLVTEFEIGDHAGIKWLNGS
                         ****:****: :*  *********:***.*.*.  .*:***.********

P_brasilianum_hmfL3      CLACEYCKTSDEPLCATPQLSGYTVDGTFQQYAIGKAAHVTILPKDIPLD
Pen_oxal_EPS34335        CLACEYCKTAEEQLCAGQQLSGYTVDGTFQQYAIGKAAHVTNLPKDVSLD
Pen_rube_XP_002557546    CLACEFCKTADEPLCPDAQLSGYTVDGTFQQYAIGKAAHVAKLPKEVSLD
Pen_digi_EKV11985        CLSCEYCKTSDEPLCPDAQLSGYTVDGTFQQYAIGKAAHVLKLSKDIPLD
Neo_fisc_XP_001262738    CLACEFCKQADEPLCQNASLSGYTVDGTFQQYTIGKATHASKIPKNVPLD
Neo_fisc_XP_001266013    CMECEFCKQSEEPLCPHATMSGYTVDGTFQQYCVAKATHASNIPKDVPLD
Asp_kawa_GAA89866        CLACEFCKQADEPLCPHASLSGYTVDGTFQQYAVAKASHASKLPKEVPLD
Asp_fumi_EDP48048        CLACEFCKQADEPLCQNALLSGYTVDGTFQQYTIGKATHASKIPKHVPLD
Asp_nige_XP_001398382    CLACEFCKQAEEPLCPHALLSGYTVDGTFQQYAIAKASHASKLPKEVPLD
Asp_clav_XP_001273959    CMECEFCRQAEEPLCPNASLSGYTVDGTFQQYCIGKATHASKIPKDVPLD
Asp_fumi_XP_746830       CLACEFCKQADEPLCQNALLSGYTVDGTFQQYTIGKATHASKIPKHVPLD
                         *: **:*: ::* **    :************ :.**:*.  :.*.:.**

P_brasilianum_hmfL3      GIAPILCAGLTVYKGLKESNARPGQTVAIVGAGGGLGVMAQQYAKAMGLR
Pen_oxal_EPS34335        GIAPILCAGVTVYRGLKESAARPGQTVAIVGAGGGLGAMAQQYAKAMGLR
Pen_rube_XP_002557546    AIAPILCAGITVYKGLKESGARPGQTVAIVGAGGGLGSLAQQYAKAMGLR
Pen_digi_EKV11985        TISPILCAGITVYKALKESGVRPGQTVAIVGAGGGLGSLGQQYAKAMGLR
Neo_fisc_XP_001262738    AVAPVLCAGITVYKGLKESGARPGQTVAIVGAGGGLGSLAQQYARAMGLR
Neo_fisc_XP_001266013    AAAPILCAGLTVYKGLKESGARPGQTVAIVGAGGGLGSLAQQYAKAMGLR
Asp_kawa_GAA89866        AVAPILCAGITVYKGLKESGARPGQTVAIVGAGGGLGSLALQYAKAMGLR
Asp_fumi_EDP48048        AVAPVLCAGITVYKGLKESGARPGQTVAIVGAGGGLGSLAQQYARAMGLR
Asp_nige_XP_001398382    AVAPILCAGITVYKGLKESGARPGQTVAIVGAGGGLGSLALQYAKAMGLR
Asp_clav_XP_001273959    AIAPVLCAGITVYKGLKESGARPGETVAIVGAGGGLGSLAVQYAKAMGLR
Asp_fumi_XP_746830       AVAPVLCAGITVYKGLKESGARPGQTVAIVGAGGGLGSLAQQYARAMGLR
                           :*:****:***:.**** .***:************ :. ***:*****

P_brasilianum_hmfL3      VISIDGGDEKRQVCEKLDSEAYIDFTKSKDLVSDVKAATPEGLGAHAVIL
Pen_oxal_EPS34335        VIAIDGGDEKREMCEKLGSEAYIDFTKSKDLIADVRAATPDNLGAHAVLL
Pen_rube_XP_002557546    VIAIDGGEEKKAMCEKLGAEAYVDFTKSTDLVADVKAATPDGLGAHAVLL
Pen_digi_EKV11985        VIAIDGGEEKKAMCLQLGAETYVDFTKSTDVIADVKAATPGGLGAHAVLL
Neo_fisc_XP_001262738    VIAIDGGDEKRVMCEQLGAEAYVDFTKSSDLVADVKAATPDGLGAHAVIL
Neo_fisc_XP_001266013    VVAIDGGDEKREMCEKLGAEAYIDFTISKNVVEDVKAATPGGLGAHAVLL
Asp_kawa_GAA89866        TISIDGGDEKRAMCEKLGSEAYIDFKTSKDVVEDVKAATPEGLGAHAVIL
Asp_fumi_EDP48048        VIAIDGGDEKRAMCEQLGAEAYVDFTKSKDLVADVKAATPDGLGAHAVIL
Asp_nige_XP_001398382    TIAIDGGDEKKAMCEKLGSEAYIDFKTSKDVVEDVKAATPEGLGAHAVIL
Asp_clav_XP_001273959    VVGIDGGDEKRELCEKLGAEAFVDFTKSKDVIEDVKANTPEGLGAHAVLL
Asp_fumi_XP_746830       VIAIDGGDEKRAMCEQLGAEAYVDFTKSKDLVADVKAATPDGLGAHAVIL
                         .:.****:**: :* :*.:*:::**. *.::: **:* ** .******:*

P_brasilianum_hmfL3      LAVSEKPFQQAVEYSRPRGTIVAIGMPANAFLKASVFETVVKMITIKGSY
Pen_oxal_EPS34335        LAVSEKPFQQAVEYARPRGNIVAIGLPAHAFLKAPVFESVTKMINIKGSY
Pen_rube_XP_002557546    LAVSEKPFQQAVEYARSRGTIVAIGLPAHAFLKAPVFETVVKMISIKGSY
Pen_digi_EKV11985        LAVAEKPFQQAVEYARSRGTIVAIGLPANAFLKAPVFETVVRMINIKGSY
Neo_fisc_XP_001262738    LAVSEKPFQQATEYVRSRGTVVAIGLPANAFLRAPVLNTVVRMINIKGSY
Neo_fisc_XP_001266013    LAVSEKPFQQATDYVRSRGTIVAIGMPAEAYLKAPVFNTVIKMITIKGSY
Asp_kawa_GAA89866        LAVAEKPFQQATEYVRSKGSVVAIGLPAGAFLRAPVFNTVVRMINIKGSY
Asp_fumi_EDP48048        LAVSEKPFQQATEYVRSRGTVVAIGLPANAFLRAPVLNTVVRMINIRGSY
Asp_nige_XP_001398382    LAVAEKPFQQATEYVRSKGSVVAIGMPAGAFLRAPVFNTVVRMINIKGSY
Asp_clav_XP_001273959    LAVSERPFQQATGYVRSRGSIVAIGLPADAFLKAPVFSTVVKMINIKGSY
Asp_fumi_XP_746830       LAVSEKPFQQATEYVRSRGTVVAIGLPANAFLRAPVLNTVVRMINIRGSY
                         ***:*:*****. * *.:*.:****:** *:*:*.*:.:* :**.*:***

P_brasilianum_hmfL3      VGNRQDASEAVDFYARGLIKAPFKTVPLEELPKVFELMGKLPNSNLLLHK
Pen_oxal_EPS34335        VGNRQDAAEAVGFYARGLIKAPFKTVPLKDLPKVFELME-----------
Pen_rube_XP_002557546    VGNRQDGVEAIDFYARGLIKAPFKTVPLKELPEVFKLME-----------
Pen_digi_EKV11985        VGNRQDGEEAVEFFARGLINAPFKTVPLKELPEVFELMK-----------
Neo_fisc_XP_001262738    VGNRQDGVEAIDFFARGLIKAPFKTAPLEDLPKIYELME-----------
Neo_fisc_XP_001266013    VGNRQDGVEAIDFFARGLINAPFKKAPLKDLPRIFELME-----------
Asp_kawa_GAA89866        VGNRQDGVEAVDFFARGLIKAPFKTAPLEDLPRIFELME-----------
Asp_fumi_EDP48048        VGNRQDGVEAIDFFARGLIKAPFKVAPLADLPKIYELME-----------
Asp_nige_XP_001398382    VGNRQDGVEAVDFFARGLIKAPFKTAPLEDLPRIFELME-----------
Asp_clav_XP_001273959    VGNRQDGVEAIEFFARGLINAPFKKAPLKDLPKIYELME-----------
Asp_fumi_XP_746830       VGNRQDGVEAIDFFARGLIKAPYKVAPLADLPKIYELME-----------
                         ******. **: *:*****:**:* .** :**.:::**

P_brasilianum_hmfL3      LLICFSQSKARLPVVMFSRCQSKCINRRAVHNRQHRMSIS
Pen_oxal_EPS34335        --------------------QGKIAGRYVLQMPE------
Pen_rube_XP_002557546    --------------------EGKIAGRYVLEIPE------
Pen_digi_EKV11985        --------------------QGKIAGRYVLEVPE------
Neo_fisc_XP_001262738    --------------------QGKIAGRYVLELPE------
Neo_fisc_XP_001266013    --------------------QGKIAGRYVLEIPE------
Asp_kawa_GAA89866        --------------------QGQIAGRYVLEVPQ------
Asp_fumi_EDP48048        --------------------QGKIAGRYVLEMPE------
Asp_nige_XP_001398382    --------------------QGQIAGRYVLEVPQ------
```

TABLE 3-continued

Amino acid sequence alignment of *Penicillium brasilianum* hmfL3 and 10 closest orthologues.

```
Asp_clav_XP_001273959 --------------------QGKIAGRYVLEVPK------
Asp_fumi_XP_746830    --------------------QGKIAGRYVLEMPEUSAGE-
                                          :.:  .* .:.  :
```

TABLE 4

Amino acid sequence alignment of *Penicillium brasilianum* hmfL4 and 10 closest orthologues.

```
P_brasilianum_hmfL4   --------------------------------------------------
Pen_oxal_EPS32591     --------------------------------------------------
Pen_rube_XP_002567675 --------------------------------------------------
Pen_digi_EKV10327     --------------------------------------------------
Asp_fumi_XP_753506    MHLSRTFVPRLSNSLAATSPALVRLSGVRCHLQPSFRPTASLRSSSQPHT
Asp_fumi_KEY78459     MHLSRTFVPRLSNSLAATSPALVRLSGVRCHLQPSFRPTASLRSSSQPHT
Neo_fisc_XP_001259550 --------------------------------------------------
Asp_oryz_EIT82010     MYLNRFFATHFASLRTTATRITSPSIARLSAIRAHLSPSPISPFSHQARA
Asp_terr_XP_001211305 --------------------------------------------------
Asp_kawa_GAA89952     --------------------------------------------------
Asp_clav_XP_001274440 --------------------------------------------------

P_brasilianum_hmfL4   MSLPTTMRAVIVEQTGGPEVLQFKTDHPVPTPGEGQLLVHNNISGVNYID
Pen_oxal_EPS32591     MSIPSTMKAVVIEQTGGPEVLQFKTDHPVPTPKEGQLLVHNNISGVNYID
Pen_rube_XP_002567675 MSVPATMKAVVVEETGGPEVLKFKTSYPVPTPRAGELLVRNNISGVNYID
Pen_digi_EKV10327     MSIPTTMKAVVVEQTGGPEVLQYKTSYPVPTPQAGQLLVRNNISGVNYID
Asp_fumi_XP_753506    MSIPTTMKAVLIEKTGGPEVLDFKTDHPVPTPQEGQLLVKNNISGINYID
Asp_fumi_KEY78459     MSIPTTMKAVLIEKTGGPEVLDFKTDYPVPTPQEGQLLVKNNISGINYID
Neo_fisc_XP_001259550 MSIPTAMKAVLVEKTGGPEVLDFKTDYPVPAPQEGQLLVKNNISGINYID
Asp_oryz_EIT82010     MSVPSTMKAVIVEKLGGPEVLEFKSDHPVPTPQEGQLLVKNNISGVNYID
Asp_terr_XP_001211305 MSVPASMKAIVVEALGGPEVLEFKTDYPVPTPKEGQLLVKNNICGINYID
Asp_kawa_GAA89952     MSVPQTMKAVLVEKLGGPEVLEFKSDHPVPTPKEGQVLVKNNISGINYID
Asp_clav_XP_001274440 MSLPSTMNAVVIEKTGGPEVLDFRTDHPVPTPQAGELLIKNNISGINFID
                      **:* :*.*:::*  ******.:::.:***:*  *::*::***.*:*:**

P_brasilianum_hmfL4   TYFRTGLYASPKPEILGREGAGIVAAIG--PNTSGFNVGDRVAWLATGGY
Pen_oxal_EPS32591     TYFRTGLYPSPKPEVLGREGAGVVAAVG--PNTSGFQVGDRVAWLGTSGY
Pen_rube_XP_002567675 TYFRTGLYPAPKPEVLGREGAGIVAAVG--PQTSGFQVGDRVAWLSTGGY
Pen_digi_EKV10327     TYFRTGLYPAPKPEILGREGAGVVAAVG--PGTSGFQVGDRVAWLSTGGY
Asp_fumi_XP_753506    TYFRTGLYPAPKPEVLGREGAGTVVALGPGPNHYNFQVGDRVAWLSTGGY
Asp_fumi_KEY78459     TYFRTGLYPAPKPEVLGREGAGTVVALGPGPNHYNFQVGDRVAWLSTGGY
Neo_fisc_XP_001259550 TYFRTGLYPAPKPEVLGREGAGTVVALGPGPNHYNFQVGDRVAWLSTGGY
Asp_oryz_EIT82010     TYFRTGLYPSAKPEILGREGAGTVVALGSGPNPYGFKVGDRVAWMTTGGY
Asp_terr_XP_001211305 TYFRTGLYPSQKPEVLGREAAGTVVALGPGPNPYNFQVGDRVAWLGTGGY
Asp_kawa_GAA89952     TYFRTGLYPSAKPEILGREGAGTIVALGDGPNPYNFQVGDRVAWLSTGGY
Asp_clav_XP_001274440 TYFRTGLYPAPKPEVLGREGAGAIVALGPGPNPYNFQVGDRVAWLSTSGY
                      ********.: ***:****.** :.*:*  *   .*:*******: *.**

P_brasilianum_hmfL4   AEYTAVPAAKTVKIPEGVSDEDVVASFLSGLTVLSFAKETYPVQKGDWVL
Pen_oxal_EPS32591     AEYTAVPADKTVKIPDGISEEDLVASFLSGLTVLTLAKETYPVQKGDWVL
Pen_rube_XP_002567675 AEYTAVPIAQTAKIPDGISDEDIMASFLSGLTVLAFAKEAYPVQKGDWVL
Pen_digi_EKV10327     AEYTAVPVALTAKIPEGISDEDIMASFLSGLTVLSFVKETYPVQKGDWVL
Asp_fumi_XP_753506    AEYTAVPAAKAVKIPDGISDEDVMASFLSGLTVLSLAKETYAVQKGDWVL
Asp_fumi_KEY78459     AEYTAVPAAKAVKIPDGISDEDVMASFLSGLTVLSLAKETYAVQKGDWVL
Neo_fisc_XP_001259550 AEYTAVPAAKAVKIPDGISDEDVMASFLSGLTVLSLAKETYAVQKGDWVL
Asp_oryz_EIT82010     AEYTAVPAAKTVKIPDEITDEDAIAGFLSGLTVITLAKETYAVQKGDWVL
Asp_terr_XP_001211305 AEYTAVPAAKTVKIPAGVSDEDVMASFLSGLTVLSFAKETYAVQKGDWVL
Asp_kawa_GAA89952     AEYTAVPMAKTIKIPEGITDENLMASFLSGLTVLTLAKETYPVQKDEWVL
Asp_clav_XP_001274440 AQYTAVPAAKAVKIPDGISDEDVMASFLSGLTVLSLVKETYAVQKGDWVL
                      *:*****   : ***  :::*: :*.*******:::.**:*.***.:***

P_brasilianum_hmfL4   LHAAAGGAGFLMTQILKSIGAKVIGTAGGAEKCALVKSLGADVVIDYRSE
Pen_oxal_EPS32591     LHAAAGGAGFLMTQVLKSMGAKVIGTAGGAEKCALVKSLGADLVIDYRSD
Pen_rube_XP_002567675 LHAAAGGAGFLMTQILKSIGANVIGTAGGAEKCALVKSLGADVVIDYRSE
Pen_digi_EKV10327     LHAAAGGAGFLMTQILKILGAKVIGTAGGPEKCALVKSLGADVVIDYRSV
Asp_fumi_XP_753506    LHAAAGGAGFLMTQILKSIGAHVIGTAGGPEKVELVKGLGADHVIDYRSE
Asp_fumi_KEY78459     LHAAAGGAGFLMTQILKSIGAHVIGTAGGPEKVELVKGLGADHVIDYRSE
Neo_fisc_XP_001259550 LHAAAGGAGFLMTQILKSIGAHVIGTAGGPEKVELVKGLGADHVIDYRSE
Asp_oryz_EIT82010     LHAAAGGAGFLMTQVLKSLGAKVIGTAGGPEKVALVKSLGADVVIDYRSE
Asp_terr_XP_001211305 LHAAAGGAGFLMTQILKSMGAKVIGTAGGPEKVALVKGLGADHVIDYRSE
Asp_kawa_GAA89952     VHAAAGGAGTLMTQVLKSIGAKVIGTAGGPEKCQLAKSLGADVVIDYRSE
Asp_clav_XP_001274440 VHAAAGGAGFLMTQVLKSIGAHVIGTAGGPEKVALVKGLGADHVIDYRSE
                      :******** ****:** :**:*******.**  *.*.**** ******
```

TABLE 4-continued

Amino acid sequence alignment of *Penicillium brasilianum* hmfL4 and 10 closest orthologues.

```
P_brasilianum_hmfL4    EGKDWVKLVKEATGGRGVDVVYDSVGKDTWEGSLEAVKRKGTIVWFGNAS
Pen_oxal_EPS32591      EGKDWVKLVKEATGGRGVDVVYDSVGKDTWEGSLEVVKRKGTVVWFGNAS
Pen_rube_XP_002567675  EDKDWVKKVKEATGGRGVDVVYDSVGKDTWEGSLEAVKRKGTIVWFGNAS
Pen_digi_EKV10327      EDKNWVRKVKEATGGRGVDVVYDSVGKDTWEGSLEAVKRKGTIVWFGNAS
Asp_fumi_XP_753506     EGKDWVKQVKEITGGRGVDVVYDSVGKDTWEGSLEVVKRKGTIVWFGNAS
Asp_fumi_KEY78459      EGKDWVKQVKEITGGRGVDVVYDSVGKDTWEGSLEVVKRKGTIVWFGNAS
Neo_fisc_XP_001259550  EGKDWVKRVKEITGGRGVDVVYDSVGKDTWEGSLEVVKRKGTIVWFGNAS
Asp_oryz_EIT82010      EGKDWVKKVKEVTDGRGVDVVYDSVGKDTWEGSLEAVKRKGTIVWFGNAS
Asp_terr_XP_001211305  EGKDWVSKVKEITGGRGVDVVYDSVGKDTWEGSLEAVKRKGTIVWFGNAS
Asp_kawa_GAA89952      EGKDWVKQVKEITGGKGVDVVFDSVGKDTWEGSLESVKRKGTIVWFGNAS
Asp_clav_XP_001274440  EGKNWVEKVKEITGGRGVDVVYDSVGKDTWEGSLEAVKRKGTIVWFGNAS
                       *.*:**  *** *.*:*****:************* ******:*******

P_brasilianum_hmfL4    GPVPPIPLPKLSPKNVKIARPTLFGYIETREEFEYYTNELFSLLQSGQLK
Pen_oxal_EPS32591      GPVPPLPLQKIAPKCVKVARPMLFGYIETREEFEFYTNELFSLLKSGQLK
Pen_rube_XP_002567675  GPVPPLPLAKLTPKCVKVARPSLFGYIQTREEFEYYTNELFNLLKSGQLK
Pen_digi_EKV10327      GPVPPLPLAKLTPKCVKIARPSLFGYIQTREEFESYTNELFSLLKSGQLK
Asp_fumi_XP_753506     GPVPPLPLNKLSPKCVKVARPQLFGYIETREEFEFYVNELFHLLQSGQLK
Asp_fumi_KEY78459      GPVPPLPLNKLSPKCVKVARPQLFGYIETREEFEFYVNELFHLLQSGQLK
Neo_fisc_XP_001259550  GPVPPLPLNKLSPKCVKVARPTLFGYIETREEFEFYVNELFNLLQSGQLK
Asp_oryz_EIT82010      GPVPPLPLQKLSPKCVKVARPQLFGYIETREEFEFYVNELFGLLKSGQLK
Asp_terr_XP_001211305  GPVPPLPLNKLSPKCVKVARPTLFGYIETREEFEYYVNELFTLLKSGQLK
Asp_kawa_GAA89952      GPVPPLPLQKLSPKCVKVARPQLFGYIETREEFEFYVNELFSLLLSNKLK
Asp_clav_XP_001274440  GPVPPLPLTKISPKCVKVARPTLFGYIETREEFEFYVNELFNQLKSGQLK
                       *****:** *::** **:*** *****:****** *.****  * *.:**

P_brasilianum_hmfL4    TKIHKVYPLEDIAQVHKDLEGRKTMGKSLLKP-----
Pen_oxal_EPS32591      TKIHKIYPMEDIVQVHQDLEARKTMGKSLLKP-----
Pen_rube_XP_002567675  TKIHKIYPLEDIAQVHKDLEGRKTMGKPLLKP-----
Pen_digi_EKV10327      TKIHKIYPLEDIAQVHKDLEGRKTMGKPLLRP-----
Asp_fumi_XP_753506     VRIHKVYPLEQVQQAHIDLEGRKTTGKSLLKP-----
Asp_fumi_KEY78459      VRIHKVYPLEQVQQAHIDLEGRKTTGKSLLKP-----
Neo_fisc_XP_001259550  VRIHKVYPLEQVQQAHIDLEGRKTTGKSLLKP-----
Asp_oryz_EIT82010      VKIHKVYPLEQAAQAHTDLEGRKTTGKLLLKP-----
Asp_terr_XP_001211305  VKIHKVYPLEQVAQAHIDLEGRKSTGKLLLKA-----
Asp_kawa_GAA89952      AKVHKVYPLEEVAQAHTDLEGRKTTGKSMLKP-----
Asp_clav_XP_001274440  ARIHKVYPLEQVRQAHTDLEGRKTTGKSLLKPUSAGE
                       .::**:**:*:  *.* ***.**: ** :*:.
```

TABLE 5

Amino acid sequence alignment of *Penicillium brasilianum* hmf1V1 and 10 closest orthologues.

```
P_brasilianum_hmfN1    ------MTQTNVHVNKSDTSLAAPQQLFISGKYQNSQRNGTFPVKNPMTG
Spo_sche_ERT02387      ---------------MSYPPVSEPLQLYISGQHVASESSTTFPVMNPMTG
Sce_apio_KEZ45623      -------MATNGGVGPKATTLSQVQELFIGGKHKPSSDNVEFQVINPMTG
Pod_anse_XP_001908521  MAPHSPTTSNNGGVSERTSTLSQPQFLFINGKYILSSDNETFPVRNPITG
Eut_lata_XP_007794079  ------------MANNGVSSLSEPQQLVIDGSYTTSSDGTTFQVVNPMKG
Sta_char_KEY72856      ----------MARPRTNNDTLSSPQHLFINGAYRPSSDNSTFHVTNPMTG
Gae_gram_XP_009217152  MVAHP--VAEKG-----PSALSQAQELVINGEAQPSSDGTTFTVRNPMTG
Sta_char_KFA73399      ----------MARPRTNNDTLSSPQHLFINGAYRPSSDNSTFHVTNPMTG
Sta_char_KFA53356      ----------MARPRTNNDTLSSPQHLFINGAYRPSSDNSTFHVTNPMTG
Cyp_euro_XP_008712551  -------MHEKNGTTERRSTLTDEQLLYVNGEYVRPEDDAKFEVLNPATG
Sta_chlo_KFA62282      ----------MAHLTASNDTLSSPQHLFINGAYRPSSNNSTFHVTNPMTG
                                          .::    * :.*    .. .  * * ** .*

P_brasilianum_hmfN1    ETIYECVSASLDDYAAAIEEADAAQPSWARLGPSARRLILLKAADIMETY
Spo_sche_ERT02387      EAIYQCASASPADYTTAIDAAYTAYQSWSRLGPSARRSVLLKAADIIESY
Sce_apio_KEZ45623      ANIYSCASATVDDVSEAIESAHTAFKSWSRMGPSARRSIFLKAADILEGY
Pod_anse_XP_001908521  SVLYNCASASKVDYETAIENAHSAYQTWSQTGPSARRRIFLKAADIMESY
Eut_lata_XP_007794079  EKIYDCASATVQDYQKAIESASEAFKTWSRTSPSARRLVFLKAADIIEGY
Sta_char_KEY72856      EPIYPCAAATAQDYLDAVAAAHAAYPRWSGTSPSARRLVLLRAADVLEGY
Gae_gram_XP_009217152  QAIYECANATVDDYSRAIDTAHEAFKSWSATGPSARRLIFLKAAEIIESY
Sta_char_KFA73399      EPIYPCAAATAQGYLDAVAAAHAAYPRWSGTSPSARRLVLLRAADVLEGY
Sta_char_KFA53356      EPIYPCAAATAQDYLDAVAAAHAAYPRWSGISPSARRLVLLRAADVLEGY
Cyp_euro_XP_008712551  GKIYDCSSAGVREYELAIKAADAAFTSWSQTAPSARRLIFLRAADTLERY
Sta_chlo_KFA62282      EPIYSCAAATSQDYLDAVAAAHAAYPSWSRTSPSARRLILLRAADVLEGY
                         :* *  *       *:  *  *   *:  .***** ::*:**: :* *

P_brasilianum_hmfN1    IETDAPAILSAEVSATRGWVRANILSTAGVFRETAALATHIKGEIVPADR
Spo_sche_ERT02387      LDQDAVAILSAEVSATRSWVKANMLSAAGVFRENAALATHIKGEIVPADR
Sce_apio_KEZ45623      IHGDAPEILASEVSATATWVKVNIFSTANVLREAAGLVTHIKGEIVPADR
```

TABLE 5-continued

Amino acid sequence alignment of *Penicillium brasilianum* hmf1V1 and 10 closest orthologues.

```
Pod_anse_XP_001908521 ITGDAPEFMSQEVSATMHWVKINVFATAGLFRETASLATQIRGEIVPADR
Eut_lata_XP_007794079 AKQDAPAILSAEVSATKSWVQVNIGATAGILRESAGLVTHIKGEIVPADR
Sta_char_KEY72856     LESDAPEILASEVSATRSWVALNIRATAGILRETAGLATHIKGEIVPADR
Gae_gram_XP_009217152 LGGDAPEVLSSEVSATAAWVRINMHATAGLFRETASLATHIRGEVVPADR
Sta_char_KFA73399     LESDAPEILASEVSATRSWVALNIRATAGILRETAGLATHIKGEIVPADR
Sta_char_KFA53356     LESDAPEILASEVSATRSWVALNIRATAGILRETAGLATHIKGEIVPADR
Cyp_euro_XP_008712551 LHDDAPEILSAEVSAVSSWIRVNIMATANILRETAGQATQMRGEIVPADR
Sta_chlo_KFA62282     LESDAPDILASEVSATRSWVALNIRATVGILRETAGLATHIKGEVVPADR
                         **  .:: ****.  *:  *: ::..::** *. .*:::**:*****

P_brasilianum_hmfN1   PGTTILVSREPVGVVLAISPWNMPATLTARAICCPLICGNSVVLRPSEFS
Spo_sche_ERT02387     PGTTILVNREAVGVVLAISPWNMPVTLTARAVCCPLICGNAVLLKPSEYS
Sce_apio_KEZ45623     PGTTVLITREPLGVMYAISPWNAPVNLTARAIACPLICGNTVVLKPSEYS
Pod_anse_XP_001908521 PGTTIWVERQPVGVVFAISPWNAPINLTARAIAVPLLCGNTVVLKPSEFS
Eut_lata_XP_007794079 PGTTILVERQPVGVVFAISPWNAPVNLTARAIATPL--------------
Sta_char_KEY72856     PGTTIMVERCPVGVVFAISPWNAPVNLTARAIATPLICGNTVVLKPSEYS
Gae_gram_XP_009217152 PGTTILVERQAVGVVLAISPWNAPVNLTARSVACPLMCGNTVVVKPSEHS
Sta_char_KFA73399     PGTTIMVERCPVGVVFAISPWNAPVNLTARAIAAPLICGNTVVLKPSEYS
Sta_char_KFA53356     PGTTIMVERCPVGVVFAISPWNAPVNLTARAIATPLICGNTVVLKPSEYS
Cyp_euro_XP_008712551 PGTMIMIMREAIGVVFAISPWNAPVNLTARAIASPLICGNTVVLKPSEFS
Sta_chlo_KFA62282     PGTTIMVERCPVGVVFAISPWNAPVNLTARAIATPLICGNTSAPLPP---
                      *** : : * .:**: ****** * .****::. **

P_brasilianum_hmfN1   PKSQHLVVRALTEAGLPAGCLQFLPTSTADTPRAIEFAIRHPKVSRANFT
Spo_sche_ERT02387     PKAQFLVVRALVEAGLPPGVLQFLPTSAADAPRATAFAIAHPKVSRTNFT
Sce_apio_KEZ45623     PKSQHLVIKALTEAGLPAGCINFVPCSPDRAAANTEFAVKHPTVRHINFT
Pod_anse_XP_001908521 PKSQDLAIRALTAAGLPPGCVNVLPTSAERTPEVTELAVKHPKVLRVNFT
Eut_lata_XP_007794079 ----HLVVRALAEAGLPPGCLNFVPTSPERAPEVTEYAVKHPLVRRVNFT
Sta_char_KEY72856     PKSQHLVIRALTAAGLPPGALNFLPTSPALAAAVTEQTVKHRHVLRVNFT
Gae_gram_XP_009217152 PKSQALVVRALLEAGLPPGAIAFLPTSPGRAAEVTEYAVKHARVLRVNFT
Sta_char_KFA73399     PKSQHLVIRALTAAGLPPGALNFLPTSPALAAAVTEQTVKHRHVLRVNFT
Sta_char_KFA53356     PKSQDLVIRALTAAGLPPGALNFLPTSPALAAAVTEQTVKHRHVLRVNFT
Cyp_euro_XP_008712551 PKSQHLVVRAFQEAGLPSGCLNFLPTKASDAAKVTEYATKHSKVRRLNYT
Sta_chlo_KFA62282     -------------PACPPGALNFLPTSPALAAAVTEQTVKHRHVLRVNFT
                                   .. *.* : .:* ..  :.     :  *  * : *:*

P_brasilianum_hmfN1   GSDRVGRIIAGLSASCLKPCVLELGGKAPVVVLEDADVEAAVEAVVYGAM
Spo_sche_ERT02387     GGHRVGGIIASLSAKHIKKCLLELGGKAAVLVLHDADLDAAADAVAFGAM
Sce_apio_KEZ45623     GSERVGKIIAGWAASCVKKCVFELGGKAPVIVREDADLDDAVESIIFGGL
Pod_anse_XP_001908521 GSDRVGRIIAGWAATCLKQCVLELGGKAPVIVFEDANIDDAVEAVVFGAL
Eut_lata_XP_007794079 GSDRVGKIIAGWAATCLKQCVLELGGKAPVLVLDDANIEDAVEAVAFGAF
Sta_char_KEY72856     GSDRVGRIIAGWAAEVLKQCVLELGGKAPVLVLEDADVRGAVEAVVFGAL
Gae_gram_XP_009217152 GSDRVGRIIAGHAAACLKQCVFELGGKAPVIVRADANLDDAVEAVVFGAL
Sta_char_KFA73399     GSDRVGRIIAGWAAEVLKQCVLELGGKAPVLVLEDADVRGAVEAVVFGAL
Sta_char_KFA53356     GSDRVGRIIAGWAAEVLKQCVLELGGKAPVLVLEDADVRGAVEAVVFGAL
Cyp_euro_XP_008712551 GSDRVGKIIAGWAASCLKQCVLELGGKAPVIVLEDANIEDAVEAVVFGGF
Sta_chlo_KFA62282     GSDRVGRIIAGWAAQVLKQCVLELGGKAPVLVLEDADVRDAVEAVVFGAL
                      *..*** ***. :*  :* *::******.*:*  **::  *.::: :*.:

P_brasilianum_hmfN1   SNSGQICMSTERAIVHRSLAADFKALLVKRAESLRVGNHLEDPDVQLSGL
Spo_sche_ERT02387     SNSGQICMSTERVLVHASVAAAFKQKLVQRVEALRVGNHLDDPTVQLSGL
Sce_apio_KEZ45623     ANNGQVCMSTERVIVHKSISGDFKSRLLARAGALKCGNHHVEKDVSISGL
Pod_anse_XP_001908521 AFSGQVCMSTERVILHKSISREFKEKLLKKVESIKTGNHLEDPAVSISGL
Eut_lata_XP_007794079 ANAGQICMSTERVLVHTSIAAKFKELLIQKSRELKTGNHEDDPEVSISGL
Sta_char_KEY72856     ANAGQICMSTERVVVHDSVAKEFTEALVEKVGDVSVGNHMETPDVAISGL
Gae_gram_XP_009217152 AYSGQVCMSTERAIVHRSVAAEFRTKVLARIAALRCGNHLDDAAVSVSGL
Sta_char_KFA73399     ANTGQICMSTERVVVHDSVAKEFTEALVEKVGDVSVGNHMETPDVAISGL
Sta_char_KFA53356     ANAGQICMSTERVVVHDSVAKEFTEALVEKVGDVSVGNHMETPDVAISGL
Cyp_euro_XP_008712551 CNSGQICMSTERVIVEKAIEQKFTATLLEKVKTINWG---DQEGVSMAGL
Sta_chlo_KFA62282     ANAGQICMSTERVVVHDSVAKEFTEALVKKVGDVSVGNHMETPDVAMSGL
                      .  **:******.::. ::    *   :: :   :  *       * ::**

P_brasilianum_hmfN1   FTAASAERVLGLIKGAVNAGATLLAGDLALHGPCQTIMAPHILTGVTRDM
Spo_sche_ERT02387     FCAASAKRILGLLQAAVDAGATALTGDLQVHGPNGTILAPHVLEGVSADM
Sce_apio_KEZ45623     FTPASASRVLGLVKSAVDTGATLLMGDMKLDGPNKTIMRPHILEGVTREM
Pod_anse_XP_001908521 FTSAHAKRVMSLVKSAVDGGAKLLAGDLQVTGPRGTIIRPHILEHVSTNM
Eut_lata_XP_007794079 YTPASATRILALMKDAVSSGAKLLCGDMSLAGPNKTIIAPHVFEGVTPEM
Sta_char_KEY72856     YTPSSCTRILGLVREAMSQGATLLTGRLTPSGPNNTILAPMVLSHVTPAM
Gae_gram_XP_009217152 FTPAHALRVLELVQDALAGGAELLAGDLATSGPCGTIVRPHVLSGVGPSA
Sta_char_KFA73399     YTPSSCTRILGLVREAMSQGATLLTGRLTPSGPNNTILAPMVLSHVTPAM
Sta_char_KFA53356     YTPSSCTRILGLVREAMSQGATLLTGRLTPSGPNNTILAPMVLSHVTPAM
Cyp_euro_XP_008712551 YTPQSAERFLAMIEQAIADGAELLAGDRSASGPNRTLVQPHVLGKVTRTM
Sta_chlo_KFA62282     YTPSSCTRILGLVREAMSKGAILLTGCLTPSGPNNTILAPIVLSHVTPAM
                      : .  . *.: ::. *:  **  * *     **  *:: * ::  *

P_brasilianum_hmfN1   DLFHRETFGPVLFVSEFDTDDEAIAQANDTEFSLCASVFSRDVLRAMDTA
Spo_sche_ERT02387     DLYQQETFGPVVIVNTFADEADAVTQANQTDFTLCGSIFSRDVLRAADLA
```

TABLE 5-continued

Amino acid sequence alignment of *Penicillium brasilianum* hmf1V1 and 10 closest orthologues.

```
Sce_apio_KEZ45623     DLYHQESFGPVMILLEFETDEEGVDLANDSDFSLCASVFSRDVMRAMELA
Pod_anse_XP_001908521 DIAHVETFGPVMLLSEFETDDEAVASANDSDFSLCGSVFSKDTMRALDIS
Eut_lata_XP_007794079 DIFHKESFGPLICLTEFNTDEDAIRLANESDFSLCASVFSRDILRALDVG
Sta_char_KEY72856     AIFHQETFGPIICLTTCSSDAEAVSLANDSDFSLAASVFSRDVMRALDVA
Gae_gram_XP_009217152 RMRREEVFGPVLMLAEFDTDDEAVAAANDSDYSLCASVFSRDVMTAMDLA
Sta_char_KFA73399     AIFHQETFGPIICLTTCSSDAEAVSLANDSDFSLAASVFSRDVMRALDVA
Sta_char_KFA53356     AIFHQETFGPIICLTTCSSDAEAVSLANDSDFSLAASVFSRDVMRALDVA
Cyp_euro_XP_008712551 DVFREESFGPVLCLTVVDSQAEAIEVANDSEFSLSAAVFSQDIMKALWLA
Sta_chlo_KFA62282     AIFHQETFGPIICLTTCSSDAEAVSLANDNDFSLAASVFSRDVMRALDVA
                       : : * ***:: :     : :.:  **:.:::*..::**:* : *   .

P_brasilianum_hmfN1   KRIRTGSCHVNGPTVYIEAPLPNGGVGGGSGYGRFGGVAGIEEFTERQIV
Spo_sche_ERT02387     KQVRVGSCHINGPTVYVEAPLPNGGIGGASGYGRFGGMAGVEEFTERQIV
Sce_apio_KEZ45623     KQVRAGSCHINGPTIYIEPTLPNGGVGGSSGYGRFGGVAGVEEFTERKIV
Pod_anse_XP_001908521 KRLRLGACHINGPSLYVESTLPQGGTGGGSGYGRFGGMAGVEAFTEKKII
Eut_lata_XP_007794079 RQVRAGSCHINGPTVYIEATLPNGGTGGSSGYGRFGGIAGVEEFTERQIL
Sta_char_KEY72856     RQVRAGSCHINGPTVYIEPTLPNGGTGGSSGYGRFGGVAGIEEFTERKII
Gae_gram_XP_009217152 RRVRAGTCHVNGPTIYVESTLPNGGTGGGSGYGRFGGMSGVEAFTEKKVI
Sta_char_KFA73399     RQVRAGSCHINGPTVYIESTLPNGGTGGSSGYGRFGGVAGIEEFTERKII
Sta_char_KFA53356     RQVRAGSCHINGPTVYIEPTLPNGGTGGSSGYGRFGGVAGIEEFTERKII
Cyp_euro_XP_008712551 KQVRAGSCHINGPTVYIEATLPNGGTGGRSGYGRLGGSAGIEEYTERKII
Sta_chlo_KFA62282     REVRAGSCHINGPTVYIEPALPNGGTGGSSGYGRFGGVAGIEEFTERKII
                      :.:* *:**:***::*:*..**:** ** *****:** :*:* :**::::

P_brasilianum_hmfN1   SLAKPGIKYAF-----
Spo_sche_ERT02387     SLTRPGLKYAF-----
Sce_apio_KEZ45623     SLAQPGMKYSF-----
Pod_anse_XP_001908521 TVVKPGLKLPL-----
Eut_lata_XP_007794079 SLGKSGMRYRF-----
Sta_char_KEY72856     TLARPGAKYPM-----
Gae_gram_XP_009217152 TLARPGMRFAF-----
Sta_char_KFA73399     TLARPGAKYPM-----
Sta_char_KFA53356     TLARPGAKYPM-----
Cyp_euro_XP_008712551 SLAQSGLKCVF-----
Sta_chlo_KFA62282     TLARPDAKHPMUSAGE
                      :: :.. :  :
```

TABLE 6

Amino acid sequence alignment of *Penicillium brasillanum* hmfN2 and 10 closest orthologues.

```
P_brasilianum_hmfN2   MSQNDS------------KAVTPLLINNESVMTDIKFEVHAPATGELSSY
Pen_rube_XP_002562108 MAQSN-------------KPVTPLIINNESIETDIKFEVHAPATGELSGY
Pen_oxal_EPS27859     MASN--------------AVTPLIINNESIVTDIKFEVHAPATGELSGY
Pen_digi_EKV07543     MASSN-------------KAVTPLIIDNESVETDVRFEVHAPATGELSGY
Asp_kawa_GAA83411     MIAKNPNGNTA---------VIPLLINNESSVTETIFDVTSPATGEVIDR
Asp_rube_EYE94383     MTIVPLSAPTGATTTTAGKLPVPLLINNQSIITGNQFNVQNPATNQVADL
Asp_nige_XP_001398866 MIAKNPNGNTA---------VIPLLINNESSVTETIFDVTSPSTGEVIDR
Asp_terr_XP_001213025 MADI-----------------VPLLINNESIVTDTVFDVYNPATGQVAHR
Neo_fisc_XP_001265293 MAANVAKADSG---------VIPLIINNESVVTENVFDVHAPATGEVLHQ
Asp_fumi_KEY77153     MAANGAKADSG---------VIPLIINNESIVTENIFDIHAPATGQVLHQ
Asp_fumi_XP_750112    MAANGAKADSG---------VIPLIINNESIVTENVFDIHAPATGQVLHQ
                      *                     **:*:*:*  *   *::  *:*.::

P_brasilianum_hmfN2   CAGASVEDAVRAVDNAKAAFPAWSKTKAYDRRDILLKAAEIMISRKEELI
Pen_rube_XP_002562108 CAGVSVDDANRAVDSAQAAFPAWSKTTANDRRDILLKAADIMASRKEELI
Pen_oxal_EPS27859     CAGASVDDAKRAVECAQAAFPAWSKTKAFDRRDILLKAGEVMLARKEELI
Pen_digi_EKV07543     CAGVSVADANRAVDSAQAAFLAWRKTKAHERRDILLKAADIMASRKEELI
Asp_kawa_GAA83411     CAGATVDDANRAVAAAKAAFPGWSKTKPYDRRDILIRAADIMLSRKEELI
Asp_rube_EYE94383     CVGATVGDALRAVDSAKAAFAPWSKTTPYARRDILLRAADIMESRKEELI
Asp_nige_XP_001398866 CAGATVDDANRAVAAAKAAFPGWSKTKPYDRRDILIRAADIMLSRKEELI
Asp_terr_XP_001213025 CAGASVDDARRAVDSAKAAFPAWSKTTPNARRDILLKAADIMLSRREELI
Neo_fisc_XP_001265293 CAAASVDHANRAVAAAKAAFPAWSRMKPYDRRDVLMKAADIMIARSEELI
Asp_fumi_KEY77153     CASASVDHANRAVAAAKAAFPAWSRMKPYDRRDVLMKAADIMFARSEELI
Asp_fumi_XP_750112    CAAASVDHANRAVAAAKAAFPAWSRMKPYDRRDVLMKAADIMFARSEELI
                      *...:* .* ***  *:***  * : ..  ***:*::*.::* :* ****

P_brasilianum_hmfN2   AYQQEETGAGRPFCEHTFNMGVNFIKDFAGRISTIEGVVPSVTLDGEGAM
Pen_rube_XP_002562108 QYQREETGAGRPFSEATFNMGVLFIKDFAGRISTIEGVVPNVSQEGEGAI
Pen_oxal_EPS27859     ALQMEETGAGRLFVEHTFHMGVNFVKDFAGRISTIEGKVPSVNVDGENAI
Pen_digi_EKV07543     QYQREETGAGRPFSEFTFNQGVLFIKEFAGRISTIEGVVPHVSGEGEEAI
Asp_kawa_GAA83411     RYQMEETGAGRMFVEKTFMLGVGFLKDFAARIPSIEGTVPSVSEDGECAM
Asp_rube_EYE94383     AYQIEETGAGRLFSEKTFDLGVSFMRDTAGRIPSIEGAVPSVSENGETAM
```

TABLE 6-continued

Amino acid sequence alignment of *Penicillium brasillanum* hmfN2 and 10 closest orthologues.

```
Asp_nige_XP_001398866 RYQMEETGAGRMFVEKTFMLGVGFLKDFAARIPSIEGTVPSVSEDGECAM
Asp_terr_XP_001213025 AYQIEETGSQRPFAEKTFEMGAAFIKDFAARIPSIEGAVPSVSEQGECAV
Neo_fisc_XP_001265293 KYQMEETGAGRMFAEKTCLLGAGFLKDFAARIPSIEGSVPSVTQDGECAM
Asp_fumi_KEY77153     KYQMEETGAGRMFAEKTCLLGAGFLKDFAARIPSIEGSVPSVTQDGECAM
Asp_fumi_XP_750112    KYQMEETGAGRMFAEKTCLLGAGFLKDFAARIPSIEGSVPSVTQDGECAM
                        * ****: * * * *   *. *::: *.**.:*** ** *. :** *:

P_brasilianum_hmfN2   IYKEPYGVILSIAPWNAPFILGTRAVALPLAAGNTVVLKGSELSPKCFWA
Pen_rube_XP_002562108 VYKEPYGVILSIAPWNAPFILGTRAVALPLAAGNTVVLKGSELSPKCFWA
Pen_oxal_EPS27859     IYKEPYGVILSIAPWNAPLILGMRAIALPLAAGNTVVFKGSELSPKCFWA
Pen_digi_EKV07543     VYKEPYGVILSIAPWNAPFILGTRAVALPLAAGNTVVLKGSELSPKCFWA
Asp_kawa_GAA83411     VIKQPYGVVLGIAPWNAPYILGTRAVALPLAAGNTTILKGSELSPKCFWA
Asp_rube_EYE94383     VFKEPYGVILGIAPWNAPYILGTRSIILPLAAGNTVVLKGSELSPKCFWA
Asp_nige_XP_001398866 VIKQPYGVVLGIAPWNAPYILGTRAVALPLAAGNTTILKGSELAPKCFWA
Asp_terr_XP_001213025 VFKEPYGVILGIAPWNAPFILGTRAVLLPLAAGNTAILKGSELSPKCFWA
Neo_fisc_XP_001265293 VFKEPYGVVLGIAPWNAPFILGVRAVALPLAAGNTTILKGSELSPKCFWA
Asp_fumi_KEY77153     VFKEPYGVVLGIAPWNAPFILGVRAVALPLAAGNTAILKGSELSPKCFWA
Asp_fumi_XP_750112    VFKEPYGVVLGIAPWNAPFILGVRAVALPLAAGNTAILKGSELAPKCFWA
                      : *:****:*.******* *** *:: ********.::*****:******

P_brasilianum_hmfN2   LGDIFRQAGLPDGCFNVIFHQPSDAAAVTTALIAHPAVRKVNFTGSTNVG
Pen_rube_XP_002562108 LGDIFRQAGLPAGCLNVVFHQPSDAPAVTNALIAHQAVRKVNFTGSTMVG
Pen_oxal_EPS27859     LGDIFREAGLPAGCLNVLYHQTSDAAAVTNTLIAHPYVRKINFTGSTHVG
Pen_digi_EKV07543     LGDIFRQAGLPAGCLNVIFHQPSDAPAVTTALIAHQAVRKVNFTGSTLVG
Asp_kawa_GAA83411     IGDIYREAGLPAGCLNVLYHRPSDAAAVTNALIAHPAVRKINFTGSTTVG
Asp_rube_EYE94383     LGDIYREAGLPAGCVNVVYRKTSDAAAVTNALIAHPAVRKINFTGSSHVG
Asp_nige_XP_001398866 IGDIYREAGLPAGCLNVLYHRPSDAAAVTNALIAHPAVRKINFTGSTTVG
Asp_terr_XP_001213025 LGDIFRQAGLPDGCLQVLYHKVTDAPAVTEALIAHPAVRKISFTGSTHIG
Neo_fisc_XP_001265293 IGDIFREAGLPAGCLNVLYHTTADAAEVTTALIAHPAVRKVNFTGSTQVG
Asp_fumi_KEY77153     IGDIFREAGLPAGCLNVLYHRTADAAEVTTALIAHPAVRKVNFTGSTQVG
Asp_fumi_XP_750112    IGDIFREAGLPAGCLNVLYHRTADAAEVTTALIAHPAVRKVNFTGSTQVG
                      :***:*:**** **.:*::*  :**. ** :****  ***:.****: :*

P_brasilianum_hmfN2   SIIASTAGKYIKPVLLELGGKASAIVLDDADLDKAAMSCALGSFLHSGQI
Pen_rube_XP_002562108 SIIASTAGKYIKPVLLELGGKASAIVLDDANLDKAAMNCAIGSFMHSGQI
Pen_oxal_EPS27859     SIIASTAGKYIKPVLLELGGKASAIVLDDADLDKAAMNCALGSFMHSGQI
Pen_digi_EKV07543     SIIASTAGKYIKPVLLELGGKASAVVLDDANLDKAAMNCAIGSFMHSGQI
Asp_kawa_GAA83411     SIIASTAGKYTKPVLLELGGKASAIVLDDANLEKAAMCCALGSFMHSGQI
Asp_rube_EYE94383     SIVAATAGKYIKPVLLELGGKAAAVVLDDANMEQAAMACTLGAFLHSGQV
Asp_nige_XP_001398866 SIVAATAGKYTKPVLLELGGKASAIVLDDANLDKAAMCCALGSFMHSGQI
Asp_terr_XP_001213025 AVVASLAGRYVKPVLLELGGKAAAIVLDDANLERAAFNCALGAFMHSGQV
Neo_fisc_XP_001265293 SIIAATAGKYTKPVLLELGGKASAIVLDDANLEKAAFCCALGSFMHSGQI
Asp_fumi_KEY77153     SIIAATAGKYTKPVLLELGGKASAIVLDDANLEKAAFCCALGSFMHSGQI
Asp_fumi_XP_750112    SIIAATAGKYTKPVLLELGGKASAIVLDDANLEKAAFCCALGSFMHSGQI
                      :::*: **:* ***********:*:*****:::**:  *::*:*:****:

P_brasilianum_hmfN2   CMSTERIVVQRAIADEFRQKVAANAEKLFGKDAPALGLVNAAAVTKNKKL
Pen_rube_XP_002562108 CMSTERIIVQRSIADEFRQKLAETAEKLFGKDAPALFLVNAAGVAKNKKL
Pen_oxal_EPS27859     CMSTERIVVQSAVADQFRQKVAEHAEKLFGKDVPALCLVNAAAVTKNKKL
Pen_digi_EKV07543     CMSTERIIVLRSIADEFRQKLAATTEKLFGKDAPALVLVNTAAVAKNKRL
Asp_kawa_GAA83411     CMSTERVIVQRSIADRFKQMMAEAVEKVFGKHGPALVLVAPAAVKKNKEL
Asp_rube_EYE94383     CMSTERIIVQSSIADKFRKLLAETAEKVFGEHAPAPVLVASAAVEKNKKL
Asp_nige_XP_001398866 CMSTERVIVQRSIADRFKQMMAEAVEKVFGKHGPALVLVAPAAVKKNKEL
Asp_terr_XP_001213025 CMSTERIIVQRGVAEKFRELLAGAAEKVFGQHTPAPVLVAAAAVSKNKAL
Neo_fisc_XP_001265293 CMSTERIVVQRAIADKFRQLLAENAEKLFGKAAPAPVLVASAAVKKNKAL
Asp_fumi_KEY77153     CMSTERIVVQRAIADKFRQLLAENAEKLFGKAAPAPVLVTSAAVKKNKTL
Asp_fumi_XP_750112    CMSTERIVVQRAIADKFRQLLAENAEKLFGKAAPAPVLVTSAAVKKNKTL
                      ******::*  .:*:.*:: :*  .**:**:  **  ** .*.* *** *

P_brasilianum_hmfN2   VADAVSRGANILFGDASANESVNTCMRPIIVDGVSKEMDLYATESFGPTV
Pen_rube_XP_002562108 VTDAVSRGATLLFGDANSSESVNTGMRPIVVEGVTKEMDMYATESFGPTV
Pen_oxal_EPS27859     VADAVSRGAKVIFGDANGNEGRDTQMRPIIVDGVTQEMDLYKTESFGPTV
Pen_digi_EKV07543     VADAVSRGASLLFGDANASESVGAGMRPIVVDGVTKEMEMYATESFGPTV
Asp_kawa_GAA83411     VEDALAKGANLVYGDTAAIDLNNSSMRPVIVGDVAKNMDMYFTESFGPTV
Asp_rube_EYE94383     VADAVSKGASVLFGNPDASETNPYSMRPLIVDGVTKEMDLYATESFGPTV
Asp_nige_XP_001398866 VEDALAKGANLIYGDTAAIDLNNSSMRPVVVGDVAKNMDMYSTESFGPTV
Asp_terr_XP_001213025 VADALAKGAEVVFGDAAATEACGSSMRPLIVGNVTKAMDLYATESFGPTV
Neo_fisc_XP_001265293 VADALSKGASVLFGDANATESSGHSLRPVIVDNVTKDMDLYSIESFGPTV
Asp_fumi_KEY77153     VADALSKGASVLFGDANATESSDHSLRPVIVDNVTKDMDLYSTESFGPTV
Asp_fumi_XP_750112    VADALSKGASVLFGDANATESSDHSLRPVIVDNVTKDMDLYSTESFGPTV
                      * **:::** :::*:. . :     :**::* .*:: *::*  *******

P_brasilianum_hmfN2   SLIVVDTEEEAIAVANDTEYGLTGAVYTQNLFRGLRVAKQIESGAIHINA
Pen_rube_XP_002562108 SLMVVDTEDDAIALANDTEYGLTAALYTNNLFRGLRVAKQIESGAVHINS
Pen_oxal_EPS27859     SLFVVDSEEEAIALANDTEYGLTAAVYTQNLFRGLRVAKQVESGAVHINA
Pen_digi_EKV07543     SLMVVDTEDEAIALANDTEYGLTAALYTNNLFRGLRVAKQIDSGAVHINS
Asp_kawa_GAA83411     SLIVVDSEEDAVTLANDTEYGLTSAVFTGNLFRGLRVAKQIEAGAVHINS
```

TABLE 6-continued

Amino acid sequence alignment of *Penicillium brasillanum* hmfN2 and 10 closest orthologues.

```
Asp_rube_EYE94383     SLIEVDTEDDAVALANDSEYGLTSAVFTGNLFRGLRVARQIESGAVHINS
Asp_nige_XP_001398866 SLIVVDSEEDAVTLANDTEYGLTSAVFTGNLFRGLRVAKQIEAGAVHINS
Asp_terr_XP_001213025 SLMVVDSEEEAVALANDTEYGLSSAVFTDNLFRGLRVAKQIESGAVHINS
Neo_fisc_XP_001265293 SLLVVDTEEDAIALANDTEYGLTSAVFTDNLFRGLRVAKQIEAGAVHINS
Asp_fumi_KEY77153     SLIVVDTEEDAIALANDTEYGLTSAVFTDNLFRGLRVAKQIEAGAVHINS
Asp_fumi_XP_750112    SLIVVDTEEDAIALANDTEYGLTSAVFTDNLFRGLRVAKQIEAGAVHINS
                      **: **:*::*:::***:****:.*::* *********:*:::**:***:

P_brasilianum_hmfN2   LTVHDEPTLPHGGWKSSGFGRFGG-VAGYDEFLQTKTVTWME-----
Pen_rube_XP_002562108 MTVHDESVLPHGGWKSSGFGRFGG-VSGYDEFLQTKTVTWHE-----
Pen_oxal_EPS27859     LTIHDEPVLPHGGWKSSGFGRFGG-VSGYDEFLQTKVVTWHE-----
Pen_digi_EKV07543     LTVHDESALPHGGWKSSGFGRFGG-SSGYDEFLQTKTITWQE-----
Asp_kawa_GAA83411     LTVHDEPVLPHGGWKSSGYGRFGG-TSGYDEWLQTKTITWVE-----
Asp_rube_EYE94383     LTIHDEPVLPHGGYKSSGLGRFGG-TKGYEEFLQTKTVTWIEP----
Asp_nige_XP_001398866 LTVHDEPVLPHGGWKSSGYGRFGG-TSGYDEWLQTKTITWVE-----
Asp_terr_XP_001213025 LTIHDEAVLPHGGYKSSGFGRFGG-AHGYDEWLQTKTVTWVE-----
Neo_fisc_XP_001265293 LTVHDEPTLPHGGWKSSGFGRFGGGTAAYDEWLQTKTVTWTQ-----
Asp_fumi_KEY77153     LTVHDEPTLPHGGWKSSGFGRFGGGTAAFDEWLQTKTVTWTQ-----
Asp_fumi_XP_750112    LTVHDEPTLPHGGWKSSGFGRFGGGTAAFDEWLQTKTVTWTQUSAGE
                      :*:***..*****:**** *****     .::*:****.:** :
```

TABLE 7

Amino acid sequence alignment of *Penicillium brasilianum* hmfP1 and 10 closest orthologues.

```
P_brasilianum_hmfP1   -------------------------------------------------M
Art_otae_XP_002842712 --------------------------------------------------
Mic_gyps_XP_003169145 --------------------------------------------------
Art_benh_XP_003013874 --------------------------------------------------
Tri_soud_EZF72840     MLCVRLVATRTVVQRCISISSHYRPRLVVKPQAYKHRTSYIRTIHIDKPS
Tri_rubr_XP_003235790 MLCVRLVATRTVVQRCISISSHYRPRLVVKPQAYKHRTSYIRTIHIDKPS
Tri_tons_EGD94050     -------------------------MVIKSRAFNHTNSSIRTIHIDKPS
Tri_inte_EZF36477     -------------------------MVIKSRAFNHTNSSIRTIHIDKPS
Tri_verr_XP_003021315 --------------------------------------------------
Tal_marn_XP_002148377 --------------------------------------------------
Tal_marn_KFX51761     --------------------------------------------------

P_brasilianum_hmfP1   TVTTTLSLIAPPEHRHEPSPFDPAVDIKDAP------SIITALNAADPSL
Art_otae_XP_002842712 -MTSSAPFSATAEHRQEPTPFDPAVDAQGSE------PIVQTLQSLDSTL
Mic_gyps_XP_003169145 -MLDSAPFSSTAEHRQEPTPFDPAVDAQGSE------PIIQTLTTLDSAL
Art_benh_XP_003013874 -MLTSTPFSSTAEHRQEPTTFDPALDAQGTE------PIIQTLKSLDSSL
Tri_soud_EZF72840     SMLTLAPFSSTAEHRQEPTPFDPAIDAQGAE------PIIQTLKSLDSSL
Tri_rubr_XP_003235790 SMLTLAPFSSTAEHRQEPTPFDPAIDAQGAE------PIIQTLKSLDSSL
Tri_tons_EGD94050     SMLTSAPFSSTVEHRQEAAPFDPAVDAQGAE------PIIQTLKSLDSSL
Tri_inte_EZF36477     SMLTSAPFSSTVEQRQEAAPFDPAVDAQGAE------PIIQTLKSLDSSL
Tri_verr_XP_003021315 -MPTSTPFSSTAEHRQEPTTFDPAIDAQGTE------PIIQTLKSLDSSL
Tal_marn_XP_002148377 MAVGPVSLTAGSQFRHAVIRYDPTTDTATTSGEDAETTIIKTLQSADSAL
Tal_marn_KFX51761     MAVGPVSLTAGSQFRHAVIRYDPTTDTATTSGEDAETTIIKTLQSADSAL
                            .: :  : *:    :**: *   :       .*: :* : *.:*

P_brasilianum_hmfP1   KVYTRSSPNFETLRGVYNKLITHQPLAICRPQTIEQIQLIVR---TAR--
Art_otae_XP_002842712 KLYTRASPHYGSLRGCFNKAIAAEPLVICRPVSVEQVQLIVR---TVGDL
Mic_gyps_XP_003169145 KLYTRSSPHYESLRGCFNKLITARPLVICRPVTIEQVQLIVR---AVSDL
Art_benh_XP_003013874 KLYTRSSPHYERLRGCFNKLITARPLVICRPVTVEQVQLIVR---AVGDL
Tri_soud_EZF72840     KLYTRSSPHYECLRGCFNKLVTARPLVICRPVTVEQVQLIVR---AVSDL
Tri_rubr_XP_003235790 KLYTRSSPHYECLRGCFNKLVTARPLVICRPVTVEQVQLIVR---AVSDL
Tri_tons_EGD94050     KLYTRSSPHYERLRGCFNKLITARPLVICRPITVEQVQLIVR---AVGDL
Tri_inte_EZF36477     KLYTRSSPHYERLRGCFNKLITARPLVICRPVTVEQVQLIVR---AVGDL
Tri_verr_XP_003021315 KLYTRSSPHYERLRGCFNKLITARPLVICRPVTVEQVQMIVR---AVSDL
Tal_marn_XP_002148377 KIYTRASSHFNTLRETYNTLITAKPLLFIRVTSVEQIQAIVRLYSAPGVP
Tal_marn_KFX51761     KIYTRASSHFNTLRETYNTLITAKPLLFIRVTSVEQIQAIVRLYSAPGVP
                      *:***:*.::  **  :*. :: .** : *  ::**:* ***   :

P_brasilianum_hmfP1   -AANPPVPIVPRCGGHDVYGRGLKPDSLSIDMRELDTQTLAEDRQSVRIG
Art_otae_XP_002842712 PDG---PPLAVRGAGHDVWGRGCIADSVTIDVRELDGQTLAEDKQSVSIG
Mic_gyps_XP_003169145 PAGNECPPLAVRGGGHDVWGRGCIADSVTIDVRELDQARLAEDKQSVTAG
Art_benh_XP_003013874 ANGDGCPPLAIRGGGHDVWGRGCIADSVTIDVRELDKATLAEDKQSVTVG
Tri_soud_EZF72840     ANGDGCPPLAIRGGGHDVWGRGCIADSVTIDVRELDTATLAEDKQSVTVG
Tri_rubr_XP_003235790 ANGDGCPPLAIRGGGHDVWGRGCIADSVTIDVRELDTATLAEDKQSVTVG
Tri_tons_EGD94050     AGGDGCPPLAIRGGGHDVWGRGCIADSVTIDVRELDKATLAEDKQSVTVG
Tri_inte_EZF36477     AGGDGCPPLAIRGGGHDVWGRGCIADSVTIDVRELDKATLAEDKQSVTVG
Tri_verr_XP_003021315 ADGDGCPPLAIRGGGHDVWGRGCIADSVTIDVRELDKATLAEDKQSVTVG
Tal_marn_XP_002148377 EDIKKKYPLNVRCGGHDVWGRGSVQDSVTIDLRELDTQVLDDTKKIVRVG
```

TABLE 7-continued

Amino acid sequence alignment of *Penicillium brasilianum* hmfP1 and 10 closest orthologues.

```
Tal_marn_KFX51761     EDIKKKYPLNVRCGGHDVWGRGSVQDSVTIDLRELDTQVLDDTKKIVRVG
                             *:  * .****:***   **::**:****   * : :: *  *

P_brasilianum_hmfP1   GGVTSQNFVGFLDEHGLCTANGTAGNVGWTGWAVWGGYGPFNDYVGLGVD
Art_otae_XP_002842712 GGVLSGNLVGFLNTHGLCTSNGTAGNVGWTGWAIWGGYGPFNDFVGLGVD
Mic_gyps_XP_003169145 GGILSGNLVGFLNNHGLCTSNGTAADVGWTGWAVWGGYGPFNDYLGLGVD
Art_benh_XP_003013874 GGILSGNLVGFLNTHGLCTSNGTAADVGWTGWAVWGGYGPFNDYLGLGVD
Tri_soud_EZF72840     GGILSGSLVGFLNTHGLCTSNGTAADVGWTGWAVWGGYGPFNDYLGLGVD
Tri_rubr_XP_003235790 GGILSGSLVGFLNTHGLCTSNGTAADVGWTGWAVWGGYGPFNDYLGLGVD
Tri_tons_EGD94050     GGILSGNLVGFLNTHGLCTSNGTAADVGWTGWAVWGGYGPFNDYLGLGVD
Tri_inte_EZF36477     GGILSGNLVGFLNTHGLCTSNGTAADVGWTGWAVWGGYGPFNDYLGLGVD
Tri_verr_XP_003021315 GGILSGNLVGFLNTHGLCTSNGTAADVGWTGWAVWGGYGPFNDYLGLGVD
Tal_marn_XP_002148377 GGLTSRNFVTFLDTHGLCTANGAAGSVGWIGNSIWGGFGPLNDYTGLGLD
Tal_marn_KFX51761     GGLTSRNFVTFLDTHGLCTANGAAGSVGWIGNSIWGGFGPLNDYTGLGLD
                      **: * .:* **: *****:**:*..*** **::***:**:**: ***:*

P_brasilianum_hmfP1   NILSARLVLADGSLVEAGPGSELLWGVRGAGGSLGVIVDVTVKVYPMPVI
Art_otae_XP_002842712 NILSARVVLADGRLVEAKAGSDLLWAIRGAGGNFGVIVETTVKVYRMPVI
Mic_gyps_XP_003169145 NILAAKVVLADGRLVEAKPESELLWAIRGAGGNFGVIVEVTVKVYHMPTI
Art_benh_XP_003013874 NILAAKVVLADGTLVEAKPESDLLWAIRGAGGNFGVIVEVTAKVYHMPTI
Tri_soud_EZF72840     NILAAKVVLADGTLAEAKPESDLLWAIRGAGGNFGAIVEVTVKVYHIPTI
Tri_rubr_XP_003235790 NILAAKVVLADSTLAEAKPESDLLWAIRGAGGNFGAIVEVTVKVYHIPTI
Tri_tons_EGD94050     NILAAKVVLADGTLVEAKPESDLLWAIRGAGGNFGAIVELTVKVYHMPAI
Tri_inte_EZF36477     NILAAKVVLADGTLVEAKPESDLLWAIRGAGGNFGAIVELTVKVYHMPAI
Tri_verr_XP_003021315 NILAAKVVLADGTLVEAKPESDLLWAIRGAGGNFGAIVEVTAKVYHIPTI
Tal_marn_XP_002148377 NIQGAKIVLANGELVEAGP--DLLWGLKGAGGNLGIVVETTVQVYPMPRI
Tal_marn_KFX51761     NIQGAKIVLANGELVEAGP--DLLWGLKGAGGNLGIVVETTVQVYPMPRI
                      ** .*::***:. *.** .  :***.::****.:* :*: *.:** :* *

P_brasilianum_hmfP1   LAGFIAYQWGESAKVLSGLQELLD----RG-IPDTMCLQMGFMKTKWGVG
Art_otae_XP_002842712 LAGFIVYKWEESEQALHRVQELLD----KG-VPDAMGMQVGFMRSRAGLG
Mic_gyps_XP_003169145 LGGFIVYKWEETEQALHRTQELLD----KG-VPDALGIQVGFNRSRVGLG
Art_benh_XP_003013874 LGGFIVFKWEETRQALHRLQELLD----KG-VPDALGIQVGFNRSKIGLG
Tri_soud_EZF72840     LGGFIVFKWEETRQALYRLQELLD----KG-VPDALGIQIGFNRSKIGLG
Tri_rubr_XP_003235790 LGGFIVFKWEETRQALYRLQELLD----KG-VPDALGIQIGFNRSKIGLG
Tri_tons_EGD94050     LGGFIVFKWEETRQALHKLQELLD----KG-VPDALGIQVGFNRSKVGLG
Tri_inte_EZF36477     LGGFIVFKWEETRQALHKLQELLD----KG-VPDALGIQVGFNRSKVGLG
Tri_verr_XP_003021315 LGGFIVFKWEETRQALNRLQELLD----KG-VPDALGIQVGFNRSKVGLG
Tal_marn_XP_002148377 LGGFINYAWDDAESVLLKLQELLDGKTEHGPVPDAACMQIGFMNGRWGMG
Tal_marn_KFX51761     LGGFINYAWDDAESVLLKLQELLDGKTEHGPVPDAACMQIGFMNGRWGMG
                      *.*** : * :: ..*   *****    :* :**:  :*:** . : *:*

P_brasilianum_hmfP1   MSLIFAWPDSETLD-EGRTWLETVRGLGAIQVDTVGETTFKAFQGITSRV
Art_otae_XP_002842712 LSLIYTWADSDRLD-EGKKWLEEVRQLATVTIDTISETTFKDFQAITTKP
Mic_gyps_XP_003169145 MSLIYTWADSNDLD-EGKKWLETLKQLATVVVDTTTETTFKDFQAMTTKP
Art_benh_XP_003013874 MSFIYTWADSSNLA-EGKKWLETLKQLATVVLDTTTETTFKDFQAMTTKP
Tri_soud_EZF72840     MSFIYTWADSGNLD-EGKKWLETLKQLATVVVDTTTETTFKDFQAMTTKP
Tri_rubr_XP_003235790 MSFIYTWADSGNLD-EGKKWLETLKQLATVVVDTTTETTFKDFQAMTTKP
Tri_tons_EGD94050     MSFIYTWADSSNLA-EGKKWLETLKQLATVVVDTTTETTFKDFQAMTTKP
Tri_inte_EZF36477     MSFIYTWADSSNLA-EGKKWLETLKQLATVVVDTTTETTFKDFQAMTTKP
Tri_verr_XP_003021315 MSFIYTWADSSNLA-EGKKWLETLKQLATVVVDTTTETTFKDFQAMTSKP
Tal_marn_XP_002148377 ISLIFIWADSSTLETEGRRWLEIVRGLGTVTFDTVKETTFKDFQNVVGAV
Tal_marn_KFX51761     ISLIFIWADSSTLETEGRRWLEIVRGLGTVTFDTVKETTFKDFQNVVGAV
                      :*:*: *.**   *  **: *** :: *.:: .**  ***** ** :.

P_brasilianum_hmfP1   VDEPVNVCTRSASVPRFTPETIALLQKYSEAIPDGRQYNVIAHIGHGKST
Art_otae_XP_002842712 VREPVNVCTRSVSIPRFTPETIAVLLKYSEAIPEGGRYNIVSHVGHGKGI
Mic_gyps_XP_003169145 FKDPIDVCTRSISIPRFTPETIAILLKYAEDIPIGGRYNVVSHVGHGKGT
Art_benh_XP_003013874 FKDPAEVCSRSVSIPRFTPETVEVLLKYIEAIPMGGRYSVLSHVGHGKGI
Tri_soud_EZF72840     FKDPTNVCSRSVSIPRFTPETVEVLLKYIEAIPMGGRYNVLSHVGHGKGT
Tri_rubr_XP_003235790 FKDPTNVCSRSVSIPRFTPETVEVLLKYIEAIPMGGRYNVLSHVGHGKGT
Tri_tons_EGD94050     FKDPTDVCCRSVSIPRFTPETIDILLKYAEAIPVGGRYNVVSHVGHGKGI
Tri_inte_EZF36477     FKDPTDVCCRSVSIPRFTPETIDILLKYAEAIPVGGRYNVVSHVGHGKGI
Tri_verr_XP_003021315 FKDPTDVCSRSVSIPRFTPEVVEVLLKYIEAIPMGGRYNVLSHVGHGKGI
Tal_marn_XP_002148377 IDEPVNVYTRCFVIPKWTPKTVDVLLNATRAIPKMRKYNIGSHIGHGKHT
Tal_marn_KFX51761     IDEPVNVYTRCFVIPKWTPKTVDVLLNATRAIPKMRKYNIGSHIGHGKHT
                      . :* :*  *.  :*::**:.: :* :  . **   :*.: :*:****

P_brasilianum_hmfP1   RPNPDTSFATREPHVLFHINA--CDEPERMDEARSWVDGLMKEMNATRQA
Art_otae_XP_002842712 QPNKESCFGTREPHILFHINAPVSDEAGSMTDAQGWVDGLMADIKGTGQA
Mic_gyps_XP_003169145 KPNNSTCFGTREPHILFHINAPVPDGAGGMERAQAWVDGLMADIKGTGQA
Art_benh_XP_003013874 QPNSTTCFGTREPHILFHINAPVADGAGSMENAQSWVDNLMADIKGTGQS
Tri_soud_EZF72840     QPNSTTCFGTREPHILFHINAPVADGADSIGKAQSWVDGLMADIKGTGQA
Tri_rubr_XP_003235790 QPNSTTCFGTREPHILFHINAPVADGADSIGKAQSWVDGLMADIKGTGQA
Tri_tons_EGD94050     KPNSKTCFGTREPHILFHINAPVADGAGSMEKAQSWVDGLMADIKGTGQS
Tri_inte_EZF36477     KPNSTTCFGTREPHILFHINAPVADGAGSMEKAQSWVDGLMADIKGTGQS
Tri_verr_XP_003021315 QPNSRTCFGTREPHILFHINAPVPDGAGSMENAQSWVDGLMADIKGTGQS
```

TABLE 7-continued

Amino acid sequence alignment of *Penicillium brasilianum* hmfP1 and 10 closest orthologues.

```
Tal_marn_XP_002148377 RENATSCFPYRKPHILFHINA--CDDTDKMDEAKAWVEKLVADLVATGEG
Tal_marn_KFX51761     RENATSCFPYRKPHILFHINA--CDDTDKMDEAKAWVEKLVADLVATGEG
                      : *  :.*  *:**:******   * .  :  *:.**: *: :: .* :.

P_brasilianum_hmfP1   MKPVYVSFMGEDEDPRVSFGSHWERLQALKQSVDPDNVFRFP--------
Art_otae_XP_002842712 LKPAYVSFMGEDEATHESFGQNWERLQALKRDMDQKNLFKFAQPKLS---
Mic_gyps_XP_003169145 LKPVYVSFMGKDEETQNSFGQNWKRLQELKGTLDKRDLFRFAQPMLGKM-
Art_benh_XP_003013874 LKPVYVSFMGTDEETHDSFGQNWKRLQELKGSLDKKNLFRFAQPMLGKM-
Tri_soud_EZF72840     LKPVYVSFMGTDEETHDSFGRNWKRLQELKGSLDKKNLFRFAQPMLGKM-
Tri_rubr_XP_003235790 LKPVYVSFMGTDEETHDSFGRNWKRLQELKGSLDKKNLFRFAQPMLGKM-
Tri_tons_EGD94050     LKPVYVSFMGTDEETHDSFGQNWKRLQELKGSLDKKNLFRFAQPMLGKM-
Tri_inte_EZF36477     LKPVYVSFMGTDEETHDSFGQNWKRLQELKGSLDKKNLFRFAQPMLGKM-
Tri_verr_XP_003021315 LKPVYVSFMGTDEETHDSFGQNWKRLQELKGSLDKKNLFRFAQPMLGKM-
Tal_marn_XP_002148377 ELGVYVSFMGEDEQTKQSFADNWDQMRAIKAKVDPNNLFQFAQPRLAD--
Tal_marn_KFX51761     ELGVYVSFMGEDEQTKQSFADNWDQMRAIKAKVDTNNLFQFAQPRLADUS
                         .****** ** .: **. :*.::: :*  :*  ::*:*.

P_brasilianum_hmfP1   ---
Art_otae_XP_002842712 ---
Mic_gyps_XP_003169145 ---
Art_benh_XP_003013874 ---
Tri_soud_EZF72840     ---
Tri_rubr_XP_003235790 ---
Tri_tons_EGD94050     ---
Tri_inte_EZF36477     ---
Tri_verr_XP_003021315 ---
Tal_marn_XP_002148377 ---
Tal_marn_KFX51761     AGE
```

TABLE 8

Amino acid sequence alignment of *Penicillium brasillanum* hmfP2 and 10 closest orthologues.

```
P_brasilianum_hmfP2        MPFLPFFKVLRLRRELDGTKAEIFTWGCDGYDESIKQWNAYLTQGA----
Asp_oryz_XP_001824539.2    MPFLSYAHILELQQQLEGTRARVICAGSDEYAESIKRWSDTCEKEA----
Asp_fumi_EDP50847          MPFMSYSHVLELRRWLEGTRANVICYGSEDYAEKIKRWSDTCERDA----
Tal_marn_XP_002149881      MPFLTYPAALELQKELRGTNAEVVTLADDEYVESLDRWSATSEKEA----
Tal_stip_XP_002484384      MPFLTYPAALELQKELSGTNAEVITLADDDYVESLDRWSATSEKEA----
Tal_marn_KFX40866          MPFLTYPAALELQKELRGTNAEVVTLADDEYVESLDRWSATSEKEA----
Tal_marn_XP_002149879      MPFLTYPAALELQKELRGTNAEVVTLADDEYVESLDRWSATSEKEAVCVS
Asp_flav_XP_002384098      --------------------------------------MSLTVPQ----
Asp_oryz_EIT77828          --------------------------------------MSLTVPQ----
Asp_terr_XP_001218425      MPFLSYRHALQLKEQLEGTAAEVITSESEDYPKSIQRWSDTCEKEA----
Asp_nige_XP_001398623      MPFLSFARALELRRQLEGTRAEVVCIGSDDYATSIRRWSDTCEKEA----

P_brasilianum_hmfP2        ------------------------------TVRVTSSDEAATVVRFAACH
Asp_oryz_XP_001824539.2    ----------------------------GAVVKVTSTSEVSEVIKFARKH
Asp_fumi_EDP50847          ----------------------------GAIVEVTSTSEVSETVQFARKH
Tal_marn_XP_002149881      ----------------------------GAIVKVTTAEEVSTVVEFAAKR
Tal_stip_XP_002484384      ----------------------------GAIVRVTSVEDVSTVVEFAAKR
Tal_marn_KFX40866          ----------------------------GAIVKVTTAEEVSTVVEFAAKR
Tal_marn_XP_002149879      SPHQSIRSLLSPIQEHHLTYADTTMLIKGAIVKVTTAEEVSTVVEFAAKR
Asp_flav_XP_002384098      ----------------------------GAVVKVTSTSEVSEVIKFARKH
Asp_oryz_EIT77828          ----------------------------GAVVKVTSTSEVSEVIKFARKH
Asp_terr_XP_001218425      ----------------------------GAIVRVTSTSEVSIVVEFAQKH
Asp_nige_XP_001398623      ----------------------------GAVVRVTSTSEVAEVVRFCRKN
                                                          *.**: .:.: .:.*.  .

P_brasilianum_hmfP2        KIPFTVKGGGYSTTGASSAHG--------------------VTAQGGALW
Asp_oryz_XP_001824539.2    RISFAVEAGGHSTTGSSASHGGIVISLSQMRKVLTDPASKTVCVQGGATW
Asp_fumi_EDP50847          HINFVTEAGGHSTTGSSATHGGLVISLAKMRRVLTDPASKTVCVQGGAIW
Tal_marn_XP_002149881      YIPFAVLSGGYSTNGASSTYGGIVIDLGRMNRVDVQSSSSIVSVEGGAKW
Tal_stip_XP_002484384      YVPFAVLSGGYSTNGASSTYGGIVIDLGRMNKVDVQPSSSTISVEGGAKW
Tal_marn_KFX40866          YIPFAVLSGGYSTNGASSTYGGIVIDLGRMNRVDVQSSSSIVSVEGGAKW
Tal_marn_XP_002149879      YIPFAVLSGGYSTNGASSTYGGIVIDLGRMNRVDVQSSSSIVSVEGGAKW
Asp_flav_XP_002384098      RISFAVEAGGHSTTGSSASHGGIVISLSQMRKVLTDPASKTVCVQGGATW
Asp_oryz_EIT77828          RISFAVEAGGHSTTGSSASHGGIVISLSQMRKVLTDPASKTVCVQGGATW
Asp_terr_XP_001218425      HVKYVVEAGGHSTTGASASHGGIVISMTTMRKVMTDTASRTVCVQGGAIW
Asp_nige_XP_001398623      HIDFVVEAGGHSTTGASSSHGGVVISMARMCKVLTDPASETVCVQGGANW
                            : :.. .**:**.*:*:::*                    : .:*** *

P_brasilianum_hmfP2        EDIDVAAAQHRLAVVGSTLNHIGVAGATLGGGYGWLTGQYGLAIDNLLWV
Asp_oryz_XP_001824539.2    QDVNSSTAPYDLVVVGATSSHAGVGGSTLGGGYGWLTGRYGLIIDSLLSV
```

TABLE 8-continued

Amino acid sequence alignment of *Penicillium brasillanum* hmfP2 and 10 closest orthologues.

```
Asp_fumi_EDP50847           DDVNESTAAYGLAVVGSTASHTGVAGTTLGGGFGWLTGRYGLISDNLLSV
Tal_marn_XP_002149881       ADVDTAAAQHGLAVVGPTASQLGVGGTTLGGGIGWLTGKYGLIIDNLVEA
Tal_stip_XP_002484384       ADVNTAAAQHGLAVVGPTVSQLGVGGTTLGGGIGWLTGKYGLVVDNLIEA
Tal_marn_KFX40866           ADVDTAAAQHGLAVVGPTASQLGVGGTTLGGGIGWLTGKYGLIIDNLVEA
Tal_marn_XP_002149879       ADVDTAAAQHGLAVVGPTASQLGVGGTTLGGGIGWLTGKYGLIIDNLVEA
Asp_flav_XP_002384098       QDVNSSTAPYDLVVVGATSSHAGVGGSTLGGGYGWLTGRYGLIIDSLLSV
Asp_oryz_EIT77828           QDVNSSTAPYDLVVVGATSSHAGVGGSTLGGGYGWLTGRYGLIIDSLLSV
Asp_terr_XP_001218425       KDVNHSTMPHGLAVVGATADQTGVAASTLGGGYGWLSGLYGLIMDSLLSV
Asp_nige_XP_001398623       DMVNHSTAPYGLAVVGATASHSGVGGSALGGGFGWLTGQHGLIADQLLSV
                              :: ::  : *.***.* .: **..::**** ***:* :**  *.*: .

P_brasilianum_hmfP2         KMILADGSVIIVSEEQYPDLFWAIRGAGQSFGVAIELAFRAHRQDHPVFA
Asp_oryz_XP_001824539.2     RMVLADGSIVEASETTSPDLFWAVRGAGQAFGVVTELVFRAYDLKHHVFG
Asp_fumi_EDP50847           RMVLADGTIVEASDEDHQDLFWAVRGAGQAFGIVTELVFRAHELAGPVYG
Tal_marn_XP_002149881       QVVLADGSITTASESENPDLFWAIRGAGQDFGVTTRFTFRAHPQQNDVFA
Tal_stip_XP_002484384       QIVLADGSITTASETENPDLFWAIRGAGQDFGVITRFTFKAHPQKNDVYA
Tal_marn_KFX40866           QVVLADGSITTASESENPDLFWAIRGAGQDFGVTTRFTFRAHPQQNDVFA
Tal_marn_XP_002149879       QVVLADGSITTASESENPDLFWAIRGAGQDFGVTTRFTFRAHPQQNDVFA
Asp_flav_XP_002384098       RMVLADGSIVEASETTSPDLFWAVRGAGQAFGVVTELVFRAYDLKHHVFG
Asp_oryz_EIT77828           RMVLADGSIVEASETTSPDLFWAVRGAGQAFGVVTELVFRAYDLKHHVFG
Asp_terr_XP_001218425       KMVLADGSVVEASDESHPDLFWAVRGAGLAFGVVTELVFRAHPIPPRLFG
Asp_nige_XP_001398623       KMVLADGSIVEASDEDNQDLFWAVRGAGQAFGVATEFVFRAHKVRDRFFG
                            :::****::  .*:    *****:****  **:  .:.*:*:     .:.

P_brasilianum_hmfP2         GTLLFSASKLSAIVEFANNFETLTNGNQGFWFGFTMPPSMDRCAILVVVF
Asp_oryz_XP_001824539.2     GALYFTPDRLAKIVEFANEFHRRMNENSGLMFGFTAPPFMEETAVLVIPF
Asp_fumi_EDP50847           GTLVFTVDRLPGILEFASRFDKLQDENSGFFFGLAAPSAADRTGILVLPF
Tal_marn_XP_002149881       GIIYLDPDKLSQLVDYVNDLDSKLEEDQGLFFGFTNT--HDQTTIVVILF
Tal_stip_XP_002484384       GMVYLEPDKLPQLVDYVNDLDSKLEEDQGLFFGFTNS--NGRTNIVLILF
Tal_marn_KFX40866           GIIYLDPDKLSQLVDYVNDLDSKLEEDQGLFFGFTNT--HDQTTIVVILF
Tal_marn_XP_002149879       GIIYLDPDKLSQLVDYVNDLDSKLEEDQGLFFGFTNT--HDQTTIVVILF
Asp_flav_XP_002384098       GALYFTPDRLAKIVEFANEFHRRMNENSGLMFGFTAPPFMEETAVLVIPF
Asp_oryz_EIT77828           GALYFTPDRLAKIVEFANEFHRRMNENSGLMFGFTAPPFMEETAVLVIPF
Asp_terr_XP_001218425       GSIYFTGDKLPQIVRFANQFHERQDPKSGLFFGFRAHPSVRGTAIVVLLF
Asp_nige_XP_001398623       GLVYYDVDKLPMLVSFANEFDKRQDPKSGFFFGFAAPREIGHMVVLAVLF
                            * :    .:*. :: :.. :.   : ..*: **:          :: : *

P_brasilianum_hmfP2         YNGPQIAARQFFSPLLSIGPVVNETGMLPYDSLNGILNMMDTVSRRRILR
Asp_oryz_XP_001824539.2     YNGSREEAEDFFEPILSAGPAAGQTDMMSYTKLNAVANVD----------
Asp_fumi_EDP50847           YNGSQEKSEEFFAPLMSLGPSINKTSMMSYKELNGIANVD----------
Tal_marn_XP_002149881       YNGPQDKAEKMFEPVLSLSTGRGETGMMPYYKTNRLFNRT----------
Tal_stip_XP_002484384       YNGPQDQAEKIFSPLLSLDSGRKEIGMMPYYKANELLNRT----------
Tal_marn_KFX40866           YNGPQDKAEKMFEPVLSLSTARGETGMMPYYKTNRLFNRT----------
Tal_marn_XP_002149879       YNGPQDKAEKMFEPVLSLSTGRGETGMMPYYKTNRLFNRT----------
Asp_flav_XP_002384098       YNGSREEAEDFFEPILSAGPAAGQTDMMSYTRLNAVANVD----------
Asp_oryz_EIT77828           YNGSREEAEDFFEPILSAGPAAGQTDMMSYTRLNAVANVD----------
Asp_terr_XP_001218425       YHGTQTEGEAFFRDLLTINAAEEGTGPMSYAELHTLANIE----------
Asp_nige_XP_001398623       YDGSAYDGEAFFEPILNPNPLINRAAMKSYIEMNSIANVD----------
                            *.*.   .. :*  ::. ..         .*   : : *

P_brasilianum_hmfP2         GADITLPTDENVGTRKSLRGSNITLPLDINFTASIYSEFDGILREFTQAR
Asp_oryz_XP_001824539.2     ------PSPE---GRKNINGTNISLPFDTDFVYDVYKQFDRIMKSCRRVG
Asp_fumi_EDP50847           ------PVPE---GRKCFSGTKVSMPLDQHLLCDLWEHFDAIMDKYPRSN
Tal_marn_XP_002149881       ------TASE---GRKRLSGTSVTLPLDMDFFQTVYQNFSHILDDHSDDA
Tal_stip_XP_002484384       ------ADSA---GRKRLSGTSVTFPLDMGFFQTVYQHFSHVLDDYPGDG
Tal_marn_KFX40866           ------TASE---GRKRLSGTSVTLPLDMDFFQTVYQNFSHILDDHSDDA
Tal_marn_XP_002149879       ------TASE---GRKRLSGTSVTLPLDMDFFQTVYQNFSHILDDHSDDA
Asp_flav_XP_002384098       ------PSPE---GRKNINGTNISLPFDTDFVYDVYKQFDRIMRSCRRVG
Asp_oryz_EIT77828           ------PSPE---GRKNINGTNISLPFDTDFVYDVYKQFDRIMRNCRRVG
Asp_terr_XP_001218425       ------PIPE---GRKSIDGTTVTFPLAMEKYLAVYDKLEHISRSYPEIR
Asp_nige_XP_001398623       ------PVPE---GRKSIGGANIMPPLETSLLQNLYSQFKEAMNTYPRME
                                  .       ** : *:.:  *:       ::..:.

P_brasilianum_hmfP2         DSILLFELLPYTQITKVPNDATAFASRGPYHNVISLFGWQDKDLDERMHS
Asp_oryz_XP_001824539.2     NSVLMFELLPYNHIIEVPLDATACANRGRYYNVGSIFCWPDPDLDQKMLT
Asp_fumi_EDP50847           NSVLMFELIPYEKTISVPIDATACADRGRYYNVALLLCWYDPEHDAAMHT
Tal_marn_XP_002149881       EAFLLFEMLPYTKVVEVPNDATAYANRGPYYNVCSIFNWQDVNADSKIRN
Tal_stip_XP_002484384       EALLFFEMLPYNKVVEVPNDATAYANRGPYYNVCSIFNWHDAKIDSKVRT
Tal_marn_KFX40866           EAFLLFEMLPYTKVVEVPNDATAYANRGPYYNVCSIFNWQDVNADSKIRN
Tal_marn_XP_002149879       EAFLLFEMLPYTKVVEVPNDATAYANRGPYYNVCSIFNWQDVNADSKIRN
Asp_flav_XP_002384098       NSVLMFELLPYNHIIEVPLDATACANRGRYYNVGSIFCWPDPDLDQKMLT
Asp_oryz_EIT77828           NSVLMFELLPYNHIIEVPLDATACANRGRYYNVGSIFCWPDPDLDQKMLT
Asp_terr_XP_001218425       ESTLVFEMLPYGKVKEVPLDATACASRGPYYNVGLVFCWRNPELDRKIVA
Asp_nige_XP_001398623       DSALVFELLPYTKAVQVPIKETACANRGPYYNVGLILCWHDSDLDAKMHA
                            :: *.**::** :  .** . ** *.** *:**  :: * : . *  :
```

TABLE 8-continued

Amino acid sequence alignment of *Penicillium brasillanum* hmfP2 and 10 closest orthologues.

```
P_brasilianum_hmfP2         LQEDIMNQIGKRAGIACTPFYNVSKHGTGLYANYAGHNVPLEAIFGDNLR
Asp_oryz_XP_001824539.2     EQQGIISKIENFGSGS----RDEGEKRVAKYANYAGHNISAANLFGENLE
Asp_fumi_EDP50847           YMRALLTQIKRSDCYA----GKK-EPVVQANANFAGHEIGATYLFRDNLP
Tal_marn_XP_002149881       LQQGLMSQIRDEHVK-----KRGPG--VGTYPNFTGFDANARDLFGDNLP
Tal_stip_XP_002484384       LQQGLMNLIREEHIK-----KSGHG--VNMYANYTGFEANAKDLFGDNLS
Tal_marn_KFX40866           LQQGLMSQIRDEHVK-----KRGPGLQVELIDYGIGFDANARDLFGDNLP
Tal_marn_XP_002149879       LQQGLMSQIRDEHVK-----KRGPG--VGTYPNFTGFDANARDLFGDNLP
Asp_flav_XP_002384098       EQQGIISKIENFGSGS----RDEGEKRVAKYANYAGHNISAANLFGENLE
Asp_oryz_EIT77828           EQQGIISKIENFGSGS----RDEGEKRVAKYANYAGHNISAANLFGENLE
Asp_terr_XP_001218425       LKRDVLDVLKRES--------SEEEAHAEIYPNLAGHEFRASQLFRGNLD
Asp_nige_XP_001398623       LQRSIISKILEAQ-------RDITDDHAVVYPNLAGHDVSAEKLFGANLP
                              . ::  :                  .       *.:     :*  **

P_brasilianum_hmfP2         RLQELKKKFDPNNVFKKWHNLNTTIGTPA-----------
Asp_oryz_XP_001824539.2     RLQQLKRAYDPNNVFRKWHDLLHQKNPV------------
Asp_fumi_EDP50847           RLQALKKKYDPHNVFSKWHDLVSHTERQP-----------
Tal_marn_XP_002149881       RLKELKKYYDPRNVFRKWHDLLLQTGSSV-----------
Tal_stip_XP_002484384       RLKELKKQYDPRNVFRKWHDLLLQTGSSV-----------
Tal_marn_KFX40866           RLKELKKYYDPRNVFRKWHDLLLQTGSSV-----------
Tal_marn_XP_002149879       RLKELKKYYDPRNVFRKWHDLLLQTGSSV-----------
Asp_flav_XP_002384098       RLQQLKRAYDPNNVFRKWHDLLHQKNPV------------
Asp_oryz_EIT77828           RLQQLKRAYDPNNVFRKWHDLLHQKNPV------------
Asp_terr_XP_001218425       RLRELKKKYDPENVFRHWHNLLN-----------------
Asp_nige_XP_001398623       RLQKLKKKYDPHNVFRKWHDLLAPARSHVEQTDKPUSAGE
                            **: **: :**.*** :**:*
```

TABLE 9

Amino acid sequence alignment of *Penicillium brasilianum* hmfP3 and 10 closest orthologues.

```
P_brasilianum_hmfP3   MMTPPILAFHLFKDFELQRTKNYFRVLNINYKADHHPHQLFHDEFTINTI
Pen_oxal_EPS33887     -------------------------MNSLSTLSRARSLRVTTRPQTVLYF
Pen_digi_EKV16227     ----------------------------MNTRSARAPWRAAAKPQ-YLHL
Pen_chry_AAR08189     ----------------------------MNTLSVRAPLRAAAKPQ-YLHL
Pen_rube_XP_002557865 ----------------------------MNTLSVRAPLRAAARPQ-YLHL
Asp_terr_XP_001215177 ----------------------------MSLSISTVPIRAAVFPKSYLLV
Neo_fisc_XP_001260128 -----------------------------------MPLRATAFPKPYLRF
Asp_fumi_XP_749637    ----------------------------MNSITATMPLRATAFPKPYLRF
Asp_kawa_GAA83790     ----------------------------MNSLTATAPIRA-AIPKSYLHI
O74180.2              ----------------------------MNSLTATAPIRA-AIPKSYMHI
Asp_nige_XP_001394472 ----------------------------MNSLTATAPIRA-AIPKSYMHI
                                                          . :          .

P_brasilianum_hmfP3   DDCTLANCCKATDLSLPGRSHLLRGRSHNDQLFMSRQTTLFTMYLHIETS
Pen_oxal_EPS33887     AIRSYSG-VATTCHGPPNFQRRSSP-------------------LTYTTK
Pen_digi_EKV16227     AVRTYSGIAATTITPAFGESKRTST-------------------FSLISK
Pen_chry_AAR08189     AVRTYSGVAATTLNPACGANKRTSI-------------------FSLTSK
Pen_rube_XP_002557865 AVRTYSGVVATTLNSSCVVSKRTSA-------------------FSLTSK
Asp_terr_XP_001215177 SSRGYASLLATTSLRYSNGSLLATKP-----------------GYHRTTK
Neo_fisc_XP_001260128 TIRTYASAVAAP--RCSR-PLLASSN-----------------HFQSITK
Asp_fumi_XP_749637    TIRTYASAAAAP--RCSR-PLLASSS-----------------HFQSFTK
Asp_kawa_GAA83790     ATRNYSGVIAMSGLRCSG-SLVANR-------------------HQTAGK
O74180.2              ATRNYSGVIAMSGLRCSG-SLVANR-------------------HQTAGK
Asp_nige_XP_001394472 ATRNYSNVIAMSGLRCSG-SLVANR-------------------HQTAGK
                           :.    .                                     .

P_brasilianum_hmfP3   DLLNASSSDQRILPSSCKPRSERGDYGMVASDYHSYTEAQMNNVKIAHRE
Pen_oxal_EPS33887     RPISSTPHPQ-IKEYFPPPENSAVKEVDSAWAHPVYTEAQVQSVRVAHRE
Pen_digi_EKV16227     RLISSTPQNQ-ITDYFPPPKTPNVKEVQTAWVHPVYTESQMRKIRVAHRQ
Pen_chry_AAR08189     RPISSTPQNQ-ITDYFPPPKAPNVKEVQTAWVHPVYTESQMQNIRIAHRQ
Pen_rube_XP_002557865 RPISSTPKSQTITDYFPAPETPNVKEVQTAWVHPVYTEAQMQSIQIAHRQ
Asp_terr_XP_001215177 RFISSTPQQQ-IKEFFPPPNTPQIKESETAWVHPVYTEEQMRQVEIAHRE
Neo_fisc_XP_001260128 RPISSTPQAQ-IKDYFPPPKAPHIKEVETAWVHPIYTEDQMRAVQIGHRE
Asp_fumi_XP_749637    RPISSTPQTQ-IKEYFPPPKAPHIKEVETAWVHPIYTEDQMRAVQIAHRE
Asp_kawa_GAA83790     RFISTTPKSQ-IKEFFPPPTAPHVKEVETAWVHPVYTEEQMKQVAIAHRD
O74180.2              RFISTTPKSQ-IKEFFPPPTAPHVKEVETAWVHPVYTEEQMKQVAIAHRD
Asp_nige_XP_001394472 RFISTTPKSQ-IKEFFPPPTAPHVKEVETAWVHPVYTEEQMKQVAIAHRD
                        :.::.  * *      *     .    *  :  *** *:. : :.**:

P_brasilianum_hmfP3   ATNWSDWVALGTVRFFRWGMDLATGYKHPQPGQEASEKFKMTERKWLTRF
Pen_oxal_EPS33887     ARDWSDWVALGTVRFFRWGMDWVTGYKHPEPGQQLSERFKMTEQKWLTRF
Pen_digi_EKV16227     ASNWADWVALGTVRMFRWGMDTATGYRHPKPGQELSGIFQMTERKWLNRF
```

TABLE 9-continued

Amino acid sequence alignment of *Penicillium brasilianum* hmfP3 and 10 closest orthologues.

```
Pen_chry_AAR08189         AANWSDWVALGTVRIFRWGMDTATGYRHPKPGQELPDMFKMTERKWMNRF
Pen_rube_XP_002557865     TANWSDWIALGTVRFFRWGMDTATGYKHPKPGEQLPARFKMTERKWLNRF
Asp_terr_XP_001215177     AKNWSDWVALGTVRMLRWGMDLVTGYRHPPPGKENDVRFRMTEQKWLTRF
Neo_fisc_XP_001260128     AKNWSDWVALGTVRVLRWGMDLVTGYRHPKPGQEHDAKFKMTEQKWLTRF
Asp_fumi_XP_749637        AKNWSDWVALGTVRVLRWGMDFVTGYRHPKPGQEHDAKFRMTEQKWLTRF
Asp_kawa_GAA83790         AKNWADWVALGTVRMLRWGMDLVTGYRHPPPGREHEARFKMTEQKWLTRF
O74180.2                  AKNWADWVALGTVRMLRWGMDLVTGYRHPPPGREHEARFKMTEQKWLTRF
Asp_nige_XP_001394472     AKNWADWVALGTVRMLRWGMDLVTGYRHPPPGREHEARFKMTEQKWLTRF
                          : :*:**:******.:***** .***:** **.:    *:***:**:.**

P_brasilianum_hmfP3       IFLESVAGVPGMVGGMLRHLRSLRRMKRDNGWIETLLEEAFNERMHLLTF
Pen_oxal_EPS33887         VFLESVAGVPGMVGGMLRHLRSLRKMKRDNGWIETLLEEAFNERMHLLTF
Pen_digi_EKV16227         IFLESVAGVPGMVGGMLRHLRSLRKMKRDNGWIETLLEEAFNERMHLLTF
Pen_chry_AAR08189         IFLESVAGVPGMVGGMLRHLRSLRKMKRDNGWIETLLEEAFNERMHLLTF
Pen_rube_XP_002557865     VFLESIAGVPGMVGGMLRHLRSLRKMKRDNGWIETLLEEAFNERMHLLTF
Asp_terr_XP_001215177     VFLESVAGVPGMVGGMLRHLRSLRRMKRDNGWIETLLEEAFNERMHLLTF
Neo_fisc_XP_001260128     VFLESVAGVPGMVGGMLRHLRSLRRMKRDNGWIETLLEEAYNERMHLLTF
Asp_fumi_XP_749637        IFLESVAGVPGMVGGMLRHLRSLRRMKRDNGWIETLLEEAYNERMHLLTF
Asp_kawa_GAA83790         IFLESVAGVPGMVGGMLRHLRSLRRMKRDNGWIETLLEEAYNERMHLLTF
O74180.2                  IFLESVAGVPGMVGGMLRHLRSLRRMKRDNGWIETLLEEAYNERMHLLTF
Asp_nige_XP_001394472     IFLESVAGVPGMVGGMLRHLRSLRRMKRDNGWIETLLEEAYNERMHLLTF
                          :****:******************:***************:*********

P_brasilianum_hmfP3       LKLAEPGWFMRLMVLGAQGVFFNGFFLSYLISPRICHRFVGYLEEEAVLT
Pen_oxal_EPS33887         LKLAEPGWFMRLMVLGAQGVFFNGFFLAYLISPRICHRFVGYLEEEAVLT
Pen_digi_EKV16227         LKLAEPGWFMRLMVIGAQGVFFNGFFLAYLISPRICHRFVGYLEEEAVIT
Pen_chry_AAR08189         LKLAEPGWFMRLMVIGAQGVFFNGFFLSYLISPRICHRFVGYLEEEAVIT
Pen_rube_XP_002557865     LKLAEPGWFMRVMVIGAQGVFFNGFFLSYLISPRICHRFVGYLEEEAVIT
Asp_terr_XP_001215177     LKLAEPGWFMRLMVLGAQGVFFNGFFLSYLVSPRTCHRFVGYLEEEAVIT
Neo_fisc_XP_001260128     LKLAEPGWFMRLMVLGAQGVFFNGFFLSYLISPRTCHRFVGYLEEEAVIT
Asp_fumi_XP_749637        LKLAEPGWFMRLMVLGAQGVFFNGFFLSYLISPRTCHRFVGYLEEEAVIT
Asp_kawa_GAA83790         LKLAEPGWFMRLMVLGAQGVFFNGFFLSYLMSPRICHRFVGYLEEEAVIT
O74180.2                  LKLAEPGWFMRLMVLGAQGVFFNGFFLSYLMSPRICHRFVGYLEEEAVIT
Asp_nige_XP_001394472     LKLAEPGWFMRLMVLGAQGVFFNGFFLSYLMSPRICHRFVGYLEEEAVIT
                          ***********:**:************:**:*** *************:*

P_brasilianum_hmfP3       YTRAIQELEDGHLPEWKELQAPEIAVHYWQMPENQRTMRDLLLYIRADEA
Pen_oxal_EPS33887         YTRAIQELENGHLPDWDKLEAPEIAVQYWKMPEDKRTMRDLLFYVRADEA
Pen_digi_EKV16227         YSRAIEELETGKLPEWKDLDAPEIAIKYWQMPEGQRQMRDLLLFVRADEA
Pen_chry_AAR08189         YTRAIEELEAGKLPQWDDLDAPEIAIKYWQMPEGQRKMKDLLMFVRADEA
Pen_rube_XP_002557865     YTRAIEELEAGNLPEWKDLDAPEIAVKYWQMPEGQRKMKDLLLFIRADEA
Asp_terr_XP_001215177     YTRAIKDLENGNLPLWEKKEAPEIAIQYWKMPEGKRTMKDLLLYVRADEA
Neo_fisc_XP_001260128     YTRAIKDIEAGKLPDWEELDAPEIAVQYWNMPEGQRKMKDLLLYVRADEA
Asp_fumi_XP_749637        YTRAIKDIETGKLPDWEKLDAPEIAVQYWNMPEGQRKMRDLLLYVRADEA
Asp_kawa_GAA83790         YTRAIKEIEAGSLPAWEKTEAPEIAVQYWKMPEGQRSMKDLLLYVRADEA
O74180.2                  YTRAIKEIEAGSLPAWEKTEAPEIAVQYWKMPEGQRSMKDLLLYVRADEA
Asp_nige_XP_001394472     YTRAIKEIEAGSLPVWEKTEAPEIAVQYWKMPEGQRSMKDLLLYVRADEA
                          *:***:::* * ** *.. :*****::**:***.:* *:***:::*****

P_brasilianum_hmfP3       KHREVNHTLSNLDQAADPNPYQTEYQDPRKDHPTRGIDNLKATGWERKDI
Pen_oxal_EPS33887         KHREVNHTLSNLNQAVDPNPYHTEYRNPARDHPSRGIENLKATGWEREDI
Pen_digi_EKV16227         KHREVNHTLANLKQTHDPNPYQIEYIDPSISHPTKGIDNLKPEGWDRKEI
Pen_chry_AAR08189         KHREVNHTLANLKQTFDPNPYQIEYTDPSISHPTKGIDNLKPEGWDRDEV
Pen_rube_XP_002557865     KHREVNHTLANLKPTQDPNPYQIEYADLSVSHPTKGIDNLRPEGWDRNEI
Asp_terr_XP_001215177     KHREVNHTLGNLSQAADPNPYTSKYKDPSKPHPSKGMENLKPTGWERDDV
Neo_fisc_XP_001260128     KHREVNHTLGNLQHNVDPNPYAAKYKDPSKPRPTKGIENLKATGWEREEV
Asp_fumi_XP_749637        KHREVNHTLGNLQHNVDPNPYAAKYKDPSKPRPTKGIENLKSTGWEREEV
Asp_kawa_GAA83790         KHREVNHTLGNLNQAIDPNPYAAKYKDPTKAHPNKGIADLKPTGWEREEV
O74180.2                  KHREVNHTLGNLNQAIDPNPYAAKYKDPTKAHPNKGIADLKPTGWEREEV
Asp_nige_XP_001394472     KHREVNHTLGNLNQAIDPNPYAAKYKDPTKAHPNKGIADLKPMGWEREEV
                          *********.**.   *****  :* :    **.:*: :*:. **:*.::

P_brasilianum_hmfP3       F---------
Pen_oxal_EPS33887         FS--------
Pen_digi_EKV16227         FTIEWGKVNP
Pen_chry_AAR08189         FITESRQVKP
Pen_rube_XP_002557865     FMGKARTEKS
Asp_terr_XP_001215177     I---------
Neo_fisc_XP_001260128     I---------
Asp_fumi_XP_749637        I---------
Asp_kawa_GAA83790         I---------
O74180.2                  I---------
Asp_nige_XP_001394472     IUSAGE----
                          :
```

TABLE 10

Amino acid sequence alignment of *Penicillium brasilianum* hmfK1 and 10 closest orthologues.

```
P_brasilianum_hmfK1   MPHASRSLNVLIVGAGLGGLAAGLALQTDGHKVTIIDAAPEFAEAGAGIR
Sce_apio_KEZ45619     MPHASRSLNIVIVGAGLGGLAAGLALQTDGHKVTILDSAPEFGEVGAGIR
Tog_mini_XP_007916105 MPQAARSLNVLVVGAGLGGLATGLALQTDGHTVTIIDAAPEFAEAGAGIR
Sta_char_KEY72859     MPAAARSLNIVIVGAGLGGLAASLALQTDGHKVTILDSALEFAEAGAGIR
Sta_char_KFA53358     MPAAARSLNIVIVGAGLGGLAASLALQTDGHKVTILDSALEFAEAGAGIR
Spo_sche_ERT02390     MPQAARSLNVVVVGAGLGGLAAGLALQTDGHKVTILDAAPEFAEAGAGIR
Eut_lata_XP_007794919 -------------------------------------MRLTLFKAGAGIR
Sta_chlo_KFA62283     MPAAARSLNIVIVGAGLGGLAASLALQTDGHKT------------GAGIR
Gro_clav_EFX06428     MPVPSRSLDILVVGAGLGGLAAGLALQTDGHKVTILDAVTEFAEVGAGIR
Cyp_euro_XP_008712555 MPQAQHPRKILIVGAGLGGLAAGLALQTDGHNVTIIDSAPEFAEAGAGIR
Bys_spec_GAD98036     MSKSVIPKEILIVGAGLGGLFASLALRQDGHSVTIIDAVPEFAEAGAGIR
                                                                 *****

P_brasilianum_hmfK1   IPPNSSRLLMRWGVDLERMKKSTSQRYHFIRWKDGSTIFDLPFNNIVETH
Sce_apio_KEZ45619     VPPNSSRLLARWGVDLEGMKKSISKRYHFIRWQDGNTIVKLPFDKIVETH
Tog_mini_XP_007916105 VPPNSSRLLLRWGVDLEKMKKSVSKRYHFIRWEDGATICKLPFDNIVETH
Sta_char_KEY72859     VPPNSSRLLIRWGVDMEGMKKSTSNKYHFIRWKDGDTIVKVPFENVVETH
Sta_char_KFA53358     VPPNSSRLLIRWGVDMEGMKKSTSNKYHFIRWKDGDTIVKVPFENVVETH
Spo_sche_ERT02390     IPPNSSRLLMRWGVDLQRMKKSTSNRYHFIRWKDGTTIFDLPFDNNVATH
Eut_lata_XP_007794919 VPPNSSRLLLRWGVDLENMKKSVSKRYHFVRWEDGSTIVKLPFENIVETH
Sta_chlo_KFA62283     LPPNSSRLLIRWGVDMEGMKKSTSNKYHFIRWKDGDTIVKVPFDNVVETH
Gro_clav_EFX06428     IPPNSSRLLIRWGVDLDRIKKSTASRYHFIRWKDGATIFNLPFVDSVQDH
Cyp_euro_XP_008712555 VPPNSSRLLLRWGVDLEKMKKSVSQCYHFLRWKDGSTIVKLPFNDIVKNH
Bys_spec_GAD98036     IPPNSSRLLMRWGVDLDKMKKSVSRSYHFVRWKDGTTITKLPFENIIEVH
                      :******** *****:: :*** :  ***:**:** ** .:** . :  *

P_brasilianum_hmfK1   GAPYWLVHRADLHAALLDATLKAGVKVLNNKLVTSYDFEAPSATTQDGET
Sce_apio_KEZ45619     GAPYYLVHRADLHKALLDAAERAAVKVLTNKRITSFDFDAPSATTDDGEV
Tog_mini_XP_007916105 GAPYYLVHRADLHAGLLEAARKAGVDIHTHKRVIEYNFEAPYAKTQEGEI
Sta_char_KEY72859     GAPYYLVHRADLHAGLVEAAVRAGVAIRNNKRVTGYDLEAPAAVTHDGEV
Sta_char_KFA53358     GAPYYLVHRADLHAGLVEAAVRAGVAIRNNKRVTGYDLEAPAAVTHDGEV
Spo_sche_ERT02390     GSPYWLVHRADLHAALLDAAHKAGVQILTNKRVTAYDMDAPSATTADGAV
Eut_lata_XP_007794919 GAPYYLVHRADLHAALLQTAEKAGVKVYNHKRVIAYDFDAPSATTQDGET
Sta_chlo_KFA62283     GAPYYLVHRADLHSGLVEAALRAGVAIHNNKRVTGYDFDAPAAVTHDGEV
Gro_clav_EFX06428     GAPYWLVHRADLHAALLDAARRAGATIVTSSRVVVYDMDAPSVTTADGTA
Cyp_euro_XP_008712555 GAPYYLVHRADLHAGLLEAATRAGVQILNDKRVVEYNFEGPFVVTADGET
Bys_spec_GAD98036     GAPYFLVHRADLHAALLDAAKKAGVEIYANQKVEKYDFSVPCAVTSEGKT
                      *:**:******** .*:::: :*.. :   . :  :::. * . * :*

P_brasilianum_hmfK1   FKADLIVGADGIKSICRPLLTGQPDVPRDTGDVAYRILIPGEKLLADPDL
Sce_apio_KEZ45619     FKADLVVAADGIKSICRPLLTGKPDVPRDTGDVAYRILIPGEKLLADPEL
Tog_mini_XP_007916105 FKADLIIGADGIKSIARPLLTGQPDIPRDTGDVAYRILIPGEKLLADPEL
Sta_char_KEY72859     WRADLVLGADGIKSLARPLLTGQPDVPRDTGDVAYRILIPGERLLADPEL
Sta_char_KFA53358     WRADLVLGADGIKSLARPLLTGQPDVPRDTGDVAYRILIPGERLLADPEL
Spo_sche_ERT02390     YTGDLVVAADGIKSLCRPLLTGQADKPRDTGDVAYRILIPAEKLLADPEL
Eut_lata_XP_007794919 FKADLVIGADGIKSIARPLLTGQPDIPRDTGDVAYRILIPGEKVLADPEL
Sta_chlo_KFA62283     WRADLVLGADGIKSLARPLLTGQPDAPRDTGDVAYRILIPGERLLADPEL
Gro_clav_EFX06428     YTADLVIGADGIKSTCRPLLTGRPDVPRDTGDVAYRILIPAEKLLADPDL
Cyp_euro_XP_008712555 WRADLVIGADGIKSLARPALTGQEDVPRDTGDVAYRILIPGKDLLADPEL
Bys_spec_GAD98036     WTADLVVCSDGIKSIARPLLTGQPDVPRDTGDVAYRILIPGKELLADSDL
                      : .**:: :***** .** ***: * **************.: :***.:*

P_brasilianum_hmfK1   AHLIRDPCTTSWCGPDAHLVGYPIRNGEMYNIVMCATSYNETTDEVWVVK
Sce_apio_KEZ45619     ADLITEPCTTSWCGPDAHLVGYPIRNGEMYNIVVCATSYNETTDEVWVVK
Tog_mini_XP_007916105 ANLITDPCTTSWCGPDAHLVGYPIRNGEMYNIVVCATSYNETTDEVWVIK
Sta_char_KEY72859     APLITDPCTTSWCGPEAHLVGYPVRGGALYNVVVCATSHNETSDEAWVIR
Sta_char_KFA53358     APLITDPCTTSWCGPEAHLVGYPVRGGALYNVVVCATSHNETSDEAWVIR
Spo_sche_ERT02390     APLIQEPCTTSWCGPDAHLVGYPIRNEDTYNIVMCVTSYNETTDEAWVVR
Eut_lata_XP_007794919 SDLITDPCTTSWCGPDAHLVGYPIRNGELYNIVVCATSYNETTDEVWVIK
Sta_chlo_KFA62283     APLITDPCTTSWCGPEAHLVGYPIRGGAMYNIVVCAASHNETSDEAWVIR
Gro_clav_EFX06428     APLITQPCSTSWCGPDAHLVGYPIRAGELYNVVVCATSRNETTSNTWVVR
Cyp_euro_XP_008712555 ADLITDPCTTSWCGPDAHLVGYPIRNGELYNIVVCATSYNETSDEAWVVQ
Bys_spec_GAD98036     KDLITEPATTSWCGPGAHLVGYPIRDGELYNIVVCATSNGETTDEVWVVK
                        ** :*.:****** *******:*    **:*:*.:* .**:.:.**::

P_brasilianum_hmfK1   GDNSELCKRFASWEPQVRKLCALTGDFMKWRLCDLPNLARWTHPSGKAVL
Sce_apio_KEZ45619     GDNSELCKRFSKWEPRVQKLCALTGDFLKWRLCDLPDLTRWVHPAGKVVL
Tog_mini_XP_007916105 GDNRELCERFGKWEKRVQKLCALTGDFMKWRLCDLPNLTRWAHPSGKAVL
Sta_char_KEY72859     GDNRELCARFAAWEPRVRKLCALTGDFMKWRLCDLPILPRWVHPAGKVAL
Sta_char_KFA53358     GDNRELCARFAAWEPRVRKLCALTGDFMKWRLCDLPILPRWVHPAGKVAL
Spo_sche_ERT02390     GDNSELCQRFAHWETKVQKLCALTGDFMKWRLCDLPNLSRWVHPAGKVVL
Eut_lata_XP_007794919 GDNRELCTRFGGWESRVRKLCALTGDFMKWRLCDLPNISRWAHPSGKVVL
Sta_chlo_KFA62283     GDNRELCTRFAAWEPRVRKLCALTGDFMKWRLCDLPILPRWVHPAGKAAL
Gro_clav_EFX06428     GDNSELRLRFASWTTQVRKLCALTGDFLKWRLCDLPNLTRWVHPSGKVVL
Cyp_euro_XP_008712555 GSPLDLLERFKTWEPRVQKLCKLTPQFMKWRLCDLPILSRWVHPSGKAAL
Bys_spec_GAD98036     GSNEELCERFASWEPRIQKLCKLTRDFMKWRLCDLPILSTWVHPSGKACL
                      *.  :*  **  *  :::*** ** :*:******** :. *.**:**. *
```

TABLE 10-continued

Amino acid sequence alignment of *Penicillium brasilianum* hmfK1 and 10 closest orthologues.

```
P_brasilianum_hmfK1   LGDSCHPMLPYLAQGAAQAVEDAAVLRQVLAQDM----------------
Sce_apio_KEZ45619     LGDSCHPMLPYLAQGAAQAFEDAATLRQVLAQGE----------------
Tog_mini_XP_007916105 LGDSCHPMLPYLAQGAAQAFEDAAVIRQCLAQDT----------------
Sta_char_KEY72859     LGDACHPMLPYLAQGAAQSFEDAATLRQCLALDLP---------------
Sta_char_KFA53358     LGDACHPMLPYLAQGAAQSFEDAATLRQCLALDLP---------------
Spo_sche_ERT02390     LGDSCHPMLPYLAQGAAQAFEDAAVLRQVLALVG-------GVDGG----
Eut_lata_XP_007794919 IGDSCHPMLPYLAQGAAQSFEDAAALRQVLAQDV----------------
Sta_chlo_KFA62283     LGDACHPMLPYLAQGAAQSFEDAATLRQCLALDLP---------------
Gro_clav_EFX06428     LGDSCHPMLPYLAQGAAQAFEDASVLRQVLRVALSSADLSMGSDGATSSL
Cyp_euro_XP_008712555 LGDSCHPMLPYLAQGAAQAVEDAAALRQCLAGASTAG-------------
Bys_spec_GAD98036     LGDSCHPMLPYLAQGAAQAAEDAAVLRRCLAKFS----------------
                      :**:**************: ***:.:*: *

P_brasilianum_hmfK1   ---DMAAALKQYEQIRMPRASLVQAKTREHQYILHVDDGHEQQDRDKKLA
Sce_apio_KEZ45619     ---DLSAALKKYEQIRMPRASLVQAKTREHQYILHIDDGEEQAIRDEKMK
Tog_mini_XP_007916105 ---DLPTGLKNYESIRMPRASLVQAKTREHQYILHIDDGEEQKARDERMR
Sta_char_KEY72859     ----LADALARYEAVRQPRASLVQTKTREHQYILHIADGDEQRLRDDLMK
Sta_char_KFA53358     ----LADALARYEAVRQPRASLVQTKTREHQYILHIADGDEQRLRDDLMK
Spo_sche_ERT02390     --VDLKTALQRYEAIRMPRATLVQAKTREHQHILHVDDGQEQATRDQELA
Eut_lata_XP_007794919 ---DLPTALKRYEQIRMPRASLVQAKTREHQYILHIPDGEEQKARDRQLQ
Sta_chlo_KFA62283     ----LADALARYESVRQPRASLVQSKTREHQYILHIADGDEQRLRDDMMK
Gro_clav_EFX06428     PPPDLHAALLRYERIRMPRASLVQSTTREHQHLLHIDDGLEQEERDHRLS
Cyp_euro_XP_008712555 -ADGLKQALLKYESIRLPRASLVQQKTREHQYILHVDDGETQKQRDVTMK
Bys_spec_GAD98036     ---DLHEALKDYEKIRLPRASTIQGKTREHQYILHIDDGEEQLERDQRMR
                          :  .*  ** :* ***: :* .*****::**: **  *  **  :

P_brasilianum_hmfK1   LDAAENPVFWGYDDRRKWLFSHDAEVIQKEGANWRDGPN-----------
Sce_apio_KEZ45619     LNAAENPVFWGYDDRRQWLFSHDAENLAKEGANWKDGLN-----------
Tog_mini_XP_007916105 VNAAENPVFWGYDDRRKWLFSHDAEILNKDGANWREASQ-----------
Sta_char_KEY72859     HNGEGNPVFWGHDDRRKWLFSHDAEVLTKEGANWMEAPN-----------
Sta_char_KFA53358     HNGEGNPVFWGHDDRRKWLFSHDAEVLTKEGANWIEAPN-----------
Spo_sche_ERT02390     LDAAENPVFWGHTDRRNWLFGHDAEIITTPGDNWREGQ------------
Eut_lata_XP_007794919 LNATENPIFWGYDERRKWLFSHDAEVLNTEGANWQKTTP-----------
Sta_chlo_KFA62283     QNGEGNPVFWGHDDRRKWLFSHDAEVLTKEGANWMEAPN-----------
Gro_clav_EFX06428     RDHPDSPVFWGYVERKNWLFGHDADVIIKEGDNWREGAGLHVVQASHVVD
Cyp_euro_XP_008712555 VNGQENPVFWGDDKRRMWLFSHDAENVDSEGANWKSGTG-----------
Bys_spec_GAD98036     QNSETNPIFWGYDKRRKWLFSHDADLLERNEVVWSQPAA-----------
                       :   .*:***  .*: ***.***: :      * .

P_brasilianum_hmfK1   ------------MNGVHVA---------
Sce_apio_KEZ45619     ------------GSAIRSH---------
Tog_mini_XP_007916105 ------------STGVAAH---------
Sta_char_KEY72859     ------------ATALKAH---------
Sta_char_KFA53358     ------------ATALKAH---------
Spo_sche_ERT02390     ------------TSGVAAH---------
Eut_lata_XP_007794919 ------------DSGVSAH---------
Sta_chlo_KFA62283     ------------ATALKAH---------
Gro_clav_EFX06428     GVQGAGTNGVGGINGVAVH---------
Cyp_euro_XP_008712555 ------------APLVGAPVATSMLAAH
Bys_spec_GAD98036     ------------ASLUSAGE--------
```

TABLE 11

Amino acid sequence alignment of *Penicillium brasilianum* hmfK2 and 10 closest orthologues.

```
P_bras._hmfK2      MSPSVTPERYPIAIVGGGIAGLTLALALEKLGVRYVLFESQSSLAPDRGASVGLQPNGLR
Fus_oxys_EMT69322  --MAKPNQHYEVIIAGGGIAGVTLALMLEKLGISYFLLEGRDTLESDRGAGIGLQPNGLR
Fus_oxys_EXK38464  --MAKPNQHYEVIIAGGGIAGVTLALMFEKLGISYFLLEGRDTLESDRGAGIGLQPNGLR
Bot_cine_CCH26290  --MAKPAQHYEVIIAGGGIAGVTLALMFEKLGISYSLLEGRDTLESDRGAGIGLQPNGLR
Fus_oxys_EXK83377  --MAKPNQHYEVIIAGGGIAGVTLALMFEKLGISYFLLEGRDTLESDRGAGIGLQPNGLR
Fus_oxys_ENH68136  --MAKPNQHYEVIIAGGGIAGVTLGLMFEKLGISYFLLEGRDTLESDRGAGIGLQPNGLR
Fus_fuji_CCT67992  --MAEPNQHYEVIIAGGGIAGVTLALMFEKLDISYFLLEGRDTLESDRGAGIGLQPNGLR
Fus_fuji_CAJ76275  --MAEPNQHYEVIIAGGGIAGVTLALMFEKLDISYFLLEGRDTLESDRGAGIGLQPNGLR
Mac_phas_EKG18528  ---MATEQHVTVGIIGGGIAGLTLANILEQAGISYVLWEAKSEIAPAEGASIGLMPNGLR
Met_robe_EXV00673  --MAH--EHYEIAIIGGGIAGLTLALLCERLGFSYILFEKRDSLEGDNGAGISLQANALR
Met_anis_KFG86875  --MAH--EHYEIAIIGGGIAGLTLALLCERLGFSYILFEKRDSLEGDNGAGIGLQANALR
                          ::  : * ******:**.   *: .. * * * :. :   .**.:.* .*.**

P_bras._hmfK2      ILDQLGLIDKIEQHTGTLQRWRHLDGQGELISETKALGYYQ-SLIGYGPLFLERRKLLEI
Fus_oxys_EMT69322  ILDQLGLVEDIEEATIPLEKWFSYDSEGNLMNDSDAMGQYR-EKIGYPVAFIERRKLLPI
Fus_oxys_EXK38464  ILDQLGLVEDIEEATIPLEKWFSYDSEGNLMNDSDAMGQYR-EKIGYPVAFIERRKLLPI
Bot_cine_CCH26290  ILDQLGLVEDIEEATIPLEKWFSYDSEGNLMNDSDAMGQYLHVRIGYPVAFIERRKLLPI
```

TABLE 11-continued

Amino acid sequence alignment of *Penicillium brasilianum* hmfK2 and 10 closest orthologues.

```
Fus_oxys_EXK83377  ILDQLGLVEDIEEATIPLEKWFSYDSEGNLMNDSDAMGQYR-EKIGYPVAFIERRKLLPI
Fus_oxys_ENH68136  ILDQLGLVEDIEEATIPLEKWFSYDSEGNLMNDSDAMGQYR-EKIGYPVAFIERRKLLPI
Fus_fuji_CCT67992  ILDQLGLVEDIEEATIPLEKWFSYDSEGNLMNDSDAMGQYR-DKIGYPVAFIERRKLLPI
Fus_fuji_CAJ76275  ILDQLGLVEDIEEATIPLEKWFSYDSEGNLMNDSDAMGQYR-DKIGYPVAFIERRKLLPI
Mac_phas_EKG18528  ILDQIGLLQDVEQYAVPHHSWEYRDSDGTLLNTLNAMSSYP-DLLGYGAFFMERQRVLEI
Met_robe_EXV00673  ILDQLGVAEKVDAEAGTLAETYRYDEDGNQIMRNSALGTSK-KRVGYGFTIMERAAFRRI
Met_anis_KFG86875  ILDQLGVAEKVDAEAGTLAETYRYDEDGNQIMRNSALGTSR-KRVGYGFTIMERAAFRRI
                   ****:*: :.::  : .       * :*  :   .*:.      :**   ::**  .  *

P_bras._hmfK2      MADELQDKTAAKTSLRVVSANESSDGVELALSDGHSITADLVIGADGVRSCIREAIDMSR
Fus_oxys_EMT69322  MVRHIQRTECVRTSARVASIEESDDHVTVTTTDGLSLTADIVVGADGVRSAVRAHIDSKL
Fus_oxys_EXK38464  MVRHIKRTECVRTSARVASIEESDDHVTVTTTDGLSLTADIVVGADGVRSAVRTHIDSKL
Bot_cine_CCH26290  MVRRIQRTECVRTSARVASIEESDDHVTVTTTDGLSLTADIVVGADGVRSTVRTHIDSKL
Fus_oxys_EXK83377  MVRHIQRTECVRTSARVASIEESDDHVTVTTTDGLSLTADIVVGADGVRSAVRTHIDSKL
Fus_oxys_ENH68136  MVRHIQRTECVRTSARVASIEESDDHVTVTTTDGLSLTADIVVGADGVRSAVRTHIDSKL
Fus_fuji_CCT67992  MVRHIQRTECVKTSARVASIEESEDHVTVTTTDGLSLTADIVVGADGVRSAVRTHIDSKL
Fus_fuji_CAJ76275  MVRHIQRTECVKTSARVASIEESEDHVTVTTTDGLSLTADIVVGADGVRTLVRTHIDSKL
Mac_phas_EKG18528  LYGGVKDKSPIHMSKRVCSVEDLGAKSVVTAADGSQYSCDFVAGADGVRSIVRQHIQEAL
Met_robe_EXV00673  LWESITRRECIMAPCLVTSVEENEDEVIVRTARG-SYRADLVVGADGVNSTLRRLVDASK
Met_anis_KFG86875  LWESITRRECIMAPCLVTSVEENEDEVIVRTARG-SYRVOLVVGADGVNSTLRRLVNASK
                   :    :         * * ::        :  : * .   *:* *****.: :*  ::

P_bras._hmfK2      TEWHSEANEY---------INTQFACIYGISGAIQGIVEGDCFSVYRPEATVLIFTGRNG
Fus_oxys_EMT69322  PEALTADDY----------ISVACSTVYGMSAPTEGIAPGERFAVYRENQTVIGFTGKDG
Fus_oxys_EXK38464  PEALTADDY----------ISVACSTVYGMSAPTEGIAPGERFAVYRENQTVIGFTGKDG
Bot_cine_CCH26290  PGALTADDY----------ISVACSTVYGMSAPTGGIAQGERFAVYRENQTVIGFTSKDG
Fus_oxys_EXK83377  PEALTADDY----------ISVACSTVYGMSAPTEGIAPGERFAVYRENQTVIGFTGKDG
Fus_oxys_ENH68136  PEALTADDY----------ISVACSTVYGMSAPTEGIAPGERFAVYRENQTVIGFTGKDG
Fus_fuji_CCT67992  PEPLTADDY----------ISVACSTVYGMSAPTEGIAPGERFAVYRENQTVIGFTGKDG
Fus_fuji_CAJ76275  PEPLTADDL----------HQRCLLHSLRHVSTHRSIAPGERFAVYRENQTVIGFTGKDG
Mac_phas_EKG18528  PHLQKTPQN----------FASKYACVYGMSDPLPEIGPGRAFTIHRANISSLIFSGMGG
Met_robe_EXV00673  PMAEY--------------MSSPFTCTYGMSSATPGILPGDHFGTHRPNGGVLAFAGKGG
Met_anis_KFG86875  PMAEYEQTNKESICQLKTDMSSPFTCTYGMSSATPGILPGDHFGTHRPNGGVLAFAGKAG
                   .                               .    *   *   *   :* :    : *:.  *

P_bras._hmfK2      TIFWFVFEDLGQTYGLSTTPRYTNDDFDALCDSIAHLRLTASVRFGDVYGNRSVAMKVPL
Fus_oxys_EMT69322  IVFWFVFENLNQNVPLSQAPRYTEAEAEALCQSVAHTQVTPKLRFGEIYKNRVVAVKIGV
Fus_oxys_EXK38464  IVFWFVFENLNHNVPLSQAPRYTEAEAEALCKSVAHTQVTPKLKFGEIYKNRVVAVKIGV
Bot_cine_CCH26290  IVFWFVFENLGQKIPLSQAPRYTEAEAEALCQSVAHTQVTPKLKFGEIYKNRVVAVKIGV
Fus_oxys_EXK83377  IVFWFVFENLNHNVPLSQAPRYTEAEAEALCQSVAHTQVTPKLKFGEIYKNRVVAVKIGV
Fus_oxys_ENH68136  IVFWFVFENLNHNVPLSQAPRYTEAEAEALCQSVAHTQVTPKLKFGEIYKNRVVAVKIGV
Fus_fuji_CCT67992  IVFWFVFENLNRNVPLSQAPRYTEAEAEALCLSVAHTQVTPKLKFGEIYKNSVVAVKIGV
Fus_fuji_CAJ76275  IVFWFVFENLNRNVPLSQAPRYTEAEAEALCLSVAHTQVTPKLKFGEIYKNSVVAVKIGV
Mac_phas_EKG18528  ALYWFVFVDLKEAVELGKTKRYVEEDVEAVFSEMADVTITDDVTFSDMYRARRAAVMTPL
Met_robe_EXV00673  TIFWFLFENQAANTQLP--PRYSASDADKACQLLADIRVMPEATFGDVDKNAIFKFKIPL
Met_anis_KFG86875  TIFWFLFENQAANTQLP--PRYSASDADKACQLLADIRVMPEATFGDVDKNAIFKFKIPL
                    ::**:* :        *     **    : :      :*.  :   .  *.::           .    :

P_bras._hmfK2      EEGLAPSWHTDRMVIVGDAAHKMVPNAAMGANQAIESSATLLNELGNIFTAKDGGS---P
Fus_oxys_EMT69322  EEGVAKGWHTDRAVIVGDAACKTTPAGGQGANQAIESCAVFVNKLIKAKKARQPGE--KL
Fus_oxys_EXK38464  EEGVAKGWHTDRAVIVGDAACKTTPAGGQGANQAIESCAVFVNKLIKAKKARQPGE--KL
Bot_cine_CCH26290  EEGVAKGWHTDRAVIVGDAACKTTPAGGQGANQAIESCAVFVNKLMKAKNACHPSE--KL
Fus_oxys_EXK83377  EEGVAKGWHTDRAVIVGDAACKTTPAGGQGANQAIESCAVFVNKLIKAKKALQPGE--KL
Fus_oxys_ENH68136  EEGVAKGWHTDRAVIVGDAACKTTPAGGQGANQAIESCAVFVNKLIKAKKALQPGE--KL
Fus_fuji_CCT67992  EEGVAKGWHTDRAVIVGDAACKTTPAGGQGANQAIESCAVFVNKLMAARKASQSGD--KL
Fus_fuji_CAJ76275  EEGVAKGWHTDRAVIVGDAACKTTPAGGQGANQAIESCAVFVNKLMAARKASQSGD--KL
Mac_phas_EKG18528  EQGLVDTWFSGRMFLLGDAAHKMLPHTAMGAMQAMESAACFASLLLELRTHVGDSLESGV
Met_robe_EXV00673  QEGVAPIWHTHRSVLVGDAACKISPASGMGACQAIEMCAVLMNELVRARRGALSRREGRI
Met_anis_KFG86875  QEGVAPIWHTHRSVLVGDAACKISPASGMGACQAIEMCAVLMNELVRARREALSRREGRI
                   ::*:.   *.: * .::**** *   *   . ** **:* .* :  . *

P_bras._hmfK2      QPEILANALKRYADIRKFRASEIVKRAGTICRAQLSHSGPAAAVREELPSLTDGDWLFRG
Fus_oxys_EMT69322  SSEAVKSVLASYAQERAQPATTALERSQMVGKALLCTPGPATTLVKDMLKLSNEDWLLRA
Fus_oxys_EXK38464  SSEAVKSVLASYAQERAQPATTALERSQMVGKALLCTPGPATTLVKDMLKLSNEDWLLRA
Bot_cine_CCH26290  SSEAVKSILVSYAQERAQPATTALERSQMVGKALLCTPGPATTLVKDMLKLSNEDWLFRA
Fus_oxys_EXK83377  SSEAVKSVLASYTQERAQPATTALERSQMVGKALLCTPGPATTLVKDMLKLSNEDWLLRA
Fus_oxys_ENH68136  SSEAVKSVLVSYTQERAQPATTALERSQMVGKALLCTPGPATTLVKDMLKLSNEDWLLRA
Fus_fuji_CCT67992  SSDVVKSVLASYAQERAQPATTALERSQMVGKALLCTPGPATTLVKDMLKLSNEDWLLRA
Fus_fuji_CAJ76275  SSDVVKSVLASYAQERAQPATTALERSQMVGKALLCTPGPATTLVKDMLKLSNEDWLLRA
Mac_phas_EKG18528  PSEDVEACLTAYAQKRHSRVAEVIQTGHFHCMTQLKIGPAADGWTRRLPALRNDMWLNIV
Met_robe_EXV00673  SRQLMRSALEKYHEIRRPFAVSMMAKAHLITQICLCTPGMPTAFGEQIRQLSEESFFSLA
Met_anis_KFG86875  SRQLMRSALEKYHGIRRPVAVSMVAKAHLITQICLCTPGMPTAFGEQMRQLSEESFFSLA
                     : :    *  *   *   .   :  .           *      .     . :  *  :  ::

P_bras._hmfK2      FMGLSESPVIDALPVP-PRGKFFGQAVEKFWKRFRARQ------ASGFKTSNLELFGIEA
Fus_oxys_EMT69322  FMALSAAPYLEDVELT-ARGHLYNKAVKEAQAEMARRQKVAKEIKEAEEKESKQAASIQE
Fus_oxys_EXK38464  FMALSAAPYLEDVELT-ARGHLYNKAVKEAQAEMARRQKVAKEIKEAEEKESKQAASIQE
```

TABLE 11-continued

Amino acid sequence alignment of *Penicillium brasilianum* hmfK2 and 10 closest orthologues.

```
Bot_cine_CCH26290  FMTLSAAPYLEDVELT-ARGHIYNKAVKEAQAEMARRQKVA---KEAEEKESKKAASIQE
Fus_oxys_EXK83377  FMALSAAPYLEDVELT-ARGHLYNKAVKEAQAEMARRQKVAKEIKEAEEKESKQAASIQE
Fus_oxys_ENH68136  FMALSAAPYLEDVELT-ARGHLYNKAVKEAQAEMARRQKVAKEIKEAEEKESKQAASIQE
Fus_fuji_CCT67992  FMALSAAPYLEDVELT-ARGHLYNKAVEEARAEMARRQRVAKEVKEAEEKESKQAASIKE
Fus_fuji_CAJ76275  FMALSAAPYLEDVELT-ARGHLYNKAVEEARAEMARRQRVAKEVKEAEEKESKQAASIKE
Mac_phas_EKG18528  LEGFCKAEKIEGWHRNSARVDYYTEQVQLMREKFEKRKQMMTMAPSGPHGGPSAQENRHQ
Met_robe_EXV00673  VENWKDSPTVEDLELT-PRARLCSEAIAKEMTQAVR---------ERTKTQTK-------
Met_anis_KFG86875  VENWKDSPTVEDLELT-PRGRLCSEAIAKEMTQAVR---------ERNKIQTKUSAGE--
                   .     :  ::      .*     : :      .             .  .

P_bras._hmfK2      -------------------------
Fus_oxys_EMT69322  SEQRNDFAGLRNPVQAATGVVEVGS
Fus_oxys_EXK38464  SEQRNDFAGLRNPVQAATGVVEVGS
Bot_cine_CCH26290  SDKRNEFASLRNPVQAATGVVEVGS
Fus_oxys_EXK83377  SEQRNDFAGLRNPVQAATGVVEVGS
Fus_oxys_ENH68136  SEQRNDFAGLRNPVQAATGVVEVGS
Fus_fuji_CCT67992  SEQRNEFVGLRNPVQAATGVVEVGS
Fus_fuji_CAJ76275  SEQRNEFVGLRNPVQAATGVVEVGS
Mac_phas_EKG18528  EPELVSAPA----------------
Met_robe_EXV00673  -------------------------
Met_anis_KFG86875  -------------------------
```

TABLE 12

Amino acid sequence alignment of *Penicillium brasilianum* hmfQ and 10 closest orthologues.

```
P_brasilianum_hmfQ     -------------------------M----SSHTLSLLEAKPYYSTELG
Gla_lozo_XP_008076942  -----------------------MGK----SPHVAFLISAEPFYNTKLG
Myc_arom_WP_036343933  --------------------MSRLKR----SEHSVSLLDGEIVEESDLG
Myc_smeg_WP_003893625  -------------------MTTSLSH----SIHATSLLDSELVEENDLG
Myc_sp_WP_029367382    -------------------MTISLTRSTTRSAHATSLLDGEIVEENDYG
Myc_smeg_WP_011728257  -------------------MTTSLSH----SIHATSLLDSELVEENDLG
Myc_smeg_AFP38668      ---------MATRFTQRRPRMTTSLSH----SIHATSLLDSELVEENDLG
Myc_sp_WP_029111475    -------------------MTAASVR----SAHVVSLLASTDVEQSDLG
Myc_mage_WP_036434064  -------------------MTVSLTR----SSHTTSLLDGEIVEENDFG
Myc_kans_WP_036402197  -------------------MATSDRS----SRHAASLVEGEIVEESDLG
Rho_opac_BAH48573      MRELLPTAEAVPRQPSDTEGTSMSTRR----SIHNTSLTDGEIVEQSDLG
                                                       * *   *  .    ... *

P_brasilianum_hmfQ     SLRAVTAEQLPILKNLSIKRVVLAPSAIREPHWHSNANELAYCLRGKLMV
Gla_lozo_XP_008076942  SLQRISSDELPILKNLSIKRLILEPGSIREPHWHANCNELTYCLSGKVLV
Myc_arom_WP_036343933  SIRRVTADNLPILSGLSIKRLVINPGAMRTPHWHANANELAYCVTGNCLV
Myc_smeg_WP_003893625  SIRRVTADNFPILRGLSIKRLVINPGAMRTPHWHANANELTYCVSGSALV
Myc_sp_WP_029367382    SIRRVTADNFPILRGMSIKRLVINPGAMRTPHWHANANELTYCVSGTALV
Myc_smeg_WP_011728257  SIRRVTADNFPILRGLSIKRLVINPGAMRTPHWHANANELTYCVSGSALV
Myc_smeg_AFP38668      SIRRVTADNFPILRGLSIKRLVINPGAMRTPHWHANANELTYCVSGSALV
Myc_sp_WP_029111475    SIHRVTADSFPILRGMSIKRLVLNPGAMRTPHWHANANELTYCVSGTALV
Myc_mage_WP_036434064  SIRRVTADNFPILRRMSIKRLVINPGAMRTPHWHANANELTYCVSGVALV
Myc_kans_WP_036402197  SIRRLTGDNFPILRGMSIKRVVIHPGAMRTPHWHANANELTYCVSGTSLV
Rho_opac_BAH48573      SITRVTADTFPILQGLSIKRVLINPGAMRTPHWHANANELTYCLSGTSLV
                       *:   ::.: :***   :****::: *.::* ****:*.***:**: *   :*

P_brasilianum_hmfQ     SILDSGNVFANFVIEAGQMFHIESGSLHHFENICDEEAEIIICFRHEKPT
Gla_lozo_XP_008076942  TQLDVGNEFMNFTITAGQMFFVKTGALHHIENIGEETAELIVAFRHEAPK
Myc_arom_WP_036343933  SILDSGSQFSSFTIGSGEMFHVDSGSLHHIENIGEEPAEFILSFRHERPE
Myc_smeg_WP_003893625  SVLDTASRFSTFTVSAGEMFHVDSGSLHHIENIGTEPAEFIITFRNERPE
Myc_sp_WP_029367382    SVLDTGNKFAAFTVSAGEMFHADSGSLHHIENIGTEPAEFIITFRHERPE
Myc_smeg_WP_011728257  SVLDTASRFSTFTVSAGEMFHVDSGSLHHIENIGTEPAEFIITFRNERPE
Myc_smeg_AFP38668      SVLDTASRFSTFTVSAGEMFHVDSGSLHHIENIGTEPAEFIITFRNERPE
Myc_sp_WP_029111475    SVLDDGSRFSSFTIGAGEMFHIDSGALHHIENIGTEPAEFIITFRNERPE
Myc_mage_WP_036434064  SMLDTGNRFSTFTVSAGEMFHADSGSLHHIENIGTEPAEFIVTFSSERPE
Myc_kans_WP_036402197  SVLDAYSQFASFVVSAGDMFHIDSGSLHHIENIGEDVAEFIIAFRSERPE
Rho_opac_BAH48573      SVLDTGSAFSTFTVGAGEMFHIDSGSLHHIENIGDEVAEFVIAFRSERPE
                       : **   . *   *.: :*:**. .:*:***:***   : **::: *   * *

P_brasilianum_hmfQ     DFALSASMGAMTDGVLGNTYGHHSSDWAKINRHTHPKYIVRRNGRPTIPS
Gla_lozo_XP_008076942  DFSLSASFGAMSDAVLGNTYDAPSSAFRGITRNTSPKYIVQRKGNPTVPD
Myc_arom_WP_036343933  DFGLGAAFGAMTDAVLGNTYDLPASDFAKIRRDTTDRKLAARVGDPSVPS
Myc_smeg_WP_003893625  DFGLGAAFGAMTDAVLGNTYDLDASDFAALRRDTTDRALAARRGDPVIPQ
Myc_sp_WP_029367382    DFALGAAFGAMTDAVLGNTYDLDASEFAKLRRDTVDRRLARRTGDPVIPD
Myc_smeg_WP_011728257  DFGLGAAFGAMTDAVLGNTYDLDASDFAALRRDTTDRALAARRGDPVIPQ
Myc_smeg_AFP38668      DFGLGAAFGAMTDAVLGNTYDLDASDFAALRRDTTDRALAARRGDPVIPQ
Myc_sp_WP_029111475    DFGLAASLGAMTDAVLGNTYDLDTGDLSTLRRSTVDRTLAARTGDAVIPS
```

TABLE 12-continued

Amino acid sequence alignment of *Penicillium brasilianum* hmfQ and 10 closest orthologues.

```
Myc_mage_WP_036434064  DFGLGASFGAMTDAVLGNTYDLDASDFAVLRRDTVDRKLAGRAGDAVVPD
Myc_kans_WP_036402197  DFGLGAAFGAMTDAVLGNTYDLPASDFAALRRDTTDRALAARVGKPNVPA
Rho_opac_BAH48573      DFGLGAAFGAMTDAVLGNTYDLDASDFAALRRNTADRALAARIGDPVVPP
                       **.*.*::***:*.******.  :.    : *  *  : :. * * . :*

P_brasilianum_hmfQ     TAYLPDPHKFDVEEMNPPVSSEFGSNRTARNQFWPALHNMSMYSLRIEDT
Gla_lozo_XP_008076942  TAELPNPHKFDVENAPNGPQVEIGSANMARKDFWPILDNMSMYSLRIEED
Myc_arom_WP_036343933  TAHFDDPHKFGVEAQSPPVGSAVGSARLARVQFWPALKDMSMYSLRIRED
Myc_smeg_WP_003893625  AAHFGDPHKFGVEAMTPPVTSAVGSARTARVQFWPALKDLSMYSLRVRED
Myc_sp_WP_029367382    TAGYPDPHKFAVEAMTPPVASAVGSARTARVQFWPALKDLSMYSLRVRED
Myc_smeg_WP_011728257  AAHFGDPHKFGVEAMTPPVTSAVGSARTARVQFWPALKDLSMYSLRVRED
Myc_smeg_AFP38668      AAHFGDPHKFGVEAMTPPVTSAVGSARTARVQFWPALKDLSMYSLRVRED
Myc_sp_WP_029111475    SARFGDPHKFGVEAMSAPVAAEYGSARTARKQFWPALKDLSMYSLRIRED
Myc_mage_WP_036434064  TAGYPDPHKFAVEAMTPPVTSAVGSARTARVQFWPALKDLSMYSLRVRED
Myc_kans_WP_036402197  TAWFNDPHKFSVEAQSPPVGIAVGSARLARVQFWPALKDLSMYSLRVRED
Rho_opac_BAH48573      AAKFSDARKFAVEEQNPVLSLAVGSAHLARVQFWPALKDLSMYSLRIRED
                       :*    :.*** **          ** . ** :*** *.::******:.:

P_brasilianum_hmfQ     GMREAHWHPETSELGYVAEGEARMTVLDPDGSTDTYYLKQGDMYYVPTAY
Gla_lozo_XP_008076942  GMREPHWHPFTAEMGYVHKGNARMSVMDPDGSVDTYTLKPGDVYFIPHAY
Myc_arom_WP_036343933  GMREPHWHPVTAEMGYVASGSSRMTVMDPDGTLDTWYLEQGDMYFIPRAY
Myc_smeg_WP_003893625  GMREPHWHPVTAEMGYVQSGSARMTVMDPDGTLDTWELQRGDVYFIPRAY
Myc_sp_WP_029367382    GMREPHWHPVTAEMGYVQSGSARMTVMDPDGTLDTWLLQRGDVYFVPRAY
Myc_smeg_WP_011728257  GMREPHWHPVTAEMGYVQSGSARMTVMDPDGTLDTWELQRGDVYFIPRAY
Myc_smeg_AFP38668      GMREPHWHPVTAEMGYVQSGSARMTVMDPDGTLDTWELQRGDVYFIPRAY
Myc_sp_WP_029111475    GMREPHWHPVTAEMGYVQSGSARMTVMNPDGSLDTWHLRRGDVYFVPRAY
Myc_mage_WP_036434064  GMREPHWHPVTAEMGYVHSGSARMTVMDPDGTLDTWHMRQGDVYFIPRAY
Myc_kans_WP_036402197  GMREPHWHPITAEMGYVQTGSARMTIMDPDGSLDTYYLNQGDVYFVPRAY
Rho_opac_BAH48573      GMREPHWHPITAEMGYVRRGSARMTVMDPDGTLDTWYLEQGDVYFIPRAY
                       ****.**** *:*:***  *.:**:::***: **: :. **:*::* **

P_brasilianum_hmfQ     PHQIEVIGSE---------RMHFLIFFDQPYPKDVGYRTSATALPRETLA
Gla_lozo_XP_008076942  PHQIEVIGDE---------EIHFLIFFDAPIPGDVGYRTSATALSREVLA
Myc_arom_WP_036343933  PHHIEVVDAP---------DLHFAIFFDQPTPGDIGYRASASAYSREVLA
Myc_smeg_WP_003893625  PHHIEVVDAP---------DLHFLIFFDQPTPADVGYRTSVSAYSREVLA
Myc_sp_WP_029367382    PHHIEVFDSPADAGSNSGSGLHFLIFFDQPTPADIGYRTSASAYSRAVLA
Myc_smeg_WP_011728257  PHHIEVVHAP---------DLHFLIFFDQPTPADVGYRTSVSAYSREVLA
Myc_smeg_AFP38668      PHHIEVVHAP---------DLHFLIFFDQPTPADVGYRTSVSAYSREVLA
Myc_sp_WP_029111475    PHHIEVVDSP---------DLHFLIFFDQPTPADIGYRASMSAYSRATLA
Myc_mage_WP_036434064  PHHIEVVDAP---------DLHFLIFFDQPTPADIGYRNSASAYSRAVLA
Myc_kans_WP_036402197  PHHIEVVDAP---------DIHFAIFFDQPTPGDIGYRASVSAYSREVLA
Rho_opac_BAH48573      PHHIEVVGSD---------DIHFLIFFDQPTPGDIGYRASVSAYSREVLA
                       **:***.             :** **** * * *:*** * :* .* .**

P_brasilianum_hmfQ     STLEVAEKDLPKFPLTVKDPLFVEKKNPVDNLRPKL-
Gla_lozo_XP_008076942  ATFGVDEDQLPEFPFTVKDPLLVGRKNPVDPVKSKI-
Myc_arom_WP_036343933  ATFNVHIDDLPNFPFTKADPLIVNRVNPLDPRD----
Myc_smeg_WP_003893625  ATFDTHIDDLPDFPLTTADPLIVGRRNPLDR------
Myc_sp_WP_029367382    AVFDTHIEDLPEFPFTATDPLIVGRRNPQDR------
Myc_smeg_WP_011728257  ATFDTHIDDLPDFPLTTADPLIVGRRNPLDR------
Myc_smeg_AFP38668      ATFDTHIDDLPDFPLTTADPLIVGRRNPLDR------
Myc_sp_WP_029111475    AVFDCHIEDLPEFPFTAADPLIVRRRNPVDSYAVGQ-
Myc_mage_WP_036434064  ATFDTHIDDLPEFPFTPADPLIVGRRNPVDR------
Myc_kans_WP_036402197  ATFNTHIDDLPQFPFTNTDPLIVTRNNPLDER-AMGE
Rho_opac_BAH48573      ATFDTHIGDLPNFPFTPADPLIVTRNNPLDDRUSAGE
                       :.:     :**.**:*  ***:* : ** *
```

TABLE 13

Amino acid sequence alignment of *Penicillium brasilianum* hmfU and 10 closest orthologues.

```
P_brasilianum_hmfU       --------------------------------------------------
Pen_oxal_EPS28195        --------------------------------------------------
Pen_rube_XP_002560238    --------------------------------------------------
Pen_digi_EKV20433        --------------------------------------------------
Pen_digi_EKV11956        --------------------------------------------------
Asp_terr_XP_001208783    --------------------------------------------------
Neo_fisc_XP_001260626    --------------------------------------------------
Asp_oryz_XP_001821930.2  --------------------------------------------------
Asp_clav_XP_001275449    --------------------------------------------------
Asp_oryz_BAE59928        --------------------------------------------------
Asp_flav_XP_002379461    MEGFRMLLDKRPDIQILWKIKPSSGTTFEDTPLPDNLRTAVAEGQVRVES
```

TABLE 13-continued

Amino acid sequence alignment of *Penicillium brasilianum* hmfU and 10 closest orthologues.

```
P_brasilianum_hmfU       --------------------------------------------------
Pen_oxal_EPS28195        --------------------------------------------------
Pen_rube_XP_002560238    --------------------------------------------------
Pen_digi_EKV20433        --------------------------------------------------
Pen_digi_EKV11956        --------------------------------------------------
Asp_terr_XP_001208783    --------------------------------------------------
Neo_fisc_XP_001260626    --------------------------------------------------
Asp_oryz_XP_001821930.2  --------------------------------------------------
Asp_clav_XP_001275449    --------------------------------------------------
Asp_oryz_BAE59928        --------------------------------------------------
Asp_flav_XP_002379461    WLAVEPICILTSGHVKCMVHHGGSNSYHEAIRAGVPQVILPVWFDTYDFA

P_brasilianum_hmfU       --------------------------------------------------
Pen_oxal_EPS28195        --------------------------------------------------
Pen_rube_XP_002560238    --------------------------------------------------
Pen_digi_EKV20433        --------------------------------------------------
Pen_digi_EKV11956        --------------------------------------------------
Asp_terr_XP_001208783    --------------------------------------------------
Neo_fisc_XP_001260626    --------------------------------------------------
Asp_oryz_XP_001821930.2  --------------------------------------------------
Asp_clav_XP_001275449    --------------------------------------------------
Asp_oryz_BAE59928        --------------------------------------------------
Asp_flav_XP_002379461    LRAEWLGIGIWASRKTAPGVNAPELGQALIRVLASAQSESMRHRAKGIAT

P_brasilianum_hmfU       ------------------------MAGIRVAWIGLGNIGRGMSSNIAQKG
Pen_oxal_EPS28195        ------------------------MSGTRVAWIGLGNIGRGMSSNIARKG
Pen_rube_XP_002560238    ------------------------MAG-RVSWIGLGNIGRGMSQNIAQKG
Pen_digi_EKV20433        ------------------------MTGPRVAWIGLGNIGRGMSQNIAQKG
Pen_digi_EKV11956        ------------------------MTGPRVAWIGLGNIGRGMSQNIAQKG
Asp_terr_XP_001208783    ------------------------MAAQRIAWIGLGNIGRGMSRNIALKG
Neo_fisc_XP_001260626    ------------------------MAGESVAFIGLGNIGRGMSKNIAQKG
Asp_oryz_XP_001821930.2  ------------------------MASERVAWLGLGNIGRGMSRNIALKG
Asp_clav_XP_001275449    ------------------------MAEERVAWLGLGNIGRGMSKNIAQKG
Asp_oryz_BAE59928        ------------------------MASERVAWLGLGNIGRGMSRNIALKG
Asp_flav_XP_002379461    KLGPKDGRVIACEKIISLLTEPCNTKMQRVAWLGLGNIGRGMSRNIALKG
                                                      ::::********** *** **

P_brasilianum_hmfU       PQS-SLILFNRTTSRATAHAEKLGG---NVTVAISLIEAVKASDLIFTCV
Pen_oxal_EPS28195        PQS-SLILYNRTTSRAVALAEKLGGS--NVTVAQSIPEAVTSSDIIFTCV
Pen_rube_XP_002560238    PQTGPLLLYNRTTARATAHASELTN----AKAVTTLAEAVNESDLIFTCV
Pen_digi_EKV20433        PQTGPLLLFNRTTARAIVHASKLIN----AQAVTTLTEAVTQSDLIFTCV
Pen_digi_EKV11956        PQTGPLLLFNRTTARAIVHASKLIN----AKAVTTLTEAVTQSDLIFTCV
Asp_terr_XP_001208783    PQTSPLILYNRTTSKASAFAQSLGPGKA--TVAETLPAAVRDASVTFICV
Neo_fisc_XP_001260626    PQSS-LTLYNRTVAKASAFAESLGSTKAPVTVASTIPEAVKDASIIFICV
Asp_oryz_XP_001821930.2  PQTTPIVLYNRTTSRATAFADSIGSNKA--TVATTIPEAVAQATITFICV
Asp_clav_XP_001275449    PQTS-LVLYNRTVAKAVAFAETLGPNKA--TVASTIPDAVRDASLVFICV
Asp_oryz_BAE59928        PQTTPIVLYNRTTSRATAFADSIGSNKA--TVATTIPEAVAQATITFICV
Asp_flav_XP_002379461    PQTTPIVLYNRTTSRATAFADSIGSNKA--TVATTIPEAVAQATITFICV
                         **:  : *:***.::* . *. :        .. ::  **  : : * **

P_brasilianum_hmfU       GDDPAIDSITETILSDK--ELDLSTKTFVDCSTVHPDTSRRTEAAYEARG
Pen_oxal_EPS28195        GDDAAIESIAEAILSDA--SIDLSGKTFVDCSTIHPDTTRRLENAFTARG
Pen_rube_XP_002560238    GDDTALDSIVTAILSDNRISQDLSDKTFIDCSTVHPDTSRRTEAAFHERG
Pen_digi_EKV20433        GDDAALNSIVTAIISDPTIPQDLSSKTFIDCSTVHPDTSRRTEAAFNQRG
Pen_digi_EKV11956        GDDAALNSIVTAIISDPTIPQDLSSKTFIDCSTVHPDTSRRTEAAFNQRG
Asp_terr_XP_001208783    GDDPAVDSIVNTLVSDS--SLDLTGKTIVDCSTVHPDTSRRSHAALTTRG
Neo_fisc_XP_001260626    GDDPALDQIITTILADS--SLDLTSKVVVDCSTVHPDTSRRIHAALNPRG
Asp_oryz_XP_001821930.2  GDDHALDQIITTIISDS--SLDLTSKLIVDCSTVHPNTSRRIHATLTERG
Asp_clav_XP_001275449    GDDHALDQIISTILADP--TIPLAGKVIADCSTVHPDTSRRMHAALADRG
Asp_oryz_BAE59928        GDDHALDQIITTIISDS--SLDLTSKLIVDCSTVHPNTSRRIHATLTERG
Asp_flav_XP_002379461    GDDHALDQIITTIISDS--SLDLTSKLIVDCSTVHPNTSRRIHATLTERG
                         *** *::.*  ::::*      *: * . ****:**:*:** . :   **

P_brasilianum_hmfU       ASFVACPVFGAPNMADAGQMIVVPAGKQSAITKVKPFFEGVVAKATIDLS
Pen_oxal_EPS28195        AGFVACPVFGAPNMADAGQMIVVPAGKQSSIAKAKPFFEGVTAKATIDLS
Pen_rube_XP_002560238    AGFVACPVFGAPNMADAGQLIVVPAGKRASIEKVRPFFDGVVSKKTIDLS
Pen_digi_EKV20433        ADFVACPVFGAPNMADAGQLIVVPAGKRAAIEKVRPFFDGVVSKKTIDLS
Pen_digi_EKV11956        ADFVACPVFGAPNMADAGQLIVVPAGKRAAIEKVRPFFDGVVSKKTIDLS
Asp_terr_XP_001208783    AAFVACPVFGAPNAAEAGQMVVVPAGDPAAVDRIKPWLEGVTSKAIIDMS
Neo_fisc_XP_001260626    ASFIACPVFGAPAFADAGQLVVVPAGDAAAINRIRPFFEGVTARATIDMS
Asp_oryz_XP_001821930.2  ATFIACPVFGAPNMADAGQMIVVPAGKQEAIDRLQPFFEGVTAKATLPLP
Asp_clav_XP_001275449    AAFVACPVFGAPAFADAGQLVVVPAGDAAAVARLKPFLDGVTARATIDMS
Asp_oryz_BAE59928        ATFIACPVFGAPNMADAGQMIVVPAGKQEAIDRLQPFFEGVTAKATLPLP
Asp_flav_XP_002379461    ATFIACPVFGAPNMADAGQMIVVPAGKQEAIDRLQPFFEGVTAKATLPLP
                         * *:********  *:***::*****.  :: : :*:::**.::  : :.
```

TABLE 13-continued

Amino acid sequence alignment of *Penicillium brasilianum* hmfU and 10 closest orthologues.

```
P_brasilianum_hmfU         AGTGADIDVGRASTLKVLGNTFILNTVGVLAEALTAADATGLGTAPFRQW
Pen_oxal_EPS28195          DGSGSDIDVGRASTLKVLGNTFILNTVGVLAESLTAADATGLGSGPFRQW
Pen_rube_XP_002560238      SGTGADVDVGRASTLKVLGNTFILNTVGVLAEALVAADASGLGVEPLQEW
Pen_digi_EKV20433          AGSEGDVDVGRASTLKVLGNTFILNTVGVLAEALVAAEASGLGVEPLQKW
Pen_digi_EKV11956          AGSEGDVDVGRASTLKVLGNTFILNTVGVLAEALVAAEASGLGVEPLQKW
Asp_terr_XP_001208783      G-----EEVGRALMLKVLGNTFILNMVETLAEGLVIAEKSGLGREVYRQW
Neo_fisc_XP_001260626      G-----HDVGRSSTLKVLGNTLILNTVESIAEGLVAAEKSGLGADVYQQW
Asp_oryz_XP_001821930.2    G-----DDVGRASQLKILGNTFILNTVETVAEGLVLAEKSGLGADMYQKW
Asp_clav_XP_001275449      GP----DDVGRATTLKILGNTFILNTVETLAEGLVAAEKAGLGADVYQQW
Asp_oryz_BAE59928          G-----DDVGRASQLKILGNTFILNTVETVAEGLVLAEKSGLGADMYQKW
Asp_flav_XP_002379461      G-----DDVGRASQLKILGNTFILNTVETVAEGLVLAEKSGLGADMYQKW
                                  :***:  **:****:*** *  :**.*. *: :***    ::*

P_brasilianum_hmfU         LELFNPGPFAKYADRMISGDYYQREEPLFAVDLARKDLRHASNIAKEGGQ
Pen_oxal_EPS28195          LELFNPGPFVKYADRMISGDYYQREDPLFAVDLARKDLRHASSLAKDGGQ
Pen_rube_XP_002560238      LGLFAPGPFANYAQRMVGGDYCTREEPLFAVDLARKDLGHAYGIAKEGGL
Pen_digi_EKV20433          LGLFAPGPFANYAERMVGGDYCTREEPLFAVDLARKDLGHAYKIAKEGGL
Pen_digi_EKV11956          LGLFAPGPFANYAERMVGGDYCTREEPLFAVDLARKDLGHAYKIAKEGGL
Asp_terr_XP_001208783      VHMFSPGPFAKYADRMCTGDYYQREEPLFAVDLARKDLRHASSLASDANM
Neo_fisc_XP_001260626      VHALVGGMFAKYADRMCTGDYYKREEPLFAVDLARKDLRHAASLAEAAGM
Asp_oryz_XP_001821930.2    IHTWLGGPFAKYADRMVEGDYHKREEPLFAVDLARKDLGHATSIAQDAGM
Asp_clav_XP_001275449      IHALIGGMFAKYADRMCSGDYYTREEPLFAVDLARKDLRHAATLAGEAGM
Asp_oryz_BAE59928          IHTWLGGPFAKYADRMVEGDYHKREEPLFAVDLARKDLGHATSIAQDAGM
Asp_flav_XP_002379461      IHTWLGGPFAKYADRMVEGDYHKREEPLFAVDLARKDLGHATSIAQDAGM
                           :     * *.:**:**  ***  **:************ **  :*  ..

P_brasilianum_hmfU         RMRNVEVTDHFLQEVKAEKGEKGDIAAVYGAARKDAGLKFENQ-------
Pen_oxal_EPS28195          RMRNVEVTDQFLQDVKAEKGEKGDIAAIYGAARKAAGLKFENQ-------
Pen_rube_XP_002560238      RMKNVEVMDGLLEHVKEVKGVKGDVAAVYGAVRKGAGMEFGNQ-------
Pen_digi_EKV20433          RMRNVEVMDGLLEGVKEVKGVKGDVAAVYGAVRKGAGMEFGNQ-------
Pen_digi_EKV11956          RMRNVEVMDGLLEGVKEVKGVKGDVAAVYGAVRKGAGMEFGNQ-------
Asp_terr_XP_001208783      RLRSVEVTDEYLKQVKAEKGEKGDIAGVYGAIRKESGLPFENQ-------
Neo_fisc_XP_001260626      RLRSVEVTDAYLQEVKAEKGEKGDIAAVYGAIRKESGLPFENEQ-------
Asp_oryz_XP_001821930.2    RLRSVEVTDAYLQEVKKEKGVKGDVAGVYGAIRKESGLEYDN--------
Asp_clav_XP_001275449      RMRSVEVTDGYLEALKEERGEKGDIAGIYGAVRKESGLPFENDK------
Asp_oryz_BAE59928          RLRSVEVTDAYLQEVKKEKGVKGDVAGVYGAIRKESGLEVAVNMDKIRIY
Asp_flav_XP_002379461      RLRSVEVTDAYLQEVKKEKGVKGDVAGVYGAIRKESGLEYDNU-------
                           *::.*** *  *: :*  :* ***:*.:*** ** :*:

P_brasilianum_hmfU         ---------------
Pen_oxal_EPS28195          ---------------
Pen_rube_XP_002560238      ---------------
Pen_digi_EKV20433          ---------------
Pen_digi_EKV11956          ---------------
Asp_terr_XP_001208783      ---------------
Neo_fisc_XP_001260626      ---------------
Asp_oryz_XP_001821930.2    ---------------
Asp_clav_XP_001275449      ---------------
Asp_oryz_BAE59928          CSHRKATITQFPNQL
Asp_flav_XP_002379461      -SAGE----------
```

TABLE 14

Amino acid sequence alignment of *Penicillium brasilianum* hmfO and 10 closest orthologues.

```
P_brasilianum_hmfO    --------------MSSTSESFTLPNGRQMAYTLSPGGSSDRVVLLSNSL
Spo_sche_ERT02389     --------------MS----SFALPCGRRMAYALSQPTTSKPVVLLSNSL
Mag_oryz_ELQ38824     ------------------MSTFTLPDSRVMAYDLTPSPTPLPIILLSNPL
Mag_oryz_XP_003712784 MTRIPGLKRSRFNKTHSKMSTFTLPDSRVMAYDLTPSPTPLPIILLSNPL
Mag_gris_ABO93629     -----------------------------MAYDLTPSPTPLPIILLSNPL
Col_fior_XP_007591389 ---------------MASAQQLNLPDGRVLSYDLSG-PDSKPVVLLANSL
Col_higg_CCF42149     ---------------MASAQQLTLSDGRILSYDLSG-PDSKPVVLLANSL
Col_gloe_EQB58465     ---------------MVTTQQVNLPDGRILSYHLSS-QGDEPLVLLANSL
Acr_chry_KFH45030     ---------------MPSS--ITLPDSRKFAYSLDTVPQDGPIVILANSL
Fus_oxys_ENH72740     ---------------MASS--LTLPDSRTLAYALDSSPKEGPLIILSNSL
Fus_oxys_EMT64805     ---------------MASS--LTLPDSRTLAYALDSSPKEGPLIILSNSL
                                                   ::* *        :::*:*.*

P_brasilianum_hmfO    AEDLTSWERVVPVVENQGFRVLRYDQPGHGRSGAPTEAELTSMTFETLVD
Spo_sche_ERT02389     CEDYTSWDRVVPVLETLGFRTLRYDQPGHGRSPAPAADQIAATTFETLAD
Mag_oryz_ELQ38824     LTSYRAWDRVTPVLQAAGFRVLRYDQPGRGSSTAPSNPE--TTTFSSIAD
Mag_oryz_XP_003712784 LTSYRAWDRVTPVLQAAGFRVLRYDQPGRGSSTAPSNPE--TTTFSSIAD
```

TABLE 14-continued

Amino acid sequence alignment of *Penicillium brasilianum* hmfO and 10 closest orthologues.

```
Mag_gris_ABO93629      LTSYRAWDRVTPVLQAAGFRVLRYDQPGRGSSTAPSNPE--TTTFSSIAD
Col_fior_XP_007591389  AAPFTLWDHVVKVLHANGFRTLRFDQPGHGKSSAPKKLN---TEFETIAD
Col_higg_CCF42149      SAPFTLWDRVVKVLHDNGFRTLRFDQPGHGKSSAPAGLD---TEFETIAD
Col_gloe_EQB58465      SAPFRVWDHVAKFLAENGFRTLRFDQPGHGQSSAPKNLD---TTFESIAD
Acr_chry_KFH45030      CATLALWDNVVPVLNKNGFRTLRYDQPGHGDSSAPAGLD---TTFDSMAD
Fus_oxys_ENH72740      TAPLSVWDHVVKVLNSNGYRTLRYDQPGHGGSSAPKDLS---PTFDSMAE
Fus_oxys_EMT64805      TAPLSVWDHVVKVLNSNGYRTLRYDQPGHGGSSAPKDLS---PTFDSMAE
                             *:.*. .:   *:*.**:****** * **    .     *.::.:

P_brasilianum_hmfO     DVYRLLGHLKINNLHAWVGVSMGGIKAVYFTARHPGIVNKIVVADAIAAS
Spo_sche_ERT02389      DVAQLLKHLHISRLHAWVGVSMGGIKGVYFAARHPGVVQKLVVADAIAAS
Mag_oryz_ELQ38824      DVAQLLRHLGVERLHAWVGVSMGAATGVYFATRHPGIISRLVVCDTISAS
Mag_oryz_XP_003712784  DVAQLLRHLGVERLHAWVGVSMGAATGVYFATRHPGIISRLVVCDTISAS
Mag_gris_ABO93629      DVAQLLRHLGVERLHAWVGVSMGAATGVYFATRHPGIISRLVVCDTISAS
Col_fior_XP_007591389  DVHSLVKSLKIEKLFAWIGVSMGAATSFYFATKYPGIIQKVAICDTISSS
Col_higg_CCF42149      DVHFLVTSLRVDKLFAWVGVSMGAATSFYFVTKYPGLVHKVAICDTISSS
Col_gloe_EQB58465      DVYHLLQALKIEKVFAWIGVSMGAATSFYFVNKYPGIVHKVAICDTIAAS
Acr_chry_KFH45030      DVRFLLQSLDITKVHAWVGVSMGAATGVVFTTKFPGVVSRLAICDTVSCS
Fus_oxys_ENH72740      DVHHLLKKLEINKVYSWIGVSMGASAGVYFTTKYPNVVSKLAICDTISAS
Fus_oxys_EMT64805      DVHHLLKKLEINKVYSWIGVSMGASAGVYFTTKYPNVVSKLAICDTISSS
                       **  *:  * : .:.:*:*****.  .. *. :.*.:: ::.:.*:::.*

P_brasilianum_hmfO     PSVVCIP-DNFAARVSAVKQSGSISDDLSNTRKRWFGEDWMAKHPEETAR
Spo_sche_ERT02389      PTVAGAPVDVFAQRVAAAKTAGSMATDLDNVGRRWFGEAWLAANPTEARR
Mag_oryz_ELQ38824      PANAGVP-DAFADRVLQARTAGNVETQVQSTLERWFGAGWLKSEEAEASR
Mag_oryz_XP_003712784  PANAGVP-DAFADRVLQARTAGNVETQVQSTLERWFGAGWLKSEEAEASR
Mag_gris_ABO93629      PANAGVP-DAFADRVLQARTAGNVETQVQSTLERWFGAGWLKSEEAEASR
Col_fior_XP_007591389  PKHAGVE-DLFGPRAKAAGEAGNMEAQVDQTMDRWFGAEWIKANPEEAAR
Col_higg_CCF42149      PKLAGVE-DAFGPRAKAAGEAGDMREQVEQTMDRWFGADWIKANPDEAGR
Col_gloe_EQB58465      PKNAGVD-DLFAPRAQQAREAGNMQEQVEGTIDRWFGQEWVKANPDEADR
Acr_chry_KFH45030      PVNAGTE-DAFGARVAAAREAGNMEATVEGTMERWFGKAWVNTNAEEAQR
Fus_oxys_ENH72740      PINAGTE-DTFGTRVAAAREAGNLDSTIQSTLERWFGKEWLENNPQETQR
Fus_oxys_EMT64805      PINAGTE-DTFGPRVAAAREAGNLDSTIQSTLERWFGKEWLENNPQETQR
                       *   .     * *. *.  .   :*.:    :. .  ****  *:  .   *: *

P_brasilianum_hmfO     MEKSMATTTIQGLEACCAALSSPSFDLRPLYTKVGHGCEEALIVAGEKDA
Spo_sche_ERT02389      MRASMDTTTLEGLEACCAALSSSSFDLRPLYPSVGKGADEALIVVGEKDA
Mag_oryz_ELQ38824      MRDLMVKTSVGGFEACVAALRSQSFDLRPLLPEVGKGCEDALLIVGENDA
Mag_oryz_XP_003712784  MRDLMVKTSVGGFEACVAALRSQSFDLRPLLPEVGKGCEDALLIVGENDA
Mag_gris_ABO93629      MRDLMVKTSVGGFEACVAALRSQSFDLRPLLPEVGKGCEDALLIVGENDA
Col_fior_XP_007591389  ARAIMNQTTVEGFQTCCFALQSDSFDIRPLFERIGSGVDEALLVVGEKDA
Col_higg_CCF42149      ARAIMNQTTVEGFQTCCHALRSDRFDIRPLYERVGSGVDEALLVVGEKDA
Col_gloe_EQB58465      VRGIMNQTSVDGFATCCHALRSDSFDIRPLFGKVGAGVDEALLVVGDKDA
Acr_chry_KFH45030      MRSLMIRTTVDGFESCCHALRSPSFDLRPLYGRVGASVDEAICVVGEKDA
Fus_oxys_ENH72740      MRIVMSGTTIDGFEACCNALRSETFDLRPRFAKIGSSVDDAICIVGEKDA
Fus_oxys_EMT64805      MRTVMSGTTIDGFEACCNALRSETFDLRPRFAKIGSSVDDAICIVGEKDA
                         .  *  *:: *: :*  ** *  **:**     :* . ::*: :.*::**

P_brasilianum_hmfO     DLPVKMQEMRQAIEESLRSCGKK-VPVRMEIIKGAGHVPYIDGFEDFCEI
Spo_sche_ERT02389      DLPVKMQDMRAAIETSLAANGKT-TPVALEIVANAGHVPYVDGFDQFCEI
Mag_oryz_ELQ38824      DLPVKMEELRAGIEDSLRKNGKEGKKVOLVVIKNAGHAVFVDGFEDFCKT
Mag_oryz_XP_003712784  DLPVKMEELRAGIEDSLRKNGKEGKKVOLVVIKNAGHAVFVDGFEDFCKT
Mag_gris_ABO93629      DLPVKMEELRAGIEDSLRKNGKEGKKVOLVVIKNAGHAVFVDGFEDFCKT
Col_fior_XP_007591389  NLPQAMQEMRDKVEKGFRAAGKD-NKIELKLIKNAGHVPFVDNFEQFKEV
Col_higg_CCF42149      NLPQAMKEMRDKVETGFRAAGKD-NKIELKVIAKAGHVPFVDNFEQFTEV
Col_gloe_EQB58465      NLPEAMKEMRQKVEEGFRAAGKD-NKIELKVIKNAGHVPFVDGYDQFKEI
Acr_chry_KFH45030      NLPQSMEEMRAQIEEGFTAAGKP-KKVELAVVKNAGHVCFIDGFDQFVRI
Fus_oxys_ENH72740      NLPETMKEMRDKIQEGFEAAGKS-NKIDLVIIKNAGHVSFVDGFEQFTAE
Fus_oxys_EMT64805      NLPETMKEMRDKIQEGFEAAGKS-NKIDLVIIKNAGHVSFVDGFEQFTAE
                       :**  *:::*  :: .:   **    : : ::  ***. ::*.:::*

P_brasilianum_hmfO     ITKFLA------
Spo_sche_ERT02389      LKTFL-------
Mag_oryz_ELQ38824      LLNFVQQ-----
Mag_oryz_XP_003712784  LLNFVQQ-----
Mag_gris_ABO93629      LLNFVQQ-----
Col_fior_XP_007591389  ILGYLKA-----
Col_higg_CCF42149      ILGYLKA-----
Col_gloe_EQB58465      ILGYLKA-----
Acr_chry_KFH45030      ITPFLTA-----
Fus_oxys_ENH72740      VLKWLKA-----
Fus_oxys_EMT64805      VLKWLKAUSAGE
                       :  ::
```

TABLE 15

Amino acid sequence alignment of *Penicillium brasilianum* hmfM and 10 closest orthologues.

```
P_brasilianum_hmfM     MSLSGKVVLITGSSKGIGKAAALRVASEGANVVINYLRDPVAANNLVDQI
Asp_nidu_XP_664054     MSLAGKVALITGASKGIGRATAQRLASEGASLVINYNTDAASAQALVDEI
Eut_lata_XP_007797627  MSLQGKVILITGGSKGIGRAIALRVAKSGASVVVNYSSDSNAANEVVSQI
Thi_terr_XP_003656972  MSLSGKVALITGGSKGIGRAVAQRLAADGASVVINFKSDSKAADELVAEI
Tri_atro_EHK50353      MQLPDKVILITGASSGIGKACAQRLYQEGARIVVNYRNDASAANALVDSF
Asp_terr_XP_001212987  MSLAGKVVLITGASKGIGKATAQHLAANGASIVINYLSDAASANALVDEI
Tri_rees_XP_006962638  MSLQDKVILITGASSGIGKATAQRLYKEGARIVVNYHSDDSAANALVESF
Fus_oxys_EMT67544      MSLNGKVVLVTGGSKGIGKAVAERVVADGASVVINYSSDSKPAEDLVIKI
Fus_oxys_EGU79882      MSLNGKVVLVTGGSKGIGKAVAERVVADGASVVINYSSDSKPAEDLVIKI
Fus_oxys_EXL52390      MSLNGKVVLVTGGSKGIGKAVAERVVADGASVVINYSSDSKPAEDLVTKI
Fus_oxys_ENH63602      MSLNGKVVLVTGGSKGIGKAVAERVVADGASVVINYSSDSKPAEDLVIKI
                       *.*  .** *:**.*.***:* *  ::   .** :*:*:   *   .*: :* .:

P_brasilianum_hmfM     GADRALAVQADASKLADLDRLVNAAVAQFGKIDVLIPNAGILPLRDLEHT
Asp_nidu_XP_664054     GQDRALAVQADASKLADIDRLVDAAVAKFGKIDILIPNAGILPMRDLEHT
Eut_lata_XP_007797627  GSDRALAVKADASTVTGVSSLVDATVKQFGKVDVVIPNAGMMPMQDLEHT
Thi_terr_XP_003656972  GADRALAVQADVSKLDDIEKLVNAAVARFGKIDIVMPNAGVMAMVPLANL
Tri_atro_EHK50353      GADRAIAVQADASNINDIERLVQATVDKFGRIDTIVANAGLMLMRDVEDT
Asp_terr_XP_001212987  GEDRALAVQADASKLDDIRRLVEAAVTKFGHIDVVIPNAGVLLMRDLATT
Tri_rees_XP_006962638  GPDRAIAVRADAANISDIDRLVRTTVDKFGRIDVVVANAGLMLMRDVEDT
Fus_oxys_EMT67544      GSDRALAFKADVSKIAEIEKLVQATVEKFGKIDCVMANAACAPMNDLEST
Fus_oxys_EGU79882      GSDRALAFKADVSNIAEIEKLVQATVEKFGKIDCVMANAACAPMNDLEST
Fus_oxys_EXL52390      GSDRALAFKADVSNIAEIEKLVQATVEKFGKIDCVMANAACAPMNDLEST
Fus_oxys_ENH63602      GSDRALAFKADVSNIAEIEKLVQATVEKFGKIDCVMANAACAPMNDLEST
                       * ***:*.:**.:.:  :   **  ::*  :**::*  ::.**.    :  :

P_brasilianum_hmfM     SEEDFDRTYNLMVKGPYFLAQ--KAVKHMPPGGRIIFVSTSTARFASVAP
Asp_nidu_XP_664054     TEEDFDFTYNLMVKGPYFLAQAQKAAKHIPAGGRIILVSTGVTVLSNIAP
Eut_lata_XP_007797627  TEATFDKIYAINVKGPYFLAQ--KAVPHMPSGGRIIFVSTGIAHNSAVPP
Thi_terr_XP_003656972  TEAEFDRHFNLNVKGALFLVQ--KAVAHVPAGGRIIFVSTGLARQSAVAP
Tri_atro_EHK50353      TEDDFAKSFDLNVKGPYFLAQ--KAVPHMPPGSHVIFISTGVCHHSSVSP
Asp_terr_XP_001212987  TEADFDTAFNLNVKGPYFLVQ--EATRHMPAGGRVIFVSTGVTVHSSISP
Tri_rees_XP_006962638  TEDDFGQMFDINVKGPYFLAQ--KAVPHMPPGSRIIFISTGVCHYSSVPA
Fus_oxys_EMT67544      TEEGFDKAFNLNVKGPYFLVQ--KAVKHMPRDGRVILVSSGVLHQSQVAP
Fus_oxys_EGU79882      TEEGFDKAFNLNVKGPYFLVQ--KAVKHMPRDGRVILVSSGVLHQSQVAP
Fus_oxys_EXL52390      TEEGFDKAFNLNVKGPYFLVQ--KAVKHMPRDGRVILVSSGVLHQSQVAP
Fus_oxys_ENH63602      TEEGFDKAFNLNVKGPYFLVQ--KAVKHMPRDGRVILVSSGVLHQSQVAP
                       :*  *    : : ***. **.*  :*. *:* ..::*::*:.     : :..

P_brasilianum_hmfM     AYLLYTSSKGAIEQMTRIMAKDLARKGILVNAVAPGPTSTELFLEGKPEQ
Asp_nidu_XP_664054     AYLLYASAKAAVEQMARVMAKDLARNGILVNCVAPGPTTTGLFLNGKSDQ
Eut_lata_XP_007797627  PYLLYASTKGAVEQMTRVMAKDLGKKGITVNCVAPGPTATELFFEGKSEA
Thi_terr_XP_003656972  GYLVYAATKGAIEQLVRVLSKDLGAKGITVNAVAPGPTGTELFYQGKSEQ
Tri_atro_EHK50353      KYLLYAATKGAIEQMTRVMAKGLAAKGIIVNAVAPGPTATELFYKGKPEG
Asp_terr_XP_001212987  TYLLYASTKGAIEQMTRITAKELAKKGIFVNAIAPGPTTTELFLRGKSEE
Tri_rees_XP_006962638  KYLLYAATKGAIEQMTRVMAKGLAAKGIIVNAVAPGPTATELFFKGKPES
Fus_oxys_EMT67544      RYLLYASSKGSIEQMTRILAKDLGPKGITVNAIAPGPTATEMFFQGKSQE
Fus_oxys_EGU79882      RYLLYASSKGSIEQMTRILAKDLGPKGITVNAIAPGPTATEMFFQGKSQE
Fus_oxys_EXL52390      RYLLYASSKGSIEQMTRILAKDLGPKGITVNAIAPGPTATEMFFQGKSQE
Fus_oxys_ENH63602      RYLLYASSKGSIEQMTRILAKDLGPKGITVNAIAPGPTATEMFFQGKSQE
                        **:*:::*.::**:.*: :* *. :** **.:***** * :* .**.:

P_brasilianum_hmfM     MIKAISGFSPFNRIGEPEEIAAVMAFLSG-------------------KD
Asp_nidu_XP_664054     MLKMVAGFSPFNRIGEPEEIANAVYFLCS-------------------KD
Eut_lata_XP_007797627  MVKGIASQSPFNRLGDPAEIAELAAFVAG-------------------PE
Thi_terr_XP_003656972  LLQTIRGWSPFNRIGEPAEIAGVVAFLAG-------------------ED
Tri_atro_EHK50353      LVNTIKAWSPFNRLGEPEDIANTVKFLAS-------------------GD
Asp_terr_XP_001212987  TLRAVAGFSPFNRIGEPGEMASVINFLCGPEFGDCPESRSTPETMTETKT
Tri_rees_XP_006962638  VVNAIKGWSPFNRLGQPEEVANTIKFLAS-------------------DE
Fus_oxys_EMT67544      LIDTIAGFSPLGRLGKPEEIAGLAAFLAG-------------------PT
Fus_oxys_EGU79882      LIDTIAGFSPLGRLGKPEEIAGLAAFLAG-------------------PT
Fus_oxys_EXL52390      LIDTIAGFSPLGRLGKPEEIAGLAAFLAG-------------------PT
Fus_oxys_ENH63602      LIDTIAGFSPLGRLGKPEEIAGLAAFLAG-------------------PT
                        :  : . **:.*:*.* ::*     *:..

P_brasilianum_hmfM     SSWISG-QVVAVNGAMA--------------------------------
Asp_nidu_XP_664054     SSWVSG-QTLRVNGGMA--------------------------------
Eut_lata_XP_007797627  SRWVSG-QVIGANGAAFV-------------------------------
Thi_terr_XP_003656972  SRWVSG-QVIGANGAMMV-------------------------------
Tri_atro_EHK50353      SSWVVG-QTVLVNGGIMV-------------------------------
Asp_terr_XP_001212987  TERVEKPQKGKVAGNTDAKPRAKSLKLTLPLPTDLSADRQPATTKNRNHF
Tri_rees_XP_006962638  SSWVVG-QTVLVNGGIMV-------------------------------
Fus_oxys_EMT67544      SSWVSG-QVIGANGGSFV-------------------------------
Fus_oxys_EGU79882      SSWVSG-QVIGVNGGSFV-------------------------------
Fus_oxys_EXL52390      SSWVSG-QVIGANGGSFV-------------------------------
Fus_oxys_ENH63602      SSWVSG-QVIGANGGSFVUSAGE--------------------------
                       :  :   *   . *
```

TABLE 15-continued

Amino acid sequence alignment of *Penicillium brasilianum* hmfM and 10 closest orthologues.

```
P_brasilianum_hmfM     --------------------------------------------------
Asp_nidu_XP_664054     --------------------------------------------------
Eut_lata_XP_007797627  --------------------------------------------------
Thi_terr_XP_003656972  --------------------------------------------------
Tri_atro_EHK50353      --------------------------------------------------
Asp_terr_XP_001212987  VKTLTGKTITLDVESSDTIDNVKAKIQDKEGIPPDQQRLIFAGKQLEDGR
Tri_rees_XP_006962638  --------------------------------------------------
Fus_oxys_EMT67544      --------------------------------------------------
Fus_oxys_EGU79882      --------------------------------------------------
Fus_oxys_EXL52390      --------------------------------------------------
Fus_oxys_ENH63602      --------------------------------------------------

P_brasilianum_hmfM     --------------------------------------------------
Asp_nidu_XP_664054     --------------------------------------------------
Eut_lata_XP_007797627  --------------------------------------------------
Thi_terr_XP_003656972  --------------------------------------------------
Tri_atro_EHK50353      --------------------------------------------------
Asp_terr_XP_001212987  TLSDYNIQKESTLHLVLRLRGGIIEPSLKALASKYNCEKSICRKCYARLP
Tri_rees_XP_006962638  --------------------------------------------------
Fus_oxys_EMT67544      --------------------------------------------------
Fus_oxys_EGU79882      --------------------------------------------------
Fus_oxys_EXL52390      --------------------------------------------------
Fus_oxys_ENH63602      --------------------------------------------------

P_brasilianum_hmfM     ------------------------
Asp_nidu_XP_664054     ------------------------
Eut_lata_XP_007797627  ------------------------
Thi_terr_XP_003656972  ------------------------
Tri_atro_EHK50353      ------------------------
Asp_terr_XP_001212987  PRATNCRKKKCGHTNQLRPKKKLK
Tri_rees_XP_006962638  ------------------------
Fus_oxys_EMT67544      ------------------------
Fus_oxys_EGU79882      ------------------------
Fus_oxys_EXL52390      ------------------------
Fus_oxys_ENH63602      ------------------------
```

TABLE 16

Amino acid sequence alignment of *Penicillium brasilianum* hmfT3 and 10 closest orthologues.

```
P_brasilianum_hmfT3    MASLIREAPFGQIVRYLTNNKYFQYPEEKPDFKLPDTWLQLLN-------
Pen_rube_XP_002560799  MASIIRDAPFGQLVRLLTNNKYFQYPEEKPDFKLPDTWLQLLN-------
Pen_oxal_EPS29964      MASVIRDAPFGQLVRYLTNNKYFQYPEERPDFELPEAWRELISGADSIKP
Asp_terr_XP_001212020  MQAVLRESAFGQLVRLVTKNKYFQYPEEKADFKLPDQWIKVMD-------
Fus_oxys_ENH73763      MSDLIRDAPLGQLIRFVTRNKYLQYPEEKPDFKLPESWVAVINNPDAIIE
Fus_oxys_EGU73369      MSDLIRDAPLGQLIRFVTRNKYLQYPEEKPDFKLPESWVAVINNPDAIIE
Fus_oxys_EXL94287      MSDLIRDAPLGQLIRFVTRNKYLQYPEEKPDFKLPESWVAVINNPDAIIE
Nec_haem_XP_003040064  MADIIRDAPLGQVIRFVTRNKYLKYPEEKEDFKLPDPWITLVNNPDAIVE
Fus_pseu_XP_009258565  MSDIIRDAPLGQLIRFVTRNRYFQYPEEKPDFKLPDAWDTVINNPNVIID
Fus_gram_XP_011323833  MSDIIRDAPLGQLIRFVTRNKYLQYPEEKPDFKLPDAWDTVINNPNVIVD
Fus_fuji_CCT64241      MSDLIRDAPLGQLIRFVTRNKYLQYPEEKPDFKLPESWVAVINNPDAIIE
                       *  ::*::.:**::* :*.*:*::****: **:**: *  ::.

P_brasilianum_hmfT3    -------------ESDAATIADPEKTEPEPEGQGYDAT------------
Pen_rube_XP_002560799  -------------SNGDE---DDEKKAIQQDSNRSPED------------
Pen_oxal_EPS29964      VRDLEKAP---VAGTPASLTDEDASVRGQSPDAESETTT-----------
Asp_terr_XP_001212020  -------------GLDAAASSEHAQTDAQTP-TRQPDS------------
Fus_oxys_ENH73763      ESSPHDNT--VLT-------------------------------------
Fus_oxys_EGU73369      ESSPHDNT--VLTGTALASSASSTVAAEEDPKLKAENENEKNEKSEKNNE
Fus_oxys_EXL94287      ESSPHDNT--VLTGTALASSASSTVAAEEDPKLKAENE--KNEKSEKTNE
Nec_haem_XP_003040064  DAPIENLT------------------------------------------
Fus_pseu_XP_009258565  ESPANNNN-ALLTGTALASSASSTVAATEDPKIKSETD----------KE
Fus_gram_XP_011323833  ESPANNNNNALLTGTALASSASSTVAATEDPKIKSETD----------KE
Fus_fuji_CCT64241      ESSPNDNT--VLTGTALASSASSTVAAEEDPKLKGDNE--KNDKSEKNDE

P_brasilianum_hmfT3    -----------SEAISRASTQNSLPFTEARLEADEQHEIEKIKSIPIQPK
Pen_rube_XP_002560799  -----------SEPLSRASTQASIEFTEARLEADEQHEIEKIKSIPIAPK
Pen_oxal_EPS29964      --------ATATEAIARVNTKETLAYTQSRLEADEEHEIQKLQSIPIQPK
Asp_terr_XP_001212020  -----------DESLSQVTTNYSLSFTEARLEADQQHEIEKVKSIPIAPK
Fus_oxys_ENH73763      ------------------------AYTVDRLEADEEHDVEKVKSIPVVPK
Fus_oxys_EGU73369      NDDIERADPQPMRLHRSRSPQETQAYTVDRLEADEEHDVEKVKSIPVVPK
Fus_oxys_EXL94287      NDDIERADPQPMRLHRSRSPQETQAYTVDRLEADEEHDVEKVKSIPVVPK
```

TABLE 16-continued

Amino acid sequence alignment of *Penicillium brasilianum* hmfT3 and 10 closest orthologues.

```
Nec_haem_XP_003040064  ---------------------DTQAYTADRMRVDEEHEIEKVQSIPIVPK
Fus_pseu_XP_009258565  TEDVERADSVPVRLHRSRSPQETQAYTIDRLEADEEHDVEKVKSIPVVPK
Fus_gram_XP_011323833  TEDVERADSVPVRLYRSRSPQETQAYTIDRLEADEEHDVEKVKSIPVVPK
Fus_fuji_CCT64241      NDDIERADPQPMRLHRSRSPQETQAYTVDRLEADEEHDVEKVKSIPVVPK
                                                :*  *:..*::*:::*::***: **

P_brasilianum_hmfT3    KTKDGAILVDWYYTDDAENPHNWSNRKRALLTTLICLYTFVVYTTSAIYT
Pen_rube_XP_002560799  KTKDGSILVDWYYTDDLENPHNWSNGKRAFITILICLYTFVVYTTSAIYT
Pen_oxal_EPS29964      KTKDGTILVDWYYTDDQENPHNWSNRKRALLTTIICLYTFVVYTTSAIYT
Asp_terr_XP_001212020  KTKDGAILVDWYYTDDAENPHNWSNLKRALVATIICLYTFVVYTTSAIYT
Fus_oxys_ENH73763      RTKDGSILVDWYFSDDNENPHNWTNNRRLGVSLIICLYTFVVYTSSAIYT
Fus_oxys_EGU73369      RTKDGSILVDWYFSDDNENPHNWTNNRRLGVSLIICLYTFVVYTSSAIYT
Fus_oxys_EXL94287      RTKDGSILVDWYFSDDNENPHNWTNNRRLGVSLIICLYTFVVYTSSAIYT
Nec_haem_XP_003040064  KTKDGAILVDWYYSDDADNPHNWSNNKRLGISLIICLYTFVVYTSSAIYT
Fus_pseu_XP_009258565  RTKDGHILVDWYYSDDNENPHNWTNNRRLGVALIICLYTFVVYTSSAIYT
Fus_gram_XP_011323833  RTKDGHILVDWYYSDDKENPHNWTNNRRLGVALIICLYTFVVYTSSAIYT
Fus_fuji_CCT64241      RTKDGSILVDWYFSDDNENPHNWTNNRRLGVSLIICLYTFVVYTSSAIYT
                       :**** ******::** :*****:* :*  :: :**********:*****

P_brasilianum_hmfT3    SSVPGIMKEFGVSDLVATLGLSLYVLGYGTGPLIFSPLSEIPVIGRNPVY
Pen_rube_XP_002560799  SSTQGVMKEFGVSTLVATLGLSLYVLGYGTGPLVFSPLSEIPVIGRNPVY
Pen_oxal_EPS29964      ASVPGVMEDFGVSNLLATLGLSLYVLGYGMGPLVFSPLSEIPLIGRNPVY
Asp_terr_XP_001212020  SSVGGIIAQFGVSELLATLGLSLYVLGYGIGPLLFSPMSEIPIIGRNPVY
Fus_oxys_ENH73763      SSTEGVMRAFGVSQLKATLGLSLYVLGYGIGPLIFSPLSEIPRIGRNPVY
Fus_oxys_EGU73369      SSTEGVMRAFGVSQLKATLGLSLYVLGYGIGPLIFSPLSEIPRIGRNPVY
Fus_oxys_EXL94287      SSTEGVMHAFGVSQLKATLGLSLYVLGYGIGPLIFSPLSEIPRIGRNPVY
Nec_haem_XP_003040064  SSTEGVMKAFGVSQLKATLGLALYVLGYGIGPLLFSPLSEIPRIGRNPVY
Fus_pseu_XP_009258565  SSTEGVMRAFGVSQLKATLGLSLYVLGYGTGPLIFSPLSEIPRIGRNPVY
Fus_gram_XP_011323833  SSTEGVMRAFGVSQLKATLGLSLYVLGYGTGPLIFSPLSEIPRIGRNPVY
Fus_fuji_CCT64241      SSTEGVMRAFGVSQLKASLGLALYVLGYGIGPLIFSPLSEIPRIGRNPVY
                       :*. *::  **** * *:***:******* ***:***:**** *******

P_brasilianum_hmfT3    IVTMFLFVILSIPTAFVGNFAGLMVLRFLQGFFGSPCLASGGASIGDMYS
Pen_rube_XP_002560799  IITMFLFVIISIPTAFVGNFAGLMVLRFLQGFFGSPCLASGGASIGDMYS
Pen_oxal_EPS29964      IVTMFLFVILSIPTALVHNFAGLIVLRFLQGFFGSPCLASGGASIGDMYS
Asp_terr_XP_001212020  IVTMFLFVIISIPTAFAGNFPGLMVLRFLQGFFGSPCLASGGASIGDMYS
Fus_oxys_ENH73763      IVTMFLFVIISIPTALVNNYPGLMVLRFLQGFFGSPCLASGGASLGDIYS
Fus_oxys_EGU73369      IVTMFLFVIISIPTALVNNYPGLMVLRFLQGFFGSPCLASGGASLGDIYS
Fus_oxys_EXL94287      IVTMFLFVIISIPTALVNNYPGLMVLRFLQGFFGSPCLASGGASLGDIYS
Nec_haem_XP_003040064  IVTMFLFVIISIPTAFVGNYPGLMVLRFLQGFFGSPCLASGGASLGDIYS
Fus_pseu_XP_009258565  IVTMFLFVIISIPTALVKNYPGLMVLRFLQGFFGSPCLASGGASLGDIYS
Fus_gram_XP_011323833  IVTMFLFVIISIPTALVKNYPGLMVLRFLQGFFGSPCLASGGASLGDIYS
Fus_fuji_CCT64241      IVTMFLFVIISIPTALVDNYPGLMVLRFLQGFFGSPCLASGGASLGDIYS
                       *:*******:*****:. *:.**:********************:**:**

P_brasilianum_hmfT3    LMSLPYAMMSWVSAAYCGPALGPLISGFAVPAETWRWSLFESIWMSAPVL
Pen_rube_XP_002560799  LMNLPFAMMAWVAAAYCGPALGPLLSGFAVPVKGWRWSLFESIWASAPVF
Pen_oxal_EPS29964      LLSLPYAMMTWVSAAYCGPALGPLLSGFAVAAKNWRWSLYESIWMSAPVF
Asp_terr_XP_001212020  LMSLPYAMMAWVAAAYCGPALGPLLSGFAVPAKSWRWSLFESIWASAPVF
Fus_oxys_ENH73763      LMALPYAMMAWVSAAYCGPALGPLISGFAVPAKNWRWSLYESIWASAPIF
Fus_oxys_EGU73369      LMALPYAMMAWVSAAYCGPALGPLISGFAVPAKNWRWSLYESIWASAPIF
Fus_oxys_EXL94287      LMALPYAMMAWVSAAYCGPALGPLISGFAVPAKNWRWSLYESIWASAPIF
Nec_haem_XP_003040064  LMALPYAMMAWVSAAYCGPALGPLLSGFAVPAKSWRWSLYESIWASAPIF
Fus_pseu_XP_009258565  FMALPYAMMAWVAAAYCGPALGPLLSGFAVPAKGWRWSLYESIWASAPIF
Fus_gram_XP_011323833  FMALPYAMMAWVAAAYCGPALGPLLSGFAVPAKGWRWSLYESIWASAPIF
Fus_fuji_CCT64241      LMALPYAMMAWVSAAYCGPALGPLISGFAVPAKNWRWSLYESIWASAPIF
                       :: **:***:**:***********:*****..: *****:**** ***::

P_brasilianum_hmfT3    ILMFFFLPETSSATILLRRAARLRKIHNNARFMAQSEIDQRNMKVSAVAV
Pen_rube_XP_002560799  ILMFMFLPETSSATILLRRAARLRKIHNTNRFMSQSELDQRNMRVSDIAV
Pen_oxal_EPS29964      ILMLVFLPETSSATILLRRAARLRKIYNTDLFMSQSEIDQRNMKVSDIAV
Asp_terr_XP_001212020  LLMFFFLPETSTSTILLRRASRLRRIFKDDRFMSQSEIDQRNMRISDVTV
Fus_oxys_ENH73763      ILMFLLLPETSGANILLRRAERLRKLTGNQRFMSQSEIDQRHMKVSAIAV
Fus_oxys_EGU73369      ILMFLLLPETSGANILLRRAERLRKLTGNQRFMSQSEIDQRHMKVSAIAV
Fus_oxys_EXL94287      ILMFLLLPETSGANILLRRAERLRKLTGNQRFMSQSEIDQRHMKVSAIAV
Nec_haem_XP_003040064  ILMFLLLPETSGANILLRRAKRLRKLTGNDRFMSQSEIDQRNMKVSSIAL
Fus_pseu_XP_009258565  ILMFLLLPETSGANILLRRAERLRKLTGNERFMSQSEIDQRHMKVSAIAL
Fus_gram_XP_011323833  ILMFLLLPETSGANILLRRAERLRKLTGNERFMSQSEIDQRHMKVSAIAL
Fus_fuji_CCT64241      ILMFLLLPETSGANILLRRAERLRKLTGNQRFMSQSEIDQRHMKVSAIAV
                       :**:.:***** :.****** ***::     **:***:***:*::* :::

P_brasilianum_hmfT3    DALIKPLEITIKDPAVLFVQVYTAIIYGIYYSFFEVFPLVYPVDYGMNLG
Pen_rube_XP_002560799  DALIKPMEITIKDPAVLFVQIYTAIIYGIYYSFFEVFPLVYPVDYNMNLG
Pen_oxal_EPS29964      DALLKPLQITIMDPAVLFVQVYTAITYGIYYSFFEVFPLVYPVYYHMNMG
Asp_terr_XP_001212020  DALIKPLEITIKDPAVLFVQIYTAIIYGIYYSFFEVFPLVYPVDYNMNLG
Fus_oxys_ENH73763      DALIKPMEITIKDPAVLFVQVYTAIIYGIYYSFFEVFPRVYPVYYNMNLG
Fus_oxys_EGU73369      DALIKPMEITIKDPAVLFVQVYTAIIYGIYYSFFEVFPRVYPVYYNMNLG
```

TABLE 16-continued

Amino acid sequence alignment of *Penicillium brasilianum* hmfT3 and 10 closest orthologues.

```
Fus_oxys_EXL94287     DALIKPMEITIKDPAVLFVQVYTAIIYGIYYSFFEVFPRVYPVYYNMNLG
Nec_haem_XP_003040064 DALIKPMEITIKDPAVLFVQVYTAIIYGIYYSFFEVFPRVYPVYYGMNLG
Fus_pseu_XP_009258565 DALIKPMEITIKDPAVLFVQIYTAIIYGIYYSFFEVFPRVYPVYYNMNLG
Fus_gram_XP_011323833 DALIKPMEITIKDPAVLFVQIYTAIIYGIYYSFFEVFPRVYPVYYNMNLG
Fus_fuji_CCT64241     DALIKPMEITIKDPAVLFVQVYTAIIY-----VFEVFPRVYPVYYNMNLG
                      ***:**::*** ********:**** *     .***** **** * **:*

P_brasilianum_hmfT3   QVGLVFLCILVSCIIGIAIYWSYLYFWMNPRIERFGFPAQESRLIPALPA
Pen_rube_XP_002560799 QIGLVFLCVLVSCIIGIAVYASYIHFWMNRRIRRFGFPVNEKLLIPALPA
Pen_oxal_EPS29964     QIGLVFLCILVSCLIGIAAYSAYLYYWMNPRIHRFGFPVQEARLIPALPA
Asp_terr_XP_001212020 QIGLVFLCILVSCILGIAIYFSYLYFWMNPRIARFGFPEQETRLVPALPA
Fus_oxys_ENH73763     QIGLVFLCVLVSCMIGVGLYVSYLYFYMDPRIAKRGWPIQESRLVPALPA
Fus_oxys_EGU73369     QIGLVFLCVLVSCMIGVGLYVSYLYFYMDPRIAKRGWPIQESRLVPALPA
Fus_oxys_EXL94287     QIGLVFLCVLVSCMIGVGLYVSYLYFYMDPRIAKRGWPIQESRLVPALPA
Nec_haem_XP_003040064 EIGLVFLCVLVSCIIGVAIYVAYLYYYMDPRIAKRGWPVQEARLAPALLA
Fus_pseu_XP_009258565 EIGLVFLCVLVSCMIGVGVYLSYLYFYMDPRIAKRGWPIQESRLVPALPA
Fus_gram_XP_011323833 EIGLVFLCVLVSCMIGVGVYLSYLYFYMDPRIAKRGWPVQESRLVPALPA
Fus_fuji_CCT64241     QIGLVFLCVLVSCMIGVGLYLSYLYFYMDPRIAKRGWPIQESRLVPALPA
                      ::******:****::*:. * :*::::*: ** : *:* :*  * *** *

P_brasilianum_hmfT3   SIGPTIGLFLFAWTARASIHWIAPTIGITIYGATVFIVMQCLFVYIPLSY
Pen_rube_XP_002560799 SFGPLIGLFLFAWTARASIHWIAPTIGITIYGATVFIVMQCIFMYIPLTY
Pen_oxal_EPS29964     ALGPTIGLFIFAWTARASIHWIVPTIGITIYGATVFVVMQCLFVYIPLSY
Asp_terr_XP_001212020 SFGPTIGLFLFAWTARASIHWIAPTIGITIYGATVFVVMQCIFVYIPLSY
Fus_oxys_ENH73763     ALGPTIGLFLFAWTARASIHWIVPTIGITIYGATVFIVMQCIFVYIPLSY
Fus_oxys_EGU73369     ALGPTIGLFLFAWTARASIHWIVPTIGITIYGATVFIVMQCIFVYIPLSY
Fus_oxys_EXL94287     ALGPTIGLFLFAWTARASIHWIVPTIGITIYGATVFIVMQCIFVYIPLSY
Nec_haem_XP_003040064 SIGPTIGLFLFAWTARKSIHWIAPTIGITIYGATVFIVMQCIFVYIPLSY
Fus_pseu_XP_009258565 SIGPTIGLFLFAWTARASIHWIVPTIGITIYGATVFVVMQCIFVYIPLSY
Fus_gram_XP_011323833 SIGPTIGLFLFAWTARASIHWIVPTIGITIYGATVFVVMQCIFVYIPLSY
Fus_fuji_CCT64241     ALGPTIGLFLFAWTARSSIHWIVPTIGITIYGATVFIVMQCIFVYIPLSY
                      ::** ****:****** *****.*************:****:*:****:*

P_brasilianum_hmfT3   PMYAASLFAANDFFRSALACGSVLFAHPLFGNLGVARGTSLLGGLSVIGI
Pen_rube_XP_002560799 PKYAASLFAANDFFRSALACGSVLFAHPLFGNLGVARGVSLLGGLSVIGI
Pen_oxal_EPS29964     PQYAASLFAANDFFRSALACGSVLFAHPLFGNLGVARGTSLLGGLSVIGI
Asp_terr_XP_001212020 PNYAASLFAANDFFRSALACGSVLFAHPLFGNLGVARGVSLLGGLSVIGI
Fus_oxys_ENH73763     PMYAASLFAANDFFRSALACGSVLFAQPLFDNLGVAKGTSLLGGLSVIGI
Fus_oxys_EGU73369     PMYAASLFAANDFFRSALACGSVLFAQPLFDNLGVAKGTSLLGGLSVIGI
Fus_oxys_EXL94287     PMYAASLFAANDFFRSALACGSVLFAQPLFDNLGVAKGTSLLGGLSVIGI
Nec_haem_XP_003040064 PMYAASLFAANDFFRSALACGSVLFAQPLFDNLGVAKGTSLLGGLSVIGI
Fus_pseu_XP_009258565 PMYAASLFAANDFFRSALACGSVLFAQPLFDNLGVDKGTSLLGGLSVIGI
Fus_gram_XP_011323833 PMYAASLFAANDFFRSALACGSVLFAQPLFDNLGVDKGTSLLGGLSVIGI
Fus_fuji_CCT64241     PMYAASLFAANDFFRSALACGSVLFAQPLFDNLGVAKGTSLLGGLSVIGI
                      * ************************:***.**** :*.***********

P_brasilianum_hmfT3   IGIWLLYYYGARLRSLSKFAISDD----
Pen_rube_XP_002560799 IGIWLLYFYGGRLRALSKFAISDPVE--
Pen_oxal_EPS29964     VGIWLLYVYGARLRSLSKFAISDD----
Asp_terr_XP_001212020 IGIWLLYFYGARLRALSKFALSPGASFE
Fus_oxys_ENH73763     IGIWLLYFYGGRLRSLSKFAISDHVE--
Fus_oxys_EGU73369     IGIWLLYFYGGKLRSLSKFAISDHVE--
Fus_oxys_EXL94287     IGIWLLYFYGGKLRSLSKFAISDHVE--
Nec_haem_XP_003040064 IGIWLLYFYGARLRALSKFAVYEHVE--
Fus_pseu_XP_009258565 IGIWLLYFYGAKLRSLSKFAVSDHVE--
Fus_gram_XP_011323833 IGIWLLYFYGAKLRSLSKFAVSDHVE--
Fus_fuji_CCT64241     IGIWLLYFYGGKLRSLSKFAISDHVE--
                      :****** **.:**:*****:
```

TABLE 17

Amino acid sequence alignment of *Penicillium brasilianum* hmfT4 and 10 closest orthologues.

```
P_brasilianum_hmfT4   -MSTTKEAFPHTDSDIMEDSEKNLPECEHIVSVEPTLKMRDGIVLMPQPS
Spo_sche_ERT02386     ---MKSDEIPRPE--VIEANEK--VSDQDATSIGNNLKTRGGVVLMPQPS
Tog_mini_XP_007915981 --MGTKQELDHVA--AMEHQEKS-GSDIEEPSLAPNLKKRDGVILMPQPS
Cap_coro_XP_007724585 MASSEKAAIADTTKSASVSDQVDKGDVEQTTADVNLKRTKDGILLVPQPT
Spo_sche_ERS98342     --MDTKHGVTVDAAGH-----HPS--SSDKTDGPPLKCNKHGIVLVPQPS
Asp_kawa_GAA83620     --MVDVKESQAVEVLQ-----TKSVSSGDREADTRIKTTAQGIPLVPQPS
Cap_coro_XP_007725190 MAVS----AADKTTSD------DQIAIEGGKDERVVKCRSDGIPLVPQPS
Asp_nige_XP_001389139 --MADVKELQSVEVLQ-----EKSMSSGDPEANARIKTTAQGIPLVPQPS
Gro_clav_EFX04858     -MNETKKIVAVDTERL-----DTSQEHSDKAEAPFVKHTKEGFLLVPQPS
Spo_sche_ERS94853     MGQPGAIDIQEQPSSE-----DFRSEKHDKPEPVFLKATKDGIPLHPQPS
```

TABLE 17-continued

Amino acid sequence alignment of *Penicillium brasilianum* hmfT4 and 10 closest orthologues.

```
Asp_nige_EHA26600      --MADVKELQSVEVLQ-----EKSMSSGDPEANARIKTTAQGIPLVPQPS
                                                                *. * ***:

P_brasilianum_hmfT4    DDPNDPLN------WSWFRKHAAMFTLSYLALVCYVAVTTLVTGTVPLAK
Spo_sche_ERT02386      DDPADPLN------WSWFEKHAAMFTISYLALICYMSVTTLVAGTVNVAE
Tog_mini_XP_007915981  DDPHDPLN------WSSFRKHMAMATISYLALTCYMTVTTLVPGTVELGK
Cap_coro_XP_007724585  DDPEEPLN------WSFAKKHGALVVLALGSFFVKFTATILAPGAHSLAK
Spo_sche_ERS98342      DDPEDPLN------WSFAKKHAAMFVLALESLLVKFSATLIAPGAHSLAA
Asp_kawa_GAA83620      DDPEDPLRGNCLQNWSTFVKHAALVVLAFESFMTKMSNTLIAPDALELAK
Cap_coro_XP_007725190  DDPEDPLN------WSSAKKHSAAVTLALMSFVLKFTTTLIAPGAHTLAA
Asp_nige_XP_001389139  DDPEDPLN------WSQFTKIAALMVLAFESFLVKFSATLIAPDALELAE
Gro_clav_EFX04858      DDPDDPLN------WSFSKKHVALFFLAMESLLVKFSATLISPGARTLAH
Spo_sche_ERS94853      DDPEDPLN------WSPLRKHAALVVLAMESLIIKFSNTVIAPGAHTLAA
Asp_nige_EHA26600      DDPEDPL-----------------------------------APDALELAE
                       *** :**                                  ..:  :.

P_brasilianum_hmfT4    SMHVSKSTAVYLGNTPVALYAVAPWFWSPLSHFIGRRPVLLMCNIIAVVG
Spo_sche_ERT02386      GLGVPKATAVYLGNTPVALYGVAPFLWSPLSHFIGRRPVLLLSNIMAMVG
Tog_mini_XP_007915981  EFNVPKETAVYLGSTPVALYGVGPFLWSPLSHSIGRRPVLLLCNIIAIVG
Cap_coro_XP_007724585  QFHVTAKRAVYIASASSIMPAVAPFFWIPMSHRYGRRPMLMAGSTMAIVF
Spo_sche_ERS98342      QFHTAASKATYIGSAPSILYAIAPFFWIPLSHRVGRRPVLLASQVIALVA
Asp_kawa_GAA83620      EFGVTKSTATYIGSAPPILNALTSFFWIPLSHRIGRRPVLLMGNLLALVS
Cap_coro_XP_007725190  QFGTPASKATYIGSTPTIMFSVAPLLWIPLSSRYGRRPITLIGNFMAIWF
Asp_nige_XP_001389139  EFNVPETTATYIGSVPSILNAITSFFWIPMSHRIGRRPVLLIGNLMTLVS
Gro_clav_EFX04858      LFHVPLSKATYIGSAPTIMNAVGPFFWIPISHRIGRRPVLLMSQIIAMVA
Spo_sche_ERS94853      QFGTAASTASYIGSAPSVLYAFAPFLWIPLSHRLGRRPVLLASHLVALLA
Asp_nige_EHA26600      EFNVPETTATYIGSVPSILNAITSFFWIPMSHRIGRRPVLLIGNLMTLVS
                         : ..    * *:....  : .. . :* *:*   ****: :    :::

P_brasilianum_hmfT4    AVVVTTSKTYASCMVGRVILGAGGSAFWTLGPASIGDIFFRHEKGKKIGV
Spo_sche_ERT02386      AGIVTSAENYGTAMAGRVILGAGGSAFWTLGPACIGDIFFRHEKGKKIGI
Tog_mini_XP_007915981  TIIVATSHSYGACMAGRIILGLGGSAFWSLGPASIGDMFFRHEKGKKIGI
Cap_coro_XP_007724585  ALIIARADTYAQALVCRLFMAFGASSAICIGPAAISDMFFLHEKGTRMGF
Spo_sche_ERS98342      AIGVARSESYAQALGCRMVMGFGGSAGLCIGPAAISDMFFLHEKGSRMGV
Asp_kawa_GAA83620      SIGVARSQTYAQALACRMVMTFGGSVGLSIGPAAISDMFFLHEKGSRMGV
Cap_coro_XP_007725190  AIGVAESESYASALVCRIFMGFCGAAGLCLGPAGIADMFFLHEKGRHMGL
Asp_nige_XP_001389139  AIGVARSQTYAQCLACRMLMNVGGSVGLSIGPAAISDMFFLHEKGSRMGV
Gro_clav_EFX04858      AIGVGRSETYAQALGCRMVMGFGGSAGLCIGPAAISDMFFLHEKGTRMGI
Spo_sche_ERS94853      AIGVGRAQSYSQALGCRMLMGFGGSAGLCISTAAISDMFFLHEKGTRLGL
Asp_nige_EHA26600      AIGVARSQTYAQCLACRMLMNVGGSVGLSIGPAAISDMFFLHEKGSRMGV
                       :  :  :..*. .:  *:.:    .:    :..* *.*:** **** ::*.

P_brasilianum_hmfT4    STLAIVIAPFLGTIIGGPIIENEKLGWPASQWIPLIFMAAGFIMQIFFLP
Spo_sche_ERT02386      STLAIVVSPFLGTLVGGAIIENPHLGWPASQWIPLIFMGVGLVMQVFFLP
Tog_mini_XP_007915981  STLAIVVSPFAGGIIGGAIIDSPKLGWRWSQWIPLILMAIGFAMQVVFLP
Cap_coro_XP_007724585  NTILLITAPYLGGVVGGSIMYNPNLGWRWTMYIAAILLAGLLICQFLFVP
Spo_sche_ERS98342      NSILLVVAPYVGGVAGGAIQQNPALGWRWSMYVSAITYAVQLTAQFCLVP
Asp_kawa_GAA83620      NSILLVIGPYVGGVAGASIAYNPNLGWRWSMYIAAILYAAQFVFQLFVP
Cap_coro_XP_007725190  NTVLLVSAPYAGGVAGGAVQFNKSLGWRWSMYIAAIIYSGLFVAQLLLVP
Asp_nige_XP_001389139  NSILLVISPYVGGVAGGSIAYNKSLGWRWSMYIAAILYATQFVAQIFFVP
Gro_clav_EFX04858      QSILLVVAPYVGGVAGGSIQYNSKLGWRWSMYVSAICYSAQFVCQFFFVP
Spo_sche_ERS94853      NGMLFVVAPYIGGVAGGAIQQNKHLGWRWAMYIAAICYAVQLVLQCLLVP
Asp_nige_EHA26600      NSILLVISPYVGGVAGGSIAYNKSLGWRWSMYIAAILYATQFVAQIFFVP
                       . : :: .*: * : *..:   .   ***  : ::. *   .   :   *   ::*

P_brasilianum_hmfT4    ETIYIRETRAHPAIMSTSTPGKPTFWDRYGIHIPKRSEEKQHSFLFIATR
Spo_sche_ERT02386      ETIYVREVQGQRAGLASKT--KATLWDRYGVRIPQRTSDKKHSFFFIFSR
Tog_mini_XP_007915981  ETVYVREIGSPGGVPQPVTPTKPTRWGRYGIHIPKRPADKRDGFWFIASR
Cap_coro_XP_007724585  ETIFDR-ALA-KPVHEK---PPPTIAARLGFRRPTAT--RNENWGHTFTR
Spo_sche_ERS98342      ETIYER-----GGHRR----QPQSVARRFGFRTPTNP--TGESWLQTFRR
Asp_kawa_GAA83620      ETIYVRDENG-QGVSRSSEPKPTTFLSRLKFRPPPPP--KGESWGRTFIK
Cap_coro_XP_007725190  ETLYPRPAAG-APAPKS---TTTGTLRKLGFRKPTYA--KDPTWLDLFSR
Asp_nige_XP_001389139  ETIYTRNEKT-SAESKPSDRKKSTFLSRMKFRKPVVP--KEETWGQTFRK
Gro_clav_EFX04858      ETIYEREVAA-AELPE----QKKTIWRRLGFRMPTNP--SGETWLQTFRR
Spo_sche_ERS94853      ETIYNKDVAA-AEPPE----AKATLYRRLGFRTPKPA--PGETWAATFRM
Asp_nige_EHA26600      ETIYTRNEKT-SAESKPSDRKKSTFLSRMKFRKPVVP--KEETWGQTFRK
                       **:: :                        :   .: *   .       :

P_brasilianum_hmfT4    PFVLFKFPAVILSAFWFGIAYMMHVGITSEIPLIFEEH--YDFSVLEIGL
Spo_sche_ERT02386      PFVLLRFPAITLGTFWFGVAYMMHVGITAEIPLIFEAK--FHFTVLDVGL
Tog_mini_XP_007915981  PFVMFKFPVVVLTSFWFGLAYWCHVGITAELPLIFEPEP-FNFSVTDVGL
Cap_coro_XP_007724585  PFAMFAYPAVVLPSFWFSVTAMTEVANTAGFPLNFGPGSRWHFNTQEIGF
Spo_sche_ERS98342      PYAMFVYPAVVVPSFWVSTAVMTEVANTAGFTLNFGVTSRFHFTTAQVGY
Asp_kawa_GAA83620      PYKMFAYPAVFLPSFWFGVACMTEVGNTAGFALNFGSDSRWGFNLAQVGF
Cap_coro_XP_007725190  PVAMFAYPTVLLPSIWFSLAAMTEVANTAGFPLNFGEHTRWNFNTRSVGF
Asp_nige_XP_001389139  PYKMFAYPAVVLPSFWFGVANMTEVGNTAGFALNFGSKSRFHFNLAQVGF
Gro_clav_EFX04858      PFVMFAYPAVVLPSFWASVAVMTEVANTAGFAINFGASSRFHFNTAQVGF
```

TABLE 17-continued

Amino acid sequence alignment of *Penicillium brasilianum* hmfT4 and 10 closest orthologues.

```
Spo_sche_ERS94853     PFSMFAYPAVVLPCFWASTCIMTEVANTAGLSLNFGSGTRFDFSVAQVGY
Asp_nige_EHA26600     PYKMFAYPAVVLPSFWFGVANMTEVGNTAGFALNFGSKSRFHFNLAQVGF
                      *  :: :*.: :  :* .     .*. *: :.: *     : *.  .:*

P_brasilianum_hmfT4   SGFSGLIGALLGEVYAGPSLDFIAKRTMKQGREWRPEYRLQAIWPALITV
Spo_sche_ERT02386     SGLSGLIGALIGEAYAGPSIDYLARRSLKQGKEWRPEYRLKVIWPALVAI
Tog_mini_XP_007915981 AAFSGLIGALIGEAYAGPAIDYIAKRCLKQGKEWRPEMRLKAIWPALVAT
Cap_coro_XP_007724585 CSFSGFIGAIVGEFFAGPLCDLVAKRHLNKGTAWKPEYLLPLTISGLITV
Spo_sche_ERS98342     CFLSGLIGAFSGELLAGPLCDLLVKRALKKEHGWRPETLLVLNVTGLVAI
Asp_kawa_GAA83620     CYFSGVIGAALGEIFGGPLCDMLAKYSIRHGKEWKPERLLHLVWSGMVTI
Cap_coro_XP_007725190 CSFSGFIGALLGEIFAGPLCDFIAGRALAKKRAWVPEKILPVTFISLVTI
Asp_nige_XP_001389139 CYFSGIIGAGIGEIFGGPLCDMVAKYSLRRGQEWRPERLLHLAWSALITI
Gro_clav_EFX04858     CFISGLIGAFTGEVCAGPLCDMAVRNSLRRNQVWRAEKLLKLAITGLVTI
Spo_sche_ERS94853     CFFAGLIGSSLGEVCAGPLCDMTAKRSLRSGVAWVPEKLLKLFLSGLFTT
Asp_nige_EHA26600     CYFSGIIGAGIGEIFGGPLCDMVAKYSLRRGQEWRPERLLHLAWSALITI
                      . ::*.**:  **  .**  *  .   :     * .*  *     .:.:

P_brasilianum_hmfT4   PAGLIMFGTSIQFGN--VWITPLIGQAVYIFGIEIATTVIQTYILECYPR
Spo_sche_ERT02386     PGGLVMFGTAIEFGN--SWVTPLVGQLIYIFGIEIATTIIQTYILESYPR
Tog_mini_XP_007915981 PIGLIMFGVSIQFGN--AWITPLVGQGIYIFGIEIATTVWY---------
Cap_coro_XP_007724585 PAGLLLYGFELQWPT--GWAAALTGVAIFTAGQEILMTVLMTYMTDCYPG
Spo_sche_ERS98342     VGGLLVYGIQLQGSAPGDWASPLAGMILFVFGQEIIVTVVMTYMTDCYPD
Asp_kawa_GAA83620     SAGLLLYGLELEYGN--NWAAALTGIGLFTFGQEVLVTVLLTYMTDCYPE
Cap_coro_XP_007725190 PAGLLLYGLELEYPT--GWAAALTGVAIFAFGQEVALTAIMTYLVDCYPQ
Asp_nige_XP_001389139 SAGLLLYGLELEYGD--SWAAALTGIGLFTFGQEVLVTVLLTYMTECYPE
Gro_clav_EFX04858     FAGLMLYGFELESSK--AWARPLAGMILFVFGQEVVVTIIMTYMTDCYPE
Spo_sche_ERS94853     FAGLLVYGFTLEYVQTSQWAVPLVGLGLFVFGQEIVVTVLLAYMTECYRD
Asp_nige_EHA26600     SAGLLLYGLELEYGD--SWAAALTGIGLFTFGQEVLVTVLLTYMTECYPE
                        **:::*  ::      *  .* *  ::  * *:  *

P_brasilianum_hmfT4   QGAEANLVFNLIRNLFSYISPFFVQPMIATLG-TTSPFGLSAALTAFFFP
Spo_sche_ERT02386     QGAEANLIFNLVRNIFSYISPFFLTPFIAKVG-YAAPFGLFAALTVVFFP
Tog_mini_XP_007915981 --------------IFEFLS--FV--------------------------
Cap_coro_XP_007724585 SASEVSIVFQCLLNAMAYHPPFYVPQWIAEPGGAKVPYIVFAVLPVVFFP
Spo_sche_ERS98342     QAAEVAIVFQFFFNLMCFHPPFYTPGWIASAG-ARTPYIVYAVIPLALFP
Asp_kawa_GAA83620     DAAEVTLVLQFFFAIQTFHVPFYLPQWIKQPGGAKVPYIVFAALPVVLYP
Cap_coro_XP_007725190 RASECSVVFQFWRNLMAFHPPFYVPQWIESGGGAKVPYIVFACLAVGLFP
Asp_nige_XP_001389139 DAAEVAIVFQFFFAVQTFHPPFYLPQWIKQPGGAKVPYIVFAALPIVLYP
Gro_clav_EFX04858     HAAEVAVVFQFFFNLMCYHPPFYTPQWIASAG-SKVPYIVYAVLPVGLFP
Spo_sche_ERS94853     RAVECTIVFQFFLNLMCFPPPFFTPLWIAKKGGAKVPYIVYALLPVAFFP
Asp_nige_EHA26600     DAAEVAIVFQFFFAVQTFHPPFYLPQWIKQPGGAKVPYIVFAALPIVLYP
                                       :    :

P_brasilianum_hmfT4   FTVGVLMWRGKQIRDKGGDPGWSRD-------------------------
Spo_sche_ERT02386     FTILVLMLRGKQLREKAGDPGWSRD-------------------------
Tog_mini_XP_007915981 --------------------------------------------------
Cap_coro_XP_007724585 LTIGVLMWKGPQLRARGPWFTI----------------------------
Spo_sche_ERS98342     LLMGPFIWKGEQIRSKGPLFRLSK--------------------------
Asp_kawa_GAA83620     ICIWIFEWKGEKIRKRGPLFRI----------------------------
Cap_coro_XP_007725190 FGVGTLLWKGSNLRARGPMFSFSHKQ------------------------
Asp_nige_XP_001389139 FCISLFTWKGPQIRKRGPFFVL----------------------------
Gro_clav_EFX04858     ILIGPFMWKGSQIREKGPLFRFISFKRKATKTSFKASSKKFFKKLLGREK
Spo_sche_ERS94853     LCILPFMLKGQAIRERGGVLAFWKRRQ-----------------------
Asp_nige_EHA26600     FCISLFTWKGPQIRKRGPFFVL----------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     KDIASNFPSQGEVVFHPPAAKEESNIEAASEEPFASTLSNTPSVQANIVS
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     SSSQNAVPQTDDIPSTPEAATEALTVSPHPISNTSLIVADNAANPVSENV
```

TABLE 17-continued

Amino acid sequence alignment of *Penicillium brasilianum* hmfT4 and 10 closest orthologues.

```
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      VLSAPQTDDIASTPPPTTAEASPSDELWTRAFGLFREKEPELARDYMTHL
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      ATLHNSVDSVDLSASRSVKDLVDRLLEKREEKLWKVSILGKSVKIREQTE
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      KLVRLLVFFDPVVKEAVSSQPYAALAWSGVSLILPLLTSGTTQNEAMLKG
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      FDTIGNEQLYWNICEKTYLESAEHEIYKPLVEPLAQLYSDMIAFQALAIC
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      HYSKAQLSRAWENIAGSNDWDVRANKIEKQSTNIQRNILNLDKQEIRILW
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
Tog_mini_XP_007915981  --------------------------------------------------
Cap_coro_XP_007724585  --------------------------------------------------
Spo_sche_ERS98342      --------------------------------------------------
Asp_kawa_GAA83620      --------------------------------------------------
Cap_coro_XP_007725190  --------------------------------------------------
Asp_nige_XP_001389139  --------------------------------------------------
Gro_clav_EFX04858      NTQLQGIQESQFALNDVRQILSENNRLNQKRYDDEKERELLKELASAYES
Spo_sche_ERS94853      --------------------------------------------------
Asp_nige_EHA26600      --------------------------------------------------

P_brasilianum_hmfT4    --------------------------------------------------
Spo_sche_ERT02386      --------------------------------------------------
```

TABLE 17-continued

Amino acid sequence alignment of *Penicillium brasilianum* hmfT4 and 10 closest orthologues.

```
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     YKNFNKQRVEGTCEWFFNDNRFRTWRDSKMSSLLWVSAGPGCGKSVLSRA
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     LVDEHRLSTNAATSTVCHFFFKDGDARRLRSTAALCAVLHQLFTQDHTGS
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     LIKHALPSYNEGMALRNNFPGLWKILINCANSPEAGQIICVLDALDECEI
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     QSRNELIGELKRFYCEQRELAKSSTLMFLITSRPYADLEFAFLKFNTTTY
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     LRFDGDEKSADIGKEISLVIDERVNTVAASFSEKHRLELADHLKSMENRT
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     YLWLHLVFSIIEGNFSYSRPLDIKKLLSQIPPEVSGAYEQILDKSSNKDL
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
```

TABLE 17-continued

Amino acid sequence alignment of *Penicillium brasilianum* hmfT4 and 10 closest orthologues.

```
Asp_nige_XP_001389139 --------------------------------------------------
Gro_clav_EFX04858     TMKLLQLVLAAEHPLTLDEVNIALALADSPQDSAAELKSALWPKGNFQTT
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     VRNFCGLFVSVYDSKLFFIHQTAREFLLSSERDGNWKGHFALPECHSILS
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     RVCIDYLLFPDLVEHPLIVEDEENEKETRPSFFEYAARYWTSHYNSQEDA
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     NAYKSRKDACMLCHKINIEPMDTTKTSALQAASLQGQLKTIRLLIDRGAN
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     VNLQGGDYGSALQAASRNGYTEIVQILLNSGADVNLDGGAALKAASRNGH
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     TEIVQILLNSGADVNLQGGEYGSALQAASSFGYKEVVQILLNSGADVNLQ
Spo_sche_ERS94853     --------------------------------------------------
Asp_nige_EHA26600     --------------------------------------------------

P_brasilianum_hmfT4   --------------------------------------------------
Spo_sche_ERT02386     --------------------------------------------------
Tog_mini_XP_007915981 --------------------------------------------------
Cap_coro_XP_007724585 --------------------------------------------------
Spo_sche_ERS98342     --------------------------------------------------
Asp_kawa_GAA83620     --------------------------------------------------
Cap_coro_XP_007725190 --------------------------------------------------
Asp_nige_XP_001389139 --------------------------------------------------
Gro_clav_EFX04858     GGEYGSALQAASIFRHKEVVQILLNSGADVNLDGGAALKAASRKGQTEIV
Spo_sche_ERS94853     --------------------------------------------------
Asp_nige_EHA26600     --------------------------------------------------
```

TABLE 17-continued

Amino acid sequence alignment of *Penicillium brasilianum* hmfT4 and 10 closest orthologues.

```
P_brasilianum_hmfT4    --------------
Spo_sche_ERT02386      --------------
Tog_mini_XP_007915981  --------------
Cap_coro_XP_007724585  --------------
Spo_sche_ERS98342      --------------
Asp_kawa_GAA83620      --------------
Cap_coro_XP_007725190  --------------
Asp_nige_XP_001389139  --------------
Gro_clav_EFX04858      EMLHASANNKTEEL
Spo_sche_ERS94853      --------------
Asp_nige_EHA26600      --------------
```

TABLE 18

Amino acid sequence alignment of *Penicillium brasilianum* hmfT5 and 10 closest orthologues.

```
P_brasilianum_hmfT5    MEDHEK--------EYDSTSPPGTATEE---------GNGGYFNTLTVPE
Pen_digi_EKV20717      MEQHPGPDDASLHSEYGTEDEDNNQDLENSLVRKLNTHDFTSVETLRSPQ
Pen_digi_EKV19541      MEQHPGPDDASLHSEYGTEDEDNNQDLENSLVRKLNTHDFTSVETLRSPQ
Pen_rube_XP_002565665  MEQHPGLDDGSLHSEYQNEDENDNKSPDNQPIHKLNTHNFTSVETLHVPQ
Asp_oryz_KDE82314      MEFH----------LHDEAPPASTAPTEYGDQSGEEFEAYSEKPTLGVPD
Asp_oryz_EIT77345      MEFH----------LHDEAPPASTAPTEYGDQSGEEFEAYSEKPTLGVPD
Asp_flav_XP_002380612  MEFH----------LHDEALPASTAPTEYGDQSGEEFEAYSGKPTLGVPD
Asp_terr_XP_001208847  -MEK----------NFDTSDDFSSSP----------LPETKSYETLAVPN
Asp_kawa_GAA86951      MNSH----------EFPEDEKSSDLP----------VPERKSLDTLNVPH
Asp_nige_XP_001400982  MNPP----------EFPEDEKSSDLP----------IPERKSLDTLNVPH
Oph_pice_EPE02908      MDQY-------------ENSDDSETPAD---------NDNYRPNRLSVPH
                                             .                      *  *.

P_brasilianum_hmfT5    INLREASSAETLTPH--ASVVQPPKKA-AEWHMTPQVIRNAERDEAAGFK
Pen_digi_EKV20717      VNIHEAKSAETLNVA-NAETSLLPKKA-AEWSMTPQVIRNAERDEAAGFK
Pen_digi_EKV19541      VNIHEAKSAETLNVA-NAETSLLPKKA-AEWSMTPQVIRNAERDEAAGFK
Pen_rube_XP_002565665  ANIHEAKSSETLNVA-HADTSIPPKKT-AEWSMTPQVIRNAERDEAAGFK
Asp_oryz_KDE82314      NNVREATSAETLAVHGSPHITPPPGRD-AEWSMTDQVIRNKERSEAAGYK
Asp_oryz_EIT77345      NNVREATSAETLAVHGSPHITPPPGRD-AEWSMTDQVIRNKERSEAAGYK
Asp_flav_XP_002380612  NNVREATSAETLAVHGSPHITPPPGRD-AEWSMTDQVIRNKERSEAAGYK
Asp_terr_XP_001208847  LNIREASSAETLAAP-HANNTPTPGKDAAEWHMTPQVIQQQEREIAAGFK
Asp_kawa_GAA86951      IDVREAPSSETLTVP-HANTTSPPGKD-AEWSMTPQVIRSQEREAAAGFK
Asp_nige_XP_001400982  INVREAPSAETLIVP-HAVNASAPGKD-AEWSMTPQVIRSQEREAAAGFK
Oph_pice_EPE02908      GNSPEASSSETLEALFPPTGSPPEKKKIAEWSMTPQVVRNAERDAAAGFK
                        :  ** *:***     .       :  *** ** **::. **. ***:*

P_brasilianum_hmfT5    RRELGVTWQDLSVEVLAAEAAVKENMISQFNVPQLIKDFRRKPPLKSILS
Pen_digi_EKV20717      RRELGVTWQNLTVDVLAAEAAVNENMISQFNVPQLIKDFRRKPPLKSILS
Pen_digi_EKV19541      RRELGVTWQNLTVDVLAAEAAVNENMISQFNVPQLIKDFRRKPPLKSILS
Pen_rube_XP_002565665  KRELGVTWQSLTVDVLAAEAAVNENMISQFNLPQLIKDFRRKPPLKSILS
Asp_oryz_KDE82314      KRELGVTWQNLTVEVLAAEAAVKENQFTQYNIIQLIQDWRRKPPLKAILQ
Asp_oryz_EIT77345      KRELGVTWQNLTVEVLAAEAAVKENQFTQYNIIQLIQDWRRKPPLKAILQ
Asp_flav_XP_002380612  KRELGVTWQNLTVEVLAAEAAVKENQFTQYNIIQLIQDWRRKPPLKAILQ
Asp_terr_XP_001208847  RRELGVTWENLSVDVLAAEAAVKENLFSQFNIPQLIKDWRRKPPMKSILS
Asp_kawa_GAA86951      KRELGVTWKNLGVDVLAAEAAVNENLFSQFNVPQRIRDFTRKPPLKSILA
Asp_nige_XP_001400982  KRELGVTWKNLGVDVLAAEAAVNENLFSQFNLPQRIRDFTRKPPLKSILT
Oph_pice_EPE02908      KRELGVTWQNLSVDVIAAEAAVKENMVSQFNVPQLVKDYLHKPPLKSIVQ
                       :*******:.* *:*:******:** .:*:*: * ::*: :***:*:*:

P_brasilianum_hmfT5    NSHGCVKPGEMLLVLGRPGSGCTTLLKMLANRREG-YQNITGDVRFGNMT
Pen_digi_EKV20717      DSHGCVKPGEMLLVLGRPGSGCTTLLKILSNRREG-YHTINGDVRFGNMT
Pen_digi_EKV19541      DSHGCVKPGEMLLVLGRPGSGCTTLLKILSNRREG-YHTINGDVRFGNMT
Pen_rube_XP_002565665  DSHGCVKPGEMLLVLGRPGSGCTTLLKMLSNRREG-YHTVNGDVRFGSMS
Asp_oryz_KDE82314      DSHGCVKPGEMLLVLGRPGSGCTTLLKMLANRREG-YHSVHGDVSFGNMN
Asp_oryz_EIT77345      DSHGCVKPGEMLLVLGRPGSGCTTLLKMLANRREG-YHSVHGDVSFGNMN
Asp_flav_XP_002380612  DSHGCVKPGEMLLVLGRPGSGCTTLLKMLANRREG-YHSVHGDVSFGNMN
Asp_terr_XP_001208847  DSHGCVKPGEMLLVLGRPGSGCTTLLKLLTNRRKG-YHTIRGDVRFGNMT
Asp_kawa_GAA86951      ESHGCVKPGEMLLVLGRPGSGCTTLLNLLSNRRHG-YHTIKGDVSFGNMS
Asp_nige_XP_001400982  ESHGCVKPGEMLLVLGRPGSGCTTLLNLLSNRRHG-YHTIKGDVSFGNMS
Oph_pice_EPE02908      DSHGCVKPGEMLLVLGRPGSGCTTLLKMLSNHRDGGYKTINGDVRFGNMT
                       :*************************::*:*:*.* *:.: *** **.*.

P_brasilianum_hmfT5    PEEASRYQGQIVMNTEEELFYPRLTVGQTMDFATKLKVPYHLPGEGKSVA
Pen_digi_EKV20717      PKEAEGYNGQIVMNTEEELFYPRLTVGQTMDFAARLKVPFHLPEGAQSVE
Pen_digi_EKV19541      PKEAEGYNGQIVMNTEEELFYPRLTVGQTMDFAARLKVPFHLPEGAQSVE
Pen_rube_XP_002565665  PKEAEDYNGQIVMNTEEELFYPRLTVGQTMDFAARLKVPFHLPEGVQSVD
Asp_oryz_KDE82314      SEEAAHYRGQIVMNTEEELFYPRLTVGQTMDFATKLKVPAHLPAETKSVH
```

TABLE 18-continued

Amino acid sequence alignment of *Penicillium brasilianum* hmfT5 and 10 closest orthologues.

```
Asp_oryz_EIT77345       SEEAAHYRGQIVMNTEEELFYPRLTVGQTMDFATKLKVPAHLPAETKSVH
Asp_flav_XP_002380612   SEEAAHYRGQIVMNTEEELFYPRLTVGQTMDFATKLKVPAHLPAETKSVH
Asp_terr_XP_001208847   HEEAVQYQSQIVMNTEEELFYPRLTVGQTMDFATRLKVPSHLPNDVKSVE
Asp_kawa_GAA86951       HEEAAQYRSHIVMNTEEELFYPRLTVGQTMDFATRLKVPSHLPDGTASVS
Asp_nige_XP_001400982   HEEAAQYRSHIVMNTEEELFYPRLTVGQTMDFATRLKVPSHLPDGAASVK
Oph_pice_EPE02908       AEEALNYHGQIIMNTEEELFYPRLTVGQTIEFATKLKIPFHLPDGIKSVE
                         :**  *..:*:*****************::**::**:* ***    **

P_brasilianum_hmfT5     EYTAETKQFLLESMGIAHTADTKVGNEFVRGVSGGERKRVSIIECLATRG
Pen_digi_EKV20717       EYTAETKEFLLQSMGIAHTADTKVGNEFVRGVSGGERKRVSIIECLATRG
Pen_digi_EKV19541       EYTAETKEFLLQSMGIAHTADTKVGNEFVRGVSGGERKRVSIIECLATRG
Pen_rube_XP_002565665   EYTAETKQFLLESMGISHTADTKVGNEFVRGVSGGERKRVSIIECLATRG
Asp_oryz_KDE82314       DYVAETKQFLLESMKIAHTADTKVGNEFVRGVSGGERKRVSIIECMATNG
Asp_oryz_EIT77345       DYVAETKQFLLESMKIAHTADTKVGNEFVRGVSGGERKRVSIIECMATNG
Asp_flav_XP_002380612   DYVAETKQFLLESMKIAHTADTKVGNEFVRGVSGGERKRVSIIECMATNG
Asp_terr_XP_001208847   EYTAETKRFLLESMGIAHTADTKVGNEFVRGVSGGERKRVSIIEVLATKG
Asp_kawa_GAA86951       EYTAETKQFLMESMGISHTADTKVGNEFVRGVSGGERKRVSIIECLATRG
Asp_nige_XP_001400982   EYTAETKQFLMESMGISHTADTKVGNEFVRGVSGGERKRVSIIECLATRG
Oph_pice_EPE02908       EYTDETRDFLLESMGITHTADTPVGNEYVRGVSGGERKRVSIIECLATRA
                        :*. **: **::** *:***** ****:**************** :**..

P_brasilianum_hmfT5     SVFTWDNSTRGLDASTALEWAKALRAMTDVQGLSTIVTLYQAGNGIYNLF
Pen_digi_EKV20717       SIYSWDNSTRGLDASTALEWAKALRAMTDILGLSTIVTLYQAGNGIYNLF
Pen_digi_EKV19541       SIYSWDNSTRGLDASTALEWAKALRAMTDILGLSTIVTLYQAGNGIYNLF
Pen_rube_XP_002565665   SVYSWDNSTRGLDASTALEWAKALRAMTDVLGLSTIVTLYQAGNGIYNLF
Asp_oryz_KDE82314       SIFTWDNSTRGLDASTALEWAKALRAMTNVMGLTTIVTLYQAGNGIYNLF
Asp_oryz_EIT77345       SIFTWDNSTRGLDASTALEWAKALRAMTNVMGLTTIVTLYQAGNGIYNLF
Asp_flav_XP_002380612   SIFTWDNSTRGLDASTALEWAKALRAMTNVMGLTTIVTLYQAGNGIYNLF
Asp_terr_XP_001208847   SVFCWDNSTRGLDASTALEWAKALRAMTDVQGLSTIVTLYQAGNGIYNLF
Asp_kawa_GAA86951       SVFCWDNSTRGLDASTALEWAKALRAMTNVLGLSTIVTLYQAGNGIYNLF
Asp_nige_XP_001400982   SVFCWDNSTRGLDASTALEWAKALRAMTNVLGLSTIVTLYQAGNGIYNLF
Oph_pice_EPE02908       SVYCWDNSTRGLDASTALEWAKALRAMTDVLGLSTIVTLYQAGNGIYNLF
                        *:: ************************:: **:****************

P_brasilianum_hmfT5     DKVLVLDEGKQIYYGPAAEAKPFMENLGFVYTDGANIGDFLTGLTVPTER
Pen_digi_EKV20717       DKILVLDEGKQIYYGPAAAAKPFMEDLGFMYTDGANVGDFLTGLTVPTER
Pen_digi_EKV19541       DKILVLDEGKQIYYGPAAAAKPFMEDLGFMYTDGANVGDFLTGLTVPTER
Pen_rube_XP_002565665   DKVLVLDEGKQIYYGPAAAAKPFMEDLGFVYTDGANIGDFLTGVTVPTER
Asp_oryz_KDE82314       DKVLVLDEGKQIYYGPAASAKPFMEDLGFVYSDGANVGDYLTGVTVPTER
Asp_oryz_EIT77345       DKVLVLDEGKQIYYGPAASAKPFMEDLGFVYSDGANVGDYLTGVTVPTER
Asp_flav_XP_002380612   DKVLVLDEGKQIYYGPAASAKPFMEDLGFVYSDGANVGDYLTGVTVPTER
Asp_terr_XP_001208847   DKVLVLDEGKQIYYGPAQAAKPFMEELGFVYSDGANIGDYLTGVTVPTER
Asp_kawa_GAA86951       DKALVLDEGKQIFYGPASAAKPFMENLGFVYTDGANVGDFLTGVTVPTER
Asp_nige_XP_001400982   DKVLVLDEGKQIFYGPAAAAKPFMENLGFVYTDGANVGDFLTGVTVPTER
Oph_pice_EPE02908       DKVLVLDEGKEIYYGPASEAKGFMESIGFVYSEGANIGDFLTGVTVPTER
                        ** *******:*:****  ** ***.:**:*::***:**:***:******

P_brasilianum_hmfT5     KIRPGWENRFPRTADAILTEYQNSATYKNEVSLYGYPDTDLAAERTEAFK
Pen_digi_EKV20717       KIRPGFENSFPRNADAILTEYIKSSTYRRMVSTYDYPDSELSRERTAAFK
Pen_digi_EKV19541       KIRPGFENSFPRNADAILTEYIKSSTYRRMVSTYDYPDSELSRERTAAFK
Pen_rube_XP_002565665   KIRPGYENTFPRNADAILAEYKKSSIYDRMVSTYDYPDSNLSRERTDAFK
Asp_oryz_KDE82314       KIRPGYENRFPKNAEAILAEYQRSTLYQTMTREYDYPSSDAARQRTEEFK
Asp_oryz_EIT77345       KIRPGYENRFPKNAEAILAEYQRSTLYQTMTREYDYPSSDAARQRTEEFK
Asp_flav_XP_002380612   KIRPGFENRFPKNAEAILAEYQRSTLYQTMTREYDYPSSDAARQRTEEFK
Asp_terr_XP_001208847   KIRPGREHRFPRNADAILAEYKNSPLYTHMISEYDYPNSEIAKARTEDFK
Asp_kawa_GAA86951       RIRPGYENRFPRNADAIMAEYKASAIYSHMTAEYDYPTSAVARERTEAFK
Asp_nige_XP_001400982   RIRPGYENRFPRNADSIMVEYKASAIYSHMTAEYDYPTSAIAQERTEAFK
Oph_pice_EPE02908       KIKPGWENRFPRTAEAIFAEYQKSTICRDAMSEYDYPDTTLAATRTEDFK
                        :*:** *: **:.*::*:.**  *.         *.** :   :  **  **

P_brasilianum_hmfT5     ESVAWEKSKHLPKGSDLTTSFWAQLMSCTARQYQILWGEKSTFLIKQILS
Pen_digi_EKV20717       ESVAWEKSKHLPKSSSLTTSFWAQLVACTKRQYQILWGEKSTFITKQVLS
Pen_digi_EKV19541       ESVAWEKSKHLPKSSSLTTSFWAQLVACTKRQYQILWGEKSTFITKQVLS
Pen_rube_XP_002565665   ESVAWEKSSHLPKGSSLTTSFWVQLIACTKRQYQILWGEKSTFIIKQVLS
Asp_oryz_KDE82314       ESVAWEKAKHLPNSSTLTVGFWDQLIACTIRQYQILWGEKSTFLIKQVLS
Asp_oryz_EIT77345       ESVAWEKAKHLPNSSTLTVGFWDQLIACTIRQYQILWGEKSTFLIKQVLS
Asp_flav_XP_002380612   ESVAWEKAKYLPNSSTLTVGFWDQLIACTIRQYQILWGEKSTFLIKQVLS
Asp_terr_XP_001208847   ESVAFEKAKYLPKNTTLTTGFGTQLWACTIRQYQILWGEKSTFLIKQVLS
Asp_kawa_GAA86951       ESVAFEKTTHQPQKSPFTTGFGTQVLACTRRQYQILWGEKSTFLIKQILS
Asp_nige_XP_001400982   ESVAFEKTTHQPKKSPFTTGFGTQVLACTRRQYQILWGEKSTFLIKQILS
Oph_pice_EPE02908       HSVAWEKSSHLPKGSRLTTSFWAQVMFCTHRQYQILWGERSTFLIRQVLS
                        .***:**:.: *: : :*..*  *:  ** *********:***: :*:**

P_brasilianum_hmfT5     CVMALIAGSCFYNSPDTSAGLFTKGGAVFFSLLYNCIVAMSEVTESFKGR
Pen_digi_EKV20717       CAMALIAGSCFYDSPDTSEGLFTKGGAVFFSLLYNCIVAMSEVTESFKGR
Pen_digi_EKV19541       CAMALIAGSCFYDSPDTSEGLFTKGGAVFFSLLYNCIFAMSEVTESFKGR
Pen_rube_XP_002565665   CVMALIAGSCFYDSPDTSAGLFTKGGAVFFSLLYNCIVAMSEVTESFKGR
```

TABLE 18-continued

Amino acid sequence alignment of *Penicillium brasilianum* hmfT5 and 10 closest orthologues.

```
Asp_oryz_KDE82314     VAMALIAGSCFYNSPDTTAGLFTKGGAVFFALLYNCIVAMSEVTESFKGR
Asp_oryz_EIT77345     VAMALIAGSCFYNSPDTTAGLFTKGGAVFFALLYNCIVAMSEVTESFKGR
Asp_flav_XP_002380612 VAMALIAGSCFYNSPDTTAGLFTKGGAVFFALLYNCIVAMSEVTESFKGR
Asp_terr_XP_001208847 LSMALIAGSCFYNSPDTTAGLFTKGGAVFFSLLYNCIVAMSEVTESFKGR
Asp_kawa_GAA86951     LVMALIAGSCFYNAPQTSAGLFTKGGAVFFSLLYNTIVAMSEVTESFKGR
Asp_nige_XP_001400982 LVMALIAGSCFYNAPQTSAGLFTKGGAVFFSLLYNTIVAMSEVTESFKGR
Oph_pice_EPE02908     LAMALIAGSCFYDAPDDSSGLFTKGGAVFFTLLYNSMAAMSEVTDSFKGR
                        **********::*: :  ***********:**** : ******:*****

P_brasilianum_hmfT5   PILTKHKSFAMYHPAAFCLAQITADFPVLLFQCTIFSVVIYWMVGLKHTA
Pen_digi_EKV20717     PVLIKHKDFAMYHPAAFCLAQIMADFPVLLFQCSIFSVVIYWMSGLKHTA
Pen_digi_EKV19541     PVLIKHKDFAMYHPAAFCLAQIMADFPVLLFQCSIFSVVIYWMSGLKHTA
Pen_rube_XP_002565665 PVLVKHKGFAMYHPAAFSLAQIMADFPVLLFQCTIFSVVIYWMSGLKHTA
Asp_oryz_KDE82314     PVLIKHKSFAMYHPSAFCLAQITADLPVLLVQCTLFAVVIYWMTGLKHTA
Asp_oryz_EIT77345     PVLIKHKSFAMYHPSAFCLAQITADLPVLLVQCTLFAVVIYWMTGLKHTA
Asp_flav_XP_002380612 PVLIKHKSFAMYHPSAFCLAQITADLPVLLVQCTLFAVVIYWMTGLKHTA
Asp_terr_XP_001208847 PVLVKHKGFGFYHPAAFCLAQITADFPVLLFQCTIFAIVMYFMVGLKVDA
Asp_kawa_GAA86951     PVLIKHKGFAFYHPAAFCLAQITADFPVLLFQCTIFSVVLYWMVGLKATA
Asp_nige_XP_001400982 PVLIKHKAFAFYHPAAFCLAQITADFPVLLFQCTIFSVVLYWMVGLKATA
Oph_pice_EPE02908     PILTKHKRFAMHHPAAFCLAQITSDIPVILFQCTIFAVVLYWMTGLKSSA
                      *:* *** *.::**:**.**** :*:**:*.**::*::*:*:* ***  *

P_brasilianum_hmfT5   AAFFTFWAILFTTTLCITALFRFIGAAFSSFEAASKISGTAVKAIVMYAG
Pen_digi_EKV20717     AAFFTFWIILFTTILCITALFRFIGSAFSTFEAASKISGTAVKGIVMYAG
Pen_digi_EKV19541     AAFFTFWIILFTTILCITALFRFIGSAFSTFEAASKISGTAVKGIVMYAG
Pen_rube_XP_002565665 AAFFTFWIILFTTTLCITALFRFIGSAFSTFEAASKISGTAVKGIVMYAG
Asp_oryz_KDE82314     AAFFTFWAILFTTTLCITALFRCIGAGFSTFEAASKISGTAVKGIVMYAG
Asp_oryz_EIT77345     AAFFTFWAILFTTTLCITALFRCIGAGFSTFEAASKISGTAVKGIVMYAG
Asp_flav_XP_002380612 AAFFTFWAILFTTTLCITALFRCIGAGFSTFEAASKISGTAVKGIVMYAG
Asp_terr_XP_001208847 AAFFTFWAILFTTTLCITALFRFCGAAFSSFEAASKISGTAVKGIVMYAG
Asp_kawa_GAA86951     AAFFTFWIILFTTTLCVTALFRCIGAAFSTFEAASKISGTAIKGIVMYAG
Asp_nige_XP_001400982 AAFFTFWIILFTTTLCVTALFRCIGAGFSTFEAASKISGTAIKGIVMYAG
Oph_pice_EPE02908     AAFFTFWAVLFTTTLCLTALFRFIGAAFSSFEAASKISGTVVKGLVMYAG
                      ******* :**** **:*****  *:.**:**********.:*.:*****

P_brasilianum_hmfT5   YMIPKPEIKNWFLEFYYTNPFAYAFQAALTNEFHDQHIDCVGGNLIPSGP
Pen_digi_EKV20717     YMIPKPEMKNWFLELYYTNPFAYAFQAALSNEFHDRHIPCVGKNLIPSGP
Pen_digi_EKV19541     YMIPKPEMKNWFLELYYTNPFAYAFQAALSNEFHDRHIPCVGKNLIPSGP
Pen_rube_XP_002565665 YMIPKPQMKNWFLELYYTNPFAYAFQAAMSNEFHGRHIPCVGNNLIPSGP
Asp_oryz_KDE82314     YMIPKGRIKNWFLELYYTNPFAYAFQAALSNEFHGQTIPCVGNNLVPSGP
Asp_oryz_EIT77345     YMIPKGRIKNWFLELYYTNPFAYAFQAALSNEFHGQTIPCVGNNLVPSGP
Asp_flav_XP_002380612 YMIPKGRIKNWFLELYYTNPFAYAFQAALSNEFHGQTIPCVGNNLVPSGP
Asp_terr_XP_001208847 YMIPKPHIKNWFLELYYTNPFAYAFQAALSNEFHDQVIPCVGNNLIPSGP
Asp_kawa_GAA86951     YMIPKPKVKNWFLELYYTNPMAYAFQAALSNEFHGQVIPCVGKNIVPTGP
Asp_nige_XP_001400982 YMIPKPKVKNWFLELYYTNPMAYAFQAALSNEFHGQHIPCVGKNIVPNGP
Oph_pice_EPE02908     YMIPKPKVKNWFLELYYTNPFAYAFQAALSNEFHDQHVDCVGPNLIPNGP
                      ***** .:******:*****:*******::****.: : *** *::*.**

P_brasilianum_hmfT5   GYEDVGSGYKACAGVGGALPGADYVTGDQYLSSLHYKHSQLWRNFGVVWA
Pen_digi_EKV20717     GYENVGAENQACAGVGGALPGANYVTGDQYLASLHYKHSQLWRNFGVVWG
Pen_digi_EKV19541     GYENVGAENQACAGVGGALPGANYVTGDQYLASLHYKHSQLWRNFGVVWG
Pen_rube_XP_002565665 GYEEVGAENQACAGVGGALPGANYVTGDQYLGSLHYKHSQMWRNFGVVWG
Asp_oryz_KDE82314     GYENVSSANKACTGVGGALPGADYVTGDQYLLSLHYKHSQMWRNYGVLWG
Asp_oryz_EIT77345     GYENVSSANKACTGVGGALPGADYVTGDQYLLSLHYKHSQMWRNYGVLWG
Asp_flav_XP_002380612 GYENVSSANKACTGVGGALPGADYVTGDQYLLSLHYKHSQMWRNYGVLWG
Asp_terr_XP_001208847 GYENVGTANKACAGVGGALPGADYVTGDQYLGSLHYKHSQLWRNYGVVWA
Asp_kawa_GAA86951     GYEDVDSANKACTGVGGALPGADYVTGDQYLSSLHYKHSQLWRNFGVVWA
Asp_nige_XP_001400982 GYEDVDSANKACTGVGGALPGADYVTGDQYLSSLHYKHSQLWRNFGVVWA
Oph_pice_EPE02908     GYLDVDSAYKACAGVAGAMPGADFVTGDQYLSSLHYNHSQMWRNFGVIWV
                      ** :*.:  :**:**.**:***::******* ****:***:***:**:*

P_brasilianum_hmfT5   WWGFFAVLTVVFTCFWKSGAASGSSLLIPRENLKKHQVGND--EEAQ-NN
Pen_digi_EKV20717     WWGFFAILTIVFTSYWKSGAGSGASLLIPREKLKNSLAGIS--DEEAQRN
Pen_digi_EKV19541     WWGFFAILTIVFTSYWKSGAGSGASLLIPREKLKNSLAGIS--DEEAQRN
Pen_rube_XP_002565665 WWGFFAILTIVFTSYWKAGAGAGSSLLIPREKLKQHHAAVS--DEEAQNN
Asp_oryz_KDE82314     WWGFFAVLTVICTCFWKGGAAAGASLLIPREKLKAHRAHLD--AEAQKEK
Asp_oryz_EIT77345     WWGFFAVLTVICTCFWKGGAAAGASLLIPREKLKAHRAHLD--AEAQKEK
Asp_flav_XP_002380612 WWGFFAVLTVICTCFWKGGAAAGASLLIPREKLKAHRAHLD--AEAQKEK
Asp_terr_XP_001208847 WWGFFAVATIVCTCFWNAGAGSGAALLIPREKLKNHQRAAD--EESQ-VK
Asp_kawa_GAA86951     WWGFFAVLTIICTTYWKAGAGGSASLLIPRENLKQHQKSID--EESQ-IK
Asp_nige_XP_001400982 WWGFFAVLTIICTTYWKAGAGGSASLLIPRENLKQHQKSID--EESQ-VK
Oph_pice_EPE02908     WWGLFAGLTVFFTSRWKDSGSSGSSLLIPRENLKAHEGKAKSGDEEAQNN
                      ***:**  *:. *  *: .....::******:**      .   *    :

P_brasilianum_hmfT5   EKHAARTTTDEPVQVEDDNLVRNTSIFTWKNLTYTVKTPTGDRVLLDNIN
Pen_digi_EKV20717     EKTTARETIDEPVQVDDENLTRNTSIFTWRNLTYTVQTPTGDRVLLDNIH
Pen_digi_EKV19541     EKTTARETIDEPVQVDDENLTRNTSIFTWRNLTYTVQTPTGDRVLLDNIH
```

TABLE 18-continued

Amino acid sequence alignment of *Penicillium brasilianum* hmfT5 and 10 closest orthologues.

```
Pen_rube_XP_002565665 EKSTTRETPDEPIQVDDENLNRNTSIFTWKNLTYTVQTPTGDRVLLDNIH
Asp_oryz_KDE82314     DPAREKGSGDALTSADEGNLTHNTSIFTWKNLTYTVNTPTGERVLLDNIH
Asp_oryz_EIT77345     DPAREKGSGDALTSADEGNLTHNTSIFTWKNLTYTVNTPTGERVLLDNIH
Asp_flav_XP_002380612 DPAREKGSGDALTSADEGNLTHNTSIFTWKNLTYTVNTPTGERVLLDNIH
Asp_terr_XP_001208847 EKEQTRGPAAGESTAQDDNLTRNTSIFTWKNLKYTVKTPTGDRLLLDNVH
Asp_kawa_GAA86951     EKEQTKAATSDTTAEVDGNLSRNTAVFTWKNLKYTVKTPSGDRVLLDNIH
Asp_nige_XP_001400982 EKEQAKAATSDTTAEVDGNLSRNTAVFTWKNLKYTVKTPSGDRVLLDNIH
Oph_pice_EPE02908     EKNTPRPQADAPVEANDNSLVRNTSIFTWKDLTYTVNTPTGERVLLNQVN
                      :    :          : .* :**::***::*.***:**:*:*:**::::

P_brasilianum_hmfT5   GWVKPGMLGALMGSSGAGKTTLLDVLAQRKTEGTIKGSILVDGRELPVSF
Pen_digi_EKV20717     GWVKPGMLGALMGSSGAGKTTLLDVLAQRKTDGTIKGSIMVDGRELPVSF
Pen_digi_EKV19541     GWVKPGMLGALMGSSGAGKTTLLDVLAQRKTDGTIKGSIMVDGRELPVSF
Pen_rube_XP_002565665 GWVKPGMLGALMGSSGAGKTTLLDVLAQRKTDGTINGSIMVDGRELPVSF
Asp_oryz_KDE82314     GWVKPGMLGALMGSSGAGKTTLLDVLAQRKTEGTIKGSVLVDGRELPVSF
Asp_oryz_EIT77345     GWVKPGMLGALMGSSGAGKTTLLDVLAQRKTEGTIKGSVLVDGRELPVSF
Asp_flav_XP_002380612 GWVKPGMLGALMGSSGAGKTTLLDVLAQRKTEGTIKGSVLVDGRELPVSF
Asp_terr_XP_001208847 GWVKPGMLGALMGSSGAGKTTLLDVLAQRKTEGTINGSILVDGRPLPVSF
Asp_kawa_GAA86951     GWVKPGMLGALMGSSGAGKTTLLDVLAQRKTEGTITGSIMVDGRPLPVSF
Asp_nige_XP_001400982 GWVKPGMLGALMGSSGAGKTTLLDVLAQRKTEGTITGSIMVDGRPLPVSF
Oph_pice_EPE02908     GWVKPGMLGALMGSSGAGKTTLLDVLAQRKTEGTIRGSILVDGRPLPLSF
                      *******************************:*** **::**** **:**

P_brasilianum_hmfT5   QRMAGYCEQLDVHESYATVREALEFSALLRQSRDTPKAEKLKYVDTIIDL
Pen_digi_EKV20717     QRMAGYCEQLDVHEPFATVREALEFSALLRQSRNISKADKLKYVDTIIDL
Pen_digi_EKV19541     QRMAGYCEQLDVHEPFATVREALEFSALLRQSRNISKADKLKYVDTIIDL
Pen_rube_XP_002565665 QRMAGYCEQLDVHEPYATVREALEFSALLRQSRNTPKADKLKYVDTIIDL
Asp_oryz_KDE82314     QRMAGYCEQLDVHEPYATVREALEFSALLRQSRDTPREEKLKYVDTIIDL
Asp_oryz_EIT77345     QRMAGYCEQLDVHEPYATVREALEFSALLRQSRDTPREEKLKYVDTIIDL
Asp_flav_XP_002380612 QRMAGYCEQLDVHEPYATVREALEFSALLRQSRDTPREEKLKYVDTIIDL
Asp_terr_XP_001208847 QRMAGYCEQLDVHEPYATVREALEFSALLRQPRTTPKEEKLKYVDTIIDL
Asp_kawa_GAA86951     QRMAGYCEQLDVHEPFATVREALEFSALLRQPRTTPREEKLKYVDTIIDL
Asp_nige_XP_001400982 QRMAGYCEQLDVHEPFATVREALEFSALLRQPRTTPKEEKLKYVETIIDL
Oph_pice_EPE02908     QRMAGYCEQLDVHEPYATVREALEFSALLRQSRDVPRAEKLKYVETIIDL
                      **************.:***************.*  .: :*****:*****

P_brasilianum_hmfT5   LELHDLADTLIGSVGNGLSVEQRKRVTIGVELVSKPSILIFLDEPTSGLD
Pen_digi_EKV20717     LELHDLADTLIGTVGNGLSVEQRKRVTIGVELVSKPSILIFLDEPTSGLD
Pen_digi_EKV19541     LELHDLADTLIGTVGNGLSVEQRKRVTIGVELVSKPSILIFLDEPTSGLD
Pen_rube_XP_002565665 LELDDLADTLIGTIGNGLSVEQRKRVTIGVELVSKPSILIFLDEPTSGLD
Asp_oryz_KDE82314     LELHDLADTLIGTVGNGLSVEQRKRVTIGVELVSKPSILIFLDEPTSGLD
Asp_oryz_EIT77345     LELHDLADTLIGTVGNGLSVEQRKRVTIGVELVSKPSILIFLDEPTSGLD
Asp_flav_XP_002380612 LELHDLADTLIGTVGNGLSVEQRKRVTIGVELVSKPSILIFLDEPTSGLD
Asp_terr_XP_001208847 LELHDLADTLIGTVGNGLSVEQRKRVTIGVELVSKPSILIFLDEPTSGLD
Asp_kawa_GAA86951     LELHDLADTLIGTVGNGLSVEQRKRVTIGVELVSKPSILIFLDEPTSGLD
Asp_nige_XP_001400982 LELHDLADTLIGTVGNGLSVEQRKRVTIGVELVSKPSILIFLDEPTSGLD
Oph_pice_EPE02908     LELHDLADTLIGAVGNGLSVEQRKRVTIGVELVAKPSILIFLDEPTSGLD
                      ***.********::*******************:****************

P_brasilianum_hmfT5   GQSAYNTVRFLRKLADVGQAVLVTIHQPSAQLFAQFDTLLLLARGGKTVY
Pen_digi_EKV20717     GQSAYNTVRFLRKLADVGQAVTI--HQPSAQLFAQFDTLLLLAKGGKTVY
Pen_digi_EKV19541     GQSAYNTVRFLRKLADVGQAVTI--HQPSAQLFAQFDTLLLLAKGGKTVY
Pen_rube_XP_002565665 GQSAYNTVRFLRKLADVGQAV-----LPSAQLFAQFDTLLLLAKGGKTVY
Asp_oryz_KDE82314     GQSAYNTVRFLRKLADVGQAVLVTIHQPSAQLFAQFDTLLLLARGGKTVY
Asp_oryz_EIT77345     GQSAYNTVRFLRKLADVGQAVLVTIHQPSAQLFAQFDTLLLLARGGKTVY
Asp_flav_XP_002380612 GQSAYNTVRFLRKLADVGQAVLVTIHQPSAQLFAQFDTLLLLARGGKTVY
Asp_terr_XP_001208847 GQSAYNTVRFLRKLADVGQAVLVTIHQPSAQLFAQFDTLLLLARGGKTVY
Asp_kawa_GAA86951     GQSAYNTVRFLRKLADVGQAVLVTIHQPSAQLFAQFDTLLLLARGGKTVY
Asp_nige_XP_001400982 GQSAYNTVRFLRKLADVGQAVLVTIHQPSAQLFAQFDTLLLLARGGKTVY
Oph_pice_EPE02908     GQSAFNTVRFLRKLADVGQAVLVTIHQPSAQLFAQFDTLLLLAKGGKTVY
                      ****:****************      ****************:******

P_brasilianum_hmfT5   FGDIGDNGSTIKQYFGNYGAICPQEANPAEFMIDVVTGGIQEVKDKDWHQ
Pen_digi_EKV20717     FGDIGENAATVKQYFGQYGAQCPTEANAAEFMIDVVTGGIEAVKDKDWHQ
Pen_digi_EKV19541     FGDIGENAATVKQYFGQYGAQCPTEANAAEFMIDVVTGGIEAVKDKDWHQ
Pen_rube_XP_002565665 FGDIGDNAACVKQYFGQYGAQCPTDANAAEFMIDVVTGGIESVKDKDWHQ
Asp_oryz_KDE82314     FGDIGDNGAAIKQYFGKYGASCPIEANPAEFMIDVVTGGIEEVKDKDWHQ
Asp_oryz_EIT77345     FGDIGDNGAAIKQYFGKYGASCPIEANPAEFMIDVVTGGIEEVKDKDWHQ
Asp_flav_XP_002380612 FGDIGDNGAAIKQYFGKYGASCPIEANPAEFMIDVVTGGIEEVKDKDWHQ
Asp_terr_XP_001208847 FGDIGENGQTIKEYFGKYGAQCPVEANPAEFMIDVVTGGIESVKHMDWHQ
Asp_kawa_GAA86951     FGDIGDNGQTIKHYFGKYGAQCPVEANPAEFMIDVVTGGIESVKDKDWHQ
Asp_nige_XP_001400982 FGDIGENGQTIKNYFGKYGAQCPIEANPAEFMIDVVTGGIESVKDKDWHH
Oph_pice_EPE02908     FGDIGDNGATVKQYFGQYGAVCPEESNPAEFMIDVVTGGIEEVKDKDWHQ
                      *****:*.  :*.***:*** ** ::*.************: **. ***:

P_brasilianum_hmfT5   IWLDSPEQHQMITELDRMIADAASKPPGTVND-GYEFSMPLWEQIKIVTQ
Pen_digi_EKV20717     IWLDSPEQTRMIAELDGMIADAAAKPPGTVDD-GFEFSMPMWEQIKIVTQ
```

TABLE 18-continued

Amino acid sequence alignment of *Penicillium brasilianum* hmfT5 and 10 closest orthologues.

| | |
|---|---|
| Pen_digi_EKV19541 | IWLDSPEQTRMIAELDGMIADAAAKPPGTVDD-GFEFSMPMWEQIKIVTQ |
| Pen_rube_XP_002565665 | IWLDSPEQTRMIAELDRMIADAASKPPGTVDD-GFEFSMPLWEQTKIVTH |
| Asp_oryz_KDE82314 | IWLESPEHEHMMVELDQLISDAAAKPPGTHDD-GYEFSMPLWDQVKIVTH |
| Asp_oryz_EIT77345 | IWLESPEHEHMMVELDQLISDAAAKPPGTHDD-GYEFSMPLWDQVKIVTH |
| Asp_flav_XP_002380612 | IWLESPEHEHMMVELDQLISDAAAKPPGTHDD-GYEFSMPLWDQVKIVTH |
| Asp_terr_XP_001208847 | VWLESPEHTRMLQELDHMVEDAASKPPGTVDD-GFEFSMSLWEQTKIVTR |
| Asp_kawa_GAA86951 | VWLESPEHQQMITELDHLISEAASKPSSVNDD-GCEFSMPLWEQTKIVTH |
| Asp_nige_XP_001400982 | VWLESPEHQQMITELDHLISEAASKPSGVNDD-GCEFSMPLWEQTKIVTH |
| Oph_pice_EPE02908 | VWMDSSEQREMATELNTMIEDAAGRPSQTSDDDGFEFAMPLWEQTKIVTY |
| | :*::*.*: .*  **: :: :**.:*. . :* * **:*.:*:* **** |
| | |
| P_brasilianum_hmfT5 | RMNVSLFRNTAYVNNKFSLHIISALLNGFSFWRPGPSVSALQLKMFTIFN |
| Pen_digi_EKV20717 | RMNVALFRNTNYINNKFSLHIISAALNGFSFWRPGPSVTALNLKMFTIFN |
| Pen_digi_EKV19541 | RMNVALFRNTNYINNKFSLHIISAALNGFSFWRPGPSVTALNLKMFTIFN |
| Pen_rube_XP_002565665 | RMNVALFRNTNYVNNKFSLHIISAMLNGFSFWRPGPSVSALNLKMFTIFN |
| Asp_oryz_KDE82314 | RMNVALFRNTNYVNNKFSLHIISALLNGFSFWHTGPSVSALNLKMFTIFN |
| Asp_oryz_EIT77345 | RMNVALFRNTNYVNNKFSLHIISALLNGFSFWHTGPSVSALNLKMFTIFN |
| Asp_flav_XP_002380612 | RMNVALFRNTNYVNNKFSLHIISALLNGFSFWHTGPSVSALNLKMFTIFN |
| Asp_terr_XP_001208847 | RMNIALFRNTNYVNNKFMLHIISALLNGFSFWRVGPSVSALNLKMFTIFN |
| Asp_kawa_GAA86951 | RMNVALFRNTNYVNNKFSLHIISALLNGFSFWRVGPSVTALQLKMFTIFN |
| Asp_nige_XP_001400982 | RMNVALFRNTNYVNNKFSLHIISALLNGFSFWRVGPSVTALQLKMFTIFN |
| Oph_pice_EPE02908 | RMNVSLFRNTAYVNNKFSLHIISALLNGFSFWRLGKSANDLQLRLFTIFN |
| | ***::***** *:**** ****** *******: * *.. *:*::***** |
| | |
| P_brasilianum_hmfT5 | FVFVAPGVINQLQPLFIQRRDIYDAREKKSKMYSWVAFVTGLIVSEFPYL |
| Pen_digi_EKV20717 | FVFVAPGVINQLQPLFIQRRDIYDTREKKSKMYSWVAFVTGLVVSEFPYL |
| Pen_digi_EKV19541 | FVFVAPGVINQLQPLFIQRRDIYDTREKKSKMYSWVAFVTGLVVSEFPYL |
| Pen_rube_XP_002565665 | FVFVAPGVINQLQPLFIQRRDIYDTREKKSKMYSWVAFVTGLIVSEFPYL |
| Asp_oryz_KDE82314 | FVFVAPGVINQLQPLFIQRRDIYDAREKKSKMYSWVAFVTGLIVSEFPYL |
| Asp_oryz_EIT77345 | FVFVAPGVINQLQPLFIQRRDIYDAREKKSKMYSWVAFVTGLIVSEFPYL |
| Asp_flav_XP_002380612 | FVFVAPGVINQLQPLFIQRRDIYDAREKKSKMYSWVAFVTGLIVSEFPYL |
| Asp_terr_XP_001208847 | FVFVAPGVINQLQPLFIQRRDIYDAREKKSKMYSWVSFVIGLIVSEFPYL |
| Asp_kawa_GAA86951 | FVFVAPGVINQLQPLFIQRRDIYDAREKKSKMYSWISFVIGLIVSEFPYL |
| Asp_nige_XP_001400982 | FVFVAPGVINQLQPLFIQRRDIYDAREKKSKMYSWISFVIGLIVSEFPYL |
| Oph_pice_EPE02908 | FVFVAPGVINQLQPLFIQRRDIYDAREKKSKMYSWVAFVTALIVSEFPYL |
| | ************************:**********::** .*:******* |
| | |
| P_brasilianum_hmfT5 | CICAVLYFVCWYWPVWRLPHDSDRSGAIFFMMLIYEFIYTGIGQFIAAYA |
| Pen_digi_EKV20717 | CICAVLYFACWYYPVWRLPHASNRSGATFFMMLIYELIYTGIGQFVAAYS |
| Pen_digi_EKV19541 | CICAVLYFACWYYPVWRLPHASNRSGATFFMMLIYELIYTGIGQFVAAYS |
| Pen_rube_XP_002565665 | CICAVLYFVCWYYPVWRLPHESSRSGATFFMMLIYELIYTGIGQFVAAYS |
| Asp_oryz_KDE82314 | CVCAVLYFACWYYCVRKLPHDSKRSGATFFIMLIYEFIYTGIGQFVAAYA |
| Asp_oryz_EIT77345 | CVCAVLYFACWYYCVR-LPHDSKRSGATFFIMLIYEFIYTGIGQFVAAYA |
| Asp_flav_XP_002380612 | CVCAVLYFACWYYCVR-LPHDSNRSGATFFIMLIYEFIYTGIGQFVAAYA |
| Asp_terr_XP_001208847 | CVCAVLYFLCWYYCVK-LPHDSNKAGATFFIMLIYEFIYTGIGQFVAAYA |
| Asp_kawa_GAA86951 | CVCAVLYFLCWYYCVR-LPHDSNKAGATFFIMLIYEFIYTGIGQFIAAYA |
| Asp_nige_XP_001400982 | CVCAVLYFLCWYYCVR-LPHDSNKAGATFFIMLIYEFIYTGIGQFIAAYA |
| Oph_pice_EPE02908 | CICAVLYFVCWYWPVWTLPHDSNRSGAIFFMMWIYEFIYTGIGQFIAAYA |
| | *:****** ***: *  *** *.::** **:* ***:********:***: |
| | |
| P_brasilianum_hmfT5 | PNPTFAALVNPLIISVLVLFCGVFVPYDQLNVFWKYWMYYLNPFNYVVNG |
| Pen_digi_EKV20717 | PNPTFAALVNPLIISTLILFCGVFVPYLQLNVFWRFWMYYLNPFNYVVSG |
| Pen_digi_EKV19541 | PNPTFAALVNPLIISTLILFCGVFVPYLQLNVFWRFWMYYLNPFNYVVSG |
| Pen_rube_XP_002565665 | PNPTFAALVNPLIISTLVLFCGIFVPYIQLNVFWRYWMYYLNPFNYVVSG |
| Asp_oryz_KDE82314 | PNPTFAALVNPLIISTLTLMCGIFVPYSQLTVFWRYWMYYLNPFNYVTSG |
| Asp_oryz_EIT77345 | PNPTFAALVNPLIISTLTLMCGIFVPYSQLTVFWRYWMYYLNPFNYVTSG |
| Asp_flav_XP_002380612 | PNPTFAALVNPLIISTLTLMCGIFVPYSQLTVFWRYWMYYLNPFNYVTSG |
| Asp_terr_XP_001208847 | PNPTFAALVNPLIISTLVLFCGIFVPYTQLNVFWKYWLYWLNPFNYVVSG |
| Asp_kawa_GAA86951 | PNPTFAALVNPMIISVLVLFCGIFVPYTQLNVFWKYWLYYLNPFNYVVSG |
| Asp_nige_XP_001400982 | PNPTFAALVNPMIISVLVLFCGIFVPYTQLNVFWKYWLYYLNPFNYVVSG |
| Oph_pice_EPE02908 | PNPTFAALINPLIISIMTLFCGVFVPYQQLNVFWKYWMYWINPFSYVVNG |
| | ********:**:*** : *:**:**** **.***::*:*::***.**..* |
| | |
| P_brasilianum_hmfT5 | MLTFGLWGQKVTCNESEYAVFDPLNG-TCGEYLATYMSGK--GSGVNLLN |
| Pen_digi_EKV20717 | MLTFGIWGAKVTCNEEEFAFFEPVNGTTCVEYLSDYMTGT--GSGINLIN |
| Pen_digi_EKV19541 | MLTFGIWGAKVTCNEEEFAFFEPVNGTTCVEYLSDYMTGT--GSGINLIN |
| Pen_rube_XP_002565665 | MLTFGLWGAKVTCNEDEFALFEPLNGTTCAQYLSDYMSGA--GSSINLVN |
| Asp_oryz_KDE82314 | MLVFGMWGAKVTCNEDEFAIFDPVNG-TCGDYLADYMAGS--GSRINLTN |
| Asp_oryz_EIT77345 | MLVFGMWGAKVTCNEDEFAIFDPVNG-TCGDYLADYMAGS--GSRINLTN |
| Asp_flav_XP_002380612 | MLVFGMWGAKVTCNEDEFAIFDPVNG-TCGDYLADYMAGS--GSRINLTN |
| Asp_terr_XP_001208847 | MLTFGIWDAKVTCNADEFAFFDPTNG-TCGEYLADYIRGD--GWRINLTN |
| Asp_kawa_GAA86951 | MLTFDMWDAKVTCNEDEFALFNPTNG-TCAEYLKDYIAGQ--GWRVNLTN |
| Asp_nige_XP_001400982 | MLTFDMWDAKVTCNEDEFALFNPTNG-TCAEYLKDYIAGQ--GWRVNLTN |
| Oph_pice_EPE02908 | MLTFGLWGQKVVCAEGEFAVFDPLNG-TCGEYLSTYMSANGMGSHVNLTN |
| | **.*.:*. **.*   *:*.*:* ** ** :**  *: .   *  :** * |

TABLE 18-continued

Amino acid sequence alignment of *Penicillium brasilianum* hmfT5 and 10 closest orthologues.

```
P_brasilianum_hmfT5   PDATSSCKVCEYTTGSDFLQTLNINHYYYGWRDAGITVIYAISGYALVFG
Pen_digi_EKV20717     PDATSACKVCQYTDGSDFLRGLHIQNYTTGWRDIGISVIFAISGYALVFG
Pen_digi_EKV19541     PDATSACKVCQYTDGSDFLRGLHIQNYTTGWRDIGISVIFAISGYALVFG
Pen_rube_XP_002565665 PDATSACKVCQYTDGSDFLRNLNIMNYTTGWRDIGISVIFAISGYALVFG
Asp_oryz_KDE82314     PDATSGCRVCEYRSGSDFLTTLNINHYYYGWRDAGICVIFAISGYALVFV
Asp_oryz_EIT77345     PDATSGCRVCEYRSGSDFLTTLNINHYYYGWRDAGICVIFAISGYALVFV
Asp_flav_XP_002380612 PDATSGCRVCEYRSGSDFLTTLNINHYYYGWRDAGICVIFAISGYALVFA
Asp_terr_XP_001208847 PDATSACKVCQYREGSDFLTTLNINDYYYGWRDAGISVIFAISGYALVFG
Asp_kawa_GAA86951     PDATSTCRVCEYRRGSDFLTTLNINHYFYGWRDAGISVIFAISGYALVFA
Asp_nige_XP_001400982 PDATSTCRVCEYRRGSDFLTTLNINHYYYGWRNAGITVIFAISGYALVFA
Oph_pice_EPE02908     PDATAGCRVCEYRDGSGFLSTLNVNHYYVGWRDAAISVLYAFSGYALVFG
                      ****: *:**:*  **.**  *:: .*  ***: .* *::*:*******

P_brasilianum_hmfT5   LMKLRTKASKKAE-----
Pen_digi_EKV20717     LMKLRTKASKKAE-----
Pen_digi_EKV19541     LMKLRTKASKKAE-----
Pen_rube_XP_002565665 LMKLRTKASKKAE-----
Asp_oryz_KDE82314     LMKLRTKASKKAE-----
Asp_oryz_EIT77345     LMKLRTKASKKAE-----
Asp_flav_XP_002380612 LMKLRTKASKKAE-----
Asp_terr_XP_001208847 LMKLRTKASKKAE-----
Asp_kawa_GAA86951     LMKLRTKASKKAE-----
Asp_nige_XP_001400982 LMKLRTKASKKAE-----
Oph_pice_EPE02908     LMKLRTKASKKAEUSAGE
                      *************
```

TABLE 19

Amino acid sequence alignment of *Penicillium brasilianum* hmfR and 10 closest orthologues.

```
P_brasilianum_hmfR    --------------------------------------------------
Spo_sche_ERT02388     MSHPAGHAAPATASVTSTRRLRRVADTSRKRSVQSCDFCRKRRCKCVPQP
Sce_apio_KEZ45621     -------MADSPPDAAARRRLRRVPEQLRKRSAHSCDLCRKRRCKCVPGP
Sta_chlo_KFA62280     ---------MPESSAAAKRRMRRIPAQLRKRNLQSCDWCRKRRCKCVPST
Ver_alfa_XP_003000413 ---------MSESVSAAKRRQRRIPDEFR---------------------
Fus_oxys_EXL68817     ---------MSES-ANAKRRLRRIPDESRKRNAQSCDRCRKRRCKCVPDP
Fus_oxys_EXK46473     ---------MSES-ANAKRRLRRIPDESRKRNAQSCDRCRKRRCKCVPDP
Fus_oxys_EGU75021     ---------MSES-ANAKRRLRRIPDESRKRNAQSCDRCRKRRCKCVPDP
Fus_oxys_EXM14771     ---------MSES-ANAKRRLRRIPDESRKRNAQSCDRCRKRRCKCVPDP
Fus_oxys_EXM09676     --------------------------------------------------
Fus_oxys_EXK77862     ---------MSES-ANAKRRLRRIPDESRKRNAQSCDRCRKRRCKCVPDP

P_brasilianum_hmfR    ------MCQDHDLECSYTLPRKTRFYGSVDDLSDRYKCLEAIVRAAFPND
Spo_sche_ERT02388     AGDGCLMCHTQGVACSYTLPRKARFYGSVEDLSDRFKCLEAIVRGAFPSD
Sce_apio_KEZ45621     AGRGCATCEKHNVECSYALPRKSRFYGSVDDLGDRHKCLEAIVRGAFPGE
Sta_chlo_KFA62280     TGQGCVSCEQHDVQCSYTAPRKTRFYGSLDELSLRYRCLEAVVKGAFHND
Ver_alfa_XP_003000413 ---------------------------------------------AFPND
Fus_oxys_EXL68817     SGAGCVNCLEHNVTCSYTAPRKTRFYGSVDDLSDRYRCLEAIVRGAFPNE
Fus_oxys_EXK46473     SGVGCVNCLEHNVTCSYTAPRKTRFYGSVDDLSDRYRCLEAIVRGAFPNE
Fus_oxys_EGU75021     SGAGCVNCLEHNVTCSYTAPRKTRFYGSVDDLSDRYRCLEAIVRGAFPNE
Fus_oxys_EXM14771     SGAGCVNCLEHNVTCSYTAPRKTRFYGSVDDLSDRYRCLEAIVRGAFPNE
Fus_oxys_EXM09676     -----MNCLEHNVTCSYTAPRKTRFYGSVDDLSDRYRCLEAIVRGAFPNE
Fus_oxys_EXK77862     SGAGCVNCLEHNVTCSYTAPRKTRFYGSVDDLSDRYRCLEAIVRGAFPNE
                                                                   ** .:

P_brasilianum_hmfR    GISTVPELIRLGERMGYAMPDLSQ-KSGESPRIEELVR--------DFPT
Spo_sche_ERT02388     PIATVPELLRLGHRLGVTMPDLAD-DARAKLSLDDLVNTPSKSVTSDQTT
Sce_apio_KEZ45621     PTATVADLRKLGERMGYSMPEPTI-PSTRPLESSEPTIS--------YPS
Sta_chlo_KFA62280     DIATAAELVQLGRRLGYAMPDINHKATYSEVKLDEIIRAP--------AV
Ver_alfa_XP_003000413 LTATAEDLVELGRRMGYAMPDFSQ-PRRKGVKIEDLVRAP--------DP
Fus_oxys_EXL68817     TLDHVSDLAQLGQKMGYKMPDVSD-PNRAHIRVEDLVQNP--------SS
Fus_oxys_EXK46473     TLDHVSDLAQLGQKMGYKMPDVSD-PNRTHIRVEDLVQNP--------SS
Fus_oxys_EGU75021     TLDHVSDLAQLGQKMGYKMPDVSD-PNRAHIRVEDLVQNP--------SS
Fus_oxys_EXM14771     TLDHVSDLAQLGQKMGYKMPDVSD-PNRTHIRVEDLVQNP--------SS
Fus_oxys_EXM09676     TLDHVSDLAQLGQKMGYKMPDVSD-PNRTHIRVEDLVQNP--------SS
Fus_oxys_EXK77862     TLDHVSDLAQLGQKMGYKMPDVSD-PNRTHIRVEDLVQNP--------SS
                          . :* .**.::*  **:            .:

P_brasilianum_hmfR    EAGDQGLAGSTQCTSSPPRTGAVNVPTESER-------------------
Spo_sche_ERT02388     AVEGAVDGGGSGGGGGDRRPSMTNAPTQSDAGHVNARPLATEPESADTVN
Sce_apio_KEZ45621     SEAPIRRPLVPSHEAVSRRNSCPDVFG-----------------------
Sta_chlo_KFA62280     TPLPIPRTPES-------DSSGQSDCVE----------------------
```

TABLE 19-continued

Amino acid sequence alignment of *Penicillium brasilianum* hmfR and 10 closest orthologues.

```
Ver_alfa_XP_003000413 VGSSRHNSVAESKISGSELGTGSKAPSE----------------------
Fus_oxys_EXL68817     K----ERTP----------STGPDIITA----------------------
Fus_oxys_EXK46473     K----ERTP----------STGPDIITA----------------------
Fus_oxys_EGU75021     K----ERTP----------STGPDIITA----------------------
Fus_oxys_EXM14771     K----ERTP----------STGPDIITA----------------------
Fus_oxys_EXM09676     K----ERTP----------STGPDIITA----------------------
Fus_oxys_EXK77862     K----ERTP----------STGPDIITA----------------------

P_brasilianum_hmfR    ----------------RHSSSQVQENNSCPD----EPVGLIRDTTGREHF
Spo_sche_ERT02388     TDNTHNTGNSGNTDNTRHTTTTDGTASSNPQDESSEAIGLVRDTTGQEHF
Sce_apio_KEZ45621     -----------------ARVPEGVDGDSSPDD--AESLGLIRDPTGRQHY
Sta_chlo_KFA62280     -----------------RGGGETWRPRTRVN-SEEPHVSLIRDTSGNEHY
Ver_alfa_XP_003000413 -----------------VGTDDAVSAAAAASGAEDAQLSLIRDTSGNEHY
Fus_oxys_EXL68817     -----------------DSRADTSPRSSKSH-SEEPQSSLVKDNSGHEHY
Fus_oxys_EXK46473     -----------------HSRADTSPRSSKSH-SEEPQSSLVKDNSGHEHY
Fus_oxys_EGU75021     -----------------DSRADTSPRSSKSH-SEEPQSSLVKDNSGHEHY
Fus_oxys_EXM14771     -----------------DSRADTSPRSSKSH-SEEPQSSLVKDNSGHEHY
Fus_oxys_EXM09676     -----------------DSRADTSPRSSKSH-SEEPQSSLVKDNSGHEHY
Fus_oxys_EXK77862     -----------------DSRADTSPRSSKSH-SEEPQSSLVKDNSGHEHY
                                                 :          .*::* :*.:*:

P_brasilianum_hmfR    IGPSGSLQFLGQLRRLLLISR-----------------SGDAVESRAPAR
Spo_sche_ERT02388     IGSSGSLQFLGQLRRLLLLSQHDNMSRNSSYHGIGYPCSGYSAPGRASQR
Sce_apio_KEZ45621     IGPSGSLQFLSQLRRLLISRN------------------QRLPVNNDNSP
Sta_chlo_KFA62280     IGPSGTLNFLSQLRKLFDTDT-----------------TANPALAAAACP
Ver_alfa_XP_003000413 IGPSGTLNFLSQLRRLMVSSE-----------------GTPEAQPEV---
Fus_oxys_EXL68817     IGPSGTLNFWNQLRNLVDSNN-----------------SPHPSPGRE---
Fus_oxys_EXK46473     IGPSGTLNFWNQLRNLVDSNN-----------------SPYPSPGRE---
Fus_oxys_EGU75021     IGPSGTLNFWNQLRNLVDSNN-----------------SPHPSPGRE---
Fus_oxys_EXM14771     IGPSGTLNFWNQLRNLVDSNN-----------------SPHPSPGRE---
Fus_oxys_EXM09676     IGPSGTLNFWNQLRNLVDSNN-----------------SPYPSPGRE---
Fus_oxys_EXK77862     IGPSGTLNFWNQLRNLVDSNN-----------------SPYPSPGRE---
                      **.**:*:* .***.*.

P_brasilianum_hmfR    -LTATFTDEDAAQALEAD---GDQSELAALPSGGTGN-----GGDEGQEI
Spo_sche_ERT02388     -LSTTFTEEDAAQALEAD---NSHDGSDAPPTLHHHT-----PLMD----
Sce_apio_KEZ45621     -TASKFTEDDTARALEADSITVDTTDPVVAAADHGGV-----AGDVVAAQ
Sta_chlo_KFA62280     AGATKFAQDDAAQALEAEGEPRDEERHDEAEAGDAMNCSRDSVPRVPQPQ
Ver_alfa_XP_003000413 --VTKFTQDDTAQALEADDSPGAPGALHPATQTDG-------------PL
Fus_oxys_EXL68817     -GATKFTQDNTSRLLEADGQDEDDQPPRTAAT----------------PP
Fus_oxys_EXK46473     -GATKFTQDNTSRLLEADGQDEDDQPPRTAAT----------------PQ
Fus_oxys_EGU75021     -GATKFTQDNTSRLLEADGQDEDDQPPRTAAT----------------PP
Fus_oxys_EXM14771     -GATKFTQDNTSRLLEADGQDEDDQPPRTAAT----------------PQ
Fus_oxys_EXM09676     -GATKFTQDNTSRLLEADGQDEDDQPPRTAAT----------------PQ
Fus_oxys_EXK77862     -GATKFTQDNTSRLLEADGQDEDDQPPRTAAT----------------PQ
                         :.*::::::: ***:

P_brasilianum_hmfR    DERSPASLG--SALVRDFSSIPVNDIDEMRRQLPPRHVLDSLMRVYFKNV
Spo_sche_ERT02388     DRPSPMSSS--SALARECATIQPEDVNGIMAQLPPRHVLDGLIRVYFKSV
Sce_apio_KEZ45621     DELSPGSIS--SSIARDFTMQPWDAAGDLFRKLPSRLVTDSLLQSYFKNA
Sta_chlo_KFA62280     DGPSPGTVT--STIARDFTQLPAADMDDMLAQFPPNHVLETLTHSYFKNV
Ver_alfa_XP_003000413 DGPSPASVTSVTSIAKDFTRMPTVDLDETLRGLPADETLELLVQSYFKNV
Fus_oxys_EXL68817     DGPSPGSIT--SAIARDFTRLPTADMDEILSQFPSNEILDLLIHSYFKNV
Fus_oxys_EXK46473     DGPSPGSIT--SAIARDFTRLPTADMDEILGQFPSNEILDLLIQSYFKNV
Fus_oxys_EGU75021     DGPSPGSIT--SAIARDFTRLPTADMDEILSQFPSNEILDLLIHSYFKNV
Fus_oxys_EXM14771     DGPSPGSIT--SAIARDFTRLPTADMDEILGQFPSNEILDLLIQSYFKNV
Fus_oxys_EXM09676     DGPSPGSIT--SAIARDFTRLPTADMDEILGQFPSNEILDLLIQSYFKNV
Fus_oxys_EXK77862     DGPSPGSIT--SAIARDFTRLPTADMDEILGQFPSNEILDLLIHSYFKNV
                      *  ** :    :::.:: :       .     :*.    : * : ***..

P_brasilianum_hmfR    HPDFALFHRGTFEEEYETFMSKGRYYHQHARAGVH---LSSPTLPEPGWL
Spo_sche_ERT02388     HPDFPLFHRGTFEEEYERYIPDFESFYHPRRR-------TDTPTADPGWL
Sce_apio_KEZ45621     HEDFPLFHRGTFEEEYESYWALLKQRITAPEP------CLQASQMEWGWV
Sta_chlo_KFA62280     HSDFPLFHRATFEDEYELFVVQARR--RPPGRRQRP-------APDWGWI
Ver_alfa_XP_003000413 HDDYPLFHRATFEDEYELYIVQARRRLQFLPQSQAQPQNRSNAVPDWGWM
Fus_oxys_EXL68817     HDDFPLFHRATFEEEYESFIVEARRSSRLPSRPLR--------LPDWGWI
Fus_oxys_EXK46473     HDDFPLFHRATFEEEYESFIVEARRSSRLPSRPLR--------LPDWGWI
Fus_oxys_EGU75021     HDDFPLFHRATFEEEYESFIVEARRSSRLPSRPLR--------LPDWGWI
Fus_oxys_EXM14771     HDDFPLFHRATFEEEYESFIVEARRSSCLPSRPLR--------LPDWGWI
Fus_oxys_EXM09676     HDDFPLFHRATFEEEYESFIVEARRSSRLPSRPLR--------LPDWGWI
Fus_oxys_EXK77862     HDDFPLFHRATFEEEYESFIVEARRSSRLPSRPLR--------LPDWGWI
                      * *:.****.***:*** :    .                     : **:

P_brasilianum_hmfR    GCLHMMIAFASLN-----------------------GSVDVAPDLDLTS
Spo_sche_ERT02388     GCLHMILAFASLVTPAVSSSASHHRPPPSTATPSTAASSRQTHDDVDLAA
Sce_apio_KEZ45621     ATLQMLIVFGSMCDP-------------------------SIPGIDHTT
Sta_chlo_KFA62280     GCLHMMCVFGSISDP-------------------------GATGLDHSE
```

TABLE 19-continued

Amino acid sequence alignment of *Penicillium brasilianum* hmfR and 10 closest orthologues.

```
Ver_alfa_XP_003000413  GCLHMILVFGSIARP--------------------------DIPGVDHSH
Fus_oxys_EXL68817      GCLHMIVVFGSIADR--------------------------SIPNVDHSA
Fus_oxys_EXK46473      GCLHMIVVFGSIADR--------------------------SIPNVDHSA
Fus_oxys_EGU75021      GCLHMIVVFGSIADR--------------------------SIPNVDHSA
Fus_oxys_EXM14771      GCLHMIVVFGSIADR--------------------------SIPNVDHSA
Fus_oxys_EXM09676      GCLHMIVVFGSIADR--------------------------SIPNVDHSA
Fus_oxys_EXK77862      GCLHMIVVFGSIADR--------------------------SIPNVDHSA
                       . *:*: .*.*:                                .:* :

P_brasilianum_hmfR     LCRHCASLTR-QLLPQFISKCTLSNVRALLLLSLFLHNHNERNAAWNLVG
Spo_sche_ERT02388      LRKHCVSLTRFRLLPRFISRCTLANIRALLLLALYLHNHNERNAAWNLVG
Sce_apio_KEZ45621      LRRQCVSVTR-SLLPQLVSKCTLSNVRALLLLSLFLHNNNERNAAWNLVG
Sta_chlo_KFA62280      LRRRCVMATR-MLLPQFVSKCTLSNVRVLLLLSLFLHNNNERNAAWNLVG
Ver_alfa_XP_003000413  LRRRSVAAAR-TLLPQFISKCTLSNVRVLMLLSLFLHNNNERNAAWNLVG
Fus_oxys_EXL68817      LRRRSIAVAR-GLLPQFISKCSLTNVRVLLLLSLFLHNNNERNAAWNIAG
Fus_oxys_EXK46473      LRRRSIAVAR-GLLPQFISKCSLTNVRVLLLLSLFLHNNNERNAAWNIAG
Fus_oxys_EGU75021      LRRRSIAVAR-GLLPQFISKCSLTNVRVLLLLSLFLHNNNERNAAWNIAG
Fus_oxys_EXM14771      LRRRSIAVAR-GLLPQFISKCSLTNVRVLLLLSLFLHNNNERNAAWNIAG
Fus_oxys_EXM09676      LRRRSIAVAR-GLLPQFISKCSLTNVRVLLLLSLFLHNNNERNAAWNIAG
Fus_oxys_EXK77862      LRRRSIAVAR-GLLPQFISKCSLTNVRVLLLLSLFLHNNNERNAAWNIAG
                       * ::.   :*  ***:::*:*:*:*:*.*:**:*:***:********:.*

P_brasilianum_hmfR     TAMRLSFAMGLHRASDNGSHFRPIEREVRKRVFCTLYGFEQFLASSLGRP
Spo_sche_ERT02388      TATRAAFAMGLHRCTVGAEHLRPVEREVRRRVFCTLFGLEQFLASSLGRP
Sce_apio_KEZ45621      TATRISFALGLHRR-DVAAYFRPIEREVRKRVFCTLYSFEQFLASSLGRP
Sta_chlo_KFA62280      TATRISFALGLHRA-TMLASLRPQEREVRKWVFCTLYAFEQFLASSLGRP
Ver_alfa_XP_003000413  TATRIAFALGLHRS-DMRSSLRPLDREVRKWVFCTLYSFEQFLASSLGRP
Fus_oxys_EXL68817      TATRISFALGLHRS-DMSVSFRPLEREVRKWVFCTLYSFEQFLASSLGRP
Fus_oxys_EXK46473      TATRISFALGLHRS-DMSVSFRPLEREVRKWVFCTLYSFEQFLASSLGRP
Fus_oxys_EGU75021      TATRISFALGLHRS-DMSVSFRPLEREVRKWVFCTLYSFEQFLASSLGRP
Fus_oxys_EXM14771      TATRISFALGLHRS-DMSVSFRPLEREVRKWVFCTLYSFEQFLASSLGRP
Fus_oxys_EXM09676      TATRISFALGLHRS-DMSASFRPLEREVRKWVFCTLYSFEQFLASSLGRP
Fus_oxys_EXK77862      TATRISFALGLHRS-DMSVSFRPLEREVRKWVFCTLYSFEQFLASSLGRP
                       ** * :**:****       :** :****: *****:.:***********

P_brasilianum_hmfR     SGFY---------DFEDVEIVPPREGVLDSG-----QDEDDEVMKLSLRL
Spo_sche_ERT02388      SGLSGLSALSSANDANEVEVVPPRAEILDGGGSADADDDDGAMATLLLRL
Sce_apio_KEZ45621      SGLN----------DFDVEIALPREGLLGTG--------TDRVVALSLKL
Sta_chlo_KFA62280      SGLQ----------DVDVEVVPPRDGFLDVG--------DAQLARLSLRL
Ver_alfa_XP_003000413  SGLQ----------EMDVEIVPPREGFLDAGT-----GTDAKLVFLSLRL
Fus_oxys_EXL68817      SGLQ----------ELDVEVVPPREGFVEGGI-----GTDARLVSWSVKL
Fus_oxys_EXK46473      SGLQ----------ELDVEVVPPREGFVEGGV-----GTDARLVSWSVKL
Fus_oxys_EGU75021      SGLQ----------ELDVEVVPPREGFVEGGI-----GTDARLVSWSVKL
Fus_oxys_EXM14771      SGLQ----------ELDVEVVPPREGFVEGGI-----GTDARLVSWSVKL
Fus_oxys_EXM09676      SGLQ----------ELDVEVVPPREGFVEGGI-----GTDARLVSWSVKL
Fus_oxys_EXK77862      SGLQ----------ELDVEVVPPREGFVEGGI-----GTDARLVSWSVKL
                       **:             :**:. **  .:  *           :    ::*

P_brasilianum_hmfR     QVILAKARVSLAVKTLAVANERGNIDGLARQQQSSRETLEILKAWREDLA
Spo_sche_ERT02388      QTILAGARVSAAVKTVGLGSRR------LRQEQSAREILQRLDEWRTAVA
Sce_apio_KEZ45621      QNILGRARISQAVRSLASGNTDT-----QRHEESAKETISALKAWRDEVA
Sta_chlo_KFA62280      DGILAKARLLHAGRARGTAADG------AGSPPDLEGVLGALEEWKKEAA
Ver_alfa_XP_003000413  QAILARTRFAYARPQRRPDAEGQD----VVPRPSVDDIMRSLAAWKRDVA
Fus_oxys_EXL68817      QAILARTRLLHVDINR-------------SSGPTLDEILTALNGWKRDIG
Fus_oxys_EXK46473      QAILARTRLLHVDINR-------------SSGPTLDEILTALNGWKRDIG
Fus_oxys_EGU75021      QAILARTRLLHVDINR-------------SSGPTLDEILTALNGWKRDIG
Fus_oxys_EXM14771      QAILARTRLLHVGINQ-------------SLGPTLDEILTALDGWKRDIG
Fus_oxys_EXM09676      QAILARTRLLHVDINR-------------SSGPTLDEILTALNGWKRDIG
Fus_oxys_EXK77862      QAILARTRLLHVGINQ-------------SSGPTLDEILTALNGWKRDIG
                       : **. :*.  .                          :  *  *:   .

P_brasilianum_hmfR     SHHILNIPLISETDDP-------LCQYAEEIPRMSLQDLKAMMGWQSRPR
Spo_sche_ERT02388      GCRCLDIPQITETTDSGRDAFVADAPPSTSTPSMDLDSLKNMLAWQSRPR
Sce_apio_KEZ45621      ASQSLNIPSISEPDDA--------FKEDDAPVTMSFTEIKLLLSWQDRTR
Sta_chlo_KFA62280      RQAGCDVPWVRTG---------KAFP--AKTAAVDMDELKAMLSWKTRAQ
Ver_alfa_XP_003000413  ENPSFHMPDIQTRVSL-RGRGSSASLHDEDGDAMEFDELKVVLSWKTRAQ
Fus_oxys_EXL68817      KAPGLDVSWIKMEG--------PALESIDHEGAVDMEELKVSLAWKTRAQ
Fus_oxys_EXK46473      KAPGLDVSWIKMEG--------PALESIDHEGAVAMEELKVSLAWKTRAQ
Fus_oxys_EGU75021      KAPGLDVSWIKMEG--------PALESIDHEGAVDMEELKVSLAWKTRAQ
Fus_oxys_EXM14771      KAPGLDVSWIKMEG--------PALESIDHEGAVDMEELKVSLAWKTRAQ
Fus_oxys_EXM09676      KAPGLDVSWIKMEG--------PALESIDHEGAVDMEELKVSLARKTRAQ
Fus_oxys_EXK77862      KAPGLDVSWIKMEG--------PALESIDHEGAVDMEGLKVSLTWKTRAQ
                            .:. :                       : :  :*  :  : *.:

P_brasilianum_hmfR     LRAALVLHLQYRYIAVLVTRSSLLRYVASAQRGEPEHEALLSRNEARTDP
Spo_sche_ERT02388      LRAALVLHMQYRYVAVLSTRSALL-YSMAARAARTAPVAHDGGPAPSPSP
Sce_apio_KEZ45621      LRAALVLNMQYRYIAIMVARPFLLRDTAMAR-----VVARTDNKNTTNDT
```

TABLE 19-continued

Amino acid sequence alignment of *Penicillium brasilianum* hmfR and 10 closest orthologues.

```
Sta_chlo_KFA62280     LRAVLLLHIQYYYINIVATRPLLLRDIAKLG---------ATTADPAPPG
Ver_alfa_XP_003000413 LRAVLMLHIQYHYIAIVATRPILLREIAAAR---------KALRDESAG-
Fus_oxys_EXL68817     LRAVLLLHIHFHYIAIVATRPLLLRDVAAAR---------KEDAPKTP--
Fus_oxys_EXK46473     LRAVLLLHIHFHYIAIVATRPLLLREVAAAR---------KEDAPKTP--
Fus_oxys_EGU75021     LRAVLLLHIHFHYIAIVATRPLLLRDVAAAR---------KEDAPKTP--
Fus_oxys_EXM14771     LRAVLLLHIHFHYIAIVATRPLLLRDVAAAR---------KEDAPKTP--
Fus_oxys_EXM09676     LRAVLLLHIHFHYIAIVATRPLLLRDVAAAR---------KEDAPKTP--
Fus_oxys_EXK77862     LRAVLLLHIHFHYIAIVATRPLLLRDVAAAR---------KEDAPKTP--
                      ***.*:*:::: *: :: :*. **

P_brasilianum_hmfR    YNSEAGERLSDICVTHATQLCRLILLADSFGLVNGISAMDVFYVYCGVMV
Spo_sche_ERT02388     ATSAAPPTLADLCVQNAVQLCRLVLLADSFGLINGVSAMDVFYAYCAAMV
Sce_apio_KEZ45621     PRSDAHSHLASVCVQNACQLAKIVLLLAEFELLNGVCGMDVFYAYSASM-
Sta_chlo_KFA62280     AGVPALSPHAESCVRHACQLAHLVVLLDGFGVINGLSGLDVFYAYCAAMV
Ver_alfa_XP_003000413 APPPAMSAVADACVRHAVQLTYMVLFLDGFELVNGLSGLDVFYAYCAAMV
Fus_oxys_EXL68817     -----VPTHAALCVKHACQLSYLMILLDHFDVINGLSGLDIFYAYCSAMI
Fus_oxys_EXK46473     -----VPTHAALCVKHACQLSYLMILLDHFDVINGLSGLDIFYAYCSAMI
Fus_oxys_EGU75021     -----VPTHAALCVKHACQLSYLMILLDHFDVINGLSGLDIFYAYCSAMI
Fus_oxys_EXM14771     -----VPTHAALCVKHACQLSYLMILLDHFDVINGLSGLDIFYAYCSAMI
Fus_oxys_EXM09676     -----VPTHAALCVKHACQLSYLMILLDHFDVINGLSGLDIFYAYCSAMI
Fus_oxys_EXK77862     -----VPTHAALCVKHACQLSYLMILLDHFDVINGLSGLDIFYAYCSAMI
                               :  ** :* **  ::::   * ::**:..:*:**.*.. *

P_brasilianum_hmfR    LILRSLRISS---SASHYHDQREAHLQLELRKLIAQTREVLIRVNKCSTM
Spo_sche_ERT02388     LILRSLNGGSEQDQGAVSVSAADAAYCAELRRLIARTRQVLMRVDKCSTM
Sce_apio_KEZ45621     -------------------------------LIQSIRLVVSKVPKSGTM
Sta_chlo_KFA62280     LILRLAR--AGRQDDGGEEEEEEKMLG-AVRELVSDLRRVMNRTQKGGSM
Ver_alfa_XP_003000413 LILRLLRR-PPAAEGAEASDQQEEQIQVVIRELVRKSQSVLNRTNKSGSM
Fus_oxys_EXL68817     LILRLLR--LRPGESAESIGPDEVMLQSKVRRLVATLRNVINHTDKCGSM
Fus_oxys_EXK46473     LILRLLR--LRPGEGAESIGPDEVILQSKVRRLVATLRNVINHTDKCGSM
Fus_oxys_EGU75021     LILRLLR--LRPGESAESIGPDEVMLQSKVRRLVATLRNVINHTDKCGSM
Fus_oxys_EXM14771     LILRLLR--LRPGEGAESIGPDEVMLQSKVRRLVATLRNVINHTDKCGSM
Fus_oxys_EXM09676     LILRLLR--LRPG---EGIGPDEVMLQSKVRRLVATLRNVINHTDKCGSM
Fus_oxys_EXK77862     LILRLLR--LRPGEGAESIGPDEVMLQSKVRRLVATLRNVINHTDKCGSM
                                                      *:   : *: :. * .:*

P_brasilianum_hmfR    KRFARVVATFEDGSR---QDNIRPADGSTNRS--------TANCEMRTAR
Spo_sche_ERT02388     KRFSRVVATFEEGSRRVGRDDVHQNSNTANTANTAGDGTVPAHPSSTTAH
Sce_apio_KEZ45621     KRFARVMATFEDSVFN---HDALPHAATPRKD------------------
Sta_chlo_KFA62280     RRFARVVDTFFEAVDKP--SPRLKMSGHG-----------HNGPSMQGVP
Ver_alfa_XP_003000413 KRFASVVDAFAECTSQTPGTQEDKVRALPGSA-------WSRGFSGGGVS
Fus_oxys_EXL68817     KRLAQVVDTFSECANNP--TDPPGIANLP-----------PQGINMNNPP
Fus_oxys_EXK46473     KRLAQVVDTFSECANNP--TDPPGIANLP-----------PQGINMNNPP
Fus_oxys_EGU75021     KRLAQVVDTFSECANNP--TDPPGIANLP-----------PQGINMNNPP
Fus_oxys_EXM14771     KRLAQVVDTFSECANNP--TDPPGIANLP-----------PQGINMNNPP
Fus_oxys_EXM09676     KRLAQVVDTFSECANNP--TDPPGIANLP-----------PQGINMNNPP
Fus_oxys_EXK77862     KRLAQVVDTFSECANNP--TDPPGIANLP-----------PQGINMNNPP
                      :*:: *: :* :

P_brasilianum_hmfR    --------QASRDPRGRFN---------------HSIHAALDGGRASNLA
Spo_sche_ERT02388     PRHPPPSPYAPPAPRQRQTPAHGPAAVHTPSQAPPSVTRRLASMSSQSSA
Sce_apio_KEZ45621     -----------------------------------SGTQLHATGQDIPAI
Sta_chlo_KFA62280     APHLQ-------------------------QQQNTSFFYPYGQRQQQMT
Ver_alfa_XP_003000413 ALPR-----------------------------------QPAALDAGQFP
Fus_oxys_EXL68817     ---------------------------------------YPAGWSADQVQ
Fus_oxys_EXK46473     ---------------------------------------YPDGWSAEKIQ
Fus_oxys_EGU75021     ---------------------------------------YPAGWSADQVQ
Fus_oxys_EXM14771     ---------------------------------------YPAGWSAEQVQ
Fus_oxys_EXM09676     ---------------------------------------YPAGWSAEQVQ
Fus_oxys_EXK77862     ---------------------------------------YPAGWSAEQVQ

P_brasilianum_hmfR    IFPGAGGSLDTSSS--LPVSQQE----PLNFQHGYGNGIGPRLG------
Spo_sche_ERT02388     LHVDESQRLHMSPS--QTSQTTQTTLPPQNQAHFASAGVGALCSNGYDQY
Sce_apio_KEZ45621     HHLGSTDPLLLAP---QPATASAFLDPSFPMMAGWPQGDWSTFG------
Sta_chlo_KFA62280     LN-DQGLVLGPDLLGEHAGAAPRLGDAGTFGDAWLELLPLSTFGGS----
Ver_alfa_XP_003000413 YGMMGTGVIG------------VPPGQAFSMTAPMGFGQATTYGVLN---
Fus_oxys_EXL68817     AQQGQGMALG-------------------SMEGLLDFLPFPGFG------
Fus_oxys_EXK46473     AQQDQGMALG-------------------SMEGLLDFLPFPGFG------
Fus_oxys_EGU75021     AQQGQGMALG-------------------SMEGLLDFLPFPGFG------
Fus_oxys_EXM14771     AQHGQGMALG-------------------SMEGLLDFLPFPGFG------
Fus_oxys_EXM09676     AQQGQGMALG-------------------SMEGLLDFLPFPGFG------
Fus_oxys_EXK77862     AQHGQGMALG-------------------SMEGLLDFLPFPGFG------
                              :                               .  .

P_brasilianum_hmfR    ----------ISDPFW-------QPNLLTSFDGEPEANGWMMDPFL-AMD
Spo_sche_ERT02388     GHAQSHLHPHSSFPPWPGQPMGPQPGLTSLFDGEPEENQWVMDTFL-GMG
Sce_apio_KEZ45621     ------------------------------ADDGREFGGWIASLLQPAMD
```

TABLE 19-continued

Amino acid sequence alignment of *Penicillium brasilianum* hmfR and 10 closest orthologues.

```
Sta_chlo_KFA62280     ----------------------------------RIVEGMFPNLEG-ASE
Ver_alfa_XP_003000413 --------------------------------VQLDDGGFYFHPFN-GSE
Fus_oxys_EXL68817     -----------------------------------MAEGSMAQYVP-GSE
Fus_oxys_EXK46473     -----------------------------------MAEGSMAQYVP-GSE
Fus_oxys_EGU75021     -----------------------------------MAEGSMAQYVP-GSE
Fus_oxys_EXM14771     -----------------------------------MAEGSMAQYVP-GSE
Fus_oxys_EXM09676     -----------------------------------MAEGSMAQYVP-GSE
Fus_oxys_EXK77862     -----------------------------------MAEGSMAQYVP-GSE
                                                                     .

P_brasilianum_hmfR    G---------------------TGVVDWGDIESLLSRNPGQ---------
Spo_sche_ERT02388     MGMGMHPGSGGSVEGDIDGVFSAGMLDWPDMDAIMRNG------------
Sce_apio_KEZ45621     T---------------------PMVTEFGDMDSILRNAPM----------
Sta_chlo_KFA62280     G---------------------VGGHDWVDMQILLGAYGGQGP-------
Ver_alfa_XP_003000413 T---------------------TAPPEWGDMEMVMAGYGMPRS-------
Fus_oxys_EXL68817     ----------------------MEMTGWHDMEFLMEGYGDQSR-------
Fus_oxys_EXK46473     ----------------------MEMTGWHDMEFLMEGYGDQSR-------
Fus_oxys_EGU75021     ----------------------MEMTGWHDMEFLMEGYGDQIIGEGVEPV
Fus_oxys_EXM14771     ----------------------MEMTGWHDMEFLMEGYGDQSK-------
Fus_oxys_EXM09676     ----------------------MEMTGWHDMEFLMEGYGDQSR-------
Fus_oxys_EXK77862     ----------------------MEMTGWHDMEFLMEGYGDQSK-------
                                                   : *:: ::

P_brasilianum_hmfR    ----------------------------------
Spo_sche_ERT02388     ----------------------------------
Sce_apio_KEZ45621     ----------------------------------
Sta_chlo_KFA62280     ---------------------------VM-----
Ver_alfa_XP_003000413 ----------------------------------
Fus_oxys_EXL68817     ---------------------------TNY----
Fus_oxys_EXK46473     ---------------------------TNY----
Fus_oxys_EGU75021     DVWRSQLQATVALEADDEPSSIQEGLTPNYTMDI
Fus_oxys_EXM14771     ---------------------------TNY----
Fus_oxys_EXM09676     ---------------------------TNY----
Fus_oxys_EXK77862     ---------------------------TNY----
```

TABLE 1A

Percentage amino acid sequence identity among *Penicillium brasilianum* hmfL1 orthologogues and accession numbers thereof.

| Species | Accession | | | | | | | | | | | |
|---|---|---|---|---|---|---|---|---|---|---|---|---|
| *Penicillium brasilianum* hmfL1 | SEQ ID NO: 1 | 100.00 | 73.80 | 49.70 | 48.30 | 48.40 | 49.80 | 51.30 | 41.50 | 41.50 | 43.30 | 43.40 |
| *Sporothrix schenckii* ATCC 58251 | ERT02385 | 73.80 | 100.00 | 48.60 | 49.10 | 49.00 | 50.80 | 51.00 | 40.20 | 40.20 | 44.60 | 43.80 |
| *Aspergillus kawachii* IFO 4308 | GAA84694 | 49.70 | 48.60 | 100.00 | 61.40 | 84.90 | 61.50 | 84.70 | 38.10 | 38.10 | 35.50 | 39.90 |
| *Byssochlamys spectabilis* No. 5 | GAD98038 | 48.30 | 49.10 | 61.40 | 100.00 | 60.90 | 66.60 | 62.30 | 41.80 | 41.80 | 39.00 | 40.50 |
| *Aspergillus niger* CBS 513.88 | XP_001397354 | 48.40 | 49.00 | 84.90 | 60.90 | 100.00 | 60.00 | 99.70 | 36.60 | 36.60 | 34.50 | 38.00 |
| *Eutypa lata* UCREL1 | XP_007796771 | 49.80 | 50.80 | 61.50 | 66.60 | 60.00 | 100.00 | 62.10 | 38.90 | 38.90 | 35.60 | 38.30 |
| *Aspergillus niger* ATCC 1015 | EHA21652 | 51.30 | 51.00 | 84.70 | 62.30 | 99.70 | 62.10 | 100.00 | 39.00 | 39.00 | 35.80 | 39.00 |
| *Fusarium graminearum* | EYB30957 | 41.50 | 40.20 | 38.10 | 41.80 | 36.60 | 38.90 | 39.00 | 100.00 | 99.70 | 41.20 | 41.30 |
| *Fusarium graminearum* PH-1 | XP_011318199 | 41.50 | 40.20 | 38.10 | 41.80 | 36.60 | 38.90 | 39.00 | 99.70 | 100.00 | 41.50 | 41.30 |
| *Rhizobium phaseoli* | WP_016737077 | 43.30 | 44.60 | 35.50 | 39.00 | 34.50 | 35.60 | 35.80 | 41.20 | 41.50 | 100.00 | 67.70 |
| *Dyella jiangningensis* | WP_038619920 | 43.40 | 43.80 | 39.90 | 40.50 | 38.00 | 38.30 | 39.00 | 41.30 | 41.30 | 67.70 | 100.00 |

TABLE 2A

Percentage amino acid sequence identity among *Penicillium brasilianum* hmfL2 orthologogues and accession numbers thereof.

| Species | Accession | | | | | | | | | | | |
|---|---|---|---|---|---|---|---|---|---|---|---|---|
| *Penicillium brasilianum* hmfL2 | SEQ ID NO: 2 | 100.00 | 69.30 | 68.10 | 67.70 | 64.00 | 64.30 | 63.70 | 64.00 | 67.10 | 67.00 | 63.90 |

TABLE 2A-continued

Percentage amino acid sequence identity among *Penicillium brasilianum* hmfL2 orthologogues and accession numbers thereof.

| Species | Accession | | | | | | | | | | | |
|---|---|---|---|---|---|---|---|---|---|---|---|---|
| *Coccidioides immitis* RS | XP_001244132 | 69.30 | 100.00 | 97.30 | 96.70 | 67.60 | 68.10 | 68.40 | 67.80 | 70.10 | 66.10 | 69.20 |
| *Coccidioides posadasii* C735 delta SOWgp | XP_003068662 | 68.10 | 97.30 | 100.00 | 98.20 | 65.00 | 65.70 | 67.80 | 65.30 | 67.60 | 66.60 | 69.50 |
| *Coccidioides posadasii* str. *Silveira* | EFW20539 | 67.70 | 96.70 | 98.20 | 100.00 | 64.70 | 65.30 | 67.40 | 65.00 | 67.20 | 66.20 | 69.10 |
| *Trichophyton rubrum* CBS 118892 | XP_003235253 | 64.00 | 67.60 | 65.00 | 64.70 | 100.00 | 97.60 | 65.20 | 97.30 | 89.10 | 65.20 | 82.00 |
| *Trichophyton equinum* CBS 127.97 | EGE05431 | 64.30 | 68.10 | 65.70 | 65.30 | 97.60 | 100.00 | 64.60 | 99.70 | 88.80 | 65.20 | 82.50 |
| *Chaetomium globosum* CBS 148.51 | XP_001220755 | 63.70 | 68.40 | 67.80 | 67.40 | 65.20 | 64.60 | 100.00 | 64.30 | 66.80 | 64.90 | 63.30 |
| *Trichophyton tonsurans* CBS 112818 | EGD92820 | 64.00 | 67.80 | 65.30 | 65.00 | 97.30 | 99.70 | 64.30 | 100.00 | 88.50 | 64.90 | 82.20 |
| *Microsporum gypseum* CBS 118893 | XP_003173798 | 67.10 | 70.10 | 67.60 | 67.20 | 89.10 | 88.80 | 66.80 | 88.50 | 100.00 | 65.60 | 85.20 |
| *Endocarpon pusillum* Z07020 | XP_007800835 | 67.00 | 66.10 | 66.60 | 66.20 | 65.20 | 65.20 | 64.90 | 64.90 | 65.60 | 100.00 | 67.60 |
| *Arthroderma otae* CBS 113480 | XP_002844685 | 63.90 | 69.20 | 69.50 | 69.10 | 82.00 | 82.50 | 63.30 | 82.20 | 85.20 | 67.60 | 100.00 |

TABLE 3A

Percentage amino acid sequence identity among *Penicillium brasilianum* hmfL3 orthologogues and accession numbers thereof.

| Species | Accession | | | | | | | | | | | |
|---|---|---|---|---|---|---|---|---|---|---|---|---|
| *Penicillium brasilianum* hmfL3 | SEQ ID NO: 3 | 100.00 | 84.40 | 81.40 | 76.40 | 75.90 | 76.30 | 76.60 | 75.00 | 76.00 | 74.90 | 73.70 |
| *Penicillium oxalicum* 114-2 | EPS34335 | 84.40 | 100.00 | 83.40 | 77.30 | 77.60 | 78.60 | 76.60 | 77.30 | 76.60 | 77.70 | 77.00 |
| *Penicillium rubens* Wisconsin 54-1255 | XP_002557546 | 81.40 | 83.40 | 100.00 | 86.30 | 82.60 | 80.20 | 80.50 | 82.10 | 81.40 | 80.50 | 81.80 |
| *Penicillium digitatum* Pd1 | EKV11985 | 76.40 | 77.30 | 86.30 | 100.00 | 77.60 | 76.60 | 78.00 | 78.50 | 78.90 | 77.40 | 78.20 |
| *Neosartorya fischeri* NRRL 181 | XP_001262738 | 75.90 | 77.60 | 82.60 | 77.60 | 100.00 | 82.30 | 84.90 | 96.30 | 84.60 | 84.60 | 96.00 |
| *Neosartorya fischeri* NRRL 181 | XP_001266013 | 76.30 | 78.60 | 80.20 | 76.60 | 82.30 | 100.00 | 84.30 | 82.60 | 84.30 | 86.60 | 82.30 |
| *Aspergillus kawachii* IFO 4308 | GAA89866 | 76.60 | 76.60 | 80.50 | 78.00 | 84.90 | 84.30 | 100.00 | 84.60 | 97.10 | 83.40 | 84.30 |
| *Aspergillus fumigatus* A1163 | EDP48048 | 75.00 | 77.30 | 82.10 | 78.50 | 96.30 | 82.60 | 84.60 | 100.00 | 84.90 | 84.00 | 99.70 |
| *Aspergillus niger* CBS 513.88 | XP_001398382 | 76.00 | 76.60 | 81.40 | 78.90 | 84.60 | 84.30 | 97.10 | 84.90 | 100.00 | 82.90 | 84.60 |
| *Aspergillus clavatus* NRRL 1 | XP_001273959 | 74.90 | 77.70 | 80.50 | 77.40 | 84.60 | 86.60 | 83.40 | 84.00 | 82.90 | 100.00 | 83.70 |
| *Aspergillus fumigatus* Af293 | XP_746830 | 73.70 | 77.00 | 81.80 | 78.20 | 96.00 | 82.30 | 84.30 | 99.70 | 84.60 | 83.70 | 100.00 |

TABLE 4A

Percentage amino acid sequence identity among *Penicillium brasilianum* hmfL4 orthologogues and accession numbers thereof.

| Species | Accession | | | | | | | | | | | |
|---|---|---|---|---|---|---|---|---|---|---|---|---|
| *Penicillium brasilianum* hmfL4 | SEQ ID NO: 4 | 100.00 | 87.90 | 87.30 | 87.30 | 84.50 | 84.20 | 84.20 | 83.90 | 83.90 | 80.90 | 80.60 |
| *Penicillium oxalicum* 114-2 | EPS32591 | 87.90 | 100.00 | 85.80 | 85.20 | 83.90 | 83.60 | 82.70 | 83.30 | 81.50 | 80.30 | 81.50 |
| *Penicillium rubens* Wisconsin 54-1255 | XP_002567675 | 87.30 | 85.80 | 100.00 | 91.80 | 82.70 | 83.00 | 83.00 | 81.80 | 82.70 | 78.80 | 80.90 |
| *Penicillium digitatum* Pd1 | EKV10327 | 87.30 | 85.20 | 91.80 | 100.00 | 81.50 | 81.80 | 81.50 | 80.90 | 80.90 | 77.90 | 79.70 |
| *Aspergillus fumigatus* Af293 | XP_753506 | 84.50 | 83.90 | 82.70 | 81.50 | 100.00 | 99.70 | 97.90 | 77.50 | 89.20 | 85.20 | 90.70 |
| *Aspergillus fumigatus* var. RP-2014 | KEY78459 | 84.20 | 83.60 | 83.00 | 81.80 | 99.70 | 100.00 | 98.20 | 77.20 | 89.50 | 84.90 | 90.40 |

TABLE 4A-continued

Percentage amino acid sequence identity among *Penicillium brasilianum* hmfL4 orthologogues and accession numbers thereof.

| Species | Accession | | | | | | | | | | | |
|---|---|---|---|---|---|---|---|---|---|---|---|---|
| *Neosartorya fischeri* NRRL 181 | XP_001259550 | 84.20 | 82.70 | 83.00 | 81.50 | 97.90 | 98.20 | 100.00 | 86.10 | 89.80 | 84.00 | 90.10 |
| *Aspergillus oryzae* 3.042 | EIT82010 | 83.90 | 83.30 | 81.80 | 80.90 | 77.50 | 77.20 | 86.10 | 100.00 | 87.00 | 86.40 | 84.00 |
| *Aspergillus terreus* NIH2624 | XP_001211305 | 83.90 | 81.50 | 82.70 | 80.90 | 89.20 | 89.50 | 89.80 | 87.00 | 100.00 | 83.10 | 85.50 |
| *Aspergillus kawachii* IFO 4308 | GAA89952 | 80.90 | 80.30 | 78.80 | 77.90 | 85.20 | 84.90 | 84.00 | 86.40 | 83.10 | 100.00 | 81.90 |
| *Aspergillus clavatus* NRRL 1 | XP_001274440 | 80.60 | 81.50 | 80.90 | 79.70 | 90.70 | 90.40 | 90.10 | 84.00 | 85.50 | 81.90 | 100.00 |

TABLE 5A

Percentage amino acid sequence identity among *Penicillium brasilianum* hmfN1 orthologogues and accession numbers thereof.

| Species | Accession | | | | | | | | | | | |
|---|---|---|---|---|---|---|---|---|---|---|---|---|
| *Penicillium brasilianum* hmfN1 | SEQ ID NO: 5 | 100.00 | 70.80 | 64.90 | 62.80 | 64.20 | 62.70 | 61.90 | 62.50 | 62.50 | 57.90 | 60.80 |
| *Sporothrix schenckii* ATCC 58251 | ERT02387 | 70.80 | 100.00 | 59.90 | 58.10 | 62.10 | 60.10 | 59.30 | 59.90 | 60.10 | 52.90 | 57.50 |
| *Scedosporium apiospermum* | KEZ45623 | 64.90 | 59.90 | 100.00 | 64.30 | 67.20 | 64.70 | 65.30 | 64.30 | 64.50 | 59.90 | 61.00 |
| *Podospora anserina* S mat+ | XP_001908521 | 62.80 | 58.10 | 64.30 | 100.00 | 64.20 | 63.50 | 67.70 | 63.50 | 63.50 | 58.10 | 60.20 |
| *Eutypa lata* UCREL1 | XP_007794079 | 64.20 | 62.10 | 67.20 | 64.20 | 100.00 | 69.00 | 64.70 | 68.40 | 68.60 | 63.20 | 66.70 |
| *Stachybotrys chartarum* IBT 7711 | KEY72856 | 62.70 | 60.10 | 64.70 | 63.50 | 69.00 | 100.00 | 63.30 | 99.20 | 99.60 | 62.20 | 92.80 |
| *Gaeumannomyces graminis* var. *tritici* R3-111a-1 | XP_009217152 | 61.90 | 59.30 | 65.30 | 67.70 | 64.70 | 63.30 | 100.00 | 63.30 | 63.10 | 59.10 | 61.20 |
| *Stachybotrys chartarum* IBT 40288 | KFA73399 | 62.50 | 59.90 | 64.30 | 63.50 | 68.40 | 99.20 | 63.30 | 100.00 | 98.80 | 62.20 | 92.00 |
| *Stachybotrys chartarum* IBT 40293 | KFA53356 | 62.50 | 60.10 | 64.50 | 63.50 | 68.60 | 99.60 | 63.10 | 98.80 | 100.00 | 61.80 | 92.60 |
| *Cyphellophora europaea* CBS 101466 | XP_008712551 | 57.90 | 52.90 | 59.90 | 58.10 | 63.20 | 62.20 | 59.10 | 62.20 | 61.80 | 100.00 | 59.50 |
| *Stachybotrys chlorohalonata* IBT 40285 | KFA62282 | 60.80 | 57.50 | 61.00 | 60.20 | 66.70 | 92.80 | 61.20 | 92.00 | 92.60 | 59.50 | 100.00 |

TABLE 6A

Percentage amino acid sequence identity among *Penicillium brasilianum* hmfN2 orthologogues and accession numbers thereof.

| Species | Accession | | | | | | | | | | | |
|---|---|---|---|---|---|---|---|---|---|---|---|---|
| *Penicillium brasilianum* hmfN2 | SEQ ID NO: 6 | 100.00 | 84.90 | 84.50 | 83.10 | 73.40 | 71.80 | 72.50 | 72.20 | 76.30 | 75.70 | 75.50 |
| *Penicillium rubens* Wisconsin 54-1255 | XP_002562108 | 84.90 | 100.00 | 82.10 | 91.00 | 73.90 | 72.60 | 73.50 | 73.20 | 74.20 | 73.90 | 73.70 |
| *Penicillium oxalicum* 114-2 | EPS27859 | 84.50 | 82.10 | 100.00 | 78.80 | 72.60 | 70.80 | 72.00 | 71.50 | 74.30 | 74.30 | 74.10 |
| *Penicillium digitatum* Pd1 | EKV07543 | 83.10 | 91.00 | 78.80 | 100.00 | 72.10 | 70.90 | 71.60 | 71.10 | 73.30 | 72.50 | 72.30 |
| *Aspergillus kawachii* IFO 4308 | GAA83411 | 73.40 | 73.90 | 72.60 | 72.10 | 100.00 | 73.70 | 98.30 | 75.90 | 79.00 | 78.80 | 78.40 |
| *Aspergillus ruber* CBS 135680 | EYE94383 | 71.80 | 72.60 | 70.80 | 70.90 | 73.70 | 100.00 | 73.20 | 76.20 | 72.00 | 72.20 | 71.80 |
| *Aspergillus niger* CBS 513.88 | XP_001398866 | 72.50 | 73.50 | 72.00 | 71.60 | 98.30 | 73.20 | 100.00 | 74.90 | 78.40 | 78.20 | 78.20 |
| *Aspergillus terreus* NIH2624 | XP_001213025 | 72.20 | 73.20 | 71.50 | 71.10 | 75.90 | 76.20 | 74.90 | 100.00 | 76.20 | 75.70 | 75.70 |
| *Neosartorya fischeri* NRRL 181 | XP_001265293 | 76.30 | 74.20 | 74.30 | 73.30 | 79.00 | 72.00 | 78.40 | 76.20 | 100.00 | 96.90 | 97.10 |
| *Aspergillus fumigatus* var. RP-2014 | KEY77153 | 75.70 | 73.90 | 74.30 | 72.50 | 78.80 | 72.20 | 78.20 | 75.70 | 96.90 | 100.00 | 99.40 |

TABLE 6A-continued

Percentage amino acid sequence identity among *Penicillium brasilianum* hmfN2 orthologogues and accession numbers thereof.

| Species | Accession | | | | | | | | | | | |
|---|---|---|---|---|---|---|---|---|---|---|---|---|
| *Aspergillus fumigatus* Af293 | XP_750112 | 75.50 | 73.70 | 74.10 | 72.30 | 78.40 | 71.80 | 78.20 | 75.70 | 97.10 | 99.40 | 100.00 |

TABLE 7A

Percentage amino acid sequence identity among *Penicillium brasilianum* hmfP1 orthologogues and accession numbers thereof.

| Species | Accession | | | | | | | | | | | |
|---|---|---|---|---|---|---|---|---|---|---|---|---|
| *Penicillium brasilianum* hmfP1 | SEQ ID NO: 7 | 100.00 | 62.60 | 60.30 | 58.40 | 59.20 | 59.00 | 59.20 | 59.00 | 58.40 | 54.90 | 54.70 |
| *Arthroderma otae* CBS 113480 | XP_002842712 | 62.60 | 100.00 | 80.30 | 79.10 | 78.00 | 77.80 | 79.10 | 79.10 | 78.20 | 55.10 | 55.10 |
| *Microsporum gypseum* CBS 118893 | XP_003169145 | 60.30 | 80.30 | 100.00 | 87.40 | 87.00 | 86.70 | 88.60 | 88.60 | 87.40 | 51.30 | 51.10 |
| *Arthroderma benhamiae* CBS 112371 | XP_003013874 | 58.40 | 79.10 | 87.40 | 100.00 | 93.80 | 93.60 | 93.80 | 94.00 | 96.30 | 51.90 | 51.80 |
| *Trichophyton soudanense* CBS 452.61 | EZF72840 | 59.20 | 78.00 | 87.00 | 93.80 | 100.00 | 99.80 | 90.70 | 90.90 | 93.80 | 51.60 | 51.50 |
| *Trichophyton rubrum* CBS 118892 | XP_003235790 | 59.00 | 77.80 | 86.70 | 93.60 | 99.80 | 100.00 | 90.60 | 90.70 | 93.60 | 51.40 | 51.30 |
| *Trichophyton tonsurans* CBS 112818 | EGD94050 | 59.20 | 79.10 | 88.60 | 93.80 | 90.70 | 90.60 | 100.00 | 99.40 | 93.60 | 51.80 | 51.70 |
| *Trichophyton interdigitale* H6 | EZF36477 | 59.00 | 79.10 | 88.60 | 94.00 | 90.90 | 90.70 | 99.40 | 100.00 | 93.60 | 52.00 | 51.90 |
| *Trichophyton verrucosum* HKI 0517 | XP_003021315 | 58.40 | 78.20 | 87.40 | 96.30 | 93.80 | 93.60 | 93.60 | 93.60 | 100.00 | 51.50 | 51.40 |
| *Talaromyces marneffei* ATCC 18224 | XP_002148377 | 54.90 | 55.10 | 51.30 | 51.90 | 51.60 | 51.40 | 51.80 | 52.00 | 51.50 | 100.00 | 99.80 |
| *Talaromyces marneffei* PM1 | KFX51761 | 54.70 | 55.10 | 51.10 | 51.80 | 51.50 | 51.30 | 51.70 | 51.90 | 51.40 | 99.80 | 100.00 |

TABLE 8A

Percentage amino acid sequence identity among *Penicillium brasilianum* hmfP2 orthologogues and accession numbers thereof.

| Species | Accession | | | | | | | | | | | |
|---|---|---|---|---|---|---|---|---|---|---|---|---|
| *Penicillium brasilianum* hmfP2 | SEQ ID NO: 8 | 100.00 | 49.20 | 46.80 | 49.00 | 46.80 | 48.30 | 49.00 | 50.00 | 50.00 | 45.20 | 46.80 |
| *Aspergillus oryzae* RIB40 | XP_001824539 | 49.20 | 100.00 | 61.90 | 50.60 | 49.60 | 50.20 | 50.60 | 97.90 | 97.70 | 57.80 | 61.10 |
| *Aspergillus fumigatus* A1163 | EDP50847 | 46.80 | 61.90 | 100.00 | 45.50 | 45.50 | 44.90 | 45.50 | 59.80 | 59.80 | 56.60 | 59.80 |
| *Talaromyces marneffei* ATCC 18224 | XP_002149881 | 49.00 | 50.60 | 45.50 | 100.00 | 83.40 | 98.30 | 100.00 | 48.70 | 48.70 | 48.90 | 47.50 |
| *Talaromyces stipitatus* ATCC 10500 | XP_002484384 | 46.80 | 49.60 | 45.50 | 83.40 | 100.00 | 82.50 | 83.40 | 47.60 | 47.60 | 49.30 | 47.10 |
| *Talaromyces marneffei* PM1 | KFX40866 | 48.30 | 50.20 | 44.90 | 98.30 | 82.50 | 100.00 | 98.30 | 48.30 | 48.30 | 48.50 | 46.70 |
| *Talaromyces marneffei* ATCC 18224 | XP_002149879 | 49.00 | 50.60 | 45.50 | 100.00 | 83.40 | 98.30 | 100.00 | 48.70 | 48.70 | 48.90 | 47.50 |
| *Aspergillus flavus* NRRL3357 | XP_002384098 | 50.00 | 97.90 | 59.80 | 48.70 | 47.60 | 48.30 | 48.70 | 100.00 | 99.80 | 56.00 | 58.50 |
| *Aspergillus oryzae* 3.042 | EIT77828 | 50.00 | 97.70 | 59.80 | 48.70 | 47.60 | 48.30 | 48.70 | 99.80 | 100.00 | 55.80 | 58.50 |
| *Aspergillus terreus* NIH2624 | XP_001218425 | 45.20 | 57.80 | 56.60 | 48.90 | 49.30 | 48.50 | 48.90 | 56.00 | 55.80 | 100.00 | 58.60 |
| *Aspergillus niger* CBS 513.88 | XP_001398623 | 46.80 | 61.10 | 59.80 | 47.50 | 47.10 | 46.70 | 47.50 | 58.50 | 58.50 | 58.60 | 100.00 |

TABLE 9A

Percentage amino acid sequence identity among *Penicillium brasilianum* hmfP3 orthologogues and accession numbers thereof.

| Species | Accession | | | | | | | | | | | |
|---|---|---|---|---|---|---|---|---|---|---|---|---|
| *Penicillium brasilianum* hmfP3 | SEQ ID NO: 9 | 100.00 | 66.80 | 65.10 | 63.90 | 63.70 | 63.40 | 65.50 | 64.20 | 63.20 | 63.20 | 63.20 |

TABLE 9A-continued

Percentage amino acid sequence identity among *Penicillium brasilianum* hmfP3 orthologogues and accession numbers thereof.

| Species | Accession | | | | | | | | | | | |
|---|---|---|---|---|---|---|---|---|---|---|---|---|
| *Penicillium oxalicum* 114-2 | EPS33887 | 66.80 | 100.00 | 70.20 | 71.00 | 71.30 | 70.70 | 72.20 | 70.80 | 69.40 | 69.10 | 68.40 |
| *Penicillium digitatum* Pd1 | EKV16227 | 65.10 | 70.20 | 100.00 | 88.40 | 82.30 | 69.30 | 72.80 | 73.10 | 71.40 | 71.10 | 69.90 |
| *Penicillium chrysogenum* | AAR08189 | 63.90 | 71.00 | 88.40 | 100.00 | 86.40 | 69.90 | 75.10 | 73.90 | 72.60 | 72.30 | 71.00 |
| *Penicillium rubens* Wisconsin 54-1255 | XP_002557865 | 63.70 | 71.30 | 82.30 | 86.40 | 100.00 | 67.60 | 72.50 | 70.20 | 70.60 | 70.30 | 69.00 |
| *Aspergillus terreus* NIH2624 | XP_001215177 | 63.40 | 70.70 | 69.30 | 69.90 | 67.60 | 100.00 | 80.00 | 79.30 | 79.50 | 79.20 | 78.90 |
| *Neosartorya fischeri* NRRL 181 | XP_001260128 | 65.50 | 72.20 | 72.80 | 75.10 | 72.50 | 80.00 | 100.00 | 96.20 | 80.70 | 80.40 | 80.10 |
| *Aspergillus fumigatus* Af293 | XP_749637 | 64.20 | 70.80 | 73.10 | 73.90 | 70.20 | 79.30 | 96.20 | 100.00 | 80.80 | 80.50 | 80.20 |
| *Aspergillus kawachii* IFO 4308 | GAA83790 | 63.20 | 69.40 | 71.40 | 72.60 | 70.60 | 79.50 | 80.70 | 80.80 | 100.00 | 99.70 | 98.90 |
| *Aspergillus niger* WU-2223L | O74180 | 63.20 | 69.10 | 71.10 | 72.30 | 70.30 | 79.20 | 80.40 | 80.50 | 99.70 | 100.00 | 99.10 |
| *Aspergillus niger* CBS 513.88 | XP_001394472 | 63.20 | 68.40 | 69.90 | 71.00 | 69.00 | 78.90 | 80.10 | 80.20 | 98.90 | 99.10 | 100.00 |

TABLE 10A

Percentage amino acid sequence identity among *Penicillium brasilianum* hmfK1 orthologogues and accession numbers thereof.

| Species | Accession | | | | | | | | | | | |
|---|---|---|---|---|---|---|---|---|---|---|---|---|
| *Penicillium brasilianum* hmfK1 | SEQ ID NO: 10 | 100.00 | 82.20 | 80.60 | 73.90 | 73.90 | 80.00 | 78.50 | 74.20 | 74.50 | 72.80 | 69.80 |
| *Scedosporium apiospermum* | KEZ45619 | 82.20 | 100.00 | 79.60 | 76.10 | 76.10 | 77.50 | 78.50 | 76.30 | 71.70 | 73.10 | 68.40 |
| *Togninia minima* UCRPA7 | XP_007916105 | 80.60 | 79.60 | 100.00 | 75.60 | 75.60 | 76.10 | 82.60 | 76.30 | 70.30 | 75.60 | 70.50 |
| *Stachybotrys chartarum* IBT 7711 | KEY72859 | 73.90 | 76.10 | 75.60 | 100.00 | 99.80 | 73.40 | 73.50 | 95.40 | 68.40 | 73.80 | 67.40 |
| *Stachybotrys chartarum* IBT 40293 | KFA53358 | 73.90 | 76.10 | 75.60 | 99.80 | 100.00 | 73.40 | 73.50 | 95.20 | 68.40 | 73.80 | 67.40 |
| *Sporothrix schenckii* ATCC 58251 | ERT02390 | 80.00 | 77.50 | 76.10 | 73.40 | 73.40 | 100.00 | 72.50 | 72.90 | 75.50 | 69.10 | 66.00 |
| *Eutypa lata* UCREL1 | XP_007794919 | 78.50 | 78.50 | 82.60 | 73.50 | 73.50 | 72.50 | 100.00 | 74.30 | 67.70 | 72.10 | 69.70 |
| *Stachybotrys chlorohalonata* IBT 40285 | KFA62283 | 74.20 | 76.30 | 76.30 | 95.40 | 95.20 | 72.90 | 74.30 | 100.00 | 67.50 | 73.00 | 67.10 |
| *Grosmannia clavigera* kw1407 | EFX06428 | 74.50 | 71.70 | 70.30 | 68.40 | 68.40 | 75.50 | 67.70 | 67.50 | 100.00 | 65.30 | 64.20 |
| *Cyphellophora europaea* CBS 101466 | XP_008712555 | 72.80 | 73.10 | 75.60 | 73.80 | 73.80 | 69.10 | 72.10 | 73.00 | 65.30 | 100.00 | 70.60 |
| *Byssochlamys spectabilis* No. 5 | GAD98036 | 69.80 | 68.40 | 70.50 | 67.40 | 67.40 | 66.00 | 69.70 | 67.10 | 64.20 | 70.60 | 100.00 |

TABLE 11A

Percentage amino acid sequence identity among *Penicillium brasilianum* hmfK2 orthologogues and accession numbers thereof.

| Species | Accession | | | | | | | | | | | |
|---|---|---|---|---|---|---|---|---|---|---|---|---|
| *Penicillium brasilianum* hmfK2 | SEQ ID NO: 11 | 100.00 | 43.30 | 42.50 | 42.70 | 42.50 | 42.20 | 42.50 | 41.10 | 35.10 | 38.10 | 37.70 |
| *Fusarium oxysporum* f. sp. *cubense* race 4 | EMT69322 | 43.30 | 100.00 | 98.80 | 93.40 | 98.80 | 98.40 | 94.50 | 90.40 | 32.60 | 41.90 | 41.70 |
| *Fusarium oxysporum* f. sp. *melonis* 26406 | EXK38464 | 42.50 | 98.80 | 100.00 | 93.40 | 99.20 | 98.80 | 94.90 | 90.80 | 32.60 | 41.70 | 41.50 |
| *Botrytis cinerea* | CCH26290 | 42.70 | 93.40 | 93.40 | 100.00 | 93.60 | 93.60 | 90.50 | 86.80 | 32.20 | 41.50 | 41.10 |
| *Fusarium oxysporum* f. sp. *raphani* 54005 | EXK83377 | 42.50 | 98.80 | 99.20 | 93.60 | 100.00 | 99.60 | 94.90 | 90.80 | 32.20 | 41.90 | 41.70 |
| *Fusarium oxysporum* f. sp. *cubense* race 1 | ENH68136 | 42.20 | 98.40 | 98.80 | 93.60 | 99.60 | 100.00 | 94.50 | 90.40 | 32.00 | 41.70 | 41.50 |

TABLE 11A-continued

Percentage amino acid sequence identity among *Penicillium brasilianum* hmfK2 orthologogues and accession numbers thereof.

| Species | Accession | | | | | | | | | | | |
|---|---|---|---|---|---|---|---|---|---|---|---|---|
| *Fusarium fujikuroi* IMI 58289 | CCT67992 | 42.50 | 94.50 | 94.90 | 90.50 | 94.90 | 94.50 | 100.00 | 95.90 | 32.40 | 41.90 | 41.70 |
| *Fusarium fujikuroi* | CAJ76275 | 41.10 | 90.40 | 90.80 | 86.80 | 90.80 | 90.40 | 95.90 | 100.00 | 30.90 | 40.30 | 40.20 |
| *Macrophomina phaseolina* M56 | EKG18528 | 35.10 | 32.60 | 32.60 | 32.20 | 32.20 | 32.00 | 32.40 | 30.90 | 100.00 | 28.90 | 28.50 |
| *Metarhizium robertsii* | EXV00673 | 38.10 | 41.90 | 41.70 | 41.50 | 41.90 | 41.70 | 41.90 | 40.30 | 28.90 | 100.00 | 97.10 |
| *Metarhizium anisopliae* | KFG86875 | 37.70 | 41.70 | 41.50 | 41.10 | 41.70 | 41.50 | 41.70 | 40.20 | 28.50 | 97.10 | 100.00 |

TABLE 12A

Percentage amino acid sequence identity among *Penicillium brasilianum* hmfQ orthologogues and accession numbers thereof.

| Species | Accession | | | | | | | | | | | |
|---|---|---|---|---|---|---|---|---|---|---|---|---|
| *Penicillium brasilianum* hmfQ | SEQ ID NO: 12 | 100.00 | 62.80 | 59.30 | 57.00 | 58.50 | 57.00 | 57.00 | 55.90 | 56.70 | 55.50 | 55.60 |
| *Glarea lozoyensis* ATCC 20868 | XP_008076942 | 62.80 | 100.00 | 59.00 | 57.30 | 57.60 | 57.30 | 57.30 | 55.60 | 58.40 | 56.60 | 57.30 |
| *Mycobacterium aromaticivorans* | WP_036343933 | 59.30 | 59.00 | 100.00 | 81.60 | 78.40 | 81.30 | 81.30 | 74.80 | 80.10 | 80.50 | 78.50 |
| *Mycobacterium smegmatis* | WP_003893625 | 57.00 | 57.30 | 81.60 | 100.00 | 87.10 | 99.70 | 99.70 | 80.20 | 87.10 | 80.50 | 80.50 |
| *Mycobacterium* sp. UM_WWY | WP_029367382 | 58.50 | 57.60 | 78.40 | 87.10 | 100.00 | 86.80 | 86.80 | 80.70 | 89.10 | 78.20 | 77.00 |
| *Mycobacterium smegmatis* | WP_011728257 | 57.00 | 57.30 | 81.30 | 99.70 | 86.80 | 100.00 | 100.00 | 79.90 | 86.80 | 80.20 | 80.50 |
| *Mycobacterium smegmatis* str. MC2 155 | AFP38668 | 57.00 | 57.30 | 81.30 | 99.70 | 86.80 | 100.00 | 100.00 | 79.90 | 86.80 | 80.20 | 78.30 |
| *Mycobacterium* sp. URHD0025 | WP_029111475 | 55.90 | 55.60 | 74.80 | 80.20 | 80.70 | 79.90 | 79.90 | 100.00 | 79.30 | 72.20 | 72.80 |
| *Mycobacterium mageritense* | WP_036434064 | 56.70 | 58.40 | 80.10 | 87.10 | 89.10 | 86.80 | 86.80 | 79.30 | 100.00 | 77.30 | 78.20 |
| *Mycobacterium kansasii* | WP_036402197 | 55.50 | 56.60 | 80.50 | 80.50 | 78.20 | 80.20 | 80.20 | 72.20 | 77.30 | 100.00 | 80.20 |
| *Rhodococcus opacus* B4 | BAH48573 | 55.60 | 57.30 | 78.50 | 80.50 | 77.00 | 80.50 | 78.30 | 72.80 | 78.20 | 80.20 | 100.00 |

TABLE 13A

Percentage amino acid sequence identity among *Penicillium brasilianum* hmfU orthologogues and accession numbers thereof.

| Species | Accession | | | | | | | | | | | |
|---|---|---|---|---|---|---|---|---|---|---|---|---|
| *Penicillium brasilianum* hmfU | SEQ ID NO: 13 | 100.00 | 85.30 | 74.60 | 73.40 | 73.40 | 67.60 | 68.40 | 65.20 | 64.40 | 64.70 | 64.40 |
| *Penicillium oxalicum* 114-2 | EPS28195 | 85.30 | 100.00 | 69.80 | 68.90 | 68.90 | 66.10 | 65.60 | 63.40 | 63.50 | 62.90 | 62.90 |
| *Penicillium rubens* Wisconsin 54-1255 | XP_002560238 | 74.60 | 69.80 | 100.00 | 89.80 | 90.10 | 60.80 | 61.80 | 63.30 | 61.40 | 62.70 | 62.40 |
| *Penicillium digitatum* Pd1 | EKV20433 | 73.40 | 68.90 | 89.80 | 100.00 | 99.70 | 60.30 | 61.60 | 63.40 | 61.20 | 62.90 | 62.90 |
| *Penicillium digitatum* PHI26 | EKV11956 | 73.40 | 68.90 | 90.10 | 99.70 | 100.00 | 60.30 | 61.60 | 63.40 | 61.20 | 62.90 | 62.90 |
| *Aspergillus terreus* NIH2624 | XP_001208783 | 67.60 | 66.10 | 60.80 | 60.30 | 60.30 | 100.00 | 75.40 | 71.50 | 73.50 | 71.00 | 71.00 |
| *Neosartorya fischeri* NRRL 181 | XP_001260626 | 68.40 | 65.60 | 61.80 | 61.60 | 61.60 | 75.40 | 100.00 | 75.00 | 80.00 | 74.20 | 73.80 |
| *Aspergillus oryzae* RIB40 | XP_001821930 | 65.20 | 63.40 | 63.30 | 63.40 | 63.40 | 71.50 | 75.00 | 100.00 | 70.80 | 99.00 | 98.70 |
| *Aspergillus clavatus* NRRL 1 | XP_001275449 | 64.40 | 63.50 | 61.40 | 61.20 | 61.20 | 73.50 | 80.00 | 70.80 | 100.00 | 70.00 | 69.60 |
| *Aspergillus oryzae* RIB40 | BAE59928 | 64.70 | 62.90 | 62.70 | 62.90 | 62.90 | 71.00 | 74.20 | 99.00 | 70.00 | 100.00 | 96.50 |
| *Aspergillus flavus* NRRL3357 | XP_002379461 | 64.40 | 62.90 | 62.40 | 62.90 | 62.90 | 71.00 | 73.80 | 98.70 | 69.60 | 96.50 | 100.00 |

TABLE 14A

Percentage amino acid sequence identity among *Penicillium brasilianum* hmfO orthologogues and accession numbers thereof.

| Species | Accession | | | | | | | | | | | |
|---|---|---|---|---|---|---|---|---|---|---|---|---|
| *Penicillium brasilianum* hmfO | SEQ ID NO: 14 | 100.00 | 67.40 | 50.70 | 50.30 | 50.90 | 45.60 | 44.60 | 44.90 | 47.20 | 44.00 | 43.70 |
| *Sporothrix schenckii* ATCC 58251 | ERT02389 | 67.40 | 100.00 | 57.30 | 56.90 | 57.70 | 52.50 | 52.10 | 49.30 | 53.60 | 48.20 | 47.90 |
| *Magnaporthe oryzae* Y34 | ELQ38824 | 50.70 | 57.30 | 100.00 | 100.00 | 100.00 | 50.90 | 49.50 | 50.90 | 55.00 | 51.80 | 51.40 |
| *Magnaporthe oryzae* 70-15 | XP_003712784 | 50.30 | 56.90 | 100.00 | 100.00 | 100.00 | 50.30 | 49.00 | 50.30 | 54.40 | 51.20 | 50.90 |
| *Magnaporthe grisea* | ABO93629 | 50.90 | 57.70 | 100.00 | 100.00 | 100.00 | 51.10 | 50.00 | 51.50 | 54.60 | 51.30 | 50.90 |
| *Colletotrichum fioriniae* PJ7 | XP_007591389 | 45.60 | 52.50 | 50.90 | 50.30 | 51.10 | 100.00 | 86.40 | 74.80 | 59.20 | 59.20 | 59.90 |
| *Colletotrichum higginsianum* | CCF42149 | 44.60 | 52.10 | 49.50 | 49.00 | 50.00 | 86.40 | 100.00 | 73.80 | 60.90 | 56.70 | 57.40 |
| *Colletotrichum gloeosporioides* Cg-14 | EQB58465 | 44.90 | 49.30 | 50.90 | 50.30 | 51.50 | 74.80 | 73.80 | 100.00 | 60.60 | 58.80 | 58.80 |
| *Acremonium chrysogenum* ATCC 11550 | KFH45030 | 47.20 | 53.60 | 55.00 | 54.40 | 54.60 | 59.20 | 60.90 | 60.60 | 100.00 | 64.20 | 64.20 |
| *Fusarium oxysporum* f. sp. *cubense* race 1 | ENH72740 | 44.00 | 48.20 | 51.80 | 51.20 | 51.30 | 59.20 | 56.70 | 58.80 | 64.20 | 100.00 | 98.90 |
| *Fusarium oxysporum* f. sp. *cubense* race 4 | EMT64805 | 43.70 | 47.90 | 51.40 | 50.90 | 50.90 | 59.90 | 57.40 | 58.80 | 64.20 | 98.90 | 100.00 |

TABLE 15A

Percentage amino acid sequence identity among *Penicillium brasilianum* hmfM orthologogues and accession numbers thereof.

| Species | Accession | | | | | | | | | | | |
|---|---|---|---|---|---|---|---|---|---|---|---|---|
| *Penicillium brasilianum* hmfM | SEQ ID NO: 15 | 100.00 | 73.50 | 64.90 | 64.50 | 60.40 | 64.50 | 59.60 | 60.80 | 60.80 | 60.40 | 60.40 |
| *Aspergillus nidulans* FGSC A4 | XP_664054 | 73.50 | 100.00 | 60.80 | 62.90 | 60.40 | 69.00 | 58.80 | 58.40 | 58.40 | 58.00 | 58.00 |
| *Eutypa lata* UCREL1 | XP_007797627 | 64.90 | 60.80 | 100.00 | 65.00 | 58.50 | 56.90 | 61.80 | 65.40 | 65.00 | 65.40 | 65.40 |
| *Thielavia terrestris* NRRL 8126 | XP_003656972 | 64.50 | 62.90 | 65.00 | 100.00 | 58.50 | 61.80 | 55.70 | 65.40 | 64.60 | 65.00 | 65.00 |
| *Trichoderma atroviride* IMI 206040 | EHK50353 | 60.40 | 60.40 | 58.50 | 58.50 | 100.00 | 59.80 | 85.00 | 57.30 | 58.10 | 57.70 | 57.70 |
| *Aspergillus terreus* NIH2624 | XP_001212987 | 64.50 | 69.00 | 56.90 | 61.80 | 59.80 | 100.00 | 59.30 | 58.90 | 58.90 | 58.50 | 57.40 |
| *Trichoderma reesei* QM6a | XP_006962638 | 59.60 | 58.80 | 61.80 | 55.70 | 85.00 | 59.30 | 100.00 | 55.70 | 56.50 | 56.10 | 56.10 |
| *Fusarium oxysporum* f. sp. *cubense* race 4 | EMT67544 | 60.80 | 58.40 | 65.40 | 65.40 | 57.30 | 58.90 | 55.70 | 100.00 | 99.20 | 99.20 | 99.60 |
| *Fusarium oxysporum* Fo5176 | EGU79882 | 60.80 | 58.40 | 65.00 | 64.60 | 58.10 | 58.90 | 56.50 | 99.20 | 100.00 | 99.20 | 99.60 |
| *Fusarium oxysporum* f. sp. *radicis-lycopersici* 26381 | EXL52390 | 60.40 | 58.00 | 65.40 | 65.00 | 57.70 | 58.50 | 56.10 | 99.20 | 99.20 | 100.00 | 99.60 |
| *Fusarium oxysporum* f. sp. *cubense* race 1 | ENH63602 | 60.40 | 58.00 | 65.40 | 65.00 | 57.70 | 57.40 | 56.10 | 99.60 | 99.60 | 99.60 | 100.00 |

TABLE 16A

Percentage amino acid sequence identity among *Penicillium brasilianum* hmfT3 orthologogues and accession numbers thereof.

| Species | Accession | | | | | | | | | | | |
|---|---|---|---|---|---|---|---|---|---|---|---|---|
| *Penicillium brasilianum* hmfT3 | SEQ ID NO: 16 | 100.00 | 85.10 | 81.90 | 81.70 | 80.50 | 75.90 | 75.90 | 80.20 | 75.20 | 75.20 | 75.20 |
| *Penicillium rubens* Wisconsin 54-1255 | XP_002560799 | 85.10 | 100.00 | 78.50 | 80.80 | 79.60 | 75.20 | 75.20 | 79.60 | 75.90 | 76.00 | 74.30 |
| *Penicillium oxalicum* 114-2 | EPS29964 | 81.90 | 78.50 | 100.00 | 77.40 | 77.10 | 72.60 | 72.70 | 76.60 | 71.90 | 72.00 | 71.60 |

TABLE 16A-continued

Percentage amino acid sequence identity among *Penicillium brasilianum* hmfT3 orthologogues and accession numbers thereof.

| Species | Accession | | | | | | | | | | | |
|---|---|---|---|---|---|---|---|---|---|---|---|---|
| *Aspergillus terreus* NIH2624 | XP_001212020 | 81.70 | 80.80 | 77.40 | 100.00 | 78.30 | 73.90 | 73.90 | 79.00 | 74.60 | 74.60 | 73.00 |
| *Fusarium oxysporum* f. sp. *cubense* race 1 | ENH73763 | 80.50 | 79.60 | 77.10 | 78.30 | 100.00 | 99.80 | 99.60 | 88.00 | 93.10 | 92.90 | 98.60 |
| *Fusarium oxysporum* Fo5176 | EGU73369 | 75.90 | 75.20 | 72.60 | 73.90 | 99.80 | 100.00 | 99.70 | 87.70 | 91.90 | 91.50 | 98.20 |
| *Fusarium oxysporum* f. sp. *cubense* tropical race 4 54006 | EXL94287 | 75.90 | 75.20 | 72.70 | 73.90 | 99.60 | 99.70 | 100.00 | 87.70 | 91.70 | 91.40 | 97.90 |
| *Nectria haematococca* mpVI 77-13-4 | XP_003040064 | 80.20 | 79.60 | 76.60 | 79.00 | 88.00 | 87.70 | 87.70 | 100.00 | 87.60 | 88.30 | 87.30 |
| *Fusarium pseudograminearum* CS3096 | XP_009258565 | 75.20 | 75.90 | 71.90 | 74.60 | 93.10 | 91.90 | 91.70 | 87.60 | 100.00 | 99.00 | 91.30 |
| *Fusarium graminearum* PH-1 | XP_011323833 | 75.20 | 76.00 | 72.00 | 74.60 | 92.90 | 91.50 | 91.40 | 88.30 | 99.00 | 100.00 | 91.00 |
| *Fusarium fujikuroi* IMI 58289 | CCT64241 | 75.20 | 74.30 | 71.60 | 73.00 | 98.60 | 98.20 | 97.90 | 87.30 | 91.30 | 91.00 | 100.00 |

TABLE 17A

Percentage amino acid sequence identity among *Penicillium brasilianum* hmfT4 orthologogues and accession numbers thereof.

| Species | Accession | | | | | | | | | | | |
|---|---|---|---|---|---|---|---|---|---|---|---|---|
| *Penicillium brasilianum* hmfT4 | SEQ ID NO: 17 | 100.00 | 68.90 | 66.40 | 38.60 | 38.50 | 36.90 | 37.40 | 37.50 | 39.10 | 36.50 | 37.80 |
| *Sporothrix schenckii* ATCC 58251 | ERT02386 | 68.90 | 100.00 | 67.00 | 35.90 | 38.40 | 37.90 | 35.90 | 38.50 | 39.50 | 38.50 | 38.80 |
| *Togninia minima* UCRPA7 | XP_007915981 | 66.40 | 67.00 | 100.00 | 36.20 | 40.30 | 40.50 | 39.10 | 41.00 | 38.80 | 38.50 | 42.10 |
| *Capronia coronata* CBS 617.96 | XP_007724585 | 38.60 | 35.90 | 36.20 | 100.00 | 57.40 | 56.80 | 60.00 | 56.40 | 57.30 | 54.10 | 56.40 |
| *Sporothrix schenckii* ATCC 58251 | ERS98342 | 38.50 | 38.40 | 40.30 | 57.40 | 100.00 | 59.20 | 55.30 | 59.60 | 71.10 | 61.80 | 58.90 |
| *Aspergillus kawachii* IFO 4308 | GAA83620 | 36.90 | 37.90 | 40.50 | 56.80 | 59.20 | 100.00 | 53.40 | 80.60 | 60.30 | 56.20 | 81.30 |
| *Capronia coronata* CBS 617.96 | XP_007725190 | 37.40 | 35.90 | 39.10 | 60.00 | 55.30 | 53.40 | 100.00 | 53.40 | 55.70 | 52.90 | 53.60 |
| *Aspergillus niger* CBS 513.88 | XP_001389139 | 37.50 | 38.50 | 41.00 | 56.40 | 59.60 | 80.60 | 53.40 | 100.00 | 61.70 | 56.00 | 100.00 |
| *Grosmannia clavigera* kw1407 | EFX04858 | 39.10 | 39.50 | 38.80 | 57.30 | 71.10 | 60.30 | 55.70 | 61.70 | 100.00 | 61.40 | 61.40 |
| *Sporothrix schenckii* ATCC 58251 | ERS94853 | 36.50 | 38.50 | 38.50 | 54.10 | 61.80 | 56.20 | 52.90 | 56.00 | 61.40 | 100.00 | 55.70 |
| *Aspergillus niger* ATCC 1015 | EHA26600 | 37.80 | 38.80 | 42.10 | 56.40 | 58.90 | 81.30 | 53.60 | 100.00 | 61.40 | 55.70 | 100.00 |

TABLE 18A

Percentage amino acid sequence identity among *Penicillium brasilianum* hmfT5 orthologogues and accession numbers thereof.

| Species | Accession | | | | | | | | | | | |
|---|---|---|---|---|---|---|---|---|---|---|---|---|
| *Penicillium brasilianum* hmfT5 | SEQ ID NO: 18 | 100.00 | 84.00 | 83.90 | 84.30 | 82.20 | 82.30 | 82.20 | 82.40 | 81.00 | 81.10 | 81.00 |
| *Penicillium digitatum* Pd1 | EKV20717 | 84.00 | 100.00 | 99.90 | 91.40 | 79.10 | 79.20 | 79.30 | 80.80 | 79.10 | 79.10 | 76.80 |
| *Penicillium digitatum* PHI26 | EKV19541 | 83.90 | 99.90 | 100.00 | 91.30 | 79.10 | 79.10 | 79.20 | 80.70 | 79.00 | 79.00 | 76.80 |
| *Penicillium rubens* Wisconsin 54-1255 | XP_002565665 | 84.30 | 91.40 | 91.30 | 100.00 | 80.10 | 80.20 | 80.00 | 81.60 | 80.90 | 80.40 | 77.90 |
| *Aspergillus oryzae* 100-8 | KDE82314 | 82.20 | 79.10 | 79.10 | 80.10 | 100.00 | 100.00 | 99.60 | 82.40 | 81.60 | 81.30 | 75.60 |

TABLE 18A-continued

Percentage amino acid sequence identity among *Penicillium brasilianum* hmfT5 orthologogues and accession numbers thereof.

| Species | Accession | | | | | | | | | | | |
|---|---|---|---|---|---|---|---|---|---|---|---|---|
| *Aspergillus oryzae* 3.042 | EIT77345 | 82.30 | 79.20 | 79.10 | 80.20 | 100.00 | 100.00 | 99.60 | 82.40 | 81.60 | 81.30 | 75.70 |
| *Aspergillus flavus* NRRL3357 | XP_002380612 | 82.20 | 79.30 | 79.20 | 80.00 | 99.60 | 99.60 | 100.00 | 82.50 | 81.60 | 81.30 | 75.70 |
| *Aspergillus terreus* NIH2624 | XP_001208847 | 82.40 | 80.80 | 80.70 | 81.60 | 82.40 | 82.40 | 82.50 | 100.00 | 84.90 | 84.80 | 76.10 |
| *Aspergillus kawachii* IFO 4308 | GAA86951 | 81.00 | 79.10 | 79.00 | 80.90 | 81.60 | 81.60 | 81.60 | 84.90 | 100.00 | 97.40 | 75.70 |
| *Aspergillus niger* CBS 513.88 | XP_001400982 | 81.10 | 79.10 | 79.00 | 80.40 | 81.30 | 81.30 | 81.30 | 84.80 | 97.40 | 100.00 | 75.40 |
| *Ophiostoma piceae* UAMH 11346 | EPE02908 | 81.00 | 76.80 | 76.80 | 77.90 | 75.60 | 75.70 | 75.70 | 76.10 | 75.70 | 75.40 | 100.00 |

TABLE 19A

Percentage amino acid sequence identity among *Penicillium brasilianum* hmfR orthologogues and accession numbers thereof.

| Species | Accession | | | | | | | | | | | |
|---|---|---|---|---|---|---|---|---|---|---|---|---|
| *Penicillium brasilianum* hmfR | SEQ ID NO: 19 | 100.00 | 52.30 | 46.40 | 41.70 | 40.60 | 41.70 | 41.80 | 41.70 | 41.70 | 41.70 | 41.70 |
| *Sporothrix schenckii* ATCC 58251 | ERT02388 | 52.30 | 100.00 | 43.10 | 39.60 | 36.70 | 41.80 | 41.90 | 41.80 | 41.90 | 40.30 | 41.80 |
| *Scedosporium apiospermum* | KEZ45621 | 46.40 | 43.10 | 100.00 | 43.50 | 42.30 | 45.90 | 45.70 | 45.90 | 46.10 | 44.80 | 45.90 |
| *Stachybotrys chlorohalonata* IBT 40285 | KFA62280 | 41.70 | 39.60 | 43.50 | 100.00 | 51.50 | 56.30 | 55.90 | 56.30 | 56.00 | 55.30 | 56.30 |
| *Verticillium alfalfae* VaMs.102 | XP_003000413 | 40.60 | 36.70 | 42.30 | 51.50 | 100.00 | 53.90 | 54.00 | 53.90 | 54.00 | 53.10 | 53.70 |
| *Fusarium oxysporum* f. sp. *conglutinans* race 2 54008 | EXL68817 | 41.70 | 41.80 | 45.90 | 56.30 | 53.90 | 100.00 | 97.90 | 99.60 | 98.40 | 98.60 | 98.50 |
| *Fusarium oxysporum* f. sp. *melonis* 26406 | EXK46473 | 41.80 | 41.90 | 45.70 | 55.90 | 54.00 | 97.90 | 100.00 | 97.50 | 97.80 | 98.20 | 97.90 |
| *Fusarium oxysporum* Fo5176 | EGU75021 | 41.70 | 41.80 | 45.90 | 56.30 | 53.90 | 99.60 | 97.50 | 100.00 | 98.10 | 98.30 | 98.30 |
| *Fusarium oxysporum* f. sp. *vasinfectum* 25433 | EXM14771 | 41.70 | 41.90 | 46.10 | 56.00 | 54.00 | 98.40 | 97.80 | 98.10 | 100.00 | 98.30 | 99.10 |
| *Fusarium oxysporum* f. sp. *cubense* tropical race 4 54006 | EXM09676 | 41.70 | 40.30 | 44.80 | 55.30 | 53.10 | 98.60 | 98.20 | 98.30 | 98.30 | 100.00 | 98.40 |
| *Fusarium oxysporum* f. sp. *raphani* 54005 | EXK77862 | 41.70 | 41.80 | 45.90 | 56.30 | 53.70 | 98.50 | 97.90 | 98.30 | 99.10 | 98.40 | 100.00 |

EXAMPLES

Methods and Materials

Cultivation Procedures

The mineral medium employed contained the following per liter of demineralized water: $(NH_4)_2SO_4$, 5 g; $K_2HPO_4$, 1.55 g; $NaH_2PO_4$ $2H_2O$, 0.85 g; $MgSO_4.7H_2O$, 0.5 g; EDTA, 15 mg; $ZnSO_4.7H_2O$, 4.5 mg; $CoCl_2$ $6H_2O$, 0.3 mg; $MnCl_2$ $4H_2O$, 1 mg; $CuSO_4$ $5H_2O$, 0.3 mg; $CaCl_2.2H_2O$, 4.5 mg; $FeSO_4$ $7H_2O$, 3 mg; $Na_2MoO_4.2H_2O$, 0.4 mg; $H_3BO_3$, 1 mg; KI, 0.1 mg. After heat sterilization at 120° C. and cooling, sterile carbon sources were added. Glucose solutions were heat-sterilized separately at 110° C. for 20 minutes, whereas other carbon sources were sterilized at 120° C. Where necessary mineral medium was supplemented with vitamins.

Media for plates (1.5% agar) contained the mineral medium to which carbon sources were added at the concentrations indicated.

Small-scale batch cultivation was done at 30° C. in 100-ml Erlenmeyer flasks. They contained 20 ml mineral salts medium supplied with carbon sources. They were incubated either stationary or on a rotary shaker at rates as indicated for the various experiments. Air could enter in the flasks via cotton plugs.

Batch cultivation of fungi in a fermenter with a working volume of 1 liter was done at 30° C. and the stirring speed could be controlled. $K_2HPO_4$ was omitted from the mineral salts medium. The pH was automatically controlled at the pH-value required by titration with either 4 M NaOH or 4 M $H_2SO_4$. Air was supplied at a rate of maximally 1 liter per minute.

Chemostat cultivation of *P. brasilianum* was also in the fermenter with a 1 liter working volume. The same medium was used except that now 0.1 g/l yeast extract was added. The cultivation vessel (1 g/l HMF) was inoculated with a preculture of *P. brasilianum* from a small-scale batch culture. After overnight batch-wise incubation, pumping was started from the medium reservoir at a desired rate. Concentrations of carbon substrates in the medium reservoir were 1 g/1. Oxygen levels in the liquid were automatically controlled by adjusting the stirrer speed. Air was supplied at a rate of maximally 1 liter per minute.

Chemostat cultivation of yeast strains was in a fermenter with a 1 liter working volume. The cultivation vessel was inoculated with a preculture of the yeasts from a small-scale batch culture. After overnight batch-wise incubation, pumping was started from the medium reservoir at a desired rate. Oxygen levels in the liquid were automatically controlled by adjusting the stirrer speed. Air was supplied at a rate of maximally 1 liter per minute.

Strains

The following strains were used: *Saccharomyces cerevisiae* CEN.PK113-1A (MATalpha; his3D1; leu2-3_112; ura3-52; trp1-289; MAL2-8c; SUC2; Euroscarf No. 30000B Orf 2463); *Yarrowia lipolytica* Po1g (commercially obtained from Yeastern Biotech Co. Ltd., www.yestern.com); *Kluyveromyces marxianus* Ky-003, DSM 70073 (type strain, isolate from butter milk); *Echerichia coli* NEB 5-alpha (commercially obtained from New England Biolabs, www.neb.com); *Pseudomonas putida* S12 (ATCC 700801); *Cupriavidus basilensis* HMF14 (Wierckx et al., 2010, Microb Biotechnol. 3(3):336-43); *Penicillium brasilianum* C1 (isolated from Dutch soil as described in Example 1).

Molecular Cloning

All molecular cloning techniques used here are similar or equivalent to methods described in Molecular Cloning: A Laboratory Manual, $4^{th}$ Edition Manual by Michael R. Green, Howard Hughes Medical Institute, University of Massachusetts Medical School; Joseph Sambrook, Peter MacCallum Cancer Institute, Melbourne, Australia. Cold Spring Harbour Laboratory Press, 2012.

Metabolite Analyses

Supernatants obtained by centrifugation and/or filtration of culture samples were analyzed for furans by HPLC. Analyses were performed with an Agilent 1100 system. Furanic compounds were measured using an Zorbax eclipse XDB C8 column, (pore size 80 Å, 180 $m^2/g$ operated at 25° C.). Compounds were quantified on an Thermo system equipped with a diode array detector.

The two eluents used were 12 mM $PO_4$ buffer pH 7 (1.293 g $K_2HPO_4$ and 0.543 g $NaH_2PO_4$ per liter) and acetonitrile (HPLC grade, Sigma E chromasolv). The flow rate was set at 1.2 ml/min and the gradient run time was 8 minutes according to the scheme: 1) Acetonitrile at 5% during the initial period of 3.5 minutes; 2) Linear increase of acetonitrile during 2.5 minutes to reach 40% acetonitrile; 3) Constant level of acetonitrile at 40% during 0.5 minutes; 4) Linear decrease of acetonitrile during 0.5 minutes to reach 5% acetonitrile; and, 5) Constant level of acetonitrile at 5% during 1 minute.

The retention times and the wavelengths for the various furanic compounds is given in the Table 20 below.

TABLE 20

HPLC retention times and wavelengths of various furanic compounds

| Compound | Wavelength (nm) | Retention time (min) |
|---|---|---|
| FDCA | 230 | 1.12 |
| HMFCA | 250 | 1.56 |
| FFCA | 285 | 1.99 |
| HMF-OH | 230 | 4.15 |
| HMF | 285 | 4.51 |

Glucose concentration in the supernatants was determined enzymatically (D-Glucose UV-Test, Boehringer Mannheim/R-Biopharm) by measuring the absorption of NADPH which is formed when D-Glucose is oxidized to Glucose-6-phosphate. Supernatants were diluted up to $10^2$ prior to analysis.

Ethanol concentration in the supernatants was determined enzymatically (Ethanol UV-Test, Boehringer Mannheim/R-Biopharm) by measuring the absorption of NADH which is formed when Ethanol is oxidized to Acetaldehyde and subsequently to Acetic acid. Supernatants were diluted up to $10^3$ prior to analysis.

Example 1: Isolation of *Penicillium brasilianum* Batista

Fungal strains with the ability to grow at the expense of HMF at low pH-values were enriched and isolated from Dutch soil. An amount of 1 g air-dried soil was supplied in a 100-ml Erlenmeyer flask containing 20 ml of liquid mineral from which $K_2HPO_4$ had been omitted. The pH of the medium was lowered to pH=3 by titrating with a solution of HCl. The initial HMF concentration was 1 g/l. Naladixic acid (20 mg/1) was included in the medium in order to suppress bacterial growth. Flasks were incubated stationary at 30° C. under air. After 2 weeks of incubation, material (1 ml) from the enrichment culture was transferred to fresh medium with the same initial composition. From this second culture, agar plates were streaked that contained mineral medium and 0.5 g/l HMF. Colonies appearing after incubating plates during 10 days at 30° C. under air were restreaked onto plates with the same initial medium until purity of the organisms. Isolates were tested for growth at the expense of HMF by growing organisms in the mineral salts medium. Erlenmeyer flasks of 100 ml containing 20 ml of liquid were employed and isolates were incubated in this medium either in the presence or absence of HMF at 1 g/l. One particular strain that showed good growth at the expense of HMF was taken for further studies.

The organism was identified and characterized at the Fungal Biodiversity Centre of CBS-KNAW. It was cultivated on Malt Extact Agar for 3 days in the dark at 25° C. DNA was extracted using the MoBio-UltraClean™ Microbial DNA Isolation Kit according to the instructions of the manufacturer. Fragments containing the ITS region were amplified using the primers LS266 (GCATTCC-CAAACAACTCGACTC; SEQ ID NO: 39) and V9G (TTACGTCCCTGCCCTTTGTA; SEQ ID NO: 40) (Gerrits van den Ende and de Hoog, 1999, Studies in Mycology, 43:151-162). Amplification of part of the β-tubulin gene was performed using the primers Bt2a (GGTAAC-CAAATCGGTGCTGCTTTC; SEQ ID NO: 41) and Bt2b (ACCCTCAGTGTAGTGACCCTTGGC; SEQ ID NO: 42), (Glass and Donaldson, 1995, Appl Environ Microbiol. 61(4): 1323-1330). Both strands of the PCR fragments were sequenced with the ABI Prism® Big Dye™ Terminator v.

3.0 Ready Reaction Cycle sequencing Kit. Samples were analysed on an ABI PRISM 3700 Genetic Analyzer and contigs were assembled using the forward and reverse sequences with the programme SeqMan from the LaserGene package. A homology search was performed on the NCBI nucleotide database and the internal database of CBS-KNAW. This gave a 100% match with the type strain of *Penicillium brasilianum* Batista for the isolate. The organism was designated *Penicillium brasilianum* C1 and employed for further studies as described herein.

Apart from HMF, the organism also grew in mineral medium at the expense of HMF-alcohol, HMFCA, FDCA, glucose, fructose, sucrose, xylose, starch and citric acid.

Example 2: Limitation for Growth of *P. brasilianum* at Low pH-Values

The *P. brasilianum* C1 strain was isolated by incubating soil in a medium with an initial pH=3. However, during growth the pH of the medium changes, also in subsequent batch experiment with the pure culture. In order to verify the pH-limits for growth, a chemostat culture was operated thus allowing a constant predetermined pH at a predetermined growth rate. The growth rate was set at 0.08 $h^{-1}$ and the pH was maintained at pH=2.9. In 3 separate experiments, either HMF, HMFCA or FDCA was used as carbon source. The organism was able to establish itself under each of the 3 conditions in a steady state; no wash-out occurred. The concentration of either of the 3 furans in the cultivation vessel was below the detection limit in either of the three runs. The results show the ability of the organism to grow at a pH-value below 3 which is a desirable property in the production of FDCA from HMF at low pH values. Furthermore, the organism grew in a homogeneous suspension further adding to the usefulness of the strain.

Example 3: Identification of *P. brasilianum* C1 Genes Encoding Enzymes Involved in HMF Catabolism Sequencing and Annotation of the Genome of *P. brasilianum* C1

DNA from *P. brasilianum* C1 was isolated and sent to BaseClear for paired-end sequencing using the Illumina HiSeq2500 system. After quality check, filtering and removing adaptors, the read sequences were assembled into contigs and linked and placed into scaffolds.

Genome annotation was performed using the BaseClear annotation pipeline, which is based on a combination of Augustus (Stanke and Waack, 2003, Bioinformatics. 19 Suppl 2:ii215-25) for structural annotation and the Prokka Prokaryotic Annotation system for functional annotation (vicbioinformatics.com). A set of *Penicillium* species was used as reference for the annotation, the annotation included information on rRNA, tRNA, signal peptides, Pfam protein family prediction, cellular localization and conserved domains.

RNA Sequencing of *P. brasilianum* C1 Cells Cultivated on HMF and on Citric Acid Cells for comparative RNA-sequencing were obtained by growing *P. brasilianum* C1 in chemostat culture on two different carbon sources. The growth rate was set at 0.1 $h^{-1}$ and the pH was maintained at pH=7. Either HMF or citric acid was used as carbon source at 2 g/l and steady state situations were obtained for both instances. The chemostat was inoculated with a 100 ml of a preculture of *P. brasilianum* C1. After 24 hours, the feed pump the was started and 36 hours later (steady state) 6 ml of cells were obtained upon centrifugation for 50 seconds at 15000 rpm at 0° C. in RNA'se-free Eppendorf-tubes. The supernatant was discarded and 1 ml RNAlater® Solutions for RNA stabilization and storage was added to the pellets. Samples were vortexed briefly and were stored overnight at 4° C. before being transferred to a −80° C. freezer.

RNA-sequencing was performed by BaseClear, based on single-end sequencing using the Illumina HiSeq2500 system. After quality check, filtering and trimming, the reads were aligned against the annotated genome. Based on this alignment the absolute expression values were calculated and subsequently the normalized RPKM (Reads per Kilobase per Million mapped reads) expression measure, to normalize between genes and between samples. To compare the two different samples, statistical tests were performed (Kal's Z-test and Baggerly's beta-binomial test) to assign the significance of expression differences between the samples.

Identification of *P. brasilianum* C1 Genes Encoding Enzymes Involved in HMF Catabolism Based on the genome annotation and blasting genes against public databases as well as on differential expression RNA-sequencing results, a list has been compiled of candidate genes that are involved in encoding enzymes that are involved in the degradation of HMF by *P. brasilianum* C1.

First the genes (from the RNAseq data) were grouped by function as predicted by automatic annotation (dehydrogenase, monooxygenase etc). Second, genes were grouped by absolute expression level (RPKM value; transcript abundance corrected for gene length) during growth on HMF. The top-100 most highly expressed genes were tagged. Third, genes were grouped by fold change during growth on HMF as compared to growth on citrate. The top-100 most highly upregulated genes were tagged. Fourth, genes were selected that scored high both with respect to absolute expression level and with respect to fold change. Fifth, a filter was applied based on function (as predicted by automatic annotation): functions that could be related to the presumed HMF degradation route (see Table 21) were selected and hits with unclear designation were discarded. Finally, a ranking was made for top hits (hmfK1, hmfL1, hmfM, hmfN1, hmfO, hmfL2, hmfP1 and hmfP2; see Table 21) that were expected to be the actual genes involved in HMF metabolism and additional potentially relevant hits, which were moderately highly expressed or upregulated but which have predicted function that relate to (possible alternative) routes for HMF metabolism (e.g., a "classical" decarboxylase and a decarboxylating dehydrogenase; hmfP3, hmfK2, hmfL3, hmfL4, hmfN2, hmfQ and hmfU). In addition a few "accesory genes" (transport/regulation) were selected (hmfR, hmfT3, hmfT4 and hmfT5).

TABLE 21

| Genes in the *P. brasilianum* C1 genome identified as being involved in HMF catabolism | | | | | | |
|---|---|---|---|---|---|---|
| Gene name | Contig | Function (annotated) | role in HMF catabolism | aa SEQ ID NO: | aa length | nt SEQ ID NO: |
| hmfL1 | 82 | alcohol dehydrogenase Zn-binding | HMFCA oxidation to FFCA | 1 | 351 | 20 |
| hmfL2 | 153 | alcohol dehydrogenase Zn-binding | HMFCA oxidation to FFCA | 2 | 339 | 21 |
| hmfL3 | 220 | alcohol dehydrogenase Zn-binding | HMFCA oxidation to FFCA | 3 | 389 | 22 |
| hmfL4 | 10 | alcohol dehydrogenase Zn-binding | HMFCA oxidation to FFCA | 4 | 330 | 23 |
| hmfN1 | 730 | salicylaldehyde dehydrogenase | HMF/FFCA oxidation to HMFCA/FDCA | 5 | 505 | 24 |
| hmfN2 | 364 | salicylaldehyde dehydrogenase | HMF/FFCA oxidation to HMFCA/FDCA | 6 | 479 | 25 |
| hmfP1 | 147 | 6-hydroxy-D-nicotine oxidase FAD binding | oxidation of HMF to HMFCA, HMF | 7 | 473 | 26 |
| hmfP2 | 819 | 6-hydroxy-D-nicotine oxidase FAD binding | to DFF, DFF to FFCA, HMFCA to FFCA, and/or | 8 | 475 | 27 |
| hmfP3 | 90 | oxidase | FFCA to FDCA | 9 | 401 | 28 |
| hmfK1 | 730 | salicylate hydroxylase FAD binding monooxygenase | FDCA decarboxylation | 10 | 427 | 29 |
| hmfK2 | 23 | 3-hydroxybenzoate 6-hydroxylase FAD binding monooxygenase | FDCA decarboxylation | 11 | 460 | 30 |
| hmfQ | 249 | oxalate decarboxylase cupin domain protein | FDCA decarboxylation | 12 | 347 | 31 |
| hmfU | 28 | 6-phosphogluconate dehydrogenase domain | oxidative decarboxylation of FDCA | 13 | 313 | 32 |
| hmfO | 730 | 3-oxoadipate enol-lactonase | hydrolysis of lactone resulting from FDCA decarboxylation | 14 | 290 | 33 |
| hmfM | 273 | short chain dehydrogenase | reduction of HMF/FFCA to the corresponding alcohol | 15 | 245 | 34 |
| hmfT3 | 254 | major superfamily facilitator protein | furan transport | 16 | 581 | 35 |
| hmfT4 | 730 | major superfamily facilitator protein | furan transport | 17 | 513 | 36 |
| hmfT5 | 1 | ABC transporter | furan transport | 18 | 1435 | 37 |
| hmfR | 730 | transcriptional activator | induction furan catabolism genes | 19 | 872 | 38 |

Example 4: Degradation of FDCA by *P. putida* S12 Containing Heterologously Expressed hmfK1 from *P. brasilianum* C1

The above described *P. brasilianum* C1 hmfK1 gene (showing homology with salicylate 1-monooxygenases nahG) was selected for expression in *P. putida* S12. The enzyme (EC 1.14.13.1) encoded for by this gene was expected to have a crucial role in the degradation of HMF via FDCA and to act as a decarboxylating monooxygenase on FDCA. In order test this hypothesis, the gene was expressed in *P. putida* S12. Subsequently, the degradation of FDCA was monitored by the strain containing the *P. brasilianum* hmfK1 gene (*P. putida* S12 ΔGCD; pBT'nahG_aldH/pjNNhmfT1) as well as by a control strain containing the empty vector (*P. putida* S12 ΔGCD; pBT'hmfH_aldH/pjNNhmfT1).

*P. putida* transformant was grown overnight in 100-ml shake flasks containing 10 ml of MM+160 mM glucose supplemented with 50 mg/L kanamycin and 30 mg/L gentamycin and 156 mg/L FDCA (1 mM). The starting pH was measured at ≈7.0. Cells were harvested at mid log phase (OD600≈0.6), washed and re-suspended in MM supplemented with 160 mM glucose and 50 mg/L kanamycin, 30 mg/L gentamicin. Aliquots (10 ml) of cell suspensions (corresponding to 0.84 g of CDW) were incubated with 1 mM of FDCA in 100-ml Erlenmeyer flasks and samples were drawn at regular intervals for analysis of FDCA. The results shown in Table 22 clearly demonstrate the involvement of the enzyme encoded by the *P. brasilianum* hmfK1 in the degradation of FDCA.

TABLE 22

Degradation of FDCA by *P. putida* S12 expressing the *P. brasilianum* hmfK1 gene compared to a control strain lacking the hmfK1 gene.

| | FDCA (mM) | |
|---|---|---|
| Time (h) | hmfK1 present | hmfK1 absent |
| 0 | 1.06 | 1.04 |
| 4 | 1.03 | 1.10 |
| 8 | 1.01 | 1.10 |
| 24 | 0.84 | 1.28 |
| 28 | 0.84 | 1.15 |
| 32 | 0.82 | 1.18 |
| 48 | 0.71 | 1.19 |
| 56 | 0.74 | 1.29 |
| 120 | 0.49 | 1.53 |

Example 5: The Metabolic Fate of HMF in Growing Cultures *P. brasilianum* and in Cell Suspensions in Buffer Solution

*P. brasilianum* C1 was cultivated in small batch cultures with mineral medium and 0.5 g/l HMF. As an initial reaction to the presence of HMF, the organism produced both HMF-alcohol and HMFCA and subsequently degraded all three compounds. This behaviour is reminiscent to the degradation of HMF by several known organisms. No FDCA was detected in such growing cultures.

In order to convincingly demonstrate the formation of FDCA from HMF by whole cells, an experiment was undertaken with concentrated cell suspensions in a buffer solution. The strain was cultivated overnight in 500-ml Erlenmeyer flasks containing 100 ml mineral medium with 0.5 g/l initial HMF. Cultures were centrifuged and washed twice in phosphate buffer (1.55 g/l of $K_2HPO_4$ and 0.85 g/l of $NaH_2PO_4$ $2H_2O$). The resulting pellets were resuspended in 10 ml of the same buffer containing HMF. These cells in this buffer were put in a 100-ml Erlenmeyer flask, which was shaken at a rotary shaker at 400 rpm. Over a period of 120 minutes, samples were taken from this incubation and analyzed by HPLC for HMF, HMF-OH, HMFCA and FDCA.

The results in Table 23 show that HMF was degraded over time and both HMF-OH and HMFCA were formed. Most importantly, it was shown that FDCA accumulated to a concentration of 0.20 mM, demonstrating the fungus *P. brasilianum* C1 is able to produce FDCA from originally HMF. Blank incubations, without initial HMF, accumulated neither of the three intermediary compounds.

TABLE 23

Degradation of HMF by *P. brasilianum* C1 in buffer solution and accumulation of FDCA in time.

| | Compounds (mM) | | | |
|---|---|---|---|---|
| Time (min) | HMF | HMF-OH | HMFCA | FDCA |
| 0 | 0.83 | <0.01 | <0.01 | <0.01 |
| 5 | 0.80 | <0.01 | 0.01 | 0.01 |
| 10 | 0.74 | 0.03 | 0.02 | 0.03 |
| 30 | 0.62 | 0.06 | 0.05 | 0.10 |
| 60 | 0.43 | 0.08 | 0.06 | 0.15 |
| 90 | 0.35 | 0.09 | 0.06 | 0.18 |
| 120 | 0.26 | 0.10 | 0.06 | 0.20 |

Example 6: Production of FDCA from HMF by *S. cerevisiae* and *K. marxianus* Upon Heterologous Expression of *Cupriavidus basilensis* HMFCA Oxidase and Aldehyde Dehydrogenase Genes Genes encoding the hmfH HMF-oxidase and the aldehyde dehydrogenase (HMF/FFCA dehydrogenase) from *Cupriavidus basilensis* HMF14 previously have been functionally expressed in *P. putida* S12 (WO 2012/064195). Bacterial strains such as *P. putida*, however, cannot be employed at low pH-range, e.g. lower than pH 5. For various reason it would be advantageous to employ microbes for FDCA production at pH-values much lower than pH 5. We therefore tested whether the yeasts *S. cerevisiae* and *K. marxianus* could be modified to produce FDCA from HMF and be used at low pH. To this effect, the two *C. basilensis* genes, coding for the oxidase and the aldehyde dehydrogenase, respectively, were expressed in *S. cerevisiae* CEN.PK113-1A and in *K. marxianus* Ky-003 and the recombinant strains were tested for their ability to produce FDCA from HMF. Initial tests were run at neutral pH and in batch culture. Subsequently, the recombinant strain were cultivated in a chemostat at varying pH-values.

An expression construct was prepared for expression of the *C. basilensis* hmfH and HMF/FFCA aldehyde dehydrogenase genes in the yeasts *S. cerevisiae* and *K. marxianus*. In this expression construct, the *C. basilensis* hmfH gene is expressed from the TEF1 promoter and transcription is terminated by the CYC1 terminator, and the *C. basilensis* HMF/FFCA aldehyde dehydrogenase gene is expressed from the TDH3 promoter and transcription is terminated by the TDH3 terminator (tandem construct depicted in SEQ ID NO: 43). The expression construct further comprises a G418 resistance marker and URA3 homologous site for chromosomal integration into the *S. cerevisiae* and *K. marxianus* URA3 locus.

Yeast strains *S. cerevisiae* CEN.PK and *K. marxianus* Ky-003 were transformed with this construct using the standard "lithium acetate/single-stranded carrier DNA/polyethylene glycol" method of Gietz and Woods (2002, Methods in Enzymology, Volume 350, pages 87-96) and transformants were selected on YE agar plates containing 300 μg/ml Geneticin (G418). Incubation of the plates was done at 30° C. for at least 3 days. Transformants were checked by colony PCR. Several clones expressing the enzymes were obtained and *S. cerevisiae* CEN.PK clone 2 and *K. marxianus* Ky-003 clone 3 were used for further studies.

Batch cultivation of the parent CEN.PK strain as well as clone 2 was done in the mineral medium supplied with 1 g/l of glucose and 4 mM of HMF. For the tandem clone 2 G418 (200 μg/ml) was added to the medium. Incubations were shaken at 150 rpm. Samples were taken from these incubations and analyzed by HPLC for HMF, HMF-OH, HMFCA, FFCA and FDCA. The yeast cell density at the start of the experiment was OD 2.2 and OD 4.1 for clone 2 and the parent strain, respectively. The results as given in Table 24 clearly demonstrate the ability of clone 2 to produce both FFCA and FDCA from HMF.

TABLE 24

Degradation of HMF and accumulation of FDCA by CEN.PK and by recombinant CEN.PK clone 2 while incubated in glucose-containing mineral medium.

| Strain | Time (h) | HMF | Concentration (mM) HMF-OH | HMFCA | FFCA | FDCA |
|---|---|---|---|---|---|---|
| CEN.PK control | 0 | 3.05 | <0.01 | <0.01 | 0.03 | <0.01 |
| CEN.PK control | 24 | 0.24 | 1.18 | 2.66 | 0.03 | 0.02 |
| CEN.PK control | 40 | 0.02 | 1.19 | 2.84 | 0.03 | 0.02 |
| CEN.PK clone 2 | 0 | 3.06 | <0.01 | 0.03 | 0.02 | <0.01 |
| CEN.PK clone 2 | 24 | 0.30 | 1.50 | 1.97 | 0.17 | 0.15 |
| CEN.PK clone 2 | 40 | 0.03 | 1.55 | 2.09 | 0.25 | 0.22 |

Batch cultivation of the parent Ky-003 strain as well as clone 3 was done in the mineral medium supplied with 1 g/l of glucose and 4 mM of HMF. For the tandem clone 3 G418 (200 μg/ml) was added to the medium. Incubations were shaken at 150 rpm. Samples were taken from these incubations and analyzed by HPLC for HMF, HMF-OH, HMFCA, FFCA and FDCA. The yeast cell density at the start of the experiment was OD 2 and OD 2.5 for clone 3 and the parent strain, respectively. Similar results as obtained with the *S. cerevisiae* CEN.PK clone 2 were obtained with the *K. marxianus* Ky-003 clone 3 (data not shown): also the *K. marxianus* was capable of producing both FFCA and FDCA from HMF.

Subsequently, the *S. cerevisiae* strains CEN.PK and CEN.PK clone 2 were cultivated in chemostat culture at a dilution rate of 0.08 $h^{-1}$. The mineral medium was used except that $K_2HPO_4$ was taken at 0.3 g/l while 0.2 g/l of yeast extract was added. The pH in the fermentation vessel was controlled automatically with NaOH (4M) and $H_2SO_4$ (4M) at pH=4.0 and the oxygen concentration in the liquid was kept between 45% and 50% of its maximal solubility under these conditions. Antifoam was used whenever required (structol 10%). The amount of glucose added to the medium reservoir was 2 g/l in each run. The first run contained glucose but no HMF. The other runs in addition to glucose also contained HMF in the medium reservoir at 0.5 g/l. For each of the runs, steady state situations were established after 4 volume changes. Both the actual concentrations in the medium reservoir and in the liquid of the fermentation vessel (after cell separation) were determined for glucose, ethanol, HMF, HMF-OH, HMFCA, FFCA and FDCA. Furthermore the yeast biomass was estimated by measuring OD-values. The results are given in Table 25 and confirm that CEN.PK clone 2 is able to produce FDCA from HMF when growing at a pH as low as pH=4.0.

TABLE 25

Measured concentrations of yeast produced as cell dry weight (CDW) and of metabolites in both the medium reservoir (medium in) and the fermentation liquid in the growth vessel (medium out) in chemostat cultures.

| | | Yeast (g/l) CDW | Compounds (mM) Gluc | EtOH | HMF | HMF-OH | HMFCA | FFCA | FDCA |
|---|---|---|---|---|---|---|---|---|---|
| Run1: CEN.PK | Medium in | ND | 11.10 | <0.01 | <0.01 | <0.01 | <0.01 | <0.01 | <0.01 |
| Clone 2 | Liquid out | 0.99 | 0.05 | <0.01 | <0.01 | <0.01 | <0.01 | <0.01 | <0.01 |
| Run 2: CEN.PK | Medium in | ND | 11.08 | <0.01 | 3.98 | <0.01 | <0.01 | <0.01 | <0.01 |
| Clone 2 | Liquid out | 1.04 | 0.07 | <0.01 | 0.71 | 0.67 | 2.87 | <0.01 | 0.21 |
| Run 3: CEN.PK | Medium in | ND | 11.23 | <0.01 | 3.88 | <0.01 | <0.01 | <0.01 | <0.01 |
| | Liquid out | 0.97 | 0.04 | <0.01 | 0.69 | 0.73 | 2.90 | <0.01 | <0.01 |

Example 7: Production of FDCA from HMF by *S. cerevisiae* CEN.PK Expressing *P. brasilianum* hmfL1, hmfL2 and/or hmfN1 Genes Codon optimised nucleotide sequences encoding the *P. brasilianum* alcohol dehydrogenase genes hmfL1 (SEQ ID NO: 57) and/or hmfL2 (SEQ ID NO: 58), as well as the *P. brasilianum* aldehyde dehydrogenase gene hmfN1 (SEQ ID NO: 59) were expressed in *S. cerevisiae* CEN.PK113-1A and the recombinant strain was tested for its ability to produce FDCA from HMF. Initial tests were run at neutral pH and in batch culture. The sequence were codon optimised for expression in yeast.

Expression vectors for the expression of the *P. brasilianum* hmfL1, hmfL2 and/or hmfN1 genes were prepared as follows. A synthetic DNA fragment containing the codon optimised *P. brasilianum* hmfN1 coding sequence (SEQ ID NO: 60) was treated with the restriction enzymes XmaI and SpeI to yield a fragment that was cloned in a yeast/*E. coli* shuttle vector pTT2 (SEQ ID NO: 61) that was treated with XmaI and SpeI followed by a dephosphorylation with calf intestinal phosphatase (CIP). After ligation and transformation of competent *E. coli* the resulting construct (pTT2-hmfN1, SEQ ID NO: 62) was used as a recipient for the synthetic DNA fragment represented by SEQ ID NO: 63 (hmfL1). For this, both DNA molecules (pTT2-hmfN1 and the SEQ ID NO: 63 DNA fragment comprising the hmfL1 coding sequence) were treated with the restriction enzymes Asc1 and MluI. The plasmid was subsequently treated with CIP. The ligation product pTT2-hmfLN1-hmfL1 (SEQ ID NO: 64) was transformed in *E. coli*. In an approach to yield a plasmid capable to express hmfN1 and hmfL2 the plasmid pTT2-hmfN1 (SEQ ID NO: 62) and a synthetic DNA fragment represented by SEQ ID NO: 65 (comprising the hmfL2 coding sequence) were incubated with BsmBI and AatII. The plasmid was subsequently incubated with CIP and ligated with the digested hmfL2-fragment to yield pTT2-hmfN1-hmfL2 (SEQ ID NO: 66). pTT2-hmfLN1-hmfL1 (SEQ ID NO: 64) and the synthetic DNA fragment (SEQ ID NO: 65) were digested with BsmBI and AatII. Again the plasmid was treated with CIP following restriction and the two DNA fragments were ligated to yield pTT2-hmfN1-hmfL1-hmfL2 (SEQ ID NO: 67). pTT2-hmfL1 was derived from pTT2-hmfLN1-hmfL1 (SEQ ID NO: 64) by digestion with the restriction enzymes SmaI and PacI to cut out a fragment containing the TDH3 promotor and the aldehyde dehydrogenase gene hmfN1. The resulting 5' overhang was filled-in using DNA Polymerase I, Large (Klenow) Fragment. The DNA fragment was then ligated and transformed into competent *E. coli*'s to result in pTT2-hmfL1 (SEQ ID NO: 68). This plasmid allows the expression of only the *P. brasilianum* hmfL1 alcohol dehydrogenase. This plasmid allows the co-expression of all three HMF-transforming *P. brasilianum* enzymes in yeast in parallel. *S. cerevisiae* CEN.PK was transformed with pTT2, pTT2-hmfN1-hmfL1-hmfL2, pTT2-hmfN1-hmfL1 and pTT2-hmfL1. Several clones for each transformant were obtained and one clone of each transformant was used for further studies.

Batch cultivation of the transformants was done in the mineral medium supplied with 1 g/l of glucose and 3 mM of HMF. Histidin (100 mg/L) and Uracil (100 mg/L) were added to the medium. Incubations were shaken at 150 rpm. Samples were taken from these incubations and analyzed by HPLC for HMF, HMF-OH, HMFCA, FFCA and FDCA The results as given in Table 26 clearly demonstrate that CEN.PK transformed with pTT2 is incapable of producing FFCA and FDCA from HMF but that each of pTT2-hmfN1-hmfL1-hmfL2, pTT2-hmfN1-hmfL1 and pTT2-hmfL1 confers to the CEN.PK host cell the ability produce both FFCA and FDCA from HMF.

TABLE 26

Determination of HMF metabolites upon incubation of CEN.PK/pTT2, CEN.PK/pTT2-hmfN1-hmfL1-hmfL2, CEN.PK/pTT2-hmfN1-hmfL1 and CEN.PK/pTT2-hmfL1, respectively, in glucose-containing mineral medium supplemented with 3 mM HMF.

| CEN.PK-transforming plasmid | Time (h) | Compounds (mM) HMF | HMF-OH | HMFCA | FFCA | FDCA |
|---|---|---|---|---|---|---|
| pTT2 control | 0 | 2.57 | <0.07 | <0.03 | <0.01 | <0.01 |
| pTT2 control | 40 | 0.20 | 1.84 | 1.78 | <0.01 | <0.01 |
| pTT2-hmfN1-hmfL1-hmfL2 | 0 | 2.71 | 0.09 | 0.01 | <0.01 | 0.05 |
| pTT2-hmfN1-hmfL1-hmfL2 | 40 | 0.35 | 1.36 | 1.25 | <0.01 | 0.87 |
| pTT2-pTT2-hmfN1-hmfL1 | 0 | 2.57 | 0.06 | 0.01 | <0.01 | 0.04 |
| pTT2-pTT2-hmfN1-hmfL1 | 40 | 0.49 | 1.11 | 1.09 | <0.01 | 1.17 |
| pTT2-hmfL1 | 0 | 3.01 | 0.08 | 0.02 | <0.01 | 0.02 |
| pTT2-hmfL1 | 40 | 0.47 | 1.03 | 1.24 | 0.03 | 0.93 |

Subsequently, the *S. cerevisiae* CEN.PK transformants CEN.PK/pTT2 and CEN.PK/pTT2-hmfN1-hmfL1 were cultivated in chemostat culture under the same conditions as described above in Example 6. The results as presented in Table 27 clearly demonstrate that CEN.PK transformed with pTT2-hmfN1-hmfL1 has the ability to efficiently produce FDCA from HMF when provided with sufficient oxygen.

TABLE 27

Measured concentrations of yeast produced as cell dry weight (CDW) and of metabolites in both the medium reservoir (medium in) and the fermentation liquid in the growth vessel (medium out) in chemostat cultures with CEN.PK/pTT2 and CEN.PK/pTT2-hmfN1-hmfL1.

| Strain | | Yeast (g/l) CDW | Compounds (mM) Gluc. | EtOH | HMF | HMF-OH | HMFCA | FFCA | FDCA |
|---|---|---|---|---|---|---|---|---|---|
| CEN.PK/pTT2 | Medium in | ND | 10.98 | <0.01 | 4.03 | <0.01 | <0.01 | <0.01 | <0.01 |
| | Liquid out | 1.05 | 0.06 | <0.01 | 0.88 | 0.76 | 2.56 | <0.01 | <0.01 |
| CEN.PK/pTT2-hmfN1-hmfL1 | Medium in | ND | 11.12 | <0.01 | 4.16 | <0.01 | <0.01 | <0.01 | <0.01 |
| | Liquid out | 1.09 | 0.07 | <0.01 | 0.60 | 0.52 | 0.23 | <0.01 | 3.02 |

Example 8: Production of FDCA from HMF by E *Lipolytica* Upon Heterologous Expression of the Gene from *P. brasilianum* Encoding for a HMFCA Dehydrogenase For expression in *Yarrowia lipolytica*, the *P. brasilianum* hmfL1 codon optimised codon sequence is amplified from pTT2-hmfN1-hmfL1 as template DNA by PCR with oligonucleotides introducing a restriction site for BamHI at the 3' end and a blunt end at the 5' end. The PCR fragment is then cloned into the pYLEX1 expression vector (obtained from Yeastern Biotech Co. Ltd., www.yeastern.com) using BamHI and PmlI as cloning sites and transformed into *E. coli*. After identification of positive *E. coli* clones the pYLEX1-hmfL1 expression vector carrying the *P. brasilianum* hmfL1 gene is prepared for integration into E *lipolytica* Po1g strain (also obtained from Yeastern Biotech Co. Ltd.) by linearising the vector with Nod. The linearized vector is integrated into Po1g using lithium acetate transformation protocol and leucine as auxotrophic marker. Transformants are checked by PCR for the presence of the hmfL1 gene.

Batch cultivation of the transformants was done in the mineral medium supplied with 1 g/l of glucose and 4 mM of HMF. Incubations were shaken at 150 rpm. Samples were taken from these incubations and analyzed by HPLC for HMF, HMF-OH, HMFCA, FFCA and FDCA. The results as presented in Table 28 clearly demonstrate that heterologous expression of the *P. brasilianum* hmfL1 in the *Y. lipolytica* Po1g strain confers the ability to produce FDCA from HMF to this yeast strain.

TABLE 28

Determination of HMF metabolites upon incubation of *Y. lipolytica* Po1g transformed with empty vector or with pYLEX1-hmfL1, respectively, in glucose-containing mineral medium supplemented with 4 mM HMF.

| Vector transforming | | Compounds (mM) | | | | |
|---|---|---|---|---|---|---|
| *Y. lipolytica* Po1g | Time (h) | HMF | HMF-OH | HMFCA | FFCA | FDCA |
| pYLEX1 | 0 | 3.98 | <0.01 | <0.03 | <0.01 | <0.01 |
| pYLEX1 | 40 | 2.01 | 0.05 | 1.78 | <0.01 | <0.01 |
| pYLEX1-hmfL1 | 0 | 4.02 | <0.01 | <0.01 | <0.01 | <0.01 |
| pYLEX1-hmfL1 | 40 | 1.88 | 0.09 | 0.69 | <0.01 | 1.55 |

The invention claimed is:

1. A fungal cell comprising a genetic modification that is:

a) a genetic modification that confers to the cell the ability to oxidize 5-hydroxymethyl-2-furancarboxylic acid (HMFCA) to 5-formyl-2-furoic acid (FFCA) or that increases in the cell the specific activity of an enzyme that oxidizes HMFCA to FFCA as compared to a corresponding wild type cell lacking the genetic modification, wherein the genetic modification is at least one of i) a modification that increases expression of a nucleotide sequence encoding a polypeptide with HMFCA dehydrogenase activity, which polypeptide comprises an amino acid sequence that has at least 73.9% sequence identity with the amino acid sequence of SEQ ID NO: 1; at least 69.4% sequence identity with the amino acid sequence of SEQ ID NO: 2; least 84.5% sequence identity with the amino acid sequence of SEQ ID NO: 3; and/or an amino acid sequence with at least 88% sequence identity with the amino acid sequence of SEQ ID NO: 4; and ii) a modification that increases expression of a nucleotide sequence encoding a polypeptide with furanic oxidase activity, which polypeptide comprises an amino acid sequence that has at least at least 62.7% sequence identity with the amino acid sequence of SEQ ID NO: 7, an amino acid sequence with at least 49.3% sequence identity with the amino acid sequence of SEQ ID NO: 8 and/or an amino acid sequence with at least 66.9% sequence identity with the amino acid sequence of SEQ ID NO: 9.

2. The cell according to claim 1, wherein the cell is a filamentous fungal cell selected from a genus from the group consisting of:

*Acremonium, Aspergillus, Aureobasidium, Cryptococcus, Filibasidium, Fusarium, Humicola, Magnaporthe, Mucor, Mycehophthora, Neocalhmastix, Neurospora, Paecilomyces, Penicillium, Piromyces, Schizophyllum, Talaromyces, Thermoascus, Thielavia, Tolypocladium, Trichoderma*, and *Ustilago*; or, wherein the cell is a yeast cell selected from a genus from the group consisting of: *Saccharomyces, Kluyveromyces, Candida, Pichia, Schizosaccharomyces, Hansenula, Kloeckera, Schwanniomyces, Yarrowia, Cryptococcus, Debaromyces, Saccharomycecopsis, Saccharomycodes, Wickerhamia, Debayomyces, Hanseniaspora, Ogataea,*

*Kuraishia, Komagataella, Metschnikowia, Williopsis, Nakazawaea, Torulaspora, Bullera, Rhodotorula*, and *Sporobolomyces*.

3. The fungal cell according to claim 1, wherein the cell further comprises a genetic modification that reduces or eliminates the expression a gene encoding an FDCA decarboxylating monooxygenase, wherein the FDCA decarboxylating monooxygenase encoding gene has an amino acid sequence with at least 82.3% sequence identity to SEQ ID NO: 10 and/or that has a an amino acid sequence having at least 45% sequence identity to SEQ ID NO: 11.

* * * * *